United States Patent
Zhang et al.

(10) Patent No.: US 11,905,327 B2
(45) Date of Patent: Feb. 20, 2024

(54) SINGLE-DOMAIN ANTIBODIES AND VARIANTS THEREOF AGAINST TIGIT

(71) Applicant: Nanjing Legend Biotech Co., Ltd., Jiangsu (CN)

(72) Inventors: Wang Zhang, Jiangsu (CN); Shu Wu, Jiangsu (CN); Shuai Yang, Jiangsu (CN); Qi Pan, New York, NY (US); Chuan-Chu Chou, Westfield, NJ (US)

(73) Assignee: Nanjing Legend Biotech Co., Ltd., Nanjing (CN)

(*) Notice: Subject to any disclaimer, the term of this patent is extended or adjusted under 35 U.S.C. 154(b) by 699 days.

(21) Appl. No.: 16/958,397

(22) PCT Filed: Dec. 28, 2018

(86) PCT No.: PCT/CN2018/124979
§ 371 (c)(1),
(2) Date: Jun. 26, 2020

(87) PCT Pub. No.: WO2019/129221
PCT Pub. Date: Jul. 4, 2019

(65) Prior Publication Data
US 2021/0054071 A1 Feb. 25, 2021

(30) Foreign Application Priority Data

| Dec. 28, 2017 | (WO) | PCT/CN2017/119506 |
| Jul. 26, 2018 | (WO) | PCT/CN2018/097159 |

(51) Int. Cl.
| C07K 16/02 | (2006.01) |
| A61K 39/395 | (2006.01) |
| A61P 35/00 | (2006.01) |
| C07K 16/28 | (2006.01) |
| A61K 39/00 | (2006.01) |

(52) U.S. Cl.
CPC .......... *C07K 16/2803* (2013.01); *A61P 35/00* (2018.01); *C07K 16/2818* (2013.01); *C07K 16/2827* (2013.01); *A61K 2039/505* (2013.01); *C07K 2317/22* (2013.01); *C07K 2317/24* (2013.01); *C07K 2317/31* (2013.01); *C07K 2317/33* (2013.01); *C07K 2317/569* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| 3,773,919 A | 11/1973 | Boswell |
| RE30,985 E | 6/1982 | Cartaya |
| 4,419,446 A | 12/1983 | Howley |
| 4,560,655 A | 12/1985 | Baker |
| 4,601,978 A | 7/1986 | Karin |
| 4,657,866 A | 4/1987 | Kumar |
| 4,676,980 A | 6/1987 | Segal |
| 4,767,704 A | 8/1988 | Cleveland |
| 4,816,567 A | 3/1989 | Cabilly |
| 4,927,762 A | 5/1990 | Darfler |
| 4,965,199 A | 10/1990 | Capon |
| 5,122,469 A | 6/1992 | Mather |
| 5,229,275 A | 7/1993 | Goroff |
| 5,264,365 A | 11/1993 | Georgiou |
| 5,500,362 A | 3/1996 | Robinson |
| 5,508,192 A | 4/1996 | Georgiou |
| 5,545,806 A | 8/1996 | Lonberg |
| 5,545,807 A | 8/1996 | Surani |
| 5,565,332 A | 10/1996 | Hoogenboom et al. |
| 5,567,610 A | 10/1996 | Borrebaeck |
| 5,569,825 A | 10/1996 | Lonberg |
| 5,571,894 A | 11/1996 | Wels |
| 5,573,905 A | 11/1996 | Lerner |
| 5,587,458 A | 12/1996 | King |
| 5,591,669 A | 1/1997 | Krimpenfort et al. |
| 5,591,828 A | 1/1997 | Bosslet |
| 5,624,821 A | 4/1997 | Winter |
| 5,625,126 A | 4/1997 | Lonberg |
| 5,633,425 A | 5/1997 | Lonberg |
| 5,639,635 A | 6/1997 | Joly |
| 5,641,870 A | 6/1997 | Rinderknecht |
| 5,648,237 A | 7/1997 | Carter |
| 5,648,260 A | 7/1997 | Winter |
| 5,661,016 A | 8/1997 | Lonberg |
| 5,731,168 A | 3/1998 | Carter |
| 5,739,277 A | 4/1998 | Presta |
| 5,750,373 A | 5/1998 | Garrard |
| 5,770,429 A | 6/1998 | Lonberg et al. |

(Continued)

FOREIGN PATENT DOCUMENTS

| CN | 1388136 A | 1/2003 |
| CN | 102369215 A | 3/2012 |

(Continued)

OTHER PUBLICATIONS

Sela-Culang et al. (2013) Frontiers in Immunology 4: 302, p. 1-13.*
Rentero et al. (2011) Chimia 2011, 65: 843-845.*
Khan et al. Sci. Rep. (2017) 7, 45163; doi: 10.1038/srep45163 (12 pages).*
Zhu et al. Cell (2015) 161: 1280-1292.*
Lee et al. Nature Medicine (2016) 22: 1456-1464.*
Abdiche et al. mAbs (2016) 8: 264-277.*

(Continued)

*Primary Examiner* — Ilia I Ouspenski

(74) *Attorney, Agent, or Firm* — Fish & Richardson P.C.

(57) ABSTRACT

Provided are constructs comprising a single-domain antibody (sdAb) moiety that specifically recognizes TIGIT. Also provided are methods of making and using these constructs.

18 Claims, 26 Drawing Sheets

Specification includes a Sequence Listing.

(56) References Cited

U.S. PATENT DOCUMENTS

| | | |
|---|---|---|
| 5,821,337 A | 10/1998 | Carter |
| 5,837,234 A | 11/1998 | Gentile |
| 5,840,523 A | 11/1998 | Simmons |
| 5,869,046 A | 2/1999 | Presta |
| 6,013,605 A | 1/2000 | Rees |
| 6,027,888 A | 2/2000 | Georgiou |
| 6,075,181 A | 6/2000 | Kucherlapati |
| 6,083,715 A | 7/2000 | Georgiou |
| 6,150,584 A | 11/2000 | Kucherlapati |
| 6,194,551 B1 | 2/2001 | Idusogie |
| 6,602,684 B1 | 8/2003 | Umana |
| 6,737,056 B1 | 5/2004 | Presta |
| 6,982,321 B2 | 1/2006 | Winter |
| 7,041,870 B2 | 5/2006 | Tomizuka |
| 7,087,409 B2 | 8/2006 | Barbas, III |
| 7,189,826 B2 | 3/2007 | Rodman |
| 7,332,581 B2 | 2/2008 | Presta |
| 7,371,826 B2 | 5/2008 | Presta |
| 7,371,849 B2 | 5/2008 | Honda |
| 7,504,256 B1 | 3/2009 | Ogawa |
| 7,521,541 B2 | 4/2009 | Eigenbrot |
| 7,527,791 B2 | 5/2009 | Adams |
| 8,502,014 B2 | 8/2013 | Grosveld |
| 8,507,748 B2 | 8/2013 | Grosveld |
| 8,754,287 B2 | 6/2014 | Macdonald |
| 8,921,522 B2 | 12/2014 | Grosveld et al. |
| 8,921,524 B2 | 12/2014 | Grosveld et al. |
| 10,385,137 B2 | 8/2019 | Baty et al. |
| 11,447,573 B2 | 9/2022 | Chou et al. |
| 11,472,881 B2 | 10/2022 | Zhang et al. |
| 2002/0164328 A1 | 11/2002 | Shinkawa |
| 2003/0115614 A1 | 6/2003 | Kanda |
| 2003/0157108 A1 | 8/2003 | Presta |
| 2004/0093621 A1 | 5/2004 | Shitara |
| 2004/0109865 A1 | 6/2004 | Niwa |
| 2004/0110282 A1 | 6/2004 | Kanda |
| 2004/0110704 A1 | 6/2004 | Yamane |
| 2004/0132140 A1 | 7/2004 | Satoh |
| 2004/0259150 A1 | 12/2004 | Nakamura |
| 2005/0014934 A1 | 1/2005 | Hinton |
| 2005/0031613 A1 | 2/2005 | Nakamura |
| 2005/0079574 A1 | 4/2005 | Bond |
| 2005/0119455 A1 | 6/2005 | Fuh |
| 2005/0123546 A1 | 6/2005 | Umana |
| 2005/0255115 A1 | 11/2005 | Huang et al. |
| 2005/0266000 A1 | 12/2005 | Bond |
| 2005/0272916 A1 | 12/2005 | Hanai |
| 2006/0025576 A1 | 2/2006 | Miller |
| 2007/0061900 A1 | 3/2007 | Murphy |
| 2007/0071675 A1 | 3/2007 | Wu |
| 2007/0117126 A1 | 5/2007 | Sidhu |
| 2007/0134759 A1 | 6/2007 | Nishiya |
| 2007/0160598 A1 | 7/2007 | Dennis |
| 2007/0178552 A1 | 8/2007 | Arathoon |
| 2007/0237764 A1 | 10/2007 | Birtalan |
| 2007/0292936 A1 | 12/2007 | Barthelemy |
| 2008/0241884 A1 | 10/2008 | Shitara |
| 2009/0002360 A1 | 1/2009 | Chen |
| 2009/0307787 A1 | 12/2009 | Grosveld |
| 2010/0122358 A1 | 5/2010 | Brueggemann |
| 2011/0028695 A1 | 2/2011 | Rivets et al. |
| 2011/0118444 A1 | 5/2011 | Grosveld et al. |
| 2011/0287009 A1 | 11/2011 | Scheer |
| 2013/0156769 A1 | 6/2013 | Kufer et al. |
| 2013/0189735 A1 | 7/2013 | Zardi |
| 2013/0323235 A1 | 12/2013 | Craig et al. |
| 2013/0344057 A1 | 12/2013 | Grosveld et al. |
| 2014/0033335 A1 | 1/2014 | Grosveld |
| 2014/0037616 A1 | 2/2014 | Grosveld |
| 2014/0127210 A1 | 5/2014 | Kim |
| 2014/0356908 A1 | 12/2014 | Grosveld et al. |
| 2015/0086541 A1 | 3/2015 | Aguilar-Cordova |
| 2015/0202291 A1 | 7/2015 | Bosch |
| 2015/0216970 A1 | 8/2015 | Grogan |
| 2015/0232555 A1 | 8/2015 | Carven |
| 2015/0289489 A1 | 10/2015 | Macdonald |
| 2016/0000842 A1 | 1/2016 | Song et al. |
| 2016/0083476 A1 | 3/2016 | Baty et al. |
| 2016/0106835 A1 | 4/2016 | Hoos et al. |
| 2016/0145355 A1 | 5/2016 | Saha et al. |
| 2016/0166685 A1 | 6/2016 | Cheung et al. |
| 2016/0176963 A1 | 6/2016 | Maurer et al. |
| 2016/0272960 A1 | 9/2016 | Thanos et al. |
| 2016/0355589 A1* | 12/2016 | Williams ........... C07K 16/2803 |
| 2019/0202935 A1 | 7/2019 | Chou |
| 2019/0233519 A1 | 8/2019 | Zhang |
| 2020/0369770 A1* | 11/2020 | Zhang .................... A61P 35/00 |
| 2022/0267475 A1* | 8/2022 | Yin .................... C07K 16/2809 |

FOREIGN PATENT DOCUMENTS

| | | |
|---|---|---|
| CN | 105754990 A | 7/2016 |
| EP | 0308936 A2 | 3/1989 |
| EP | 0368684 A1 | 5/1990 |
| EP | 0404097 A2 | 12/1990 |
| EP | 1792991 A1 | 6/2007 |
| EP | 3263702 A1 | 1/2018 |
| EP | 3459597 A1 | 3/2019 |
| JP | 2008523795 A | 7/2008 |
| JP | 2009504191 A | 2/2009 |
| JP | 2010-527597 | 8/2010 |
| JP | 2010530753 A | 9/2010 |
| JP | 2011504742 A | 2/2011 |
| JP | 2013505923 A | 2/2013 |
| JP | 2014090721 A | 5/2014 |
| JP | 2014519029 A | 8/2014 |
| JP | 2014525918 A | 10/2014 |
| JP | 2015-501135 | 1/2015 |
| JP | 2015504306 A | 2/2015 |
| JP | 2015-509097 | 3/2015 |
| JP | 2015-524790 | 8/2015 |
| KR | 20100097720 A | 9/2010 |
| WO | 1987000195 A1 | 1/1987 |
| WO | 1991000360 A | 1/1991 |
| WO | 1991010741 A1 | 7/1991 |
| WO | 199308829 A1 | 5/1993 |
| WO | 1993011161 A1 | 6/1993 |
| WO | 199316185 A2 | 8/1993 |
| WO | 199404678 A1 | 3/1994 |
| WO | 1994004678 A1 | 3/1994 |
| WO | 1994004690 A1 | 3/1994 |
| WO | 1994011026 A2 | 5/1994 |
| WO | 199429351 A2 | 12/1994 |
| WO | 1996016673 A1 | 6/1996 |
| WO | 1996027011 A1 | 9/1996 |
| WO | 1996033735 A1 | 10/1996 |
| WO | 1996034096 A1 | 10/1996 |
| WO | 1996034103 A1 | 10/1996 |
| WO | 1997017852 A1 | 5/1997 |
| WO | 1997030087 A1 | 8/1997 |
| WO | 1997049805 A2 | 12/1997 |
| WO | 1998022141 A2 | 5/1998 |
| WO | 1998024893 A2 | 6/1998 |
| WO | 1998050431 A2 | 11/1998 |
| WO | 1998058964 A1 | 12/1998 |
| WO | 1999022764 A1 | 5/1999 |
| WO | 1999037681 A2 | 7/1999 |
| WO | 1999051642 A1 | 10/1999 |
| WO | 2000027435 A1 | 5/2000 |
| WO | 2000043507 A1 | 7/2000 |
| WO | 2000061739 A1 | 10/2000 |
| WO | 2001029246 A1 | 4/2001 |
| WO | 2001077137 A1 | 10/2001 |
| WO | 2002031140 A1 | 4/2002 |
| WO | 2002085945 A2 | 3/2003 |
| WO | 2003025020 A1 | 3/2003 |
| WO | 2003035694 A2 | 5/2003 |
| WO | 2003014161 A2 | 8/2003 |
| WO | 2003084570 A1 | 10/2003 |
| WO | 2003085107 A1 | 10/2003 |
| WO | 2003011878 A2 | 11/2003 |
| WO | 2004042072 A2 | 5/2004 |
| WO | 2004049794 A2 | 6/2004 |
| WO | 2004056312 A2 | 7/2004 |

(56) References Cited

FOREIGN PATENT DOCUMENTS

| | | |
|---|---|---|
| WO | 2004092219 A2 | 10/2004 |
| WO | 2005035586 A1 | 4/2005 |
| WO | 2003085119 A1 | 8/2005 |
| WO | 2005100402 A1 | 10/2005 |
| WO | 2001090190 A2 | 1/2006 |
| WO | 2006003388 A2 | 1/2006 |
| WO | 2006008548 A2 | 1/2006 |
| WO | 2006029879 A2 | 3/2006 |
| WO | 2006030220 A1 | 3/2006 |
| WO | 2005035778 A1 | 12/2006 |
| WO | 2006138670 A2 | 12/2006 |
| WO | 2007024715 A2 | 3/2007 |
| WO | 2005053742 A1 | 6/2007 |
| WO | WO 2007112940 | 10/2007 |
| WO | 2008077546 A1 | 7/2008 |
| WO | 2009068649 A2 | 6/2009 |
| WO | 2009089004 A1 | 7/2009 |
| WO | 2010097597 A1 | 9/2010 |
| WO | 2010112193 A1 | 10/2010 |
| WO | 2011036460 A1 | 3/2011 |
| WO | 2012155019 A1 | 11/2012 |
| WO | 2012158818 A2 | 11/2012 |
| WO | 2013019906 A1 | 2/2013 |
| WO | 2014209804 A1 | 12/2014 |
| WO | 2016024231 A1 | 2/2016 |
| WO | 2016028656 A1 | 2/2016 |
| WO | 2016061142 A1 | 4/2016 |
| WO | 2016106302 A1 | 6/2016 |
| WO | WO 2016115274 | 7/2016 |
| WO | 2016154473 A1 | 9/2016 |
| WO | 2016187594 A1 | 11/2016 |
| WO | 2017037707 A1 | 3/2017 |
| WO | 2017053748 A2 | 3/2017 |
| WO | 2017059095 A1 | 4/2017 |
| WO | 2017143406 A1 | 8/2017 |
| WO | 2017165681 A1 | 9/2017 |
| WO | WO 2017215590 | 12/2017 |
| WO | 2018014260 A1 | 1/2018 |
| WO | 2018014855 A1 | 1/2018 |
| WO | 2018068201 A1 | 4/2018 |
| WO | 2018068695 A1 | 4/2018 |
| WO | 2019129221 A1 | 7/2019 |

OTHER PUBLICATIONS

Konitzer et al. mAbs (2017) 9: 536-549.*
Ferrara et al. mAbs (2015) 7: 32-41.*
Parola et al. Immunology (2018) 153: 31-41.*
Boyd et al. Current Opinion in Immunology 2016, 40: 103-109.*
Damschroder et al. Molecular Immunology (2004) 41: 985-1000.*
Van Regenmortel MHV. Front. Immunol. (2018) vol. 8, Article 2009 (11 pages).*
Kanyavuz et al. Nat Rev Immunol. 2019; 19(6): 355-368.*
Conroy et al. Methods (2017) 116: 12-22.*
Sheehan et al. Microbiol. Spectr. (2015) 3(1): AID-0028-2014; 17 pages.*
Almagro, J. et al. (Jan. 1, 2008). "Humanization of Antibodies," Frontiers in Bioscience 13:1619-1633.
Anderson, A. C. et al. (May 17, 2016). "Lag-3, Tim-3, and TIGIT: Co-Inhibitory Receptors with Specialized Functions in Immune Regulation," Immunity 44(5):989-1004.
Arie, J-P. et al. (Jan. 1, 2001). "Chaperone Function of FkpA, A Heat Shock Prolyl Isomerase, in the Periplasm of *Escherichia coli*," Molecular Micorbiology 39(1):199-210.
Armour, K.L. et al. (1999). "Recombinant Human IgG Molecules Lacking Fcγ Receptor I Binding and Monocte Triggering Activities," Eur. J. Immunol. 29:2613-2624.
Baca, M. et al. (Apr. 18, 1997). "Antibody Humanization Using Monovalent Phage Display," J. Biol. Chem 272(16):10678-10684.
Bachmann, B.J. (1987). "Section G. Strains and Useful Strain Constructions. Derivations and Genotypes (of Some Mutant Derivatives of *Escherichia coli* K-12," Cellular and Molecular Biology, vol. 2, Neidhardt, F. C. et al., Washington, D.C., American Society for Microbiology, pp. 1190-1219.
Balzano, C. et al. (1992). "CTLA-4 and CD28: Similar Proteins, Neighbouring Genes," Int. J. Cancer Suppl. 7:28-32. (Abstract Only).
Bao, F. et al. (May 27, 2017). "Construction and Identification of Natural Single Domain Antibody Library of Bactrian Camel," Animal Husbandry and Feed Science 38(5):1-7. (English Abstract Only).
Barbas III, C.F. et al. (Apr. 1994). "In Vitro Evolution of a Neutralizing Human Antibody to Human Immunodeficiency Virus Type 1 to Enhance Affinity and Broaden Strain Cross-Reactivity," Proc Nat. Acad. Sci. USA 91:3809-3813.
Barnes, D. et al. (Mar. 1, 1980). "Methods for Growth of Cultured Cells in Serum-Free Medium," Anal. Biochem. 102(2):255-270.
Barthelemy, P.A. et al. (Feb. 8, 2008). "Comprehensive Analysis of the Factors Contributing to the Stability and Solubility of Autonomous Human VH Domains," Journal of Biological Chemistry 283(6):3639-3654.
Bass, S. et al. (1990). "Hormone Phage: An Enrichment Method for Variant Proteins With Altered Binding Properties," Proteins 8:309-314.
Beiboer, S.H.W. et al. (2000). "Guided Selection of a Pan Carcinoma Specific Antibody Reveals Similar Binding Characteristics Yet Structural Divergence Between the Original Murine Antibody and Its Human Equivalent," J Mol Biol. 296(3):833-849.
Boerner, P. et al. (Jul. 1, 1991). "Production of a Antigen-Specific Human Monoclonal Antibodies from In Vitro-Primed Human Splenocytes," J. Immunol. 147(1):86-95.
Bothmann, H. et al., (Jun. 2, 2000). "The Periplasmic *Escherichia coli* Peptidylprolyl cis, trans-Isomerase FkpA," The Journal of Biological Chemistry 275(22):17100-17105.
Brennan, M. et al. (Jul. 5, 1985). "Preparation of Bispecific Antibodies by Chemical Recombination of Monoclonal Immunoglobulin G1 Fragments," Science 229:81-83.
Brown, M. et al. (1996) "Tolerance to Single, but Not Multiple, Amino Acid Replacements in Antibody VH CDR2," J. Immunol. 156:3285-3291.
Brüggemann, M. et al. (1993). "Designer Mice: The Production of Human Antibody Repertoires in Transgenic Animals," Year in Immuno. 7:33-40.
Brüggemann, M. et al. (Nov. 1, 1987). "Comparison of the Effector Functions of Human Immunoglobulins Using a Matched Set of Chimeric Antibodies," J. Exp. Med. 166:1351-1361.
Caljon, G. et al. (Nov. 15, 2012). "Affinity Is an Important Determinant of the Anti-Trypanosome Activity of Nanobodies", Plos Neglected Tropical Diseases 6(11):e1902, 8 pages.
Capel, P.J. et al. (Feb. 1994). "Heterogeneity of Human IgG Fc Receptors," Immunomethods 4(1):25-34.
Caron, P.C. et al. (Oct. 1, 1992). "Engineering Humanized Dimeric Forms of IgG Are More Effective Antibodies," J. Exp Med. 176:1191-1195.
Carter, P. et al. (Feb. 1992). "High Level *Escherichia coli* Expression and Production of a Bivalent Humanized Antibody Fragment," Bio/Technology 10:163-167.
Carter, P. et al. (May 1992). "Humanization of an Anti-p185HER2 Antibody for Human Cancer Therapy," Proc. Natl. Acad. Sci. USA 89:4285-4289.
Chen, W. et al. (Jan. 2010). "A Large Human Domain Antibody Library Combining Heavy and Light Chain CDR3 Diversity," Mol. Immunol. 47(4):912-921, 23 pages.
Chen, Y. et al. (1999). "Selection and Analysis of an Optimized Anti-VEGF Antibody: Crystal Structure of an Affinity-Matured Fab In Complex With Antigen," J. Mol. Biol 293:865-881.
Choi, Y. et al. (2011). "Predicting Antibody Complementarity Determining Region Structures Without Classification," Molecular BioSystems 7:3327-3334.
Chothia, C. et al. (Aug. 20, 1987). "Canonical Structures for the Hypervariable Regions of Immunoglobulins," J. Mol. Biol. 196(4):901-917.
Chowdhury, P.S. (2008). "Engineering Hot Spots for Affinity Enhancement of Antibodies," Methods Mol. Biol. 207:179-196.

(56) References Cited

OTHER PUBLICATIONS

Clackson, T. et al. (Aug. 15, 1991). "Making Antibody Fragments Using Phage Display Libraries," Nature 352:624-628.
Clynes, R. et al. (Jan. 1998). "Fc Receptors are Required in Passive and Active Immunity to Melanoma," Proc. Natl. Acad. Sci. U.S.A. 95:652-656.
Cole, R.D. (Aug. 1960). "The Chromatography of Insulin in Urea-Containing Buffer," Journal of Biological Chemistry 235(8):2294-2299.
Conrath, K.E. et al. (Mar. 9, 2001). "Camel Single-domain Antibodies as Modular Building Units in Bispecific and Bivalent Antibody Constructs" J. Biol. Chem. 276(10):7346-7350.
Cragg, M.S. et al. (Apr. 1, 2004). "Antibody Specificity Controls In Vivo Effector Mechanisms of Anti-CD20 Reagents," Blood 103(7):2738-2743.
Cragg, M.S. et al. (Feb. 1, 2003). "Complement-Mediated Lysis by Anti-CD20 Mab Correlates With Segregation Into Lipid Rafts," Blood 101(3):1045-1052.
Cunningham, B.C. et al. (Jun. 2, 1989). "High-Resolution Epitope Mapping of hGH-Receptor Interactions by Alanine-Scanning Mutagenesis," Science 244:1081-1085.
Dall'Acqua, W.F. et al. (2005). "Antibody Humanization by Framework Shuffling," Methods 36:43-60.
Davies, J. et al. (1996). "Single Antibody Domains as Small Recognition Units: Design and In Vitro Antigen Selection of Camelized, Human VH Domains with Improved Protein Stability," Protein Engineering 9(6):531-537.
Davies, J. et al. (Feb. 21, 1994). "Camelising' Human Antibody Fragments: NMR Studies on VH Domains," FEBS Letters 339(3):285-290.
Daëron, M. (1997). "Fc Receptor Biology," Ann. Rev. Immunol. 15:203-234.
De Genst, E. et al. (2006, e-pub. Jul. 11, 2005). "Antibody Repertoire Development in Camelids," Developmental and Comparative Immunology 30:187-198.
De Haas, M. et al. (Oct. 1995). "Fc Gamma receptors of Phagocytes," J. Lab. Clin. Med. 126:330-341.
Duncan, A.R. et al. (Apr. 21, 1988). "The Binding Site for C1q on IgG," Nature 322:738-740.
Fan, G. et al. (2015). "Bispecific Antibodies and their Applications," J. Hematol & Oncol. 8(130):1-14.
Fellouse, F.A. et al. (Aug. 24, 2004). "Synthetic Antibodies from a Four-Amino-Acid Code: A Dominant Role for Tyrosine in Antigen Recognition," Proc. Natl. Acad. Sci. USA 101(34):12467-12472.
Fishwild, D.M. et al. (Jul. 1996). "High-Avidity Human IgGK Monoclonal Antibodies from a Novel Strain of Minilocus Transgenic Mice," Nature Biotechnol. 14:845-851.
Fromentin, R. et al. (Jul. 14, 2016). "CD4+ T Cells Expressing PD-1, Tigit and LAG-3 Contribute to HIV Persistence during Art," Plos Athogens 12(7):1-19.
Fulkerson, P.C. et al. (2013, e-pub. Jan. 21, 2013). "Targeting Eosinophils in Allergy, Inflammation (and Beyond," Nat Rev Drug Discov 12(2):117-129, 23 pages.
Gazzano-Santoro, H. et al. (Mar. 28, 1997). "A Non-Radioactive Complement-Dependent Cytotoxicity Assay for Anti-CD20 Monoclonal Antibody," J. Immunol. Methods 202:163-171.
Geering, B. et al. (Feb. 2015). "Synthetic Immunology: Modulating the Human Immune System," Trends Biotechnol. 33(2):65-79.
Ghetie, V. et al. (1997). "Increasing the Serum Persistence of an IgG Fragment by Random Mutagenesis," Nat Biotech 15:637-640.
Ghetie, V. et al. (Jul. 15, 1997). "FcRn: the MHC Class I-related Receptor That is More Than An IgG Transporter," Immunol. Today 18(12):592-598.
Goding, J.W. (1983). "Production of Monoclonal Antibodies," Chapter 3 in Monoclonal Antibodies: Principles and Practice, Academic Press, pp. 59-103, 27 pages.
Graham, F.L. et al. (1977). "Characteristics of a Human Cell Line Transformed by DNA From Human Adenovirus Type 5," Journal General Virology 36(1):59-74.
Greenberg, A.S. et al. (Mar. 9, 1995). "A New Antigen Receptor Gene Family That Undergoes Rearrangement and Extensive Somatic Diversification In Sharks" Nature 374(6518):168-173.
Griffiths, A.D. et al. (1993). "Human Anti-Self Antibodies with High Specificity from Phage Display Libraries," EMBO J. 12(2):725-734.
Gruber, M. et al. (1994). "Efficient Tumor Cell Lysis Mediated by a Bispecific Single Chain Antibody Expressed in Escherichia coli," J. Immunol. 152:5368-5374.
Guss, B. et al. (Jul. 1986). "Structure of the IgG-Binding Regions of Streptococcal Protein G," EMBO J. 5(7):1567-1575.
Guyer, R.L. et al. (Aug. 1976). "Immunoglobulin Binding by Mouse Intestinal Epithelial Cell Receptors," J. Immunol. 117(2):587-593.
Ham, R.G. et al. (1979). "Media and Growth Requirements," Meth. Enzymol. 58:44-93.
Hamers-Casterman, C. et al. (Jun. 3, 1993). "Naturally Occurring Antibodies Devoid of Light Chains," Nature 363:446-448.
Hammerling, G. et al. (1981). "Monoclonal Antibodies and T-Cell Hybridomas," in Monoclonal Antibodies and T-Cell Hybridomas, Elsevier/North Holland Biomedical Press, New York, pp. 563-586.
Hara, H. et al. (Nov. 1, 1996) "Overproduction Of Penicillin-Binding Protein 7 Suppresses Thermosensitive Grovvth Defect at Low Osmolarity Due to An Spr Mutation of Escherichia coli," Microbial Drug Resistance 2(1):63-72.
Harris, W.J. (1995). "Production of Humanized Monoclonal and Antibodies for in vivo Imaging and Therapy," Biochem. Soc. Transactions 23:1035-1038.
Hassanzadeh-Ghassabeh, G. et al. (2013, e-pub. Jun. 4, 2013). "Nanobodies and their Potential Applications," Nanomedicine (Lond) 8(6):1013-1026.
Hawkins, R.E. et al. (1992). "Selection of Phage Antibodies by Binding Affinity: Mimicking Affinity Maturations," J. Mol. Biol. 226:889-896.
Hellstrom, I. et al. (Mar. 1985). "Strong Antitumor Activities of IgG3 Antibodies to a Human Melanoma-associated Ganglioside," Proc. Natl. Acad. Sci. USA 82:1499-1502.
Hellstrom, I. et al. (Sep. 1986). "Antitumor Effects of L6, an IgG2a Antibody That Reacts With Most Human Carcinomas," Proc. Natl. Acad. Sci. USA 83:7059-7063.
Hinton, P.R. et al. (Feb. 20, 2004). "Engineered Human IgG Antibodies with Longer Serum Half-lives in Primates," J. Biol. Chem. 279(8):6213-6216.
Hmila, I. et al. (Aug. 2008, e-pub. Jul. 9, 2008). "VHH Bivalent Domains And Chimeric Heavy Chain-Only Antibodies With High Neutralizing Efficacy for Scorpion Toxin Aahi," Molecular Immunology 45(14):3847-3856.
Holliger, P. et al. (Jul. 1993). "Diabodies: Small Bivalent and Bispecific Antibody Fragments," Proc. Natl. Acad. Sci. USA 90:6444-6448.
Holt, L.J. et al. (Nov. 2003) "Domain Antibodies: Proteins For Therapy," Trends in Biotechnology 21(11): 484-490.
Hongo, J.A.S. et al. (1995). "Development and Characterization of Murine Monoclonal Antibodies to the Latency-Associated Peptide of Transforming Growth Factor Beta1," Hybridoma, 14(3):253-260.
Hoogenboom, H.R. (2002). "Overview of Antibody Phage-Display Technology and its Applications," in Chapter 1 of Methods in Molecular Biology, O'Brien, P.M. (ed.) et al., Humana Press Inc., Totowa, NJ, 178:1-37.
Hoogenboom, H.R. et al. (1991) "Multi-Subunit Proteins on the Surface of Filamentous Phage: Methodologies for Displaying Antibody (Fab) Heavy and Light Chains," Nucleic Acids Research 19(15):4133-4137.
Hoogenboom, H.R. et al. (Sep. 20, 1992). "By-Passing Immunisation Human Antibodies From Synthetic Repertoires of Germline VH Gene Segments Rearranged In Vitro," J. Mol. Biol. 227(2):381-388.
Hurle, M.R. et al. (1994). "Protein Engineering Techniques for Antibody Humanization," Curr. Op. Biotech. 5(4):428-433.
Idusogie, E.E. et al. (2000). "Mapping of the C1q Binding Site on Rituxan, a Chimeric Antibody With a Human lgG1 Fc," J. Immunol. 164:4178-4184.

(56) References Cited

OTHER PUBLICATIONS

International Preliminary Report on Patentability dated Jul. 14, 2020, for PCT Patent Application No. PCT/CN2019/070873, filed Jan. 8, 2019, 7 pages.
International Preliminary Report on Patentability dated Jun. 30, 2020 for PCT Application No. PCT/CN2018/124979 filed on Dec. 28, 2018, 5 pages.
International Preliminary Report on Patentability dated Apr. 16, 2019, for PCT Patent Application No. PCT/CN2017/105506, filed Oct. 10, 2017, 7 pages.
International Preliminary Report on Patentability dated Apr. 25, 2019, for PCT Patent Application No. PCT/CN2016/101777, filed Oct. 11, 2016, 9 pages.
International Preliminary Report on Patentability dated Jan. 22, 2019, for PCT Patent Application No. PCT/CN2016/090703, filed Jul. 20, 2016, 6 pages.
International Preliminary Report on Patentability dated Jan. 22, 2019, for PCT Patent Application No. PCT/CN2017/093644, filed Jul. 20, 2017, 6 pages.
International Search Report and Written Opinion dated Apr. 11, 2019, for PCT Patent Application No. PCT/CN2019/070873, filed Jan. 8, 2019, 15 pages.
International Search Report and Written Opinion of the International Searching Authority dated Mar. 18, 2019 for PCT Application No. PCT/CN2018/124979 filed on Dec. 28, 2018, 10 pages.
International Search Report dated Apr. 12, 2017, for PCT Patent Application No. PCT/CN2016/090703, filed Jul. 20, 2016, 7 pages.
International Search Report dated Jan. 19, 2018, for PCT Patent Application No. PCT/CN2017/105506, filed Oct. 10, 2017, 6 pages.
International Search Report dated Jul. 11, 2017, for PCT Patent Application No. PCT/CN2016/101777, filed Oct. 11, 2016, 7 pages.
International Search Report dated Oct. 11, 2017, for PCT Patent Application No. PCT/CN2017/093644, filed Jul. 20, 2017, 7 pages.
Iwai, Y. et al. (Feb. 2005, e-pub. Dec. 20, 2004). "PD-1 Blockade Inhibits Hematogenous Spread of Poorly Immunogenic Tumor Cells by Enhanced Recruitment of Effector T Cells," International Immunology 17(2):133-144.
Jackson, J.R. et al. (Apr. 1, 1995). "In Vitro Antibody Maturation. Improvement of a High Affinity, Neutralizing Antibody Against IL-1 Beta," J. Immunol. 154(7):3310-3319.
Jakobovits, A. et al. (Mar. 18, 1993). "Germ-Line Transmission and Expression of a Human-Derived Yeast Artificial Chromosome," Nature 362:255-258.
Jakobovits, A. et al. (Mar. 1993). "Analysis of Homozygous Mutant Chimeric Mice: Deletion of the Immunoglobulin Heavy-Chain Joining Region Blocks B-Cell Development and Antibody Production," Proc. Natl. Acad. Sci. USA 90:2551-2555.
Janssens, R. et al. (Oct. 10, 2006). "Generation Of Heavy-Chain-Only Antibodies In Mice," Proc. Natl. Acad. Sci. USA 103(41):15130-15135.
Jin, H. (Dec. 31, 2013, e-pub. Apr. 23, 2015). "Construction and Characterization of a CTLA-4-Targeted scFv-Melittin Fusion Protein as a Potential Immunosuppressive Agent for Organ Transplant," Cell Biochemistry and Biophysics 3(67):1067-1074.
Johnson, G. et al. (2003). "The Kabat Database and a Bioinformatics Example," Methods in Molecular Biology 248:11-25, 15 pages.
Johnson, K.S. et al. (1993). "Human Antibody Engineering," Current Opinion in Structural Biology 3:564- 571.
Jones, A.J.S. (1993). "Analysis of Polypeptides and Proteins," Adv. Drug Delivery Rev. 10:29-90.
Jones, P. et al. (May 29, 1986). "Replacing the Complementarity-Determining Regions in a Human Antibody With Those From a Mouse," Nature 321:522-525.
Kam, N.W.S. et al. (Aug. 16, 2005). "Carbon Nanotubes as Multifunctional Biological Transporters and Near-Infrared Agents for Selective Cancer Cell Destruction," PNAS 102(33):11600-11605, 6 pages.
Kanda, Y. et al. (Jul. 5, 2006, e-pub. Apr. 11, 2006). "Comparison of Cell Line for Stable Production of Fucose-Negative Antibodies with Enhanced ADCC," Biotechnol. Bioeng. 94(4):680-688.
Kashmiri, S.V. et al. (2005). "SDR grafting—A New Approach to Antibody Humanization," Methods 36:25-34.
Kim, J-K. et al. (1994). "Localization of the Site of the Murine IgGl Molecule That is Involved in Binding to the Murine Intestinal Fc Receptor," Eur. J. Immunol. 24:2429-2434.
Klimka, A. et al. (2000). "Human Anti-CD30 Recombinant Antibodies by Guided Phage Antibody Selection Using Cell Panning," Br. J. Cancer 83(2):252-260.
Kohler, G. et al. (Aug. 7, 1975) "Continuous Cultures of Fused Cells Secreting Antibody of Predefined Specificity," Nature 256:495-497.
Kostelny, S.A. et al. (Mar. 1, 1992). "Formation of a Bispecific Antibody by the Use of Leucine Zippers," J. Immunol. 148(5):1547-1553.
Kozbor, D. (Dec. 1984). "A Human Hybrid Myeloma for Production of Human Monoclonal Antibodies," J. Immunol. 133(6):3001-3005.
Lauwereys, M. et al. (Jul. 1, 1998). "Potent Enzyme Inhibitors Derived From Dromedary Heavy-Chain Antibodies," The EMBO Journal 17(13):3512-3520.
Lee, C.V. et al. (2004). "Bivalent Antibody Phage Display Mimics Natural Immunoglobulin," .J. Immunol. Methods 284(1-2):119-132.
Lee, C.V. et al. (2004). "High-Affinity Human Antibodies From Phage-Displayed Synthetic Fab Libraries With a Single Framework Scaffold," J. Mol. Biol. 340:1073-1093.
Li, A. et al. (Apr. 26, 2016). "A Single-Domain Antibody-Linked Fab Bispecific Antibody Her2-S-Fab Has Potent Cytotoxicity Against Her2-Expressing Tumor Cells," AMB Express 6(32):1-8.
Li, J. et al. (Mar. 7, 2006). "Human Antibodies for Immunotherapy Development Generated via a Human B Cell Hybridoma Technology," Proc. Natl. Acad. Sci. USA 103:3557-3562, 6 pages.
Li, L. et al. (Nov./Dec. 2015). "A Novel Bispecific Antibody, S-Fab, Induces Potent Cancer Cell Killing", J. of Immunotherapy 38(9):350-356.
Lindmark, R. et al. (1983). "Binding of Immunoglobulins to Protein A and Immunoglobulin Levels in Mammalian Sera," J. Immunol. Meth. 62:1-13.
Lonberg, N. (Sep. 2005). "Human Antibodies From Transgenic Animals," Nat. Biotech. 23(9):1117- 1125.
Lonberg, N. et al. (1995, e-pub. Jul. 10, 2009). "Human Antibodies From Transgenic Mice," Int. Rev. Immunol. 13(1):65-93.
Lonberg, N. et al. (Apr. 28, 1994). "Antigen-Specific Human Antibodies From Mice Comprising Four Distinct Genetic Modifications," Nature 368(6474):856-859.
Mabry, R. et al. (2010, e-pub. Dec. 18, 2009). "Engineering Of Stable Bispecific Antibodies Targeting IL-17A and IL-23," Protein Engineering, Design & Selection 23(3):115-127.
Lonberg, N. et al. (2008, e-pub. Jul. 21, 2008). "Fully Human Antibodies From Transgenic Mouse and Phage Display Platforms," Curr. Opin. Immunol. 20:450-459.
Malia, T.J. et al. (2016, e-pub. Jan. 21, 2016). "Epitope Mapping and Structural Basis for the Recognition of Phosphorylated tau by the Anti-tau Antibody ATB," Proteins 84:427-434.
Marks, J.D. et al. (1991). "By-Passing Immunization Human Antibodies from V-gene Libraries Displayed on Phage," J. Mol. Biol. 222:581-597.
Marks, J.D. et al. (2004) "Selection of Human Antibodies from Phage Display Libraries," Chapter 8 in Methods in Molecular Biology, Lo, B.K.C. (ed.), Humana Press Inc., Totowa, NJ, 248:161-176, 29 pages.
Marks, J.D. et al. (Jul. 1992). "By-Passing Immunization: Building High Affinity Human Antibodies by Chain Shuffling," Bio/Technology 10:779-783.
Mather, J.P. (1980). "Establishment and Characterization of Two Distinct Mouse Testicular Epithelial Cell Lines," Biology of Reproduction 23:243-252.
Mather, J.P et al. (1982). "Culture of Testicular Cells in Hormone-Supplemented Serum-Free Medium," Annals New York Academy of Sciences pp. 44-68.
McCafferty, J. et al. (Dec. 6, 1990). "Phage Antibodies: Filamentous Phage Displaying Antibody Variable Domains," Nature 348:552-554.

(56) References Cited

OTHER PUBLICATIONS

Milstein, C. et al. (Oct. 6, 1983). "Hybrid Hybridomas and Their Use in Immunohistochemistry," Nature 305:537-539.

Mitchell, L.S. et al. (2018). "Comparative Analysis of Nanobody Sequence and Structure Data", Proteins: Structure, Function, and Bioinformatics 86(7):697-706.

Molhoj, M. (Sep. 2011). "Ang2/VEGF CrossMAbCH1-CL, a novel bispecific monovalent human IgG1 format aiming at neutralizing Ang2 and VEGF-A to treat solid tumors", Presentations Outline in CrossMAB Technology, 35 pages.

Mordenti, J. et al. (1989). "The Use of Interspecies Scaling in Toxicokinetics," Chapter 4 in Toxicokinetics and New Drug Development, Yacobi A. ed et al.; Pergamon Press, New York, pp. 42-96.

Morimoto, K. et al. (1992). "Single-Step Purification of F(AB')2 Fragments of Mouse Monoclonal Antibodies (Immunoglobulins G1) By Hydrophobic Interaction High Performance Liquid Chromatography Using TSKgel Phenyl-5PW," J. Biochem. Biophys. Method 24:107-117.

Morrison, S.C. et al. (Nov. 1984). "Chimeric Human Antibody Molecules: Mouse Antigen-Binding Domains With Human Constant Region Domains," Proc. Natl. Acad. Sci. USA 81:6851-6855.

Morrison, S.L. (Apr. 28, 1994). "Success in Specification," Nature 368:812-813.

Munson, P.J. et al. (1980). "Ligand: A Versatile Computerized Approach for Characterization of Ligand-Binding Systems," Anal. Biochem. 107:220-239.

Murata, K.Y. (Aug. 1999). " Expression of the Costimulatory Molecule BB-1, the Ligands CTLA-4 and CD28, and their mRNA in Inflammatory Myopathies," Am. J. Pathol. 155(2):453-460.

Neuberger, M. (Jul. 1996). "Generating High-Avidity Human Mabs in Mice," Nature Biotechnology 14:826.

Ni, J. (Oct. 23, 2006). "Research Progress and Future Perspectives in Antibodmics and Antibodomic Drugs," J. General Review 26(4):265-268, 3 pages.

Okazaki, A. et al. (Mar. 5, 2004). "Fucose Depletion From Human IgG1 Oligosaccharide Enhances Binding Enthalpy And Association Rate Between IgG1 and FcγRIIIa," J. Mol. Biol. 336(5):1239-1249.

Osbourn, J. et al. (2005). "From Rodent Regents to Human Therapeutics Using Antibody Guided Selection," Methods 36:61-68.

Padlan, E.D. (1991). "A Possible Procedure for Reducing the Immunogenicity of Antibody Variable Domains While Preserving Their Ligand-Binding Properties," Mol. Immunol. 28(4/5):489-498.

Pardon, E. et al. (Mar. 2014, e-pub. Feb. 27, 2014). "A General Protocol for the Generation of Nanobodies for Structural Biology," Nature Protocol 9(3):674-693, 40 pages.

Perrin, P.J. et al. (Aug. 15, 1996). "CTLA-4 Blockade Enhances Clinical Disease and CytokineProduction During Experimental Allergic Encephalomyelitis," The Journal of Immunology 157(4):1333-1336.

Petkova, S.B. et al. (2006, e-pub. Oct. 31, 2006). "Enhanced Half-Life of Genetically Engineered Human IgG1 Antibodies in a Humanized FcRn Mouse Model: Potential Application in Humorally Mediated Autoimmune Disease," Int'l. Immunol. 18(12):1759-1769.

Plückthun, A. (1992). "Mono- and Bivalent Antibody Fragments Producted in *Escherichia coli*: Engineering, Folding and Antigen Binding," Immunol. Revs. 130:151-188.

Plückthun, A. (1994) "Antibodies from *Escherichia coli*," Chapter 11 in Handbook of Experimental Pharmacology 113:269-315.

Presta, L.G. (1992). "Antibody Engineering," Current Opinion in Structural Biology 2:593-596.

Presta, L.G. et al. (Oct. 15, 1997). "Humanization of an Anti-Vascular Endothelial Growth Factor Monoclonal Antibody for the Therapy of Solid Tumors and Other Disorders," Cancer Res. 57:4593-4599.

Presta, L.G. et al. (Sep. 1, 1993). "Humanization of an Antibody Directed Against IgE," J. Immunol. 151(5):2623-2632.

Proba, K. et al. (1995). "Functional Antibody Single-chain Fragments From the Cytoplasm of *Escherichia coli*: Influence of Thioredoxin Reductase (trxb)," Gene 159(2):203-207.

Queen, C. et al. (Dec. 1989). "A Humanized Antibody That Binds to the Interleukin 2 Receptor," Proc. Natl Acad. Sci. USA 86:10029-10033.

Ramm, K. et al. (Jun. 2, 2000). "The Periplasmic *Escherichia coli* Peptidylprolyl cis, Trans-Isomerase FkpA," The Journal of Biological Chemistry 275(22):17106-17113.

Ravetch, J.V. et al. (1991). "Fc Receptors," Annu. Rev. Immunol. 9:457-492.

Reyes, G.R. et al. (Jun. 17, 1982) "Expression of Human β-interferon cDNA Under the Control of a Thymidine Kinase Promoter from Herpes Simplex Virus," Nature 297:598-601.

Richard, G. et al. (Jul. 22, 2013) "In vivo Neutralization of a-cobratoxin With High-Affinity Llama Single-Domain Antibodies (VHHs) and a VHH-Fc Antibody," PLOS One. 8(7):e69495, 14 pages.

Riechmann, L. (Jun. 28, 1996). "Rearrangement Of The Former VL Interface In The Solution Structure of a Camelised, Single Antibody VH Domain," Journal of Molecular Biology 259(5):957-969.

Riechmann, L. et al. (Dec. 10, 1999). "Single Domain Antibodies: Comparison of Camel VH and Camelised Human VH Domains," Journal of Immunological Methods 231(1-2):25-38.

Riechmann, L. et al. (Mar. 24, 1988). "Reshaping Human Antibodies for Therapy," Nature 33(6162):323-327.

Ripka, J. et al. (Sep. 1986). "Two Chinese Hamster Ovary Glycosylation Mutants Affected in the Conversion of GDP-Mannose to GDP-Fucose," Arch Biochem Biophys. 249(2):533-545.

Rosenberg, S.A. et al. (Dec. 22, 1988). "Use of Tumor-Infiltrating Lymphocytes And Interleukin-2 in the Immunotherapy of Patients With Metastatic Melanoma. A Preliminary Report," N Engl J Med. 319(25):1676-1680.

Rosok, M.J. et al. (Sep. 13, 1996). "A Combinatorial Library Strategy for the Rapid Humanization of Anticarcinoma BR96 Fab," J. Biol. Chem. 271(37):22611-22618.

Schaefer, W. et al. (Jul. 5, 2011, e-pub. Jun. 20, 2011). "Immunoglobulin Domain Crossover as a Generic Approach for the Production of Bispecific IgG Antibodies," Proc. Natl. Acad. Sci. U.S.A. 108(27):11187-11192.

Schier, R. et al. (1995). "Identification of Functional and Structural Amino-Acid Residues by Parsimonious Mutagenesis," Gene 169:147-155.

Shalaby, M.R. et al. (Jan. 1, 1992). "Development of Humanized Bispecific Antibodies Reactive With Cytotoxic Lymphocytes and Tumor Cells Overexpressing the HER2 Protooncogene, "J. Exp. Med. 175:217-225.

Sheriff, S. et al. (Sep. 1996). "Redefining the Minimal Antigen-Binding Fragment," Nature Struct. Biol. 3(9):733-736.

Shields, R.L. et al. (Mar. 2, 2001). "High Resolution Mapping of the Binding Site on Human IgG1 for FcγRI, FcγRII. FcγRIII, and FcRn and Design of IgG1 Variants With Improved Binding to the FcγR," J. Biol.Chem. 276(9):6591-6604.

Shinkawa, T. et al. (Jan. 31, 2003). "The Absence of Fucose But Not The Presence of Galactose OrBisecting N-Acetylglucosamine of Human Lgg1 Complex-Type Oligosaccharides Shows the Critical Role of Enhancing Antibody-Dependent Cellular Cytotoxicity," Journal of Biological Chemistry 278(5):3466-3473.

Shopes, B. et al. (May 1, 1992). "A Genetically Engineered Human IgG Mutant With Enhanced Cytolytic Activity," J. Imniunol. 148:2918-2922.

Siebenlist, U. et al. (Jun. 1980). "*E. Coli* RNA Polymerase Interacts Homologously With Two Different Promoters," Cell 20(2):269-281.

Simmons, L.C. et al. (May 1, 2002). "Expression of Full-Length Immunoglobulins in *Escherichia coli*: Rapid and Efficient Production of Aglycosylaled Antibodies," J. Immunol. Meth. 263(1-2):133-147.

Sims, M.J. et al. (Aug. 15, 1993). "A Humanized CD18 Antibody Can Block Function Without Cell Destruction," J. Immunol. 151(4):2296-2308.

Skerra, A. (1993) "Bacterial Expression of Immunoglobulin Fragments," Current Opinion in Immunology 5:256-262.

Stamova, S. et al. (Jul. 18, 2012). "Cancer Immunotherapy by Retargeting of Immune Effector Cells via Recombinant Bispecific Antibody Constructs," Antibodies 1(2):172-198.

(56) References Cited

OTHER PUBLICATIONS

Stevenson, G.T. et al. (Mar. 1989). "A Chimeric Antibody With Dual Fc Regions (bisFabFc) Prepared by Manipulations at the IgG Hinge," Anti-cancer Drug Des.3(4):219-230.
Streltsov, V.A. (Nov. 2005). "Structure of a Shark Ignar Antibody Variable Domain And Modeling of an Early-Developmental Isotype," Protein Sci. 14:2901-2909.
Suresh, M.R. et al. (1986). "Bispecific Monoclonal Antibodies From Hybrid Hybridomas," Methods in Enzymology 121:210-228, 19 pages.
Transue, T.R. et al. (1998). "Camel Single-Domain Antibody Inhibits Enzyme by Mimicking Carbohydrate Substrate," Proteins 32(4):515-522.
Traunecker, A. et al. (1991). "Bispecific Single Chain Molecules (Janusins) Target Cytotoxic Lymphocytes on HIV Infected Cells," Embo J. 10(12):3655-3659.
Turnis, M.E. (2012, e-pub. Oct. 1, 2012). "Combinatorial Immunotherapy PD-1 May Not Be LAG-ing Behind Any More," Combinatorial Immunotherapy, OncoImmunology 1(7):1172-1174.
Tutt, A. et al. (Jul. 1, 1991) "Trispecific F(ab')3 Derivatives that use Cooperative Signaling via the TCR/CD3 Complex and CD2 to Activate and Redirect Resting Cytotoxic T Cells," J. Immunol. 147(1):60-69.
U.S. Appl. No. 16/960,521, filed Jul. 7, 2020, by Zhang et al.(A copy of U.S. Patent Application document is not submitted herewith pursuant to the waiver of 37 C.F.R. § 1.98(a)(2)(iii) issued by the Office on Sep. 21, 2004.).
U.S. Appl. No. 17/818,942, filed Aug. 10, 2022, by Chou et al.(A copy of U.S. Patent Application document is not submitted herewith pursuant to the waiver of 37 C.F.R. § 1.98(a)(2)(iii) issued by the Office on Sep. 21, 2004.).
Urlaub, G et al. (Jul. 1980). "Isolation of Chinese Hamster Cell Mutants Deficient in Dihydrofolate Reductase Activity," Proc. Natl. Acad. Sci. USA 77(7):4216-4220.
Vajdos, F. et al. (2002) "Comprehensive Functional Maps of the Antigen Binding Site of an Anti-ErbB2 Antibody Obtained with Shotgun Scanning Mutagenesis," J. Mol. Biol. 320:415-428.
Van Der Linden, R. (Jun. 23, 2000, e-pub. Jun. 13, 2000). "Induction Of Immune Responses and Molecular Cloning of the Heavy Chain Antibody Repertoire of Lama Glama," J. Immunol. Methods 240(1-2):185-195.
Van Dijk, M.A. et al. (Aug. 2001). "Human Antibodies as Next Generation Therapeutics," Curr. Opin. Che. Biology 5(4):368-374.
Vaswani, S.K. et al. (Aug. 1998) "Humanized Antibodies as Potential Therapeutic Drugs," Annals of Allergy, Asthma, & Immunology 81:105-115.
Verhoeyen, M. et al. (Oct. 23, 1987) "Reshaping Human Antibodies: Grafting an Antilysozyme Activity," Science 239:1534-1536.
Vollmers, H.P. et al. (2005) "Death by Stress: Natural IgM-induced Apoptosis," Methods Find Exp Clin Pharmacol. 27(3):1-7.
Vollmers, H.P. et al. (2005). "The 'Early Birds': Natural IgM Antibodies and Immune Surveillance," Histology and Histopathology, 20(3):927-937.
Walunas, T.L. et al. (Jun. 1996). "CTLA-4 Ligation Blocks CD28-Dependent T Cell Activation," The Journal of Experimental Medicine 183(6):2541-2550.
Ward, E.S. et al. (Oct. 12, 1989). "Binding Activities of a Repertoire of Single Immunoglobulin Variable Domains Secreted From *Escherichia coli*," Nature 341(6242): 544-546.
Waterhouse, P. et al. (1993). "Combinatorial Infection and In Vivo Recombination: A Strategy for Making Large Phage Antibody Repertoires," Nucleic Acids Research 21(9):2265-2266.
Weidle, U.H. et al. (January-Feb. 2013). "The Intriguing Options of Multispecific Antibody Formats for Treatment of Cancer," Cancer Genomics Proteomics 10(1):1-18.
Weidner K. M. et al. (Nov. 1, 2010). "Anti-Angiogenic Activity of a Tetravalent Bispecific Antibody (TAvi6) Targeting VEGF and Angiopoietin-211," Blood 116(21):1746 (abstract 4303), 2 pages.
Wesolowski, J. et al. (Aug. 2009, e-pub. Jun. 16, 2009). "Single Domain Antibodies: Promising Experimental and Therapeutic Tools in Infection and Immunity," Med Microbiol Immunol 198:157-174.
Winter, G. el al. (1994). "Making Antibodies by Phage Display Technology," Ann. Rev. Immunol. 12:433- 455.
Wolff, E.A. et al. (Jun. 1, 1993). "Monoclonal Antibody Homodimers: Enhanced Antitumor Activity in Nude Mice," Can Res 53:2560-2565.
Wright, A. et al. (Jan. 1997). "Effect of Glycosylation on Antibody Function: Implications for Genetics Engineering," Trends Biotechnol. 15:26-32.
Written Opinion of the International Searching Authority dated Apr. 12, 2017, for PCT Patent Application No. PCT/CN2016/090703, filed Jul. 20, 2016, 5 pages.
Written Opinion of the International Searching Authority dated Jan. 19, 2018, for PCT Patent Application No. PCT/CN2017/105506, filed Oct. 10, 2017, 6 pages.
Written Opinion of the International Searching Authority dated Jul. 11, 2017, for PCT Patent Application No. PCT/CN2016/101777, filed Oct. 11, 2016, 7 pages.
Written Opinion of the International Searching Authority dated Oct. 11, 2017, for PCT Patent Application No. PCT/CN2017/093644, filed Jul. 20, 2017, 5 pages.
Xu, J.L. et al. (Jul. 2000). "Diversity in the CDR3 Region of V(H) Is Sufficient for Most Antibody Specificities," Immunity 13:37-45.
Yamane-Ohnuki, N. et al. (Sep. 5, 2004, e-pub Aug. 6, 2004). "Establishment of FUT8 Knockout Chinese Hamster Ovary Cells: An Ideal Host Cell Line For Producing Completely Defucosylated Antibodies With Enhanced Antibody-Dependent Cellular Cytotoxicity," Biotechnology and Bioengineering 87(5):614-622.
Yaniv, M. (May 6, 1982). "Enhancing Elements for Activation of Eukaryotic Promoters," Nature 297:17-18.
Yansura, D.G. et al. (1992). "Nucleotide Sequence Selection for Increased Expression of Heterologous Genes in *Escherichia coli*," Methods: A Companion to Methods in Enzymol 4:151-158.
Yelton, D.E. et al. (1995). "Affinity Maturation of the BR96 Anti-Carcinoma Antibody by Codon-Based Mutagenesis," J. Immunol. 155:1994-2004.
Zapata, G. et al. (1995). "Engineering Linear F(ab')2 Fragments for Efficient Production In *Escherichia coli* And Enhanced Antiproliferative Activity," Protein Engineering 8(10):1057-1062.
Zhu, Z. et al. (1997). "Remodeling Domain Interfaces to Enhance Heterodimer Formation," Protein Science 6:781-788.
JP Office Action in Japanese Appln. No. 2020-536043, dated Jun. 13, 2023, 7 pages (with English translation).
Kim et al., "Identifying amino acid residues that influence plasma clearance of murine IgG1 fragments by site-directed mutagenesis." European Journal of Immunology, 1994, 24(3):542-548.
Kishimoto et al., "Therapeutic applications of antigen binding domain VHH derived from heavy chain antibodies of Camelidae," Medchem News, Feb. 1, 2017, 27(1):35-41 (English Summary).
NCBI Reference Sequence: NP_776160.2.
Reisfeld et al., "Monoclonal antibodies and cancer therapy," UCLA Symposia on Molecular and Cellular Biology, New Series (Liss, New York), 1985, vol. 27, 5 pages.
Riechmann et al., "Single domain antibodies: comparison of camel VH and camelised human VH domains." Journal of Immunological Methods, 1999, 231(1-2):25-38.

\* cited by examiner

FIG. 1 Serum titration assay
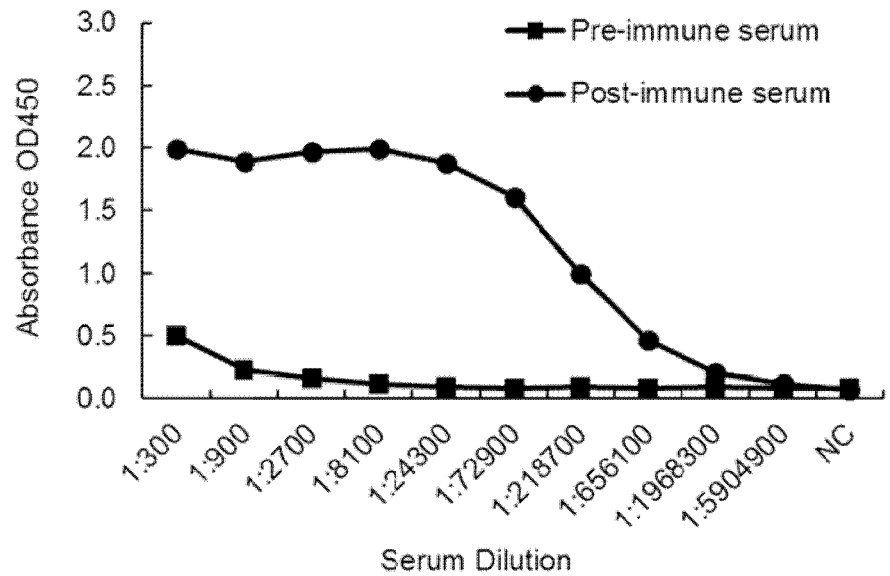
FIG. 2 Purified IgG immune response test
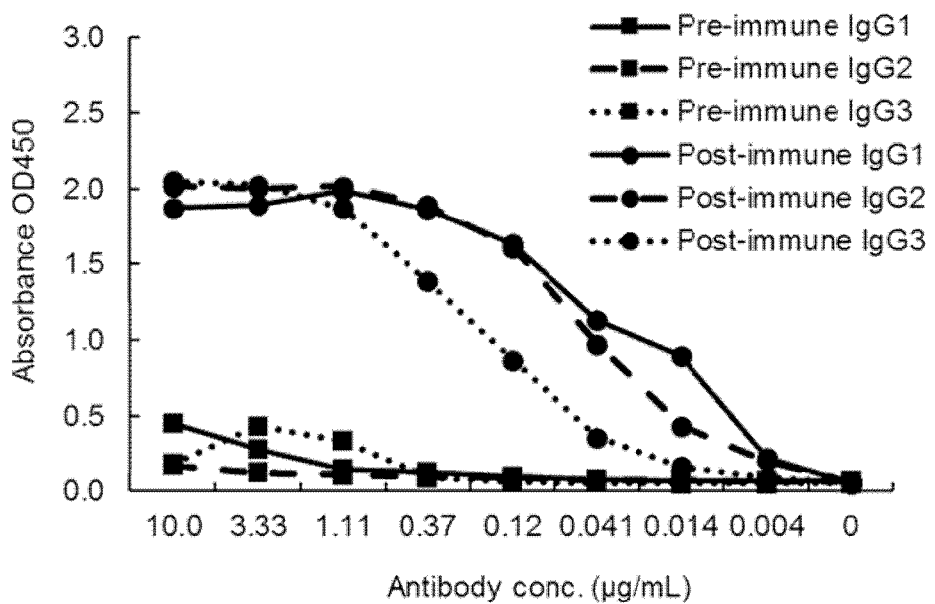

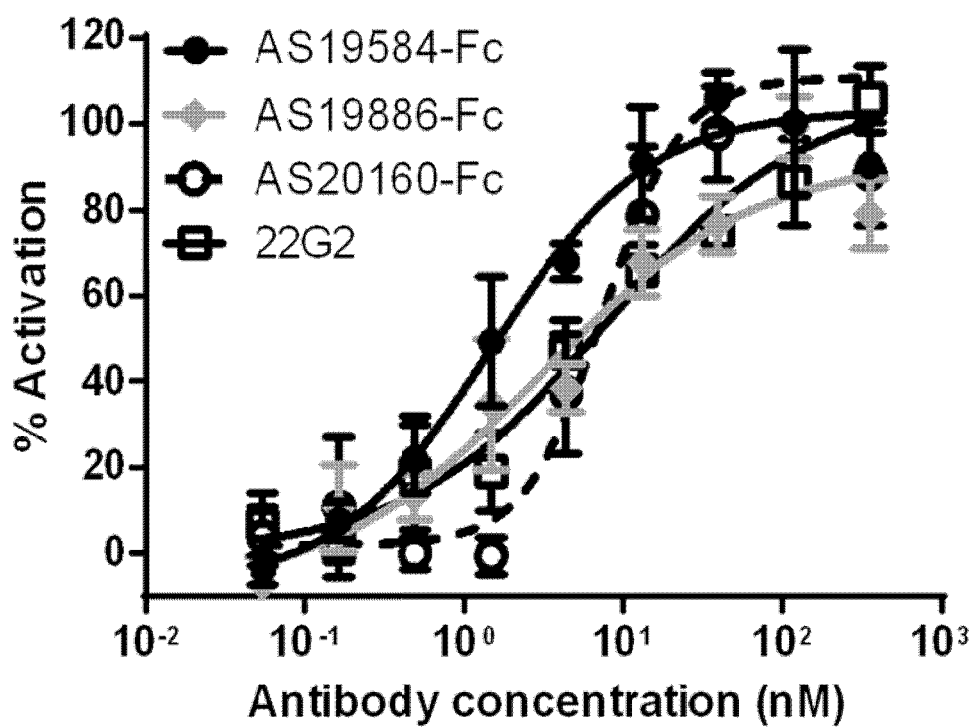
FIG. 3 TIGIT/CD155 blockade reporter assay for unhumanized anti-TIGIT sdAb-Fc fusion proteins and 22G2

Efficacy of unhumanized anti-TIGIT sdAb-Fc fusion protein and 10A7 in CT26 syngeneic tumor model

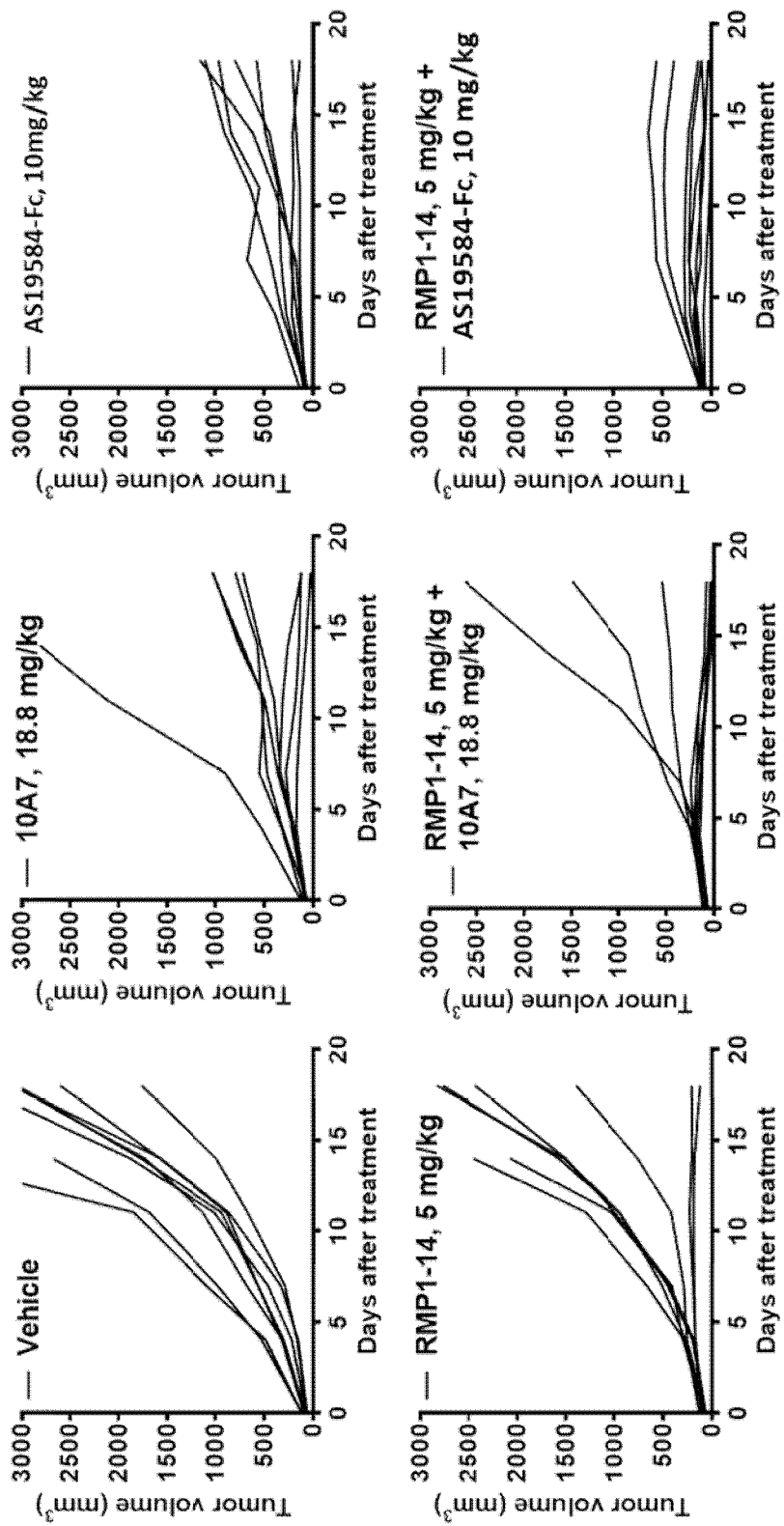

Efficacy of unhumanized anti-TIGIT sdAb-Fc fusion protein in CT26 syngeneic tumor model Efficacy of unhumanized anti-TIGIT sdAb-Fc fusion protein in MC38 syngeneic tumor model

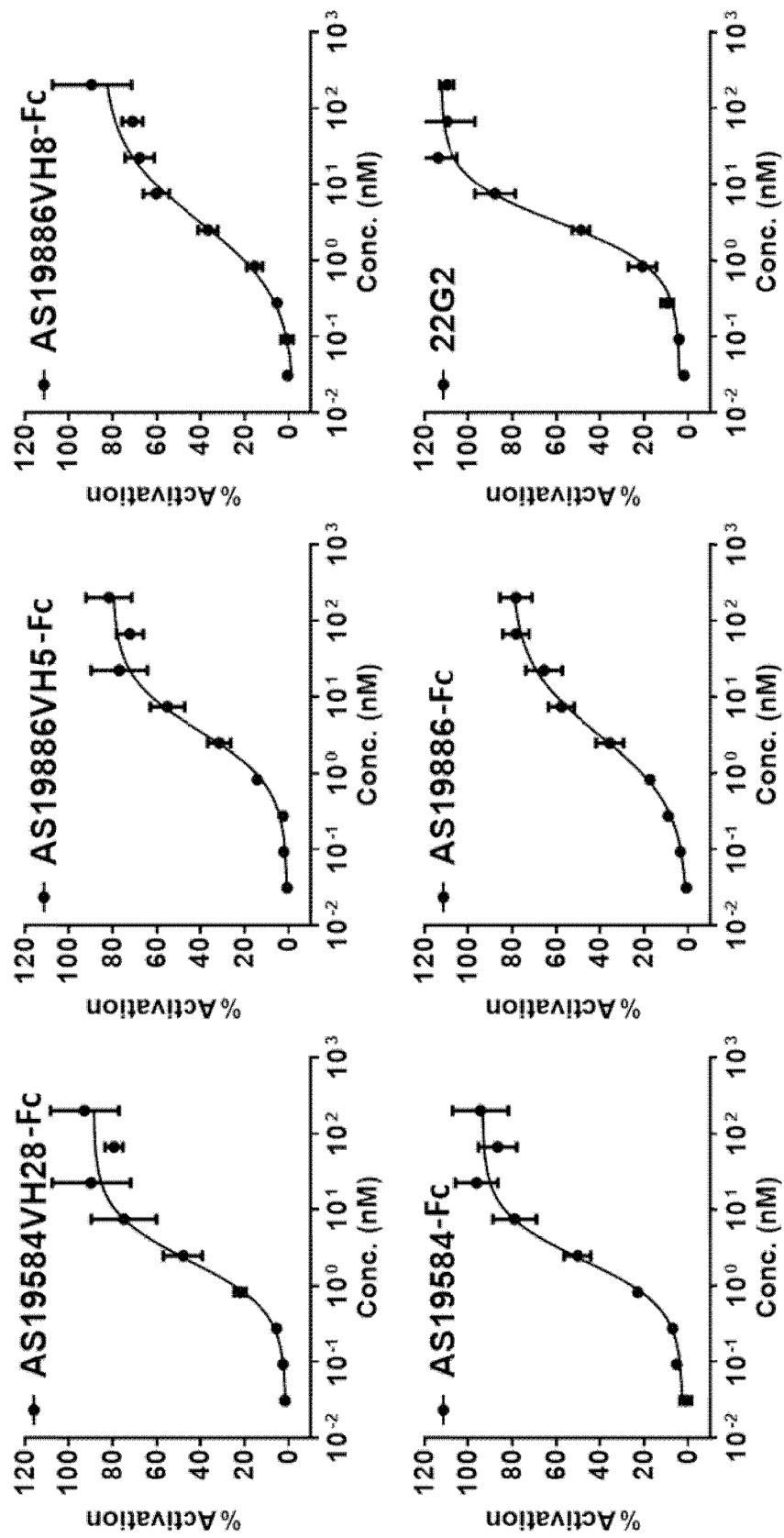
FIG. 7 TIGIT/CD155 blockade reporter assay for anti-TIGIT sdAb-Fc fusion proteins

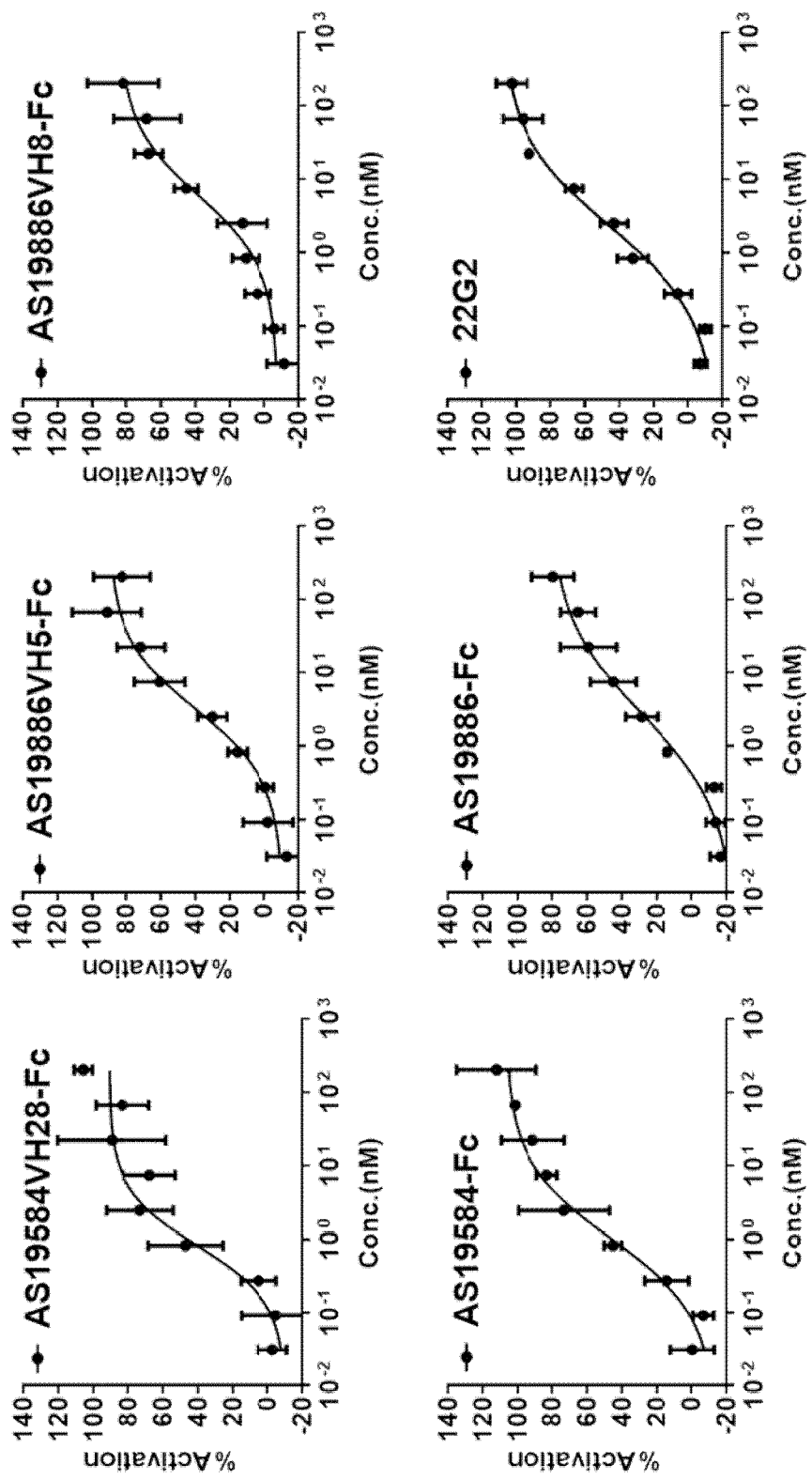

FIG. 9 Pharmacokinetic curve of humanized anti-TIGIT sdAb-Fc fusion protein vs. anti-TIGIT full length antibody 22G2
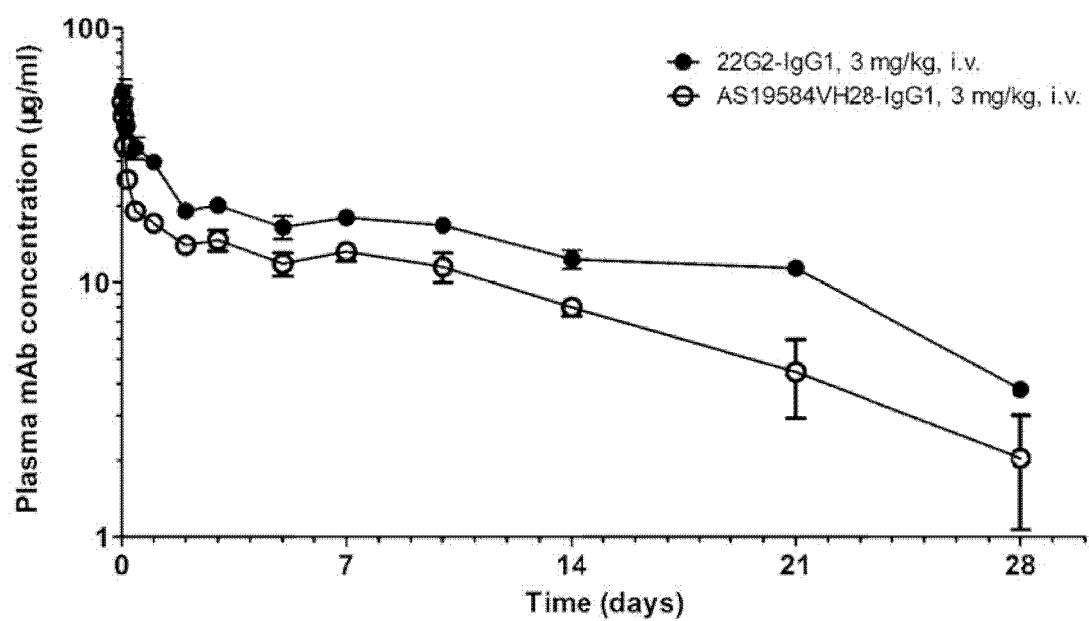

Efficacy of humanized anti-TIGIT sdAb-Fc fusion proteins in human TIGIT KI mice bearing MC38 tumor

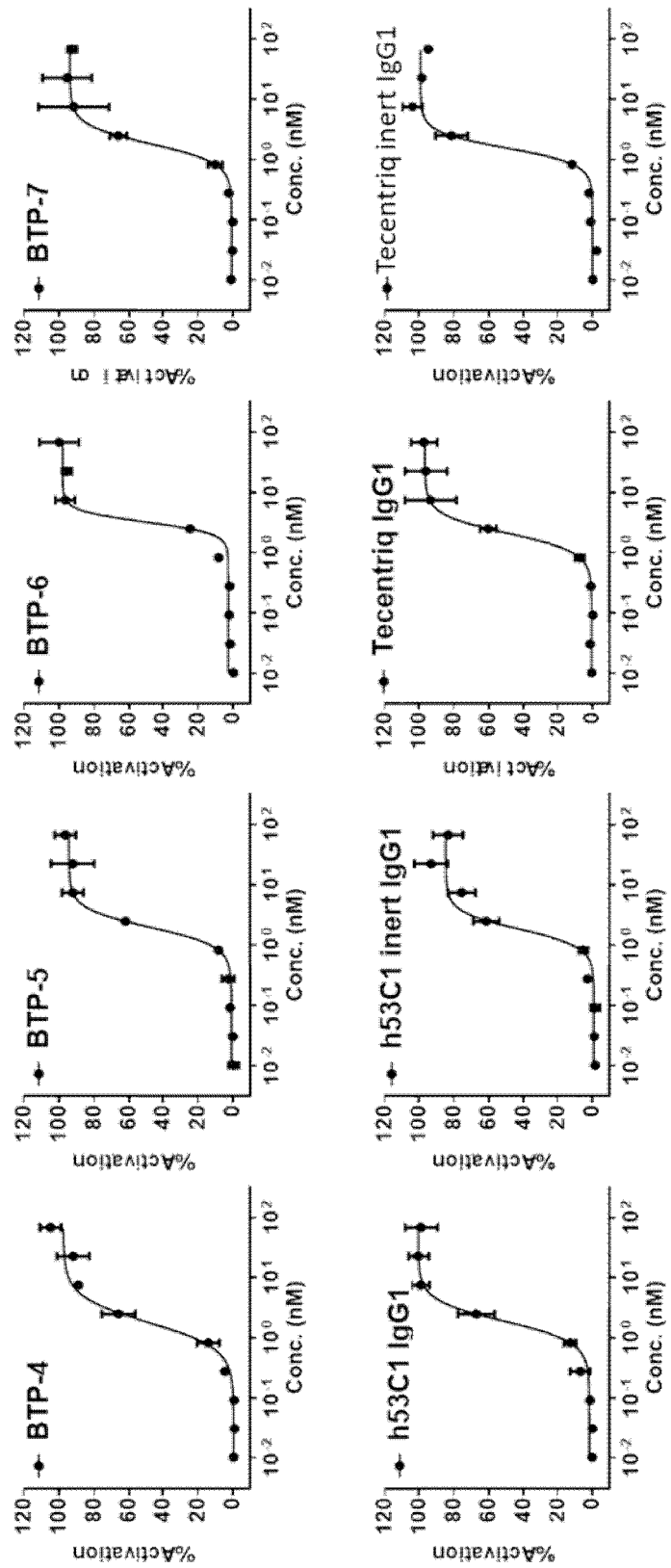
FIG. 11 PD-L1 functional assay for POC PD-L1×TIGIT BABPs

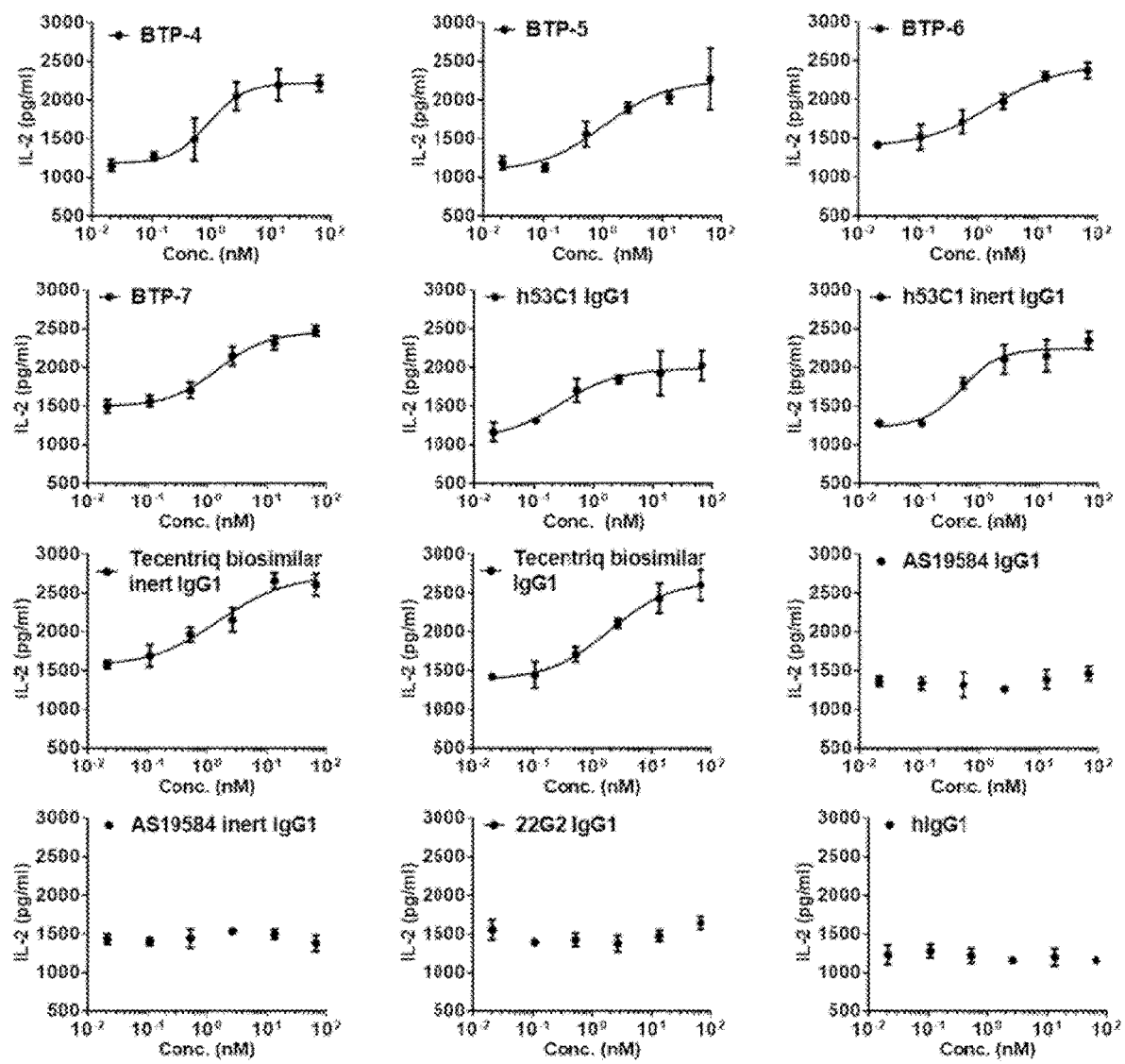
FIG. 12 MLR assay for POC PD-L1×TIGIT BABPs

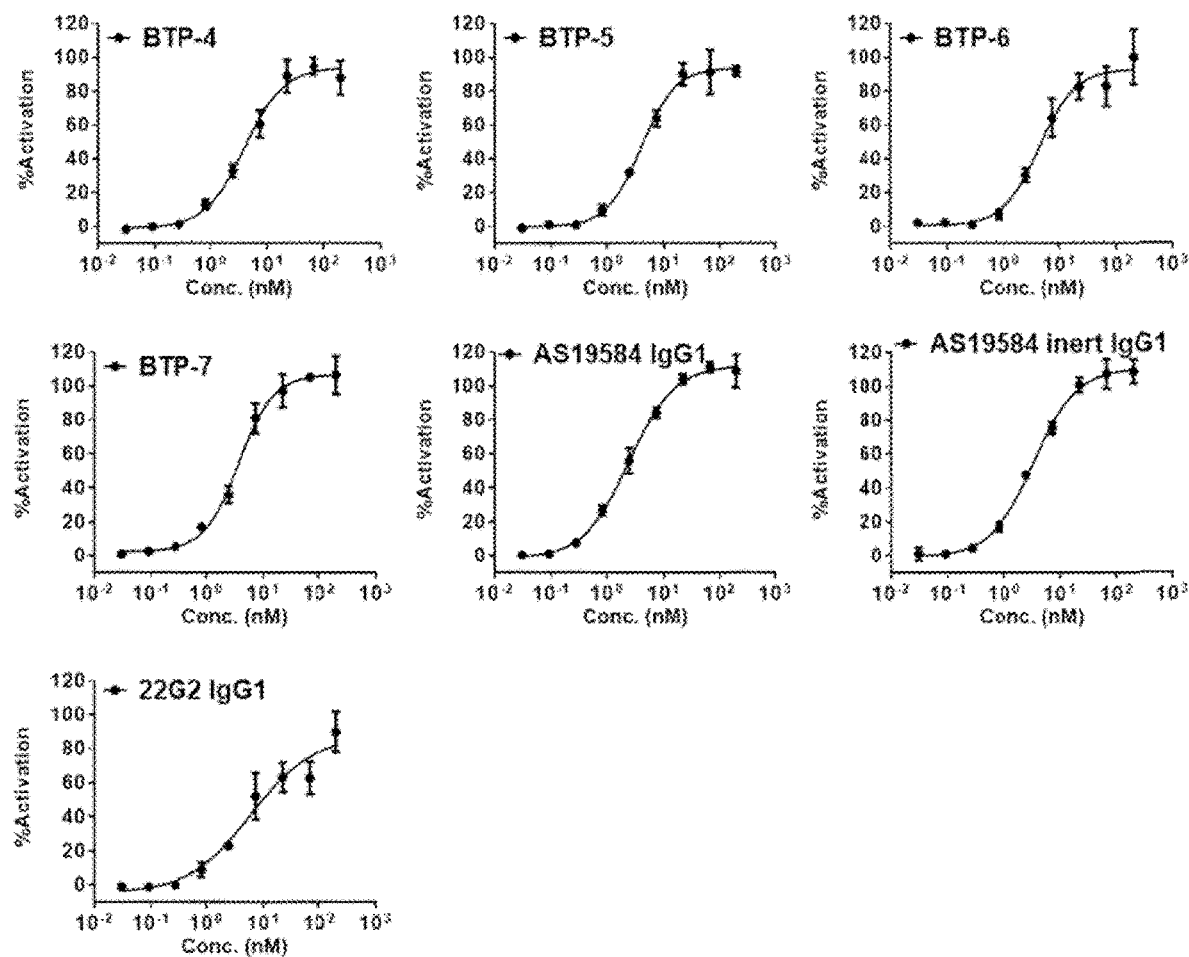
FIG. 13 TIGIT/CD155 blockade reporter assay for POC PD-L1×TIGIT BABPs

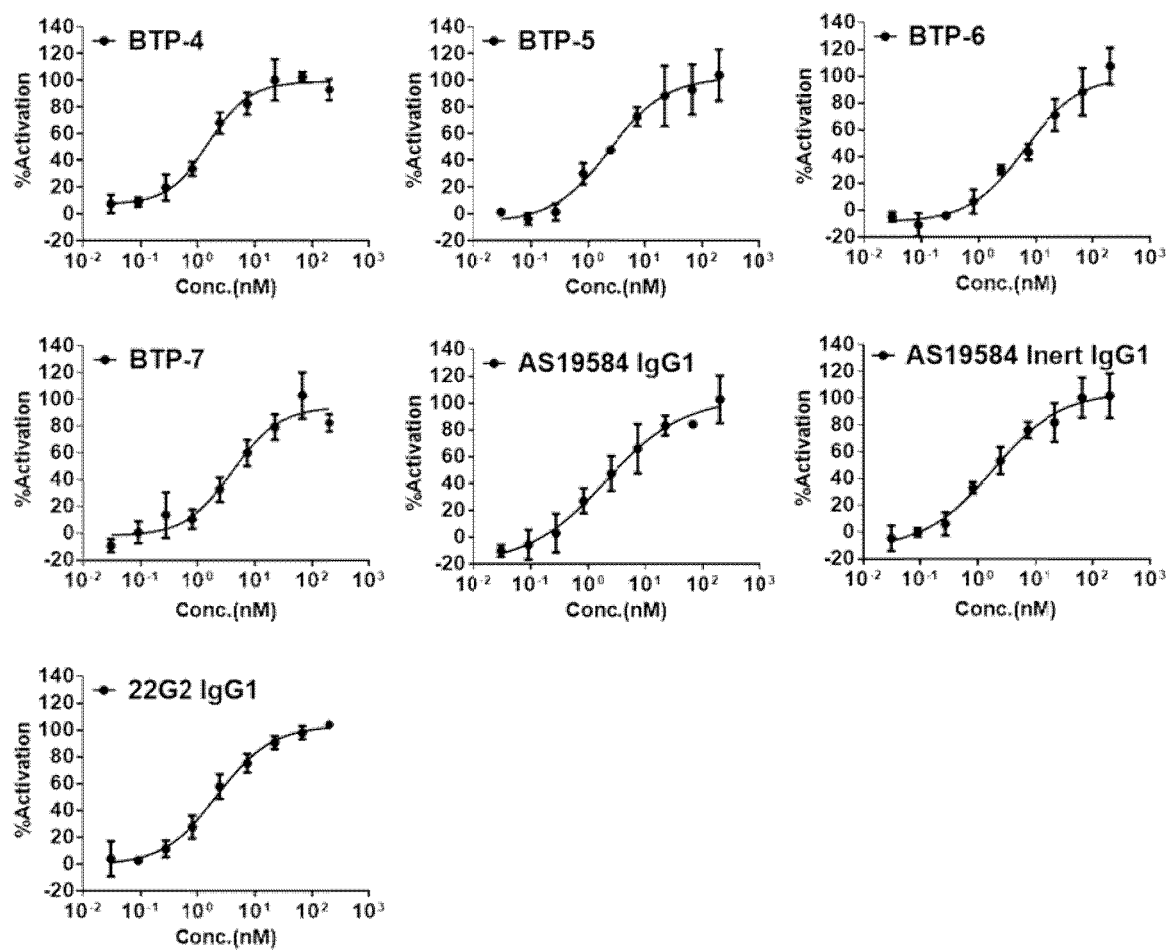
FIG. 14 IL-2-release assay for POC PD-L1×TIGIT BABPs

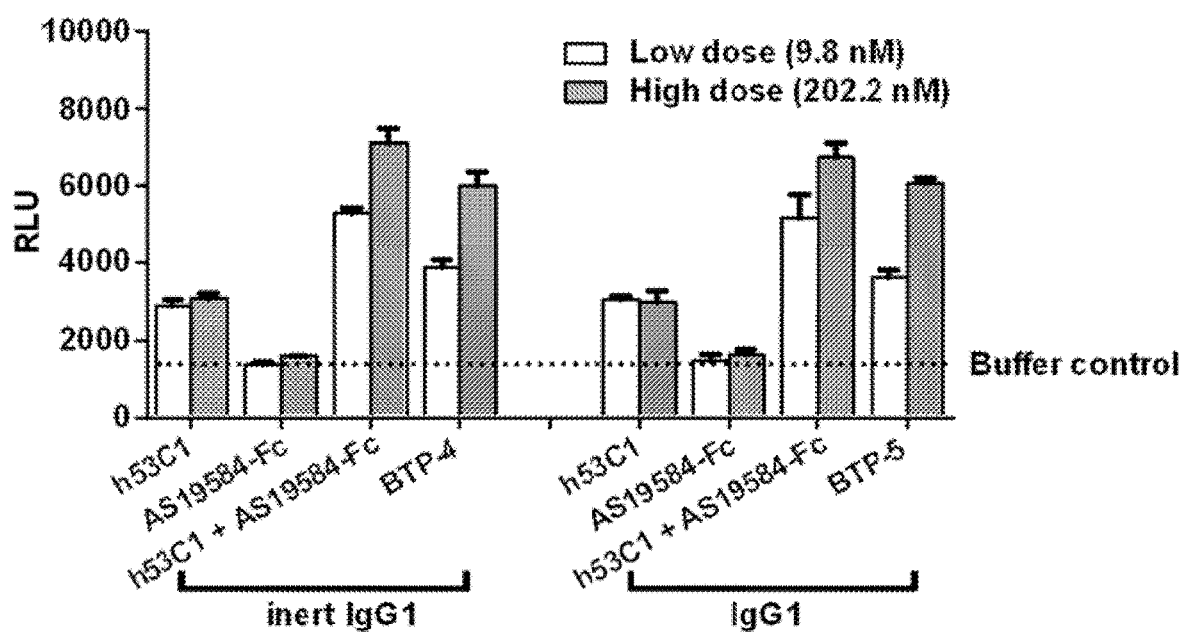
FIG. 15 PD-L1/TIGIT bifunctional reporter assay for POC PD-L1×TIGIT BABPs Fig. 16 Efficacy of POC SMABs in C57BL/6 human PD-1 KI mice bearing MC38-hPD-L1 tumor

FIG. 27 PD-1/TIGIT, PD-L1/TIGIT bifunctional reporter assay

FIG. 28 Primary T cell binding assay

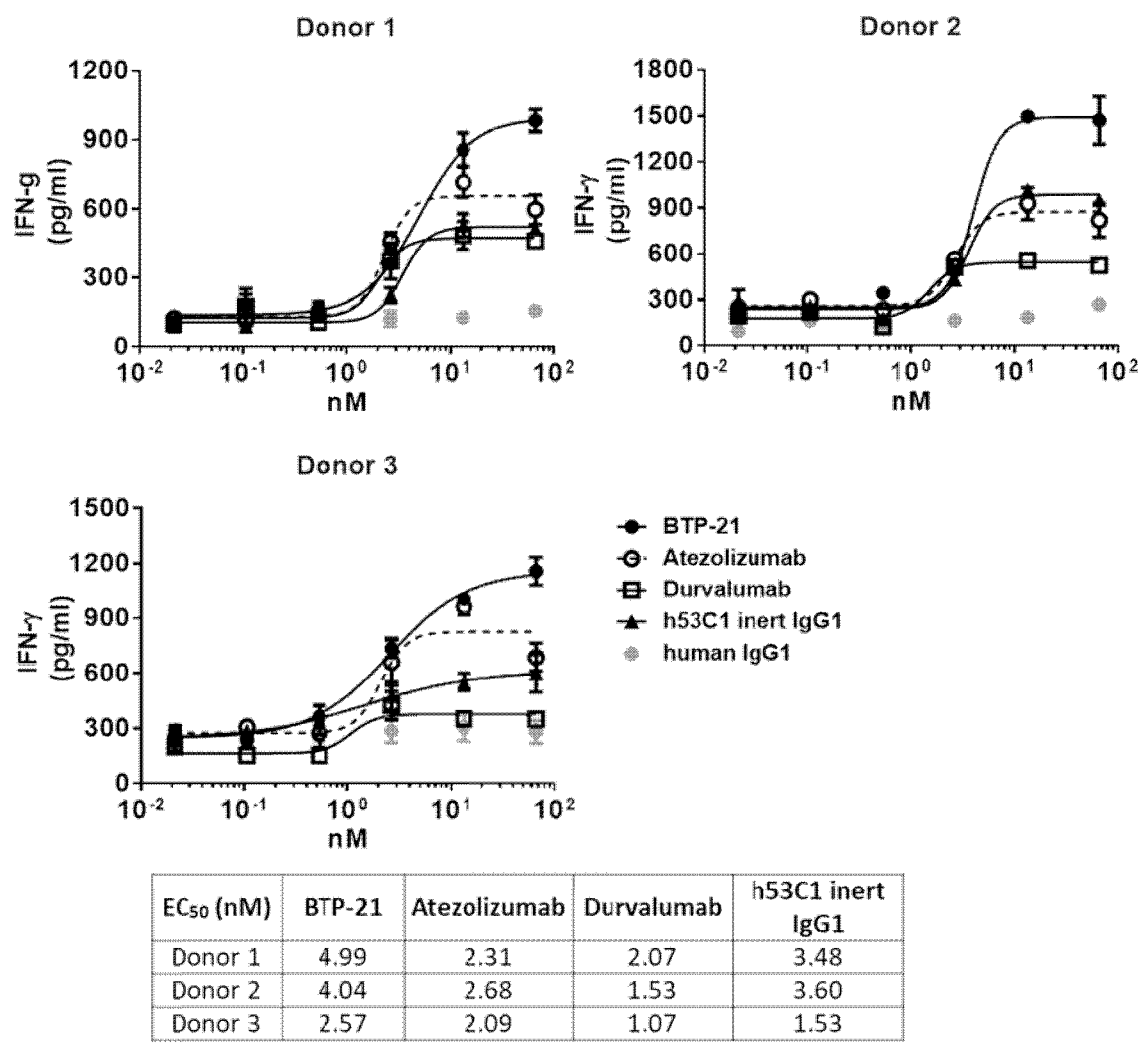
FIG. 29 PBMC IFN-γ release assay

FIG. 30 Efficacy of BTP-11 in Balb/c human PD-1 KI mice bearing CT26 tumor
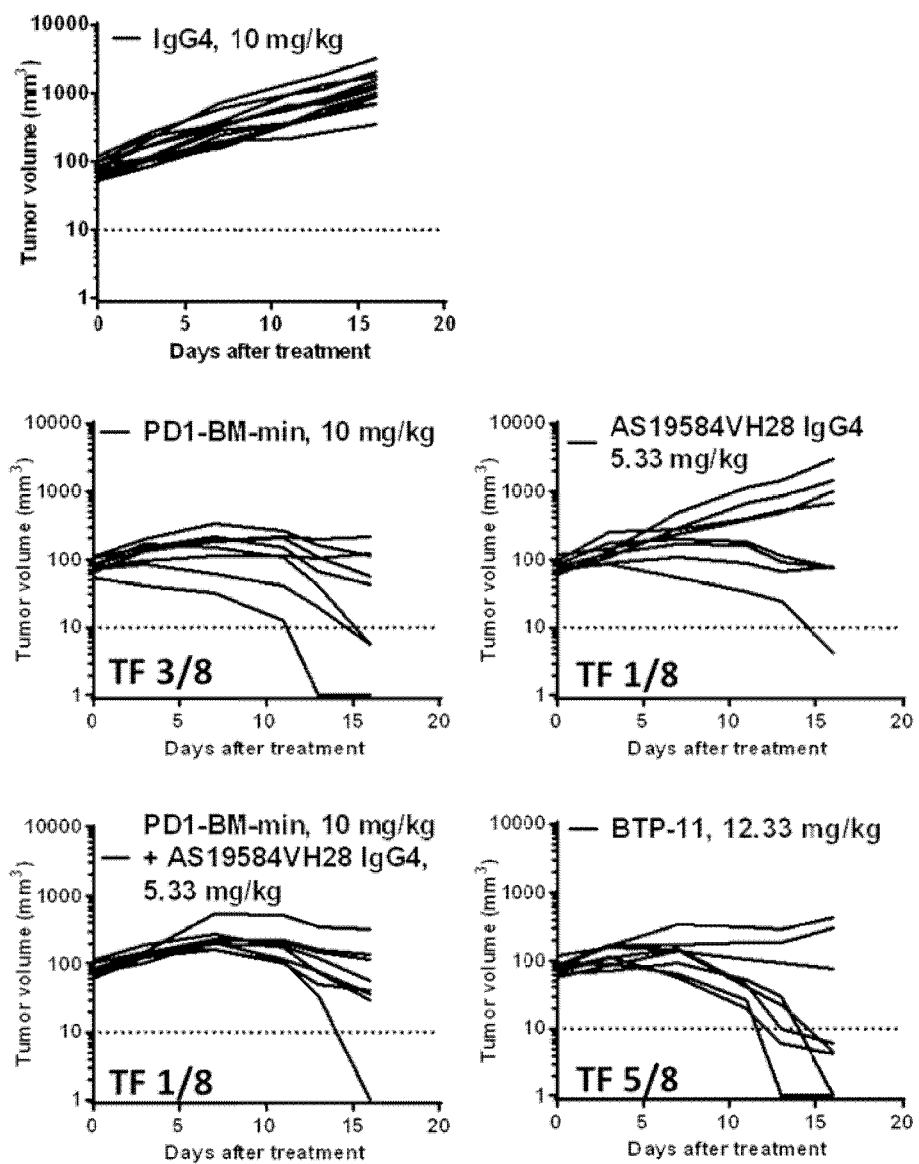

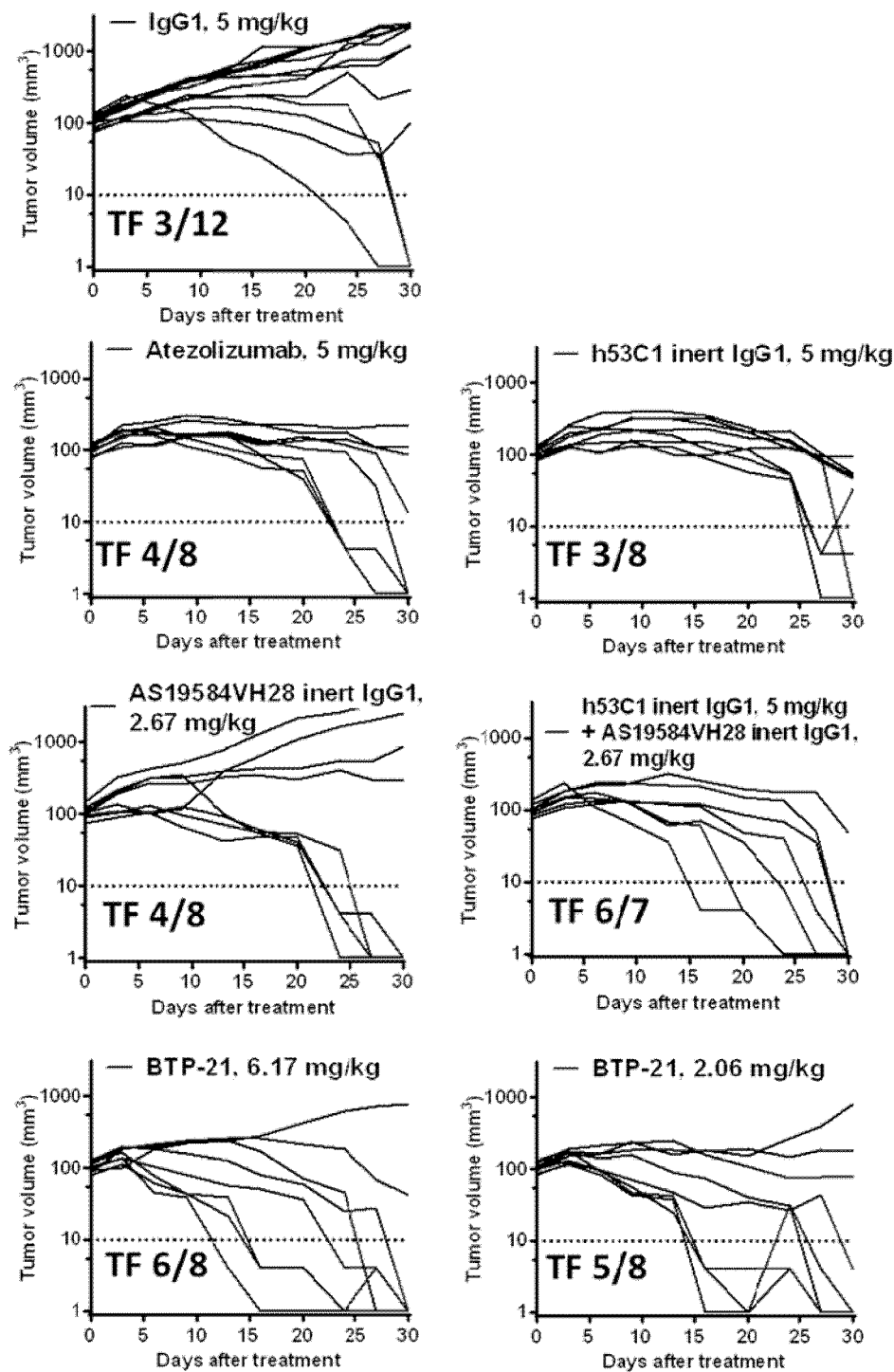
FIG. 31 Efficacy of BTP-21 in C57BL/6 human PD-1/PD-L1 double KI mice bearing MC38-hPDL1 tumor

SEQUENCE LISTING

<160> NUMBER OF SEQ ID NOS: 407

<210> SEQ ID NO 1
<211> LENGTH: 25
<212> TYPE: PRT
<213> ORGANISM: Artificial Sequence
<220> FEATURE:
<223> OTHER INFORMATION: Synthetic Construct

<400> SEQUENCE: 1

Gln Val Gln Leu Ala Glu Ser Gly Gly Gly Ser Val Gln Ala Gly Gly
1               5                   10                  15

Ser Leu Arg Leu Ser Cys Ala Ala Ser
            20                  25

<210> SEQ ID NO 2
<211> LENGTH: 25
<212> TYPE: PRT
<213> ORGANISM: Artificial Sequence
<220> FEATURE:
<223> OTHER INFORMATION: Synthetic Construct

<400> SEQUENCE: 2

Gln Val Gln Leu Ala Glu Ser Gly Gly Gly Ser Val Gln Thr Gly Gly
1               5                   10                  15

Ser Leu Arg Leu Ser Cys Ala Ala Ser
            20                  25

<210> SEQ ID NO 3
<211> LENGTH: 25
<212> TYPE: PRT
<213> ORGANISM: Artificial Sequence
<220> FEATURE:
<223> OTHER INFORMATION: Synthetic Construct

<400> SEQUENCE: 3

Gln Ile Gln Leu Val Glu Ser Gly Gly Gly Ser Val Gln Ala Gly Gly
1               5                   10                  15

Ser Leu Arg Leu Ser Cys Ala Thr Ser
            20                  25

<210> SEQ ID NO 4
<211> LENGTH: 24
<212> TYPE: PRT

```
<213> ORGANISM: Artificial Sequence
<220> FEATURE:
<223> OTHER INFORMATION: Synthetic Construct

<400> SEQUENCE: 4

Gln Val Gln Leu Val Glu Ser Gly Gly Gly Ser Val Gln Ala Gly Gly
1               5                   10                  15

Ser Leu Arg Leu Ser Cys Val Ala
            20

<210> SEQ ID NO 5
<211> LENGTH: 25
<212> TYPE: PRT
<213> ORGANISM: Artificial Sequence
<220> FEATURE:
<223> OTHER INFORMATION: Synthetic Construct

<400> SEQUENCE: 5

Gln Val Gln Leu Ala Glu Ser Gly Gly Gly Ser Val Gln Ala Gly Gly
1               5                   10                  15

Ser Leu Arg Leu Ser Cys Ala Ala Ser
            20                  25

<210> SEQ ID NO 6
<211> LENGTH: 25
<212> TYPE: PRT
<213> ORGANISM: Artificial Sequence
<220> FEATURE:
<223> OTHER INFORMATION: Synthetic Construct

<400> SEQUENCE: 6

Gln Val Gln Leu Ala Glu Ser Gly Gly Gly Ser Val Gln Thr Gly Gly
1               5                   10                  15

Ser Leu Arg Leu Ser Cys Glu Ala Ser
            20                  25

<210> SEQ ID NO 7
<211> LENGTH: 25
<212> TYPE: PRT
<213> ORGANISM: Artificial Sequence
<220> FEATURE:
<223> OTHER INFORMATION: Synthetic Construct

<400> SEQUENCE: 7

Glu Val Gln Leu Ala Glu Ser Gly Gly Gly Ser Val Gln Ala Gly Gly
1               5                   10                  15

Ser Leu Arg Leu Ser Cys Thr Thr Ser
            20                  25

<210> SEQ ID NO 8
<211> LENGTH: 25
<212> TYPE: PRT
<213> ORGANISM: Artificial Sequence
<220> FEATURE:
<223> OTHER INFORMATION: Synthetic Construct

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 9
<211> LENGTH: 25
```

<212> TYPE: PRT
<213> ORGANISM: Artificial Sequence
<220> FEATURE:
<223> OTHER INFORMATION: Synthetic Construct

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 10
<211> LENGTH: 25
<212> TYPE: PRT
<213> ORGANISM: Artificial Sequence
<220> FEATURE:
<223> OTHER INFORMATION: Synthetic Construct

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 11
<211> LENGTH: 25
<212> TYPE: PRT
<213> ORGANISM: Artificial Sequence
<220> FEATURE:
<223> OTHER INFORMATION: Synthetic Construct

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 12
<211> LENGTH: 25
<212> TYPE: PRT
<213> ORGANISM: Artificial Sequence
<220> FEATURE:
<223> OTHER INFORMATION: Synthetic Construct

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 13
<211> LENGTH: 25
<212> TYPE: PRT
<213> ORGANISM: Artificial Sequence
<220> FEATURE:
<223> OTHER INFORMATION: Synthetic Construct

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 14

```
<211> LENGTH: 25
<212> TYPE: PRT
<213> ORGANISM: Artificial Sequence
<220> FEATURE:
<223> OTHER INFORMATION: Synthetic Construct

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 15
<211> LENGTH: 25
<212> TYPE: PRT
<213> ORGANISM: Artificial Sequence
<220> FEATURE:
<223> OTHER INFORMATION: Synthetic Construct

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 16
<211> LENGTH: 25
<212> TYPE: PRT
<213> ORGANISM: Artificial Sequence
<220> FEATURE:
<223> OTHER INFORMATION: Synthetic Construct

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 17
<211> LENGTH: 25
<212> TYPE: PRT
<213> ORGANISM: Artificial Sequence
<220> FEATURE:
<223> OTHER INFORMATION: Synthetic Construct

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 18
<211> LENGTH: 25
<212> TYPE: PRT
<213> ORGANISM: Artificial Sequence
<220> FEATURE:
<223> OTHER INFORMATION: Synthetic Construct

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25
```

<210> SEQ ID NO 19
<211> LENGTH: 25
<212> TYPE: PRT
<213> ORGANISM: Artificial Sequence
<220> FEATURE:
<223> OTHER INFORMATION: Synthetic Construct

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 20
<211> LENGTH: 25
<212> TYPE: PRT
<213> ORGANISM: Artificial Sequence
<220> FEATURE:
<223> OTHER INFORMATION: Synthetic Construct

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 21
<211> LENGTH: 25
<212> TYPE: PRT
<213> ORGANISM: Artificial Sequence
<220> FEATURE:
<223> OTHER INFORMATION: Synthetic Construct

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 22
<211> LENGTH: 25
<212> TYPE: PRT
<213> ORGANISM: Artificial Sequence
<220> FEATURE:
<223> OTHER INFORMATION: Synthetic Construct

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 23
<211> LENGTH: 25
<212> TYPE: PRT
<213> ORGANISM: Artificial Sequence
<220> FEATURE:
<223> OTHER INFORMATION: Synthetic Construct

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 24
<211> LENGTH: 25
<212> TYPE: PRT
<213> ORGANISM: Artificial Sequence
<220> FEATURE:
<223> OTHER INFORMATION: Synthetic Construct

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 25
<211> LENGTH: 25
<212> TYPE: PRT
<213> ORGANISM: Artificial Sequence
<220> FEATURE:
<223> OTHER INFORMATION: Synthetic Construct

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 26
<211> LENGTH: 25
<212> TYPE: PRT
<213> ORGANISM: Artificial Sequence
<220> FEATURE:
<223> OTHER INFORMATION: Synthetic Construct

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 27
<211> LENGTH: 25
<212> TYPE: PRT
<213> ORGANISM: Artificial Sequence
<220> FEATURE:
<223> OTHER INFORMATION: Synthetic Construct

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 28
<211> LENGTH: 25
<212> TYPE: PRT
<213> ORGANISM: Artificial Sequence
<220> FEATURE:
<223> OTHER INFORMATION: Synthetic Construct

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

```
<210> SEQ ID NO 29
<211> LENGTH: 25
<212> TYPE: PRT
<213> ORGANISM: Artificial Sequence
<220> FEATURE:
<223> OTHER INFORMATION: Synthetic Construct

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Val Ala Ser
            20                  25

<210> SEQ ID NO 30
<211> LENGTH: 25
<212> TYPE: PRT
<213> ORGANISM: Artificial Sequence
<220> FEATURE:
<223> OTHER INFORMATION: Synthetic Construct

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 31
<211> LENGTH: 25
<212> TYPE: PRT
<213> ORGANISM: Artificial Sequence
<220> FEATURE:
<223> OTHER INFORMATION: Synthetic Construct

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 32
<211> LENGTH: 25
<212> TYPE: PRT
<213> ORGANISM: Artificial Sequence
<220> FEATURE:
<223> OTHER INFORMATION: Synthetic Construct

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 33
<211> LENGTH: 25
<212> TYPE: PRT
<213> ORGANISM: Artificial Sequence
<220> FEATURE:
<223> OTHER INFORMATION: Synthetic Construct

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser
```

```
                            20                  25

<210> SEQ ID NO 34
<211> LENGTH: 25
<212> TYPE: PRT
<213> ORGANISM: Artificial Sequence
<220> FEATURE:
<223> OTHER INFORMATION: Synthetic Construct

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 35
<211> LENGTH: 25
<212> TYPE: PRT
<213> ORGANISM: Artificial Sequence
<220> FEATURE:
<223> OTHER INFORMATION: Synthetic Construct

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 36
<211> LENGTH: 10
<212> TYPE: PRT
<213> ORGANISM: Artificial Sequence
<220> FEATURE:
<223> OTHER INFORMATION: Synthetic Construct

<400> SEQUENCE: 36

Gly Tyr Lys Tyr Gly Val Tyr Ser Met Gly
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Synthetic Construct

<400> SEQUENCE: 37

Gly Asn Thr Gly Ser Arg Arg Tyr Val Ala
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Synthetic Construct

<400> SEQUENCE: 38

Gly Tyr Thr Tyr Arg Gln Lys Cys Met Gly
1               5                   10

<210> SEQ ID NO 39
<211> LENGTH: 11
<212> TYPE: PRT
<213> ORGANISM: Artificial Sequence
<220> FEATURE:
```

```
<223> OTHER INFORMATION: Synthetic Construct

<400> SEQUENCE: 39

Ser Gly Tyr Thr Tyr Ser Arg Lys Cys Arg Gly
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Synthetic Construct

<400> SEQUENCE: 40

Gly Val Thr Ser Asp Ser Tyr His Met Gly
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Synthetic Construct

<400> SEQUENCE: 41

Gly Val Ala Ala Ser Gly Tyr Cys Met Ala
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Synthetic Construct

<400> SEQUENCE: 42

Gly Tyr Thr Tyr Ser Arg Asn Cys Met Gly
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Synthetic Construct

<400> SEQUENCE: 43

Gly Tyr Lys Tyr Gly Val Tyr Ser Met Gly
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Synthetic Construct

<400> SEQUENCE: 44

Gly Tyr Lys Tyr Gly Val Tyr Ser Met Gly
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Synthetic Construct
```

<400> SEQUENCE: 45

Gly Tyr Lys Tyr Gly Val Tyr Ser Met Gly
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Synthetic Construct

<400> SEQUENCE: 46

Gly Tyr Lys Tyr Gly Val Tyr Ser Met Gly
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Synthetic Construct

<400> SEQUENCE: 47

Gly Tyr Lys Tyr Gly Val Tyr Ser Met Gly
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Synthetic Construct

<400> SEQUENCE: 48

Gly Tyr Lys Tyr Gly Val Tyr Ser Met Gly
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Synthetic Construct

<400> SEQUENCE: 49

Gly Tyr Lys Tyr Gly Val Tyr Ser Met Gly
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Synthetic Construct

<400> SEQUENCE: 50

Gly Tyr Lys Tyr Gly Val Tyr Ser Met Gly
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Synthetic Construct

<400> SEQUENCE: 51

Gly Tyr Lys Tyr Gly Val Tyr Ser Met Gly
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Synthetic Construct

<400> SEQUENCE: 52

Gly Tyr Lys Tyr Gly Val Tyr Ser Met Gly
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Synthetic Construct

<400> SEQUENCE: 53

Gly Tyr Lys Tyr Gly Val Tyr Ser Met Gly
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Synthetic Construct

<400> SEQUENCE: 54

Gly Tyr Lys Tyr Gly Val Tyr Ser Met Gly
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Synthetic Construct

<400> SEQUENCE: 55

Gly Tyr Lys Tyr Gly Val Tyr Ser Met Gly
1               5                   10

<210> SEQ ID NO 56
<211> LENGTH: 10
<212> TYPE: PRT
<213> ORGANISM: Artificial Sequence
<220> FEATURE:
<223> OTHER INFORMATION: Synthetic Construct

<400> SEQUENCE: 56

Gly Tyr Lys Tyr Gly Val Tyr Ser Met Gly
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Synthetic Construct

<400> SEQUENCE: 57

```
Gly Tyr Lys Tyr Gly Val Tyr Ser Met Gly
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Synthetic Construct

<400> SEQUENCE: 58

Gly Tyr Lys Tyr Gly Val Tyr Ser Met Gly
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Synthetic Construct

<400> SEQUENCE: 59

Gly Tyr Lys Tyr Gly Val Tyr Ser Met Gly
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Synthetic Construct

<400> SEQUENCE: 60

Gly Tyr Lys Tyr Gly Val Tyr Ser Met Gly
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Synthetic Construct

<400> SEQUENCE: 61

Gly Tyr Thr Tyr Ser Arg Lys Cys Arg Gly
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Synthetic Construct

<400> SEQUENCE: 62

Gly Tyr Thr Tyr Ser Arg Lys Cys Arg Gly
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Synthetic Construct

<400> SEQUENCE: 63
```

```
Gly Tyr Thr Tyr Ser Arg Lys Cys Arg Gly
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Synthetic Construct

<400> SEQUENCE: 64

Gly Tyr Thr Tyr Ser Arg Lys Cys Arg Gly
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Synthetic Construct

<400> SEQUENCE: 65

Gly Tyr Thr Tyr Ser Arg Lys Cys Arg Gly
1               5                   10

<210> SEQ ID NO 66
<211> LENGTH: 10
<212> TYPE: PRT
<213> ORGANISM: Artificial Sequence
<220> FEATURE:
<223> OTHER INFORMATION: Synthetic Construct

<400> SEQUENCE: 66

Gly Tyr Thr Tyr Ser Arg Lys Cys Arg Gly
1               5                   10

<210> SEQ ID NO 67
<211> LENGTH: 10
<212> TYPE: PRT
<213> ORGANISM: Artificial Sequence
<220> FEATURE:
<223> OTHER INFORMATION: Synthetic Construct

<400> SEQUENCE: 67

Gly Tyr Thr Tyr Ser Arg Lys Cys Arg Gly
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Synthetic Construct

<400> SEQUENCE: 68

Gly Tyr Thr Tyr Ser Arg Lys Cys Arg Gly
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Synthetic Construct

<400> SEQUENCE: 69

Gly Tyr Thr Tyr Ser Arg Lys Cys Arg Gly
```

```
<210> SEQ ID NO 70
<211> LENGTH: 10
<212> TYPE: PRT
<213> ORGANISM: Artificial Sequence
<220> FEATURE:
<223> OTHER INFORMATION: Synthetic Construct

<400> SEQUENCE: 70

Gly Tyr Thr Tyr Ser Arg Lys Cys Arg Gly
1               5                   10

<210> SEQ ID NO 71
<211> LENGTH: 14
<212> TYPE: PRT
<213> ORGANISM: Artificial Sequence
<220> FEATURE:
<223> OTHER INFORMATION: Synthetic Construct

<400> SEQUENCE: 71

Trp Phe Arg Leu Ala Pro Gly Lys Glu Arg Glu Gly Val Ala
1               5                   10

<210> SEQ ID NO 72
<211> LENGTH: 14
<212> TYPE: PRT
<213> ORGANISM: Artificial Sequence
<220> FEATURE:
<223> OTHER INFORMATION: Synthetic Construct

<400> SEQUENCE: 72

Trp Phe Arg Gln Ala Pro Gly Lys Glu Arg Glu Gly Val Ala
1               5                   10

<210> SEQ ID NO 73
<211> LENGTH: 14
<212> TYPE: PRT
<213> ORGANISM: Artificial Sequence
<220> FEATURE:
<223> OTHER INFORMATION: Synthetic Construct

<400> SEQUENCE: 73

Trp Phe Arg Gln Ala Pro Gly Lys Glu Arg Glu Gly Val Ala
1               5                   10

<210> SEQ ID NO 74
<211> LENGTH: 14
<212> TYPE: PRT
<213> ORGANISM: Artificial Sequence
<220> FEATURE:
<223> OTHER INFORMATION: Synthetic Construct

<400> SEQUENCE: 74

Trp Phe Arg Gln Ala Pro Gly Lys Glu Arg Glu Gly Val Ala
1               5                   10

<210> SEQ ID NO 75
<211> LENGTH: 14
<212> TYPE: PRT
<213> ORGANISM: Artificial Sequence
<220> FEATURE:
<223> OTHER INFORMATION: Synthetic Construct

<400> SEQUENCE: 75

Trp Phe Arg Gln Ala Pro Gly Lys Glu Arg Glu Gly Val Ala
1               5                   10
```

<210> SEQ ID NO 76
<211> LENGTH: 14
<212> TYPE: PRT
<213> ORGANISM: Artificial Sequence
<220> FEATURE:
<223> OTHER INFORMATION: Synthetic Construct

<400> SEQUENCE: 76

Trp Phe Arg Gln Ala Pro Gly Lys Glu Arg Glu Arg Val Ala
1               5                   10

<210> SEQ ID NO 77
<211> LENGTH: 14
<212> TYPE: PRT
<213> ORGANISM: Artificial Sequence
<220> FEATURE:
<223> OTHER INFORMATION: Synthetic Construct

<400> SEQUENCE: 77

Trp Phe Arg Gln Ala Pro Gly Lys Glu Arg Glu Gly Val Ala
1               5                   10

<210> SEQ ID NO 78
<211> LENGTH: 14
<212> TYPE: PRT
<213> ORGANISM: Artificial Sequence
<220> FEATURE:
<223> OTHER INFORMATION: Synthetic Construct

<400> SEQUENCE: 78

Trp Phe Arg Gln Ala Pro Gly Lys Gly Leu Glu Gly Val Ser
1               5                   10

<210> SEQ ID NO 79
<211> LENGTH: 14
<212> TYPE: PRT
<213> ORGANISM: Artificial Sequence
<220> FEATURE:
<223> OTHER INFORMATION: Synthetic Construct

<400> SEQUENCE: 79

Trp Phe Arg Gln Ala Pro Gly Lys Gly Leu Glu Gly Val Ser
1               5                   10

<210> SEQ ID NO 80
<211> LENGTH: 14
<212> TYPE: PRT
<213> ORGANISM: Artificial Sequence
<220> FEATURE:
<223> OTHER INFORMATION: Synthetic Construct

<400> SEQUENCE: 80

Trp Phe Arg Gln Ala Pro Gly Lys Gly Leu Glu Gly Val Ala
1               5                   10

<210> SEQ ID NO 81
<211> LENGTH: 14
<212> TYPE: PRT
<213> ORGANISM: Artificial Sequence
<220> FEATURE:
<223> OTHER INFORMATION: Synthetic Construct

<400> SEQUENCE: 81

Trp Phe Arg Leu Ala Pro Gly Lys Gly Leu Glu Gly Val Ser
1               5                   10

<210> SEQ ID NO 82
<211> LENGTH: 14
<212> TYPE: PRT
<213> ORGANISM: Artificial Sequence
<220> FEATURE:
<223> OTHER INFORMATION: Synthetic Construct

<400> SEQUENCE: 82

Trp Phe Arg Gln Ala Pro Gly Lys Gly Leu Glu Gly Val Ser
1               5                   10

<210> SEQ ID NO 83
<211> LENGTH: 14
<212> TYPE: PRT
<213> ORGANISM: Artificial Sequence
<220> FEATURE:
<223> OTHER INFORMATION: Synthetic Construct

<400> SEQUENCE: 83

Trp Phe Arg Gln Ala Pro Gly Lys Glu Leu Glu Gly Val Ser
1               5                   10

<210> SEQ ID NO 84
<211> LENGTH: 14
<212> TYPE: PRT
<213> ORGANISM: Artificial Sequence
<220> FEATURE:
<223> OTHER INFORMATION: Synthetic Construct

<400> SEQUENCE: 84

Trp Phe Arg Gln Ala Pro Gly Lys Gly Arg Glu Gly Val Ser
1               5                   10

<210> SEQ ID NO 85
<211> LENGTH: 14
<212> TYPE: PRT
<213> ORGANISM: Artificial Sequence
<220> FEATURE:
<223> OTHER INFORMATION: Synthetic Construct

<400> SEQUENCE: 85

Trp Phe Arg Gln Ala Pro Gly Lys Glu Arg Glu Gly Val Ser
1               5                   10

<210> SEQ ID NO 86
<211> LENGTH: 14
<212> TYPE: PRT
<213> ORGANISM: Artificial Sequence
<220> FEATURE:
<223> OTHER INFORMATION: Synthetic Construct

<400> SEQUENCE: 86

Trp Phe Arg Gln Ala Pro Gly Lys Gly Leu Glu Gly Val Ser
1               5                   10

<210> SEQ ID NO 87
<211> LENGTH: 14
<212> TYPE: PRT
<213> ORGANISM: Artificial Sequence
<220> FEATURE:
<223> OTHER INFORMATION: Synthetic Construct

<400> SEQUENCE: 87

Trp Phe Arg Gln Ala Pro Gly Lys Gly Leu Glu Gly Val Ser
1               5                   10

```
<210> SEQ ID NO 88
<211> LENGTH: 14
<212> TYPE: PRT
<213> ORGANISM: Artificial Sequence
<220> FEATURE:
<223> OTHER INFORMATION: Synthetic Construct

<400> SEQUENCE: 88

Trp Phe Arg Gln Ala Pro Gly Lys Gly Leu Glu Gly Val Ser
1               5                   10

<210> SEQ ID NO 89
<211> LENGTH: 14
<212> TYPE: PRT
<213> ORGANISM: Artificial Sequence
<220> FEATURE:
<223> OTHER INFORMATION: Synthetic Construct

<400> SEQUENCE: 89

Trp Phe Arg Gln Ala Pro Gly Lys Gly Leu Glu Gly Val Ser
1               5                   10

<210> SEQ ID NO 90
<211> LENGTH: 14
<212> TYPE: PRT
<213> ORGANISM: Artificial Sequence
<220> FEATURE:
<223> OTHER INFORMATION: Synthetic Construct

<400> SEQUENCE: 90

Trp Phe Arg Gln Ala Pro Gly Lys Gly Leu Glu Gly Val Ser
1               5                   10

<210> SEQ ID NO 91
<211> LENGTH: 14
<212> TYPE: PRT
<213> ORGANISM: Artificial Sequence
<220> FEATURE:
<223> OTHER INFORMATION: Synthetic Construct

<400> SEQUENCE: 91

Trp Phe Arg Gln Ala Pro Gly Lys Gly Leu Glu Gly Val Ser
1               5                   10

<210> SEQ ID NO 92
<211> LENGTH: 14
<212> TYPE: PRT
<213> ORGANISM: Artificial Sequence
<220> FEATURE:
<223> OTHER INFORMATION: Synthetic Construct

<400> SEQUENCE: 92

Trp Phe Arg Gln Ala Pro Gly Lys Glu Arg Glu Gly Val Ser
1               5                   10

<210> SEQ ID NO 93
<211> LENGTH: 14
<212> TYPE: PRT
<213> ORGANISM: Artificial Sequence
<220> FEATURE:
<223> OTHER INFORMATION: Synthetic Construct

<400> SEQUENCE: 93

Trp Phe Arg Gln Ala Pro Gly Lys Glu Arg Glu Gly Val Ser
1               5                   10

<210> SEQ ID NO 94
```

<211> LENGTH: 14
<212> TYPE: PRT
<213> ORGANISM: Artificial Sequence
<220> FEATURE:
<223> OTHER INFORMATION: Synthetic Construct

<400> SEQUENCE: 94

Trp Phe Arg Gln Ala Pro Gly Lys Glu Arg Glu Gly Val Ser
1               5                   10

<210> SEQ ID NO 95
<211> LENGTH: 14
<212> TYPE: PRT
<213> ORGANISM: Artificial Sequence
<220> FEATURE:
<223> OTHER INFORMATION: Synthetic Construct

<400> SEQUENCE: 95

Trp Phe Arg Gln Ala Pro Gly Lys Glu Arg Glu Gly Val Ser
1               5                   10

<210> SEQ ID NO 96
<211> LENGTH: 14
<212> TYPE: PRT
<213> ORGANISM: Artificial Sequence
<220> FEATURE:
<223> OTHER INFORMATION: Synthetic Construct

<400> SEQUENCE: 96

Trp Phe Arg Gln Ala Pro Gly Lys Gly Leu Glu Trp Val Ser
1               5                   10

<210> SEQ ID NO 97
<211> LENGTH: 14
<212> TYPE: PRT
<213> ORGANISM: Artificial Sequence
<220> FEATURE:
<223> OTHER INFORMATION: Synthetic Construct

<400> SEQUENCE: 97

Trp Phe Arg Gln Ala Pro Gly Lys Gly Leu Glu Gly Val Ser
1               5                   10

<210> SEQ ID NO 98
<211> LENGTH: 14
<212> TYPE: PRT
<213> ORGANISM: Artificial Sequence
<220> FEATURE:
<223> OTHER INFORMATION: Synthetic Construct

<400> SEQUENCE: 98

Trp Phe Arg Gln Ala Pro Gly Lys Gly Leu Glu Gly Val Ala
1               5                   10

<210> SEQ ID NO 99
<211> LENGTH: 14
<212> TYPE: PRT
<213> ORGANISM: Artificial Sequence
<220> FEATURE:
<223> OTHER INFORMATION: Synthetic Construct

<400> SEQUENCE: 99

Trp Phe Arg Gln Ala Pro Gly Lys Gly Leu Glu Gly Val Ser
1               5                   10

<210> SEQ ID NO 100
<211> LENGTH: 14

<212> TYPE: PRT
<213> ORGANISM: Artificial Sequence
<220> FEATURE:
<223> OTHER INFORMATION: Synthetic Construct

<400> SEQUENCE: 100

Trp Phe Arg Gln Ala Pro Gly Lys Gly Leu Glu Gly Val Ala
1               5                   10

<210> SEQ ID NO 101
<211> LENGTH: 14
<212> TYPE: PRT
<213> ORGANISM: Artificial Sequence
<220> FEATURE:
<223> OTHER INFORMATION: Synthetic Construct

<400> SEQUENCE: 101

Trp Phe Arg Gln Ala Pro Gly Lys Gly Leu Glu Gly Val Ala
1               5                   10

<210> SEQ ID NO 102
<211> LENGTH: 14
<212> TYPE: PRT
<213> ORGANISM: Artificial Sequence
<220> FEATURE:
<223> OTHER INFORMATION: Synthetic Construct

<400> SEQUENCE: 102

Trp Phe Arg Gln Ala Pro Gly Lys Gly Leu Glu Gly Val Ala
1               5                   10

<210> SEQ ID NO 103
<211> LENGTH: 14
<212> TYPE: PRT
<213> ORGANISM: Artificial Sequence
<220> FEATURE:
<223> OTHER INFORMATION: Synthetic Construct

<400> SEQUENCE: 103

Trp Phe Arg Gln Ala Pro Gly Lys Gly Arg Glu Gly Val Ser
1               5                   10

<210> SEQ ID NO 104
<211> LENGTH: 14
<212> TYPE: PRT
<213> ORGANISM: Artificial Sequence
<220> FEATURE:
<223> OTHER INFORMATION: Synthetic Construct

<400> SEQUENCE: 104

Trp Phe Arg Gln Ala Pro Gly Lys Gly Arg Glu Gly Val Ala
1               5                   10

<210> SEQ ID NO 105
<211> LENGTH: 14
<212> TYPE: PRT
<213> ORGANISM: Artificial Sequence
<220> FEATURE:
<223> OTHER INFORMATION: Synthetic Construct

<400> SEQUENCE: 105

Trp Phe Arg Gln Ala Pro Gly Lys Gly Arg Glu Gly Val Ala
1               5                   10

<210> SEQ ID NO 106
<211> LENGTH: 16
<212> TYPE: PRT

<213> ORGANISM: Artificial Sequence
<220> FEATURE:
<223> OTHER INFORMATION: Synthetic Construct

<400> SEQUENCE: 106

Ala Ile Cys Ser Gly Gly Arg Thr Thr Tyr Ser Asp Ser Val Lys Gly
1               5                   10                  15

<210> SEQ ID NO 107
<211> LENGTH: 17
<212> TYPE: PRT
<213> ORGANISM: Artificial Sequence
<220> FEATURE:
<223> OTHER INFORMATION: Synthetic Construct

<400> SEQUENCE: 107

Arg Leu Ile Thr Asp Ser Gly Ser Thr Tyr Tyr Ala Asp Ser Val Lys
1               5                   10                  15

Gly

<210> SEQ ID NO 108
<211> LENGTH: 19
<212> TYPE: PRT
<213> ORGANISM: Artificial Sequence
<220> FEATURE:
<223> OTHER INFORMATION: Synthetic Construct

<400> SEQUENCE: 108

Ala Ile Tyr Thr Ser Val Gly Gly Ser Arg Thr Tyr Val Ala Asp Ser
1               5                   10                  15

Ala Lys Gly

<210> SEQ ID NO 109
<211> LENGTH: 20
<212> TYPE: PRT
<213> ORGANISM: Artificial Sequence
<220> FEATURE:
<223> OTHER INFORMATION: Synthetic Construct

<400> SEQUENCE: 109

Thr Leu Tyr Thr Ser Ser Gly Gly Thr Tyr Phe Asp Thr Tyr Ala Asp
1               5                   10                  15

Ser Val Arg Gly
            20

<210> SEQ ID NO 110
<211> LENGTH: 17
<212> TYPE: PRT
<213> ORGANISM: Artificial Sequence
<220> FEATURE:
<223> OTHER INFORMATION: Synthetic Construct

<400> SEQUENCE: 110

Val Ile Lys Thr Gly Asp Ala Ser Thr Tyr Tyr Thr Asp Ser Val Lys
1               5                   10                  15

Gly

<210> SEQ ID NO 111
<211> LENGTH: 16
<212> TYPE: PRT
<213> ORGANISM: Artificial Sequence
<220> FEATURE:
<223> OTHER INFORMATION: Synthetic Construct

<400> SEQUENCE: 111

```
Ala Ile Ser Ser Asn Asp Leu Val Ala Tyr Ala Asp Ser Val Lys Gly
1               5                   10                  15

<210> SEQ ID NO 112
<211> LENGTH: 20
<212> TYPE: PRT
<213> ORGANISM: Artificial Sequence
<220> FEATURE:
<223> OTHER INFORMATION: Synthetic Construct

<400> SEQUENCE: 112

Thr Ile Tyr Val Ser Ala Ala Ser Thr Ser Phe Ala Thr Tyr Ala Asp
1               5                   10                  15

Ser Val Lys Gly
            20

<210> SEQ ID NO 113
<211> LENGTH: 16
<212> TYPE: PRT
<213> ORGANISM: Artificial Sequence
<220> FEATURE:
<223> OTHER INFORMATION: Synthetic Construct

<400> SEQUENCE: 113

Ala Ile Cys Ser Gly Gly Arg Thr Thr Tyr Ser Asp Ser Val Lys Gly
1               5                   10                  15

<210> SEQ ID NO 114
<211> LENGTH: 16
<212> TYPE: PRT
<213> ORGANISM: Artificial Sequence
<220> FEATURE:
<223> OTHER INFORMATION: Synthetic Construct

<400> SEQUENCE: 114

Ala Ile Cys Ser Gly Gly Arg Thr Thr Tyr Ser Asp Ser Val Lys Gly
1               5                   10                  15

<210> SEQ ID NO 115
<211> LENGTH: 16
<212> TYPE: PRT
<213> ORGANISM: Artificial Sequence
<220> FEATURE:
<223> OTHER INFORMATION: Synthetic Construct

<400> SEQUENCE: 115

Ala Ile Cys Ser Gly Gly Arg Thr Thr Tyr Ser Asp Ser Val Lys Gly
1               5                   10                  15

<210> SEQ ID NO 116
<211> LENGTH: 16
<212> TYPE: PRT
<213> ORGANISM: Artificial Sequence
<220> FEATURE:
<223> OTHER INFORMATION: Synthetic Construct

<400> SEQUENCE: 116

Ala Ile Cys Ser Gly Gly Arg Thr Thr Tyr Ser Asp Ser Val Lys Gly
1               5                   10                  15

<210> SEQ ID NO 117
<211> LENGTH: 16
<212> TYPE: PRT
<213> ORGANISM: Artificial Sequence
<220> FEATURE:
<223> OTHER INFORMATION: Synthetic Construct
```

<400> SEQUENCE: 117

Ala Ile Cys Ser Gly Gly Arg Thr Thr Tyr Ser Asp Ser Val Lys Gly
1               5                   10                  15

<210> SEQ ID NO 118
<211> LENGTH: 16
<212> TYPE: PRT
<213> ORGANISM: Artificial Sequence
<220> FEATURE:
<223> OTHER INFORMATION: Synthetic Construct

<400> SEQUENCE: 118

Ala Ile Cys Ser Gly Gly Arg Thr Thr Tyr Ser Asp Ser Val Lys Gly
1               5                   10                  15

<210> SEQ ID NO 119
<211> LENGTH: 16
<212> TYPE: PRT
<213> ORGANISM: Artificial Sequence
<220> FEATURE:
<223> OTHER INFORMATION: Synthetic Construct

<400> SEQUENCE: 119

Ala Ile Cys Ser Gly Gly Arg Thr Thr Tyr Ser Asp Ser Val Lys Gly
1               5                   10                  15

<210> SEQ ID NO 120
<211> LENGTH: 16
<212> TYPE: PRT
<213> ORGANISM: Artificial Sequence
<220> FEATURE:
<223> OTHER INFORMATION: Synthetic Construct

<400> SEQUENCE: 120

Ala Ile Cys Ser Gly Gly Arg Thr Thr Tyr Ser Asp Ser Val Lys Gly
1               5                   10                  15

<210> SEQ ID NO 121
<211> LENGTH: 16
<212> TYPE: PRT
<213> ORGANISM: Artificial Sequence
<220> FEATURE:
<223> OTHER INFORMATION: Synthetic Construct

<400> SEQUENCE: 121

Ala Ile Cys Ser Gly Gly Arg Thr Thr Tyr Ser Asp Ser Val Lys Gly
1               5                   10                  15

<210> SEQ ID NO 122
<211> LENGTH: 16
<212> TYPE: PRT
<213> ORGANISM: Artificial Sequence
<220> FEATURE:
<223> OTHER INFORMATION: Synthetic Construct

<400> SEQUENCE: 122

Ala Ile Cys Ser Gly Gly Arg Thr Thr Tyr Ser Asp Ser Val Lys Gly
1               5                   10                  15

<210> SEQ ID NO 123
<211> LENGTH: 16
<212> TYPE: PRT
<213> ORGANISM: Artificial Sequence
<220> FEATURE:
<223> OTHER INFORMATION: Synthetic Construct

```
<400> SEQUENCE: 123

Ala Ile Cys Ser Gly Gly Arg Thr Thr Tyr Ser Asp Ser Val Lys Gly
1               5                   10                  15

<210> SEQ ID NO 124
<211> LENGTH: 16
<212> TYPE: PRT
<213> ORGANISM: Artificial Sequence
<220> FEATURE:
<223> OTHER INFORMATION: Synthetic Construct

<400> SEQUENCE: 124

Ala Ile Cys Ser Gly Gly Arg Thr Thr Tyr Ser Asp Ser Val Lys Gly
1               5                   10                  15

<210> SEQ ID NO 125
<211> LENGTH: 16
<212> TYPE: PRT
<213> ORGANISM: Artificial Sequence
<220> FEATURE:
<223> OTHER INFORMATION: Synthetic Construct

<400> SEQUENCE: 125

Ala Ile Cys Ser Gly Gly Arg Thr Thr Tyr Ser Asp Ser Val Lys Gly
1               5                   10                  15

<210> SEQ ID NO 126
<211> LENGTH: 16
<212> TYPE: PRT
<213> ORGANISM: Artificial Sequence
<220> FEATURE:
<223> OTHER INFORMATION: Synthetic Construct

<400> SEQUENCE: 126

Ala Ile Cys Ser Gly Gly Arg Thr Thr Tyr Ser Asp Ser Val Lys Gly
1               5                   10                  15

<210> SEQ ID NO 127
<211> LENGTH: 16
<212> TYPE: PRT
<213> ORGANISM: Artificial Sequence
<220> FEATURE:
<223> OTHER INFORMATION: Synthetic Construct

<400> SEQUENCE: 127

Ala Ile Cys Ser Gly Gly Arg Thr Thr Tyr Ser Asp Ser Val Lys Gly
1               5                   10                  15

<210> SEQ ID NO 128
<211> LENGTH: 16
<212> TYPE: PRT
<213> ORGANISM: Artificial Sequence
<220> FEATURE:
<223> OTHER INFORMATION: Synthetic Construct

<400> SEQUENCE: 128

Ala Ile Cys Ser Gly Gly Arg Thr Thr Tyr Ser Asp Ser Val Lys Gly
1               5                   10                  15

<210> SEQ ID NO 129
<211> LENGTH: 16
<212> TYPE: PRT
<213> ORGANISM: Artificial Sequence
<220> FEATURE:
<223> OTHER INFORMATION: Synthetic Construct

<400> SEQUENCE: 129
```

Ala Ile Cys Ser Gly Gly Arg Thr Thr Tyr Ser Asp Ser Val Lys Gly
1               5                   10                  15

<210> SEQ ID NO 130
<211> LENGTH: 16
<212> TYPE: PRT
<213> ORGANISM: Artificial Sequence
<220> FEATURE:
<223> OTHER INFORMATION: Synthetic Construct

<400> SEQUENCE: 130

Ala Ile Cys Ser Gly Gly Arg Thr Thr Tyr Ser Asp Ser Val Lys Gly
1               5                   10                  15

<210> SEQ ID NO 131
<211> LENGTH: 20
<212> TYPE: PRT
<213> ORGANISM: Artificial Sequence
<220> FEATURE:
<223> OTHER INFORMATION: Synthetic Construct

<400> SEQUENCE: 131

Thr Leu Tyr Thr Ser Ser Gly Gly Thr Tyr Phe Asp Thr Tyr Ala Asp
1               5                   10                  15

Ser Val Arg Gly
            20

<210> SEQ ID NO 132
<211> LENGTH: 20
<212> TYPE: PRT
<213> ORGANISM: Artificial Sequence
<220> FEATURE:
<223> OTHER INFORMATION: Synthetic Construct

<400> SEQUENCE: 132

Thr Leu Tyr Thr Ser Ser Gly Gly Thr Tyr Phe Asp Thr Tyr Ala Asp
1               5                   10                  15

Ser Val Arg Gly
            20

<210> SEQ ID NO 133
<211> LENGTH: 20
<212> TYPE: PRT
<213> ORGANISM: Artificial Sequence
<220> FEATURE:
<223> OTHER INFORMATION: Synthetic Construct

<400> SEQUENCE: 133

Thr Leu Tyr Thr Ser Ser Gly Gly Thr Tyr Phe Asp Thr Tyr Ala Asp
1               5                   10                  15

Ser Val Arg Gly
            20

<210> SEQ ID NO 134
<211> LENGTH: 20
<212> TYPE: PRT
<213> ORGANISM: Artificial Sequence
<220> FEATURE:
<223> OTHER INFORMATION: Synthetic Construct

<400> SEQUENCE: 134

Thr Leu Tyr Thr Ser Ser Gly Gly Thr Tyr Phe Asp Thr Tyr Ala Asp
1               5                   10                  15

Ser Val Arg Gly

```
<210> SEQ ID NO 135
<211> LENGTH: 20
<212> TYPE: PRT
<213> ORGANISM: Artificial Sequence
<220> FEATURE:
<223> OTHER INFORMATION: Synthetic Construct

<400> SEQUENCE: 135

Thr Leu Tyr Thr Ser Ser Gly Gly Thr Tyr Phe Asp Thr Tyr Ala Asp
1               5                   10                  15

Ser Val Arg Gly
            20

<210> SEQ ID NO 136
<211> LENGTH: 20
<212> TYPE: PRT
<213> ORGANISM: Artificial Sequence
<220> FEATURE:
<223> OTHER INFORMATION: Synthetic Construct

<400> SEQUENCE: 136

Thr Leu Tyr Thr Ser Ser Gly Gly Thr Tyr Phe Asp Thr Tyr Ala Asp
1               5                   10                  15

Ser Val Arg Gly
            20

<210> SEQ ID NO 137
<211> LENGTH: 20
<212> TYPE: PRT
<213> ORGANISM: Artificial Sequence
<220> FEATURE:
<223> OTHER INFORMATION: Synthetic Construct

<400> SEQUENCE: 137

Thr Leu Tyr Thr Ser Ser Gly Gly Thr Tyr Phe Asp Thr Tyr Ala Asp
1               5                   10                  15

Ser Val Arg Gly
            20

<210> SEQ ID NO 138
<211> LENGTH: 20
<212> TYPE: PRT
<213> ORGANISM: Artificial Sequence
<220> FEATURE:
<223> OTHER INFORMATION: Synthetic Construct

<400> SEQUENCE: 138

Thr Leu Tyr Thr Ser Ser Gly Gly Thr Tyr Phe Asp Thr Tyr Ala Asp
1               5                   10                  15

Ser Val Arg Gly
            20

<210> SEQ ID NO 139
<211> LENGTH: 20
<212> TYPE: PRT
<213> ORGANISM: Artificial Sequence
<220> FEATURE:
<223> OTHER INFORMATION: Synthetic Construct

<400> SEQUENCE: 139

Thr Leu Tyr Thr Ser Ser Gly Gly Thr Tyr Phe Asp Thr Tyr Ala Asp
1               5                   10                  15
```

Ser Val Arg Gly
        20

<210> SEQ ID NO 140
<211> LENGTH: 20
<212> TYPE: PRT
<213> ORGANISM: Artificial Sequence
<220> FEATURE:
<223> OTHER INFORMATION: Synthetic Construct

<400> SEQUENCE: 140

Thr Leu Tyr Thr Ser Ser Gly Gly Thr Tyr Phe Asp Thr Tyr Ala Asp
1               5                   10                  15

Ser Val Arg Gly
        20

<210> SEQ ID NO 141
<211> LENGTH: 32
<212> TYPE: PRT
<213> ORGANISM: Artificial Sequence
<220> FEATURE:
<223> OTHER INFORMATION: Synthetic Construct

<400> SEQUENCE: 141

Arg Phe Thr Ile Ser Lys Asp Ser Ala Asn Gln Ile Leu Tyr Leu Gln
1               5                   10                  15

Met Asn Ser Leu Lys Pro Glu Asp Thr Ala Met Tyr Tyr Cys Ala Ala
            20                  25                  30

<210> SEQ ID NO 142
<211> LENGTH: 32
<212> TYPE: PRT
<213> ORGANISM: Artificial Sequence
<220> FEATURE:
<223> OTHER INFORMATION: Synthetic Construct

<400> SEQUENCE: 142

Arg Phe Ile Ile Ser Gln Asp Asn Ala Lys Asn Thr Val Tyr Leu Gln
1               5                   10                  15

Met Asn Thr Leu Lys Pro Glu Asp Thr Ala Met Tyr Tyr Cys Ala Glu
            20                  25                  30

<210> SEQ ID NO 143
<211> LENGTH: 32
<212> TYPE: PRT
<213> ORGANISM: Artificial Sequence
<220> FEATURE:
<223> OTHER INFORMATION: Synthetic Construct

<400> SEQUENCE: 143

Arg Phe Thr Val Ser Gln Asp Asn Ala Lys Asn Thr Val Tyr Leu Gln
1               5                   10                  15

Met Asn Ser Leu Lys Pro Glu Asp Thr Ala Met Tyr Tyr Cys Ala Ala
            20                  25                  30

<210> SEQ ID NO 144
<211> LENGTH: 32
<212> TYPE: PRT
<213> ORGANISM: Artificial Sequence
<220> FEATURE:
<223> OTHER INFORMATION: Synthetic Construct

<400> SEQUENCE: 144

Arg Phe Thr Ile Ser Gln Asp Asn Ala Lys Asn Thr Val Tyr Leu Gln
1               5                   10                  15

```
Met Asn Asn Leu Lys Pro Glu Asp Ser Gly Ile Tyr Tyr Cys Ala Ala
            20                  25                  30
```

<210> SEQ ID NO 145
<211> LENGTH: 32
<212> TYPE: PRT
<213> ORGANISM: Artificial Sequence
<220> FEATURE:
<223> OTHER INFORMATION: Synthetic Construct

<400> SEQUENCE: 145

```
Arg Phe Thr Ile Ser Gln Asp Asn Ala Lys Asn Thr Leu Tyr Leu Gln
1               5                   10                  15

Met Asn Ser Leu Lys Pro Glu Asp Thr Ala Met Tyr Tyr Cys Ala Ala
            20                  25                  30
```

<210> SEQ ID NO 146
<211> LENGTH: 32
<212> TYPE: PRT
<213> ORGANISM: Artificial Sequence
<220> FEATURE:
<223> OTHER INFORMATION: Synthetic Construct

<400> SEQUENCE: 146

```
Arg Phe Thr Ile Ser Lys Asp Asn Ala Lys Thr Thr Leu Tyr Leu Gln
1               5                   10                  15

Met Asn Asn Leu Lys Pro Glu Asp Thr Ala Met Tyr Tyr Cys Ala Ala
            20                  25                  30
```

<210> SEQ ID NO 147
<211> LENGTH: 32
<212> TYPE: PRT
<213> ORGANISM: Artificial Sequence
<220> FEATURE:
<223> OTHER INFORMATION: Synthetic Construct

<400> SEQUENCE: 147

```
Arg Phe Thr Ile Ser Leu Asp Lys Ala Lys Asn Thr Val Tyr Leu Gln
1               5                   10                  15

Met Asn Ser Leu Lys Pro Glu Asp Thr Ala Met Tyr Tyr Cys Ala Ala
            20                  25                  30
```

<210> SEQ ID NO 148
<211> LENGTH: 32
<212> TYPE: PRT
<213> ORGANISM: Artificial Sequence
<220> FEATURE:
<223> OTHER INFORMATION: Synthetic Construct

<400> SEQUENCE: 148

```
Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ala
            20                  25                  30
```

<210> SEQ ID NO 149
<211> LENGTH: 32
<212> TYPE: PRT
<213> ORGANISM: Artificial Sequence
<220> FEATURE:
<223> OTHER INFORMATION: Synthetic Construct

<400> SEQUENCE: 149

```
Arg Phe Thr Ile Ser Lys Asp Asn Ser Lys Asn Thr Leu Tyr Leu Gln
```

```
                1               5                  10                  15
Met Asn Ser Leu Arg Ala Glu Asp Thr Ala Val Tyr Tyr Cys Ala Ala
            20                  25                  30
```

<210> SEQ ID NO 150
<211> LENGTH: 32
<212> TYPE: PRT
<213> ORGANISM: Artificial Sequence
<220> FEATURE:
<223> OTHER INFORMATION: Synthetic Construct

<400> SEQUENCE: 150

```
Arg Phe Thr Ile Ser Lys Asp Asn Ser Lys Asn Thr Leu Tyr Leu Gln
1               5                  10                  15

Met Asn Ser Leu Arg Ala Glu Asp Thr Ala Val Tyr Tyr Cys Ala Ala
            20                  25                  30
```

<210> SEQ ID NO 151
<211> LENGTH: 32
<212> TYPE: PRT
<213> ORGANISM: Artificial Sequence
<220> FEATURE:
<223> OTHER INFORMATION: Synthetic Construct

<400> SEQUENCE: 151

```
Arg Phe Thr Ile Ser Arg Asp Asn Ser Lys Asn Thr Leu Tyr Leu Gln
1               5                  10                  15

Met Asn Ser Leu Arg Ala Glu Asp Thr Ala Val Tyr Tyr Cys Ala Ala
            20                  25                  30
```

<210> SEQ ID NO 152
<211> LENGTH: 32
<212> TYPE: PRT
<213> ORGANISM: Artificial Sequence
<220> FEATURE:
<223> OTHER INFORMATION: Synthetic Construct

<400> SEQUENCE: 152

```
Arg Phe Thr Ile Ser Arg Asp Asn Ser Lys Asn Thr Leu Tyr Leu Gln
1               5                  10                  15

Met Asn Ser Leu Arg Ala Glu Asp Thr Ala Met Tyr Tyr Cys Ala Ala
            20                  25                  30
```

<210> SEQ ID NO 153
<211> LENGTH: 32
<212> TYPE: PRT
<213> ORGANISM: Artificial Sequence
<220> FEATURE:
<223> OTHER INFORMATION: Synthetic Construct

<400> SEQUENCE: 153

```
Arg Phe Thr Ile Ser Arg Asp Asn Ser Lys Asn Thr Leu Tyr Leu Gln
1               5                  10                  15

Met Asn Ser Leu Arg Ala Glu Asp Thr Ala Val Tyr Tyr Cys Ala Ala
            20                  25                  30
```

<210> SEQ ID NO 154
<211> LENGTH: 32
<212> TYPE: PRT
<213> ORGANISM: Artificial Sequence
<220> FEATURE:
<223> OTHER INFORMATION: Synthetic Construct

<400> SEQUENCE: 154

Arg Phe Thr Ile Ser Arg Asp Asn Ala Lys Asn Thr Leu Tyr Leu Gln
1               5                   10                  15

Met Asn Ser Leu Arg Pro Glu Asp Thr Ala Val Tyr Tyr Cys Ala Ala
            20                  25                  30

<210> SEQ ID NO 155
<211> LENGTH: 32
<212> TYPE: PRT
<213> ORGANISM: Artificial Sequence
<220> FEATURE:
<223> OTHER INFORMATION: Synthetic Construct

<400> SEQUENCE: 155

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ala
            20                  25                  30

<210> SEQ ID NO 156
<211> LENGTH: 32
<212> TYPE: PRT
<213> ORGANISM: Artificial Sequence
<220> FEATURE:
<223> OTHER INFORMATION: Synthetic Construct

<400> SEQUENCE: 156

Arg Phe Thr Ile Ser Arg Asp Ser Ala Lys Asn Thr Leu Tyr Leu Gln
1               5                   10                  15

Met Asn Ser Leu Arg Ala Glu Asp Thr Ala Val Tyr Tyr Cys Ala Ala
            20                  25                  30

<210> SEQ ID NO 157
<211> LENGTH: 32
<212> TYPE: PRT
<213> ORGANISM: Artificial Sequence
<220> FEATURE:
<223> OTHER INFORMATION: Synthetic Construct

<400> SEQUENCE: 157

Arg Phe Thr Ile Ser Arg Asp Asn Ser Asn Gln Thr Leu Tyr Leu Gln
1               5                   10                  15

Met Asn Ser Leu Arg Ala Glu Asp Thr Ala Val Tyr Tyr Cys Ala Ala
            20                  25                  30

<210> SEQ ID NO 158
<211> LENGTH: 32
<212> TYPE: PRT
<213> ORGANISM: Artificial Sequence
<220> FEATURE:
<223> OTHER INFORMATION: Synthetic Construct

<400> SEQUENCE: 158

Arg Phe Thr Ile Ser Arg Asp Asn Ser Lys Asn Ile Leu Tyr Leu Gln
1               5                   10                  15

Met Asn Ser Leu Arg Ala Glu Asp Thr Ala Val Tyr Tyr Cys Ala Ala
            20                  25                  30

<210> SEQ ID NO 159
<211> LENGTH: 32
<212> TYPE: PRT
<213> ORGANISM: Artificial Sequence
<220> FEATURE:
<223> OTHER INFORMATION: Synthetic Construct

<400> SEQUENCE: 159

Arg Phe Thr Ile Ser Arg Asp Asn Ser Lys Gln Thr Leu Tyr Leu Gln
1               5                   10                  15

Met Asn Ser Leu Arg Ala Glu Asp Thr Ala Val Tyr Tyr Cys Ala Ala
            20                  25                  30

<210> SEQ ID NO 160
<211> LENGTH: 32
<212> TYPE: PRT
<213> ORGANISM: Artificial Sequence
<220> FEATURE:
<223> OTHER INFORMATION: Synthetic Construct

<400> SEQUENCE: 160

Arg Phe Thr Ile Ser Arg Asp Asn Ser Asn Asn Ile Leu Tyr Leu Gln
1               5                   10                  15

Met Asn Ser Leu Arg Ala Glu Asp Thr Ala Val Tyr Tyr Cys Ala Ala
            20                  25                  30

<210> SEQ ID NO 161
<211> LENGTH: 32
<212> TYPE: PRT
<213> ORGANISM: Artificial Sequence
<220> FEATURE:
<223> OTHER INFORMATION: Synthetic Construct

<400> SEQUENCE: 161

Arg Phe Thr Ile Ser Arg Asp Asn Ser Asn Gln Ile Leu Tyr Leu Gln
1               5                   10                  15

Met Asn Ser Leu Arg Ala Glu Asp Thr Ala Val Tyr Tyr Cys Ala Ala
            20                  25                  30

<210> SEQ ID NO 162
<211> LENGTH: 32
<212> TYPE: PRT
<213> ORGANISM: Artificial Sequence
<220> FEATURE:
<223> OTHER INFORMATION: Synthetic Construct

<400> SEQUENCE: 162

Arg Phe Thr Ile Ser Arg Asp Asn Ser Lys Gln Thr Leu Tyr Leu Gln
1               5                   10                  15

Met Asn Ser Leu Arg Ala Glu Asp Thr Ala Val Tyr Tyr Cys Ala Ala
            20                  25                  30

<210> SEQ ID NO 163
<211> LENGTH: 32
<212> TYPE: PRT
<213> ORGANISM: Artificial Sequence
<220> FEATURE:
<223> OTHER INFORMATION: Synthetic Construct

<400> SEQUENCE: 163

Arg Phe Thr Ile Ser Arg Asp Asn Ser Asn Asn Ile Leu Tyr Leu Gln
1               5                   10                  15

Met Asn Ser Leu Arg Ala Glu Asp Thr Ala Val Tyr Tyr Cys Ala Ala
            20                  25                  30

<210> SEQ ID NO 164
<211> LENGTH: 32
<212> TYPE: PRT
<213> ORGANISM: Artificial Sequence
<220> FEATURE:
<223> OTHER INFORMATION: Synthetic Construct

```
<400> SEQUENCE: 164

Arg Phe Thr Ile Ser Arg Asp Asn Ser Asn Gln Ile Leu Tyr Leu Gln
1               5                   10                  15

Met Asn Ser Leu Arg Ala Glu Asp Thr Ala Val Tyr Tyr Cys Ala Ala
                20                  25                  30

<210> SEQ ID NO 165
<211> LENGTH: 32
<212> TYPE: PRT
<213> ORGANISM: Artificial Sequence
<220> FEATURE:
<223> OTHER INFORMATION: Synthetic Construct

<400> SEQUENCE: 165

Arg Phe Thr Ile Ser Arg Asp Asn Ser Lys Asn Ile Leu Tyr Leu Gln
1               5                   10                  15

Met Asn Ser Leu Arg Ala Glu Asp Thr Ala Val Tyr Tyr Cys Ala Ala
                20                  25                  30

<210> SEQ ID NO 166
<211> LENGTH: 32
<212> TYPE: PRT
<213> ORGANISM: Artificial Sequence
<220> FEATURE:
<223> OTHER INFORMATION: Synthetic Construct

<400> SEQUENCE: 166

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ala
                20                  25                  30

<210> SEQ ID NO 167
<211> LENGTH: 32
<212> TYPE: PRT
<213> ORGANISM: Artificial Sequence
<220> FEATURE:
<223> OTHER INFORMATION: Synthetic Construct

<400> SEQUENCE: 167

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ala
                20                  25                  30

<210> SEQ ID NO 168
<211> LENGTH: 32
<212> TYPE: PRT
<213> ORGANISM: Artificial Sequence
<220> FEATURE:
<223> OTHER INFORMATION: Synthetic Construct

<400> SEQUENCE: 168

Arg Phe Thr Ile Ser Arg Asp Asn Ser Lys Asn Thr Val Tyr Leu Gln
1               5                   10                  15

Met Asn Ser Leu Arg Ala Glu Asp Thr Gly Val Tyr Tyr Cys Ala Ala
                20                  25                  30

<210> SEQ ID NO 169
<211> LENGTH: 32
<212> TYPE: PRT
<213> ORGANISM: Artificial Sequence
<220> FEATURE:
<223> OTHER INFORMATION: Synthetic Construct
```

```
<400> SEQUENCE: 169

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ala
            20                  25                  30

<210> SEQ ID NO 170
<211> LENGTH: 32
<212> TYPE: PRT
<213> ORGANISM: Artificial Sequence
<220> FEATURE:
<223> OTHER INFORMATION: Synthetic Construct

<400> SEQUENCE: 170

Arg Phe Thr Ile Ser Gln Asp Asn Ser Lys Asn Thr Leu Tyr Leu Gln
1               5                   10                  15

Met Asn Ser Leu Arg Ala Glu Asp Thr Ala Val Tyr Tyr Cys Ala Ala
            20                  25                  30

<210> SEQ ID NO 171
<211> LENGTH: 32
<212> TYPE: PRT
<213> ORGANISM: Artificial Sequence
<220> FEATURE:
<223> OTHER INFORMATION: Synthetic Construct

<400> SEQUENCE: 171

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ala
            20                  25                  30

<210> SEQ ID NO 172
<211> LENGTH: 32
<212> TYPE: PRT
<213> ORGANISM: Artificial Sequence
<220> FEATURE:
<223> OTHER INFORMATION: Synthetic Construct

<400> SEQUENCE: 172

Arg Phe Thr Ile Ser Arg Asp Asn Ser Lys Asn Thr Val Tyr Leu Gln
1               5                   10                  15

Met Asn Ser Leu Arg Ala Glu Asp Thr Ala Val Tyr Tyr Cys Ala Ala
            20                  25                  30

<210> SEQ ID NO 173
<211> LENGTH: 32
<212> TYPE: PRT
<213> ORGANISM: Artificial Sequence
<220> FEATURE:
<223> OTHER INFORMATION: Synthetic Construct

<400> SEQUENCE: 173

Arg Phe Thr Ile Ser Arg Asp Asn Ala Lys Asn Thr Leu Tyr Leu Gln
1               5                   10                  15

Met Asn Ser Leu Arg Ala Glu Asp Thr Ala Val Tyr Tyr Cys Ala Ala
            20                  25                  30

<210> SEQ ID NO 174
<211> LENGTH: 32
<212> TYPE: PRT
<213> ORGANISM: Artificial Sequence
<220> FEATURE:
```

<223> OTHER INFORMATION: Synthetic Construct

<400> SEQUENCE: 174

Arg Phe Thr Ile Ser Arg Asp Asn Ala Lys Asn Thr Leu Tyr Leu Gln
1               5                   10                  15
Met Asn Ser Leu Arg Pro Glu Asp Thr Ala Val Tyr Tyr Cys Ala Ala
            20                  25                  30

<210> SEQ ID NO 175
<211> LENGTH: 32
<212> TYPE: PRT
<213> ORGANISM: Artificial Sequence
<220> FEATURE:
<223> OTHER INFORMATION: Synthetic Construct

<400> SEQUENCE: 175

Arg Phe Thr Ile Ser Arg Asp Asn Ala Lys Asn Thr Val Tyr Leu Gln
1               5                   10                  15
Met Asn Ser Leu Arg Pro Glu Asp Thr Ala Val Tyr Tyr Cys Ala Ala
            20                  25                  30

<210> SEQ ID NO 176
<211> LENGTH: 17
<212> TYPE: PRT
<213> ORGANISM: Artificial Sequence
<220> FEATURE:
<223> OTHER INFORMATION: Synthetic Construct

<400> SEQUENCE: 176

Arg Pro Leu Trp Thr Gly Asp Cys Asp Leu Ser Ser Trp Tyr Lys
1               5                   10                  15
Thr

<210> SEQ ID NO 177
<211> LENGTH: 19
<212> TYPE: PRT
<213> ORGANISM: Artificial Sequence
<220> FEATURE:
<223> OTHER INFORMATION: Synthetic Construct

<400> SEQUENCE: 177

Glu Leu Ala Pro Ala Arg Ser Gly Gly Ile Trp Phe Gly Gly Arg Tyr
1               5                   10                  15
Phe Ser Tyr

<210> SEQ ID NO 178
<211> LENGTH: 16
<212> TYPE: PRT
<213> ORGANISM: Artificial Sequence
<220> FEATURE:
<223> OTHER INFORMATION: Synthetic Construct

<400> SEQUENCE: 178

Lys Ser Pro Tyr Asp Gly Ala Cys Ser Tyr Glu Ala Asp Phe Thr Tyr
1               5                   10                  15

<210> SEQ ID NO 179
<211> LENGTH: 15
<212> TYPE: PRT
<213> ORGANISM: Artificial Sequence
<220> FEATURE:
<223> OTHER INFORMATION: Synthetic Construct

<400> SEQUENCE: 179

Arg Leu Ser Thr Asp Phe Cys Gly Pro Arg Ala Asp Phe Asp Tyr
1               5                   10                  15

<210> SEQ ID NO 180
<211> LENGTH: 16
<212> TYPE: PRT
<213> ORGANISM: Artificial Sequence
<220> FEATURE:
<223> OTHER INFORMATION: Synthetic Construct

<400> SEQUENCE: 180

Arg Arg Gly Trp Val Pro Ala Pro Leu Ser Gln Tyr Asn Tyr Asn Tyr
1               5                   10                  15

<210> SEQ ID NO 181
<211> LENGTH: 17
<212> TYPE: PRT
<213> ORGANISM: Artificial Sequence
<220> FEATURE:
<223> OTHER INFORMATION: Synthetic Construct

<400> SEQUENCE: 181

Asp Gly Gly Tyr Gly Gly Tyr Cys Gly Arg Leu Arg Pro Gly Thr Gly
1               5                   10                  15
Tyr

<210> SEQ ID NO 182
<211> LENGTH: 19
<212> TYPE: PRT
<213> ORGANISM: Artificial Sequence
<220> FEATURE:
<223> OTHER INFORMATION: Synthetic Construct

<400> SEQUENCE: 182

Asp Pro Pro Asp Arg Ile Ser Asn Pro Cys Gly Pro Arg Arg Pro Asp
1               5                   10                  15
Phe Gly Tyr

<210> SEQ ID NO 183
<211> LENGTH: 17
<212> TYPE: PRT
<213> ORGANISM: Artificial Sequence
<220> FEATURE:
<223> OTHER INFORMATION: Synthetic Construct

<400> SEQUENCE: 183

Arg Pro Leu Trp Thr Gly Asp Cys Asp Leu Ser Ser Ser Trp Tyr Lys
1               5                   10                  15
Thr

<210> SEQ ID NO 184
<211> LENGTH: 17
<212> TYPE: PRT
<213> ORGANISM: Artificial Sequence
<220> FEATURE:
<223> OTHER INFORMATION: Synthetic Construct

<400> SEQUENCE: 184

Arg Pro Leu Trp Thr Gly Asp Cys Asp Leu Ser Ser Ser Trp Tyr Lys
1               5                   10                  15
Thr

<210> SEQ ID NO 185
<211> LENGTH: 17

<212> TYPE: PRT
<213> ORGANISM: Artificial Sequence
<220> FEATURE:
<223> OTHER INFORMATION: Synthetic Construct

<400> SEQUENCE: 185

Arg Pro Leu Trp Thr Gly Asp Cys Asp Leu Ser Ser Ser Trp Tyr Lys
1               5                   10                  15
Thr

<210> SEQ ID NO 186
<211> LENGTH: 17
<212> TYPE: PRT
<213> ORGANISM: Artificial Sequence
<220> FEATURE:
<223> OTHER INFORMATION: Synthetic Construct

<400> SEQUENCE: 186

Arg Pro Leu Trp Thr Gly Asp Cys Asp Leu Ser Ser Ser Trp Tyr Lys
1               5                   10                  15
Thr

<210> SEQ ID NO 187
<211> LENGTH: 17
<212> TYPE: PRT
<213> ORGANISM: Artificial Sequence
<220> FEATURE:
<223> OTHER INFORMATION: Synthetic Construct

<400> SEQUENCE: 187

Arg Pro Leu Trp Thr Gly Asp Cys Asp Leu Ser Ser Ser Trp Tyr Lys
1               5                   10                  15
Thr

<210> SEQ ID NO 188
<211> LENGTH: 17
<212> TYPE: PRT
<213> ORGANISM: Artificial Sequence
<220> FEATURE:
<223> OTHER INFORMATION: Synthetic Construct

<400> SEQUENCE: 188

Arg Pro Leu Trp Thr Gly Asp Cys Asp Leu Ser Ser Ser Trp Tyr Lys
1               5                   10                  15
Thr

<210> SEQ ID NO 189
<211> LENGTH: 17
<212> TYPE: PRT
<213> ORGANISM: Artificial Sequence
<220> FEATURE:
<223> OTHER INFORMATION: Synthetic Construct

<400> SEQUENCE: 189

Arg Pro Leu Trp Thr Gly Asp Cys Asp Leu Ser Ser Ser Trp Tyr Lys
1               5                   10                  15
Thr

<210> SEQ ID NO 190
<211> LENGTH: 17
<212> TYPE: PRT
<213> ORGANISM: Artificial Sequence
<220> FEATURE:
<223> OTHER INFORMATION: Synthetic Construct

<400> SEQUENCE: 190

Arg Pro Leu Trp Thr Gly Asp Cys Asp Leu Ser Ser Ser Trp Tyr Lys
1               5                   10                  15

Thr

<210> SEQ ID NO 191
<211> LENGTH: 17
<212> TYPE: PRT
<213> ORGANISM: Artificial Sequence
<220> FEATURE:
<223> OTHER INFORMATION: Synthetic Construct

<400> SEQUENCE: 191

Arg Pro Leu Trp Thr Gly Asp Cys Asp Leu Ser Ser Ser Trp Tyr Lys
1               5                   10                  15

Thr

<210> SEQ ID NO 192
<211> LENGTH: 17
<212> TYPE: PRT
<213> ORGANISM: Artificial Sequence
<220> FEATURE:
<223> OTHER INFORMATION: Synthetic Construct

<400> SEQUENCE: 192

Arg Pro Leu Trp Thr Gly Asp Cys Asp Leu Ser Ser Ser Trp Tyr Lys
1               5                   10                  15

Thr

<210> SEQ ID NO 193
<211> LENGTH: 17
<212> TYPE: PRT
<213> ORGANISM: Artificial Sequence
<220> FEATURE:
<223> OTHER INFORMATION: Synthetic Construct

<400> SEQUENCE: 193

Arg Pro Leu Trp Thr Gly Asp Cys Asp Leu Ser Ser Ser Trp Tyr Lys
1               5                   10                  15

Thr

<210> SEQ ID NO 194
<211> LENGTH: 17
<212> TYPE: PRT
<213> ORGANISM: Artificial Sequence
<220> FEATURE:
<223> OTHER INFORMATION: Synthetic Construct

<400> SEQUENCE: 194

Arg Pro Leu Trp Thr Gly Asp Cys Asp Leu Ser Ser Ser Trp Tyr Lys
1               5                   10                  15

Thr

<210> SEQ ID NO 195
<211> LENGTH: 17
<212> TYPE: PRT
<213> ORGANISM: Artificial Sequence
<220> FEATURE:
<223> OTHER INFORMATION: Synthetic Construct

<400> SEQUENCE: 195

Arg Pro Leu Trp Thr Gly Asp Cys Asp Leu Ser Ser Ser Trp Tyr Lys

Thr

<210> SEQ ID NO 196
<211> LENGTH: 17
<212> TYPE: PRT
<213> ORGANISM: Artificial Sequence
<220> FEATURE:
<223> OTHER INFORMATION: Synthetic Construct

<400> SEQUENCE: 196

Arg Pro Leu Trp Thr Gly Asp Cys Asp Leu Ser Ser Ser Trp Tyr Lys
1               5                   10                  15

Thr

<210> SEQ ID NO 197
<211> LENGTH: 17
<212> TYPE: PRT
<213> ORGANISM: Artificial Sequence
<220> FEATURE:
<223> OTHER INFORMATION: Synthetic Construct

<400> SEQUENCE: 197

Arg Pro Leu Trp Thr Gly Asp Cys Asp Leu Ser Ser Ser Trp Tyr Lys
1               5                   10                  15

Thr

<210> SEQ ID NO 198
<211> LENGTH: 17
<212> TYPE: PRT
<213> ORGANISM: Artificial Sequence
<220> FEATURE:
<223> OTHER INFORMATION: Synthetic Construct

<400> SEQUENCE: 198

Arg Pro Leu Trp Thr Gly Asp Cys Asp Leu Ser Ser Ser Trp Tyr Lys
1               5                   10                  15

Thr

<210> SEQ ID NO 199
<211> LENGTH: 17
<212> TYPE: PRT
<213> ORGANISM: Artificial Sequence
<220> FEATURE:
<223> OTHER INFORMATION: Synthetic Construct

<400> SEQUENCE: 199

Arg Pro Leu Trp Thr Gly Asp Cys Asp Leu Ser Ser Ser Trp Tyr Lys
1               5                   10                  15

Thr

<210> SEQ ID NO 200
<211> LENGTH: 17
<212> TYPE: PRT
<213> ORGANISM: Artificial Sequence
<220> FEATURE:
<223> OTHER INFORMATION: Synthetic Construct

<400> SEQUENCE: 200

Arg Pro Leu Trp Thr Gly Asp Cys Asp Leu Ser Ser Ser Trp Tyr Lys
1               5                   10                  15

Thr

```
<210> SEQ ID NO 201
<211> LENGTH: 15
<212> TYPE: PRT
<213> ORGANISM: Artificial Sequence
<220> FEATURE:
<223> OTHER INFORMATION: Synthetic Construct

<400> SEQUENCE: 201

Arg Leu Ser Thr Asp Phe Cys Gly Pro Arg Ala Asp Phe Asp Tyr
1               5                   10                  15

<210> SEQ ID NO 202
<211> LENGTH: 15
<212> TYPE: PRT
<213> ORGANISM: Artificial Sequence
<220> FEATURE:
<223> OTHER INFORMATION: Synthetic Construct

<400> SEQUENCE: 202

Arg Leu Ser Thr Asp Phe Cys Gly Pro Arg Ala Asp Phe Asp Tyr
1               5                   10                  15

<210> SEQ ID NO 203
<211> LENGTH: 15
<212> TYPE: PRT
<213> ORGANISM: Artificial Sequence
<220> FEATURE:
<223> OTHER INFORMATION: Synthetic Construct

<400> SEQUENCE: 203

Arg Leu Ser Thr Asp Phe Cys Gly Pro Arg Ala Asp Phe Asp Tyr
1               5                   10                  15

<210> SEQ ID NO 204
<211> LENGTH: 15
<212> TYPE: PRT
<213> ORGANISM: Artificial Sequence
<220> FEATURE:
<223> OTHER INFORMATION: Synthetic Construct

<400> SEQUENCE: 204

Arg Leu Ser Thr Asp Phe Cys Gly Pro Arg Ala Asp Phe Asp Tyr
1               5                   10                  15

<210> SEQ ID NO 205
<211> LENGTH: 15
<212> TYPE: PRT
<213> ORGANISM: Artificial Sequence
<220> FEATURE:
<223> OTHER INFORMATION: Synthetic Construct

<400> SEQUENCE: 205

Arg Leu Ser Thr Asp Phe Cys Gly Pro Arg Ala Asp Phe Asp Tyr
1               5                   10                  15

<210> SEQ ID NO 206
<211> LENGTH: 15
<212> TYPE: PRT
<213> ORGANISM: Artificial Sequence
<220> FEATURE:
<223> OTHER INFORMATION: Synthetic Construct

<400> SEQUENCE: 206

Arg Leu Ser Thr Asp Phe Cys Gly Pro Arg Ala Asp Phe Asp Tyr
1               5                   10                  15
```

<210> SEQ ID NO 207
<211> LENGTH: 15
<212> TYPE: PRT
<213> ORGANISM: Artificial Sequence
<220> FEATURE:
<223> OTHER INFORMATION: Synthetic Construct

<400> SEQUENCE: 207

Arg Leu Ser Thr Asp Phe Cys Gly Pro Arg Ala Asp Phe Asp Tyr
1               5                   10                  15

<210> SEQ ID NO 208
<211> LENGTH: 15
<212> TYPE: PRT
<213> ORGANISM: Artificial Sequence
<220> FEATURE:
<223> OTHER INFORMATION: Synthetic Construct

<400> SEQUENCE: 208

Arg Leu Ser Thr Asp Phe Cys Gly Pro Arg Ala Asp Phe Asp Tyr
1               5                   10                  15

<210> SEQ ID NO 209
<211> LENGTH: 15
<212> TYPE: PRT
<213> ORGANISM: Artificial Sequence
<220> FEATURE:
<223> OTHER INFORMATION: Synthetic Construct

<400> SEQUENCE: 209

Arg Leu Ser Thr Asp Phe Cys Gly Pro Arg Ala Asp Phe Asp Tyr
1               5                   10                  15

<210> SEQ ID NO 210
<211> LENGTH: 15
<212> TYPE: PRT
<213> ORGANISM: Artificial Sequence
<220> FEATURE:
<223> OTHER INFORMATION: Synthetic Construct

<400> SEQUENCE: 210

Arg Leu Ser Thr Asp Phe Cys Gly Pro Arg Ala Asp Phe Asp Tyr
1               5                   10                  15

<210> SEQ ID NO 211
<211> LENGTH: 11
<212> TYPE: PRT
<213> ORGANISM: Artificial Sequence
<220> FEATURE:
<223> OTHER INFORMATION: Synthetic Construct

<400> SEQUENCE: 211

Trp Gly Gln Gly Thr Gln Val Thr Val Ser Ser
1               5                   10

<210> SEQ ID NO 212
<211> LENGTH: 11
<212> TYPE: PRT
<213> ORGANISM: Artificial Sequence
<220> FEATURE:
<223> OTHER INFORMATION: Synthetic Construct

<400> SEQUENCE: 212

Trp Gly Gln Gly Thr Gln Val Thr Val Ser Ser
1               5                   10

<210> SEQ ID NO 213

```
<211> LENGTH: 11
<212> TYPE: PRT
<213> ORGANISM: Artificial Sequence
<220> FEATURE:
<223> OTHER INFORMATION: Synthetic Construct

<400> SEQUENCE: 213

Trp Gly Gln Gly Thr Gln Val Thr Val Ser Ser
1               5                   10

<210> SEQ ID NO 214
<211> LENGTH: 11
<212> TYPE: PRT
<213> ORGANISM: Artificial Sequence
<220> FEATURE:
<223> OTHER INFORMATION: Synthetic Construct

<400> SEQUENCE: 214

Trp Gly Gln Gly Thr Gln Val Thr Val Ser Ser
1               5                   10

<210> SEQ ID NO 215
<211> LENGTH: 11
<212> TYPE: PRT
<213> ORGANISM: Artificial Sequence
<220> FEATURE:
<223> OTHER INFORMATION: Synthetic Construct

<400> SEQUENCE: 215

Trp Gly Gln Gly Thr Gln Val Thr Val Ser Ser
1               5                   10

<210> SEQ ID NO 216
<211> LENGTH: 11
<212> TYPE: PRT
<213> ORGANISM: Artificial Sequence
<220> FEATURE:
<223> OTHER INFORMATION: Synthetic Construct

<400> SEQUENCE: 216

Trp Gly Gln Gly Thr Gln Val Thr Val Ser Ser
1               5                   10

<210> SEQ ID NO 217
<211> LENGTH: 11
<212> TYPE: PRT
<213> ORGANISM: Artificial Sequence
<220> FEATURE:
<223> OTHER INFORMATION: Synthetic Construct

<400> SEQUENCE: 217

Trp Gly Gln Gly Thr Gln Val Thr Val Ser Ser
1               5                   10

<210> SEQ ID NO 218
<211> LENGTH: 11
<212> TYPE: PRT
<213> ORGANISM: Artificial Sequence
<220> FEATURE:
<223> OTHER INFORMATION: Synthetic Construct

<400> SEQUENCE: 218

Trp Gly Gln Gly Thr Leu Val Thr Val Ser Ser
1               5                   10

<210> SEQ ID NO 219
<211> LENGTH: 11
```

```
<212> TYPE: PRT
<213> ORGANISM: Artificial Sequence
<220> FEATURE:
<223> OTHER INFORMATION: Synthetic Construct

<400> SEQUENCE: 219

Trp Gly Gln Gly Thr Leu Val Thr Val Ser Ser
1               5                   10

<210> SEQ ID NO 220
<211> LENGTH: 11
<212> TYPE: PRT
<213> ORGANISM: Artificial Sequence
<220> FEATURE:
<223> OTHER INFORMATION: Synthetic Construct

<400> SEQUENCE: 220

Trp Gly Gln Gly Thr Leu Val Thr Val Ser Ser
1               5                   10

<210> SEQ ID NO 221
<211> LENGTH: 11
<212> TYPE: PRT
<213> ORGANISM: Artificial Sequence
<220> FEATURE:
<223> OTHER INFORMATION: Synthetic Construct

<400> SEQUENCE: 221

Trp Gly Gln Gly Thr Leu Val Thr Val Ser Ser
1               5                   10

<210> SEQ ID NO 222
<211> LENGTH: 11
<212> TYPE: PRT
<213> ORGANISM: Artificial Sequence
<220> FEATURE:
<223> OTHER INFORMATION: Synthetic Construct

<400> SEQUENCE: 222

Trp Gly Gln Gly Thr Leu Val Thr Val Ser Ser
1               5                   10

<210> SEQ ID NO 223
<211> LENGTH: 11
<212> TYPE: PRT
<213> ORGANISM: Artificial Sequence
<220> FEATURE:
<223> OTHER INFORMATION: Synthetic Construct

<400> SEQUENCE: 223

Trp Gly Gln Gly Thr Leu Val Thr Val Ser Ser
1               5                   10

<210> SEQ ID NO 224
<211> LENGTH: 11
<212> TYPE: PRT
<213> ORGANISM: Artificial Sequence
<220> FEATURE:
<223> OTHER INFORMATION: Synthetic Construct

<400> SEQUENCE: 224

Trp Gly Gln Gly Thr Leu Val Thr Val Ser Ser
1               5                   10

<210> SEQ ID NO 225
<211> LENGTH: 11
<212> TYPE: PRT
```

```
<213> ORGANISM: Artificial Sequence
<220> FEATURE:
<223> OTHER INFORMATION: Synthetic Construct

<400> SEQUENCE: 225

Trp Gly Gln Gly Thr Leu Val Thr Val Ser Ser
1               5                   10

<210> SEQ ID NO 226
<211> LENGTH: 11
<212> TYPE: PRT
<213> ORGANISM: Artificial Sequence
<220> FEATURE:
<223> OTHER INFORMATION: Synthetic Construct

<400> SEQUENCE: 226

Trp Gly Gln Gly Thr Leu Val Thr Val Ser Ser
1               5                   10

<210> SEQ ID NO 227
<211> LENGTH: 11
<212> TYPE: PRT
<213> ORGANISM: Artificial Sequence
<220> FEATURE:
<223> OTHER INFORMATION: Synthetic Construct

<400> SEQUENCE: 227

Trp Gly Gln Gly Thr Leu Val Thr Val Ser Ser
1               5                   10

<210> SEQ ID NO 228
<211> LENGTH: 11
<212> TYPE: PRT
<213> ORGANISM: Artificial Sequence
<220> FEATURE:
<223> OTHER INFORMATION: Synthetic Construct

<400> SEQUENCE: 228

Trp Gly Gln Gly Thr Leu Val Thr Val Ser Ser
1               5                   10

<210> SEQ ID NO 229
<211> LENGTH: 11
<212> TYPE: PRT
<213> ORGANISM: Artificial Sequence
<220> FEATURE:
<223> OTHER INFORMATION: Synthetic Construct

<400> SEQUENCE: 229

Trp Gly Gln Gly Thr Leu Val Thr Val Ser Ser
1               5                   10

<210> SEQ ID NO 230
<211> LENGTH: 11
<212> TYPE: PRT
<213> ORGANISM: Artificial Sequence
<220> FEATURE:
<223> OTHER INFORMATION: Synthetic Construct

<400> SEQUENCE: 230

Trp Gly Gln Gly Thr Leu Val Thr Val Ser Ser
1               5                   10

<210> SEQ ID NO 231
<211> LENGTH: 11
<212> TYPE: PRT
<213> ORGANISM: Artificial Sequence
```

```
<220> FEATURE:
<223> OTHER INFORMATION: Synthetic Construct

<400> SEQUENCE: 231

Trp Gly Gln Gly Thr Leu Val Thr Val Ser Ser
1               5                   10

<210> SEQ ID NO 232
<211> LENGTH: 11
<212> TYPE: PRT
<213> ORGANISM: Artificial Sequence
<220> FEATURE:
<223> OTHER INFORMATION: Synthetic Construct

<400> SEQUENCE: 232

Trp Gly Gln Gly Thr Leu Val Thr Val Ser Ser
1               5                   10

<210> SEQ ID NO 233
<211> LENGTH: 11
<212> TYPE: PRT
<213> ORGANISM: Artificial Sequence
<220> FEATURE:
<223> OTHER INFORMATION: Synthetic Construct

<400> SEQUENCE: 233

Trp Gly Gln Gly Thr Leu Val Thr Val Ser Ser
1               5                   10

<210> SEQ ID NO 234
<211> LENGTH: 11
<212> TYPE: PRT
<213> ORGANISM: Artificial Sequence
<220> FEATURE:
<223> OTHER INFORMATION: Synthetic Construct

<400> SEQUENCE: 234

Trp Gly Gln Gly Thr Leu Val Thr Val Ser Ser
1               5                   10

<210> SEQ ID NO 235
<211> LENGTH: 11
<212> TYPE: PRT
<213> ORGANISM: Artificial Sequence
<220> FEATURE:
<223> OTHER INFORMATION: Synthetic Construct

<400> SEQUENCE: 235

Trp Gly Gln Gly Thr Leu Val Thr Val Ser Ser
1               5                   10

<210> SEQ ID NO 236
<211> LENGTH: 11
<212> TYPE: PRT
<213> ORGANISM: Artificial Sequence
<220> FEATURE:
<223> OTHER INFORMATION: Synthetic Construct

<400> SEQUENCE: 236

Trp Gly Gln Gly Thr Leu Val Thr Val Ser Ser
1               5                   10

<210> SEQ ID NO 237
<211> LENGTH: 11
<212> TYPE: PRT
<213> ORGANISM: Artificial Sequence
<220> FEATURE:
```

<223> OTHER INFORMATION: Synthetic Construct

<400> SEQUENCE: 237

Trp Gly Gln Gly Thr Leu Val Thr Val Ser Ser
1               5                   10

<210> SEQ ID NO 238
<211> LENGTH: 11
<212> TYPE: PRT
<213> ORGANISM: Artificial Sequence
<220> FEATURE:
<223> OTHER INFORMATION: Synthetic Construct

<400> SEQUENCE: 238

Trp Gly Gln Gly Thr Leu Val Thr Val Ser Ser
1               5                   10

<210> SEQ ID NO 239
<211> LENGTH: 11
<212> TYPE: PRT
<213> ORGANISM: Artificial Sequence
<220> FEATURE:
<223> OTHER INFORMATION: Synthetic Construct

<400> SEQUENCE: 239

Trp Gly Gln Gly Thr Leu Val Thr Val Ser Ser
1               5                   10

<210> SEQ ID NO 240
<211> LENGTH: 11
<212> TYPE: PRT
<213> ORGANISM: Artificial Sequence
<220> FEATURE:
<223> OTHER INFORMATION: Synthetic Construct

<400> SEQUENCE: 240

Trp Gly Gln Gly Thr Leu Val Thr Val Ser Ser
1               5                   10

<210> SEQ ID NO 241
<211> LENGTH: 11
<212> TYPE: PRT
<213> ORGANISM: Artificial Sequence
<220> FEATURE:
<223> OTHER INFORMATION: Synthetic Construct

<400> SEQUENCE: 241

Trp Gly Gln Gly Thr Leu Val Thr Val Ser Ser
1               5                   10

<210> SEQ ID NO 242
<211> LENGTH: 11
<212> TYPE: PRT
<213> ORGANISM: Artificial Sequence
<220> FEATURE:
<223> OTHER INFORMATION: Synthetic Construct

<400> SEQUENCE: 242

Trp Gly Gln Gly Thr Leu Val Thr Val Ser Ser
1               5                   10

<210> SEQ ID NO 243
<211> LENGTH: 11
<212> TYPE: PRT
<213> ORGANISM: Artificial Sequence
<220> FEATURE:
<223> OTHER INFORMATION: Synthetic Construct

<400> SEQUENCE: 243

Trp Gly Gln Gly Thr Leu Val Thr Val Ser Ser
1               5                   10

<210> SEQ ID NO 244
<211> LENGTH: 11
<212> TYPE: PRT
<213> ORGANISM: Artificial Sequence
<220> FEATURE:
<223> OTHER INFORMATION: Synthetic Construct

<400> SEQUENCE: 244

Trp Gly Gln Gly Thr Leu Val Thr Val Ser Ser
1               5                   10

<210> SEQ ID NO 245
<211> LENGTH: 11
<212> TYPE: PRT
<213> ORGANISM: Artificial Sequence
<220> FEATURE:
<223> OTHER INFORMATION: Synthetic Construct

<400> SEQUENCE: 245

Trp Gly Gln Gly Thr Leu Val Thr Val Ser Ser
1               5                   10

<210> SEQ ID NO 246
<211> LENGTH: 375
<212> TYPE: DNA
<213> ORGANISM: Artificial Sequence
<220> FEATURE:
<223> OTHER INFORMATION: Synthetic Construct

<400> SEQUENCE: 246
caggtgcaac tggcggagtc tgggggaggc tcggtgcagg ctggagggtc tctgagactc      60
tcctgtgcag cctctggata caagtacggt gtctactcca tggctggtt ccgcctggct      120 ccagggaagg agcgcgaggg ggtcgcagcc atttgtagtg gcggtagaac cacatactca      180
gactccgtga agggccgatt caccatctcc aaagacagcg ccaaccaaat tctgtatcta      240
cagatgaaca gcctgaaacc tgaagacact gccatgtact actgtgcggc ccgacctcta      300
tggactgggg actgcgattt aagctcatct tggtatataaa cctggggcca ggggacccag      360
gtcaccgtct cctca                                                       375

<210> SEQ ID NO 247
<211> LENGTH: 384
<212> TYPE: DNA
<213> ORGANISM: Artificial Sequence
<220> FEATURE:
<223> OTHER INFORMATION: Synthetic Construct

<400> SEQUENCE: 247
caggtgcagc tggcggagtc tgaggaggc tcggtgcaga ctggagggtc tctgagactc       60
tcctgtgcag cctctggaaa caccggtagt cgccggtatg tggcatggtt ccgccaggcg     120
ccagggaagg agcgcgaggg tgtcgcacga ctcattactg atagtggcag cacatactat    180
gccgactccg tgaagggccg attcatcatc tcccaagaca cgccaagaa cacggtgtat    240 ctgcaaatga acaccctgaa acctgaggac actgccatgt actactgtgc ggaagaatta   300
gcaccagctc gcagcggtgg tatttggttt ggtggacggt acttcagtta ctggggccag   360
gggacccagg tcaccgtctc ctca                                            384

<210> SEQ ID NO 248
<211> LENGTH: 381
<212> TYPE: DNA
<213> ORGANISM: Artificial Sequence
<220> FEATURE:
<223> OTHER INFORMATION: Synthetic Construct

<400> SEQUENCE: 248

```
cagattcagc tggtggagtc tgggggaggc tcggtgcagg ctggagggtc tctgagactc      60
tcctgtgcaa cgtctggata cacgtacaga cagaaatgca tgggctggtt ccgccaggct     120
ccagggaagg agcgcgaggg ggtcgcagcg atttatactt ctgttggtgg tagtaggaca     180
tacgttgccg actccgcgaa gggccgattc accgtctccc aagacaacgc caaaaacacg     240
gtgtatctgc aaatgaacag cctgaaacct gaggacactg ccatgtacta ctgtgcggcc     300
aagagtccgt acgatggtgc atgctcttac gaagctgact ttacttactg gggccagggg     360
acccaggtca ccgtctcctc a                                               381
```

<210> SEQ ID NO 249
<211> LENGTH: 381
<212> TYPE: DNA
<213> ORGANISM: Artificial Sequence
<220> FEATURE:
<223> OTHER INFORMATION: Synthetic Construct

<400> SEQUENCE: 249

```
caggttcagc tggtggagtc tgggggaggc tcggtgcagg ctggagggtc tctgagactc      60
tcctgtgtag cctctggata cacctatagt aggaaatgta ggggctggtt ccgccaggct     120
ccagggaagg agcgcgaggg ggtcgcgact ctttatacta gttcagggggg gacatatttt    180
gacacctatg ccgactccgt gagggccgg ttcaccatct cccaagacaa cgccaagaac      240
acggtgtatc tgcaaatgaa caacctgaaa ccggaggaca gtggcatata ctactgtgcg     300
gcacgcctga gtacggactt tgcggacca agagctgact ttgattactg gggccagggg     360
acccaggtca ccgtctcctc a                                               381
```

<210> SEQ ID NO 250
<211> LENGTH: 375
<212> TYPE: DNA
<213> ORGANISM: Artificial Sequence
<220> FEATURE:
<223> OTHER INFORMATION: Synthetic Construct

<400> SEQUENCE: 250

```
caggtgcagc tggcggagtc tgggggaggc tcggtgcagg ctggagggtc tctgagactc      60
tcctgtgcag cctctggagt cacctccgat agtaccaca tgggctggtt ccgccaggct      120
ccagggaagg agcgcgaggg ggtcgcagtt attaaaactg gtgatgccag cacatactat     180
accgactccg tgaagggccg attcaccatc tcccaagaca cgccaagaa cacgctgtac      240
ctgcaaatga acagcctgaa acctgaggac actgccatgt actactgtgc ggcaagacgg     300
ggttgggtgc cggctcccct ctcgcaatat aattataact attggggcca ggggacccag     360
gtcaccgtct cctca                                                      375
```

<210> SEQ ID NO 251
<211> LENGTH: 375
<212> TYPE: DNA
<213> ORGANISM: Artificial Sequence
<220> FEATURE:

<223> OTHER INFORMATION: Synthetic Construct

<400> SEQUENCE: 251

```
caggtgcaac tggcggagtc tgggggaggc tcggtgcaga ctggagggtc tctgagactt    60
tcctgtgaag cctctggagt ggccgccagt ggctactgca tggcctggtt ccgccaggct   120
ccggggaagg agcgcgaaag ggtcgcagct attagtagta atgatctagt tgcttacgca   180
gactccgtga agggccgatt caccatctcc aaggacaacg ccaagaccac tctgtatcta   240
caaatgaaca acctgaaacc tgaggacact gccatgtact actgtgcggc agatggaggt   300
tatggtggtt actgcggacg gttgcgacct ggcactggtt actggggcca ggggacccag   360
gtcaccgtct cctca                                                    375
```

<210> SEQ ID NO 252
<211> LENGTH: 393
<212> TYPE: DNA
<213> ORGANISM: Artificial Sequence
<220> FEATURE:
<223> OTHER INFORMATION: Synthetic Construct

<400> SEQUENCE: 252

```
gaggtgcagc tggcggagtc tgggggaggc tcggtgcagg ctggagggtc tctgagactc    60
tcctgtacaa cctctggata cacctacagt cgcaactgca tgggctggtt ccgccaggct   120
ccagggaagg agcgcgaggg ggtcgcaact atttatgtaa gtgctgcaag cacaagcttt   180
gccacatatg ccgactccgt aaagggccga ttcaccatct ccctagacaa ggccaagaac   240
acggtatatc tgcaaatgaa cagcctgaaa cctgaggaca ctgccatgta ctactgtgcg   300
gcagatcccc ccgatcgtat ctcgaacccc tgcggacccc gccgcctga ctttggatac    360
tggggccagg gaacccaggt caccgtctcc tca                                 393
```

<210> SEQ ID NO 253
<211> LENGTH: 125
<212> TYPE: PRT
<213> ORGANISM: Artificial Sequence
<220> FEATURE:
<223> OTHER INFORMATION: Synthetic Construct

<400> SEQUENCE: 253

```
Gln Val Gln Leu Ala Glu Ser Gly Gly Gly Ser Val Gln Ala Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Leu Ala Pro Gly Lys Glu Arg Glu Gly Val
        35                  40                  45

Ala Ala Ile Cys Ser Gly Gly Arg Thr Thr Tyr Ser Asp Ser Val Lys
    50                  55                  60

Gly Arg Phe Thr Ile Ser Lys Asp Ser Ala Asn Gln Ile Leu Tyr Leu
65                  70                  75                  80

Gln Met Asn Ser Leu Lys Pro Glu Asp Thr Ala Met Tyr Tyr Cys Ala
                85                  90                  95

Ala Arg Pro Leu Trp Thr Gly Asp Cys Asp Leu Ser Ser Ser Trp Tyr
            100                 105                 110

Lys Thr Trp Gly Gln Gly Thr Gln Val Thr Val Ser Ser
        115                 120                 125
```

<210> SEQ ID NO 254
<211> LENGTH: 128

```
<212> TYPE: PRT
<213> ORGANISM: Artificial Sequence
<220> FEATURE:
<223> OTHER INFORMATION: Synthetic Construct

<400> SEQUENCE: 254

Gln Val Gln Leu Ala Glu Ser Gly Gly Gly Ser Val Gln Thr Gly Gly
1               5                   10                  15

Ser Leu Arg Leu Ser Cys Ala Ala Ser Gly Asn Thr Gly Ser Arg Arg
            20                  25                  30

Tyr Val Ala Trp Phe Arg Gln Ala Pro Gly Lys Glu Arg Glu Gly Val
        35                  40                  45

Ala Arg Leu Ile Thr Asp Ser Gly Ser Thr Tyr Tyr Ala Asp Ser Val
    50                  55                  60

Lys Gly Arg Phe Ile Ile Ser Gln Asp Asn Ala Lys Asn Thr Val Tyr
65                  70                  75                  80

Leu Gln Met Asn Thr Leu Lys Pro Glu Asp Thr Ala Met Tyr Tyr Cys
                85                  90                  95

Ala Glu Glu Leu Ala Pro Ala Arg Ser Gly Gly Ile Trp Phe Gly Gly
            100                 105                 110

Arg Tyr Phe Ser Tyr Trp Gly Gln Gly Thr Gln Val Thr Val Ser Ser
        115                 120                 125

<210> SEQ ID NO 255
<211> LENGTH: 127
<212> TYPE: PRT
<213> ORGANISM: Artificial Sequence
<220> FEATURE:
<223> OTHER INFORMATION: Synthetic Construct

<400> SEQUENCE: 255

Gln Ile Gln Leu Val Glu Ser Gly Gly Gly Ser Val Gln Ala Gly Gly
1               5                   10                  15

Ser Leu Arg Leu Ser Cys Ala Thr Ser Gly Tyr Thr Tyr Arg Gln Lys
            20                  25                  30

Cys Met Gly Trp Phe Arg Gln Ala Pro Gly Lys Glu Arg Glu Gly Val
        35                  40                  45

Ala Ala Ile Tyr Thr Ser Val Gly Gly Ser Arg Thr Tyr Val Ala Asp
    50                  55                  60

Ser Ala Lys Gly Arg Phe Thr Val Ser Gln Asp Asn Ala Lys Asn Thr
65                  70                  75                  80

Val Tyr Leu Gln Met Asn Ser Leu Lys Pro Glu Asp Thr Ala Met Tyr
                85                  90                  95

Tyr Cys Ala Ala Lys Ser Pro Tyr Asp Gly Ala Cys Ser Tyr Glu Ala
            100                 105                 110

Asp Phe Thr Tyr Trp Gly Gln Gly Thr Gln Val Thr Val Ser Ser
        115                 120                 125

<210> SEQ ID NO 256
<211> LENGTH: 127
<212> TYPE: PRT
<213> ORGANISM: Artificial Sequence
<220> FEATURE:
<223> OTHER INFORMATION: Synthetic Construct

<400> SEQUENCE: 256

Gln Val Gln Leu Val Glu Ser Gly Gly Gly Ser Val Gln Ala Gly Gly
1               5                   10                  15

Ser Leu Arg Leu Ser Cys Val Ala Ser Gly Tyr Thr Tyr Ser Arg Lys
```

```
                    20                  25                  30
Cys Arg Gly Trp Phe Arg Gln Ala Pro Gly Lys Glu Arg Glu Gly Val
                35                  40                  45

Ala Thr Leu Tyr Thr Ser Ser Gly Thr Tyr Phe Asp Thr Tyr Ala
        50                  55                  60

Asp Ser Val Arg Gly Arg Phe Thr Ile Ser Gln Asp Asn Ala Lys Asn
65                  70                  75                  80

Thr Val Tyr Leu Gln Met Asn Asn Leu Lys Pro Glu Asp Ser Gly Ile
                85                  90                  95

Tyr Tyr Cys Ala Ala Arg Leu Ser Thr Asp Phe Cys Gly Pro Arg Ala
            100                 105                 110

Asp Phe Asp Tyr Trp Gly Gln Gly Thr Gln Val Thr Val Ser Ser
            115                 120                 125

<210> SEQ ID NO 257
<211> LENGTH: 125
<212> TYPE: PRT
<213> ORGANISM: Artificial Sequence
<220> FEATURE:
<223> OTHER INFORMATION: Synthetic Construct

<400> SEQUENCE: 257

Gln Val Gln Leu Ala Glu Ser Gly Gly Gly Ser Val Gln Ala Gly Gly
1               5                   10                  15

Ser Leu Arg Leu Ser Cys Ala Ala Ser Gly Val Thr Ser Asp Ser Tyr
                20                  25                  30

His Met Gly Trp Phe Arg Gln Ala Pro Gly Lys Glu Arg Glu Gly Val
                35                  40                  45

Ala Val Ile Lys Thr Gly Asp Ala Ser Thr Tyr Tyr Thr Asp Ser Val
        50                  55                  60

Lys Gly Arg Phe Thr Ile Ser Gln Asp Asn Ala Lys Asn Thr Leu Tyr
65                  70                  75                  80

Leu Gln Met Asn Ser Leu Lys Pro Glu Asp Thr Ala Met Tyr Tyr Cys
                85                  90                  95

Ala Ala Arg Arg Gly Trp Val Pro Ala Pro Leu Ser Gly Tyr Asn Tyr
            100                 105                 110

Asn Tyr Trp Gly Gln Gly Thr Gln Val Thr Val Ser Ser
            115                 120                 125

<210> SEQ ID NO 258
<211> LENGTH: 125
<212> TYPE: PRT
<213> ORGANISM: Artificial Sequence
<220> FEATURE:
<223> OTHER INFORMATION: Synthetic Construct

<400> SEQUENCE: 258

Gln Val Gln Leu Ala Glu Ser Gly Gly Gly Ser Val Gln Thr Gly Gly
1               5                   10                  15

Ser Leu Arg Leu Ser Cys Glu Ala Ser Gly Val Ala Ala Ser Gly Tyr
                20                  25                  30

Cys Met Ala Trp Phe Arg Gln Ala Pro Gly Lys Glu Arg Glu Arg Val
                35                  40                  45

Ala Ala Ile Ser Ser Asn Asp Leu Val Ala Tyr Ala Asp Ser Val Lys
        50                  55                  60

Gly Arg Phe Thr Ile Ser Lys Asp Asn Ala Lys Thr Thr Leu Tyr Leu
65                  70                  75                  80
```

```
Gln Met Asn Asn Leu Lys Pro Glu Asp Thr Ala Met Tyr Tyr Cys Ala
                85                  90                  95

Ala Asp Gly Gly Tyr Gly Gly Tyr Cys Gly Arg Leu Arg Pro Gly Thr
            100                 105                 110

Gly Tyr Trp Gly Gln Gly Thr Gln Val Thr Val Ser Ser
        115                 120                 125

<210> SEQ ID NO 259
<211> LENGTH: 131
<212> TYPE: PRT
<213> ORGANISM: Artificial Sequence
<220> FEATURE:
<223> OTHER INFORMATION: Synthetic Construct

<400> SEQUENCE: 259

Glu Val Gln Leu Ala Glu Ser Gly Gly Gly Ser Val Gln Ala Gly Gly
1               5                   10                  15

Ser Leu Arg Leu Ser Cys Thr Thr Ser Gly Tyr Thr Tyr Ser Arg Asn
            20                  25                  30

Cys Met Gly Trp Phe Arg Gln Ala Pro Gly Lys Glu Arg Glu Gly Val
        35                  40                  45

Ala Thr Ile Tyr Val Ser Ala Ala Ser Thr Ser Phe Ala Thr Tyr Ala
    50                  55                  60

Asp Ser Val Lys Gly Arg Phe Thr Ile Ser Leu Asp Lys Ala Lys Asn
65                  70                  75                  80

Thr Val Tyr Leu Gln Met Asn Ser Leu Lys Pro Glu Asp Thr Ala Met
                85                  90                  95

Tyr Tyr Cys Ala Ala Asp Pro Pro Asp Arg Ile Ser Asn Pro Cys Gly
            100                 105                 110

Pro Arg Arg Pro Asp Phe Gly Tyr Trp Gly Gln Gly Thr Gln Val Thr
        115                 120                 125

Val Ser Ser
    130

<210> SEQ ID NO 260
<211> LENGTH: 125
<212> TYPE: PRT
<213> ORGANISM: Artificial Sequence
<220> FEATURE:
<223> OTHER INFORMATION: Synthetic Construct

<400> SEQUENCE: 260

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Gln Ala Pro Gly Lys Gly Leu Glu Gly Val
        35                  40                  45

Ser Ala Ile Cys Ser Gly Gly Arg Thr Thr Tyr Ser Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ala Arg Pro Leu Trp Thr Gly Asp Cys Asp Leu Ser Ser Ser Trp Tyr
            100                 105                 110

Lys Thr Trp Gly Gln Gly Thr Leu Val Thr Val Ser Ser
        115                 120                 125
```

<210> SEQ ID NO 261
<211> LENGTH: 125
<212> TYPE: PRT
<213> ORGANISM: Artificial Sequence
<220> FEATURE:
<223> OTHER INFORMATION: Synthetic Construct

<400> SEQUENCE: 261

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Gln Ala Pro Gly Lys Gly Leu Glu Gly Val
        35                  40                  45

Ser Ala Ile Cys Ser Gly Gly Arg Thr Thr Tyr Ser Asp Ser Val Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ala Arg Pro Leu Trp Thr Gly Asp Cys Asp Leu Ser Ser Ser Trp Tyr
            100                 105                 110

Lys Thr Trp Gly Gln Gly Thr Leu Val Thr Val Ser Ser
        115                 120                 125

<210> SEQ ID NO 262
<211> LENGTH: 125
<212> TYPE: PRT
<213> ORGANISM: Artificial Sequence
<220> FEATURE:
<223> OTHER INFORMATION: Synthetic Construct

<400> SEQUENCE: 262

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Gln Ala Pro Gly Lys Gly Leu Glu Gly Val
        35                  40                  45

Ala Ala Ile Cys Ser Gly Gly Arg Thr Thr Tyr Ser Asp Ser Val Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ala Arg Pro Leu Trp Thr Gly Asp Cys Asp Leu Ser Ser Ser Trp Tyr
            100                 105                 110

Lys Thr Trp Gly Gln Gly Thr Leu Val Thr Val Ser Ser
        115                 120                 125

<210> SEQ ID NO 263
<211> LENGTH: 125
<212> TYPE: PRT
<213> ORGANISM: Artificial Sequence
<220> FEATURE:
<223> OTHER INFORMATION: Synthetic Construct

<400> SEQUENCE: 263

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Leu Ala Pro Gly Lys Gly Leu Glu Gly Val
        35                  40                  45

Ser Ala Ile Cys Ser Gly Gly Arg Thr Thr Tyr Ser Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ala Arg Pro Leu Trp Thr Gly Asp Cys Asp Leu Ser Ser Ser Trp Tyr
            100                 105                 110

Lys Thr Trp Gly Gln Gly Thr Leu Val Thr Val Ser Ser
            115                 120                 125
```

<210> SEQ ID NO 264
<211> LENGTH: 125
<212> TYPE: PRT
<213> ORGANISM: Artificial Sequence
<220> FEATURE:
<223> OTHER INFORMATION: Synthetic Construct

<400> SEQUENCE: 264

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Gln Ala Pro Gly Lys Gly Leu Glu Gly Val
        35                  40                  45

Ser Ala Ile Cys Ser Gly Gly Arg Thr Thr Tyr Ser Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Met Tyr Tyr Cys Ala
                85                  90                  95

Ala Arg Pro Leu Trp Thr Gly Asp Cys Asp Leu Ser Ser Ser Trp Tyr
            100                 105                 110

Lys Thr Trp Gly Gln Gly Thr Leu Val Thr Val Ser Ser
            115                 120                 125
```

<210> SEQ ID NO 265
<211> LENGTH: 125
<212> TYPE: PRT
<213> ORGANISM: Artificial Sequence
<220> FEATURE:
<223> OTHER INFORMATION: Synthetic Construct

<400> SEQUENCE: 265

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Gln Ala Pro Gly Lys Glu Leu Glu Gly Val
        35                  40                  45

Ser Ala Ile Cys Ser Gly Gly Arg Thr Thr Tyr Ser Asp Ser Val Lys
    50                  55                  60
```

```
Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Ala Arg Pro Leu Trp Thr Gly Asp Cys Asp Leu Ser Ser Trp Tyr
            100                 105                 110

Lys Thr Trp Gly Gln Gly Thr Leu Val Thr Val Ser Ser
        115                 120                 125
```

<210> SEQ ID NO 266
<211> LENGTH: 125
<212> TYPE: PRT
<213> ORGANISM: Artificial Sequence
<220> FEATURE:
<223> OTHER INFORMATION: Synthetic Construct

<400> SEQUENCE: 266

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Tyr Lys Tyr Gly Val Tyr
                 20                  25                  30

Ser Met Gly Trp Phe Arg Gln Ala Pro Gly Lys Gly Arg Glu Gly Val
             35                  40                  45

Ser Ala Ile Cys Ser Gly Gly Arg Thr Thr Tyr Ser Asp Ser Val Lys
         50                  55                  60

Gly Arg Phe Thr Ile Ser Arg Asp Asn Ala Lys Asn Thr Leu Tyr Leu
 65                  70                  75                  80

Gln Met Asn Ser Leu Arg Pro Glu Asp Thr Ala Val Tyr Tyr Cys Ala
                 85                  90                  95

Ala Arg Pro Leu Trp Thr Gly Asp Cys Asp Leu Ser Ser Trp Tyr
            100                 105                 110

Lys Thr Trp Gly Gln Gly Thr Leu Val Thr Val Ser Ser
        115                 120                 125
```

<210> SEQ ID NO 267
<211> LENGTH: 125
<212> TYPE: PRT
<213> ORGANISM: Artificial Sequence
<220> FEATURE:
<223> OTHER INFORMATION: Synthetic Construct

<400> SEQUENCE: 267

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Tyr Lys Tyr Gly Val Tyr
                 20                  25                  30

Ser Met Gly Trp Phe Arg Gln Ala Pro Gly Lys Glu Arg Glu Gly Val
             35                  40                  45

Ser Ala Ile Cys Ser Gly Gly Arg Thr Thr Tyr Ser Asp Ser Val Lys
         50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Ala Arg Pro Leu Trp Thr Gly Asp Cys Asp Leu Ser Ser Trp Tyr
            100                 105                 110

Lys Thr Trp Gly Gln Gly Thr Leu Val Thr Val Ser Ser
```

-continued

```
                115                 120                 125

<210> SEQ ID NO 268
<211> LENGTH: 125
<212> TYPE: PRT
<213> ORGANISM: Artificial Sequence
<220> FEATURE:
<223> OTHER INFORMATION: Synthetic Construct

<400> SEQUENCE: 268

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Gln Ala Pro Gly Lys Gly Leu Glu Gly Val
        35                  40                  45

Ser Ala Ile Cys Ser Gly Gly Arg Thr Thr Tyr Ser Asp Ser Val Lys
    50                  55                  60

Gly Arg Phe Thr Ile Ser Arg Asp Ser Ala Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ala Arg Pro Leu Trp Thr Gly Asp Cys Asp Leu Ser Ser Ser Trp Tyr
            100                 105                 110

Lys Thr Trp Gly Gln Gly Thr Leu Val Thr Val Ser Ser
        115                 120                 125

<210> SEQ ID NO 269
<211> LENGTH: 125
<212> TYPE: PRT
<213> ORGANISM: Artificial Sequence
<220> FEATURE:
<223> OTHER INFORMATION: Synthetic Construct

<400> SEQUENCE: 269

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Gln Ala Pro Gly Lys Gly Leu Glu Gly Val
        35                  40                  45

Ser Ala Ile Cys Ser Gly Gly Arg Thr Thr Tyr Ser Asp Ser Val Lys
    50                  55                  60

Gly Arg Phe Thr Ile Ser Arg Asp Asn Ser Asn Gln Thr Leu Tyr Leu
65                  70                  75                  80

Gln Met Asn Ser Leu Arg Ala Glu Asp Thr Ala Val Tyr Tyr Cys Ala
                85                  90                  95

Ala Arg Pro Leu Trp Thr Gly Asp Cys Asp Leu Ser Ser Ser Trp Tyr
            100                 105                 110

Lys Thr Trp Gly Gln Gly Thr Leu Val Thr Val Ser Ser
        115                 120                 125

<210> SEQ ID NO 270
<211> LENGTH: 125
<212> TYPE: PRT
<213> ORGANISM: Artificial Sequence
<220> FEATURE:
<223> OTHER INFORMATION: Synthetic Construct

<400> SEQUENCE: 270
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Gln Ala Pro Gly Lys Gly Leu Glu Gly Val
        35                  40                  45

Ser Ala Ile Cys Ser Gly Gly Arg Thr Thr Tyr Ser Asp Ser Val Lys
50                  55                  60

Gly Arg Phe Thr Ile Ser Arg Asp Asn Ser Lys Asn Ile Leu Tyr Leu
65                  70                  75                  80

Gln Met Asn Ser Leu Arg Ala Glu Asp Thr Ala Val Tyr Tyr Cys Ala
                85                  90                  95

Ala Arg Pro Leu Trp Thr Gly Asp Cys Asp Leu Ser Ser Trp Tyr
                100                 105                 110

Lys Thr Trp Gly Gln Gly Thr Leu Val Thr Val Ser Ser
            115                 120                 125

<210> SEQ ID NO 271
<211> LENGTH: 125
<212> TYPE: PRT
<213> ORGANISM: Artificial Sequence
<220> FEATURE:
<223> OTHER INFORMATION: Synthetic Construct

<400> SEQUENCE: 271

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Gln Ala Pro Gly Lys Gly Leu Glu Gly Val
        35                  40                  45

Ser Ala Ile Cys Ser Gly Gly Arg Thr Thr Tyr Ser Asp Ser Val Lys
50                  55                  60

Gly Arg Phe Thr Ile Ser Arg Asp Asn Ser Lys Gln Thr Leu Tyr Leu
65                  70                  75                  80

Gln Met Asn Ser Leu Arg Ala Glu Asp Thr Ala Val Tyr Tyr Cys Ala
                85                  90                  95

Ala Arg Pro Leu Trp Thr Gly Asp Cys Asp Leu Ser Ser Trp Tyr
                100                 105                 110

Lys Thr Trp Gly Gln Gly Thr Leu Val Thr Val Ser Ser
            115                 120                 125

<210> SEQ ID NO 272
<211> LENGTH: 125
<212> TYPE: PRT
<213> ORGANISM: Artificial Sequence
<220> FEATURE:
<223> OTHER INFORMATION: Synthetic Construct

<400> SEQUENCE: 272

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Gln Ala Pro Gly Lys Gly Leu Glu Gly Val
        35                  40                  45

Ser Ala Ile Cys Ser Gly Gly Arg Thr Thr Tyr Ser Asp Ser Val Lys

```
                    50                  55                  60
Gly Arg Phe Thr Ile Ser Arg Asp Asn Ser Asn Asn Ile Leu Tyr Leu
 65                  70                  75                  80

Gln Met Asn Ser Leu Arg Ala Glu Asp Thr Ala Val Tyr Tyr Cys Ala
                 85                  90                  95

Ala Arg Pro Leu Trp Thr Gly Asp Cys Asp Leu Ser Ser Ser Trp Tyr
            100                 105                 110

Lys Thr Trp Gly Gln Gly Thr Leu Val Thr Val Ser Ser
            115                 120                 125

<210> SEQ ID NO 273
<211> LENGTH: 125
<212> TYPE: PRT
<213> ORGANISM: Artificial Sequence
<220> FEATURE:
<223> OTHER INFORMATION: Synthetic Construct

<400> SEQUENCE: 273

Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Lys Tyr Gly Val Tyr
             20                  25                  30

Ser Met Gly Trp Phe Arg Gln Ala Pro Gly Lys Gly Leu Glu Gly Val
         35                  40                  45

Ser Ala Ile Cys Ser Gly Gly Arg Thr Thr Tyr Ser Asp Ser Val Lys
     50                  55                  60

Gly Arg Phe Thr Ile Ser Arg Asp Asn Ser Asn Gln Ile Leu Tyr Leu
 65                  70                  75                  80

Gln Met Asn Ser Leu Arg Ala Glu Asp Thr Ala Val Tyr Tyr Cys Ala
                 85                  90                  95

Ala Arg Pro Leu Trp Thr Gly Asp Cys Asp Leu Ser Ser Ser Trp Tyr
            100                 105                 110

Lys Thr Trp Gly Gln Gly Thr Leu Val Thr Val Ser Ser
            115                 120                 125

<210> SEQ ID NO 274
<211> LENGTH: 125
<212> TYPE: PRT
<213> ORGANISM: Artificial Sequence
<220> FEATURE:
<223> OTHER INFORMATION: Synthetic Construct

<400> SEQUENCE: 274

Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Lys Tyr Gly Val Tyr
             20                  25                  30

Ser Met Gly Trp Phe Arg Gln Ala Pro Gly Lys Glu Arg Glu Gly Val
         35                  40                  45

Ser Ala Ile Cys Ser Gly Gly Arg Thr Thr Tyr Ser Asp Ser Val Lys
     50                  55                  60

Gly Arg Phe Thr Ile Ser Arg Asp Asn Ser Lys Gln Thr Leu Tyr Leu
 65                  70                  75                  80

Gln Met Asn Ser Leu Arg Ala Glu Asp Thr Ala Val Tyr Tyr Cys Ala
                 85                  90                  95

Ala Arg Pro Leu Trp Thr Gly Asp Cys Asp Leu Ser Ser Ser Trp Tyr
            100                 105                 110
```

```
Lys Thr Trp Gly Gln Gly Thr Leu Val Thr Val Ser Ser
        115                 120                 125
```

<210> SEQ ID NO 275
<211> LENGTH: 125
<212> TYPE: PRT
<213> ORGANISM: Artificial Sequence
<220> FEATURE:
<223> OTHER INFORMATION: Synthetic Construct

<400> SEQUENCE: 275

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Gln Ala Pro Gly Lys Glu Arg Glu Gly Val
        35                  40                  45

Ser Ala Ile Cys Ser Gly Gly Arg Thr Thr Tyr Ser Asp Ser Val Lys
    50                  55                  60

Gly Arg Phe Thr Ile Ser Arg Asp Asn Ser Asn Asn Ile Leu Tyr Leu
65                  70                  75                  80

Gln Met Asn Ser Leu Arg Ala Glu Asp Thr Ala Val Tyr Tyr Cys Ala
                85                  90                  95

Ala Arg Pro Leu Trp Thr Gly Asp Cys Asp Leu Ser Ser Ser Trp Tyr
            100                 105                 110

Lys Thr Trp Gly Gln Gly Thr Leu Val Thr Val Ser Ser
        115                 120                 125
```

<210> SEQ ID NO 276
<211> LENGTH: 125
<212> TYPE: PRT
<213> ORGANISM: Artificial Sequence
<220> FEATURE:
<223> OTHER INFORMATION: Synthetic Construct

<400> SEQUENCE: 276

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Gln Ala Pro Gly Lys Glu Arg Glu Gly Val
        35                  40                  45

Ser Ala Ile Cys Ser Gly Gly Arg Thr Thr Tyr Ser Asp Ser Val Lys
    50                  55                  60

Gly Arg Phe Thr Ile Ser Arg Asp Asn Ser Asn Gln Ile Leu Tyr Leu
65                  70                  75                  80

Gln Met Asn Ser Leu Arg Ala Glu Asp Thr Ala Val Tyr Tyr Cys Ala
                85                  90                  95

Ala Arg Pro Leu Trp Thr Gly Asp Cys Asp Leu Ser Ser Ser Trp Tyr
            100                 105                 110

Lys Thr Trp Gly Gln Gly Thr Leu Val Thr Val Ser Ser
        115                 120                 125
```

<210> SEQ ID NO 277
<211> LENGTH: 125
<212> TYPE: PRT
<213> ORGANISM: Artificial Sequence
<220> FEATURE:
<223> OTHER INFORMATION: Synthetic Construct

<400> SEQUENCE: 277

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Gln Ala Pro Gly Lys Glu Arg Glu Gly Val
        35                  40                  45

Ser Ala Ile Cys Ser Gly Gly Arg Thr Thr Tyr Ser Asp Ser Val Lys
    50                  55                  60

Gly Arg Phe Thr Ile Ser Arg Asp Asn Ser Lys Asn Ile Leu Tyr Leu
65                  70                  75                  80

Gln Met Asn Ser Leu Arg Ala Glu Asp Thr Ala Val Tyr Tyr Cys Ala
                85                  90                  95

Ala Arg Pro Leu Trp Thr Gly Asp Cys Asp Leu Ser Ser Ser Trp Tyr
            100                 105                 110

Lys Thr Trp Gly Gln Gly Thr Leu Val Thr Val Ser Ser
            115                 120                 125

<210> SEQ ID NO 278
<211> LENGTH: 127
<212> TYPE: PRT
<213> ORGANISM: Artificial Sequence
<220> FEATURE:
<223> OTHER INFORMATION: Synthetic Construct

<400> SEQUENCE: 278

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Tyr Ser Arg Lys
            20                  25                  30

Cys Arg Gly Trp Phe Arg Gln Ala Pro Gly Lys Gly Leu Glu Trp Val
        35                  40                  45

Ser Thr Leu Tyr Thr Ser Ser Gly Thr Tyr Phe Asp Thr Tyr Ala
    50                  55                  60

Asp Ser Val Arg Gly Arg Phe Thr Ile Ser Arg Asp Asn Ser Lys Asn
65                  70                  75                  80

Thr Leu Tyr Leu Gln Met Asn Ser Leu Arg Ala Glu Asp Thr Ala Val
                85                  90                  95

Tyr Tyr Cys Ala Ala Arg Leu Ser Thr Asp Phe Cys Gly Pro Arg Ala
            100                 105                 110

Asp Phe Asp Tyr Trp Gly Gln Gly Thr Leu Val Thr Val Ser Ser
            115                 120                 125

<210> SEQ ID NO 279
<211> LENGTH: 127
<212> TYPE: PRT
<213> ORGANISM: Artificial Sequence
<220> FEATURE:
<223> OTHER INFORMATION: Synthetic Construct

<400> SEQUENCE: 279

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Tyr Ser Arg Lys
            20                  25                  30

Cys Arg Gly Trp Phe Arg Gln Ala Pro Gly Lys Gly Leu Glu Gly Val
        35                  40                  45

```
Ser Thr Leu Tyr Thr Ser Ser Gly Gly Thr Tyr Phe Asp Thr Tyr Ala
    50                  55                  60

Asp Ser Val Arg Gly Arg Phe Thr Ile Ser Arg Asp Asn Ser Lys Asn
 65                  70                  75                  80

Thr Leu Tyr Leu Gln Met Asn Ser Leu Arg Ala Glu Asp Thr Ala Val
                85                  90                  95

Tyr Tyr Cys Ala Ala Arg Leu Ser Thr Asp Phe Cys Gly Pro Arg Ala
            100                 105                 110

Asp Phe Asp Tyr Trp Gly Gln Gly Thr Leu Val Thr Val Ser Ser
            115                 120                 125
```

<210> SEQ ID NO 280
<211> LENGTH: 127
<212> TYPE: PRT
<213> ORGANISM: Artificial Sequence
<220> FEATURE:
<223> OTHER INFORMATION: Synthetic Construct

<400> SEQUENCE: 280

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Tyr Thr Tyr Ser Arg Lys
                20                  25                  30

Cys Arg Gly Trp Phe Arg Gln Ala Pro Gly Lys Gly Leu Glu Gly Val
            35                  40                  45

Ala Thr Leu Tyr Thr Ser Ser Gly Gly Thr Tyr Phe Asp Thr Tyr Ala
    50                  55                  60

Asp Ser Val Arg Gly Arg Phe Thr Ile Ser Arg Asp Asn Ser Lys Asn
 65                  70                  75                  80

Thr Val Tyr Leu Gln Met Asn Ser Leu Arg Ala Glu Asp Thr Gly Val
                85                  90                  95

Tyr Tyr Cys Ala Ala Arg Leu Ser Thr Asp Phe Cys Gly Pro Arg Ala
            100                 105                 110

Asp Phe Asp Tyr Trp Gly Gln Gly Thr Leu Val Thr Val Ser Ser
            115                 120                 125
```

<210> SEQ ID NO 281
<211> LENGTH: 127
<212> TYPE: PRT
<213> ORGANISM: Artificial Sequence
<220> FEATURE:
<223> OTHER INFORMATION: Synthetic Construct

<400> SEQUENCE: 281

```
Glu Val Gln Leu Val Glu Ser Gly Gly Gly Leu Val Gln Pro Gly Gly
  1               5                  10                  15

Ser Leu Arg Leu Ser Cys Val Ala Ser Gly Tyr Thr Tyr Ser Arg Lys
                20                  25                  30

Cys Arg Gly Trp Phe Arg Gln Ala Pro Gly Lys Gly Leu Glu Gly Val
            35                  40                  45

Ser Thr Leu Tyr Thr Ser Ser Gly Gly Thr Tyr Phe Asp Thr Tyr Ala
    50                  55                  60

Asp Ser Val Arg Gly Arg Phe Thr Ile Ser Arg Asp Asn Ser Lys Asn
 65                  70                  75                  80

Thr Leu Tyr Leu Gln Met Asn Ser Leu Arg Ala Glu Asp Thr Ala Val
                85                  90                  95

Tyr Tyr Cys Ala Ala Arg Leu Ser Thr Asp Phe Cys Gly Pro Arg Ala
            100                 105                 110
```

Asp Phe Asp Tyr Trp Gly Gln Gly Thr Leu Val Thr Val Ser Ser
            115                 120                 125

<210> SEQ ID NO 282
<211> LENGTH: 127
<212> TYPE: PRT
<213> ORGANISM: Artificial Sequence
<220> FEATURE:
<223> OTHER INFORMATION: Synthetic Construct

<400> SEQUENCE: 282

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Tyr Ser Arg Lys
            20                  25                  30

Cys Arg Gly Trp Phe Arg Gln Ala Pro Gly Lys Gly Leu Glu Gly Val
        35                  40                  45

Ala Thr Leu Tyr Thr Ser Ser Gly Gly Thr Tyr Phe Asp Thr Tyr Ala
    50                  55                  60

Asp Ser Val Arg Gly Arg Phe Thr Ile Ser Gln Asp Asn Ser Lys Asn
65                  70                  75                  80

Thr Leu Tyr Leu Gln Met Asn Ser Leu Arg Ala Glu Asp Thr Ala Val
                85                  90                  95

Tyr Tyr Cys Ala Ala Arg Leu Ser Thr Asp Phe Cys Gly Pro Arg Ala
            100                 105                 110

Asp Phe Asp Tyr Trp Gly Gln Gly Thr Leu Val Thr Val Ser Ser
            115                 120                 125

<210> SEQ ID NO 283
<211> LENGTH: 127
<212> TYPE: PRT
<213> ORGANISM: Artificial Sequence
<220> FEATURE:
<223> OTHER INFORMATION: Synthetic Construct

<400> SEQUENCE: 283

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Tyr Ser Arg Lys
            20                  25                  30

Cys Arg Gly Trp Phe Arg Gln Ala Pro Gly Lys Gly Leu Glu Gly Val
        35                  40                  45

Ala Thr Leu Tyr Thr Ser Ser Gly Gly Thr Tyr Phe Asp Thr Tyr Ala
    50                  55                  60

Asp Ser Val Arg Gly Arg Phe Thr Ile Ser Arg Asp Asn Ser Lys Asn
65                  70                  75                  80

Thr Leu Tyr Leu Gln Met Asn Ser Leu Arg Ala Glu Asp Thr Ala Val
                85                  90                  95

Tyr Tyr Cys Ala Ala Arg Leu Ser Thr Asp Phe Cys Gly Pro Arg Ala
            100                 105                 110

Asp Phe Asp Tyr Trp Gly Gln Gly Thr Leu Val Thr Val Ser Ser
            115                 120                 125

<210> SEQ ID NO 284
<211> LENGTH: 127
<212> TYPE: PRT
<213> ORGANISM: Artificial Sequence
<220> FEATURE:
<223> OTHER INFORMATION: Synthetic Construct

<400> SEQUENCE: 284

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Tyr Ser Arg Lys
            20                  25                  30

Cys Arg Gly Trp Phe Arg Gln Ala Pro Gly Lys Gly Leu Glu Gly Val
        35                  40                  45

Ala Thr Leu Tyr Thr Ser Ser Gly Thr Tyr Phe Asp Thr Tyr Ala
50                  55                  60

Asp Ser Val Arg Gly Arg Phe Thr Ile Ser Arg Asp Asn Ser Lys Asn
65                  70                  75                  80

Thr Val Tyr Leu Gln Met Asn Ser Leu Arg Ala Glu Asp Thr Ala Val
                85                  90                  95

Tyr Tyr Cys Ala Ala Arg Leu Ser Thr Asp Phe Cys Gly Pro Arg Ala
            100                 105                 110

Asp Phe Asp Tyr Trp Gly Gln Gly Thr Leu Val Thr Val Ser Ser
            115                 120                 125
```

<210> SEQ ID NO 285
<211> LENGTH: 127
<212> TYPE: PRT
<213> ORGANISM: Artificial Sequence
<220> FEATURE:
<223> OTHER INFORMATION: Synthetic Construct

<400> SEQUENCE: 285

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Tyr Ser Arg Lys
            20                  25                  30

Cys Arg Gly Trp Phe Arg Gln Ala Pro Gly Lys Gly Arg Glu Gly Val
        35                  40                  45

Ser Thr Leu Tyr Thr Ser Ser Gly Gly Thr Tyr Phe Asp Thr Tyr Ala
50                  55                  60

Asp Ser Val Arg Gly Arg Phe Thr Ile Ser Arg Asp Asn Ala Lys Asn
65                  70                  75                  80

Thr Leu Tyr Leu Gln Met Asn Ser Leu Arg Ala Glu Asp Thr Ala Val
                85                  90                  95

Tyr Tyr Cys Ala Ala Arg Leu Ser Thr Asp Phe Cys Gly Pro Arg Ala
            100                 105                 110

Asp Phe Asp Tyr Trp Gly Gln Gly Thr Leu Val Thr Val Ser Ser
            115                 120                 125
```

<210> SEQ ID NO 286
<211> LENGTH: 127
<212> TYPE: PRT
<213> ORGANISM: Artificial Sequence
<220> FEATURE:
<223> OTHER INFORMATION: Synthetic Construct

<400> SEQUENCE: 286

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Tyr Ser Arg Lys
            20                  25                  30

Cys Arg Gly Trp Phe Arg Gln Ala Pro Gly Lys Gly Arg Glu Gly Val
        35                  40                  45
```

```
Ala Thr Leu Tyr Thr Ser Ser Gly Gly Thr Tyr Phe Asp Thr Tyr Ala
         50                  55                  60

Asp Ser Val Arg Gly Arg Phe Thr Ile Ser Arg Asp Asn Ala Lys Asn
 65                  70                  75                  80

Thr Leu Tyr Leu Gln Met Asn Ser Leu Arg Pro Glu Asp Thr Ala Val
                 85                  90                  95

Tyr Tyr Cys Ala Ala Arg Leu Ser Thr Asp Phe Cys Gly Pro Arg Ala
             100                 105                 110

Asp Phe Asp Tyr Trp Gly Gln Gly Thr Leu Val Thr Val Ser Ser
             115                 120                 125
```

<210> SEQ ID NO 287
<211> LENGTH: 127
<212> TYPE: PRT
<213> ORGANISM: Artificial Sequence
<220> FEATURE:
<223> OTHER INFORMATION: Synthetic Construct

<400> SEQUENCE: 287

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Thr Tyr Ser Arg Lys
                 20                  25                  30

Cys Arg Gly Trp Phe Arg Gln Ala Pro Gly Lys Gly Arg Glu Gly Val
             35                  40                  45

Ala Thr Leu Tyr Thr Ser Ser Gly Gly Thr Tyr Phe Asp Thr Tyr Ala
         50                  55                  60

Asp Ser Val Arg Gly Arg Phe Thr Ile Ser Arg Asp Asn Ala Lys Asn
 65                  70                  75                  80

Thr Val Tyr Leu Gln Met Asn Ser Leu Arg Pro Glu Asp Thr Ala Val
                 85                  90                  95

Tyr Tyr Cys Ala Ala Arg Leu Ser Thr Asp Phe Cys Gly Pro Arg Ala
             100                 105                 110

Asp Phe Asp Tyr Trp Gly Gln Gly Thr Leu Val Thr Val Ser Ser
             115                 120                 125
```

<210> SEQ ID NO 288
<211> LENGTH: 357
<212> TYPE: PRT
<213> ORGANISM: Artificial Sequence
<220> FEATURE:
<223> OTHER INFORMATION: Synthetic Construct

<400> SEQUENCE: 288

```
Gln Val Gln Leu Ala Glu Ser Gly Gly Gly Ser Val Gln Ala Gly Gly
 1               5                  10                  15

Ser Leu Arg Leu Ser Cys Ala Ala Ser Gly Tyr Lys Tyr Gly Val Tyr
                 20                  25                  30

Ser Met Gly Trp Phe Arg Leu Ala Pro Gly Lys Glu Arg Glu Gly Val
             35                  40                  45

Ala Ala Ile Cys Ser Gly Gly Arg Thr Thr Tyr Ser Asp Ser Val Lys
         50                  55                  60

Gly Arg Phe Thr Ile Ser Lys Asp Ser Ala Asn Gln Ile Leu Tyr Leu
 65                  70                  75                  80

Gln Met Asn Ser Leu Lys Pro Glu Asp Thr Ala Met Tyr Tyr Cys Ala
                 85                  90                  95

Ala Arg Pro Leu Trp Thr Gly Asp Cys Asp Leu Ser Ser Ser Trp Tyr
```

```
            100                 105                 110
Lys Thr Trp Gly Gln Gly Thr Gln Val Thr Val Ser Ser Glu Pro Lys
        115                 120                 125

Ser Cys Asp Lys Thr His Thr Cys Pro Pro Cys Pro Ala Pro Glu Leu
130                 135                 140

Leu Gly Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
        355

<210> SEQ ID NO 289
<211> LENGTH: 360
<212> TYPE: PRT
<213> ORGANISM: Artificial Sequence
<220> FEATURE:
<223> OTHER INFORMATION: Synthetic Construct

<400> SEQUENCE: 289

Gln Val Gln Leu Ala Glu Ser Gly Gly Gly Ser Val Gln Thr Gly Gly
1               5                   10                  15

Ser Leu Arg Leu Ser Cys Ala Ala Ser Gly Asn Thr Gly Ser Arg Arg
            20                  25                  30

Tyr Val Ala Trp Phe Arg Gln Ala Pro Gly Lys Glu Arg Glu Gly Val
        35                  40                  45

Ala Arg Leu Ile Thr Asp Ser Gly Ser Thr Tyr Tyr Ala Asp Ser Val
    50                  55                  60

Lys Gly Arg Phe Ile Ile Ser Gln Asp Asn Ala Lys Asn Thr Val Tyr
65                  70                  75                  80

Leu Gln Met Asn Thr Leu Lys Pro Glu Asp Thr Ala Met Tyr Tyr Cys
                85                  90                  95

Ala Glu Glu Leu Ala Pro Ala Arg Ser Gly Gly Ile Trp Phe Gly Gly
```

100                 105                 110
Arg Tyr Phe Ser Tyr Trp Gly Gln Gly Thr Gln Val Thr Val Ser Ser
            115                 120                 125

Glu Pro Lys Ser Cys Asp Lys Thr His Thr Cys Pro Pro Cys Pro Ala
        130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205

Tyr Asn Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
                245                 250                 255

Arg Glu Pro Gln Val Tyr Thr Leu Pro Pro Ser Arg Asp Glu Leu Thr
            260                 265                 270

Lys Asn Gln Val Ser Leu Thr Cys Leu Val Lys Gly Phe Tyr Pro Ser
        275                 280                 285

Asp Ile Ala Val Glu Trp Glu Ser Asn Gly Gln Pro Glu Asn Asn Tyr
    290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly Lys
        355                 360

<210> SEQ ID NO 290
<211> LENGTH: 359
<212> TYPE: PRT
<213> ORGANISM: Artificial Sequence
<220> FEATURE:
<223> OTHER INFORMATION: Synthetic Construct

<400> SEQUENCE: 290

Gln Ile Gln Leu Val Glu Ser Gly Gly Gly Ser Val Gln Ala Gly Gly
1               5                   10                  15

Ser Leu Arg Leu Ser Cys Ala Thr Ser Gly Tyr Thr Tyr Arg Gln Lys
            20                  25                  30

Cys Met Gly Trp Phe Arg Gln Ala Pro Gly Lys Glu Arg Glu Gly Val
        35                  40                  45

Ala Ala Ile Tyr Thr Ser Val Gly Gly Ser Arg Thr Tyr Val Ala Asp
    50                  55                  60

Ser Ala Lys Gly Arg Phe Thr Val Ser Gln Asp Asn Ala Lys Asn Thr
65                  70                  75                  80

Val Tyr Leu Gln Met Asn Ser Leu Lys Pro Glu Asp Thr Ala Met Tyr
                85                  90                  95

Tyr Cys Ala Ala Lys Ser Pro Tyr Asp Gly Ala Cys Ser Tyr Glu Ala

```
                100                 105                 110
Asp Phe Thr Tyr Trp Gly Gln Gly Thr Gln Val Thr Val Ser Ser Glu
            115                 120                 125

Pro Lys Ser Cys Asp Lys Thr His Thr Cys Pro Pro Cys Pro Ala Pro
130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Asp Glu Leu Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys
        355

<210> SEQ ID NO 291
<211> LENGTH: 359
<212> TYPE: PRT
<213> ORGANISM: Artificial Sequence
<220> FEATURE:
<223> OTHER INFORMATION: Synthetic Construct

<400> SEQUENCE: 291

Gln Val Gln Leu Val Glu Ser Gly Gly Gly Ser Val Gln Ala Gly Gly
1               5                   10                  15

Ser Leu Arg Leu Ser Cys Val Ala Ser Gly Tyr Thr Tyr Ser Arg Lys
            20                  25                  30

Cys Arg Gly Trp Phe Arg Gln Ala Pro Gly Lys Glu Arg Glu Gly Val
        35                  40                  45

Ala Thr Leu Tyr Thr Ser Ser Gly Gly Thr Tyr Phe Asp Thr Tyr Ala
    50                  55                  60

Asp Ser Val Arg Gly Arg Phe Thr Ile Ser Gln Asp Asn Ala Lys Asn
65                  70                  75                  80

Thr Val Tyr Leu Gln Met Asn Asn Leu Lys Pro Glu Asp Ser Gly Ile
                85                  90                  95

Tyr Tyr Cys Ala Ala Arg Leu Ser Thr Asp Phe Cys Gly Pro Arg Ala
```

```
                100             105             110
Asp Phe Asp Tyr Trp Gly Gln Gly Thr Gln Val Thr Val Ser Ser Glu
            115                 120                 125

Pro Lys Ser Cys Asp Lys Thr His Thr Cys Pro Pro Cys Pro Ala Pro
        130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Asp Glu Leu Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys
            355

<210> SEQ ID NO 292
<211> LENGTH: 357
<212> TYPE: PRT
<213> ORGANISM: Artificial Sequence
<220> FEATURE:
<223> OTHER INFORMATION: Synthetic Construct

<400> SEQUENCE: 292

Gln Val Gln Leu Ala Glu Ser Gly Gly Gly Ser Val Gln Ala Gly Gly
1               5                   10                  15

Ser Leu Arg Leu Ser Cys Ala Ala Ser Gly Val Thr Ser Asp Ser Tyr
            20                  25                  30

His Met Gly Trp Phe Arg Gln Ala Pro Gly Lys Glu Arg Glu Gly Val
        35                  40                  45

Ala Val Ile Lys Thr Gly Asp Ala Ser Thr Tyr Tyr Thr Asp Ser Val
    50                  55                  60

Lys Gly Arg Phe Thr Ile Ser Gln Asp Asn Ala Lys Asn Thr Leu Tyr
65                  70                  75                  80

Leu Gln Met Asn Ser Leu Lys Pro Glu Asp Thr Ala Met Tyr Tyr Cys
                85                  90                  95

Ala Ala Arg Arg Gly Trp Val Pro Ala Pro Leu Ser Gln Tyr Asn Tyr
```

```
                100                 105                 110
Asn Tyr Trp Gly Gln Gly Thr Gln Val Thr Val Ser Ser Glu Pro Lys
            115                 120                 125

Ser Cys Asp Lys Thr His Thr Cys Pro Pro Cys Pro Ala Pro Glu Leu
130                 135                 140

Leu Gly Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
            165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Gln Tyr Asn Ser
            195                 200                 205

Thr Tyr Arg Val Val Ser Val Leu Thr Val Leu His Gln Asp Trp Leu
            210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
            275                 280                 285

Val Glu Trp Glu Ser Asn Gly Gln Pro Glu Asn Asn Tyr Lys Thr Thr
            290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
            355

<210> SEQ ID NO 293
<211> LENGTH: 357
<212> TYPE: PRT
<213> ORGANISM: Artificial Sequence
<220> FEATURE:
<223> OTHER INFORMATION: Synthetic Construct

<400> SEQUENCE: 293

Gln Val Gln Leu Ala Glu Ser Gly Gly Gly Ser Val Gln Thr Gly Gly
1               5                   10                  15

Ser Leu Arg Leu Ser Cys Glu Ala Ser Gly Val Ala Ala Ser Gly Tyr
            20                  25                  30

Cys Met Ala Trp Phe Arg Gln Ala Pro Gly Lys Glu Arg Glu Arg Val
            35                  40                  45

Ala Ala Ile Ser Ser Asn Asp Leu Val Ala Tyr Ala Asp Ser Val Lys
        50                  55                  60

Gly Arg Phe Thr Ile Ser Lys Asp Asn Ala Lys Thr Thr Leu Tyr Leu
65                  70                  75                  80

Gln Met Asn Asn Leu Lys Pro Glu Asp Thr Ala Met Tyr Tyr Cys Ala
            85                  90                  95

Ala Asp Gly Gly Tyr Gly Gly Tyr Cys Gly Arg Leu Arg Pro Gly Thr
```

```
                100                 105                 110
Gly Tyr Trp Gly Gln Gly Thr Gln Val Thr Val Ser Ser Glu Pro Lys
            115                 120                 125

Ser Cys Asp Lys Thr His Thr Cys Pro Pro Cys Pro Ala Pro Glu Leu
        130                 135                 140

Leu Gly Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
            355

<210> SEQ ID NO 294
<211> LENGTH: 363
<212> TYPE: PRT
<213> ORGANISM: Artificial Sequence
<220> FEATURE:
<223> OTHER INFORMATION: Synthetic Construct

<400> SEQUENCE: 294

Glu Val Gln Leu Ala Glu Ser Gly Gly Gly Ser Val Gln Ala Gly Gly
1               5                   10                  15

Ser Leu Arg Leu Ser Cys Thr Thr Ser Gly Tyr Thr Tyr Ser Arg Asn
            20                  25                  30

Cys Met Gly Trp Phe Arg Gln Ala Pro Gly Lys Glu Arg Glu Gly Val
        35                  40                  45

Ala Thr Ile Tyr Val Ser Ala Ala Ser Thr Ser Phe Ala Thr Tyr Ala
    50                  55                  60

Asp Ser Val Lys Gly Arg Phe Thr Ile Ser Leu Asp Lys Ala Lys Asn
65                  70                  75                  80

Thr Val Tyr Leu Gln Met Asn Ser Leu Lys Pro Glu Asp Thr Ala Met
                85                  90                  95

Tyr Tyr Cys Ala Ala Asp Pro Pro Asp Arg Ile Ser Asn Pro Cys Gly
```

```
                100                 105                 110
Pro Arg Arg Pro Asp Phe Gly Tyr Trp Gly Gln Gly Thr Gln Val Thr
            115                 120                 125

Val Ser Ser Glu Pro Lys Ser Cys Asp Lys Thr His Thr Cys Pro Pro
        130                 135                 140

Cys Pro Ala Pro Glu Leu Leu Gly Gly Pro Ser Val Phe Leu Phe Pro
145                 150                 155                 160

Pro Lys Pro Lys Asp Thr Leu Met Ile Ser Arg Thr Pro Glu Val Thr
                165                 170                 175

Cys Val Val Val Asp Val Ser His Glu Asp Pro Glu Val Lys Phe Asn
            180                 185                 190

Trp Tyr Val Asp Gly Val Glu Val His Asn Ala Lys Thr Lys Pro Arg
        195                 200                 205

Glu Glu Gln Tyr Asn Ser Thr Tyr Arg Val Val Ser Val Leu Thr Val
    210                 215                 220

Leu His Gln Asp Trp Leu Asn Gly Lys Glu Tyr Lys Cys Lys Val Ser
225                 230                 235                 240

Asn Lys Ala Leu Pro Ala Pro Ile Glu Lys Thr Ile Ser Lys Ala Lys
                245                 250                 255

Gly Gln Pro Arg Glu Pro Gln Val Tyr Thr Leu Pro Pro Ser Arg Asp
            260                 265                 270

Glu Leu Thr Lys Asn Gln Val Ser Leu Thr Cys Leu Val Lys Gly Phe
        275                 280                 285

Tyr Pro Ser Asp Ile Ala Val Glu Trp Glu Ser Asn Gly Gln Pro Glu
    290                 295                 300

Asn Asn Tyr Lys Thr Thr Pro Pro Val Leu Asp Ser Asp Gly Ser Phe
305                 310                 315                 320

Phe Leu Tyr Ser Lys Leu Thr Val Asp Lys Ser Arg Trp Gln Gln Gly
                325                 330                 335

Asn Val Phe Ser Cys Ser Val Met His Glu Ala Leu His Asn His Tyr
            340                 345                 350

Thr Gln Lys Ser Leu Ser Leu Ser Pro Gly Lys
        355                 360

<210> SEQ ID NO 295
<211> LENGTH: 357
<212> TYPE: PRT
<213> ORGANISM: Artificial Sequence
<220> FEATURE:
<223> OTHER INFORMATION: Synthetic Construct

<400> SEQUENCE: 295

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Gln Ala Pro Gly Lys Gly Leu Glu Gly Val
        35                  40                  45

Ser Ala Ile Cys Ser Gly Gly Arg Thr Thr Tyr Ser Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ala Arg Pro Leu Trp Thr Gly Asp Cys Asp Leu Ser Ser Ser Trp Tyr
```

```
            100                 105                 110
Lys Thr Trp Gly Gln Gly Thr Leu Val Thr Val Ser Ser Glu Pro Lys
        115                 120                 125

Ser Cys Asp Lys Thr His Thr Cys Pro Pro Cys Pro Ala Pro Glu Leu
130                 135                 140

Leu Gly Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
        355

<210> SEQ ID NO 296
<211> LENGTH: 357
<212> TYPE: PRT
<213> ORGANISM: Artificial Sequence
<220> FEATURE:
<223> OTHER INFORMATION: Synthetic Construct

<400> SEQUENCE: 296

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Gln Ala Pro Gly Lys Gly Leu Glu Gly Val
        35                  40                  45

Ser Ala Ile Cys Ser Gly Gly Arg Thr Thr Tyr Ser Asp Ser Val Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ala Arg Pro Leu Trp Thr Gly Asp Cys Asp Leu Ser Ser Ser Trp Tyr
```

```
                100                 105                 110
Lys Thr Trp Gly Gln Gly Thr Leu Val Thr Val Ser Ser Glu Pro Lys
            115                 120                 125

Ser Cys Asp Lys Thr His Thr Cys Pro Pro Cys Pro Ala Pro Glu Leu
130                 135                 140

Leu Gly Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
            165                 170                 175

Ser His Glu Asp Pro Glu Val Lys Phe Asn Trp Tyr Val Asp Gly Val
        180                 185                 190

Glu Val His Asn Ala Lys Thr Lys Pro Arg Glu Glu Gln Tyr Asn Ser
    195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
            245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
            325                 330                 335

Val Met His Glu Ala Leu His Asn His Tyr Thr Gln Lys Ser Leu Ser
            340                 345                 350

Leu Ser Pro Gly Lys
            355

<210> SEQ ID NO 297
<211> LENGTH: 357
<212> TYPE: PRT
<213> ORGANISM: Artificial Sequence
<220> FEATURE:
<223> OTHER INFORMATION: Synthetic Construct

<400> SEQUENCE: 297

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Gln Ala Pro Gly Lys Gly Leu Glu Gly Val
        35                  40                  45

Ala Ala Ile Cys Ser Gly Gly Arg Thr Thr Tyr Ser Asp Ser Val Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Ala Arg Pro Leu Trp Thr Gly Asp Cys Asp Leu Ser Ser Ser Trp Tyr
```

100                 105                 110
Lys Thr Trp Gly Gln Gly Thr Leu Val Thr Val Ser Ser Glu Pro Lys
            115                 120                 125

Ser Cys Asp Lys Thr His Thr Cys Pro Pro Cys Pro Ala Pro Glu Leu
130                 135                 140

Leu Gly Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
            165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
            195                 200                 205

Thr Tyr Arg Val Val Ser Val Leu Thr Val Leu His Gln Asp Trp Leu
            210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
            245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
            275                 280                 285

Val Glu Trp Glu Ser Asn Gly Gln Pro Glu Asn Asn Tyr Lys Thr Thr
290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
            325                 330                 335

Val Met His Glu Ala Leu His Asn His Tyr Thr Gln Lys Ser Leu Ser
            340                 345                 350

Leu Ser Pro Gly Lys
            355

<210> SEQ ID NO 298
<211> LENGTH: 357
<212> TYPE: PRT
<213> ORGANISM: Artificial Sequence
<220> FEATURE:
<223> OTHER INFORMATION: Synthetic Construct

<400> SEQUENCE: 298

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Leu Ala Pro Gly Lys Gly Leu Glu Gly Val
            35                  40                  45

Ser Ala Ile Cys Ser Gly Gly Arg Thr Thr Tyr Ser Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Ala Arg Pro Leu Trp Thr Gly Asp Cys Asp Leu Ser Ser Ser Trp Tyr

```
            100                 105                 110
Lys Thr Trp Gly Gln Gly Thr Leu Val Thr Val Ser Ser Glu Pro Lys
        115                 120                 125

Ser Cys Asp Lys Thr His Thr Cys Pro Pro Cys Pro Ala Pro Glu Leu
    130                 135                 140

Leu Gly Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
        355

<210> SEQ ID NO 299
<211> LENGTH: 357
<212> TYPE: PRT
<213> ORGANISM: Artificial Sequence
<220> FEATURE:
<223> OTHER INFORMATION: Synthetic Construct

<400> SEQUENCE: 299

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Gln Ala Pro Gly Lys Gly Leu Glu Gly Val
        35                  40                  45

Ser Ala Ile Cys Ser Gly Gly Arg Thr Thr Tyr Ser Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Met Tyr Tyr Cys Ala
                85                  90                  95

Ala Arg Pro Leu Trp Thr Gly Asp Cys Asp Leu Ser Ser Ser Trp Tyr
```

```
                100             105             110
Lys Thr Trp Gly Gln Gly Thr Leu Val Thr Val Ser Ser Glu Pro Lys
            115                 120                 125

Ser Cys Asp Lys Thr His Thr Cys Pro Pro Cys Pro Ala Pro Glu Leu
130                 135                 140

Leu Gly Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
        355

<210> SEQ ID NO 300
<211> LENGTH: 357
<212> TYPE: PRT
<213> ORGANISM: Artificial Sequence
<220> FEATURE:
<223> OTHER INFORMATION: Synthetic Construct

<400> SEQUENCE: 300

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Gln Ala Pro Gly Lys Glu Leu Glu Gly Val
        35                  40                  45

Ser Ala Ile Cys Ser Gly Gly Arg Thr Thr Tyr Ser Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ala Arg Pro Leu Trp Thr Gly Asp Cys Asp Leu Ser Ser Ser Trp Tyr
```

```
            100                 105                 110
Lys Thr Trp Gly Gln Gly Thr Leu Val Thr Val Ser Ser Glu Pro Lys
        115                 120                 125

Ser Cys Asp Lys Thr His Thr Cys Pro Pro Cys Pro Ala Pro Glu Leu
    130                 135                 140

Leu Gly Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
        355

<210> SEQ ID NO 301
<211> LENGTH: 357
<212> TYPE: PRT
<213> ORGANISM: Artificial Sequence
<220> FEATURE:
<223> OTHER INFORMATION: Synthetic Construct

<400> SEQUENCE: 301

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Gln Ala Pro Gly Lys Gly Arg Glu Gly Val
        35                  40                  45

Ser Ala Ile Cys Ser Gly Gly Arg Thr Thr Tyr Ser Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Ala Arg Pro Leu Trp Thr Gly Asp Cys Asp Leu Ser Ser Ser Trp Tyr
```

```
                 100                 105                 110
Lys Thr Trp Gly Gln Gly Thr Leu Val Thr Val Ser Ser Glu Pro Lys
            115                 120                 125

Ser Cys Asp Lys Thr His Thr Cys Pro Pro Cys Pro Ala Pro Glu Leu
        130                 135                 140

Leu Gly Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
        355

<210> SEQ ID NO 302
<211> LENGTH: 357
<212> TYPE: PRT
<213> ORGANISM: Artificial Sequence
<220> FEATURE:
<223> OTHER INFORMATION: Synthetic Construct

<400> SEQUENCE: 302

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Gln Ala Pro Gly Lys Glu Arg Glu Gly Val
        35                  40                  45

Ser Ala Ile Cys Ser Gly Gly Arg Thr Thr Tyr Ser Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ala Arg Pro Leu Trp Thr Gly Asp Cys Asp Leu Ser Ser Ser Trp Tyr
```

```
            100                 105                 110
Lys Thr Trp Gly Gln Gly Thr Leu Val Thr Val Ser Ser Glu Pro Lys
        115                 120                 125

Ser Cys Asp Lys Thr His Thr Cys Pro Pro Cys Pro Ala Pro Glu Leu
    130                 135                 140

Leu Gly Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
        355

<210> SEQ ID NO 303
<211> LENGTH: 357
<212> TYPE: PRT
<213> ORGANISM: Artificial Sequence
<220> FEATURE:
<223> OTHER INFORMATION: Synthetic Construct

<400> SEQUENCE: 303

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Gln Ala Pro Gly Lys Gly Leu Glu Gly Val
        35                  40                  45

Ser Ala Ile Cys Ser Gly Gly Arg Thr Thr Tyr Ser Asp Ser Val Lys
    50                  55                  60

Gly Arg Phe Thr Ile Ser Arg Asp Ser Ala Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ala Arg Pro Leu Trp Thr Gly Asp Cys Asp Leu Ser Ser Ser Trp Tyr
```

```
            100                 105                 110
Lys Thr Trp Gly Gln Gly Thr Leu Val Thr Val Ser Ser Glu Pro Lys
        115                 120                 125

Ser Cys Asp Lys Thr His Thr Cys Pro Pro Cys Pro Ala Pro Glu Leu
    130                 135                 140

Leu Gly Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
        355

<210> SEQ ID NO 304
<211> LENGTH: 357
<212> TYPE: PRT
<213> ORGANISM: Artificial Sequence
<220> FEATURE:
<223> OTHER INFORMATION: Synthetic Construct

<400> SEQUENCE: 304

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Gln Ala Pro Gly Lys Gly Leu Glu Gly Val
        35                  40                  45

Ser Ala Ile Cys Ser Gly Gly Arg Thr Thr Tyr Ser Asp Ser Val Lys
    50                  55                  60

Gly Arg Phe Thr Ile Ser Arg Asp Asn Ser Gln Thr Leu Tyr Leu
65                  70                  75                  80

Gln Met Asn Ser Leu Arg Ala Glu Asp Thr Ala Val Tyr Tyr Cys Ala
                85                  90                  95

Ala Arg Pro Leu Trp Thr Gly Asp Cys Asp Leu Ser Ser Ser Trp Tyr
```

```
                100             105             110
Lys Thr Trp Gly Gln Gly Thr Leu Val Thr Val Ser Ser Glu Pro Lys
            115                 120                 125

Ser Cys Asp Lys Thr His Thr Cys Pro Pro Cys Pro Ala Pro Glu Leu
    130                 135                 140

Leu Gly Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
            355

<210> SEQ ID NO 305
<211> LENGTH: 357
<212> TYPE: PRT
<213> ORGANISM: Artificial Sequence
<220> FEATURE:
<223> OTHER INFORMATION: Synthetic Construct

<400> SEQUENCE: 305

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Gln Ala Pro Gly Lys Gly Leu Glu Gly Val
        35                  40                  45

Ser Ala Ile Cys Ser Gly Gly Arg Thr Thr Tyr Ser Asp Ser Val Lys
    50                  55                  60

Gly Arg Phe Thr Ile Ser Arg Asp Asn Ser Lys Asn Ile Leu Tyr Leu
65                  70                  75                  80

Gln Met Asn Ser Leu Arg Ala Glu Asp Thr Ala Val Tyr Tyr Cys Ala
                85                  90                  95

Ala Arg Pro Leu Trp Thr Gly Asp Cys Asp Leu Ser Ser Ser Trp Tyr
```

```
                100             105             110
Lys Thr Trp Gly Gln Gly Thr Leu Val Thr Val Ser Ser Glu Pro Lys
            115                 120                 125

Ser Cys Asp Lys Thr His Thr Cys Pro Pro Cys Pro Ala Pro Glu Leu
            130                 135             140

Leu Gly Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
                180                 185                 190

Glu Val His Asn Ala Lys Thr Lys Pro Arg Glu Glu Gln Tyr Asn Ser
                195                 200                 205

Thr Tyr Arg Val Val Ser Val Leu Thr Val Leu His Gln Asp Trp Leu
            210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
                260                 265                 270

Val Ser Leu Thr Cys Leu Val Lys Gly Phe Tyr Pro Ser Asp Ile Ala
            275                 280                 285

Val Glu Trp Glu Ser Asn Gly Gln Pro Glu Asn Asn Tyr Lys Thr Thr
            290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
                340                 345                 350

Leu Ser Pro Gly Lys
            355

<210> SEQ ID NO 306
<211> LENGTH: 357
<212> TYPE: PRT
<213> ORGANISM: Artificial Sequence
<220> FEATURE:
<223> OTHER INFORMATION: Synthetic Construct

<400> SEQUENCE: 306

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Gln Ala Pro Gly Lys Gly Leu Glu Gly Val
            35                  40                  45

Ser Ala Ile Cys Ser Gly Gly Arg Thr Thr Tyr Ser Asp Ser Val Lys
        50                  55                  60

Gly Arg Phe Thr Ile Ser Arg Asp Asn Ser Lys Gln Thr Leu Tyr Leu
65                  70                  75                  80

Gln Met Asn Ser Leu Arg Ala Glu Asp Thr Ala Val Tyr Tyr Cys Ala
                85                  90                  95

Ala Arg Pro Leu Trp Thr Gly Asp Cys Asp Leu Ser Ser Ser Trp Tyr
```

```
                    100                 105                 110
Lys Thr Trp Gly Gln Gly Thr Leu Val Thr Val Ser Ser Glu Pro Lys
            115                 120                 125

Ser Cys Asp Lys Thr His Thr Cys Pro Pro Cys Pro Ala Pro Glu Leu
            130                 135                 140

Leu Gly Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
            165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
            195                 200                 205

Thr Tyr Arg Val Val Ser Val Leu Thr Val Leu His Gln Asp Trp Leu
            210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
            245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
            275                 280                 285

Val Glu Trp Glu Ser Asn Gly Gln Pro Glu Asn Asn Tyr Lys Thr Thr
            290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
            325                 330                 335

Val Met His Glu Ala Leu His Asn His Tyr Thr Gln Lys Ser Leu Ser
            340                 345                 350

Leu Ser Pro Gly Lys
            355

<210> SEQ ID NO 307
<211> LENGTH: 357
<212> TYPE: PRT
<213> ORGANISM: Artificial Sequence
<220> FEATURE:
<223> OTHER INFORMATION: Synthetic Construct

<400> SEQUENCE: 307

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Gln Ala Pro Gly Lys Gly Leu Glu Gly Val
            35                  40                  45

Ser Ala Ile Cys Ser Gly Gly Arg Thr Thr Tyr Ser Asp Ser Val Lys
            50                  55                  60

Gly Arg Phe Thr Ile Ser Arg Asp Asn Ser Asn Ile Leu Tyr Leu
65                  70                  75                  80

Gln Met Asn Ser Leu Arg Ala Glu Asp Thr Ala Val Tyr Tyr Cys Ala
            85                  90                  95

Ala Arg Pro Leu Trp Thr Gly Asp Cys Asp Leu Ser Ser Ser Trp Tyr
```

```
                100             105             110
Lys Thr Trp Gly Gln Gly Thr Leu Val Thr Val Ser Ser Glu Pro Lys
            115                 120                 125

Ser Cys Asp Lys Thr His Thr Cys Pro Pro Cys Pro Ala Pro Glu Leu
    130                 135                 140

Leu Gly Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
        355

<210> SEQ ID NO 308
<211> LENGTH: 357
<212> TYPE: PRT
<213> ORGANISM: Artificial Sequence
<220> FEATURE:
<223> OTHER INFORMATION: Synthetic Construct

<400> SEQUENCE: 308

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Gln Ala Pro Gly Lys Gly Leu Glu Gly Val
        35                  40                  45

Ser Ala Ile Cys Ser Gly Gly Arg Thr Thr Tyr Ser Asp Ser Val Lys
    50                  55                  60

Gly Arg Phe Thr Ile Ser Arg Asp Asn Ser Gln Ile Leu Tyr Leu
65                  70                  75                  80

Gln Met Asn Ser Leu Arg Ala Glu Asp Thr Ala Val Tyr Tyr Cys Ala
                85                  90                  95

Ala Arg Pro Leu Trp Thr Gly Asp Cys Asp Leu Ser Ser Ser Trp Tyr
```

```
            100                 105                 110
Lys Thr Trp Gly Gln Gly Thr Leu Val Thr Val Ser Ser Glu Pro Lys
        115                 120                 125

Ser Cys Asp Lys Thr His Thr Cys Pro Pro Cys Pro Ala Pro Glu Leu
130                 135                 140

Leu Gly Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
        355

<210> SEQ ID NO 309
<211> LENGTH: 357
<212> TYPE: PRT
<213> ORGANISM: Artificial Sequence
<220> FEATURE:
<223> OTHER INFORMATION: Synthetic Construct

<400> SEQUENCE: 309

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Gln Ala Pro Gly Lys Glu Arg Glu Gly Val
        35                  40                  45

Ser Ala Ile Cys Ser Gly Gly Arg Thr Thr Tyr Ser Asp Ser Val Lys
    50                  55                  60

Gly Arg Phe Thr Ile Ser Arg Asp Asn Ser Lys Gln Thr Leu Tyr Leu
65                  70                  75                  80

Gln Met Asn Ser Leu Arg Ala Glu Asp Thr Ala Val Tyr Tyr Cys Ala
                85                  90                  95

Ala Arg Pro Leu Trp Thr Gly Asp Cys Asp Leu Ser Ser Ser Trp Tyr
```

```
                100             105             110
Lys Thr Trp Gly Gln Gly Thr Leu Val Thr Val Ser Ser Glu Pro Lys
            115             120             125

Ser Cys Asp Lys Thr His Thr Cys Pro Pro Cys Pro Ala Pro Glu Leu
130             135             140

Leu Gly Gly Pro Ser Val Phe Leu Phe Pro Pro Lys Pro Lys Asp Thr
145             150             155             160

Leu Met Ile Ser Arg Thr Pro Glu Val Thr Cys Val Val Val Asp Val
            165             170             175

Ser His Glu Asp Pro Glu Val Lys Phe Asn Trp Tyr Val Asp Gly Val
            180             185             190

Glu Val His Asn Ala Lys Thr Lys Pro Arg Glu Glu Gln Tyr Asn Ser
            195             200             205

Thr Tyr Arg Val Val Ser Val Leu Thr Val Leu His Gln Asp Trp Leu
            210             215             220

Asn Gly Lys Glu Tyr Lys Cys Lys Val Ser Asn Lys Ala Leu Pro Ala
225             230             235             240

Pro Ile Glu Lys Thr Ile Ser Lys Ala Lys Gly Gln Pro Arg Glu Pro
            245             250             255

Gln Val Tyr Thr Leu Pro Pro Ser Arg Asp Glu Leu Thr Lys Asn Gln
            260             265             270

Val Ser Leu Thr Cys Leu Val Lys Gly Phe Tyr Pro Ser Asp Ile Ala
            275             280             285

Val Glu Trp Glu Ser Asn Gly Gln Pro Glu Asn Asn Tyr Lys Thr Thr
            290             295             300

Pro Pro Val Leu Asp Ser Asp Gly Ser Phe Phe Leu Tyr Ser Lys Leu
305             310             315             320

Thr Val Asp Lys Ser Arg Trp Gln Gln Gly Asn Val Phe Ser Cys Ser
            325             330             335

Val Met His Glu Ala Leu His Asn His Tyr Thr Gln Lys Ser Leu Ser
            340             345             350

Leu Ser Pro Gly Lys
            355

<210> SEQ ID NO 310
<211> LENGTH: 357
<212> TYPE: PRT
<213> ORGANISM: Artificial Sequence
<220> FEATURE:
<223> OTHER INFORMATION: Synthetic Construct

<400> SEQUENCE: 310

Glu Val Gln Leu Val Glu Ser Gly Gly Gly Leu Val Gln Pro Gly Gly
1               5               10              15

Ser Leu Arg Leu Ser Cys Ala Ala Ser Gly Tyr Lys Tyr Gly Val Tyr
            20              25              30

Ser Met Gly Trp Phe Arg Gln Ala Pro Gly Lys Glu Arg Glu Gly Val
            35              40              45

Ser Ala Ile Cys Ser Gly Gly Arg Thr Thr Tyr Ser Asp Ser Val Lys
        50              55              60

Gly Arg Phe Thr Ile Ser Arg Asp Asn Ser Asn Ile Leu Tyr Leu
65              70              75              80

Gln Met Asn Ser Leu Arg Ala Glu Asp Thr Ala Val Tyr Tyr Cys Ala
            85              90              95

Ala Arg Pro Leu Trp Thr Gly Asp Cys Asp Leu Ser Ser Ser Trp Tyr
```

```
                    100                 105                 110
Lys Thr Trp Gly Gln Gly Thr Leu Val Thr Val Ser Ser Glu Pro Lys
            115                 120                 125

Ser Cys Asp Lys Thr His Thr Cys Pro Pro Cys Pro Ala Pro Glu Leu
        130                 135                 140

Leu Gly Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
            355

<210> SEQ ID NO 311
<211> LENGTH: 357
<212> TYPE: PRT
<213> ORGANISM: Artificial Sequence
<220> FEATURE:
<223> OTHER INFORMATION: Synthetic Construct

<400> SEQUENCE: 311

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Gln Ala Pro Gly Lys Glu Arg Glu Gly Val
        35                  40                  45

Ser Ala Ile Cys Ser Gly Gly Arg Thr Thr Tyr Ser Asp Ser Val Lys
    50                  55                  60

Gly Arg Phe Thr Ile Ser Arg Asp Asn Ser Gln Ile Leu Tyr Leu
65                  70                  75                  80

Gln Met Asn Ser Leu Arg Ala Glu Asp Thr Ala Val Tyr Tyr Cys Ala
                85                  90                  95

Ala Arg Pro Leu Trp Thr Gly Asp Cys Asp Leu Ser Ser Ser Trp Tyr
```

```
                  100                 105                 110
Lys Thr Trp Gly Gln Gly Thr Leu Val Thr Val Ser Glu Pro Lys
            115                 120                 125

Ser Cys Asp Lys Thr His Thr Cys Pro Pro Cys Pro Ala Pro Glu Leu
130                 135                 140

Leu Gly Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
            165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
            195                 200                 205

Thr Tyr Arg Val Val Ser Val Leu Thr Val Leu His Gln Asp Trp Leu
            210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
            245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
            275                 280                 285

Val Glu Trp Glu Ser Asn Gly Gln Pro Glu Asn Asn Tyr Lys Thr Thr
            290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
            325                 330                 335

Val Met His Glu Ala Leu His Asn His Tyr Thr Gln Lys Ser Leu Ser
            340                 345                 350

Leu Ser Pro Gly Lys
            355

<210> SEQ ID NO 312
<211> LENGTH: 357
<212> TYPE: PRT
<213> ORGANISM: Artificial Sequence
<220> FEATURE:
<223> OTHER INFORMATION: Synthetic Construct

<400> SEQUENCE: 312

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Gln Ala Pro Gly Lys Glu Arg Glu Gly Val
            35                  40                  45

Ser Ala Ile Cys Ser Gly Gly Arg Thr Thr Tyr Ser Asp Ser Val Lys
            50                  55                  60

Gly Arg Phe Thr Ile Ser Arg Asp Asn Ser Lys Asn Ile Leu Tyr Leu
65                  70                  75                  80

Gln Met Asn Ser Leu Arg Ala Glu Asp Thr Ala Val Tyr Tyr Cys Ala
            85                  90                  95

Ala Arg Pro Leu Trp Thr Gly Asp Cys Asp Leu Ser Ser Ser Trp Tyr
```

```
                100                 105                 110
Lys Thr Trp Gly Gln Gly Thr Leu Val Thr Val Ser Ser Glu Pro Lys
            115                 120                 125

Ser Cys Asp Lys Thr His Thr Cys Pro Pro Cys Pro Ala Pro Glu Leu
130                 135                 140

Leu Gly Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
            165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
            195                 200                 205

Thr Tyr Arg Val Val Ser Val Leu Thr Val Leu His Gln Asp Trp Leu
            210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
            245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
            275                 280                 285

Val Glu Trp Glu Ser Asn Gly Gln Pro Glu Asn Asn Tyr Lys Thr Thr
            290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
            325                 330                 335

Val Met His Glu Ala Leu His Asn His Tyr Thr Gln Lys Ser Leu Ser
            340                 345                 350

Leu Ser Pro Gly Lys
            355

<210> SEQ ID NO 313
<211> LENGTH: 359
<212> TYPE: PRT
<213> ORGANISM: Artificial Sequence
<220> FEATURE:
<223> OTHER INFORMATION: Synthetic Construct

<400> SEQUENCE: 313

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Tyr Ser Arg Lys
            20                  25                  30

Cys Arg Gly Trp Phe Arg Gln Ala Pro Gly Lys Gly Leu Glu Trp Val
            35                  40                  45

Ser Thr Leu Tyr Thr Ser Ser Gly Gly Thr Tyr Phe Asp Thr Tyr Ala
            50                  55                  60

Asp Ser Val Arg Gly Arg Phe Thr Ile Ser Arg Asp Asn Ser Lys Asn
65                  70                  75                  80

Thr Leu Tyr Leu Gln Met Asn Ser Leu Arg Ala Glu Asp Thr Ala Val
            85                  90                  95

Tyr Tyr Cys Ala Ala Arg Leu Ser Thr Asp Phe Cys Gly Pro Arg Ala
```

```
                    100                 105                 110
Asp Phe Asp Tyr Trp Gly Gln Gly Thr Leu Val Thr Val Ser Ser Glu
            115                 120                 125

Pro Lys Ser Cys Asp Lys Thr His Thr Cys Pro Pro Cys Pro Ala Pro
130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Asp Glu Leu Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys
        355

<210> SEQ ID NO 314
<211> LENGTH: 359
<212> TYPE: PRT
<213> ORGANISM: Artificial Sequence
<220> FEATURE:
<223> OTHER INFORMATION: Synthetic Construct

<400> SEQUENCE: 314

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Tyr Ser Arg Lys
            20                  25                  30

Cys Arg Gly Trp Phe Arg Gln Ala Pro Gly Lys Gly Leu Glu Gly Val
        35                  40                  45

Ser Thr Leu Tyr Thr Ser Ser Gly Gly Thr Tyr Phe Asp Thr Tyr Ala
    50                  55                  60

Asp Ser Val Arg Gly Arg Phe Thr Ile Ser Arg Asp Asn Ser Lys Asn
65                  70                  75                  80

Thr Leu Tyr Leu Gln Met Asn Ser Leu Arg Ala Glu Asp Thr Ala Val
                85                  90                  95

Tyr Tyr Cys Ala Ala Arg Leu Ser Thr Asp Phe Cys Gly Pro Arg Ala
```

```
            100                 105                 110
Asp Phe Asp Tyr Trp Gly Gln Gly Thr Leu Val Thr Val Ser Ser Glu
            115                 120                 125

Pro Lys Ser Cys Asp Lys Thr His Thr Cys Pro Pro Cys Pro Ala Pro
130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Asp Glu Leu Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys
            355

<210> SEQ ID NO 315
<211> LENGTH: 359
<212> TYPE: PRT
<213> ORGANISM: Artificial Sequence
<220> FEATURE:
<223> OTHER INFORMATION: Synthetic Construct

<400> SEQUENCE: 315

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Tyr Ser Arg Lys
            20                  25                  30

Cys Arg Gly Trp Phe Arg Gln Ala Pro Gly Lys Gly Leu Glu Gly Val
        35                  40                  45

Ala Thr Leu Tyr Thr Ser Ser Gly Gly Thr Tyr Phe Asp Thr Tyr Ala
    50                  55                  60

Asp Ser Val Arg Gly Arg Phe Thr Ile Ser Arg Asp Asn Ser Lys Asn
65                  70                  75                  80

Thr Val Tyr Leu Gln Met Asn Ser Leu Arg Ala Glu Asp Thr Gly Val
                85                  90                  95

Tyr Tyr Cys Ala Ala Arg Leu Ser Thr Asp Phe Cys Gly Pro Arg Ala
```

```
                    100                 105                 110
Asp Phe Asp Tyr Trp Gly Gln Gly Thr Leu Val Thr Val Ser Ser Glu
                115                 120                 125

Pro Lys Ser Cys Asp Lys Thr His Thr Cys Pro Pro Cys Pro Ala Pro
        130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Asp Glu Leu Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys
        355

<210> SEQ ID NO 316
<211> LENGTH: 359
<212> TYPE: PRT
<213> ORGANISM: Artificial Sequence
<220> FEATURE:
<223> OTHER INFORMATION: Synthetic Construct

<400> SEQUENCE: 316

Glu Val Gln Leu Val Glu Ser Gly Gly Gly Leu Val Gln Pro Gly Gly
1               5                   10                  15

Ser Leu Arg Leu Ser Cys Val Ala Ser Gly Tyr Thr Tyr Ser Arg Lys
            20                  25                  30

Cys Arg Gly Trp Phe Arg Gln Ala Pro Gly Lys Gly Leu Glu Gly Val
        35                  40                  45

Ser Thr Leu Tyr Thr Ser Gly Gly Thr Tyr Phe Asp Thr Tyr Ala
    50                  55                  60

Asp Ser Val Arg Gly Arg Phe Thr Ile Ser Arg Asp Asn Ser Lys Asn
65                  70                  75                  80

Thr Leu Tyr Leu Gln Met Asn Ser Leu Arg Ala Glu Asp Thr Ala Val
                85                  90                  95

Tyr Tyr Cys Ala Ala Arg Leu Ser Thr Asp Phe Cys Gly Pro Arg Ala
```

```
                  100                 105                 110
Asp Phe Asp Tyr Trp Gly Gln Gly Thr Leu Val Thr Val Ser Ser Glu
            115                 120                 125

Pro Lys Ser Cys Asp Lys Thr His Thr Cys Pro Pro Cys Pro Ala Pro
        130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Asp Glu Leu Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys
        355

<210> SEQ ID NO 317
<211> LENGTH: 359
<212> TYPE: PRT
<213> ORGANISM: Artificial Sequence
<220> FEATURE:
<223> OTHER INFORMATION: Synthetic Construct

<400> SEQUENCE: 317

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Tyr Ser Arg Lys
            20                  25                  30

Cys Arg Gly Trp Phe Arg Gln Ala Pro Gly Lys Gly Leu Glu Gly Val
        35                  40                  45

Ala Thr Leu Tyr Thr Ser Ser Gly Gly Thr Tyr Phe Asp Thr Tyr Ala
    50                  55                  60

Asp Ser Val Arg Gly Arg Phe Thr Ile Ser Gln Asp Asn Ser Lys Asn
65                  70                  75                  80

Thr Leu Tyr Leu Gln Met Asn Ser Leu Arg Ala Glu Asp Thr Ala Val
                85                  90                  95

Tyr Tyr Cys Ala Ala Arg Leu Ser Thr Asp Phe Cys Gly Pro Arg Ala
```

```
            100                 105                 110
Asp Phe Asp Tyr Trp Gly Gln Gly Thr Leu Val Thr Val Ser Ser Glu
            115                 120                 125

Pro Lys Ser Cys Asp Lys Thr His Thr Cys Pro Pro Cys Pro Ala Pro
130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
                180                 185                 190

Gly Val Glu Val His Asn Ala Lys Thr Lys Pro Arg Glu Glu Gln Tyr
            195                 200                 205

Asn Ser Thr Tyr Arg Val Val Ser Val Leu Thr Val Leu His Gln Asp
            210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Asp Glu Leu Thr Lys
                260                 265                 270

Asn Gln Val Ser Leu Thr Cys Leu Val Lys Gly Phe Tyr Pro Ser Asp
            275                 280                 285

Ile Ala Val Glu Trp Glu Ser Asn Gly Gln Pro Glu Asn Asn Tyr Lys
            290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
                340                 345                 350

Leu Ser Leu Ser Pro Gly Lys
            355

<210> SEQ ID NO 318
<211> LENGTH: 359
<212> TYPE: PRT
<213> ORGANISM: Artificial Sequence
<220> FEATURE:
<223> OTHER INFORMATION: Synthetic Construct

<400> SEQUENCE: 318

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Tyr Ser Arg Lys
            20                  25                  30

Cys Arg Gly Trp Phe Arg Gln Ala Pro Gly Lys Gly Leu Glu Gly Val
        35                  40                  45

Ala Thr Leu Tyr Thr Ser Ser Gly Gly Thr Tyr Phe Asp Thr Tyr Ala
    50                  55                  60

Asp Ser Val Arg Gly Arg Phe Thr Ile Ser Arg Asp Asn Ser Lys Asn
65                  70                  75                  80

Thr Leu Tyr Leu Gln Met Asn Ser Leu Arg Ala Glu Asp Thr Ala Val
                85                  90                  95

Tyr Tyr Cys Ala Ala Arg Leu Ser Thr Asp Phe Cys Gly Pro Arg Ala
```

```
                    100                 105                 110
Asp Phe Asp Tyr Trp Gly Gln Gly Thr Leu Val Thr Val Ser Ser Glu
            115                 120                 125

Pro Lys Ser Cys Asp Lys Thr His Thr Cys Pro Pro Cys Pro Ala Pro
130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Asp Glu Leu Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys
        355

<210> SEQ ID NO 319
<211> LENGTH: 359
<212> TYPE: PRT
<213> ORGANISM: Artificial Sequence
<220> FEATURE:
<223> OTHER INFORMATION: Synthetic Construct

<400> SEQUENCE: 319

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Tyr Ser Arg Lys
            20                  25                  30

Cys Arg Gly Trp Phe Arg Gln Ala Pro Gly Lys Gly Leu Glu Gly Val
        35                  40                  45

Ala Thr Leu Tyr Thr Ser Ser Gly Gly Thr Tyr Phe Asp Thr Tyr Ala
    50                  55                  60

Asp Ser Val Arg Gly Arg Phe Thr Ile Ser Arg Asp Asn Ser Lys Asn
65                  70                  75                  80

Thr Val Tyr Leu Gln Met Asn Ser Leu Arg Ala Glu Asp Thr Ala Val
                85                  90                  95

Tyr Tyr Cys Ala Ala Arg Leu Ser Thr Asp Phe Cys Gly Pro Arg Ala
```

```
              100                 105                 110
Asp Phe Asp Tyr Trp Gly Gln Gly Thr Leu Val Thr Val Ser Ser Glu
            115                 120                 125

Pro Lys Ser Cys Asp Lys Thr His Thr Cys Pro Pro Cys Pro Ala Pro
130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Asp Glu Leu Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys
        355

<210> SEQ ID NO 320
<211> LENGTH: 359
<212> TYPE: PRT
<213> ORGANISM: Artificial Sequence
<220> FEATURE:
<223> OTHER INFORMATION: Synthetic Construct

<400> SEQUENCE: 320

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Tyr Ser Arg Lys
            20                  25                  30

Cys Arg Gly Trp Phe Arg Gln Ala Pro Gly Lys Gly Arg Glu Gly Val
        35                  40                  45

Ser Thr Leu Tyr Thr Ser Ser Gly Gly Thr Tyr Phe Asp Thr Tyr Ala
    50                  55                  60

Asp Ser Val Arg Gly Arg Phe Thr Ile Ser Arg Asp Asn Ala Lys Asn
65                  70                  75                  80

Thr Leu Tyr Leu Gln Met Asn Ser Leu Arg Ala Glu Asp Thr Ala Val
                85                  90                  95

Tyr Tyr Cys Ala Ala Arg Leu Ser Thr Asp Phe Cys Gly Pro Arg Ala
```

```
            100                 105                 110
Asp Phe Asp Tyr Trp Gly Gln Gly Thr Leu Val Thr Val Ser Ser Glu
            115                 120                 125

Pro Lys Ser Cys Asp Lys Thr His Thr Cys Pro Pro Cys Pro Ala Pro
        130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Asp Glu Leu Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys
        355

<210> SEQ ID NO 321
<211> LENGTH: 359
<212> TYPE: PRT
<213> ORGANISM: Artificial Sequence
<220> FEATURE:
<223> OTHER INFORMATION: Synthetic Construct

<400> SEQUENCE: 321

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Tyr Ser Arg Lys
            20                  25                  30

Cys Arg Gly Trp Phe Arg Gln Ala Pro Gly Lys Gly Arg Glu Gly Val
        35                  40                  45

Ala Thr Leu Tyr Thr Ser Ser Gly Gly Thr Tyr Phe Asp Thr Tyr Ala
    50                  55                  60

Asp Ser Val Arg Gly Arg Phe Thr Ile Ser Arg Asp Asn Ala Lys Asn
65                  70                  75                  80

Thr Leu Tyr Leu Gln Met Asn Ser Leu Arg Pro Glu Asp Thr Ala Val
                85                  90                  95

Tyr Tyr Cys Ala Ala Arg Leu Ser Thr Asp Phe Cys Gly Pro Arg Ala
```

```
                        100                 105                  110
Asp Phe Asp Tyr Trp Gly Gln Gly Thr Leu Val Thr Val Ser Ser Glu
                    115                 120                 125

Pro Lys Ser Cys Asp Lys Thr His Thr Cys Pro Pro Cys Pro Ala Pro
        130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Asp Glu Leu Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys
        355

<210> SEQ ID NO 322
<211> LENGTH: 359
<212> TYPE: PRT
<213> ORGANISM: Artificial Sequence
<220> FEATURE:
<223> OTHER INFORMATION: Synthetic Construct

<400> SEQUENCE: 322

Glu Val Gln Leu Val Glu Ser Gly Gly Gly Leu Val Gln Pro Gly Gly
1               5                  10                  15

Ser Leu Arg Leu Ser Cys Ala Ala Ser Gly Tyr Thr Tyr Ser Arg Lys
            20                  25                  30

Cys Arg Gly Trp Phe Arg Gln Ala Pro Gly Lys Gly Arg Glu Gly Val
        35                  40                  45

Ala Thr Leu Tyr Thr Ser Ser Gly Gly Thr Tyr Phe Asp Thr Tyr Ala
    50                  55                  60

Asp Ser Val Arg Gly Arg Phe Thr Ile Ser Arg Asp Asn Ala Lys Asn
65                  70                  75                  80

Thr Val Tyr Leu Gln Met Asn Ser Leu Arg Pro Glu Asp Thr Ala Val
                85                  90                  95

Tyr Tyr Cys Ala Ala Arg Leu Ser Thr Asp Phe Cys Gly Pro Arg Ala
```

```
                100                 105                 110
Asp Phe Asp Tyr Trp Gly Gln Gly Thr Leu Val Thr Val Ser Ser Glu
            115                 120                 125

Pro Lys Ser Cys Asp Lys Thr His Thr Cys Pro Pro Cys Pro Ala Pro
        130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Asp Glu Leu Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys
        355

<210> SEQ ID NO 323
<211> LENGTH: 449
<212> TYPE: PRT
<213> ORGANISM: Artificial Sequence
<220> FEATURE:
<223> OTHER INFORMATION: Synthetic Construct

<400> SEQUENCE: 323

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Met
        35                  40                  45

Gly Glu Ile Phe Pro Arg Arg Val Gln Thr Tyr Tyr Ser Glu Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
```

```
            100                 105                 110
Thr Thr Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 324
<211> LENGTH: 12
<212> TYPE: PRT
<213> ORGANISM: Artificial Sequence
<220> FEATURE:
<223> OTHER INFORMATION: Synthetic Construct

<400> SEQUENCE: 324

Glu Ser Lys Tyr Gly Pro Pro Cys Pro Pro Cys Pro
1               5                   10
```

<210> SEQ ID NO 325
<211> LENGTH: 447
<212> TYPE: PRT
<213> ORGANISM: Artificial Sequence
<220> FEATURE:
<223> OTHER INFORMATION: Synthetic Construct

<400> SEQUENCE: 325

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Tyr Met Tyr Trp Val Arg Gln Ala Pro Gly Gln Gly Leu Glu Trp Met
            35                  40                  45

Gly Gly Ile Asn Pro Ser Asn Gly Gly Thr Asn Phe Asn Glu Lys Phe
        50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys
            435                 440                 445

<210> SEQ ID NO 326
<211> LENGTH: 218
<212> TYPE: PRT
<213> ORGANISM: Artificial Sequence
<220> FEATURE:
<223> OTHER INFORMATION: Synthetic Construct

<400> SEQUENCE: 326

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
                20                  25                  30

Gly Tyr Ser Tyr Leu His Trp Tyr Gln Gln Lys Pro Gly Gln Ala Pro
            35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 327
<211> LENGTH: 449
<212> TYPE: PRT
<213> ORGANISM: Artificial Sequence
<220> FEATURE:
<223> OTHER INFORMATION: Synthetic Construct

<400> SEQUENCE: 327

Glu Val Gln Leu Val Gln Ser Gly Ala Glu Val Lys Lys Pro Gly Ala

-continued

```
1               5                   10                  15
Ser Val Lys Val Ser Cys Lys Ala Ser Gly Tyr Ile Phe Thr Gly Tyr
                20                  25                  30
Gly Ile Thr Trp Val Arg Gln Ala Pro Gly Gln Gly Leu Glu Trp Met
                35                  40                  45
Gly Glu Ile Phe Pro Arg Arg Val Gln Thr Tyr Tyr Ser Glu Lys Phe
                50                  55                  60
Lys Gly Arg Val Thr Met Thr Thr Asp Thr Ser Thr Ser Thr Ala Tyr
65                  70                  75                  80
Met Glu Leu Arg Ser Leu Arg Ser Asp Thr Ala Val Tyr Tyr Cys
                85                  90                  95
Ala Arg Asp Tyr Asp Pro Tyr Phe Ala Leu Asp Tyr Trp Gly Gln Gly
                100                 105                 110
Thr Thr Val Thr Val Ser Ser Ala Ser Thr Lys Gly Pro Ser Val Phe
                115                 120                 125
Pro Leu Ala Pro Ser Ser Lys Ser Thr Ser Gly Gly Thr Ala Ala Leu
                130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
                180                 185                 190
Ser Ser Leu Gly Thr Gln Thr Tyr Ile Cys Asn Val Asn His Lys Pro
                195                 200                 205
Ser Asn Thr Lys Val Asp Lys Arg Val Glu Pro Lys Ser Cys Asp Lys
210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
                260                 265                 270
Pro Glu Val Lys Phe Asn Trp Tyr Val Asp Gly Val Glu Val His Asn
                275                 280                 285
Ala Lys Thr Lys Pro Arg Glu Glu Gln Tyr Asn Ser Thr Tyr Arg Val
                290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
                340                 345                 350
Leu Pro Pro Ser Arg Asp Glu Leu Thr Lys Asn Gln Val Ser Leu Thr
                355                 360                 365
Cys Leu Val Lys Gly Phe Tyr Pro Ser Asp Ile Ala Val Glu Trp Glu
                370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
                420                 425                 430
```

Ala Leu His Asn His Tyr Thr Gln Lys Ser Leu Ser Leu Ser Pro Gly
            435                 440                 445

Lys

<210> SEQ ID NO 328
<211> LENGTH: 214
<212> TYPE: PRT
<213> ORGANISM: Artificial Sequence
<220> FEATURE:
<223> OTHER INFORMATION: Synthetic Construct

<400> SEQUENCE: 328

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Asp Trp Tyr Gln Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Ile Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 329
<211> LENGTH: 449
<212> TYPE: PRT
<213> ORGANISM: Artificial Sequence
<220> FEATURE:
<223> OTHER INFORMATION: Synthetic Construct

<400> SEQUENCE: 329

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Met
        35                  40                  45

Gly Glu Ile Phe Pro Arg Arg Val Gln Thr Tyr Tyr Ser Glu Lys Phe
    50                  55                  60

```
Lys Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Asp Tyr Asp Pro Tyr Phe Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 330
<211> LENGTH: 214
<212> TYPE: PRT
```

```
<213> ORGANISM: Artificial Sequence
<220> FEATURE:
<223> OTHER INFORMATION: Synthetic Construct

<400> SEQUENCE: 330

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Asp Trp Tyr Gln Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Ile Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 331
<211> LENGTH: 448
<212> TYPE: PRT
<213> ORGANISM: Artificial Sequence
<220> FEATURE:
<223> OTHER INFORMATION: Synthetic Construct

<400> SEQUENCE: 331

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110
```

```
Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 332
<211> LENGTH: 214
<212> TYPE: PRT
<213> ORGANISM: Artificial Sequence
<220> FEATURE:
<223> OTHER INFORMATION: Synthetic Construct

<400> SEQUENCE: 332

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30
```

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
 50                      55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 333
<211> LENGTH: 448
<212> TYPE: PRT
<213> ORGANISM: Artificial Sequence
<220> FEATURE:
<223> OTHER INFORMATION: Synthetic Construct

<400> SEQUENCE: 333

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

```
Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Ala Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 334
<211> LENGTH: 214
<212> TYPE: PRT
<213> ORGANISM: Artificial Sequence
<220> FEATURE:
<223> OTHER INFORMATION: Synthetic Construct

<400> SEQUENCE: 334

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
            85                  90                  95
```

Thr Phe Gly Gln Gly Thr Lys Val Glu Ile Lys Arg Thr Val Ala Ala
               100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 335
<211> LENGTH: 461
<212> TYPE: PRT
<213> ORGANISM: Artificial Sequence
<220> FEATURE:
<223> OTHER INFORMATION: Synthetic Construct

<400> SEQUENCE: 335

Ser Gln Val Gln Leu Gln Glu Ser Gly Pro Gly Leu Val Lys Pro Ser
1               5                   10                  15

Glu Thr Leu Ser Leu Thr Cys Thr Val Ser Gly Gly Ser Val Ser Ser
            20                  25                  30

Gly Ile Tyr Tyr Trp Ser Trp Ile Arg Gln Pro Pro Gly Lys Gly Leu
        35                  40                  45

Glu Trp Ile Gly Tyr Ile Tyr Tyr Ser Gly Ser Thr Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Arg Asp Tyr Tyr Val Ser Gly Asn Tyr Tyr Asn Val Asp
            100                 105                 110

Tyr Tyr Phe Phe Gly Val Asp Val Trp Gly Gln Gly Thr Thr Val Thr
        115                 120                 125

Val Ser Ser Ala Ser Thr Lys Gly Pro Ser Val Phe Pro Leu Ala Pro
    130                 135                 140

Ser Ser Lys Ser Thr Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Ser Leu Gly
        195                 200                 205

Thr Gln Thr Tyr Ile Cys Asn Val Asn His Lys Pro Ser Asn Thr Lys
    210                 215                 220

Val Asp Lys Arg Val Glu Pro Lys Ser Cys Asp Lys Thr His Thr Cys
225                 230                 235                 240

```
Pro Pro Cys Pro Ala Pro Glu Leu Leu Gly Pro Ser Val Phe Leu
            245                 250                 255

Phe Pro Pro Lys Pro Lys Asp Thr Leu Met Ile Ser Arg Thr Pro Glu
        260                 265                 270

Val Thr Cys Val Val Val Asp Val Ser His Glu Asp Pro Glu Val Lys
    275                 280                 285

Phe Asn Trp Tyr Val Asp Gly Val Glu Val His Asn Ala Lys Thr Lys
    290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Pro Ile Glu Lys Thr Ile Ser Lys
            340                 345                 350

Ala Lys Gly Gln Pro Arg Glu Pro Gln Val Tyr Thr Leu Pro Pro Ser
        355                 360                 365

Arg Asp Glu Leu Thr Lys Asn Gln Val Ser Leu Thr Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn
        435                 440                 445

His Tyr Thr Gln Lys Ser Leu Ser Leu Ser Pro Gly Lys
    450                 455                 460

<210> SEQ ID NO 336
<211> LENGTH: 216
<212> TYPE: PRT
<213> ORGANISM: Artificial Sequence
<220> FEATURE:
<223> OTHER INFORMATION: Synthetic Construct

<400> SEQUENCE: 336

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Leu Phe Thr Phe Gly Pro Gly Thr Lys Val Asp Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140
```

```
Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
            165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
            195                 200                 205

Lys Ser Phe Asn Arg Gly Glu Cys
    210                 215

<210> SEQ ID NO 337
<211> LENGTH: 449
<212> TYPE: PRT
<213> ORGANISM: Artificial Sequence
<220> FEATURE:
<223> OTHER INFORMATION: Synthetic Construct

<400> SEQUENCE: 337

Glu Val Gln Leu Val Glu Ser Gly Gly Gly Leu Thr Gln Pro Gly Lys
1               5                   10                  15

Ser Leu Lys Leu Ser Cys Glu Ala Ser Gly Phe Thr Phe Ser Ser Phe
            20                  25                  30

Thr Met His Trp Val Arg Gln Ser Pro Gly Lys Gly Leu Glu Trp Val
            35                  40                  45

Ala Phe Ile Arg Ser Gly Ser Gly Ile Val Phe Tyr Ala Asp Ala Val
    50                  55                  60

Arg Gly Arg Phe Thr Ile Ser Arg Asp Asn Ala Lys Asn Leu Leu Phe
65                  70                  75                  80

Leu Gln Met Asn Asp Leu Lys Ser Glu Asp Thr Ala Met Tyr Tyr Cys
                85                  90                  95

Ala Arg Arg Pro Leu Gly His Asn Thr Phe Asp Ser Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285
```

```
Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 338
<211> LENGTH: 220
<212> TYPE: PRT
<213> ORGANISM: Artificial Sequence
<220> FEATURE:
<223> OTHER INFORMATION: Synthetic Construct

<400> SEQUENCE: 338

Asp Ile Val Met Thr Gln Ser Pro Ser Ser Leu Ala Val Ser Pro Gly
1               5                   10                  15

Glu Lys Val Thr Met Thr Cys Lys Ser Ser Gln Ser Leu Tyr Tyr Ser
            20                  25                  30

Gly Val Lys Glu Asn Leu Leu Ala Trp Tyr Gln Gln Lys Pro Gly Gln
        35                  40                  45

Ser Pro Lys Leu Leu Ile Tyr Tyr Ala Ser Ile Arg Phe Thr Gly Val
    50                  55                  60

Pro Asp Arg Phe Thr Gly Ser Gly Ser Gly Thr Asp Tyr Thr Leu Thr
65                  70                  75                  80

Ile Thr Ser Val Gln Ala Glu Asp Met Gly Gln Tyr Phe Cys Gln Gln
                85                  90                  95

Gly Ile Asn Asn Pro Leu Thr Phe Gly Asp Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
```

```
              195                 200                 205

Ser Pro Val Thr Lys Ser Phe Asn Arg Gly Glu Cys
    210                 215                 220

<210> SEQ ID NO 339
<211> LENGTH: 119
<212> TYPE: PRT
<213> ORGANISM: Artificial Sequence
<220> FEATURE:
<223> OTHER INFORMATION: Synthetic Construct

<400> SEQUENCE: 339

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Met
        35                  40                  45

Gly Glu Ile Phe Pro Arg Arg Val Gln Thr Tyr Tyr Ser Glu Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser
        115

<210> SEQ ID NO 340
<211> LENGTH: 107
<212> TYPE: PRT
<213> ORGANISM: Artificial Sequence
<220> FEATURE:
<223> OTHER INFORMATION: Synthetic Construct

<400> SEQUENCE: 340

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Asp Trp Tyr Gln Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Ile Pro Phe
                85                  90                  95

Thr Phe Gly Gln Gly Thr Lys Leu Glu Ile Lys
            100                 105

<210> SEQ ID NO 341
<211> LENGTH: 589
<212> TYPE: PRT
<213> ORGANISM: Artificial Sequence
<220> FEATURE:
<223> OTHER INFORMATION: Synthetic Construct

<400> SEQUENCE: 341
```

```
Gln Val Gln Leu Ala Glu Ser Gly Gly Gly Val Gln Ala Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Leu Ala Pro Gly Lys Glu Arg Glu Gly Val
        35                  40                  45

Ala Ala Ile Cys Ser Gly Gly Arg Thr Thr Tyr Ser Asp Ser Val Lys
50                  55                  60

Gly Arg Phe Thr Ile Ser Lys Asp Ser Ala Asn Gln Ile Leu Tyr Leu
65                  70                  75                  80

Gln Met Asn Ser Leu Lys Pro Glu Asp Thr Ala Met Tyr Tyr Cys Ala
            85                  90                  95

Ala Arg Pro Leu Trp Thr Gly Asp Cys Asp Leu Ser Ser Ser Trp Tyr
        100                 105                 110

Lys Thr Trp Gly Gln Gly Thr Gln Val Thr Val Ser Ser Glu Pro Lys
        115                 120                 125

Ser Ser Asp Lys Thr His Thr Ser Pro Pro Ser Pro Glu Val Gln Leu
    130                 135                 140

Val Gln Ser Gly Ala Glu Val Lys Lys Pro Gly Ala Ser Val Lys Val
145                 150                 155                 160

Ser Cys Lys Ala Ser Gly Tyr Ile Phe Thr Gly Tyr Gly Ile Thr Trp
            165                 170                 175

Val Arg Gln Ala Pro Gly Gln Gly Leu Glu Trp Met Gly Glu Ile Phe
        180                 185                 190

Pro Arg Arg Val Gln Thr Tyr Tyr Ser Glu Lys Phe Lys Gly Arg Val
        195                 200                 205

Thr Met Thr Thr Asp Thr Ser Thr Ser Thr Ala Tyr Met Glu Leu Arg
210                 215                 220

Ser Leu Arg Ser Asp Asp Thr Ala Val Tyr Tyr Cys Ala Arg Asp Tyr
225                 230                 235                 240

Asp Pro Tyr Phe Ala Leu Asp Tyr Trp Gly Gln Gly Thr Thr Val Thr
            245                 250                 255

Val Ser Ser Ala Ser Thr Lys Gly Pro Ser Val Phe Pro Leu Ala Pro
        260                 265                 270

Ser Ser Lys Ser Thr Ser Gly Gly Thr Ala Ala Leu Gly Cys Leu Val
        275                 280                 285

Lys Asp Tyr Phe Pro Glu Pro Val Thr Val Ser Trp Asn Ser Gly Ala
    290                 295                 300

Leu Thr Ser Gly Val His Thr Phe Pro Ala Val Leu Gln Ser Ser Gly
305                 310                 315                 320

Leu Tyr Ser Leu Ser Ser Val Val Thr Val Pro Ser Ser Ser Leu Gly
            325                 330                 335

Thr Gln Thr Tyr Ile Cys Asn Val Asn His Lys Pro Ser Asn Thr Lys
        340                 345                 350

Val Asp Lys Lys Val Glu Pro Lys Ser Cys Asp Lys Thr His Thr Cys
        355                 360                 365

Pro Pro Cys Pro Ala Pro Glu Leu Leu Gly Gly Pro Ser Val Phe Leu
370                 375                 380

Phe Pro Pro Lys Pro Lys Asp Thr Leu Met Ile Ser Arg Thr Pro Glu
385                 390                 395                 400

Val Thr Cys Val Val Val Asp Val Ser His Glu Asp Pro Glu Val Lys
            405                 410                 415
```

```
Phe Asn Trp Tyr Val Asp Gly Val Glu Val His Asn Ala Lys Thr Lys
                420                 425                 430

Pro Arg Glu Glu Gln Tyr Ala Ser Thr Tyr Arg Val Val Ser Val Leu
            435                 440                 445

Thr Val Leu His Gln Asp Trp Leu Asn Gly Lys Glu Tyr Lys Cys Lys
        450                 455                 460

Val Ser Asn Lys Ala Leu Pro Ala Pro Ile Glu Lys Thr Ile Ser Lys
465                 470                 475                 480

Ala Lys Gly Gln Pro Arg Glu Pro Gln Val Tyr Thr Leu Pro Pro Ser
                485                 490                 495

Arg Glu Glu Met Thr Lys Asn Gln Val Ser Leu Thr Cys Leu Val Lys
            500                 505                 510

Gly Phe Tyr Pro Ser Asp Ile Ala Val Glu Trp Glu Ser Asn Gly Gln
        515                 520                 525

Pro Glu Asn Asn Tyr Lys Thr Thr Pro Pro Val Leu Asp Ser Asp Gly
            530                 535                 540

Ser Phe Phe Leu Tyr Ser Lys Leu Thr Val Asp Lys Ser Arg Trp Gln
545                 550                 555                 560

Gln Gly Asn Val Phe Ser Cys Ser Val Met His Glu Ala Leu His Asn
                565                 570                 575

His Tyr Thr Gln Lys Ser Leu Ser Leu Ser Pro Gly Lys
            580                 585

<210> SEQ ID NO 342
<211> LENGTH: 214
<212> TYPE: PRT
<213> ORGANISM: Artificial Sequence
<220> FEATURE:
<223> OTHER INFORMATION: Synthetic Construct

<400> SEQUENCE: 342

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Asp Trp Tyr Gln Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Ile Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

Ala Cys Glu Val Thr His Gln Gly Leu Ser Ser Pro Val Thr Lys Ser
            195                 200                 205

Phe Asn Arg Gly Glu Cys
            210

<210> SEQ ID NO 343
<211> LENGTH: 589
<212> TYPE: PRT
<213> ORGANISM: Artificial Sequence
<220> FEATURE:
<223> OTHER INFORMATION: Synthetic Construct

<400> SEQUENCE: 343

Gln Val Gln Leu Ala Glu Ser Gly Gly Gly Ser Val Gln Ala Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Leu Ala Pro Gly Lys Glu Arg Glu Gly Val
        35                  40                  45

Ala Ala Ile Cys Ser Gly Gly Arg Thr Thr Tyr Ser Asp Ser Val Lys
    50                  55                  60

Gly Arg Phe Thr Ile Ser Lys Asp Ser Ala Asn Gln Ile Leu Tyr Leu
65                  70                  75                  80

Gln Met Asn Ser Leu Lys Pro Glu Asp Thr Ala Met Tyr Tyr Cys Ala
                85                  90                  95

Ala Arg Pro Leu Trp Thr Gly Asp Cys Asp Leu Ser Ser Ser Trp Tyr
            100                 105                 110

Lys Thr Trp Gly Gln Gly Thr Gln Val Thr Val Ser Ser Glu Pro Lys
        115                 120                 125

Ser Ser Asp Lys Thr His Thr Ser Pro Pro Ser Pro Glu Val Gln Leu
    130                 135                 140

Val Gln Ser Gly Ala Glu Val Lys Lys Pro Gly Ala Ser Val Lys Val
145                 150                 155                 160

Ser Cys Lys Ala Ser Gly Tyr Ile Phe Thr Gly Tyr Gly Ile Thr Trp
                165                 170                 175

Val Arg Gln Ala Pro Gly Gln Gly Leu Glu Trp Met Gly Glu Ile Phe
            180                 185                 190

Pro Arg Arg Val Gln Thr Tyr Tyr Ser Glu Lys Phe Lys Gly Arg Val
        195                 200                 205

Thr Met Thr Thr Asp Thr Ser Thr Ser Thr Ala Tyr Met Glu Leu Arg
    210                 215                 220

Ser Leu Arg Ser Asp Asp Thr Ala Val Tyr Tyr Cys Ala Arg Asp Tyr
225                 230                 235                 240

Asp Pro Tyr Phe Ala Leu Asp Tyr Trp Gly Gln Gly Thr Thr Val Thr
                245                 250                 255

Val Ser Ser Ala Ser Thr Lys Gly Pro Ser Val Phe Pro Leu Ala Pro
            260                 265                 270

Ser Ser Lys Ser Thr Ser Gly Gly Thr Ala Ala Leu Gly Cys Leu Val
        275                 280                 285

Lys Asp Tyr Phe Pro Glu Pro Val Thr Val Ser Trp Asn Ser Gly Ala
    290                 295                 300

Leu Thr Ser Gly Val His Thr Phe Pro Ala Val Leu Gln Ser Ser Gly
305                 310                 315                 320

Leu Tyr Ser Leu Ser Ser Val Val Thr Val Pro Ser Ser Leu Gly
                325                 330                 335

```
Thr Gln Thr Tyr Ile Cys Asn Val Asn His Lys Pro Ser Asn Thr Lys
                340                 345                 350

Val Asp Lys Arg Val Glu Pro Lys Ser Cys Asp Lys Thr His Thr Cys
            355                 360                 365

Pro Pro Cys Pro Ala Pro Glu Leu Leu Gly Gly Pro Ser Val Phe Leu
        370                 375                 380

Phe Pro Pro Lys Pro Lys Asp Thr Leu Met Ile Ser Arg Thr Pro Glu
385                 390                 395                 400

Val Thr Cys Val Val Val Asp Val Ser His Glu Asp Pro Glu Val Lys
                405                 410                 415

Phe Asn Trp Tyr Val Asp Gly Val Glu Val His Asn Ala Lys Thr Lys
            420                 425                 430

Pro Arg Glu Glu Gln Tyr Asn Ser Thr Tyr Arg Val Val Ser Val Leu
        435                 440                 445

Thr Val Leu His Gln Asp Trp Leu Asn Gly Lys Glu Tyr Lys Cys Lys
    450                 455                 460

Val Ser Asn Lys Ala Leu Pro Ala Pro Ile Glu Lys Thr Ile Ser Lys
465                 470                 475                 480

Ala Lys Gly Gln Pro Arg Glu Pro Gln Val Tyr Thr Leu Pro Pro Ser
                485                 490                 495

Arg Asp Glu Leu Thr Lys Asn Gln Val Ser Leu Thr Cys Leu Val Lys
            500                 505                 510

Gly Phe Tyr Pro Ser Asp Ile Ala Val Glu Trp Glu Ser Asn Gly Gln
        515                 520                 525

Pro Glu Asn Asn Tyr Lys Thr Thr Pro Pro Val Leu Asp Ser Asp Gly
    530                 535                 540

Ser Phe Phe Leu Tyr Ser Lys Leu Thr Val Asp Lys Ser Arg Trp Gln
545                 550                 555                 560

Gln Gly Asn Val Phe Ser Cys Ser Val Met His Glu Ala Leu His Asn
                565                 570                 575

His Tyr Thr Gln Lys Ser Leu Ser Leu Ser Pro Gly Lys
            580                 585

<210> SEQ ID NO 344
<211> LENGTH: 214
<212> TYPE: PRT
<213> ORGANISM: Artificial Sequence
<220> FEATURE:
<223> OTHER INFORMATION: Synthetic Construct

<400> SEQUENCE: 344

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Asp Trp Tyr Gln Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Ile Pro Phe
                85                  90                  95

Thr Phe Gly Gln Gly Thr Lys Leu Glu Ile Lys Arg Thr Val Ala Ala
            100                 105                 110
```

```
Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 345
<211> LENGTH: 588
<212> TYPE: PRT
<213> ORGANISM: Artificial Sequence
<220> FEATURE:
<223> OTHER INFORMATION: Synthetic Construct

<400> SEQUENCE: 345

Gln Val Gln Leu Ala Glu Ser Gly Gly Gly Ser Val Gln Ala Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Leu Ala Pro Gly Lys Glu Arg Glu Gly Val
        35                  40                  45

Ala Ala Ile Cys Ser Gly Gly Arg Thr Thr Tyr Ser Asp Ser Val Lys
    50                  55                  60

Gly Arg Phe Thr Ile Ser Lys Asp Ser Ala Asn Gln Ile Leu Tyr Leu
65                  70                  75                  80

Gln Met Asn Ser Leu Lys Pro Glu Asp Thr Ala Met Tyr Tyr Cys Ala
                85                  90                  95

Ala Arg Pro Leu Trp Thr Gly Asp Cys Asp Leu Ser Ser Ser Trp Tyr
            100                 105                 110

Lys Thr Trp Gly Gln Gly Thr Gln Val Thr Val Ser Ser Glu Pro Lys
        115                 120                 125

Ser Ser Asp Lys Thr His Thr Ser Pro Pro Ser Pro Glu Val Gln Leu
    130                 135                 140

Val Glu Ser Gly Gly Gly Leu Val Gln Pro Gly Gly Ser Leu Arg Leu
145                 150                 155                 160

Ser Cys Ala Ala Ser Gly Phe Thr Phe Ser Asp Ser Trp Ile His Trp
                165                 170                 175

Val Arg Gln Ala Pro Gly Lys Gly Leu Glu Trp Val Ala Trp Ile Ser
            180                 185                 190

Pro Tyr Gly Gly Ser Thr Tyr Tyr Ala Asp Ser Val Lys Gly Arg Phe
        195                 200                 205

Thr Ile Ser Ala Asp Thr Ser Lys Asn Thr Ala Tyr Leu Gln Met Asn
    210                 215                 220

Ser Leu Arg Ala Glu Asp Thr Ala Val Tyr Tyr Cys Ala Arg Arg His
225                 230                 235                 240

Trp Pro Gly Gly Phe Asp Tyr Trp Gly Gln Gly Thr Leu Val Thr Val
                245                 250                 255
```

```
Ser Ser Ala Ser Thr Lys Gly Pro Ser Val Phe Pro Leu Ala Pro Ser
            260                 265                 270

Ser Lys Ser Thr Ser Gly Gly Thr Ala Ala Leu Gly Cys Leu Val Lys
        275                 280                 285

Asp Tyr Phe Pro Glu Pro Val Thr Val Ser Trp Asn Ser Gly Ala Leu
    290                 295                 300

Thr Ser Gly Val His Thr Phe Pro Ala Val Leu Gln Ser Ser Gly Leu
305                 310                 315                 320

Tyr Ser Leu Ser Ser Val Val Thr Val Pro Ser Ser Ser Leu Gly Thr
                325                 330                 335

Gln Thr Tyr Ile Cys Asn Val Asn His Lys Pro Ser Asn Thr Lys Val
            340                 345                 350

Asp Lys Lys Val Glu Pro Lys Ser Cys Asp Lys Thr His Thr Cys Pro
        355                 360                 365

Pro Cys Pro Ala Pro Glu Leu Leu Gly Gly Pro Ser Val Phe Leu Phe
    370                 375                 380

Pro Pro Lys Pro Lys Asp Thr Leu Met Ile Ser Arg Thr Pro Glu Val
385                 390                 395                 400

Thr Cys Val Val Val Asp Val Ser His Glu Asp Pro Glu Val Lys Phe
                405                 410                 415

Asn Trp Tyr Val Asp Gly Val Glu Val His Asn Ala Lys Thr Lys Pro
            420                 425                 430

Arg Glu Glu Gln Tyr Ala Ser Thr Tyr Arg Val Val Ser Val Leu Thr
        435                 440                 445

Val Leu His Gln Asp Trp Leu Asn Gly Lys Glu Tyr Lys Cys Lys Val
    450                 455                 460

Ser Asn Lys Ala Leu Pro Ala Pro Ile Glu Lys Thr Ile Ser Lys Ala
465                 470                 475                 480

Lys Gly Gln Pro Arg Glu Pro Gln Val Tyr Thr Leu Pro Pro Ser Arg
                485                 490                 495

Glu Glu Met Thr Lys Asn Gln Val Ser Leu Thr Cys Leu Val Lys Gly
            500                 505                 510

Phe Tyr Pro Ser Asp Ile Ala Val Glu Trp Glu Ser Asn Gly Gln Pro
        515                 520                 525

Glu Asn Asn Tyr Lys Thr Thr Pro Pro Val Leu Asp Ser Asp Gly Ser
    530                 535                 540

Phe Phe Leu Tyr Ser Lys Leu Thr Val Asp Lys Ser Arg Trp Gln Gln
545                 550                 555                 560

Gly Asn Val Phe Ser Cys Ser Val Met His Glu Ala Leu His Asn His
                565                 570                 575

Tyr Thr Gln Lys Ser Leu Ser Leu Ser Pro Gly Lys
            580                 585

<210> SEQ ID NO 346
<211> LENGTH: 214
<212> TYPE: PRT
<213> ORGANISM: Artificial Sequence
<220> FEATURE:
<223> OTHER INFORMATION: Synthetic Construct

<400> SEQUENCE: 346

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30
```

```
Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 347
<211> LENGTH: 588
<212> TYPE: PRT
<213> ORGANISM: Artificial Sequence
<220> FEATURE:
<223> OTHER INFORMATION: Synthetic Construct

<400> SEQUENCE: 347

Gln Val Gln Leu Ala Glu Ser Gly Gly Gly Ser Val Gln Ala Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Leu Ala Pro Gly Lys Glu Arg Glu Gly Val
            35                  40                  45

Ala Ala Ile Cys Ser Gly Gly Arg Thr Thr Tyr Ser Asp Ser Val Lys
 50                  55                  60

Gly Arg Phe Thr Ile Ser Lys Asp Ser Ala Asn Gln Ile Leu Tyr Leu
65                  70                  75                  80

Gln Met Asn Ser Leu Lys Pro Glu Asp Thr Ala Met Tyr Tyr Cys Ala
                85                  90                  95

Ala Arg Pro Leu Trp Thr Gly Asp Cys Asp Leu Ser Ser Ser Trp Tyr
            100                 105                 110

Lys Thr Trp Gly Gln Gly Thr Gln Val Thr Val Ser Ser Glu Pro Lys
            115                 120                 125

Ser Ser Asp Lys Thr His Thr Ser Pro Pro Ser Pro Glu Val Gln Leu
130                 135                 140

Val Glu Ser Gly Gly Gly Leu Val Gln Pro Gly Gly Ser Leu Arg Leu
145                 150                 155                 160

Ser Cys Ala Ala Ser Gly Phe Thr Phe Ser Asp Ser Trp Ile His Trp
                165                 170                 175
```

-continued

```
Val Arg Gln Ala Pro Gly Lys Gly Leu Glu Trp Val Ala Trp Ile Ser
            180                 185                 190
Pro Tyr Gly Ser Thr Tyr Tyr Ala Asp Ser Val Lys Gly Arg Phe
        195                 200                 205
Thr Ile Ser Ala Asp Thr Ser Lys Asn Thr Ala Tyr Leu Gln Met Asn
        210                 215                 220
Ser Leu Arg Ala Glu Asp Thr Ala Val Tyr Tyr Cys Ala Arg Arg His
225                 230                 235                 240
Trp Pro Gly Gly Phe Asp Tyr Trp Gly Gln Gly Thr Leu Val Thr Val
                245                 250                 255
Ser Ser Ala Ser Thr Lys Gly Pro Ser Val Phe Pro Leu Ala Pro Ser
            260                 265                 270
Ser Lys Ser Thr Ser Gly Gly Thr Ala Ala Leu Gly Cys Leu Val Lys
        275                 280                 285
Asp Tyr Phe Pro Glu Pro Val Thr Val Ser Trp Asn Ser Gly Ala Leu
        290                 295                 300
Thr Ser Gly Val His Thr Phe Pro Ala Val Leu Gln Ser Ser Gly Leu
305                 310                 315                 320
Tyr Ser Leu Ser Ser Val Val Thr Val Pro Ser Ser Ser Leu Gly Thr
                325                 330                 335
Gln Thr Tyr Ile Cys Asn Val Asn His Lys Pro Ser Asn Thr Lys Val
            340                 345                 350
Asp Lys Lys Val Glu Pro Lys Ser Cys Asp Lys Thr His Thr Cys Pro
        355                 360                 365
Pro Cys Pro Ala Pro Glu Leu Leu Gly Gly Pro Ser Val Phe Leu Phe
        370                 375                 380
Pro Pro Lys Pro Lys Asp Thr Leu Met Ile Ser Arg Thr Pro Glu Val
385                 390                 395                 400
Thr Cys Val Val Val Asp Val Ser His Glu Asp Pro Glu Val Lys Phe
                405                 410                 415
Asn Trp Tyr Val Asp Gly Val Glu Val His Asn Ala Lys Thr Lys Pro
            420                 425                 430
Arg Glu Glu Gln Tyr Asn Ser Thr Tyr Arg Val Val Ser Val Leu Thr
        435                 440                 445
Val Leu His Gln Asp Trp Leu Asn Gly Lys Glu Tyr Lys Cys Lys Val
        450                 455                 460
Ser Asn Lys Ala Leu Pro Ala Pro Ile Glu Lys Thr Ile Ser Lys Ala
465                 470                 475                 480
Lys Gly Gln Pro Arg Glu Pro Gln Val Tyr Thr Leu Pro Pro Ser Arg
                485                 490                 495
Asp Glu Leu Thr Lys Asn Gln Val Ser Leu Thr Cys Leu Val Lys Gly
            500                 505                 510
Phe Tyr Pro Ser Asp Ile Ala Val Glu Trp Glu Ser Asn Gly Gln Pro
        515                 520                 525
Glu Asn Asn Tyr Lys Thr Thr Pro Pro Val Leu Asp Ser Asp Gly Ser
        530                 535                 540
Phe Phe Leu Tyr Ser Lys Leu Thr Val Asp Lys Ser Arg Trp Gln Gln
545                 550                 555                 560
Gly Asn Val Phe Ser Cys Ser Val Met His Glu Ala Leu His Asn His
                565                 570                 575
Tyr Thr Gln Lys Ser Leu Ser Leu Ser Pro Gly Lys
            580                 585
```

```
<210> SEQ ID NO 348
<211> LENGTH: 214
<212> TYPE: PRT
<213> ORGANISM: Artificial Sequence
<220> FEATURE:
<223> OTHER INFORMATION: Synthetic Construct

<400> SEQUENCE: 348

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 349
<211> LENGTH: 10
<212> TYPE: PRT
<213> ORGANISM: Artificial Sequence
<220> FEATURE:
<223> OTHER INFORMATION: Synthetic Construct

<400> SEQUENCE: 349

Gly Tyr Ile Phe Thr Gly Tyr Gly Ile Thr
1               5                   10

<210> SEQ ID NO 350
<211> LENGTH: 17
<212> TYPE: PRT
<213> ORGANISM: Artificial Sequence
<220> FEATURE:
<223> OTHER INFORMATION: Synthetic Construct

<400> SEQUENCE: 350

Glu Ile Phe Pro Arg Arg Val Gln Thr Tyr Tyr Ser Glu Lys Phe Lys
1               5                   10                  15

Gly
```

```
<210> SEQ ID NO 351
<211> LENGTH: 10
<212> TYPE: PRT
<213> ORGANISM: Artificial Sequence
<220> FEATURE:
<223> OTHER INFORMATION: Synthetic Construct

<400> SEQUENCE: 351

Asp Tyr Asp Pro Tyr Phe Ala Leu Asp Tyr
1               5                   10

<210> SEQ ID NO 352
<211> LENGTH: 11
<212> TYPE: PRT
<213> ORGANISM: Artificial Sequence
<220> FEATURE:
<223> OTHER INFORMATION: Synthetic Construct

<400> SEQUENCE: 352

Arg Ala Ser Gln Asp Val Ser Thr Ala Val Asp
1               5                   10

<210> SEQ ID NO 353
<211> LENGTH: 7
<212> TYPE: PRT
<213> ORGANISM: Artificial Sequence
<220> FEATURE:
<223> OTHER INFORMATION: Synthetic Construct

<400> SEQUENCE: 353

Ser Ala Ser Tyr Arg Tyr Thr
1               5

<210> SEQ ID NO 354
<211> LENGTH: 10
<212> TYPE: PRT
<213> ORGANISM: Artificial Sequence
<220> FEATURE:
<223> OTHER INFORMATION: Synthetic Construct

<400> SEQUENCE: 354

Gln Gln His Tyr Ser Ile Pro Phe Thr Phe
1               5                   10

<210> SEQ ID NO 355
<211> LENGTH: 217
<212> TYPE: PRT
<213> ORGANISM: Artificial Sequence
<220> FEATURE:
<223> OTHER INFORMATION: Synthetic Construct

<400> SEQUENCE: 355

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Ala Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95
```

```
Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
                180                 185                 190

Phe Ser Cys Ser Val Met His Glu Ala Leu His Asn His Tyr Thr Gln
            195                 200                 205

Lys Ser Leu Ser Leu Ser Pro Gly Lys
    210                 215
```

<210> SEQ ID NO 356
<211> LENGTH: 217
<212> TYPE: PRT
<213> ORGANISM: Artificial Sequence
<220> FEATURE:
<223> OTHER INFORMATION: Synthetic Construct

<400> SEQUENCE: 356

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
                180                 185                 190

Phe Ser Cys Ser Val Met His Glu Ala Leu His Asn His Tyr Thr Gln
            195                 200                 205

Lys Ser Leu Ser Leu Ser Pro Gly Lys
    210                 215
```

<210> SEQ ID NO 357

<211> LENGTH: 589
<212> TYPE: PRT
<213> ORGANISM: Artificial Sequence
<220> FEATURE:
<223> OTHER INFORMATION: Synthetic Construct

<400> SEQUENCE: 357

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Gln Ala Pro Gly Lys Gly Leu Glu Gly Val
        35                  40                  45

Ser Ala Ile Cys Ser Gly Gly Arg Thr Thr Tyr Ser Asp Ser Val Lys
    50                  55                  60

Gly Arg Phe Thr Ile Ser Arg Asp Asn Ser Asn Gln Ile Leu Tyr Leu
65                  70                  75                  80

Gln Met Asn Ser Leu Arg Ala Glu Asp Thr Ala Val Tyr Tyr Cys Ala
                85                  90                  95

Ala Arg Pro Leu Trp Thr Gly Asp Cys Asp Leu Ser Ser Trp Tyr
            100                 105                 110

Lys Thr Trp Gly Gln Gly Thr Leu Val Thr Val Ser Ser Glu Pro Lys
            115                 120                 125

Ser Ser Asp Lys Thr His Thr Ser Pro Pro Ser Pro Glu Val Gln Leu
130                 135                 140

Val Gln Ser Gly Ala Glu Val Lys Lys Pro Gly Ala Ser Val Lys Val
145                 150                 155                 160

Ser Cys Lys Ala Ser Gly Tyr Ile Phe Thr Gly Tyr Gly Ile Thr Trp
                165                 170                 175

Val Arg Gln Ala Pro Gly Gln Gly Leu Glu Trp Met Gly Glu Ile Phe
            180                 185                 190

Pro Arg Arg Val Gln Thr Tyr Tyr Ser Glu Lys Phe Lys Gly Arg Val
        195                 200                 205

Thr Met Thr Thr Asp Thr Ser Thr Ser Thr Ala Tyr Met Glu Leu Arg
    210                 215                 220

Ser Leu Arg Ser Asp Asp Thr Ala Val Tyr Tyr Cys Ala Arg Asp Tyr
225                 230                 235                 240

Asp Pro Tyr Phe Ala Leu Asp Tyr Trp Gly Gln Gly Thr Thr Val Thr
                245                 250                 255

Val Ser Ser Ala Ser Thr Lys Gly Pro Ser Val Phe Pro Leu Ala Pro
            260                 265                 270

Ser Ser Lys Ser Thr Ser Gly Gly Thr Ala Ala Leu Gly Cys Leu Val
        275                 280                 285

Lys Asp Tyr Phe Pro Glu Pro Val Thr Val Ser Trp Asn Ser Gly Ala
    290                 295                 300

Leu Thr Ser Gly Val His Thr Phe Pro Ala Val Leu Gln Ser Ser Gly
305                 310                 315                 320

Leu Tyr Ser Leu Ser Ser Val Val Thr Val Pro Ser Ser Ser Leu Gly
                325                 330                 335

Thr Gln Thr Tyr Ile Cys Asn Val Asn His Lys Pro Ser Asn Thr Lys
            340                 345                 350

Val Asp Lys Lys Val Glu Pro Lys Ser Cys Asp Lys Thr His Thr Cys
        355                 360                 365

Pro Pro Cys Pro Ala Pro Glu Leu Leu Gly Gly Pro Ser Val Phe Leu
    370                 375                 380

-continued

Phe Pro Pro Lys Pro Lys Asp Thr Leu Met Ile Ser Arg Thr Pro Glu
385                 390                 395                 400

Val Thr Cys Val Val Val Asp Val Ser His Glu Asp Pro Glu Val Lys
            405                 410                 415

Phe Asn Trp Tyr Val Asp Gly Val Glu Val His Asn Ala Lys Thr Lys
        420                 425                 430

Pro Arg Glu Glu Gln Tyr Asn Ser Thr Tyr Arg Val Val Ser Val Leu
    435                 440                 445

Thr Val Leu His Gln Asp Trp Leu Asn Gly Lys Glu Tyr Lys Cys Lys
450                 455                 460

Val Ser Asn Lys Ala Leu Pro Ala Pro Ile Glu Lys Thr Ile Ser Lys
465                 470                 475                 480

Ala Lys Gly Gln Pro Arg Glu Pro Gln Val Tyr Thr Leu Pro Pro Ser
            485                 490                 495

Arg Asp Glu Leu Thr Lys Asn Gln Val Ser Leu Thr Cys Leu Val Lys
        500                 505                 510

Gly Phe Tyr Pro Ser Asp Ile Ala Val Glu Trp Glu Ser Asn Gly Gln
    515                 520                 525

Pro Glu Asn Asn Tyr Lys Thr Thr Pro Pro Val Leu Asp Ser Asp Gly
    530                 535                 540

Ser Phe Phe Leu Tyr Ser Lys Leu Thr Val Asp Lys Ser Arg Trp Gln
545                 550                 555                 560

Gln Gly Asn Val Phe Ser Cys Ser Val Met His Glu Ala Leu His Asn
            565                 570                 575

His Tyr Thr Gln Lys Ser Leu Ser Leu Ser Pro Gly Lys
        580                 585

<210> SEQ ID NO 358
<211> LENGTH: 214
<212> TYPE: PRT
<213> ORGANISM: Artificial Sequence
<220> FEATURE:
<223> OTHER INFORMATION: Synthetic Construct

<400> SEQUENCE: 358

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Asp Trp Tyr Gln Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Ile Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 359
<211> LENGTH: 589
<212> TYPE: PRT
<213> ORGANISM: Artificial Sequence
<220> FEATURE:
<223> OTHER INFORMATION: Synthetic Construct

<400> SEQUENCE: 359

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Met
        35                  40                  45

Gly Glu Ile Phe Pro Arg Val Gln Thr Tyr Tyr Ser Glu Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Thr Ala Val Tyr Tyr Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

```
Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys Glu Pro Lys Ser Ser Asp Lys Thr His Thr Ser Pro Pro Ser Pro
450                 455                 460

Glu Val Gln Leu Val Glu Ser Gly Gly Leu Val Gln Pro Gly Gly
465                 470                 475                 480

Ser Leu Arg Leu Ser Cys Ala Ala Ser Gly Tyr Lys Tyr Gly Val Tyr
                485                 490                 495

Ser Met Gly Trp Phe Arg Gln Ala Pro Gly Lys Gly Leu Glu Gly Val
            500                 505                 510

Ser Ala Ile Cys Ser Gly Gly Arg Thr Thr Tyr Ser Asp Ser Val Lys
            515                 520                 525

Gly Arg Phe Thr Ile Ser Arg Asp Asn Ser Asn Gln Ile Leu Tyr Leu
530                 535                 540

Gln Met Asn Ser Leu Arg Ala Glu Asp Thr Ala Val Tyr Tyr Cys Ala
545                 550                 555                 560

Ala Arg Pro Leu Trp Thr Gly Asp Cys Asp Leu Ser Ser Ser Trp Tyr
                565                 570                 575

Lys Thr Trp Gly Gln Gly Thr Leu Val Thr Val Ser Ser
            580                 585

<210> SEQ ID NO 360
<211> LENGTH: 214
<212> TYPE: PRT
<213> ORGANISM: Artificial Sequence
<220> FEATURE:
<223> OTHER INFORMATION: Synthetic Construct

<400> SEQUENCE: 360

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
                20                  25                  30

Val Asp Trp Tyr Gln Gln Lys Pro Gly Lys Ala Pro Lys Leu Leu Ile
            35                  40                  45

Tyr Ser Ala Ser Tyr Arg Tyr Thr Gly Val Pro Asp Arg Phe Ser Gly
        50                  55                  60

Ser Gly Ser Gly Thr Asp Phe Thr Phe Thr Ile Ser Ser Leu Gln Pro
65                  70                  75                  80
```

Glu Asp Ile Ala Thr Tyr Tyr Cys Gln Gln His Tyr Ser Ile Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 361
<211> LENGTH: 449
<212> TYPE: PRT
<213> ORGANISM: Artificial Sequence
<220> FEATURE:
<223> OTHER INFORMATION: Synthetic Construct

<400> SEQUENCE: 361

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Met
        35                  40                  45

Gly Glu Ile Phe Pro Arg Arg Val Gln Thr Tyr Tyr Ser Glu Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 362
<211> LENGTH: 354
<212> TYPE: PRT
<213> ORGANISM: Artificial Sequence
<220> FEATURE:
<223> OTHER INFORMATION: Synthetic Construct

<400> SEQUENCE: 362

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Gln Ala Pro Gly Lys Gly Leu Glu Gly Val
        35                  40                  45

Ser Ala Ile Cys Ser Gly Gly Arg Thr Thr Tyr Ser Asp Ser Val Lys
    50                  55                  60

Gly Arg Phe Thr Ile Ser Arg Asp Asn Ser Asn Gln Ile Leu Tyr Leu
65                  70                  75                  80

Gln Met Asn Ser Leu Arg Ala Glu Asp Thr Ala Val Tyr Tyr Cys Ala
                85                  90                  95

Ala Arg Pro Leu Trp Thr Gly Asp Cys Asp Leu Ser Ser Ser Trp Tyr
            100                 105                 110

Lys Thr Trp Gly Gln Gly Thr Leu Val Thr Val Ser Ser Glu Pro Lys
        115                 120                 125

```
Ser Ser Asp Lys Thr His Thr Ser Pro Pro Ser Pro Asp Ile Gln Met
    130                 135                 140

Thr Gln Ser Pro Ser Ser Leu Ser Ala Ser Val Gly Asp Arg Val Thr
145                 150                 155                 160

Ile Thr Cys Arg Ala Ser Gln Asp Val Ser Thr Ala Val Asp Trp Tyr
                165                 170                 175

Gln Gln Lys Pro Gly Lys Ala Pro Lys Leu Leu Ile Tyr Ser Ala Ser
                180                 185                 190

Tyr Arg Tyr Thr Gly Val Pro Asp Arg Phe Ser Gly Ser Gly Ser Gly
            195                 200                 205

Thr Asp Phe Thr Phe Thr Ile Ser Ser Leu Gln Pro Glu Asp Ile Ala
    210                 215                 220

Thr Tyr Tyr Cys Gln Gln His Tyr Ser Ile Pro Phe Thr Phe Gly Gln
225                 230                 235                 240

Gly Thr Lys Leu Glu Ile Lys Arg Thr Val Ala Ala Pro Ser Val Phe
                245                 250                 255

Ile Phe Pro Pro Ser Asp Glu Gln Leu Lys Ser Gly Thr Ala Ser Val
                260                 265                 270

Val Cys Leu Leu Asn Asn Phe Tyr Pro Arg Glu Ala Lys Val Gln Trp
            275                 280                 285

Lys Val Asp Asn Ala Leu Gln Ser Gly Asn Ser Gln Glu Ser Val Thr
    290                 295                 300

Glu Gln Asp Ser Lys Asp Ser Thr Tyr Ser Leu Ser Ser Thr Leu Thr
305                 310                 315                 320

Leu Ser Lys Ala Asp Tyr Glu Lys His Lys Val Tyr Ala Cys Glu Val
                325                 330                 335

Thr His Gln Gly Leu Ser Ser Pro Val Thr Lys Ser Phe Asn Arg Gly
            340                 345                 350

Glu Cys

<210> SEQ ID NO 363
<211> LENGTH: 449
<212> TYPE: PRT
<213> ORGANISM: Artificial Sequence
<220> FEATURE:
<223> OTHER INFORMATION: Synthetic Construct

<400> SEQUENCE: 363

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
                20                  25                  30

Gly Ile Thr Trp Val Arg Gln Ala Pro Gly Gln Gly Leu Glu Trp Met
            35                  40                  45

Gly Glu Ile Phe Pro Arg Arg Val Gln Thr Tyr Tyr Ser Glu Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
                100                 105                 110

Thr Thr Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
```

```
            130                 135                 140
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 364
<211> LENGTH: 354
<212> TYPE: PRT
<213> ORGANISM: Artificial Sequence
<220> FEATURE:
<223> OTHER INFORMATION: Synthetic Construct

<400> SEQUENCE: 364

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Asp Trp Tyr Gln Gln Lys Pro Gly Lys Ala Pro Lys Leu Leu Ile
        35                  40                  45
```

Tyr Ser Ala Ser Tyr Arg Tyr Thr Gly Val Pro Asp Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Ile Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Glu Pro Lys Ser Ser Asp Lys Thr His Thr
    210                 215                 220

Ser Pro Pro Ser Pro Glu Val Gln Leu Val Glu Ser Gly Gly Gly Leu
225                 230                 235                 240

Val Gln Pro Gly Gly Ser Leu Arg Leu Ser Cys Ala Ala Ser Gly Tyr
                245                 250                 255

Lys Tyr Gly Val Tyr Ser Met Gly Trp Phe Arg Gln Ala Pro Gly Lys
            260                 265                 270

Gly Leu Glu Gly Val Ser Ala Ile Cys Ser Gly Gly Arg Thr Thr Tyr
        275                 280                 285

Ser Asp Ser Val Lys Gly Arg Phe Thr Ile Ser Arg Asp Asn Ser Asn
    290                 295                 300

Gln Ile Leu Tyr Leu Gln Met Asn Ser Leu Arg Ala Glu Asp Thr Ala
305                 310                 315                 320

Val Tyr Tyr Cys Ala Ala Arg Pro Leu Trp Thr Gly Asp Cys Asp Leu
                325                 330                 335

Ser Ser Ser Trp Tyr Lys Thr Trp Gly Gln Gly Thr Leu Val Thr Val
            340                 345                 350

Ser Ser

<210> SEQ ID NO 365
<211> LENGTH: 357
<212> TYPE: PRT
<213> ORGANISM: Artificial Sequence
<220> FEATURE:
<223> OTHER INFORMATION: Synthetic Construct

<400> SEQUENCE: 365

Gln Val Gln Leu Ala Glu Ser Gly Gly Gly Ser Val Gln Ala Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Leu Ala Pro Gly Lys Glu Arg Glu Gly Val
        35                  40                  45

Ala Ala Ile Cys Ser Gly Gly Arg Thr Thr Tyr Ser Asp Ser Val Lys
 50                  55                  60

Gly Arg Phe Thr Ile Ser Lys Asp Ser Ala Asn Gln Ile Leu Tyr Leu
 65                  70                  75                  80

Gln Met Asn Ser Leu Lys Pro Glu Asp Thr Ala Met Tyr Tyr Cys Ala
                 85                  90                  95

Ala Arg Pro Leu Trp Thr Gly Asp Cys Asp Leu Ser Ser Ser Trp Tyr
            100                 105                 110

Lys Thr Trp Gly Gln Gly Thr Gln Val Thr Val Ser Ser Glu Pro Lys
        115                 120                 125

Ser Cys Asp Lys Thr His Thr Cys Pro Pro Cys Pro Ala Pro Glu Leu
130                 135                 140

Leu Gly Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Ala Ser
        195                 200                 205

Thr Tyr Arg Val Val Ser Val Leu Thr Val Leu His Gln Asp Trp Leu
210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Glu Glu Met Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
        355

<210> SEQ ID NO 366
<211> LENGTH: 354
<212> TYPE: PRT
<213> ORGANISM: Artificial Sequence
<220> FEATURE:
<223> OTHER INFORMATION: Synthetic Construct

<400> SEQUENCE: 366

Gln Val Gln Leu Ala Glu Ser Gly Gly Gly Ser Val Gln Ala Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Leu Ala Pro Gly Lys Glu Arg Glu Gly Val
        35                  40                  45

Ala Ala Ile Cys Ser Gly Gly Arg Thr Thr Tyr Ser Asp Ser Val Lys
 50                  55                  60

Gly Arg Phe Thr Ile Ser Lys Asp Ser Ala Asn Gln Ile Leu Tyr Leu
 65                  70                  75                  80

Gln Met Asn Ser Leu Lys Pro Glu Asp Thr Ala Met Tyr Tyr Cys Ala
                 85                  90                  95

Ala Arg Pro Leu Trp Thr Gly Asp Cys Asp Leu Ser Ser Trp Tyr
            100                 105                 110

Lys Thr Trp Gly Gln Gly Thr Gln Val Thr Val Ser Ser Glu Ser Lys
                115                 120                 125

Tyr Gly Pro Pro Cys Pro Pro Cys Pro Ala Pro Glu Phe Leu Gly Gly
130                 135                 140

Pro Ser Val Phe Leu Phe Pro Pro Lys Pro Lys Asp Thr Leu Met Ile
145                 150                 155                 160

Ser Arg Thr Pro Glu Val Thr Cys Val Val Val Asp Val Ser Gln Glu
                165                 170                 175

Asp Pro Glu Val Gln Phe Asn Trp Tyr Val Asp Gly Val Glu Val His
            180                 185                 190

Asn Ala Lys Thr Lys Pro Arg Glu Glu Gln Phe Asn Ser Thr Tyr Arg
        195                 200                 205

Val Val Ser Val Leu Thr Val Leu His Gln Asp Trp Leu Asn Gly Lys
210                 215                 220

Glu Tyr Lys Cys Lys Val Ser Asn Lys Gly Leu Pro Ser Ser Ile Glu
225                 230                 235                 240

Lys Thr Ile Ser Lys Ala Lys Gly Gln Pro Arg Glu Pro Gln Val Tyr
                245                 250                 255

Thr Leu Pro Pro Ser Gln Glu Glu Met Thr Lys Asn Gln Val Ser Leu
            260                 265                 270

Thr Cys Leu Val Lys Gly Phe Tyr Pro Ser Asp Ile Ala Val Glu Trp
        275                 280                 285

Glu Ser Asn Gly Gln Pro Glu Asn Asn Tyr Lys Thr Thr Pro Pro Val
290                 295                 300

Leu Asp Ser Asp Gly Ser Phe Phe Leu Tyr Ser Arg Leu Thr Val Asp
305                 310                 315                 320

Lys Ser Arg Trp Gln Glu Gly Asn Val Phe Ser Cys Ser Val Met His
                325                 330                 335

Glu Ala Leu His Asn His Tyr Thr Gln Lys Ser Leu Ser Leu Ser Leu
            340                 345                 350

Gly Lys

<210> SEQ ID NO 367
<211> LENGTH: 354
<212> TYPE: PRT
<213> ORGANISM: Artificial Sequence
<220> FEATURE:
<223> OTHER INFORMATION: Synthetic Construct

<400> SEQUENCE: 367

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Gln Ala Pro Gly Lys Gly Leu Glu Gly Val
        35                  40                  45

Ser Ala Ile Cys Ser Gly Gly Arg Thr Thr Tyr Ser Asp Ser Val Lys

```
                50                  55                  60
Gly Arg Phe Thr Ile Ser Arg Asp Asn Ser Asn Gln Ile Leu Tyr Leu
 65                  70                  75                  80

Gln Met Asn Ser Leu Arg Ala Glu Asp Thr Ala Val Tyr Tyr Cys Ala
                 85                  90                  95

Ala Arg Pro Leu Trp Thr Gly Asp Cys Asp Leu Ser Ser Trp Tyr
            100                 105                 110

Lys Thr Trp Gly Gln Gly Thr Leu Val Thr Val Ser Ser Glu Ser Lys
                115                 120                 125

Tyr Gly Pro Pro Cys Pro Pro Cys Pro Ala Pro Glu Phe Leu Gly Gly
            130                 135                 140

Pro Ser Val Phe Leu Phe Pro Pro Lys Pro Lys Asp Thr Leu Met Ile
145                 150                 155                 160

Ser Arg Thr Pro Glu Val Thr Cys Val Val Val Asp Val Ser Gln Glu
                165                 170                 175

Asp Pro Glu Val Gln Phe Asn Trp Tyr Val Asp Gly Val Glu Val His
            180                 185                 190

Asn Ala Lys Thr Lys Pro Arg Glu Glu Gln Phe Asn Ser Thr Tyr Arg
            195                 200                 205

Val Val Ser Val Leu Thr Val Leu His Gln Asp Trp Leu Asn Gly Lys
            210                 215                 220

Glu Tyr Lys Cys Lys Val Ser Asn Lys Gly Leu Pro Ser Ser Ile Glu
225                 230                 235                 240

Lys Thr Ile Ser Lys Ala Lys Gly Gln Pro Arg Glu Pro Gln Val Tyr
                245                 250                 255

Thr Leu Pro Pro Ser Gln Glu Glu Met Thr Lys Asn Gln Val Ser Leu
            260                 265                 270

Thr Cys Leu Val Lys Gly Phe Tyr Pro Ser Asp Ile Ala Val Glu Trp
            275                 280                 285

Glu Ser Asn Gly Gln Pro Glu Asn Asn Tyr Lys Thr Thr Pro Pro Val
            290                 295                 300

Leu Asp Ser Asp Gly Ser Phe Phe Leu Tyr Ser Arg Leu Thr Val Asp
305                 310                 315                 320

Lys Ser Arg Trp Gln Glu Gly Asn Val Phe Ser Cys Ser Val Met His
                325                 330                 335

Glu Ala Leu His Asn His Tyr Thr Gln Lys Ser Leu Ser Leu Ser Leu
            340                 345                 350

Gly Lys

<210> SEQ ID NO 368
<211> LENGTH: 223
<212> TYPE: PRT
<213> ORGANISM: Homo sapiens

<400> SEQUENCE: 368

Met Met Thr Gly Thr Ile Glu Thr Gly Asn Ile Ser Ala Glu Lys
  1               5                  10                  15

Gly Gly Ser Ile Ile Leu Gln Cys His Leu Ser Ser Thr Thr Ala Gln
                 20                  25                  30

Val Thr Gln Val Asn Trp Glu Gln Asp Gln Leu Leu Ala Ile Cys
             35                  40                  45

Asn Ala Asp Leu Gly Trp His Ile Ser Pro Ser Phe Lys Asp Arg Val
 50                  55                  60

Ala Pro Gly Pro Gly Leu Gly Leu Thr Leu Gln Ser Leu Thr Val Asn
```

```
                65                  70                  75                  80
Asp Thr Gly Glu Tyr Phe Cys Ile Tyr His Thr Tyr Pro Asp Gly Thr
                    85                  90                  95

Tyr Thr Gly Arg Ile Phe Leu Glu Val Leu Glu Ser Ser Val Ala Glu
                    100                 105                 110

His Gly Ala Arg Phe Gln Ile Pro Leu Leu Gly Ala Met Ala Ala Thr
                    115                 120                 125

Leu Val Val Ile Cys Thr Ala Val Ile Val Val Ala Leu Thr Arg
                    130                 135                 140

Lys Lys Lys Ala Leu Arg Ile His Ser Val Glu Gly Asp Leu Arg Arg
145                 150                 155                 160

Lys Ser Ala Gly Gln Glu Trp Ser Pro Ser Ala Pro Ser Pro Pro
                    165                 170                 175

Gly Ser Cys Val Gln Ala Glu Ala Pro Ala Gly Leu Cys Gly Glu
                    180                 185                 190

Gln Arg Gly Glu Asp Cys Ala Glu Leu His Asp Tyr Phe Asn Val Leu
                    195                 200                 205

Ser Tyr Arg Ser Leu Gly Asn Cys Ser Phe Phe Thr Glu Thr Gly
                    210                 215                 220
```

<210> SEQ ID NO 369
<211> LENGTH: 120
<212> TYPE: PRT
<213> ORGANISM: Homo sapiens

<400> SEQUENCE: 369

```
Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
                20                  25                  30

Val Thr Gln Val Asn Trp Glu Gln Gln Asp Gln Leu Leu Ala Ile Cys
                35                  40                  45

Asn Ala Asp Leu Gly Trp His Ile Ser Pro Ser Phe Lys Asp Arg Val
        50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Thr
                    85                  90                  95

Tyr Thr Gly Arg Ile Phe Leu Glu Val Leu Glu Ser Ser Val Ala Glu
                    100                 105                 110

His Gly Ala Arg Phe Gln Ile Pro
                    115                 120
```

<210> SEQ ID NO 370
<211> LENGTH: 15
<212> TYPE: PRT
<213> ORGANISM: Artificial Sequence
<220> FEATURE:
<223> OTHER INFORMATION: Synthetic Construct

<400> SEQUENCE: 370

```
Glu Pro Lys Ser Cys Asp Lys Thr His Thr Cys Pro Pro Cys Pro
1               5                   10                  15
```

<210> SEQ ID NO 371
<211> LENGTH: 15
<212> TYPE: PRT
<213> ORGANISM: Artificial Sequence

```
<220> FEATURE:
<223> OTHER INFORMATION: Synthetic Construct

<400> SEQUENCE: 371

Glu Pro Lys Ser Ser Asp Lys Thr His Thr Ser Pro Pro Ser Pro
1               5                   10                  15

<210> SEQ ID NO 372
<211> LENGTH: 9
<212> TYPE: PRT
<213> ORGANISM: Artificial Sequence
<220> FEATURE:
<223> OTHER INFORMATION: Synthetic Construct

<400> SEQUENCE: 372

Gly Gly Gly Gly Ser Gly Gly Gly Ser
1               5

<210> SEQ ID NO 373
<211> LENGTH: 15
<212> TYPE: PRT
<213> ORGANISM: Artificial Sequence
<220> FEATURE:
<223> OTHER INFORMATION: Synthetic Construct

<400> SEQUENCE: 373

Gly Gly Gly Gly Ser Gly Gly Gly Gly Ser Gly Gly Gly Gly Ser
1               5                   10                  15

<210> SEQ ID NO 374
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Can be present in repeat of at least 1

<400> SEQUENCE: 374

Gly
1

<210> SEQ ID NO 375
<211> LENGTH: 2
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2
<223> OTHER INFORMATION: Can be present in repeat of at least 1

<400> SEQUENCE: 375

Gly Ser
1

<210> SEQ ID NO 376
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 4, 5
<223> OTHER INFORMATION: Can be present in repeat of at least 1
```

-continued

```
<400> SEQUENCE: 376

Gly Ser Gly Gly Ser
1               5

<210> SEQ ID NO 377
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 4
<223> OTHER INFORMATION: Can be present in repeat of at least 1

<400> SEQUENCE: 377

Gly Gly Gly Ser
1

<210> SEQ ID NO 378
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 4, 5
<223> OTHER INFORMATION: Can be present in repeat of at least 1

<400> SEQUENCE: 378

Gly Gly Gly Gly Ser
1               5

<210> SEQ ID NO 379
<211> LENGTH: 121
<212> TYPE: PRT
<213> ORGANISM: Artificial Sequence
<220> FEATURE:
<223> OTHER INFORMATION: Synthetic Construct

<400> SEQUENCE: 379

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser
        115                 120

<210> SEQ ID NO 380
<211> LENGTH: 108
<212> TYPE: PRT
<213> ORGANISM: Artificial Sequence
```

```
<220> FEATURE:
<223> OTHER INFORMATION: Synthetic Construct

<400> SEQUENCE: 380

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys
            100                 105

<210> SEQ ID NO 381
<211> LENGTH: 118
<212> TYPE: PRT
<213> ORGANISM: Artificial Sequence
<220> FEATURE:
<223> OTHER INFORMATION: Synthetic Construct

<400> SEQUENCE: 381

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser
        115

<210> SEQ ID NO 382
<211> LENGTH: 107
<212> TYPE: PRT
<213> ORGANISM: Artificial Sequence
<220> FEATURE:
<223> OTHER INFORMATION: Synthetic Construct

<400> SEQUENCE: 382

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45
```

```
Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys
                100                 105
```

<210> SEQ ID NO 383
<211> LENGTH: 120
<212> TYPE: PRT
<213> ORGANISM: Artificial Sequence
<220> FEATURE:
<223> OTHER INFORMATION: Synthetic Construct

<400> SEQUENCE: 383

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Val Asp Tyr Trp Gly Gln
                100                 105                 110

Gly Thr Leu Val Thr Val Ser Ser
            115                 120
```

<210> SEQ ID NO 384
<211> LENGTH: 110
<212> TYPE: PRT
<213> ORGANISM: Artificial Sequence
<220> FEATURE:
<223> OTHER INFORMATION: Synthetic Construct

<400> SEQUENCE: 384

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu
                100                 105                 110
```

<210> SEQ ID NO 385

```
<211> LENGTH: 120
<212> TYPE: PRT
<213> ORGANISM: Artificial Sequence
<220> FEATURE:
<223> OTHER INFORMATION: Synthetic Construct

<400> SEQUENCE: 385

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser
        115                 120

<210> SEQ ID NO 386
<211> LENGTH: 111
<212> TYPE: PRT
<213> ORGANISM: Artificial Sequence
<220> FEATURE:
<223> OTHER INFORMATION: Synthetic Construct

<400> SEQUENCE: 386

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys
            100                 105                 110

<210> SEQ ID NO 387
<211> LENGTH: 113
<212> TYPE: PRT
<213> ORGANISM: Artificial Sequence
<220> FEATURE:
<223> OTHER INFORMATION: Synthetic Construct

<400> SEQUENCE: 387

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30
```

```
Gly Met His Trp Val Arg Gln Ala Pro Gly Lys Gly Leu Glu Trp Val
            35                  40                  45

Ala Val Ile Trp Tyr Asp Gly Ser Lys Arg Tyr Tyr Ala Asp Ser Val
 50                  55                  60

Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
                 85                  90                  95

Ala Thr Asn Asp Asp Tyr Trp Gly Gln Gly Thr Leu Val Thr Val Ser
            100                 105                 110

Ser

<210> SEQ ID NO 388
<211> LENGTH: 107
<212> TYPE: PRT
<213> ORGANISM: Artificial Sequence
<220> FEATURE:
<223> OTHER INFORMATION: Synthetic Construct

<400> SEQUENCE: 388

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
                 20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Ser Asn Trp Pro Arg
                 85                  90                  95

Thr Phe Gly Gln Gly Thr Lys Val Glu Ile Lys
            100                 105

<210> SEQ ID NO 389
<211> LENGTH: 217
<212> TYPE: PRT
<213> ORGANISM: Artificial Sequence
<220> FEATURE:
<223> OTHER INFORMATION: Synthetic Construct

<400> SEQUENCE: 389

Ala Pro Glu Phe Leu Gly Gly Pro Ser Val Phe Leu Phe Pro Pro Lys
  1               5                  10                  15

Pro Lys Asp Thr Leu Met Ile Ser Arg Thr Pro Glu Val Thr Cys Val
                 20                  25                  30

Val Val Asp Val Ser Gln Glu Asp Pro Glu Val Gln Phe Asn Trp Tyr
             35                  40                  45

Val Asp Gly Val Glu Val His Asn Ala Lys Thr Lys Pro Arg Glu Glu
 50                  55                  60

Gln Phe Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Gly Leu Pro Ser Ser Ile Glu Lys Thr Ile Ser Lys Ala Lys Gly Gln
            100                 105                 110
```

```
Pro Arg Glu Pro Gln Val Tyr Thr Leu Pro Pro Ser Gln Glu Met
            115                 120                 125
Thr Lys Asn Gln Val Ser Leu Thr Cys Leu Val Lys Gly Phe Tyr Pro
            130                 135                 140
Ser Asp Ile Ala Val Glu Trp Glu Ser Asn Gly Gln Pro Glu Asn Asn
145                 150                 155                 160
Tyr Lys Thr Thr Pro Pro Val Leu Asp Ser Asp Gly Ser Phe Phe Leu
                165                 170                 175
Tyr Ser Arg Leu Thr Val Asp Lys Ser Arg Trp Gln Glu Gly Asn Val
            180                 185                 190
Phe Ser Cys Ser Val Met His Glu Ala Leu His Asn His Tyr Thr Gln
            195                 200                 205
Lys Ser Leu Ser Leu Ser Leu Gly Lys
            210                 215

<210> SEQ ID NO 390
<211> LENGTH: 444
<212> TYPE: PRT
<213> ORGANISM: Artificial Sequence
<220> FEATURE:
<223> OTHER INFORMATION: Synthetic Construct

<400> SEQUENCE: 390

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Val Phe Ser Arg Tyr
            20                  25                  30
Asp Met Ala Trp Val Arg Gln Ala Pro Gly Lys Gly Leu Glu Trp Val
        35                  40                  45
Ser Phe Ile Ser Gly Gly Gly Ser Asn Thr Tyr Tyr Pro Asp Thr Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ile Ser Pro Tyr Tyr Tyr Ala Met Glu Tyr Trp Gly Gln Gly Thr Thr
            100                 105                 110
Val Thr Val Ser Ser Ala Ser Thr Lys Gly Pro Ser Val Phe Pro Leu
        115                 120                 125
Ala Pro Cys Ser Arg Ser Thr Ser Glu Ser Thr Ala Ala Leu Gly Cys
    130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Lys Thr Tyr Thr Cys Asn Val Asp His Lys Pro Ser Asn
        195                 200                 205
Thr Lys Val Asp Lys Arg Val Glu Ser Lys Tyr Gly Pro Pro Cys Pro
    210                 215                 220
Pro Cys Pro Ala Pro Glu Phe Leu Gly Gly Pro Ser Val Phe Leu Phe
225                 230                 235                 240
Pro Pro Lys Pro Lys Asp Thr Leu Met Ile Ser Arg Thr Pro Glu Val
                245                 250                 255
```

```
Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440

<210> SEQ ID NO 391
<211> LENGTH: 214
<212> TYPE: PRT
<213> ORGANISM: Artificial Sequence
<220> FEATURE:
<223> OTHER INFORMATION: Synthetic Construct

<400> SEQUENCE: 391

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asp Val Asp Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Phe Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 392
<211> LENGTH: 456
<212> TYPE: PRT
<213> ORGANISM: Artificial Sequence
<220> FEATURE:
<223> OTHER INFORMATION: Synthetic Construct

<400> SEQUENCE: 392

Glu Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Lys Thr Tyr Tyr Arg Phe Lys Trp Tyr Ser Asp Tyr Ala
    50                  55                  60

Val Ser Val Lys Gly Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
            85                  90                  95

Phe Tyr Cys Thr Arg Glu Ser Thr Thr Tyr Asp Leu Leu Ala Gly Pro
        100                 105                 110

Phe Asp Tyr Trp Gly Gln Gly Thr Leu Val Thr Val Ser Ser Ala Ser
    115                 120                 125

Thr Lys Gly Pro Ser Val Phe Pro Leu Ala Pro Ser Ser Lys Ser Thr
130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320
```

```
Asp Trp Leu Asn Gly Lys Glu Tyr Lys Cys Lys Val Ser Asn Lys Ala
            325                 330                 335

Leu Pro Ala Pro Ile Glu Lys Thr Ile Ser Lys Ala Lys Gly Gln Pro
        340                 345                 350

Arg Glu Pro Gln Val Tyr Thr Leu Pro Pro Ser Arg Glu Glu Met Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 393
<211> LENGTH: 220
<212> TYPE: PRT
<213> ORGANISM: Artificial Sequence
<220> FEATURE:
<223> OTHER INFORMATION: Synthetic Construct

<400> SEQUENCE: 393

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Val Leu Tyr Ser
            20                  25                  30

Ser Asn Asn Lys Lys Tyr Leu Ala Trp Tyr Gln Gln Lys Pro Gly Gln
        35                  40                  45

Pro Pro Asn Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Phe Thr Phe Gly Pro Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 394
<211> LENGTH: 584
<212> TYPE: PRT
<213> ORGANISM: Artificial Sequence
<220> FEATURE:
<223> OTHER INFORMATION: Synthetic Construct

<400> SEQUENCE: 394

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Gln Ala Pro Gly Lys Gly Leu Glu Gly Val
        35                  40                  45

Ser Ala Ile Cys Ser Gly Gly Arg Thr Thr Tyr Ser Asp Ser Val Lys
    50                  55                  60

Gly Arg Phe Thr Ile Ser Arg Asp Asn Ser Asn Gln Ile Leu Tyr Leu
65                  70                  75                  80

Gln Met Asn Ser Leu Arg Ala Glu Asp Thr Ala Val Tyr Tyr Cys Ala
                85                  90                  95

Ala Arg Pro Leu Trp Thr Gly Asp Cys Asp Leu Ser Ser Trp Tyr
            100                 105                 110

Lys Thr Trp Gly Gln Gly Thr Leu Val Thr Val Ser Ser Glu Pro Lys
        115                 120                 125

Ser Ser Asp Lys Thr His Thr Ser Pro Pro Ser Pro Glu Val Gln Leu
    130                 135                 140

Val Glu Ser Gly Gly Gly Leu Val Gln Pro Gly Gly Ser Leu Arg Leu
145                 150                 155                 160

Ser Cys Ala Ala Ser Gly Phe Val Phe Ser Arg Tyr Asp Met Ala Trp
                165                 170                 175

Val Arg Gln Ala Pro Gly Lys Gly Leu Glu Trp Val Ser Phe Ile Ser
            180                 185                 190

Gly Gly Gly Ser Asn Thr Tyr Tyr Pro Asp Thr Val Lys Gly Arg Phe
        195                 200                 205

Thr Ile Ser Arg Asp Asn Ser Lys Asn Thr Leu Tyr Leu Gln Met Asn
    210                 215                 220

Ser Leu Arg Ala Glu Asp Thr Ala Val Tyr Tyr Cys Ile Ser Pro Tyr
225                 230                 235                 240

Tyr Tyr Ala Met Glu Tyr Trp Gly Gln Gly Thr Thr Val Thr Val Ser
                245                 250                 255

Ser Ala Ser Thr Lys Gly Pro Ser Val Phe Pro Leu Ala Pro Cys Ser
            260                 265                 270

Arg Ser Thr Ser Glu Ser Thr Ala Ala Leu Gly Cys Leu Val Lys Asp
        275                 280                 285

Tyr Phe Pro Glu Pro Val Thr Val Ser Trp Asn Ser Gly Ala Leu Thr
    290                 295                 300

Ser Gly Val His Thr Phe Pro Ala Val Leu Gln Ser Ser Gly Leu Tyr
305                 310                 315                 320

Ser Leu Ser Ser Val Val Thr Val Pro Ser Ser Ser Leu Gly Thr Lys
                325                 330                 335

Thr Tyr Thr Cys Asn Val Asp His Lys Pro Ser Asn Thr Lys Val Asp
            340                 345                 350

Lys Arg Val Glu Ser Lys Tyr Gly Pro Pro Cys Pro Pro Cys Pro Ala
        355                 360                 365
```

```
Pro Glu Phe Leu Gly Gly Pro Ser Val Phe Leu Phe Pro Pro Lys Pro
    370                 375                 380

Lys Asp Thr Leu Met Ile Ser Arg Thr Pro Glu Val Thr Cys Val Val
385                 390                 395                 400

Val Asp Val Ser Gln Glu Asp Pro Glu Val Gln Phe Asn Trp Tyr Val
                405                 410                 415

Asp Gly Val Glu Val His Asn Ala Lys Thr Lys Pro Arg Glu Glu Gln
                420                 425                 430

Phe Asn Ser Thr Tyr Arg Val Val Ser Val Leu Thr Val Leu His Gln
            435                 440                 445

Asp Trp Leu Asn Gly Lys Glu Tyr Lys Cys Lys Val Ser Asn Lys Gly
450                 455                 460

Leu Pro Ser Ser Ile Glu Lys Thr Ile Ser Lys Ala Lys Gly Gln Pro
465                 470                 475                 480

Arg Glu Pro Gln Val Tyr Thr Leu Pro Pro Ser Gln Glu Glu Met Thr
                485                 490                 495

Lys Asn Gln Val Ser Leu Thr Cys Leu Val Lys Gly Phe Tyr Pro Ser
                500                 505                 510

Asp Ile Ala Val Glu Trp Glu Ser Asn Gly Gln Pro Glu Asn Asn Tyr
            515                 520                 525

Lys Thr Thr Pro Pro Val Leu Asp Ser Asp Gly Ser Phe Phe Leu Tyr
530                 535                 540

Ser Arg Leu Thr Val Asp Lys Ser Arg Trp Gln Gln Gly Asn Val Phe
545                 550                 555                 560

Ser Cys Ser Val Met His Glu Ala Leu His Asn His Tyr Thr Gln Lys
                565                 570                 575

Ser Leu Ser Leu Ser Leu Gly Lys
            580

<210> SEQ ID NO 395
<211> LENGTH: 214
<212> TYPE: PRT
<213> ORGANISM: Artificial Sequence
<220> FEATURE:
<223> OTHER INFORMATION: Synthetic Construct

<400> SEQUENCE: 395

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asp Val Asp Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Phe Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210
```

<210> SEQ ID NO 396
<211> LENGTH: 584
<212> TYPE: PRT
<213> ORGANISM: Artificial Sequence
<220> FEATURE:
<223> OTHER INFORMATION: Synthetic Construct

<400> SEQUENCE: 396

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Val Phe Ser Arg Tyr
            20                  25                  30

Asp Met Ala Trp Val Arg Gln Ala Pro Gly Lys Gly Leu Glu Trp Val
        35                  40                  45

Ser Phe Ile Ser Gly Gly Ser Asn Thr Tyr Tyr Pro Asp Thr Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ile Ser Pro Tyr Tyr Tyr Ala Met Glu Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285
```

Arg Glu Gln Phe Asn Ser Thr Tyr Arg Val Val Ser Val Leu Thr
            290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys Glu Pro Lys Ser
            435                 440                 445

Ser Asp Lys Thr His Thr Ser Pro Pro Ser Pro Glu Val Gln Leu Val
450                 455                 460

Glu Ser Gly Gly Gly Leu Val Gln Pro Gly Gly Ser Leu Arg Leu Ser
465                 470                 475                 480

Cys Ala Ala Ser Gly Tyr Lys Tyr Gly Val Tyr Ser Met Gly Trp Phe
                485                 490                 495

Arg Gln Ala Pro Gly Lys Gly Leu Glu Gly Val Ser Ala Ile Cys Ser
            500                 505                 510

Gly Gly Arg Thr Thr Tyr Ser Asp Ser Val Lys Gly Arg Phe Thr Ile
            515                 520                 525

Ser Arg Asp Asn Ser Asn Gln Ile Leu Tyr Leu Gln Met Asn Ser Leu
530                 535                 540

Arg Ala Glu Asp Thr Ala Val Tyr Tyr Cys Ala Ala Arg Pro Leu Trp
545                 550                 555                 560

Thr Gly Asp Cys Asp Leu Ser Ser Ser Trp Tyr Lys Thr Trp Gly Gln
                565                 570                 575

Gly Thr Leu Val Thr Val Ser Ser
            580

<210> SEQ ID NO 397
<211> LENGTH: 214
<212> TYPE: PRT
<213> ORGANISM: Artificial Sequence
<220> FEATURE:
<223> OTHER INFORMATION: Synthetic Construct

<400> SEQUENCE: 397

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asp Val Asp Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Phe Pro Trp
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 398
<211> LENGTH: 444
<212> TYPE: PRT
<213> ORGANISM: Artificial Sequence
<220> FEATURE:
<223> OTHER INFORMATION: Synthetic Construct

<400> SEQUENCE: 398

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Val Phe Ser Arg Tyr
             20                  25                  30

Asp Met Ala Trp Val Arg Gln Ala Pro Gly Lys Gly Leu Glu Trp Val
         35                  40                  45

Ser Phe Ile Ser Gly Gly Gly Ser Asn Thr Tyr Tyr Pro Asp Thr Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ile Ser Pro Tyr Tyr Ala Met Glu Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205
```

Thr Lys Val Asp Lys Arg Val Glu Ser Lys Tyr Gly Pro Cys Pro
210             215                 220

Pro Cys Pro Ala Pro Glu Phe Leu Gly Gly Pro Ser Val Phe Leu Phe
225             230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
                275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
                340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly Lys
            435                 440

<210> SEQ ID NO 399
<211> LENGTH: 354
<212> TYPE: PRT
<213> ORGANISM: Artificial Sequence
<220> FEATURE:
<223> OTHER INFORMATION: Synthetic Construct

<400> SEQUENCE: 399

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Gln Ala Pro Gly Lys Gly Leu Glu Gly Val
        35                  40                  45

Ser Ala Ile Cys Ser Gly Gly Arg Thr Thr Tyr Ser Asp Ser Val Lys
    50                  55                  60

Gly Arg Phe Thr Ile Ser Arg Asp Asn Ser Gln Ile Leu Tyr Leu
65                  70                  75                  80

Gln Met Asn Ser Leu Arg Ala Glu Asp Thr Ala Val Tyr Tyr Cys Ala
                85                  90                  95

Ala Arg Pro Leu Trp Thr Gly Asp Cys Asp Leu Ser Ser Ser Trp Tyr
            100                 105                 110

Lys Thr Trp Gly Gln Gly Thr Leu Val Thr Val Ser Ser Glu Pro Lys
        115                 120                 125

```
Ser Ser Asp Lys Thr His Thr Ser Pro Pro Ser Pro Asp Ile Gln Met
    130                 135                 140

Thr Gln Ser Pro Ser Ser Val Ser Ala Ser Val Gly Asp Arg Val Thr
145                 150                 155                 160

Ile Thr Cys Lys Ala Ser Gln Asp Val Asp Thr Ala Val Ala Trp Tyr
            165                 170                 175

Gln Gln Lys Pro Gly Lys Ala Pro Lys Leu Leu Ile Tyr Trp Ala Ser
                180                 185                 190

Thr Arg His Thr Gly Val Pro Ser Arg Phe Ser Gly Ser Gly Ser Gly
            195                 200                 205

Thr Asp Phe Thr Leu Thr Ile Ser Ser Leu Gln Pro Glu Asp Phe Ala
    210                 215                 220

Thr Tyr Tyr Cys Gln Gln Tyr Ser Thr Phe Pro Trp Thr Phe Gly Gly
225                 230                 235                 240

Gly Thr Lys Val Glu Ile Lys Arg Thr Val Ala Ala Pro Ser Val Phe
            245                 250                 255

Ile Phe Pro Pro Ser Asp Glu Gln Leu Lys Ser Gly Thr Ala Ser Val
                260                 265                 270

Val Cys Leu Leu Asn Asn Phe Tyr Pro Arg Glu Ala Lys Val Gln Trp
            275                 280                 285

Lys Val Asp Asn Ala Leu Gln Ser Gly Asn Ser Gln Glu Ser Val Thr
    290                 295                 300

Glu Gln Asp Ser Lys Asp Ser Thr Tyr Ser Leu Ser Ser Thr Leu Thr
305                 310                 315                 320

Leu Ser Lys Ala Asp Tyr Glu Lys His Lys Val Tyr Ala Cys Glu Val
            325                 330                 335

Thr His Gln Gly Leu Ser Ser Pro Val Thr Lys Ser Phe Asn Arg Gly
                340                 345                 350

Glu Cys

<210> SEQ ID NO 400
<211> LENGTH: 444
<212> TYPE: PRT
<213> ORGANISM: Artificial Sequence
<220> FEATURE:
<223> OTHER INFORMATION: Synthetic Construct

<400> SEQUENCE: 400

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Val Phe Ser Arg Tyr
            20                  25                  30

Asp Met Ala Trp Val Arg Gln Ala Pro Gly Lys Gly Leu Glu Trp Val
        35                  40                  45

Ser Phe Ile Ser Gly Gly Gly Ser Asn Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ile Ser Pro Tyr Tyr Tyr Ala Met Glu Tyr Trp Gly Gln Gly Thr Thr
                100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
```

```
                130                 135                 140
Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440

<210> SEQ ID NO 401
<211> LENGTH: 354
<212> TYPE: PRT
<213> ORGANISM: Artificial Sequence
<220> FEATURE:
<223> OTHER INFORMATION: Synthetic Construct

<400> SEQUENCE: 401

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asp Val Asp Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
```

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Phe Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Glu Pro Lys Ser Ser Asp Lys Thr His Thr
    210                 215                 220

Ser Pro Pro Ser Pro Glu Val Gln Leu Val Glu Ser Gly Gly Gly Leu
225                 230                 235                 240

Val Gln Pro Gly Gly Ser Leu Arg Leu Ser Cys Ala Ala Ser Gly Tyr
                245                 250                 255

Lys Tyr Gly Val Tyr Ser Met Gly Trp Phe Arg Gln Ala Pro Gly Lys
            260                 265                 270

Gly Leu Glu Gly Val Ser Ala Ile Cys Ser Gly Gly Arg Thr Thr Tyr
        275                 280                 285

Ser Asp Ser Val Lys Gly Arg Phe Thr Ile Ser Arg Asp Asn Ser Asn
    290                 295                 300

Gln Ile Leu Tyr Leu Gln Met Asn Ser Leu Arg Ala Glu Asp Thr Ala
305                 310                 315                 320

Val Tyr Tyr Cys Ala Ala Arg Pro Leu Trp Thr Gly Asp Cys Asp Leu
                325                 330                 335

Ser Ser Ser Trp Tyr Lys Thr Trp Gly Gln Gly Thr Leu Val Thr Val
            340                 345                 350

Ser Ser

<210> SEQ ID NO 402
<211> LENGTH: 589
<212> TYPE: PRT
<213> ORGANISM: Artificial Sequence
<220> FEATURE:
<223> OTHER INFORMATION: Synthetic Construct

<400> SEQUENCE: 402

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Gln Ala Pro Gly Lys Gly Leu Glu Gly Val
        35                  40                  45

Ser Ala Ile Cys Ser Gly Gly Arg Thr Thr Tyr Ser Asp Ser Val Lys
    50                  55                  60

-continued

```
Gly Arg Phe Thr Ile Ser Arg Asp Asn Ser Asn Gln Ile Leu Tyr Leu
 65                  70                  75                  80

Gln Met Asn Ser Leu Arg Ala Glu Asp Thr Ala Val Tyr Tyr Cys Ala
             85                  90                  95

Ala Arg Pro Leu Trp Thr Gly Asp Cys Asp Leu Ser Ser Trp Tyr
        100                 105                 110

Lys Thr Trp Gly Gln Gly Thr Leu Val Thr Val Ser Ser Glu Pro Lys
        115                 120                 125

Ser Ser Asp Lys Thr His Thr Ser Pro Pro Ser Pro Glu Val Gln Leu
130                 135                 140

Val Gln Ser Gly Ala Glu Val Lys Lys Pro Gly Ala Ser Val Lys Val
145                 150                 155                 160

Ser Cys Lys Ala Ser Gly Tyr Ile Phe Thr Gly Tyr Gly Ile Thr Trp
                165                 170                 175

Val Arg Gln Ala Pro Gly Gln Gly Leu Glu Trp Met Gly Glu Ile Phe
                180                 185                 190

Pro Arg Arg Val Gln Thr Tyr Tyr Ser Glu Lys Phe Lys Gly Arg Val
            195                 200                 205

Thr Met Thr Thr Asp Thr Ser Thr Ser Thr Ala Tyr Met Glu Leu Arg
210                 215                 220

Ser Leu Arg Ser Asp Asp Thr Ala Val Tyr Tyr Cys Ala Arg Asp Tyr
225                 230                 235                 240

Asp Pro Tyr Phe Ala Leu Asp Tyr Trp Gly Gln Gly Thr Thr Val Thr
                245                 250                 255

Val Ser Ser Ala Ser Thr Lys Gly Pro Ser Val Phe Pro Leu Ala Pro
            260                 265                 270

Ser Ser Lys Ser Thr Ser Gly Gly Thr Ala Ala Leu Gly Cys Leu Val
        275                 280                 285

Lys Asp Tyr Phe Pro Glu Pro Val Thr Val Ser Trp Asn Ser Gly Ala
290                 295                 300

Leu Thr Ser Gly Val His Thr Phe Pro Ala Val Leu Gln Ser Ser Gly
305                 310                 315                 320

Leu Tyr Ser Leu Ser Ser Val Val Thr Val Pro Ser Ser Leu Gly
                325                 330                 335

Thr Gln Thr Tyr Ile Cys Asn Val Asn His Lys Pro Ser Asn Thr Lys
                340                 345                 350

Val Asp Lys Lys Val Glu Pro Lys Ser Cys Asp Lys Thr His Thr Cys
        355                 360                 365

Pro Pro Cys Pro Ala Pro Glu Leu Leu Gly Gly Pro Ser Val Phe Leu
        370                 375                 380

Phe Pro Pro Lys Pro Lys Asp Thr Leu Met Ile Ser Arg Thr Pro Glu
385                 390                 395                 400

Val Thr Cys Val Val Val Asp Val Ser His Glu Asp Pro Glu Val Lys
                405                 410                 415

Phe Asn Trp Tyr Val Asp Gly Val Glu Val His Asn Ala Lys Thr Lys
                420                 425                 430

Pro Arg Glu Glu Gln Tyr Ala Ser Thr Tyr Arg Val Val Ser Val Leu
            435                 440                 445

Thr Val Leu His Gln Asp Trp Leu Asn Gly Lys Glu Tyr Lys Cys Lys
        450                 455                 460

Val Ser Asn Lys Ala Leu Pro Ala Pro Ile Glu Lys Thr Ile Ser Lys
465                 470                 475                 480
```

```
Ala Lys Gly Gln Pro Arg Glu Pro Gln Val Tyr Thr Leu Pro Pro Ser
                485                 490                 495

Arg Glu Glu Met Thr Lys Asn Gln Val Ser Leu Thr Cys Leu Val Lys
            500                 505                 510

Gly Phe Tyr Pro Ser Asp Ile Ala Val Glu Trp Glu Ser Asn Gly Gln
        515                 520                 525

Pro Glu Asn Asn Tyr Lys Thr Thr Pro Pro Val Leu Asp Ser Asp Gly
    530                 535                 540

Ser Phe Phe Leu Tyr Ser Lys Leu Thr Val Asp Lys Ser Arg Trp Gln
545                 550                 555                 560

Gln Gly Asn Val Phe Ser Cys Ser Val Met His Glu Ala Leu His Asn
                565                 570                 575

His Tyr Thr Gln Lys Ser Leu Ser Leu Ser Pro Gly Lys
            580                 585

<210> SEQ ID NO 403
<211> LENGTH: 214
<212> TYPE: PRT
<213> ORGANISM: Artificial Sequence
<220> FEATURE:
<223> OTHER INFORMATION: Synthetic Construct

<400> SEQUENCE: 403

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Asp Trp Tyr Gln Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Ile Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 404
<211> LENGTH: 449
<212> TYPE: PRT
<213> ORGANISM: Artificial Sequence
<220> FEATURE:
```

<223> OTHER INFORMATION: Synthetic Construct

<400> SEQUENCE: 404

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Met
        35                  40                  45

Gly Glu Ile Phe Pro Arg Arg Val Gln Thr Tyr Tyr Ser Glu Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 405
<211> LENGTH: 354
<212> TYPE: PRT
<213> ORGANISM: Artificial Sequence
<220> FEATURE:
<223> OTHER INFORMATION: Synthetic Construct

<400> SEQUENCE: 405

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Gln Ala Pro Gly Lys Gly Leu Glu Gly Val
            35                  40                  45

Ser Ala Ile Cys Ser Gly Gly Arg Thr Thr Tyr Ser Asp Ser Val Lys
    50                  55                  60

Gly Arg Phe Thr Ile Ser Arg Asp Asn Ser Asn Gln Ile Leu Tyr Leu
65                  70                  75                  80

Gln Met Asn Ser Leu Arg Ala Glu Asp Thr Ala Val Tyr Tyr Cys Ala
            85                  90                  95

Ala Arg Pro Leu Trp Thr Gly Asp Cys Asp Leu Ser Ser Ser Trp Tyr
            100                 105                 110

Lys Thr Trp Gly Gln Gly Thr Leu Val Thr Val Ser Ser Glu Pro Lys
            115                 120                 125

Ser Ser Asp Lys Thr His Thr Ser Pro Pro Ser Pro Asp Ile Gln Met
    130                 135                 140

Thr Gln Ser Pro Ser Ser Leu Ser Ala Ser Val Gly Asp Arg Val Thr
145                 150                 155                 160

Ile Thr Cys Arg Ala Ser Gln Asp Val Ser Thr Ala Val Asp Trp Tyr
            165                 170                 175

Gln Gln Lys Pro Gly Lys Ala Pro Lys Leu Leu Ile Tyr Ser Ala Ser
            180                 185                 190

Tyr Arg Tyr Thr Gly Val Pro Asp Arg Phe Ser Gly Ser Gly Ser Gly
            195                 200                 205

Thr Asp Phe Thr Phe Thr Ile Ser Ser Leu Gln Pro Glu Asp Ile Ala
    210                 215                 220

Thr Tyr Tyr Cys Gln Gln His Tyr Ser Ile Pro Phe Thr Phe Gly Gln
225                 230                 235                 240

Gly Thr Lys Leu Glu Ile Lys Arg Thr Val Ala Ala Pro Ser Val Phe
            245                 250                 255

Ile Phe Pro Pro Ser Asp Glu Gln Leu Lys Ser Gly Thr Ala Ser Val
            260                 265                 270

Val Cys Leu Leu Asn Asn Phe Tyr Pro Arg Glu Ala Lys Val Gln Trp
            275                 280                 285

Lys Val Asp Asn Ala Leu Gln Ser Gly Asn Ser Gln Glu Ser Val Thr
    290                 295                 300

Glu Gln Asp Ser Lys Asp Ser Thr Tyr Ser Leu Ser Ser Thr Leu Thr

```
                305                 310                 315                 320
Leu Ser Lys Ala Asp Tyr Glu Lys His Lys Val Tyr Ala Cys Glu Val
                325                 330                 335
Thr His Gln Gly Leu Ser Ser Pro Val Thr Lys Ser Phe Asn Arg Gly
            340                 345                 350
Glu Cys

<210> SEQ ID NO 406
<211> LENGTH: 117
<212> TYPE: PRT
<213> ORGANISM: Artificial Sequence
<220> FEATURE:
<223> OTHER INFORMATION: Synthetic Construct

<400> SEQUENCE: 406

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Val Phe Ser Arg Tyr
            20                  25                  30

Asp Met Ala Trp Val Arg Gln Ala Pro Gly Lys Gly Leu Glu Trp Val
        35                  40                  45

Ser Phe Ile Ser Gly Gly Gly Ser Asn Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ile Ser Pro Tyr Tyr Tyr Ala Met Glu Tyr Trp Gly Gln Gly Thr Thr
            100                 105                 110

Val Thr Val Ser Ser
        115

<210> SEQ ID NO 407
<211> LENGTH: 107
<212> TYPE: PRT
<213> ORGANISM: Artificial Sequence
<220> FEATURE:
<223> OTHER INFORMATION: Synthetic Construct

<400> SEQUENCE: 407

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asp Val Asp Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Phe Pro Trp
                85                  90                  95

Thr Phe Gly Gly Gly Thr Lys Val Glu Ile Lys
            100                 105
```

SINGLE-DOMAIN ANTIBODIES AND VARIANTS THEREOF AGAINST TIGIT

CROSS REFERENCE TO RELATED APPLICATIONS

This application is a national stage application under 35 U.S.C. § 371 of International Patent Application No. PCT/CN2018/124979, filed internationally on Dec. 28, 2018, which claims priority benefits of International Patent Application Nos. PCT/CN2017/119506 filed on Dec. 28, 2017 and PCT/CN2018/097159 filed on Jul. 26, 2018, the contents of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 761422000700 SEQLISTING.TXT, date recorded: May 14, 2020, size: 392 KB).

FIELD OF THE INVENTION

The present invention relates to constructs comprising a single-domain antibody (sdAb) moiety that specifically recognize TIGIT, and methods of making and using thereof.

BACKGROUND OF THE INVENTION

T cell immunoreceptor with Ig and ITIM domains (TIGIT, also known as Vstm3 or WUCAM) is an immune receptor belonging to the CD28 family. This 26 KDa protein contains an extracellular IgV domain, a type I transmembrane region, an intracellular immunoglobulin tail tyrosine (ITT)-like motif, and a C-terminal immunereceptor tyrosine-based inhibition motif (ITIM) motif in cytoplasm. In naïve T cells and NK cells, TIGIT is barely detectable on the cell surface but is upregulated upon T cell and NK cell activation. In tumor microenvironment, TIGIT is highly detected on regulatory T cells (Treg), exhausted T cells and NK cells. TIGIT has multiple ligands, including CD155 (nec1-5 or poliovirus receptor (PVR)), CD112 (Nectin-2 or Poliovirus receptor-related 2 (PVRL2)), and CD113 (Nectin-3 or PVRL3). TIGIT can bind to CD155 (PVR) with high affinity, while to CD112 and CD113 with lower affinity Recent reports also indicate that TIGIT interacts with CD226 (PTA1 or DNAM-1) in cis.

TIGIT exerts its inhibitory immune checkpoint function via several mechanisms. First, upon binding to its major ligand CD155 (PVR), the subsequent phosphorylation of TIGIT in its ITIM domain transduces inhibitory signals to downregulate IFN-γ expression in T cells and NK cells via NF-κB pathway. Second, as TIGIT interacts with PVR at higher affinity than with CD226, it competes with CD226 and attenuates the stimulatory signal transduced by CD226. Third, PVR binding to TIGIT on dendritic cells may lead to upregulation of IL-10 expression and downregulation of IL-12 expression, therefore impairing the anti-tumor immune response of dendritic cells. Lastly, recent research indicated that TIGIT can directly bind to CD226 in cis to inhibit CD226 dimerization, which is required for T cell activation. Therefore, TIGIT acts as an important negative regulator in immune responses in infection and cancer, and blockade of TIGIT signaling has been proposed as an approach to enhance T cell and NK cell immunity for cancer treatment.

Programmed Cell Death Receptor 1 (PD-1) is another inhibitory immune checkpoint molecule with important negative regulation on T cell functions. T-cell responses can be attenuated by PD-1 signaling when PD-1 binds to Programmed Cell Death Ligand 1 (PD-L1) and/or Programmed Cell Death Ligand 2 (PD-L2), which regulates T-cell receptor (TCR) signaling. Blockade of the PD-1/PD-L1 axis using antibodies targeting either PD-1 or PD-L1 has been shown to promote tumor-specific T cell immunity with significant clinical benefit to cancer patients. However, there are still huge unmet clinical needs due to the resistance or relapse upon PD-1/PD-L1 blockade.

The disclosures of all publications, patents, patent applications and published patent applications referred to herein are hereby incorporated herein by reference in their entirety.

BRIEF SUMMARY OF THE INVENTION

The present invention relates to anti-TIGIT constructs comprising an sdAb moiety that specifically recognizes TIGIT (hereinafter referred to as "anti-TIGIT sdAb"), such as anti-TIGIT sdAb, anti-TIGIT sdAb-Fc fusion protein comprising an anti-TIGIT sdAb fused to a crystalline fragment (Fc) fragment of human immunoglobulin G (IgG), and multispecific (such as bispecific) antigen binding proteins comprising an anti-TIGIT sdAb, for example fused to other sdAbs or fused to a full-length four-chain antibody, and methods of making and using thereof.

One aspect of the present application provides an isolated anti-TIGIT construct comprising an sdAb moiety specifically recognizing TIGIT, wherein the sdAb moiety comprises a CDR1 comprising the amino acid sequence of any one of SEQ ID NOs: 36-42, 54, 56-59, 63, 65-67, 69-70, or a variant thereof comprising up to about 3 (such as about any of 1, 2, or 3) amino acid substitutions; a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210, or a variant thereof comprising up to about 3 (such as about any of 1, 2, or 3) amino acid substitutions. In some embodiments, the isolated anti-TIGIT construct comprises an sdAb moiety specifically recognizing TIGIT, wherein the sdAb moiety comprises a CDR1 comprising the amino acid sequence of any one of SEQ ID NOs: 36-42, 54, 56-59, 63, 65-67, 69-70, or a variant thereof comprising up to about 3 (such as about any of 1, 2, or 3) amino acid substitutions; a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210. In some embodiments, the sdAb moiety specifically recognizing TIGIT comprises a CDR1 comprising the amino acid sequence of any one of SEQ ID NOs: 36-42, 54, 56-59, 63, 65-67, 69-70; a CDR2 comprising the amino acid sequence of any one of SEQ ID NOs: 106-112, 124, 126-129, 133, 135-137, 139-140; and a CDR3 comprising the amino acid sequence of any one of SEQ ID NOs: 176-182, 194, 196-199, 203, 205-207, 209-210; or a variant thereof comprising up to about 3 (such as about any of 1, 2, or 3) amino acid substitutions in the CDR regions. In some embodiments, the amino acid substitutions are in CDR1 and/or CDR2, wherein CDR3 comprises the amino acid sequence of any one of SEQ ID NOs: 176-182, 194, 196-199, 203, 205-207, 209-210. In some embodiments, the sdAb moiety specifically recognizing TIGIT comprises a CDR1 comprising the amino acid sequence of any one of SEQ ID NOs: 36-42, 54, 56-59, 63, 65-67, 69-70; a CDR2 comprising the amino acid sequence of any one of SEQ ID NOs: 106-112, 124, 126-129, 133, 135-137, 139-140; and a CDR3 comprising the amino acid sequence of any one of SEQ ID NOs: 176-182, 194, 196-199, 203, 205-207, 209-210.

In some embodiments according to any one of the isolated anti-TIGIT constructs described above, the sdAb moiety specifically recognizing TIGIT comprises any one of the following:

(1) a CDR1 comprising the amino acid sequence of SEQ ID NO: 36; a CDR2 comprising the amino acid sequence of SEQ ID NO: 106; and a CDR3 comprising the amino acid sequence of SEQ ID NO: 176; or a variant thereof comprising up to about 3 (such as about any of 1, 2, or 3) amino acid substitutions in the CDR regions;

(2) a CDR1 comprising the amino acid sequence of SEQ ID NO: 37; a CDR2 comprising the amino acid sequence of SEQ ID NO: 107; and a CDR3 comprising the amino acid sequence of SEQ ID NO: 177; or a variant thereof comprising up to about 3 (such as about any of 1, 2, or 3) amino acid substitutions in the CDR regions;

(3) a CDR1 comprising the amino acid sequence of SEQ ID NO: 38; a CDR2 comprising the amino acid sequence of SEQ ID NO: 108; and a CDR3 comprising the amino acid sequence of SEQ ID NO: 178; or a variant thereof comprising up to about 3 (such as about any of 1, 2, or 3) amino acid substitutions in the CDR regions;

(4) a CDR1 comprising the amino acid sequence of SEQ ID NO: 39; a CDR2 comprising the amino acid sequence of SEQ ID NO: 109; and a CDR3 comprising the amino acid sequence of SEQ ID NO: 179; or a variant thereof comprising up to about 3 (such as about any of 1, 2, or 3) amino acid substitutions in the CDR regions;

(5) a CDR1 comprising the amino acid sequence of SEQ ID NO: 40; a CDR2 comprising the amino acid sequence of SEQ ID NO: 110; and a CDR3 comprising the amino acid sequence of SEQ ID NO: 180; or a variant thereof comprising up to about 3 (such as about any of 1, 2, or 3) amino acid substitutions in the CDR regions;

(6) a CDR1 comprising the amino acid sequence of SEQ ID NO: 41; a CDR2 comprising the amino acid sequence of SEQ ID NO: 111; and a CDR3 comprising the amino acid sequence of SEQ ID NO: 181; or a variant thereof comprising up to about 3 (such as about any of 1, 2, or 3) amino acid substitutions in the CDR regions;

(7) a CDR1 comprising the amino acid sequence of SEQ ID NO: 42; a CDR2 comprising the amino acid sequence of SEQ ID NO: 112; and a CDR3 comprising the amino acid sequence of SEQ ID NO: 182; or a variant thereof comprising up to about 3 (such as about any of 1, 2, or 3) amino acid substitutions in the CDR regions;

(8) a CDR1 comprising the amino acid sequence of SEQ ID NO: 54; a CDR2 comprising the amino acid sequence of SEQ ID NO: 124; and a CDR3 comprising the amino acid sequence of SEQ ID NO: 194; or a variant thereof comprising up to about 3 (such as about any of 1, 2, or 3) amino acid substitutions in the CDR regions;

(9) a CDR1 comprising the amino acid sequence of SEQ ID NO: 56; a CDR2 comprising the amino acid sequence of SEQ ID NO: 126; and a CDR3 comprising the amino acid sequence of SEQ ID NO: 196; or a variant thereof comprising up to about 3 (such as about any of 1, 2, or 3) amino acid substitutions in the CDR regions;

(10) a CDR1 comprising the amino acid sequence of SEQ ID NO: 57; a CDR2 comprising the amino acid sequence of SEQ ID NO: 127; and a CDR3 comprising the amino acid sequence of SEQ ID NO: 197; or a variant thereof comprising up to about 3 (such as about any of 1, 2, or 3) amino acid substitutions in the CDR regions;

(11) a CDR1 comprising the amino acid sequence of SEQ ID NO: 58; a CDR2 comprising the amino acid sequence of SEQ ID NO: 128; and a CDR3 comprising the amino acid sequence of SEQ ID NO: 198; or a variant thereof comprising up to about 3 (such as about any of 1, 2, or 3) amino acid substitutions in the CDR regions;

(12) a CDR1 comprising the amino acid sequence of SEQ ID NO: 59; a CDR2 comprising the amino acid sequence of SEQ ID NO: 129; and a CDR3 comprising the amino acid sequence of SEQ ID NO: 199; or a variant thereof comprising up to about 3 (such as about any of 1, 2, or 3) amino acid substitutions in the CDR regions;

(13) a CDR1 comprising the amino acid sequence of SEQ ID NO: 63; a CDR2 comprising the amino acid sequence of SEQ ID NO: 133; and a CDR3 comprising the amino acid sequence of SEQ ID NO: 203; or a variant thereof comprising up to about 3 (such as about any of 1, 2, or 3) amino acid substitutions in the CDR regions;

(14) a CDR1 comprising the amino acid sequence of SEQ ID NO: 65; a CDR2 comprising the amino acid sequence of SEQ ID NO: 135; and a CDR3 comprising the amino acid sequence of SEQ ID NO: 205; or a variant thereof comprising up to about 3 (such as about any of 1, 2, or 3) amino acid substitutions in the CDR regions;

(15) a CDR1 comprising the amino acid sequence of SEQ ID NO: 66; a CDR2 comprising the amino acid sequence of SEQ ID NO: 136; and a CDR3 comprising the amino acid sequence of SEQ ID NO: 206; or a variant thereof comprising up to about 3 (such as about any of 1, 2, or 3) amino acid substitutions in the CDR regions;

(16) a CDR1 comprising the amino acid sequence of SEQ ID NO: 67; a CDR2 comprising the amino acid sequence of SEQ ID NO: 137; and a CDR3 comprising the amino acid sequence of SEQ ID NO: 207; or a variant thereof comprising up to about 3 (such as about any of 1, 2, or 3) amino acid substitutions in the CDR regions;

(17) a CDR1 comprising the amino acid sequence of SEQ ID NO: 69; a CDR2 comprising the amino acid sequence of SEQ ID NO: 139; and a CDR3 comprising the amino acid sequence of SEQ ID NO: 209; or a variant thereof comprising up to about 3 (such as about any of 1, 2, or 3) amino acid substitutions in the CDR regions; or

(18) a CDR1 comprising the amino acid sequence of SEQ ID NO: 70; a CDR2 comprising the amino acid sequence of SEQ ID NO: 140; and a CDR3 comprising the amino acid sequence of SEQ ID NO: 210; or a variant thereof comprising up to about 3 (such as about any of 1, 2, or 3) amino acid substitutions in the CDR regions.

In some embodiments according to any one of the isolated anti-TIGIT constructs described above, the sdAb moiety specifically recognizing TIGIT comprises a $V_HH$ domain comprising the amino acid sequence of any one of the following: a-1) the amino acid residue at position 37 is selected from the group consisting of F, Y, V, L, A, H, S, I, W, C, N, G, D, T, and P (such as F, Y, L, I, or V, such as F or Y, or such as F); a-2) the amino acid residue at position 44 is selected from the group consisting of E, Q, G, D, A, K, R, L, P, S, V, H, T, N, W, M, and I (such as A, G, E, D, Q, R, S, or L, or such as G, E, or Q); a-3) the amino acid residue at position 45 is selected from the group consisting of L, R, P, H, F, G, Q, S, E, T, Y, C, I, D, and V (such as L, C, or R, or such as L or R); a-4) the amino acid residue at position 103 is selected from the group consisting of W, R, G, S, K, A, M, Y, I, F, T, N, V, Q, P, E, and C (such as W, G, or R, or such as W); and a-5) the amino acid residue at position 108 is selected from the group consisting of Q, L, R, P, E, K, S, T, M, A, and H (such as Q); or b-1) the amino acid residue at position 37 is selected from the group consisting of F, Y, L, I, and V (such as F or Y, or such as F); b-2) the amino acid residue at position 44 is selected from the group consisting of E and Q; b-3) the amino acid residue at position 45 is selected from the group consisting of R and L (such as R); b-4) the amino acid residue at position 103 is selected from the group consisting of W, R, G, and S (such as W); and b-5) the amino acid residue at position 108 is selected from the group consisting of Q and L (such as Q); or c-1) the amino acid residue at position 37 is selected from the group consisting of F, Y, L, I, and V (such as F or Y, or such as F); c-2) the amino acid residue at position 44 is selected from the group consisting of A, G, E, D, Q, R, S and L (such as G, E, or Q); c-3) the amino acid residue at position 45 is selected from the group consisting of L, R and C (such as L or R); c-4) the amino acid residue at position 103 is selected from the group consisting of P, R and S (such as R or S); and c-5) the amino acid residue at position 108 is selected from the group consisting of Q and L (such as Q); wherein the amino acid position is according to Kabat numbering. In some embodiments, position 108 can be optionally humanized to L when position 108 is Q.

In some embodiments according to any one of the isolated anti-TIGIT constructs described above, the sdAb moiety specifically recognizing TIGIT comprises a $V_HH$ domain comprising the amino acid sequence of any one of SEQ ID NOs: 253-259, 271, 273-276, 280, 282-284, 286-287, or a variant thereof having at least about 80% (such as at least about any of 80%, 85%, 90%, 91%, 92%, 93%, 94%, 95%, 96%, 97%, 98%, or 99%) sequence identify to any one of SEQ ID NOs: 253-259, 271, 273-276, 280, 282-284, 286-287. In some embodiments, the sdAb moiety specifically recognizing TIGIT comprises a $V_HH$ domain comprising the amino acid sequence of any one of SEQ ID NOs: 253-259, 271, 273-276, 280, 282-284, 286-287, or a variant thereof comprising up to about 3 (such as about any of 1, 2, or 3) amino acid substitutions in the $V_HH$ domain. In some embodiments, the amino acid substitutions are in the CDRs, such as the CDR1, and/or the CDR2, and/or the CDR3 of any one of SEQ ID NOs: 253-259, 271, 273-276, 280, 282-284, 286-287. In some embodiments, the amino acid substitutions are in the FRs, such as the FR1, and/or the FR2, and/or the FR3, and/or the FR4 of any one of SEQ ID NOs: 253-259, 271, 273-276, 280, 282-284, 286-287. In some embodiments, the amino acid substitutions are in both CDRs and FRs. In some embodiments, the sdAb moiety specifically recognizing TIGIT comprises a $V_HH$ domain comprising the amino acid sequence of any one of SEQ ID NOs: 253-259, 271, 273-276, 280, 282-284, 286-287.

In some embodiments according to any one of the isolated anti-TIGIT constructs described above, the $K_d$ of the binding between the sdAb moiety specifically recognizing TIGIT and TIGIT is about $10^{-5}$ M to about $10^{-12}$ M (such as about $10^{-5}$ M to about $10^{-12}$ M, about $10^{-7}$ M to about $10^{-12}$ M, or about $10^{-8}$ M to about $10^{-12}$ M).

In some embodiments according to any one of the isolated anti-TIGIT constructs described above, the sdAb moiety specifically recognizing TIGIT is camelid, chimeric, human, partially humanized, or fully humanized.

In some embodiments according to any one of the isolated anti-TIGIT constructs described above, the isolated anti-TIGIT construct is an sdAb-Fc fusion protein. In some embodiments, sdAb-Fc fusion protein is monomeric. In some embodiments, the sdAb-Fc fusion protein is dimeric. In some embodiments, the Fc fragment is a human IgG1 (hIgG1) Fc, effectorless (inert) hIgG1 Fc, or hIgG4 Fc. In some embodiments, the Fc fragment comprises the amino acid sequence of any one of SEQ ID NOs: 355, 356, and 389. In some embodiments, the sdAb moiety specifically recognizing TIGIT and the Fc fragment are optionally connected by a peptide linker, such as peptide linker comprising the amino acid sequence of any one of SEQ ID NOs: 324 and 370-378. In some embodiments, the sdAb-Fc fusion protein comprises the amino acid sequence of any one of SEQ ID NOs: 288-294, 306, 308-311, 315, 317-319, 321-322 and 365-367.

In some embodiments according to any one of the isolated anti-TIGIT construct described above, the isolated anti-TIGIT construct further comprises a second antibody moiety specifically recognizing a second epitope. In some embodiments, the second antibody moiety is a full-length antibody, a Fab, a Fab', a (Fab')2, an Fv, a single chain Fv (scFv), an scFv-scFv, a minibody, a diabody, or an sdAb. In some embodiments, the anti-TIGIT construct is monospecific. In some embodiments, the anti-TIGIT construct is multispecific (such as bispecific). In some embodiments, the second epitope is not from TIGIT. In some embodiments, the second epitope is from TIGIT but different from that specifically recognized by the anti-TIGIT sdAb moiety. In some embodiments, the second epitope is the same as that specifically recognized by the anti-TIGIT sdAb moiety. In some embodiments, the sdAb moiety specifically recognizing TIGIT and the second antibody moiety are optionally connected by a peptide linker, such as peptide linker comprising the amino acid sequence of any one of SEQ ID NOs: 324 and 370-378. In some embodiments, the second antibody moiety is an sdAb. In some embodiments, the second antibody moiety is a Fab. In some embodiments, the second antibody moiety is an scFv. In some embodiments, the second antibody moiety is a full-length antibody consisting of two heavy chains and two light chains. In some embodiments, the Fc fragment of the heavy chain is IgG1 Fc, effectorless IgG1 Fc, IgG2 Fc, or IgG4 Fc. In some embodiments, the N-terminus of the sdAb moiety specifically recognizing TIGIT is fused to the C-terminus of at least one of the heavy chains of the full-length antibody. In some embodiments, the C-terminus of the sdAb moiety specifically recognizing TIGIT is fused to the N-terminus of at least one of the heavy chains of the full-length antibody. In some embodiments, the N-terminus of the sdAb moiety specifically recognizing TIGIT is fused to the C-terminus of at least one of the light chains of the full-length antibody. In some embodiments, the C-terminus of the sdAb moiety specifically recognizing TIGIT is fused to the N-terminus of at least one of the light chains of the full-length antibody. In some embodiments, the isolated anti-TIGIT construct comprises four identical sdAb moieties specifically recognizing TIGIT as described above, the C-terminus of each anti-TIGIT sdAb moiety is fused to the N-terminus of each chain of the full-length antibody via an optional peptide linker. In some embodiments, the isolated anti-TIGIT construct comprises four identical sdAb moieties specifically recognizing TIGIT as described above, two anti-TIGIT sdAb moieties are fused to each other via an optional peptide linker, the other two anti-TIGIT sdAb moieties are fused to each other via an optional peptide linker, and the C-terminus of each of the anti-TIGIT sdAb moiety fusion polypeptide is fused to the N-terminus of each heavy chain of the full-length antibody via an optional peptide linker. In some embodiments the isolated anti-TIGIT construct consists of four polypeptide chains with structures from the N-terminus to the C-terminus as follows: (1) $V_L$—$C_L$; (2) anti-TIGIT sdAb-$V_H$—$C_H1$-$C_H2$-$C_H3$; (3) anti-TIGIT sdAb-$V_H$—$C_H1$-$C_H2$-$C_H3$; and (4) $V_L$—$C_L$, wherein $V_H$ and $V_L$ of polypeptide chains (1) and (2) forms an antigen binding site that specifically binds a first copy of the second epitope (e.g., PD-1, PD-L1), $V_H$ and $V_L$ of polypeptide chains (3) and (4) forms an antigen binding site that specifically binds a second copy of the second epitope (e.g., PD-1, PD-L1), and each anti-TIGIT sdAb specifically binds a copy of TIGIT. In some embodiments the isolated anti-TIGIT construct consists of four polypeptide chains with structures from the N-terminus to the C-terminus as follows: (1) $V_L$—$C_L$; (2) $V_H$—$C_H1$-$C_H2$-$C_H3$-anti-TIGIT sdAb; (3) $V_H$—$C_H1$-$C_H2$-$C_H3$-anti-TIGIT sdAb; and (4) $V_L$—$C_L$, wherein $V_H$ and $V_L$ of polypeptide chains (1) and (2) forms an antigen binding site that specifically binds a first copy of the second epitope (e.g., PD-1, PD-L1), $V_H$ and $V_L$ of polypeptide chains (3) and (4) forms an antigen binding site that specifically binds a second copy of the second epitope (e.g., PD-1, PD-L1), and each anti-TIGIT sdAb specifically binds a copy of TIGIT. In some embodiments the isolated anti-TIGIT construct consists of four polypeptide chains with structures from the N-terminus to the C-terminus as follows: (1) anti-TIGIT sdAb-$V_L$—$C_L$; (2) $V_H$—$C_H1$-$C_H2$-$C_H3$; (3) $V_H$—$C_H1$-$C_H2$-$C_H3$; and (4) anti-TIGIT sdAb-$V_L$—$C_L$, wherein $V_H$ and $V_L$ of polypeptide chains (1) and (2) forms an antigen binding site that specifically binds a first copy of the second epitope (e.g., PD-1, PD-L1), $V_H$ and $V_L$ of polypeptide chains (3) and (4) forms an antigen binding site that specifically binds a second copy of the second epitope (e.g., PD-1, PD-L1), and each anti-TIGIT sdAb specifically binds a copy of TIGIT. In some embodiments the isolated anti-TIGIT construct consists of four polypeptide chains with structures from the N-terminus to the C-terminus as follows: (1) $V_L$—$C_L$-anti-TIGIT sdAb; (2) $V_H$—$C_H1$-$C_H2$-$C_H3$; (3) $V_H$—$C_H1$-$C_H2$-$C_H3$; and (4) $V_L$—$C_L$-anti-TIGIT sdAb, wherein $V_H$ and $V_L$ of polypeptide chains (1) and (2) forms an antigen binding site that specifically binds a first copy of the second epitope (e.g. PD-1, PD-L1), $V_H$ and $V_L$ of polypeptide chains (3) and (4) forms an antigen binding site that specifically binds a second copy of the second epitope (e.g. PD-1, PD-L1), and each anti-TIGIT sdAb specifically binds a copy of TIGIT. In some embodiments the isolated anti-TIGIT construct consists of four polypeptide chains with structures from the N-terminus to the C-terminus as follows: (1) anti-TIGIT sdAb-$V_L$—$C_L$; (2) anti-TIGIT sdAb-$V_H$—$C_H1$-$C_H2$-$C_H3$; (3) anti-TIGIT sdAb-$V_H$—$C_H1$-$C_H2$-$C_H3$; and (4) anti-TIGIT sdAb-$V_L$—$C_L$, wherein $V_H$ and $V_L$ of polypeptide chains (1) and (2) forms an antigen binding site that specifically binds a first copy of the second epitope (e.g. PD-1, PD-L1), $V_H$ and $V_L$ of polypeptide chains (3) and (4) forms an antigen binding site that specifically binds a second copy of the second epitope (e.g. PD-1, PD-L1), and each anti-TIGIT sdAb specifically binds a copy of TIGIT. In some embodiments the isolated anti-TIGIT construct consists of four polypeptide chains with structures from the N-terminus to the C-terminus as follows: (1) $V_L$—$C_L$; (2) anti-TIGIT sdAb-anti-TIGIT sdAb-$V_H$—$C_H1$-$C_H2$-$C_H3$; (3) anti-TIGIT sdAb-anti-TIGIT sdAb-$V_H$—$C_H1$-$C_H2$-$C_H3$; and (4) $V_L$—$C_L$, wherein $V_H$ and $V_L$ of polypeptide chains (1) and (2) forms an antigen binding site that specifically binds a first copy of the second epitope (e.g. PD-1, PD-L1), $V_H$ and $V_L$ of polypeptide chains (3) and (4) forms an antigen binding site that specifically binds a second copy of the second epitope (e.g. PD-1, PD-L1), and each anti-TIGIT sdAb specifically binds a copy of TIGIT. In some embodiments the isolated anti-TIGIT construct consists of four polypeptide chains with structures from the N-terminus to the C-terminus as follows: (1) $V_L$—$C_L$; (2) $V_H$—$C_H1$-anti-TIGIT sdAb-$C_H2$-$C_H3$; (3) $V_H$—$C_H1$-anti-TIGIT sdAb-$C_H2$-$C_H3$; and (4) $V_L$—$C_L$, wherein $V_H$ and $V_L$ of polypeptide chains (1) and (2) forms an antigen binding site that specifically binds a first copy of the second epitope (e.g. PD-1, PD-L1), $V_H$ and $V_L$ of polypeptide chains (3) and (4) forms an antigen binding site that specifically binds a second copy of the second epitope (e.g. PD-1, PD-L1), and each anti-TIGIT sdAb specifically binds a copy of TIGIT. In some embodiments the isolated anti-TIGIT construct consists of two polypeptide chains each with a structure from the N-terminus to the C-terminus as follows: $V_L$—$V_H$-anti-TIGIT sdAb-$C_H2$-$C_H3$, wherein $V_H$ and $V_L$ of each polypeptide chain forms a scFv domain that specifically binds a copy of the second epitope (e.g. PD-1, PD-L1), and each anti-TIGIT sdAb specifically binds a copy of TIGIT. In some embodiments the isolated anti-TIGIT construct consists of four polypeptide chains with structures from the N-terminus to the C-terminus as follows: (1) $V_L$—$C_L$-anti-TIGIT sdAb-$C_L$; (2) $V_H$—$C_H1$-anti-TIGIT sdAb-$C_H1$-$C_H2$-$C_H3$; (3) $V_H$—$C_H1$-anti-TIGIT sdAb-$C_H1$-$C_H2$-$C_H3$; and (4) $V_L$—$C_L$-anti-TIGIT sdAb-$C_L$, wherein $V_H$ and $V_L$ of polypeptide chains (1) and (2) forms an antigen binding site that specifically binds a first copy of the second epitope (e.g. PD-1, PD-L1), $V_H$ and $V_L$ of polypeptide chains (3) and (4) forms an antigen binding site that specifically binds a second copy of the second epitope (e.g. PD-1, PD-L1), and each anti-TIGIT sdAb specifically binds a copy of TIGIT. In some embodiments the isolated anti-TIGIT construct consists of four polypeptide chains with structures from the N-terminus to the C-terminus as follows: (1) anti-TIGIT sdAb-$C_L$; (2) $V_L$—$V_H$-anti-TIGIT sdAb-$C_H1$-$C_H2$-$C_H3$; (3) $V_L$—$V_H$-anti-TIGIT sdAb-$C_H1$-$C_H2$-$C_H3$; and (4) anti-TIGIT sdAb-$C_L$, wherein $V_H$ and $V_L$ of polypeptide chains (2) and (3) each forms an scFv that specifically binds a copy of the second epitope (e.g. PD-1, PD-L1), and each anti-TIGIT sdAb specifically binds a copy of TIGIT. In some embodiments, the full-length antibody (or antigen binding portion comprising a $V_H$ and a $V_L$) specifically recognizes PD-1. In some embodiments, the anti-PD-1 full-length antibody (or antigen binding portion comprising a $V_H$ and a $V_L$) comprises a $V_H$ comprising the amino acid sequence of SEQ ID NO: 385, and a $V_L$ comprising the amino acid sequence of SEQ ID NO: 386. In some embodiments, the anti-PD-1 full-length antibody comprises a heavy chain comprising the amino acid sequence of SEQ ID NO: 325, and a light chain comprising the amino acid sequence of SEQ ID NO: 326. In some embodiments, the anti-PD-1 full-length antibody (or antigen binding portion comprising a $V_H$ and a $V_L$) comprises a $V_H$ comprising the amino acid sequence of SEQ ID NO: 387, and a $V_L$ comprising the amino acid sequence of SEQ ID NO: 388. In some embodiments, the anti-PD-1 full-length antibody comprises a heavy chain comprising the amino acid sequence of SEQ ID NO: 390, and a light chain comprising the amino acid sequence of SEQ ID NO: 391. In some embodiments, the anti-PD-1 full-length antibody (or antigen binding portion comprising a $V_H$ and a $V_L$) comprises a $V_H$ comprising the amino acid sequence of SEQ ID NO: 406, and a $V_L$ comprising the amino acid sequence of SEQ ID NO: 407. In some embodiments, the full-length antibody comprises a heavy chain comprising the amino acid sequence of SEQ ID NO: 390, and a light chain comprising the amino acid sequence of SEQ ID NO: 391, wherein at least one of the heavy chains of the full-length antibody is fused to the sdAb moiety specifically recognizing TIGIT described above, and wherein the heavy chain fusion polypeptide comprises the amino acid sequence of SEQ ID NO: 394 or 396. In some embodiments, the full-length antibody comprises a heavy chain comprising the amino acid sequence of SEQ ID NO: 390, and a light chain comprising the amino acid sequence of SEQ ID NO: 391, wherein at least one of the light chains of the full-length antibody is fused to the sdAb moiety specifically recognizing TIGIT described above, and wherein the light chain fusion polypeptide comprises the amino acid sequence of SEQ ID NO: 399 or 401. In some embodiments, the full-length antibody (or antigen binding portion comprising a $V_H$ and a $V_L$) specifically recognizes PD-L1. In some embodiments, the anti-PD-L1 full-length antibody (or antigen binding portion comprising a $V_H$ and a $V_L$) comprises 1) a $V_H$ comprising an HC-CDR1 comprising the amino acid sequence of SEQ ID NO: 349, an HC-CDR2 comprising the amino acid sequence of SEQ ID NO: 350, and an HC-CDR3 comprising the amino acid sequence of SEQ ID NO: 351, and 2) a $V_L$ comprising an LC-CDR1 comprising the amino acid sequence of SEQ ID NO: 352, an LC-CDR2 comprising the amino acid sequence of SEQ ID NO: 353, and an LC-CDR3 comprising the amino acid sequence of SEQ ID NO: 354. In some embodiments, the anti-PD-L1 full-length antibody (or antigen binding portion comprising a $V_H$ and a $V_L$) comprises a $V_H$ comprising the amino acid sequence of SEQ ID NO: 339, and a $V_L$ comprising the amino acid sequence of SEQ ID NO: 340. In some embodiments, the anti-PD-L1 full-length antibody comprises a heavy chain comprising the amino acid sequence of SEQ ID NO: 323 or 327, and a light chain comprising the amino acid sequence of SEQ ID NO: 328. In some embodiments, the anti-PD-L1 full-length antibody comprises a heavy chain comprising the amino acid sequence of SEQ ID NO: 329, and a light chain comprising the amino acid sequence of SEQ ID NO: 330. In some embodiments, the anti-PD-L1 full-length antibody (or antigen binding portion comprising a $V_H$ and a $V_L$) comprises a $V_H$ comprising the amino acid sequence of SEQ ID NO: 379, and a $V_L$ comprising the amino acid sequence of SEQ ID NO: 380. In some embodiments, the anti-PD-L1 full-length antibody (or antigen binding portion comprising a $V_H$ and a $V_L$) comprises a $V_H$ comprising the amino acid sequence of SEQ ID NO: 383, and a $V_L$ comprising the amino acid sequence of SEQ ID NO: 384. In some embodiments, the anti-PD-L1 full-length antibody (or antigen binding portion comprising a $V_H$ and a $V_L$) comprises a $V_H$ comprising the amino acid sequence of SEQ ID NO: 381, and a $V_L$ comprising the amino acid sequence of SEQ ID NO: 382. In some embodiments, the anti-PD-L1 full-length antibody comprises a heavy chain comprising the amino acid sequence of SEQ ID NO: 331, and a light chain comprising the amino acid sequence of SEQ ID NO: 332. In some embodiments, the anti-PD-L1 full-length antibody comprises a heavy chain comprising the amino acid sequence of SEQ ID NO: 333, and a light chain comprising the amino acid sequence of SEQ ID NO: 334. In some embodiments, the full-length antibody comprises a heavy chain comprising the amino acid sequence of SEQ ID NO: 327, and a light chain comprising the amino acid sequence of SEQ ID NO: 328, wherein at least one of the heavy chains of the full-length antibody is fused to the sdAb moiety specifically recognizing TIGIT described above, and wherein the heavy chain fusion polypeptide comprises the amino acid sequence of SEQ ID NO: 343. In some embodiments, the full-length antibody comprises a heavy chain comprising the amino acid sequence of SEQ ID NO: 323, and a light chain comprising the amino acid sequence of SEQ ID NO: 328, wherein at least one of the heavy chains of the full-length antibody is fused to the sdAb moiety specifically recognizing TIGIT described above, and wherein the heavy chain fusion polypeptide comprises the amino acid sequence of SEQ ID NO: 357 or 359. In some embodiments, the full-length antibody comprises a heavy chain comprising the amino acid sequence of SEQ ID NO: 329, and a light chain comprising the amino acid sequence of SEQ ID NO: 330, wherein at least one of the heavy chains of the full-length antibody is fused to the sdAb moiety specifically recognizing TIGIT described above, and wherein the heavy chain fusion polypeptide comprises the amino acid sequence of SEQ ID NO: 341 or 402. In some embodiments, the full-length antibody comprises a heavy chain comprising the amino acid sequence of SEQ ID NO: 323, and a light chain comprising the amino acid sequence of SEQ ID NO: 328, wherein at least one of the light chains of the full-length antibody is fused to the sdAb moiety specifically recognizing TIGIT described above, and wherein the light chain fusion polypeptide comprises the amino acid sequence of SEQ ID NO: 362 or 364. In some embodiments, the full-length antibody comprises a heavy chain comprising the amino acid sequence of SEQ ID NO: 329, and a light chain comprising the amino acid sequence of SEQ ID NO: 330, wherein at least one of the light chains of the full-length antibody is fused to the sdAb moiety specifically recognizing TIGIT described above, and wherein the light chain fusion polypeptide comprises the amino acid sequence of SEQ ID NO: 405. In some embodiments, the full-length antibody comprises a heavy chain comprising the amino acid sequence of SEQ ID NO: 331, and a light chain comprising the amino acid sequence of SEQ ID NO: 332, wherein at least one of the heavy chains of the full-length antibody is fused to the sdAb moiety specifically recognizing TIGIT described above, and wherein the heavy chain fusion polypeptide comprises the amino acid sequence of SEQ ID NO: 347. In some embodiments, the full-length antibody comprises a heavy chain comprising the amino acid sequence of SEQ ID NO: 333, and a light chain comprising the amino acid sequence of SEQ ID NO: 334, wherein at least one of the heavy chains of the full-length antibody is fused to the sdAb moiety specifically recognizing TIGIT described above, and wherein the heavy chain fusion polypeptide comprises the amino acid sequence of SEQ ID NO: 345.

In some embodiments according to any one of the isolated anti-TIGIT constructs described above, the isolated anti-TIGIT construct further comprises a biologically active protein or fragments thereof.

Further provided is an isolated anti-TIGIT construct comprising an sdAb moiety specifically recognizing TIGIT, wherein the sdAb moiety comprises CDR1, CDR2, and CDR3 of any one of SEQ ID NOs: 253-259, 271, 273-276, 280, 282-284, 286-287.

Further provided is an isolated anti-TIGIT construct (e.g., anti-TIGIT sdAb, anti-TIGIT sdAb-Fc fusion, PD-1×TIGIT BABP, or PD-L1×TIGIT BABP) that specifically binds to TIGIT competitively with the any of the isolated anti-TIGIT construct described above.

Further provided is a pharmaceutical composition comprising any one of the isolated anti-TIGIT constructs described above, and optionally a pharmaceutical acceptable carrier.

Another aspect of the present application provides a method of treating an individual having a TIGIT-related disease (such as cancer, or immune-related disease), comprising administering to the individual an effective amount of any one of the pharmaceutical compositions described above. In some embodiments, the TIGIT-related disease is cancer. In some embodiments, the cancer is a solid tumor, such as a colon cancer. In some embodiments, the TIGIT-related disease is an immune-related disease. In some embodiments, immune-related disease is associated with a T cell dysfunctional disorder. In some embodiments, the T cell dysfunctional disorder is characterized by T cell exhaustion. In some embodiments, the immune-related disease is selected from the group consisting of unresolved acute infection, chronic infection, and tumor immunity. In some embodiments, the TIGIT related disease is a pathogenic infection. In some embodiments, the method further comprises administering to the individual an additional therapy (e.g., cancer therapy), such as surgery, radiation, chemotherapy, immunotherapy, hormone therapy, or a combination thereof. In some embodiments, the additional therapy is immunotherapy. In some embodiments, the immunotherapy comprises administering to the individual an effective amount of a second pharmaceutical composition comprising an immunomodulator, such as an immune checkpoint inhibitor (e.g., antibody specifically recognizing PD-1 or PD-L1). In some embodiments, the pharmaceutical composition is administered systemically, such as intravenously (i.v.) or intraperitoneally (i.p.). In some embodiments, the pharmaceutical composition is administered locally, such as intratumorally. In some embodiments, the individual is a human.

Further provided is an isolated nucleic acid encoding any one of the isolated anti-TIGIT construct described above. In some embodiments, the isolated nucleic acid comprises the nucleic acid sequence of any one of SEQ ID NOs: 246-252.

Further provided is a vector comprising any one of the isolated nucleic acids described above.

Further provided is an isolated host cell comprising any one of the isolated nucleic acid or vector described above.

Further provided is a kit comprising any one of the isolated anti-TIGIT construct, isolated nucleic acid, vector, or isolated host cell described above.

Another aspect of the present application provides a method of producing any one of isolated anti-TIGIT constructs described above, comprising culturing a host cell comprising any one of the isolated nucleic acid or vector described above, or culturing any one of the isolated host cell described above, under conditions effective to express the encoded anti-TIGIT construct; and obtaining the expressed anti-TIGIT construct from said host cell. In some embodiments, the method further comprises producing a host cell comprising any one of the isolated nucleic acid or vector described above.

BRIEF DESCRIPTION OF THE DRAWINGS

FIG. 1 depicts immune response evaluation of pre-immune serum and post-immune serum after final boost.

FIG. 2 depicts the immune response evaluation of regular antibodies (IgG1) and heavy chain antibodies (IgG2 and IgG3) after final boost. Corresponding immunoglobulin fragment isolated from pre-immune serum were used as negative controls.

FIG. 3 depicts function of unhumanized anti-TIGIT sdAb-Fc fusion proteins in Promega TIGIT/CD155 blockade reporter assay. 22G2 was used as positive anti-TIGIT control.

FIGS. 4A-4C depict in vivo efficacy of unhumanized anti-TIGIT sdAb-Fc fusion protein (AS19584-Fc) in CT26 syngeneic tumor model, alone or in combination with mouse PD-1 blocking antibody RMP1-14. 10A7 was used as a positive control of anti-TIGIT antibody. FIG. 4A shows average tumor volume in each treatment group. FIG. 4B shows the percent of tumor infiltrating $CD8^+$ or $CD4^+$ T lymphocytes under each treatment. FIG. 4C shows spider plot for each animal.

FIG. 5A shows average tumor volume in each treatment group. FIG. 5B shows spider plot of tumor volume in log scale for each animal under different treatments.

FIG. 6A shows average tumor volume in each treatment group. FIG. 6B shows spider plot of tumor volume in log scale for each animal under different treatments.

FIG. 7 depicts in vitro functional activity of humanized anti-TIGIT sdAb-Fc fusion proteins (AS19584VH28-Fc, AS19886VH5-Fc, AS19886VH8-Fc) using Promega TIGIT/CD155 blockade reporter assay, compared to their unhumanized parental anti-TIGIT sdAb-Fc fusion proteins (AS19584-Fc, AS19886-Fc). 22G2 was used as positive anti-TIGIT antibody control.

FIG. 8 depicts in vitro functional activity of humanized anti-TIGIT sdAb-Fc fusion proteins (AS19584VH28-Fc, AS19886VH5-Fc, AS19886VH8-Fc) using IL-2 release assay, compared to their unhumanized parental anti-TIGIT sdAb-Fc fusion proteins (AS19584-Fc, AS19886-Fc). 22G2 was used as positive anti-TIGIT antibody control.

FIG. 9 depicts in vivo pharmacokinetic curve of humanized anti-TIGIT sdAb-Fc fusion protein AS19584VH28-Fc. 22G2 was used as positive anti-TIGIT antibody control.

FIG. 10A shows average tumor volume in each treatment group. FIG. 10B shows spider plot of tumor volume for each animal 22G2 was used as positive anti-TIGIT antibody control. hIgG1 was used as a negative control.

FIG. 11 depicts in vitro function of proof-of-concept (POC) PD-L1×TIGIT bispecific antigen binding proteins (BABPs) and their parental anti-PD-L1 antibody elements using cell-based functional assay for PD-L1. Tecentriq biosimilar (with either IgG1 Fc or inert IgG1 Fc) was used as positive anti-PD-L1 antibody control. h53C1 (with either IgG1 Fc or inert IgG1 Fc) is an in-house developed anti-PD-L1 antibody.

FIG. 12 depicts in vitro function of POC PD-L1×TIGIT BABPs and corresponding parental elements (anti-PD-L1 antibody and anti-TIGIT sdAb-Fc fusion protein) using Mixed Lymphocyte Reaction (MLR). Tecentriq biosimilar (with either IgG1 Fc or inert IgG1 Fc) was used as positive anti-PD-L1 antibody control. 22G2 was used as positive anti-TIGIT antibody control. hIgG1 was used as a negative control.

FIG. 13 depicts in vitro function of POC PD-L1×TIGIT BABPs and corresponding parental elements (anti-TIGIT sdAb-Fc fusion protein) using Promega TIGIT/CD155 blockade reporter assay. 22G2 was used as positive anti-TIGIT antibody control.

FIG. 14 depicts in vitro function of POC PD-L1×TIGIT BABPs and corresponding parental elements (anti-TIGIT sdAb-Fc fusion protein) using IL-2-release assay for TIGIT targeting. 22G2 was used as positive anti-TIGIT antibody control.

FIG. 15 depicts in vitro function of POC PD-L1×TIGIT BABP BTP-5, its corresponding parental elements (h53C1 and AS19584-Fc fusion protein), and their combinations using PD-L1/TIGIT bifunctional reporter assay.

FIG. 16A shows average tumor volume in each treatment group. FIG. 16B shows spider plot of tumor volume for each animal IgG1 was used as a negative control.

FIG. 29 depicts the capability of BTP-21, Atezolizumab, Durvalumab, and h53C1 in inducing IFN-γ release ex vivo by primary human PBMCs from 3 healthy individuals.

FIG. 30 depicts in vivo efficacy of PD-1×TIGIT BABP BTP-11 in Balb/c human PD-1 KI mice bearing CT26 tumor, compared to its parental elements (PD1-BM-min and AS19584VH28) and their combination. Data are shown in spider plot. TF indicates tumor-free mice.

FIG. 31 depicts in vivo efficacy of PD-L1×TIGIT BABP BTP-21 in C57BL/6 human PD-1/PD-L1 double KI mice bearing MC38 tumor overexpressing human PD-L1 (MC38-hPDL1), compared to Atezolizumab, its parental elements (h53C1 and AS19584VH28) and their combination. Data are shown in spider plot. TF indicates tumor-free mice.

DETAILED DESCRIPTION OF THE INVENTION

Figure 4A:
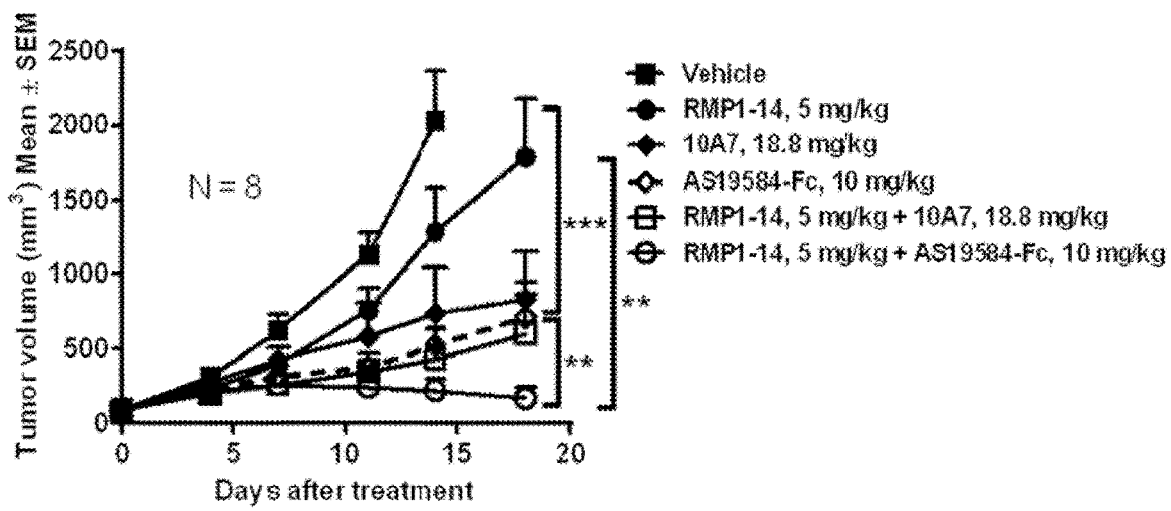

The present invention provides novel sdAbs specifically recognizing TIGIT (hereinafter also referred to as "anti-TIGIT sdAb") and its antibody variants (for example, a larger protein or polypeptide comprising the anti-TIGIT sdAb, such as anti-TIGIT sdAb-Fc fusion protein, anti-TIGIT sdAb fused to a full-length antibody, Fab, or scFv, or multispecific antigen binding proteins (MABPs, such as bispecific antigen binding proteins (BABPs)) comprising the anti-TIGIT sdAb), uses thereof for treating TIGIT-related diseases (such as cancer) and methods of making thereof.

sdAbs are different from conventional 4-chain antibodies by having a single monomeric antibody variable domain, such as heavy chain variable domain ($V_H$H), which can exhibit high affinity to an antigen without the aid of a light chain. Camelid $V_H$H is known as the smallest functional antigen-binding fragment with a molecular weight of approximately 15 kDa.

Accordingly, one aspect of the present application provides an isolated anti-TIGIT construct comprising an sdAb moiety specifically recognizing TIGIT. The isolated anti-TIGIT construct can be, for example, an anti-TIGIT sdAb (e.g. natural or humanized), a polypeptide comprising multiple anti-TIGIT sdAbs described herein fused together, an anti-TIGIT sdAb-Fc fusion protein comprising an anti-TIGIT sdAb described herein fused to an Fc fragment (e.g., a human IgG1 Fc, effectorless (inert) IgG1 Fc, hIgG2 Fc, or IgG4 Fc), or a MABP comprising the anti-TIGIT sdAb described herein fused to a full-length antibody (such as anti-PD-1 antibody or anti-PD-L1 antibody) or antigen binding fragment that comprises a heavy chain variable domain ($V_H$) and a light chain variable domain ($V_L$). The anti-TIGIT construct can be monospecific or multispecific (such as bispecific), monovalent or multivalent (such as bivalent).

Also provided are compositions (such as pharmaceutical compositions), kits and articles of manufacture comprising the anti-TIGIT construct described herein, methods of making thereof, and methods of treating TIGIT-related disease (such as cancer) using the anti-TIGIT construct described herein.

I. Definitions

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing the quality of life, and/or prolonging survival. Also encompassed by "treatment" is a reduction of pathological consequence of cancer. The methods of the invention contemplate any one or more of these aspects of treatment.

The term "effective amount" used herein refers to an amount of an agent or a combination of agents, sufficient to treat a specified disorder, condition or disease such as ameliorate, palliate, lessen, and/or delay one or more of its symptoms. In reference to cancer, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay recurrence. An effective amount can be administered in one or more administrations. The effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

As used herein, an "individual" or a "subject" refers to a mammal, including, but not limited to, human, bovine, horse, feline, canine, rodent, or primate. In some embodiments, the individual is a human.

The terms "antibody," "antigen binding portion," or "antibody moiety" are used in their broadest sense and encompasses various antibody structures, including but not limited to monoclonal antibodies, polyclonal antibodies, multispecific antibodies (e.g., bispecific antibodies), full-length antibodies and antigen-binding fragments thereof, so long as they exhibit the desired antigen-binding activity.

The term "heavy chain-only antibody" or "HCAb" refers to a functional antibody, which comprises heavy chains, but lacks the light chains usually found in 4-chain antibodies. Camelid animals (such as camels, llamas, or alpacas) are known to produce HCAbs.

The term "single-domain antibody" or "sdAb" refers to a single antigen-binding polypeptide having three complementary determining regions (CDRs). The sdAb alone is capable of binding to the antigen without pairing with a corresponding CDR-containing polypeptide. In some cases, single-domain antibodies are engineered from camelid HCAbs, and their heavy chain variable domains are referred herein as "$V_HHs$" (Variable domain of the heavy chain of the Heavy chain antibody). Camelid sdAb is one of the smallest known antigen-binding antibody fragments (see, e.g., Hamers-Casterman et al., Nature 363:446-8 (1993); Greenberg et al., Nature 374:168-73 (1995); Hassanzadeh-Ghassabeh et al., Nanomedicine (Lond), 8:1013-26 (2013)). A basic $V_HH$ has the following structure from the N-terminus to the C-terminus: FR1-CDR1-FR2-CDR2-FR3-CDR3-FR4, in which FR1 to FR4 refer to framework regions 1 to 4, respectively, and in which CDR1 to CDR3 refer to the complementarity determining regions 1 to 3.

An "isolated" antibody (or construct) is one that has been identified, separated and/or recovered from a component of its production environment (e.g., natural or recombinant). Preferably, the isolated polypeptide is free of association with all other components from its production environment. Contaminant components of its production environment, such as that resulting from recombinant transfected cells, are materials that would typically interfere with research, diagnostic or therapeutic uses for the antibody, and may include enzymes, hormones, and other proteinaceous or non-proteinaceous solutes. In preferred embodiments, the polypeptide will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator; or (3) to homogeneity by SDS-PAGE under non-reducing or reducing conditions using Coomassie Blue or, preferably, silver stain. Isolated antibody (or construct) includes the antibody in situ within recombinant cells since at least one component of the antibody's natural environment will not be present. Ordinarily, however, an isolated polypeptide, antibody, or construct will be prepared by at least one purification step.

The "variable region" or "variable domain" of an antibody refers to the amino-terminal domains of the heavy or light chain of the antibody. The variable domains of the heavy chain and light chain may be referred to as "$V_H$" and "$V_L$", respectively. These domains are generally the most variable parts of the antibody (relative to other antibodies of the same class) and contain the antigen binding sites. Heavy-chain only antibodies from the Camelid species have a single heavy chain variable region, which is referred to as "$V_HH$". $V_HH$ is thus a special type of $V_H$.

The terms "full-length antibody", "intact antibody", or "whole antibody" are used interchangeably to refer to an antibody in its substantially intact form, as opposed to an antibody fragment. Specifically, full-length 4-chain antibodies include those with heavy and light chains including an Fc region. Full-length heavy-chain only antibodies include the heavy chain variable domain (such as $V_HH$) and an Fc region. The constant domains may be native sequence constant domains (e.g., human native sequence constant domains) or amino acid sequence variants thereof. In some cases, the intact antibody may have one or more effector functions.

An "antibody fragment" or "antigen-binding fragment" comprises a portion of an intact antibody, preferably the antigen binding and/or the variable region of the intact antibody. Examples of antibody fragments include, but are not limited to Fab, Fab', F(ab')$_2$ and Fv fragments; diabodies; linear antibodies (see U.S. Pat. No. 5,641,870, Example 2; Zapata et al., Protein Eng. 8(10): 1057-1062 (1995)); single-chain antibody (scFv) molecules; single-domain antibodies (such as $V_HH$), and multispecific antibodies formed from antibody fragments. Papain digestion of antibodies produced two identical antigen-binding fragments, called "Fab" fragments, and a residual "Fc" fragment, a designation reflecting the ability to crystallize readily. The Fab fragment consists of an entire L chain along with the variable domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy-terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The term "constant domain" refers to the portion of an immunoglobulin molecule having a more conserved amino acid sequence relative to the other portion of the immunoglobulin, the variable domain, which contains the antigen-binding site. The constant domain contains the $C_H1$, $C_H2$ and $C_H3$ domains (collectively, $C_H$) of the heavy chain and the CHL (or $C_L$) domain of the light chain.

The "light chains" of antibodies (immunoglobulins) from any mammalian species can be assigned to one of two clearly distinct types, called kappa ("κ") and lambda ("λ"), based on the amino acid sequences of their constant domains.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hyper-variable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the scFv polypeptide further comprises a polypeptide linker between the $V_H$ and $V_L$ domains which enables the scFv to form the desired structure for antigen binding. For a review of the scFv, see Pluckthun in The Pharmacology of Monoclonal Antibodies, vol. 113, Rosenburg and Moore eds., Springer-Verlag, New York, pp. 269-315 (1994).

The term "hypervariable region," "HVR," or "HV," when used herein refers to the regions of an antibody variable domain which are hypervariable in sequence and/or form structurally defined loops. Generally, single-domain antibodies comprise three HVRs (or CDRs): HVR1 (or CDR1), HVR2 (or CDR2), and HVR3 (or CDR3). HVR3 (or CDR3) displays the most diversity of the three HVRs, and is believed to play a unique role in conferring fine specificity to antibodies. See, e.g., Hamers-Casterman et al., *Nature* 363:446-448 (1993); Sheriff et al., *Nature Struct. Biol.* 3:733-736 (1996).

The term "Complementarity Determining Region" or "CDR" are used to refer to hypervariable regions as defined by the Kabat system. See Kabat et al., *Sequences of Proteins of Immunological Interest*, 5th Ed. Public Health Service, National Institutes of Health, Bethesda, Md. (1991).

A number of HVR delineations are in use and are encompassed herein. The Kabat Complementarity Determining Regions (CDRs) are based on sequence variability and are the most commonly used (Kabat et al., *Sequences of Proteins of Immunological Interest*, 5th Ed. Public Health Service, National Institutes of Health, Bethesda, Md. (1991)). Chothia refers instead to the location of the structural loops (Chothia and Lesk, *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below in Table 1.

TABLE 1

HVR delineations.

| Loop | Kabat | AbM | Chothia | Contact |
|------|-------|-----|---------|---------|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B |
|    |          | (Kabat Numbering) | | |
| H1 | H31-H35 | H26-H35 | H26-H32 | H30-H35 |
|    |         | (Chothia Numbering) | | |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the $V_L$ and 26-35 (H1), 50-65 or 49-65 (H2) and 93-102, 94-102, or 95-102 (H3) in the $V_H$. The variable domain residues are numbered according to Kabat et al., supra, for each of these definitions.

The amino acid residues of a single-domain antibody (such as $V_HH$) are numbered according to the general numbering for $V_H$ domains given by Kabat et al. ("Sequence of proteins of immunological interest", US Public Health Services, NIH Bethesda, Md., Publication No. 91), as applied to $V_HH$ domains from Camelids in the article of Riechmann and Muyldermans, J. Immunol. Methods 2000 Jun. 23; 240 (1-2): 185-195. According to this numbering, FR1 of a $V_HH$ comprises the amino acid residues at positions 1-30, CDR1 of a $V_HH$ comprises the amino acid residues at positions 31-35, FR2 of a $V_HH$ comprises the amino acids at positions 36-49, CDR2 of a $V_HH$ comprises the amino acid residues at positions 50-65, FR3 of a $V_HH$ comprises the amino acid residues at positions 66-94, CDR3 of a $V_HH$ comprises the amino acid residues at positions 95-102, and FR4 of a $V_HH$ comprises the amino acid residues at positions 103-113. In this respect, it should be noted that—as is well known in the art for $V_H$ domains and for $V_HH$ domains—the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering).

The expression "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g. residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

Unless indicated otherwise herein, the numbering of the residues in an immunoglobulin heavy chain is that of the EU index as in Kabat et al., supra. The "EU index as in Kabat" refers to the residue numbering of the human IgG1 EU antibody.

"Framework" or "FR" residues are those variable-domain residues other than the HVR residues as herein defined.

As used herein, the term "specifically binds," "specifically recognizes," or is "specific for" refers to measurable and reproducible interactions such as binding between a target and an antigen binding protein (such as an sdAb), which is determinative of the presence of the target in the presence of a heterogeneous population of molecules including biological molecules. For example, an antigen binding protein (such as an sdAb) that specifically binds a target (which can be an epitope) is an antigen binding protein (such as an sdAb) that binds this target with greater affinity, avidity, more readily, and/or with greater duration than it binds other targets. In some embodiments, the extent of binding of an antigen binding protein (such as an sdAb) to an unrelated target is less than about 10% of the binding of the antigen binding protein (such as an sdAb) to the target as measured, e.g., by a radioimmunoassay (RIA). In some embodiments, an antigen binding protein (such as an sdAb) that specifically binds a target has a dissociation constant ($K_d$) of $\leq 10^{-5}$ M, $\leq 10^{-6}$ M, $\leq 10^{-7}$ M, $\leq 10^{-8}$ M, $\leq 10^{-9}$ M, $\leq 10^{-10}$ M, $\leq 10^{-11}$ M, or $\leq 10^{-12}$ M. In some embodiments, an antigen binding protein specifically binds an epitope on a protein that is conserved among the protein from different species. In some embodiments, specific binding can include, but does not require exclusive binding. Binding specificity of the antibody or antigen-binding domain can be determined experimentally by methods known in the art. Such methods comprise, but are not limited to Western blots, ELISA-, RIA-, ECL-, IRMA-, EIA-, BIAcore-tests and peptide scans.

The term "specificity" refers to selective recognition of an antigen binding protein (such as an sdAb) for a particular epitope of an antigen. Natural antibodies, for example, are monospecific. The term "multispecific" as used herein denotes that an antigen binding protein has polyepitopic specificity (i.e., is capable of specifically binding to two, three, or more, different epitopes on one biological molecule or is capable of specifically binding to epitopes on two, three, or more, different biological molecules). "Bispecific" as used herein denotes that an antigen binding protein has two different antigen-binding specificities. Unless otherwise indicated, the order in which the antigens bound by a bispecific antibody listed is arbitrary. That is, for example, the terms "anti-TIGIT/PD-L1," "anti-PD-L1/TIGIT," "TIGIT×PD-L1," "PD-L1×TIGIT," "PD-L1/TIGIT," "TIGIT/PD-L1," "PD-L1-TIGIT," and "TIGIT-PD-L1" may be used interchangeably to refer to bispecific antibodies that specifically bind to both TIGIT and PD-L1. The term "monospecific" as used herein denotes an antigen binding protein (such as a sdAb) that has one or more binding sites each of which bind the same epitope of the same antigen.

The term "valent" as used herein denotes the presence of a specified number of binding sites in an antigen binding protein. A natural antibody for example or a full length antibody has two binding sites and is bivalent. As such, the terms "trivalent", "tetravalent", "pentavalent" and "hexavalent" denote the presence of two binding site, three binding sites, four binding sites, five binding sites, and six binding sites, respectively, in an antigen binding protein.

The term "Fc region" or "fragment crystallizable region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies described herein include human IgG1, IgG2 (IgG2A, IgG2B), IgG3 and IgG4.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity that reflects a 1:1 interaction between members of a binding pair. Binding affinity can be indicated by $K_d$, $K_{off}$, $K_{on}$, or $K_a$. The term "$K_{off}$", as used herein, is intended to refer to the off rate constant for dissociation of an antibody (or antigen-binding domain) from the antibody/antigen complex, as determined from a kinetic selection set up, expressed in units of $s^{-1}$. The term "$K_{on}$", as used herein, is intended to refer to the on rate constant for association of an antibody (or antigen-binding domain) to the antigen to form the antibody/antigen complex, expressed in units of $M^{-1} s^{-1}$. The term equilibrium dissociation constant "$K_D$" or "$K_d$", as used herein, refers to the dissociation constant of a particular antibody-antigen interaction, and describes the concentration of antigen required to occupy one half of all of the antibody-binding domains present in a solution of antibody molecules at equilibrium, and is equal to $K_{off}/K_{on}$, expressed in units of M. The measurement of $K_d$ presupposes that all binding agents are in solution. In the case where the antibody is tethered to a cell wall, e.g., in a yeast expression system, the corresponding equilibrium rate constant is expressed as EC50, which gives a good approximation of $K_d$. The affinity constant, $K_a$, is the inverse of the dissociation constant, $K_d$, expressed in units of $M^{-1}$. The dissociation constant ($K_D$ or $K_d$) is used as an indicator showing affinity of antibodies to antigens. For example, easy analysis is possible by the Scatchard method using antibodies marked with a variety of marker agents, as well as by using BiacoreX (made by Amersham Biosciences), which is an over-the-counter, measuring kit, or similar kit, according to the user's manual and experiment operation method attached with the kit. The $K_D$ value that can be derived using these methods is expressed in units of M (Mols). An antibody or antigen-binding fragment thereof that specifically binds to a target may have a dissociation constant ($K_d$) of, for example, $\leq 10^{-5}$ M, $\leq 10^{-6}$ M, $\leq 10^{-7}$ M, $\leq 10^{-8}$ M, $\leq 10^{-9}$ M, $\leq 10^{-10}$ M, $\leq 10^{-11}$ M, or $\leq 10^{-12}$ M.

Half maximal inhibitory concentration ($IC_{50}$) is a measure of the effectiveness of a substance (such as an antibody) in inhibiting a specific biological or biochemical function. It indicates how much of a particular drug or other substance (inhibitor, such as an antibody) is needed to inhibit a given biological process (e.g., the binding between TIGIT and CD155, or component of a process, i.e. an enzyme, cell, cell receptor or microorganism) by half. The values are typically expressed as molar concentration. $IC_{50}$ is comparable to an "$EC_{50}$" for agonist drug or other substance (such as an antibody). $EC_{50}$ also represents the plasma concentration required for obtaining 50% of a maximum effect in vivo. As used herein, an "$IC_{50}$" is used to indicate the effective concentration of an antibody (such as an anti-TIGIT sdAb) needed to neutralize 50% of the antigen bioactivity (such as TIGIT bioactivity) in vitro. $IC_{50}$ or $EC_{50}$ can be measured by bioassays such as inhibition of ligand binding by FACS analysis (competition binding assay), cell based cytokine release assay, or amplified luminescent proximity homogeneous assay (AlphaLISA).

"Percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

An "isolated" nucleic acid molecule encoding a construct, antibody, or antigen-binding fragment thereof described herein is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies described herein is in a form other than in the form or setting in which it is found in nature. Isolated nucleic acid molecules therefore are distinguished from nucleic acid encoding the polypeptides and antibodies described herein existing naturally in cells. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

It is understood that embodiments of the invention described herein include "consisting" and/or "consisting essentially of" embodiments.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter. For example, the method is not used to treat cancer of type X means the method is used to treat cancer of types other than X.

The term "about X—Y" used herein has the same meaning as "about X to about Y."

As used herein and in the appended claims, the singular forms "a," "or," and "the" include plural referents unless the context clearly dictates otherwise.

II. Anti-TIGIT Construct (I) Anti-TIGIT Single-Domain Antibody Moiety

The isolated anti-TIGIT construct described herein comprises a single-domain antibody (sdAb) moiety that specifically recognizes TIGIT (or "anti-TIGIT sdAb"). In some embodiments, the isolated anti-TIGIT construct is an anti-TIGIT sdAb.

In some embodiments, there is provided an anti-TIGIT sdAb moiety comprising a CDR1 comprising the amino acid sequence of any one of SEQ ID NOs: 36-42, 54, 56-59, 63, 65-67, 69-70, or a variant thereof comprising up to about 3 (such as about any of 1, 2, or 3) amino acid substitutions; a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210, or a variant thereof comprising up to about 3 (such as about any of 1, 2, or 3) amino acid substitutions. In some embodiments, the $K_d$ of the binding between the anti-TIGIT sdAb moiety and TIGIT is about $10^{-5}$ M to about $10^{-12}$ M (such as about $10^{-7}$ M to about $10^{-12}$ M, or about $10^{-8}$ M to about $10^{-12}$ M). In some embodiments, the anti-TIGIT sdAb moiety is camelid, chimeric, human, partially humanized, or fully humanized.

In some embodiments, the anti-TIGIT sdAb moiety comprises a CDR3 comprising the amino acid sequence of any one of SEQ ID NOs: 176-182, 194, 196-199, 203, 205-207, 209-210, and the amino acid substitutions are in CDR1 and/or CDR2. Thus, in some embodiments, there is provided an anti-TIGIT sdAb moiety comprising a CDR1 comprising the amino acid sequence of any one of SEQ ID NOs: 36-42, 54, 56-59, 63, 65-67, 69-70, or a variant thereof comprising up to about 3 (such as about any of 1, 2, or 3) amino acid substitutions; a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210. In some embodiments, the $K_d$ of the binding between the anti-TIGIT sdAb moiety and TIGIT is about $10^{-5}$ M to about $10^{-12}$ M (such as about $10^{-7}$ M to about $10^{-12}$ M, or about $10^{-8}$ M to about $10^{-12}$ M). In some embodiments, the anti-TIGIT sdAb moiety is camelid, chimeric, human, partially humanized, or fully humanized.

In some embodiments, there is provided an anti-TIGIT sdAb moiety comprising a CDR1 comprising the amino acid sequence of any one of SEQ ID NOs: 36-42, 54, 56-59, 63, 65-67, 69-70; a CDR2 comprising the amino acid sequence of any one of SEQ ID NOs: 106-112, 124, 126-129, 133, 135-137, 139-140; and a CDR3 comprising the amino acid sequence of any one of SEQ ID NOs: 176-182, 194, 196-199, 203, 205-207, 209-210; or a variant thereof comprising up to about 3 (such as about any of 1, 2, or 3) amino acid substitutions in the CDR regions. In some embodiments, the amino acid substitutions are in CDR1 and/or CDR2.

In some embodiments, there is provided an anti-TIGIT sdAb moiety comprising a CDR1 comprising the amino acid sequence of any one of SEQ ID NOs: 36-42, 54, 56-59, 63, 65-67, 69-70; a CDR2 comprising the amino acid sequence of any one of SEQ ID NOs: 106-112, 124, 126-129, 133, 135-137, 139-140; and a CDR3 comprising the amino acid sequence of any one of SEQ ID NOs: 176-182, 194, 196-199, 203, 205-207, 209-210.

The sequences of the CDRs noted herein are provided in Table 22. The CDRs can be combined in various pair-wise combinations to generate a number of anti-TIGIT sdAb moieties.

For example, in some embodiments, there is provided an anti-TIGIT sdAb moiety comprising a CDR1 comprising the amino acid sequence of SEQ ID NO: 36, or a variant thereof comprising up to about 3 (such as about any of 1, 2, or 3) amino acid substitutions; a CDR2 comprising the amino acid sequence of SEQ ID NO: 106, or a variant thereof comprising up to about 3 (such as about any of 1, 2, or 3) amino acid substitutions; and a CDR3 comprising the amino acid sequence of SEQ ID NO: 176, or a variant thereof comprising up to about 3 (such as about any of 1, 2, or 3) amino acid substitutions. In some embodiments, there is provided an anti-TIGIT sdAb moiety comprising a CDR1 comprising the amino acid sequence of SEQ ID NO: 36; a CDR2 comprising the amino acid sequence of SEQ ID NO: 106; and a CDR3 comprising the amino acid sequence of SEQ ID NO: 176; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-TIGIT sdAb moiety comprising a CDR1 comprising the amino acid sequence of SEQ ID NO: 36; a CDR2 comprising the amino acid sequence of SEQ ID NO: 106; and a CDR3 comprising the amino acid sequence of SEQ ID NO: 176.

In some embodiments, there is provided an anti-TIGIT sdAb moiety comprising a CDR1 comprising the amino acid sequence of SEQ ID NO: 37, or a variant thereof comprising up to about 3 (such as about any of 1, 2, or 3) amino acid substitutions; a CDR2 comprising the amino acid sequence of SEQ ID NO: 107, or a variant thereof comprising up to about 3 (such as about any of 1, 2, or 3) amino acid substitutions; and a CDR3 comprising the amino acid sequence of SEQ ID NO: 177, or a variant thereof comprising up to about 3 (such as about any of 1, 2, or 3) amino acid substitutions. In some embodiments, there is provided an anti-TIGIT sdAb moiety comprising a CDR1 comprising the amino acid sequence of SEQ ID NO: 37; a CDR2 comprising the amino acid sequence of SEQ ID NO: 107; and a CDR3 comprising the amino acid sequence of SEQ ID NO:

177; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-TIGIT sdAb moiety comprising a CDR1 comprising the amino acid sequence of SEQ ID NO: 37; a CDR2 comprising the amino acid sequence of SEQ ID NO: 107; and a CDR3 comprising the amino acid sequence of SEQ ID NO: 177.

In some embodiments, there is provided an anti-TIGIT sdAb moiety comprising a CDR1 comprising the amino acid sequence of SEQ ID NO: 38, or a variant thereof comprising up to about 3 (such as about any of 1, 2, or 3) amino acid substitutions; a CDR2 comprising the amino acid sequence of SEQ ID NO: 108, or a variant thereof comprising up to about 3 (such as about any of 1, 2, or 3) amino acid substitutions; and a CDR3 comprising the amino acid sequence of SEQ ID NO: 178, or a variant thereof comprising up to about 3 (such as about any of 1, 2, or 3) amino acid substitutions. In some embodiments, there is provided an anti-TIGIT sdAb moiety comprising a CDR1 comprising the amino acid sequence of SEQ ID NO: 38; a CDR2 comprising the amino acid sequence of SEQ ID NO: 108; and a CDR3 comprising the amino acid sequence of SEQ ID NO: 178; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-TIGIT sdAb moiety comprising a CDR1 comprising the amino acid sequence of SEQ ID NO: 38; a CDR2 comprising the amino acid sequence of SEQ ID NO: 108; and a CDR3 comprising the amino acid sequence of SEQ ID NO: 178.

In some embodiments, there is provided an anti-TIGIT sdAb moiety comprising a CDR1 comprising the amino acid sequence of SEQ ID NO: 39, or a variant thereof comprising up to about 3 (such as about any of 1, 2, or 3) amino acid substitutions; a CDR2 comprising the amino acid sequence of SEQ ID NO: 109, or a variant thereof comprising up to about 3 (such as about any of 1, 2, or 3) amino acid substitutions; and a CDR3 comprising the amino acid sequence of SEQ ID NO: 179, or a variant thereof comprising up to about 3 (such as about any of 1, 2, or 3) amino acid substitutions. In some embodiments, there is provided an anti-TIGIT sdAb moiety comprising a CDR1 comprising the amino acid sequence of SEQ ID NO: 39; a CDR2 comprising the amino acid sequence of SEQ ID NO: 109; and a CDR3 comprising the amino acid sequence of SEQ ID NO: 179; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-TIGIT sdAb moiety comprising a CDR1 comprising the amino acid sequence of SEQ ID NO: 39; a CDR2 comprising the amino acid sequence of SEQ ID NO: 109; and a CDR3 comprising the amino acid sequence of SEQ ID NO: 179.

In some embodiments, there is provided an anti-TIGIT sdAb moiety comprising a CDR1 comprising the amino acid sequence of SEQ ID NO: 40, or a variant thereof comprising up to about 3 (such as about any of 1, 2, or 3) amino acid substitutions; a CDR2 comprising the amino acid sequence of SEQ ID NO: 110, or a variant thereof comprising up to about 3 (such as about any of 1, 2, or 3) amino acid substitutions; and a CDR3 comprising the amino acid sequence of SEQ ID NO: 180, or a variant thereof comprising up to about 3 (such as about any of 1, 2, or 3) amino acid substitutions. In some embodiments, there is provided an anti-TIGIT sdAb moiety comprising a CDR1 comprising the amino acid sequence of SEQ ID NO: 40; a CDR2 comprising the amino acid sequence of SEQ ID NO: 110; and a CDR3 comprising the amino acid sequence of SEQ ID NO: 180; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-TIGIT sdAb moiety comprising a CDR1 comprising the amino acid sequence of SEQ ID NO: 40; a CDR2 comprising the amino acid sequence of SEQ ID NO: 110; and a CDR3 comprising the amino acid sequence of SEQ ID NO: 180.

In some embodiments, there is provided an anti-TIGIT sdAb moiety comprising a CDR1 comprising the amino acid sequence of SEQ ID NO: 41, or a variant thereof comprising up to about 3 (such as about any of 1, 2, or 3) amino acid substitutions; a CDR2 comprising the amino acid sequence of SEQ ID NO: 111, or a variant thereof comprising up to about 3 (such as about any of 1, 2, or 3) amino acid substitutions; and a CDR3 comprising the amino acid sequence of SEQ ID NO: 181, or a variant thereof comprising up to about 3 (such as about any of 1, 2, or 3) amino acid substitutions. In some embodiments, there is provided an anti-TIGIT sdAb moiety comprising a CDR1 comprising the amino acid sequence of SEQ ID NO: 41; a CDR2 comprising the amino acid sequence of SEQ ID NO: 111; and a CDR3 comprising the amino acid sequence of SEQ ID NO: 181; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-TIGIT sdAb moiety comprising a CDR1 comprising the amino acid sequence of SEQ ID NO: 41; a CDR2 comprising the amino acid sequence of SEQ ID NO: 111; and a CDR3 comprising the amino acid sequence of SEQ ID NO: 181.

In some embodiments, there is provided an anti-TIGIT sdAb moiety comprising a CDR1 comprising the amino acid sequence of SEQ ID NO: 42, or a variant thereof comprising up to about 3 (such as about any of 1, 2, or 3) amino acid substitutions; a CDR2 comprising the amino acid sequence of SEQ ID NO: 112, or a variant thereof comprising up to about 3 (such as about any of 1, 2, or 3) amino acid substitutions; and a CDR3 comprising the amino acid sequence of SEQ ID NO: 182, or a variant thereof comprising up to about 3 (such as about any of 1, 2, or 3) amino acid substitutions. In some embodiments, there is provided an anti-TIGIT sdAb moiety comprising a CDR1 comprising the amino acid sequence of SEQ ID NO: 42; a CDR2 comprising the amino acid sequence of SEQ ID NO: 112; and a CDR3 comprising the amino acid sequence of SEQ ID NO: 182; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-TIGIT sdAb moiety comprising a CDR1 comprising the amino acid sequence of SEQ ID NO: 42; a CDR2 comprising the amino acid sequence of SEQ ID NO: 112; and a CDR3 comprising the amino acid sequence of SEQ ID NO: 182.

In some embodiments, there is provided an anti-TIGIT sdAb moiety comprising a CDR1 comprising the amino acid sequence of SEQ ID NO: 54, or a variant thereof comprising up to about 3 (such as about any of 1, 2, or 3) amino acid substitutions; a CDR2 comprising the amino acid sequence of SEQ ID NO: 124, or a variant thereof comprising up to about 3 (such as about any of 1, 2, or 3) amino acid substitutions; and a CDR3 comprising the amino acid sequence of SEQ ID NO: 194, or a variant thereof comprising up to about 3 (such as about any of 1, 2, or 3) amino acid substitutions. In some embodiments, there is provided an anti-TIGIT sdAb moiety comprising a CDR1 comprising the amino acid sequence of SEQ ID NO: 54; a CDR2 comprising the amino acid sequence of SEQ ID NO: 124; and a CDR3 comprising the amino acid sequence of SEQ ID NO: 194; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-TIGIT sdAb moiety comprising a CDR1 comprising the amino acid sequence of SEQ ID NO: 54; a CDR2 comprising the amino acid sequence of SEQ ID NO: 124; and a CDR3 comprising the amino acid sequence of SEQ ID NO: 194.

In some embodiments, there is provided an anti-TIGIT sdAb moiety comprising a CDR1 comprising the amino acid sequence of SEQ ID NO: 56, or a variant thereof comprising up to about 3 (such as about any of 1, 2, or 3) amino acid substitutions; a CDR2 comprising the amino acid sequence of SEQ ID NO: 126, or a variant thereof comprising up to about 3 (such as about any of 1, 2, or 3) amino acid substitutions; and a CDR3 comprising the amino acid sequence of SEQ ID NO: 196, or a variant thereof comprising up to about 3 (such as about any of 1, 2, or 3) amino acid substitutions. In some embodiments, there is provided an anti-TIGIT sdAb moiety comprising a CDR1 comprising the amino acid sequence of SEQ ID NO: 56; a CDR2 comprising the amino acid sequence of SEQ ID NO: 126; and a CDR3 comprising the amino acid sequence of SEQ ID NO: 196; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-TIGIT sdAb moiety comprising a CDR1 comprising the amino acid sequence of SEQ ID NO: 56; a CDR2 comprising the amino acid sequence of SEQ ID NO: 126; and a CDR3 comprising the amino acid sequence of SEQ ID NO: 196.

In some embodiments, there is provided an anti-TIGIT sdAb moiety comprising a CDR1 comprising the amino acid sequence of SEQ ID NO: 57, or a variant thereof comprising up to about 3 (such as about any of 1, 2, or 3) amino acid substitutions; a CDR2 comprising the amino acid sequence of SEQ ID NO: 127, or a variant thereof comprising up to about 3 (such as about any of 1, 2, or 3) amino acid substitutions; and a CDR3 comprising the amino acid sequence of SEQ ID NO: 197, or a variant thereof comprising up to about 3 (such as about any of 1, 2, or 3) amino acid substitutions. In some embodiments, there is provided an anti-TIGIT sdAb moiety comprising a CDR1 comprising the amino acid sequence of SEQ ID NO: 57; a CDR2 comprising the amino acid sequence of SEQ ID NO: 127; and a CDR3 comprising the amino acid sequence of SEQ ID NO: 197; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-TIGIT sdAb moiety comprising a CDR1 comprising the amino acid sequence of SEQ ID NO: 57; a CDR2 comprising the amino acid sequence of SEQ ID NO: 127; and a CDR3 comprising the amino acid sequence of SEQ ID NO: 197.

In some embodiments, there is provided an anti-TIGIT sdAb moiety comprising a CDR1 comprising the amino acid sequence of SEQ ID NO: 58, or a variant thereof comprising up to about 3 (such as about any of 1, 2, or 3) amino acid substitutions; a CDR2 comprising the amino acid sequence of SEQ ID NO: 128, or a variant thereof comprising up to about 3 (such as about any of 1, 2, or 3) amino acid substitutions; and a CDR3 comprising the amino acid sequence of SEQ ID NO: 198, or a variant thereof comprising up to about 3 (such as about any of 1, 2, or 3) amino acid substitutions. In some embodiments, there is provided an anti-TIGIT sdAb moiety comprising a CDR1 comprising the amino acid sequence of SEQ ID NO: 58; a CDR2 comprising the amino acid sequence of SEQ ID NO: 128; and a CDR3 comprising the amino acid sequence of SEQ ID NO: 198; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-TIGIT sdAb moiety comprising a CDR1 comprising the amino acid sequence of SEQ ID NO: 58; a CDR2 comprising the amino acid sequence of SEQ ID NO: 128; and a CDR3 comprising the amino acid sequence of SEQ ID NO: 198.

In some embodiments, there is provided an anti-TIGIT sdAb moiety comprising a CDR1 comprising the amino acid sequence of SEQ ID NO: 59, or a variant thereof comprising up to about 3 (such as about any of 1, 2, or 3) amino acid substitutions; a CDR2 comprising the amino acid sequence of SEQ ID NO: 129, or a variant thereof comprising up to about 3 (such as about any of 1, 2, or 3) amino acid substitutions; and a CDR3 comprising the amino acid sequence of SEQ ID NO: 199, or a variant thereof comprising up to about 3 (such as about any of 1, 2, or 3) amino acid substitutions. In some embodiments, there is provided an anti-TIGIT sdAb moiety comprising a CDR1 comprising the amino acid sequence of SEQ ID NO: 59; a CDR2 comprising the amino acid sequence of SEQ ID NO: 129; and a CDR3 comprising the amino acid sequence of SEQ ID NO: 199; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-TIGIT sdAb moiety comprising a CDR1 comprising the amino acid sequence of SEQ ID NO: 59; a CDR2 comprising the amino acid sequence of SEQ ID NO: 129; and a CDR3 comprising the amino acid sequence of SEQ ID NO: 199.

In some embodiments, there is provided an anti-TIGIT sdAb moiety comprising a CDR1 comprising the amino acid sequence of SEQ ID NO: 63, or a variant thereof comprising up to about 3 (such as about any of 1, 2, or 3) amino acid substitutions; a CDR2 comprising the amino acid sequence of SEQ ID NO: 133, or a variant thereof comprising up to about 3 (such as about any of 1, 2, or 3) amino acid substitutions; and a CDR3 comprising the amino acid sequence of SEQ ID NO: 203, or a variant thereof comprising up to about 3 (such as about any of 1, 2, or 3) amino acid substitutions. In some embodiments, there is provided an anti-TIGIT sdAb moiety comprising a CDR1 comprising the amino acid sequence of SEQ ID NO: 63; a CDR2 comprising the amino acid sequence of SEQ ID NO: 133; and a CDR3 comprising the amino acid sequence of SEQ ID NO: 203; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-TIGIT sdAb moiety comprising a CDR1 comprising the amino acid sequence of SEQ ID NO: 63; a CDR2 comprising the amino acid sequence of SEQ ID NO: 133; and a CDR3 comprising the amino acid sequence of SEQ ID NO: 203.

In some embodiments, there is provided an anti-TIGIT sdAb moiety comprising a CDR1 comprising the amino acid sequence of SEQ ID NO: 65, or a variant thereof comprising up to about 3 (such as about any of 1, 2, or 3) amino acid substitutions; a CDR2 comprising the amino acid sequence of SEQ ID NO: 135, or a variant thereof comprising up to about 3 (such as about any of 1, 2, or 3) amino acid substitutions; and a CDR3 comprising the amino acid sequence of SEQ ID NO: 205, or a variant thereof comprising up to about 3 (such as about any of 1, 2, or 3) amino acid substitutions. In some embodiments, there is provided an anti-TIGIT sdAb moiety comprising a CDR1 comprising the amino acid sequence of SEQ ID NO: 65; a CDR2 comprising the amino acid sequence of SEQ ID NO: 135; and a CDR3 comprising the amino acid sequence of SEQ ID NO: 205; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-TIGIT sdAb moiety comprising a CDR1 comprising the amino acid sequence of SEQ ID NO: 65; a CDR2 comprising the amino acid sequence of SEQ ID NO: 135; and a CDR3 comprising the amino acid sequence of SEQ ID NO: 205.

In some embodiments, there is provided an anti-TIGIT sdAb moiety comprising a CDR1 comprising the amino acid sequence of SEQ ID NO: 66, or a variant thereof comprising up to about 3 (such as about any of 1, 2, or 3) amino acid substitutions; a CDR2 comprising the amino acid sequence of SEQ ID NO: 136, or a variant thereof comprising up to about 3 (such as about any of 1, 2, or 3) amino acid substitutions; and a CDR3 comprising the amino acid sequence of SEQ ID NO: 206, or a variant thereof comprising up to about 3 (such as about any of 1, 2, or 3) amino acid substitutions. In some embodiments, there is provided an anti-TIGIT sdAb moiety comprising a CDR1 comprising the amino acid sequence of SEQ ID NO: 66; a CDR2 comprising the amino acid sequence of SEQ ID NO: 136; and a CDR3 comprising the amino acid sequence of SEQ ID NO: 206; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-TIGIT sdAb moiety comprising a CDR1 comprising the amino acid sequence of SEQ ID NO: 66; a CDR2 comprising the amino acid sequence of SEQ ID NO: 136; and a CDR3 comprising the amino acid sequence of SEQ ID NO: 206.

In some embodiments, there is provided an anti-TIGIT sdAb moiety comprising a CDR1 comprising the amino acid sequence of SEQ ID NO: 67, or a variant thereof comprising up to about 3 (such as about any of 1, 2, or 3) amino acid substitutions; a CDR2 comprising the amino acid sequence of SEQ ID NO: 137, or a variant thereof comprising up to about 3 (such as about any of 1, 2, or 3) amino acid substitutions; and a CDR3 comprising the amino acid sequence of SEQ ID NO: 207, or a variant thereof comprising up to about 3 (such as about any of 1, 2, or 3) amino acid substitutions. In some embodiments, there is provided an anti-TIGIT sdAb moiety comprising a CDR1 comprising the amino acid sequence of SEQ ID NO: 67; a CDR2 comprising the amino acid sequence of SEQ ID NO: 137; and a CDR3 comprising the amino acid sequence of SEQ ID NO: 207; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-TIGIT sdAb moiety comprising a CDR1 comprising the amino acid sequence of SEQ ID NO: 67; a CDR2 comprising the amino acid sequence of SEQ ID NO: 137; and a CDR3 comprising the amino acid sequence of SEQ ID NO: 207.

In some embodiments, there is provided an anti-TIGIT sdAb moiety comprising a CDR1 comprising the amino acid sequence of SEQ ID NO: 69, or a variant thereof comprising up to about 3 (such as about any of 1, 2, or 3) amino acid substitutions; a CDR2 comprising the amino acid sequence of SEQ ID NO: 139, or a variant thereof comprising up to about 3 (such as about any of 1, 2, or 3) amino acid substitutions; and a CDR3 comprising the amino acid sequence of SEQ ID NO: 209, or a variant thereof comprising up to about 3 (such as about any of 1, 2, or 3) amino acid substitutions. In some embodiments, there is provided an anti-TIGIT sdAb moiety comprising a CDR1 comprising the amino acid sequence of SEQ ID NO: 69; a CDR2 comprising the amino acid sequence of SEQ ID NO: 139; and a CDR3 comprising the amino acid sequence of SEQ ID NO: 209; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-TIGIT sdAb moiety comprising a CDR1 comprising the amino acid sequence of SEQ ID NO: 69; a CDR2 comprising the amino acid sequence of SEQ ID NO: 139; and a CDR3 comprising the amino acid sequence of SEQ ID NO: 209.

In some embodiments, there is provided an anti-TIGIT sdAb moiety comprising a CDR1 comprising the amino acid sequence of SEQ ID NO: 70, or a variant thereof comprising up to about 3 (such as about any of 1, 2, or 3) amino acid substitutions; a CDR2 comprising the amino acid sequence of SEQ ID NO: 140, or a variant thereof comprising up to about 3 (such as about any of 1, 2, or 3) amino acid substitutions; and a CDR3 comprising the amino acid sequence of SEQ ID NO: 210, or a variant thereof comprising up to about 3 (such as about any of 1, 2, or 3) amino acid substitutions. In some embodiments, there is provided an anti-TIGIT sdAb moiety comprising a CDR1 comprising the amino acid sequence of SEQ ID NO: 70; a CDR2 comprising the amino acid sequence of SEQ ID NO: 140; and a CDR3 comprising the amino acid sequence of SEQ ID NO: 210; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-TIGIT sdAb moiety comprising a CDR1 comprising the amino acid sequence of SEQ ID NO: 70; a CDR2 comprising the amino acid sequence of SEQ ID NO: 140; and a CDR3 comprising the amino acid sequence of SEQ ID NO: 210.

The anti-TIGIT sdAb moiety may comprise one or more "hallmark residues" in one or more of the FR sequences. In some embodiments, the anti-TIGIT sdAb moiety comprises a $V_HH$ domain comprising the amino acid sequence of any one of the following: a-1) the amino acid residue at position 37 is selected from the group consisting of F, Y, V, L, A, H, S, I, W, C, N, G, D, T, and P (such as F, Y, L, I, or V, such as F or Y, or such as F); a-2) the amino acid residue at position 44 is selected from the group consisting of E, Q, G, D, A, K, R, L, P, S, V, H, T, N, W, M, and I (such as A, G, E, D, Q, R, S, or L, or such as G, E, or Q); a-3) the amino acid residue at position 45 is selected from the group consisting of L, R, P, H, F, G, Q, S, E, T, Y, C, I, D, and V (such as L, C, or R, or such as L or R); a-4) the amino acid residue at position 103 is selected from the group consisting of W, R, G, S, K, A, M, Y, I, F, T, N, V, Q, P, E, and C (such as W, G, or R, or such as W); and a-5) the amino acid residue at position 108 is selected from the group consisting of Q, L, R, P, E, K, S, T, M, A, and H (such as Q); or b-1) the amino acid residue at position 37 is selected from the group consisting of F, Y, L, I, and V (such as F or Y, or such as F); b-2) the amino acid residue at position 44 is selected from the group consisting of E and Q; b-3) the amino acid residue at position 45 is selected from the group consisting of R and L (such as R); b-4) the amino acid residue at position 103 is selected from the group consisting of W, R, G, and S (such as W); and b-5) the amino acid residue at position 108 is selected from the group consisting of Q and L (such as Q); or c-1) the amino acid residue at position 37 is selected from the group consisting of F, Y, L, I, and V (such as F or Y, or such as F); c-2) the amino acid residue at position 44 is selected from the group consisting of A, G, E, D, Q, R, S and L (such as G, E, or Q); c-3) the amino acid residue at position 45 is selected from the group consisting of L, R and C (such as L or R); c-4) the amino acid residue at position 103 is selected from the group consisting of P, R and S (such as R or S); and c-5) the amino acid residue at position 108 is selected from the group consisting of Q and L (such as Q); wherein the amino acid position is according to Kabat numbering. It should be noted that these "hallmark residues" at amino acid positions 37, 44, 45, 103 and 108 according to Kabat numbering apply to anti-TIGIT sdAb moieties of natural $V_HH$ sequences, and can be substituted during humanization. For example, Q at amino acid position 108 according to Kabat numbering can be optionally humanized to L. Other humanized substitutions will be clear to those skilled in the art. For example, potentially useful humanizing substitutions can be determined by comparing the FR sequences of a naturally occurring $V_HH$ with the corresponding FR sequences of one or more closely related human $V_H$, then introducing one or more of such potentially useful humanizing substitutions into said $V_HH$ using methods known in the art (also as described herein). The resulting humanized $V_HH$ sequences can be tested for their TIGIT binding affinity, for stability, for ease and level of expression, and/or for other desired properties. Possible residue substitutions may also come from an antibody $V_H$ domain wherein the $V_H/V_L$ interface comprises one or more highly charged amino acid residues. The anti-TIGIT sdAb moiety described herein can be partially or fully humanized Preferably, the resulting humanized anti-TIGIT sdAb binds to TIGIT with $K_d$, $K_{on}$, and $K_{off}$ as described herein.

In some embodiments, there is provided an anti-TIGIT sdAb moiety comprising a $V_HH$ domain comprising the amino acid sequence of any one of SEQ ID NOs: 253-259, 271, 273-276, 280, 282-284, 286-287, or a variant thereof having at least about 80% (such as at least about any of 80%, 85%, 90%, 91%, 92%, 93%, 94%, 95%, 96%, 97%, 98%, or 99%) sequence identify to any one of SEQ ID NOs: 253-259, 271, 273-276, 280, 282-284, 286-287. In some embodiments, there is provided an anti-TIGIT sdAb moiety comprising a $V_HH$ domain comprising the amino acid sequence of any one of SEQ ID NOs: 253-259, 271, 273-276, 280, 282-284, 286-287, or a variant thereof comprising up to about 3 (such as about any of 1, 2, or 3) amino acid substitutions in the $V_HH$ domain. In some embodiments, the anti-TIGIT sdAb moiety comprising the $V_HH$ domain comprising the amino acid sequence of any one of SEQ ID NOs: 253-259, 271, 273-276, 280, 282-284, 286-287, or a variant thereof comprises amino acid substitutions in CDRs, such as the CDR1, and/or the CDR2, and/or the CDR3 of any one of SEQ ID NOs: 253-259, 271, 273-276, 280, 282-284, 286-287. In some embodiments, the anti-TIGIT sdAb moiety comprising the $V_HH$ domain comprising the amino acid sequence of any one of SEQ ID NOs: 253-259, 271, 273-276, 280, 282-284, 286-287, or a variant thereof comprises CDR1, CDR2, and CDR3 of any one of SEQ ID NOs: 253-259, 271, 273-276, 280, 282-284, 286-287, and the amino acid substitutions are in FRs, such as the FR1, and/or the FR2, and/or the FR3, and/or the FR4 of any one of SEQ ID NOs: 253-259, 271, 273-276, 280, 282-284, 286-287. In some embodiments, the anti-TIGIT sdAb moiety comprising the $V_HH$ domain comprising the amino acid sequence of any one of SEQ ID NOs: 253-259, 271, 273-276, 280, 282-284, 286-287, or a variant thereof comprises amino acid substitutions in both CDRs and FRs. In some embodiments, there is provided an anti-TIGIT sdAb moiety comprising a $V_HH$ domain comprising the amino acid sequence of any one of SEQ ID NOs: 253-259, 271, 273-276, 280, 282-284, 286-287. In some embodiments, there is provided an anti-TIGIT sdAb moiety comprising CDR1, CDR2, and CDR3 of any one of SEQ ID NO: 253-259, 271, 273-276, 280, 282-284, 286-287. In some embodiments, the $K_d$ of the binding between the anti-TIGIT sdAb moiety and TIGIT is about $10^{-5}$ M to about $10^{-12}$ M (such as about $10^{-7}$ M to about $10^{-12}$ M, or about $10^{-8}$ M to about $10^{-12}$ M). In some embodiments, the anti-TIGIT sdAb moiety is camelid, chimeric, human, partially humanized, or fully humanized.

In some embodiments, there is provided an anti-TIGIT sdAb moiety (hereinafter referred to as "competing anti-TIGIT sdAb moiety" or "competing anti-TIGIT sdAb") or anti-TIGIT construct comprising an anti-TIGIT sdAb moiety (hereinafter referred to as "competing anti-TIGIT construct") that specifically binds to TIGIT competitively with any one of the anti-TIGIT sdAb moiety described herein. In some embodiments, competitive binding may be determined using an ELISA assay. In some embodiments, there is provided an anti-TIGIT sdAb moiety (or an anti-TIGIT construct comprising an anti-TIGIT sdAb moiety) that specifically binds to TIGIT competitively with an anti-TIGIT sdAb moiety comprising the amino acid sequence of any one of SEQ ID NOs: 253-259, 271, 273-276, 280, 282-284, 286-287. In some embodiments, there is provided an anti-TIGIT sdAb moiety (or an anti-TIGIT construct comprising an anti-TIGIT sdAb moiety) that specifically binds to TIGIT competitively with an anti-TIGIT sdAb moiety comprising a CDR1 comprising the amino acid sequence of any one of SEQ ID NOs: 36-42, 54, 56-59, 63, 65-67, 69-70; a CDR2 comprising the amino acid sequence of any one of SEQ ID NOs: 106-112, 124, 126-129, 133, 135-137, 139-140; and a CDR3 comprising the amino acid sequence of any one of SEQ ID NOs: 176-182, 194, 196-199, 203, 205-207, 209-210. In some embodiments, the $K_d$ of the binding between the competing anti-TIGIT sdAb moiety and TIGIT is about $10^{-5}$ M to about $10^{-12}$ M (such as about $10^{-7}$ M to about $10^{-12}$ M, or about $10^{-8}$ M to about $10^{-12}$ M). In some embodiments, the competing anti-TIGIT sdAb moiety is camelid, chimeric, human, partially humanized, or fully humanized Single-Domain Antibodies Exemplary sdAbs include, but are not limited to, heavy chain variable domains from heavy-chain only antibodies (e.g., $V_HH$ (Variable domain of the heavy chain of the Heavy chain antibody) in Camelidae or $V_{NAR}$ (Variable domain of the shark New Antigen Receptor) in cartilaginous fish), binding molecules naturally devoid of light chains, single domains (such as $V_H$ or $V_L$) derived from conventional 4-chain antibodies, humanized heavy-chain only antibodies, human single-domain antibodies produced by transgenic mice or rats expressing human heavy chain segments, and engineered domains and single domain scaffolds other than those derived from antibodies. The sdAbs may be derived from any species including, but not limited to mouse, rat, human, camel, llama, lamprey, fish, shark, goat, rabbit, and bovine. sdAbs contemplated herein also include naturally occurring sdAb molecules from species other than Camelidae and sharks.

In some embodiments, the sdAb is derived from a naturally occurring single-domain antigen binding molecule known as heavy chain antibody devoid of light chains (also referred herein as "heavy chain-only antibodies", or "HCAb"). Such single domain molecules are disclosed in WO 94/04678 and Hamers-Casterman, C. et al. (1993) Nature 363:446-448, for example. For clarity reasons, the variable domain derived from a heavy chain molecule naturally devoid of light chain is known herein as a $V_H$H to distinguish it from the conventional $V_H$ of four chain immunoglobulins. Such a $V_H$H molecule can be derived from antibodies raised in Camelidae species, for example, camel, llama, vicuna, dromedary, alpaca and guanaco. Other species besides Camelidae may produce heavy chain molecules naturally devoid of light chain, and such $V_H$Hs are within the scope of the present application.

In some embodiments, the sdAb is derived from a variable region of the immunoglobulin found in cartilaginous fish. For example, the sdAb can be derived from the immunoglobulin isotype known as Novel Antigen Receptor (NAR) found in the serum of shark. Methods of producing single domain molecules derived from a variable region of NAR ("IgNARs") are described in WO 03/014161 and Streltsov (2005) Protein Sci. 14:2901-2909.

In some embodiments, the sdAb is recombinant, CDR-grafted, humanized, camelized, de-immunized and/or in vitro generated (e.g., selected by phage display). In some embodiments, the amino acid sequence of the framework regions may be altered by "camelization" of specific amino acid residues in the framework regions. Camelization refers to the replacing or substitution of one or more amino acid residues in the amino acid sequence of a (naturally occurring) $V_H$ domain from a conventional 4-chain antibody by one or more of the amino acid residues that occur at the corresponding position(s) in a $V_H$H domain of a heavy chain antibody. This can be performed in a manner known per se, which will be clear to the skilled person, for example on the basis of the further description herein. Such "camelizing" substitutions are preferably inserted at amino acid positions that form and/or are present at the $V_H$—$V_L$ interface, and/or at the so-called Camelidae hallmark residues, as defined herein (see for example WO 94/04678, Davies and Riechmann FEBS Letters 339: 285-290, 1994; Davies and Riechmann Protein Engineering 9 (6): 531-537, 1996; Riechmann J. Mol. Biol. 259: 957-969, 1996; and Riechmann and Muyldermans J. Immunol. Meth. 231: 25-38, 1999).

In some embodiments, the sdAb is a human sdAb produced by transgenic mice or rats expressing human heavy chain segments. See, e.g., US20090307787A1, U.S. Pat. No. 8,754,287, US20150289489A1, US20100122358A1, and WO2004049794. In some embodiments, the sdAb is affinity-matured.

In some embodiments, naturally occurring $V_H$H domains against a particular antigen or target, can be obtained from (naïve or immune) libraries of Camelid $V_H$H sequences. Such methods may or may not involve screening such a library using said antigen or target, or at least one part, fragment, antigenic determinant or epitope thereof using one or more screening techniques known per se. Such libraries and techniques are for example described in WO 99/37681, WO 01/90190, WO 03/025020 and WO 03/035694. Alternatively, improved synthetic or semi-synthetic libraries derived from (naïve or immune) $V_H$H libraries may be used, such as $V_H$H libraries obtained from (naïve or immune) $V_H$H libraries by techniques such as random mutagenesis and/or CDR shuffling, as for example described in WO 00/43507.

In some embodiments, the sdAbs are generated from conventional 4-chain antibodies. See, for example, EP 0 368 684, Ward et al. (Nature 1989 Oct. 12; 341 (6242): 544-6), Holt et al., Trends Biotechnol., 2003, 21(11):484-490; WO 06/030220; and WO 06/003388.

Because of the unique properties of sdAbs, using $V_H$H domains as single antigen-binding proteins or as antigen-binding domains (i.e. as part of a larger protein or polypeptide) offers a number of significant advantages over the conventional $V_H$ and $V_L$, scFv and conventional antibody fragments (such as Fab or (Fab')2): 1) only a single domain is required to bind an antigen with high affinity, so there is no need to have a second domain, nor to assure that these two domains are present in the correct spatial conformation and configuration (e.g. no need to pair the heavy chain and light chain during folding, no need to use a specially designed linker such as for scFv); 2) $V_H$H domains and other sdAbs can be expressed from a single gene and require no post-translational folding or modifications; 3) $V_H$H domains and other sdAbs can be easily engineered into multivalent and/or multispecific formats (such as those described in the present application); 4) $V_H$H domains and other sdAbs are highly soluble and do not have a tendency to aggregate (as with the mouse-derived "dAbs" described by Ward et al., Nature. 1989 Oct. 12; 341(6242):544-6); 5) $V_H$H domains and other sdAbs are highly stable against heat, pH, proteases and other denaturing agents or conditions; 6) $V_H$H domains and other sdAbs are easy and relatively cheap to prepare (even on a large production scale), such as using microbial fermentation, there is no need to use mammalian expression system (required by production of, for example, conventional antibody fragments); 7) $V_H$H domains and other sdAbs are relatively small (approximately 15 kDa, or 10 times smaller than a conventional IgG) compared to conventional 4-chain antibodies and antigen-binding fragments thereof, thus have high(er) tissue penetration ability, such as for solid tumors and other dense tissues; and 8) $V_H$H domains and other sdAbs can exhibit so-called "cavity-binding properties" (due to their extended CDR3 loop compared to that of conventional $V_H$ domains) and can therefore access targets and epitopes not accessible to conventional 4-chain antibodies and antigen-binding fragments thereof, for example, it has been shown that $V_H$H domains and other sdAbs can inhibit enzymes (see for example WO1997049805; Transue et al., Proteins. 1998 Sep. 1; 32(4):515-22; Lauwereys et al., EMBO J. 1998 Jul. 1; 17(13):3512-20).

TIGIT

TIGIT belongs to CD28 family. The protein with 26 kDa is composed of an extracellular IgV domain, a type I transmembrane region, an intracellular immunoglobulin tail tyrosine (ITT)-like motif, and a C-terminal immunoreceptor tyrosine-based inhibition motif (ITIM) motif in cytoplasm. In naïve T cells and NK cells, TIGIT is barely detectable on the cell surface but is upregulated upon T cell and NK cell activation.

The terms "T-cell immunoreceptor with Ig and ITIM domains", "TIGIT", "TIGIT antigen", "TIGIT epitope", "Vstm3" and "WUCAM" are used interchangeably, and include variants, isoforms, species homologs of human TIGIT, and analogs having at least one common epitope with TIGIT.

The amino acid sequence of human TIGIT is disclosed at Genbank Accession Number NP_776160. The region of amino acids 1-21 is the signal peptide; 22-141 is the extracellular domain; 142-162 is the transmembrane domain; and 163-244 is the cytoplasmic domain. A variant of amino acid sequence with 170 amino acids by alternative splicing of mRNA has been reported. The nucleotide sequence of human TIGIT mRNA is disclosed at NM_173799. A variant of the nucleotide sequence with an A to G transition at position 173 have been reported.

A particular human TIGIT sequence will generally be at least 90% identical in amino acids sequence to human TIGIT of Genbank Accession Number NP_776160 and contains amino acid residues that identify the amino acid sequence as being human when compared to TIGIT amino acid sequences of other species (e.g., murine). In some embodiments, a human TIGIT may be at least about 95%, 96%, 97%, 98%, or 99% identical in amino acid sequence to the human TIGIT of Genbank Accession Number NP_776160. In some embodiments, a human TIGIT sequence will display no more than 10 amino acid differences from the human TIGIT of Genbank Accession Number NP_776160. In some embodiments, the human TIGIT may display no more than 5, 4, 3, 2, or 1 amino acid difference from the human TIGIT of Genbank Accession Number NP_776160. Percent identity can be determined as described herein. In some embodiments, a human TIGIT sequence may differ from the human TIGIT of Genbank Accession Number NP_776160 by having, for example, conserved mutations or mutations in non-conserved regions and the TIGIT has substantially the same biological function as the human TIGIT of Genbank Accession Number NP_776160. For example, a biological function of human TIGIT is having an epitope in the extracellular domain of TIGIT that is specifically bound by an anti-TIGIT construct of the instant disclosure or a biological function of human TIGIT is modulation of T cell activity. In some embodiments, the anti-TIGIT sdAb moiety described herein specifically recognizes a TIGIT polypeptide with 100% amino acid sequence identity to the human TIGIT of Genbank Accession Number NP_776160. In some embodiments, the anti-TIGIT sdAb moiety described herein specifically recognizes a TIGIT polypeptide comprising an amino acid sequence of SEQ ID NO: 368.

In some embodiments, the anti-TIGIT sdAb moiety may cross-react with TIGIT from species other than human, or other proteins which are structurally related to human TIGIT (e.g., human TIGIT homologs). In some embodiments, the anti-TIGIT sdAb moiety is completely specific for human TIGIT and not exhibit species or other types of cross-reactivity.

In some embodiments, the anti-TIGIT sdAb moiety described herein specifically recognizes the extracellular domain (ECD) of TIGIT. In some embodiments, the anti-TIGIT sdAb moiety specifically recognizes the N-terminal portion of the TIGIT ECD. In some embodiments, the anti-TIGIT sdAb moiety specifically recognizes the C-terminal portion of the TIGIT ECD. In some embodiments, the anti-TIGIT sdAb moiety specifically recognizes the middle portion of the TIGIT ECD. In some embodiments, the ECD of TIGIT specifically recognized by the anti-TIGIT sdAb moiety is at least about 95%, 96%, 97%, 98%, or 99% identical in amino acid sequence to the ECD of the human TIGIT of Genbank Accession Number NP_776160. In some embodiments, the ECD of TIGIT specifically recognized by the anti-TIGIT sdAb moiety is 100% identical in amino acid sequence to the ECD of the human TIGIT of Genbank Accession Number NP_776160. In some embodiments, the anti-TIGIT sdAb moiety specifically recognizes a TIGIT polypeptide comprising an amino acid sequence of SEQ ID NO: 369.

Antibody Affinity

Binding specificity of the antibody or antigen-binding domain can be determined experimentally by methods known in the art. Such methods comprise, but are not limited to Western blots, ELISA-, RIA-, ECL-, IRMA-, EIA-, BIAcore-tests and peptide scans.

In some embodiments, the $K_d$ of the binding between the anti-TIGIT sdAb moiety and TIGIT is about $10^{-5}$ M to about $10^{-6}$ M, about $10^{-6}$ M to about $10^{-7}$ M, about $10^{-7}$ M to about $10^{-8}$ M, about $10^{-8}$ M to about $10^{-9}$ M, about $10^{-9}$ M to about $10^{-10}$ M, about $10^{-10}$ M to about $10^{-11}$ M, about $10^{-11}$ M to about $10^{-12}$ M, about $10^{-5}$ M to about $10^{-12}$ M, about $10^{-6}$ M to about $10^{-12}$ M, about $10^{-7}$ M to about $10^{-12}$ M, about $10^{-8}$ M to about $10^{-12}$ M, about $10^{-9}$ M to about $10^{-12}$ M, about $10^{-10}$ M to about $10^{-12}$ M, about $10^{-5}$ M to about $10^{-11}$ M, about $10^{-7}$ M to about $10^{-11}$ M, about $10^{-8}$ M to about $10^{-11}$ M, about $10^{-9}$ M to about $10^{-11}$ M, about $10^{-5}$ M to about $10^{-10}$ M, about $10^{-7}$ M to about $10^{-10}$ M, about $10^{-8}$ M to about $10^{-10}$ M, about $10^{-5}$ M to about $10^{-9}$ M, about $10^{-7}$ M to about $10^{-9}$ M, about $10^{-5}$ M to about $10^{-8}$ M, or about $10^{-6}$ M to about $10^{-8}$ M.

In some embodiments, the $K_{on}$ of the binding between the anti-TIGIT sdAb moiety and TIGIT is about $10^2$ M$^{-1}$s$^{-1}$ to about $10^4$ M$^{-1}$s$^{-1}$, about $10^4$ M$^{-1}$s$^{-1}$ to about $10^6$ M$^{-1}$s$^{-1}$, about $10^6$ M$^{-1}$s$^{-1}$ to about $10^7$ M$^{-1}$s$^{-1}$, about $10^2$ M$^{-1}$s$^{-1}$ to about $10^7$ M$^{-1}$s$^{-1}$, about $10^3$ M$^{-1}$s$^{-1}$ to about $10^7$ M$^{-1}$s$^{-1}$, about $10^4$ M$^{-1}$s$^{-1}$ to about $10^7$ M$^{-1}$s$^{-1}$, about $10^5$ M$^{-1}$s$^{-1}$ to about $10^7$ M$^{-1}$s$^{-1}$, about 103 M$^{-1}$s$^{-1}$ to about $10^6$ M$^{-1}$s$^{-1}$, or about $10^4$ M$^{-1}$s$^{-1}$ to about $10^6$ M$^{-1}$s$^{-1}$.

In some embodiments, the $K_{off}$ of the binding between the anti-TIGIT sdAb moiety and TIGIT is about 1 s$^{-1}$ to about $10^{-2}$ s$^{-1}$, about $10^{-2}$ s$^{-1}$ to about $10^{-4}$ s$^{-1}$, about $10^{-4}$ s$^{-1}$ to about $10^{-5}$ s$^{-1}$, about $10^{-5}$ s$^{-1}$ to about $10^{-6}$ S$^{-1}$, about 1 s$^{-1}$ to about $10^{-6}$ s$^{-1}$, about $10^{-2}$ s$^{-1}$ to about $10^{-6}$ s$^{-1}$, about $10^{-3}$ s$^{-1}$ to about $10^{-6}$ s$^{-1}$, about $10^{-4}$ s$^{-1}$ to about $10^{-6}$ s$^{-1}$, about $10^{-2}$ s$^{-1}$ to about $10^{-5}$ s$^{-1}$, or about $10^{-3}$ s$^{-1}$ to about $10^{-5}$ s$^{-1}$.

In some embodiments, the $EC_{50}$ of the anti-TIGIT sdAb moiety is less than 10 nM in an amplified luminescent proximity homogeneous assay (AlphaLISA). In some embodiments, the $EC_{50}$ of the anti-TIGIT sdAb moiety is less than 500 nM in an inhibition of ligand binding by FACS analysis (competition binding assay), or cell based cytokine release assay. In some embodiments, the $EC_{50}$ of the anti-TIGIT sdAb moiety is less than 1 nM (such as about 0.001 nM to about 0.01 nM, about 0.01 nM to about 0.1 nM, about 0.1 nM to about 1 nM, etc.), about 1 nM to about 10 nM, about 10 nM to about 50 nM, about 50 nM to about 100 nM, about 100 nM to about 200 nM, about 200 nM to about 300 nM, about 300 nM to about 400 nM, or about 400 nM to about 500 nM.

Chimeric or Humanized Antibodies

In some embodiments, the anti-TIGIT sdAb moiety provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a camelid species, such as llama) and a human constant region. In a further example, a chimeric antibody is a "class switched" antibody in which the class or subclass has been changed from that of the parent antibody. Chimeric antibodies include antigen-binding fragments thereof.

In some embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008). Human framework regions that may be used for humanization include but are not limited to: framework regions selected using the "best-fit" method; framework regions derived from the consensus sequence of human antibodies of a particular subgroup of light or heavy chain variable regions; human mature (somatically mutated) framework regions or human germline framework regions; and framework regions derived from screening FR libraries.

In some embodiments, the anti-TIGIT sdAbs are modified, such as humanized, without diminishing the native affinity of the domain for antigen and while reducing its immunogenicity with respect to a heterologous species. For example, the amino acid residues of the antibody variable domain ($V_HH$) of an llama antibody can be determined, and one or more of the Camelid amino acids, for example, in the framework regions, are replaced by their human counterpart as found in the human consensus sequence, without that polypeptide losing its typical character, i.e. the humanization does not significantly affect the antigen binding capacity of the resulting polypeptide. Humanization of Camelid single-domain antibodies requires the introduction and mutagenesis of a limited amount of amino acids in a single polypeptide chain. This is in contrast to humanization of scFv, Fab', (Fab')2 and IgG, which requires the introduction of amino acid changes in two chains, the light and the heavy chain and the preservation of the assembly of both chains.

sdAbs comprising a $V_HH$ domain can be humanized to have human-like sequences. In some embodiments, the FR regions of the $V_HH$ domain used herein comprise at least about any one of 50%, 60%, 70%, 80%, 90%, 95% or more of amino acid sequence homology to human VH framework regions. One exemplary class of humanized $V_HH$ domains is characterized in that the $V_HH$s carry an amino acid from the group consisting of glycine, alanine, valine, leucine, isoleucine, proline, phenylalanine, tyrosine, tryptophan, methionine, serine, threonine, asparagine, or glutamine at position 45, such as, for example, L45 and a tryptophan at position 103, according to the Kabat numbering. As such, polypeptides belonging to this class show a high amino acid sequence homology to human VH framework regions and said polypeptides might be administered to a human directly without expectation of an unwanted immune response therefrom, and without the burden of further humanization.

Another exemplary class of humanized Camelid single-domain antibodies has been described in WO 03/035694 and contains hydrophobic FR2 residues typically found in conventional antibodies of human origin or from other species, but compensating this loss in hydrophilicity by the charged arginine residue on position 103 that substitutes the conserved tryptophan residue present in $V_H$ from double-chain antibodies. As such, peptides belonging to these two classes show a high amino acid sequence homology to human $V_H$ framework regions and said peptides might be administered to a human directly without expectation of an unwanted immune response therefrom, and without the burden of further humanization.

Human Domain Antibodies

In some embodiments, the anti-TIGIT sdAb moiety provided herein is a human antibody (known as human domain antibody, or human DAb). Human antibodies can be produced using various techniques known in the art. Human antibodies are described generally in Chen, *Mol. Immunol.* 47(4):912-21 (2010). Transgenic mice or rats capable of producing fully human single-domain antibodies (or DAb) are known in the art. See, e.g., US20090307787A1, U.S. Pat. No. 8,754,287, US20150289489A1, US20100122358A1, and WO2004049794.

Human antibodies (e.g., human DAbs) may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). Human variable regions from intact antibodies generated by such animals may be further modified, e.g., by combining with a different human constant region.

Human antibodies (e.g., human DAbs) can also be made by hybridoma-based methods. Human myeloma and mouse-human heteromyeloma cell lines for the production of human monoclonal antibodies are known in the art.

Human antibodies (e.g., human DAbs) may also be generated by isolating Fv clone variable domain sequences selected from human-derived phage display libraries. Such variable domain sequences may then be combined with a desired human constant domain. Techniques for selecting human antibodies from antibody libraries are described below.

One technique for obtaining $V_HH$ sequences directed against a particular antigen or target involves suitably immunizing a transgenic mammal that is capable of expressing heavy chain antibodies (i.e. so as to raise an immune response and/or heavy chain antibodies directed against said antigen or target), obtaining a suitable biological sample from said transgenic mammal that contains (nucleic acid sequences encoding) said $V_HH$ sequences (such as a blood sample, serum sample or sample of B-cells), and then generating $V_HH$ sequences directed against said antigen or target, starting from said sample, using any suitable technique known per se (such as any of the methods described herein or a hybridoma technique). For example, for this purpose, the heavy chain antibody-expressing mice and the further methods and techniques described in WO 02/085945, WO 04/049794 and WO 06/008548 and Janssens et al., Proc. Natl. Acad. Sci. USA. 2006 Oct. 10; 103(41):15130-5 can be used. For example, such heavy chain antibody expressing mice can express heavy chain antibodies with any suitable (single) variable domain, such as (single) variable domains from natural sources (e.g. human (single) variable domains, Camelid (single) variable domains or shark (single) variable domains), as well as for example synthetic or semi-synthetic (single) variable domains.

Library-Derived Antibodies

Antibodies of the present application may be isolated by screening combinatorial libraries for antibodies with the desired activity or activities. For example, a variety of methods are known in the art for generating phage display libraries and screening such libraries for antibodies possessing the desired binding characteristics. Methods for constructing single-domain antibody libraries have been described, for example, see U.S. Pat. No. 7,371,849.

In certain phage display methods, repertoires of $V_H$ and $V_L$ genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Repertoires of $V_HH$ genes can be similarly cloned by PCR, recombined randomly in phage libraries, and screened for antigen-binding phage. Phage typically display antibody fragments, either as scFv fragments or as Fab fragments. Libraries from immunized sources provide high-affinity antibodies to the immunogen without the requirement of constructing hybridomas. Alternatively, the naïve repertoire can be cloned (e.g., from human) to provide a single source of antibodies to a wide range of non-self and also self-antigens without any immunization as described by Griffiths et al., *EMBO J,* 12: 725-734 (1993). Finally, naïve libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992).

Antibodies or antibody fragments isolated from human antibody libraries are considered human antibodies or human antibody fragments herein.

Biological Activities

The biological activity of anti-TIGIT sdAb moiety described herein can be determined by measuring its half maximal effective concentration ($EC_{50}$), which is a measure of the effectiveness of an antibody in binding to its target or inhibiting a specific biological or biochemical function (such as inhibiting the binding between TIGIT and its major ligand CD155). For example, here $EC_{50}$ can be used to indicate the effective concentration of anti-TIGIT sdAb needed to bind 50% TIGIT on cell surface or neutralize 50% of TIGIT bioactivity in vitro. $EC_{50}$ also represents the plasma concentration required for obtaining 50% of a maximum effect in vivo. $EC_{50}$ can be measured by assays known in the art, for example, bioassays such as FACS binding analysis, inhibition of ligand binding by FACS analysis (competition binding assay), cell based cytokine release assay, or amplified luminescent proximity homogeneous assay (AlphaLISA).

For example, the blockade of ligand binding can be studied using flow cytometry (also see Example 2). CHO cells expressing human TIGIT can be dissociated from adherent culture flasks and mixed with varying concentrations of anti-TIGIT sdAb for test, and a constant concentration of labeled-CD155 protein (such as biotin-labeled human CD155-Fc protein). An anti-TIGIT antibody positive control can be employed, such as 22G2 (see SEQ ID Nos.: 7 and 9 in US 2016/0176963). The mixture is equilibrated for 30 minutes at room temperature, washed three times with FACS buffer (PBS containing 1% BSA). Then, an antibody specifically recognizing the labeled CD155 protein of constant concentration (such as PE/Cy5 Streptavidin secondary antibody) is added and incubated for 15 minutes at room temperature. Cells are washed with FACS buffer and analyzed by flow cytometry. Data can be analyzed with Prism (GraphPad Software, San Diego, CA) using non-linear regression to calculate $EC_{50}$. The results from the competition assay can demonstrate the ability of anti-TIGIT sdAbs in inhibiting the interaction between labeled-CD155 and TIGIT.

The biological activity of anti-TIGIT sdAb moiety can also be tested by TIGIT/CD155 blockade reporter assay or IL-2 release assay (also see Example 2). Upon binding with its major ligand, CD155, the subsequent phosphorylation of TIGIT in its ITIM domain transduces inhibitory signals to downregulate IL-2 expression in T cells. For example, TIGIT Effector Cells can be plated overnight and then incubated with a serial dilution of anti-TIGIT construct comprising anti-TIGIT sdAb, followed by addition of CD155 aAPC/CHO—K1 Cells at a suitable E:T ratio. After 6 hours induction at 37° C., 5% $CO_2$, Bio-Glo™ Luciferase Assay Reagent can be added and luminescence can be determined. The results can demonstrate the ability of anti-TIGIT sdAbs in inhibiting the interaction between CD155 and TIGIT.

In some embodiments, the anti-TIGIT sdAb moiety blocks or antagonizes signals transduced by the TIGIT receptor. In some embodiments, the anti-TIGIT sdAb moiety can bind to an epitope on TIGIT so as to inhibit TIGIT from interacting with CD155. In some embodiments, the anti-TIGIT sdAb moiety can reduce the binding of TIGIT to CD155 by at least about any of 5%, 10%, 20%, 25%, 30%, 40%, 50%, 60%, 70%, 75%, 80%, 90%, 95%, 99% or 99.9% under conditions in which the ratio of antibody combining site to TIGIT ligand binding site is greater than 1:1 and the concentration of antibody is greater than $10^{-8}$ M.

(II) Construct Comprising the Anti-TIGIT sdAb Moiety

The anti-TIGIT construct comprising the anti-TIGIT sdAb moiety can be of any possible format.

In some embodiments, the anti-TIGIT construct comprising the anti-TIGIT sdAb moiety may further comprise additional polypeptide sequences, such as one or more antibody moieties (or antigen binding portions), or Fc fragment of immunoglobulin. Such additional polypeptide sequences may or may not change or otherwise influence the (biological) properties of the anti-TIGIT sdAb, and may or may not add further functionality to the anti-TIGIT sdAb described herein. In some embodiments, the additional polypeptide sequences confer one or more desired properties or functionalities to the anti-TIGIT sdAb of the present invention.

In some embodiments, the additional polypeptide sequences may comprise a second antibody moiety or second antigen binding portion (such as sdAb, scFv, Fab, full-length antibody) that specifically recognizes a second epitope. In some embodiments, the second epitope is from TIGIT. In some embodiments, the second epitope is not from TIGIT. In some embodiments, the second antibody moiety (or second antigen binding portion) specifically recognizes the same epitope on TIGIT as the anti-TIGIT sdAb described herein. In some embodiments, the second antibody moiety (or second antigen binding portion) specifically recognizes a different epitope on TIGIT as the anti-TIGIT sdAb described herein. In some embodiments, the anti-TIGIT construct comprises two or more anti-TIGIT-sdAb moieties described herein linked together via optional linkers (such as peptide linkers). The two or more anti-TIGIT-sdAb moieties linked together can be the same or different.

In some embodiments, the additional polypeptide sequences may increase the antibody construct half-life, solubility, or absorption, reduce immunogenicity or toxicity, eliminate or attenuate undesirable side effects, and/or confer other advantageous properties to and/or reduce undesired properties of the anti-TIGIT construct of the invention, compared to the anti-TIGIT sdAb described herein per se. Some non-limiting examples of such additional polypeptide sequences are serum proteins, such as human serum albumin (HSA; see e.g. WO 00/27435) or haptenic molecules (e.g. haptens that are recognized by circulating antibodies, see e.g. WO 98/22141). It was shown that linking fragments of immunoglobulins (such as $V_H$ domains) to serum albumin or fragments thereof may increase antibody half-life (see e.g. WO 00/27435 and WO 01/077137). Thus, in some embodiments, the anti-TIGIT construct of the present invention may comprise an anti-TIGIT sdAb moiety described herein linked to serum albumin (or to a suitable fragment thereof), optionally via a suitable linker (such as peptide linker). In some embodiments, the anti-TIGIT sdAb moiety described herein can be linked to a fragment of serum albumin at least comprising serum albumin domain III (see PCT/EP2007/002817). The anti-TIGIT sdAb-HSA fusion protein can be of any format, such as (sdAb) HSA (n is an integer of at least 1), sdAb-HSA-sdAb, etc.

Anti-TIGIT sdAb-Fc Fusion Protein

In some embodiments, anti-TIGIT sdAb moiety described herein can be linked to one or more (preferably human) $C_H2$ and/or $C_H3$ domains, e.g., an Fc fragment, optionally via a linker sequence, to increase its half-life in vivo.

Thus in some embodiments, the anti-TIGIT construct is an anti-TIGIT sdAb-Fc fusion protein comprising an anti-TIGIT sdAb moiety described herein fused to an Fc fragment of an immunoglobulin, such as IgA, IgD, IgE, IgG, and IgM. In some embodiments, the anti-TIGIT sdAb-Fc fusion protein comprises an Fc fragment of IgG, such as any of IgG1, IgG2, IgG3, or IgG4. In some embodiments, the Fc fragment is a human Fc, such as human IgG1 (hIgG1) Fc, hIgG2Fc, or hIgG4 Fc. In some embodiments, the Fc fragment is effectorless, with reduced, minimized, or eliminated antibody effector functions such as ADCC, CDC, and/or ADCP (antibody-dependent cellular phagocytosis). For example, in some embodiments, the effectorless Fc comprises an N297A or DANA mutation (D265A+N297A) in the $C_H2$ region. In some embodiments, the effectorless Fc comprises K322A and L234A/L235A (LALA) mutations. In some embodiments, the Fc fragment is an effectorless (inert) IgG1 Fc, such as effectorless hIgG1 Fc. In some embodiments, the Fc fragment comprises the amino acid sequence of any one of SEQ ID NOs: 355, 356, and 389. In some embodiments, the anti-TIGIT sdAb-Fc fusion protein is monomeric. In some embodiments, the anti-TIGIT sdAb-Fc fusion protein is dimeric. In some embodiments, the anti-TIGIT sdAb moiety and the Fc fragment are optionally connected by a peptide linker. In some embodiments, the peptide linker is a human IgG1 hinge (SEQ ID NO: 370). In some embodiments, the peptide linker is a mutated human IgG1 hinge (SEQ ID NO: 371). In some embodiments, the peptide linker is a human IgG4 hinge (SEQ ID NO: 324). In some embodiments, the peptide linker is an hIgG2 hinge. In some embodiments, the peptide linker comprises the amino acid sequence of any one of SEQ ID NOs: 372-378, such as SEQ ID NO: 372 or 373.

Thus for example, in some embodiments, there is provided an anti-TIGIT sdAb-Fc fusion protein comprising a sdAb moiety specifically recognizing TIGIT, wherein the anti-TIGIT sdAb moiety comprises a CDR1 comprising the amino acid sequence of any one of SEQ ID NOs: 36-42, 54, 56-59, 63, 65-67, 69-70, or a variant thereof comprising up to about 3 (such as about any of 1, 2, or 3) amino acid substitutions; a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210, or a variant thereof comprising up to about 3 (such as about any of 1, 2, or 3) amino acid substitutions, and wherein the anti-TIGIT sdAb moiety is fused to an Fc fragment of an immunoglobulin via an optional linker. In some embodiments, there is provided an anti-TIGIT sdAb-Fc fusion protein comprising an sdAb moiety specifically recognizing TIGIT, wherein the sdAb moiety comprises a CDR1 comprising the amino acid sequence of any one of SEQ ID NOs: 36-42, 54, 56-59, 63, 65-67, 69-70; a CDR2 comprising the amino acid sequence of any one of SEQ ID NOs: 106-112, 124, 126-129, 133, 135-137, 139-140; and a CDR3 comprising the amino acid sequence of any one of SEQ ID NOs: 176-182, 194, 196-199, 203, 205-207, 209-210; or a variant thereof comprising up to about 3 (such as about any of 1, 2, or 3) amino acid substitutions in the CDR regions, and wherein the anti-TIGIT sdAb moiety is fused to an Fc fragment of an immunoglobulin via an optional linker. In some embodiments, the amino acid substitutions are in CDR1 and/or CDR2. In some embodiments, there is provided an anti-TIGIT sdAb-Fc fusion protein comprising an sdAb moiety specifically recognizing TIGIT, wherein the sdAb moiety comprises a CDR1 comprising the amino acid sequence of any one of SEQ ID NOs: 36-42, 54, 56-59, 63, 65-67, 69-70; a CDR2 comprising the amino acid sequence of any one of SEQ ID NOs: 106-112, 124, 126-129, 133, 135-137, 139-140; and a CDR3 comprising the amino acid sequence of any one of SEQ ID NOs: 176-182, 194, 196-199, 203, 205-207, 209-210, and wherein the anti-TIGIT sdAb moiety is fused to an Fc fragment of an immunoglobulin via an optional linker. In some embodiments, the Fc fragment is a human IgG1 Fc, human effectorless IgG1 Fc, hIgG2 Fc, or human IgG4 Fc. In some embodiments, the Fc fragment comprises the amino acid sequence of any one of SEQ ID NOs: 355, 356, and 389. In some embodiments, the anti-TIGIT sdAb-Fc fusion protein is monomeric. In some embodiments, the anti-TIGIT sdAb-Fc fusion protein is dimeric. In some embodiments, the anti-TIGIT sdAb moiety and the Fc fragment are optionally connected by a peptide linker. In some embodiments, the peptide linker comprises the amino acid sequence of any one of SEQ ID NOs: 324 and 370-378. In some embodiments, the $K_d$ of the binding between the anti-TIGIT sdAb moiety and TIGIT is about $10^{-5}$ M to about $10^{-12}$ M (such as about $10^{-7}$ M to about $10^{-12}$ M, or about $10^{-8}$ M to about $10^{-12}$ M). In some embodiments, the anti-TIGIT sdAb moiety is camelid, chimeric, human, partially humanized, or fully humanized.

In some embodiments, there is provided an anti-TIGIT sdAb-Fc fusion protein comprising an sdAb moiety specifically recognizing TIGIT, wherein the sdAb moiety comprises a $V_HH$ domain comprising the amino acid sequence of any one of SEQ ID NOs: 253-259, 271, 273-276, 280, 282-284, 286-287, or a variant thereof having at least about 80% (such as at least about any of 80%, 85%, 90%, 91%, 92%, 93%, 94%, 95%, 96%, 97%, 98%, or 99%) sequence identify to any one of SEQ ID NOs: 253-259, 271, 273-276, 280, 282-284, 286-287, and wherein the anti-TIGIT sdAb moiety is fused to an Fc fragment of an immunoglobulin via an optional linker. In some embodiments, there is provided an anti-TIGIT sdAb-Fc fusion protein comprising a sdAb moiety specifically recognizing TIGIT, wherein the sdAb moiety comprises a $V_HH$ domain comprising the amino acid sequence of any one of SEQ ID NOs: 253-259, 271, 273-276, 280, 282-284, 286-287, or a variant thereof comprising up to about 3 (such as about any of 1, 2, or 3) amino acid substitutions in the $V_HH$ domain, and wherein the anti-TIGIT sdAb moiety is fused to an Fc fragment of an immunoglobulin via an optional linker. In some embodiments, the amino acid substitutions in the $V_HH$ domain are in CDRs, such as the CDR1, and/or the CDR2, and/or the CDR3 of any one of SEQ ID NOs: 253-259, 271, 273-276, 280, 282-284, 286-287. In some embodiments, the amino acid substitutions in the $V_HH$ domain are in FRs, such as the FR1, and/or the FR2, and/or the FR3, and/or the FR4 of any one of SEQ ID NOs: 253-259, 271, 273-276, 280, 282-284, 286-287. In some embodiments, the amino acid substitutions are in both CDRs and FRs of any one of SEQ ID NOs: 253-259, 271, 273-276, 280, 282-284, 286-287. In some embodiments, there is provided an anti-TIGIT sdAb-Fc fusion protein comprising an sdAb moiety specifically recognizing TIGIT, wherein the sdAb moiety comprises a $V_HH$ domain comprising the amino acid sequence of any one of SEQ ID NOs: 253-259, 271, 273-276, 280, 282-284, 286-287, and wherein the anti-TIGIT sdAb moiety is fused to an Fc fragment of an immunoglobulin via an optional linker. In some embodiments, there is provided an anti-TIGIT sdAb-Fc fusion protein comprising an sdAb moiety specifically recognizing TIGIT, wherein the sdAb moiety comprises CDR1, CDR2, and CDR3 of any one of SEQ ID NOs: 253-259, 271, 273-276, 280, 282-284, 286-287, and wherein the anti-TIGIT sdAb moiety is fused to an Fc fragment of an immunoglobulin via an optional linker. In some embodiments, the Fc fragment is a human IgG1 Fc, effectorless human IgG1 Fc, hIgG2 Fc, or human IgG4 Fc. In some embodiments, the Fc fragment comprises the amino acid sequence of any one of SEQ ID NOs: 355, 356, and 389. In some embodiments, the anti-TIGIT sdAb-Fc fusion protein is monomeric. In some embodiments, the anti-TIGIT sdAb-Fc fusion protein is dimeric. In some embodiments, the anti-TIGIT sdAb moiety and the Fc fragment are optionally connected by a peptide linker. In some embodiments, the peptide linker comprises the amino acid sequence of any one of SEQ ID NOs: 324 and 370-378. In some embodiments, the $K_d$ of the binding between the anti-TIGIT sdAb moiety and TIGIT is about $10^{-5}$ M to about $10^{-12}$ M (such as about $10^{-7}$ M to about $10^{-12}$ M, or about $10^{-8}$ M to about $10^{-12}$ M). In some embodiments, the anti-TIGIT sdAb moiety is camelid, chimeric, human, partially humanized, or fully humanized.

In some embodiments, there is provided an anti-TIGIT sdAb-Fc fusion protein comprising the amino acid sequence of any one of SEQ ID NOs: 288-294, 306, 308-311, 315, 317-319, 321-322 and 365-367.

In some embodiments, there is also provided an anti-TIGIT sdAb-Fc fusion protein (hereinafter referred to as "competing anti-TIGIT sdAb-Fc fusion protein") that specifically binds to TIGIT competitively with any one of the anti-TIGIT sdAb-Fc fusion proteins, anti-TIGIT sdAbs, or anti-TIGIT constructs comprising the anti-TIGIT sdAb moiety described herein. Competitive binding may be determined using an ELISA assay. For example, in some embodiments, there is provided an anti-TIGIT sdAb-Fc fusion protein that specifically binds to TIGIT competitively with an anti-TIGIT sdAb-Fc fusion protein comprising the amino acid sequence of any one of SEQ ID NOs: 288-294, 306, 308-311, 315, 317-319, 321-322 and 365-367. In some embodiments, there is provided an anti-TIGIT sdAb-Fc fusion protein that specifically binds to TIGIT competitively with an anti-TIGIT sdAb-Fc fusion protein comprising an anti-TIGIT sdAb comprising a CDR1 comprising the amino acid sequence of any one of SEQ ID NOs: 36-42, 54, 56-59, 63, 65-67, 69-70; a CDR2 comprising the amino acid sequence of any one of SEQ ID NOs: 106-112, 124, 126-129, 133, 135-137, 139-140; and a CDR3 comprising the amino acid sequence of any one of SEQ ID NOs: 176-182, 194, 196-199, 203, 205-207, 209-210. In some embodiments, there is provided an anti-TIGIT sdAb-Fc fusion protein that specifically binds to TIGIT competitively with an anti-TIGIT sdAb (or an anti-TIGIT construct comprising an anti-TIGIT sdAb) comprising a CDR1 comprising the amino acid sequence of any one of SEQ ID NOs: 36-42, 54, 56-59, 63, 65-67, 69-70; a CDR2 comprising the amino acid sequence of any one of SEQ ID NOs: 106-112, 124, 126-129, 133, 135-137, 139-140; and a CDR3 comprising the amino acid sequence of any one of SEQ ID NOs: 176-182, 194, 196-199, 203, 205-207, 209-210. In some embodiments, the Fc fragment of the competing anti-TIGIT sdAb-Fc fusion protein comprises the amino acid sequence of any one of SEQ ID NOs: 355, 356, and 389. In some embodiments, the $K_d$ of the binding between the competing anti-TIGIT sdAb-Fc fusion protein and TIGIT is about $10^{-5}$ M to about $10^{-12}$ M (such as about $10^{-7}$ M to about $10^{-12}$ M, or about 10 M to about $10^{-12}$ M). In some embodiments, the competing anti-TIGIT sdAb-Fc fusion protein is camelid, chimeric, human, partially humanized, or fully humanized Multivalent and/or Multispecific Antibodies In some embodiments, the anti-TIGIT construct comprises an anti-TIGIT sdAb moiety described herein fused to one or more other antibody moiety or antigen binding portion (such as an antibody moiety that specifically recognizes another epitope). The one or more other antibody moiety can be of any antibody or antibody fragment format, such as a full-length antibody, a Fab, a Fab', a (Fab')2, an Fv, an scFv, an scFv-scFv, a minibody, a diabody, or an sdAb. In some embodiments, the one or more antibody moiety (or antigen binding portion) comprises a heavy chain variable domain ($V_H$) and a light chain variable domain ($V_L$). Antibody fragments can be made by various techniques, including but not limited to proteolytic digestion of an intact antibody as well as production by recombinant host cells (e.g. *E. coli* or phage), as described herein.

Techniques for making multispecific antibodies include, but are not limited to, recombinant co-expression of two immunoglobulin heavy chain-light chain pairs having different specificities, and "knob-in-hole" engineering; using leucine zippers to produce bi-specific antibodies; using "diabody" technology for making bispecific antibody fragments; and using single-chain Fv (sFv) dimers; and preparing trispecific antibodies as described, e.g., in Tutt et al. *J. Immunol.* 147: 60 (1991); and creating polypeptides comprising tandem single-domain antibodies. Engineered antibodies with three or more functional antigen binding sites, including "Octopus antibodies," are also included herein (see, e.g., US 2006/0025576A1).

Peptide Linkers

In some embodiments, the anti-TIGIT sdAb and the other one or more antibody moieties (such as a full-length antibody, sdAb, or an antigen binding portion comprising a $V_H$ and a $V_L$) within the anti-TIGIT construct can be optionally connected by a peptide linker. The length, the degree of flexibility and/or other properties of the peptide linker(s) used in the anti-TIGIT construct may have some influence on properties, including but not limited to the affinity, specificity or avidity for one or more particular antigens or epitopes. For example, longer peptide linkers may be selected to ensure that two adjacent domains do not sterically interfere with one another. In some embodiment, a peptide linker comprises flexible residues (such as glycine and serine) so that the adjacent domains are free to move relative to each other. For example, a glycine-serine doublet can be a suitable peptide linker.

The peptide linker can be of any suitable length. In some embodiments, the peptide linker is at least about any of 1, 2, 3, 4, 5, 6, 7, 8, 9, 10, 11, 12, 13, 14, 15, 16, 17, 18, 19, 20, 25, 30, 35, 40, 50, 75, 100 or more amino acids long. In some embodiments, the peptide linker is no more than about any of 100, 75, 50, 40, 35, 30, 25, 20, 19, 18, 17, 16, 15, 14, 13, 12, 11, 10, 9, 8, 7, 6, 5 or fewer amino acids long. In some embodiments, the length of the peptide linker is any of about 1 amino acid to about 10 amino acids, about 1 amino acid to about 20 amino acids, about 1 amino acid to about 30 amino acids, about 5 amino acids to about 15 amino acids, about 10 amino acids to about 25 amino acids, about 5 amino acids to about 30 amino acids, about 10 amino acids to about 30 amino acids long, about 30 amino acids to about 50 amino acids, about 50 amino acids to about 100 amino acids, or about 1 amino acid to about 100 amino acids.

The peptide linker may have a naturally occurring sequence, or a non-naturally occurring sequence. For example, a sequence derived from the hinge region of heavy chain only antibodies may be used as the linker. See, for example, WO1996/34103. In some embodiments, the peptide linker is a human IgG1 hinge (SEQ ID NO: 370). In some embodiments, the peptide linker is a mutated human IgG1 hinge (SEQ ID NO: 371). In some embodiments, the peptide linker is a human IgG4 hinge (SEQ ID NO: 324). In some embodiments, the peptide liner is a human IgG2 hinge. In some embodiments, the peptide linker is a flexible linker. Exemplary flexible linkers include glycine polymers $(G)_n$ (SEQ ID NO: 374), glycine-serine polymers (including, for example, $(GS)_n$ (SEQ ID NO: 375), $(GSGGS)_n$ (SEQ ID NO: 376), $(GGGS)_n$ (SEQ ID NO: 377), and $(GGGGS)_n$ (SEQ ID NO: 378), where n is an integer of at least one), glycine-alanine polymers, alanine-serine polymers, and other flexible linkers known in the art. In some embodiments, the peptide linker comprises the amino acid sequence of SEQ ID NO: 372 (GGGGSGGGS) or 373 (GGGGSGGGGSGGGGS).

In some embodiments, the anti-TIGIT construct comprising an anti-TIGIT sdAb moiety described herein and one or more other antibody moiety (such as a full-length antibody, sdAb, or an antigen binding portion comprising a $V_H$ and a $V_L$) is monospecific. In some embodiments, the anti-TIGIT construct comprising an anti-TIGIT sdAb moiety described herein and one or more other antibody moiety (such as a full-length antibody, sdAb, or an antigen binding portion comprising a $V_H$ and a $V_L$) is multispecific (such as bispecific). Multispecific molecules are molecules that have binding specificities for at least two different epitopes (e.g., bispecific antibodies have binding specificities for two epitopes). Multispecific molecules with more than two valencies and/or specificities are also contemplated. For example, trispecific antibodies can be prepared. Tuft et al. *J. Immunol.* 147: 60 (1991). It is to be appreciated that one of skill in the art could select appropriate features of individual multispecific molecules described herein to combine with one another to form a multispecific anti-TIGIT molecule of the invention.

In some embodiments, the anti-TIGIT construct is multivalent but monospecific, i.e., the anti-TIGIT construct comprises an anti-TIGIT sdAb moiety described herein and at least a second antibody moiety (such as a full-length antibody, sdAb, or an antigen binding portion comprising a $V_H$ and a $V_L$) specifically recognizing the same TIGIT epitope as the anti-TIGIT sdAb moiety described herein. In some embodiments, the one or more antibody moiety that specifically recognizes the same TIGIT epitope as the anti-TIGIT sdAb moiety described herein may comprise the same CDRs and/or the same $V_H$H amino acid sequence as the anti-TIGIT sdAb moiety. For example, the anti-TIGIT construct may comprise two or more anti-TIGIT sdAb moieties described herein, wherein the two or more anti-TIGIT sdAb moieties are the same, and are optionally connected by peptide linker(s). In some embodiments, the peptide linker comprises the amino acid sequence of any one of SEQ ID NOs: 324 and 370-378.

In some embodiments, the anti-TIGIT construct is multivalent and multispecific, i.e., the anti-TIGIT construct comprises an anti-TIGIT sdAb moiety described herein and at least a second antibody moiety (such as a full-length antibody, sdAb, or an antigen binding portion comprising a $V_H$ and a $V_L$) specifically recognizing a second antigen other than TIGIT, or a different TIGIT epitope recognized by the anti-TIGIT sdAb moiety described herein. In some embodiments, the second antibody moiety is an sdAb. In some embodiments, the second antibody moiety specifically recognizes human serum albumin (HSA). In some embodiments, the anti-TIGIT sdAb moiety described herein is fused to the N-terminus and/or C-terminus of the second antibody moiety. In some embodiments, the anti-TIGIT construct is trivalent and bispecific. In some embodiments, the anti-TIGIT construct comprises two anti-TIGIT sdAb moieties described herein and a second antibody moiety (such as an anti-HSA sdAb), wherein the second antibody moiety is between the two anti-TIGIT sdAb moieties. In some embodiments, the antibody moieties are optionally connected by peptide linker(s). In some embodiments, the peptide linker comprises the amino acid sequence of any one of SEQ ID NOs: 324 and 370-378.

The monospecific or multispecific anti-TIGIT construct comprising two or more anti-TIGIT sdAb moieties may have increase avidity compared to that of a single anti-TIGIT sdAb moiety described here.

Bispecific Antibodies Comprising an Anti-TIGIT sdAb Moiety Fused to a Full-Length Antibody In some embodiments, the anti-TIGIT construct comprises an anti-TIGIT sdAb moiety described herein fused to a second antibody moiety, wherein the second antibody moiety is a full-length antibody consisting of two heavy chains and two light chains (such as anti-PD-1 or anti-PD-L1 full-length antibody). The Fc fragment of the full-length antibody can be, for example, IgG1 Fc, effectorless IgG1 Fc, IgG2 Fc, or IgG4 Fc. In some embodiments, the Fc fragment comprises the amino acid sequence of any one of SEQ ID NOs: 355, 356, and 389. In some embodiments, the full-length antibody is an activator of a stimulatory immune checkpoint molecule. In some embodiments, the full-length antibody is an immune checkpoint inhibitor, such as an inhibitor of PD-1 or PD-L1.

The construct comprising bispecificity against TIGIT and PD-1 will be hereinafter referred to as "anti-TIGIT/PD-1 antibody", "anti-TIGIT/PD-1 construct", "PD-1×TIGIT antibody", or "PD-1×TIGIT BABP". The construct comprising bispecificity against TIGIT and PD-L1 will be hereinafter referred to as "anti-TIGIT/PD-L1 antibody", "anti-TIGIT/PD-L1 construct", "PD-L1×TIGIT antibody", or "PD-L1×TIGIT BABP".

PD-1 and PD-L1, similar to TIGIT, are inhibitory immune checkpoint molecules.

PD-1 is a part of the B7/CD28 family of co-stimulatory molecules that regulate T-cell activation and tolerance, and thus antagonistic anti-PD-1 antibodies can be useful for overcoming tolerance. PD-1 has been defined as a receptor for B7-4. B7-4 can inhibit immune cell activation upon binding to an inhibitory receptor on an immune cell. Engagement of the PD-1/PD-L1 pathway results in inhibition of T-cell effector function, cytokine secretion and proliferation. (Turnis et al., OncoImmunology 1(7):1172-1174, 2012). High levels of PD-1 are associated with exhausted or chronically stimulated T cells. Moreover, increased PD-1 expression correlates with reduced survival in cancer patients. Agents for down modulating PD-1, B7-4, and the interaction between B7-4 and PD-1 inhibitory signal in an immune cell can result in enhancement of the immune response. Exemplary anti-PD-1 antibodies that can be applied in the present application include, but are not limited to, pembrolizumab (e.g., Keytruda®), PD1-BM-min, and nivolumab (e.g., Opdivo®).

PD-L1 (Programmed cell death-ligand 1) is also known as cluster of differentiation 274 (CD274) or B7 homolog 1 (B7-H1). PD-L1 serves as a ligand for PD-1 to play a major role in suppressing the immune system during particular events such as pregnancy, tissue allographs, autoimmune disease and other disease states such as hepatitis and cancer. The formation of PD-1 receptor/PD-L1 ligand complex transmits an inhibitory signal which reduces the proliferation of CD8+ T cells at the lymph nodes. Exemplary anti-PD-L1 antibodies that can be applied in the present application include, but are not limited to, atezolizumab (e.g., Tecentriq®), Durvalumab (e.g., MEDI4736, IMFINZI™), avelumab (e.g., Bavencio®), and h53C1 (humanized 53C1). In some embodiments, the h53C1 anti-PD-L1 antibody comprises 1) a $V_H$ comprising an HC-CDR1 comprising the amino acid sequence of SEQ ID NO: 349, an HC-CDR2 comprising the amino acid sequence of SEQ ID NO: 350, and an HC-CDR3 comprising the amino acid sequence of SEQ ID NO: 351, and 2) a $V_L$ comprising an LC-CDR1 comprising the amino acid sequence of SEQ ID NO: 352, an LC-CDR2 comprising the amino acid sequence of SEQ ID NO: 353, and an LC-CDR3 comprising the amino acid sequence of SEQ ID NO: 354. In some embodiments, the h53C1 anti-PD-L1 antibody comprises a $V_H$ comprising the amino acid sequence of SEQ ID NO: 339, and a $V_L$ comprising the amino acid sequence of SEQ ID NO: 340. In some embodiments, the h53C1 anti-PD-L1 antibody comprises a heavy chain comprising the amino acid sequence of SEQ ID NO: 323 or 327, and a light chain comprising the amino acid sequence of SEQ ID NO: 328. In some embodiments, the h53C1 anti-PD-L1 antibody comprises a heavy chain comprising the amino acid sequence of SEQ ID NO: 329, and a light chain comprising the amino acid sequence of SEQ ID NO: 330.

In some embodiments, there is provided an isolated anti-TIGIT construct comprising an sdAb moiety specifically recognizing TIGIT and an anti-PD-1 full-length antibody, wherein the anti-TIGIT sdAb moiety comprises a CDR1 comprising the amino acid sequence of any one of SEQ ID NOs: 36-42, 54, 56-59, 63, 65-67, 69-70, or a variant thereof comprising up to about 3 (such as about any of 1, 2, or 3) amino acid substitutions; a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210, or a variant thereof comprising up to about 3 (such as about any of 1, 2, or 3) amino acid substitutions. In some embodiments, there is provided an isolated anti-TIGIT construct comprising an sdAb moiety specifically recognizing TIGIT and an anti-PD-1 full-length antibody, wherein the anti-TIGIT sdAb moiety comprises a CDR1 comprising the amino acid sequence of any one of SEQ ID NOs: 36-42, 54, 56-59, 63, 65-67, 69-70; a CDR2 comprising the amino acid sequence of any one of SEQ ID NOs: 106-112, 124, 126-129, 133, 135-137, 139-140; and a CDR3 comprising the amino acid sequence of any one of SEQ ID NOs: 176-182, 194, 196-199, 203, 205-207, 209-210; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an isolated anti-TIGIT construct comprising an sdAb moiety specifically recognizing TIGIT and an anti-PD-1 full-length antibody, wherein the anti-TIGIT sdAb moiety comprises a CDR1 comprising the amino acid sequence of any one of SEQ ID NOs: 36-42, 54, 56-59, 63, 65-67, 69-70; a CDR2 comprising the amino acid sequence of any one of SEQ ID NOs: 106-112, 124, 126-129, 133, 135-137, 139-140; and a CDR3 comprising the amino acid sequence of any one of SEQ ID NOs: 176-182, 194, 196-199, 203, 205-207, 209-210. In some embodiments, there is provided an isolated anti-TIGIT construct comprising a sdAb moiety specifically recognizing TIGIT and an anti-PD-1 full-length antibody, wherein the sdAb comprises a $V_H H$ domain comprising the amino acid sequence of any one of SEQ ID NOs: 253-259, 271, 273-276, 280, 282-284, 286-287, or a variant thereof having at least about 80% (such as at least about any of 80%, 85%, 90%, 91%, 92%, 93%, 94%, 95%, 96%, 97%, 98%, or 99%) sequence identify to any one of SEQ ID NOs: 253-259, 271, 273-276, 280, 282-284, 286-287. In some embodiments, there is provided an isolated anti-TIGIT construct comprising a sdAb moiety specifically recognizing TIGIT and an anti-PD-1 full-length antibody, wherein the sdAb comprises a $V_H H$ domain comprising the amino acid sequence of any one of SEQ ID NOs: 253-259, 271, 273-276, 280, 282-284, 286-287, or a variant thereof comprising up to about 3 (such as about any of 1, 2, or 3) amino acid substitutions in the $V_H H$ domain. In some embodiments, the amino acid substitutions are in CDRs, such as the CDR1, and/or the CDR2, and/or the CDR3 of any one of SEQ ID NOs: 253-259, 271, 273-276, 280, 282-284, 286-287. In some embodiments, the amino acid substitutions are in FRs, such as the FR1, and/or the FR2, and/or the FR3, and/or the FR4 of any one of SEQ ID NOs: 253-259, 271, 273-276, 280, 282-284, 286-287. In some embodiments, the amino acid substitutions are in both CDRs and FRs of any one of SEQ ID NOs: 253-259, 271, 273-276, 280, 282-284, 286-287. In some embodiments, there is provided an isolated anti-TIGIT construct comprising an sdAb moiety specifically recognizing TIGIT and an anti-PD-1 full-length antibody, wherein the sdAb comprises a $V_HH$ domain comprising the amino acid sequence of any one of SEQ ID NOs: 253-259, 271, 273-276, 280, 282-284, 286-287. In some embodiments, there is provided an isolated anti-TIGIT construct comprising an sdAb moiety specifically recognizing TIGIT and an anti-PD-1 full-length antibody, wherein the sdAb moiety comprises CDR1, CDR2, and CDR3 of any one of SEQ ID NOs: 253-259, 271, 273-276, 280, 282-284, 286-287. In some embodiments, the anti-PD-1 antibody comprises a $V_H$ comprising HC-CDR1, HC-CDR2, and HC-CDR3 of the amino acid sequence of SEQ ID NO: 385, and a $V_L$ comprising LC-CDR1, LC-CDR2, and LC-CDR3 of the amino acid sequence of SEQ ID NO: 386. In some embodiments, the anti-PD-1 antibody comprises a $V_H$ comprising the amino acid sequence of SEQ ID NO: 385, and a $V_L$ comprising the amino acid sequence of SEQ ID NO: 386. In some embodiments, the anti-PD-1 antibody comprises a heavy chain comprising the amino acid sequence of SEQ ID NO: 325, and a light chain comprising the amino acid sequence of SEQ ID NO: 326. In some embodiments, the anti-PD-1 antibody comprises a $V_H$ comprising HC-CDR1, HC-CDR2, and HC-CDR3 of the amino acid sequence of SEQ ID NO: 387, and a $V_L$ comprising LC-CDR1, LC-CDR2, and LC-CDR3 of the amino acid sequence of SEQ ID NO: 388. In some embodiments, the anti-PD-1 antibody comprises a $V_H$ comprising the amino acid sequence of SEQ ID NO: 387, and a $V_L$ comprising the amino acid sequence of SEQ ID NO: 388. In some embodiments, the anti-PD-1 antibody comprises a $V_H$ comprising HC-CDR1, HC-CDR2, and HC-CDR3 of the amino acid sequence of SEQ ID NO: 406, and a $V_L$ comprising LC-CDR1, LC-CDR2, and LC-CDR3 of the amino acid sequence of SEQ ID NO: 407. In some embodiments, the anti-PD-1 antibody comprises a $V_H$ comprising the amino acid sequence of SEQ ID NO: 406, and a $V_L$ comprising the amino acid sequence of SEQ ID NO: 407. In some embodiments, the Fc fragment of the full-length antibody is hIgG1 Fc, effectorless hIgG1 Fc, hIgG2 Fc, or hIgG4 Fc. In some embodiments, the Fc fragment of the full-length antibody comprises the amino acid sequence of any one of SEQ ID NOs: 355, 356, and 389. In some embodiments, the N-terminus of the anti-TIGIT sdAb moiety is fused to the C-terminus of at least one of the heavy chains of the full-length antibody. In some embodiments, the C-terminus of the anti-TIGIT sdAb moiety is fused to the N-terminus of at least one of the heavy chains of the full-length antibody. In some embodiments, the N-terminus of the anti-TIGIT sdAb moiety is fused to the C-terminus of at least one of the light chains of the full-length antibody. In some embodiments, the C-terminus of the anti-TIGIT sdAb moiety is fused to the N-terminus of at least one of the light chains of the full-length antibody. In some embodiments, the anti-TIGIT construct comprises four anti-TIGIT sdAb moieties described herein, and the C-terminus of the anti-TIGIT sdAb moiety is fused to the N-terminus of both heavy and light chains of the full-length antibody (exemplified as FIG. 21). In some embodiments, the anti-TIGIT construct comprises four anti-TIGIT sdAb moieties described herein, wherein two anti-TIGIT sdAb moieties are fused together via a first optional linker, and the other two anti-TIGIT sdAb moieties are fused together via a second optional linker, wherein the C-terminus of each set of two anti-TIGIT sdAb fusion is fused to the N-terminus of each heavy chain of the full-length antibody via a third and fourth optional linkers (exemplified as FIG. 22). In some embodiments, the four anti-TIGIT sdAb moieties are identical. In some embodiments, the anti-TIGIT sdAb moiety and the full-length antibody are optionally connected by a peptide linker. In some embodiments, the peptide linker comprises the amino acid sequence of any one of SEQ ID NOs: 324 and 370-378. In some embodiments, the $K_d$ of the binding between the anti-TIGIT sdAb moiety and TIGIT is about $10^{-5}$ M to about $10^{-12}$ M (such as about $10^{-7}$ M to about $10^{-12}$ M, or about $10^{-8}$ M to about $10^{-12}$ M). In some embodiments, the anti-TIGIT sdAb moiety is camelid, chimeric, human, partially humanized, or fully humanized.

Figure 17:
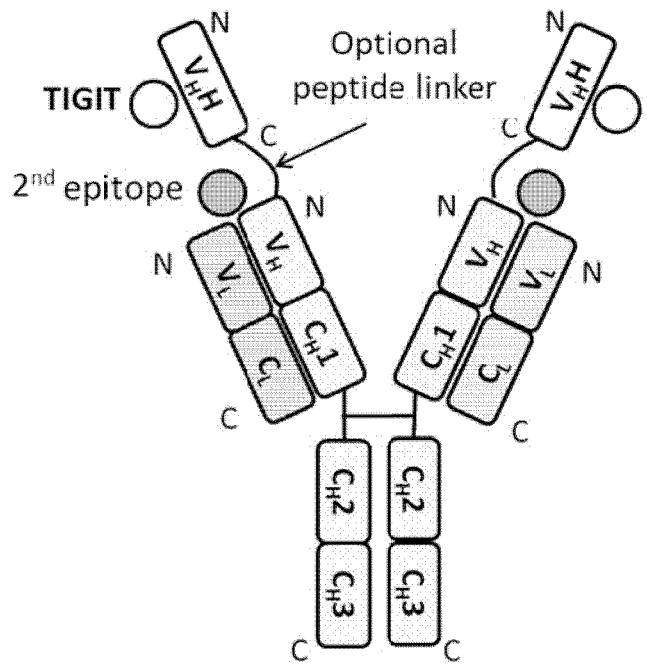
FIG. 17 depicts a schematic structure of an exemplary BABP comprising a monospecific full-length antibody having two identical heavy chains and two identical light chains, and two identical anti-TIGIT sdAbs, wherein the C-terminus of each anti-TIGIT sdAb is fused to the N-terminus of one heavy chain via an optional peptide linker. The two anti-TIGIT sdAbs specifically bind a first epitope (TIGIT). The full-length antibody has two antigen binding sites that specifically bind a second epitope. For example, the BABP can consist of four polypeptide chains with structures from the N-terminus to the C-terminus as follows: (1) $V_L$—$C_L$; (2) $V_HH$—$V_H$—$C_H1$-$C_H2$-$C_H3$; (3) $V_HH$—$V_H$—$C_H1$-$C_H2$-$C_H3$; and (4) $V_L$—$C_L$, wherein $V_H$ and $V_L$ of polypeptide chains (1) and (2) forms an antigen binding site that specifically binds a first copy of the second epitope, $V_H$ and $V_L$ of polypeptide chains (3) and (4) forms an antigen binding site that specifically binds a second copy of the second epitope, and each $V_HH$ specifically binds a copy of the first epitope (TIGIT). In alternative formats, each anti-TIGIT sdAb may be omitted, or replaced with two identical or different anti-TIGIT sdAbs fused to each other. The monospecific full-length antibody may be replaced with a bispecific full-length antibody to further expand binding specificity.
Figure 18:
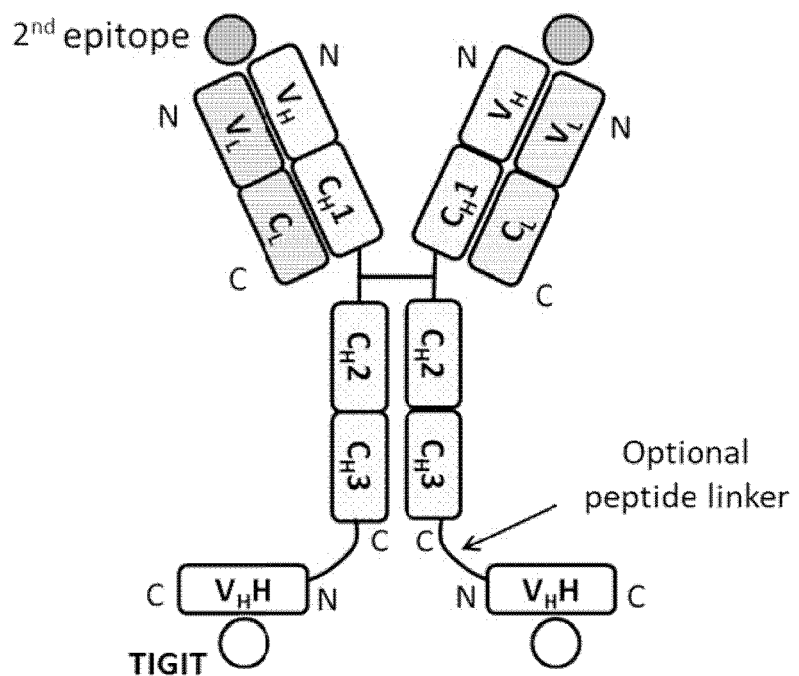
FIG. 18 depicts a schematic structure of an exemplary BABP comprising a monospecific full-length antibody having two identical heavy chains and two identical light chains, and two identical anti-TIGIT sdAbs, wherein the N-terminus of each anti-TIGIT sdAb is fused to the C-terminus of one heavy chain via an optional peptide linker. The two anti-TIGIT sdAbs specifically bind a first epitope (TIGIT). The full-length antibody has two antigen binding sites that specifically bind a second epitope. For example, the BABP can consist of four polypeptide chains with structures from the N-terminus to the C-terminus as follows: (1) $V_L$—$C_L$; (2) $V_H$—$C_H1$-$C_H2$-$C_H3$-$V_HH$; (3) $V_H$—$C_H1$-$C_H2$-$C_H3$-$V_HH$; and (4) $V_L$—$C_L$, wherein $V_H$ and $V_L$ of polypeptide chains (1) and (2) forms an antigen binding site that specifically binds a first copy of the second epitope, $V_H$ and $V_L$ of polypeptide chains (3) and (4) forms an antigen binding site that specifically binds a second copy of the second epitope, and each $V_HH$ specifically binds a copy of the first epitope (TIGIT). In alternative formats, each anti-TIGIT sdAb may be omitted, or replaced with two identical or different anti-TIGIT sdAbs fused to each other. The monospecific full-length antibody may be replaced with a bispecific full-length antibody to further expand binding specificity.
Figure 19:
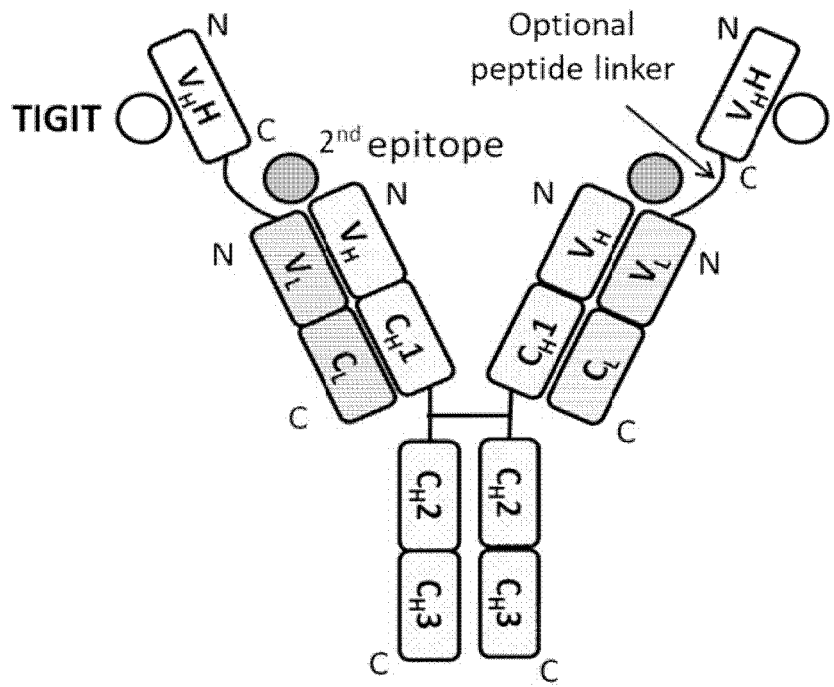
FIG. 19 depicts a schematic structure of an exemplary BABP comprising a monospecific full-length antibody having two identical heavy chains and two identical light chains, and two identical anti-TIGIT sdAbs, wherein the C-terminus of each anti-TIGIT sdAb is fused to the N-terminus of one light chain via an optional peptide linker. The two anti-TIGIT sdAbs specifically bind a first epitope (TIGIT). The full-length antibody has two antigen binding sites that specifically bind a second epitope. For example, the BABP can consist of four polypeptide chains with structures from the N-terminus to the C-terminus as follows: (1) $V_HH$—$V_L$—$C_L$; (2) $V_H$—$C_H1$-$C_H2$-$C_H3$; (3) $V_H$—$C_H1$-$C_H2$-$C_H3$; and (4) $V_HH$—$V_L$—$C_L$, wherein $V_H$ and $V_L$ of polypeptide chains (1) and (2) forms an antigen binding site that specifically binds a first copy of the second epitope, $V_H$ and $V_L$ of polypeptide chains (3) and (4) forms an antigen binding site that specifically binds a second copy of the second epitope, and each $V_HH$ specifically binds a copy of the first epitope (TIGIT). In alternative formats, each anti-TIGIT sdAb may be omitted, or replaced with two identical or different anti-TIGIT sdAbs fused to each other. The monospecific full-length antibody may be replaced with a bispecific full-length antibody to further expand binding specificity.
Figure 20:
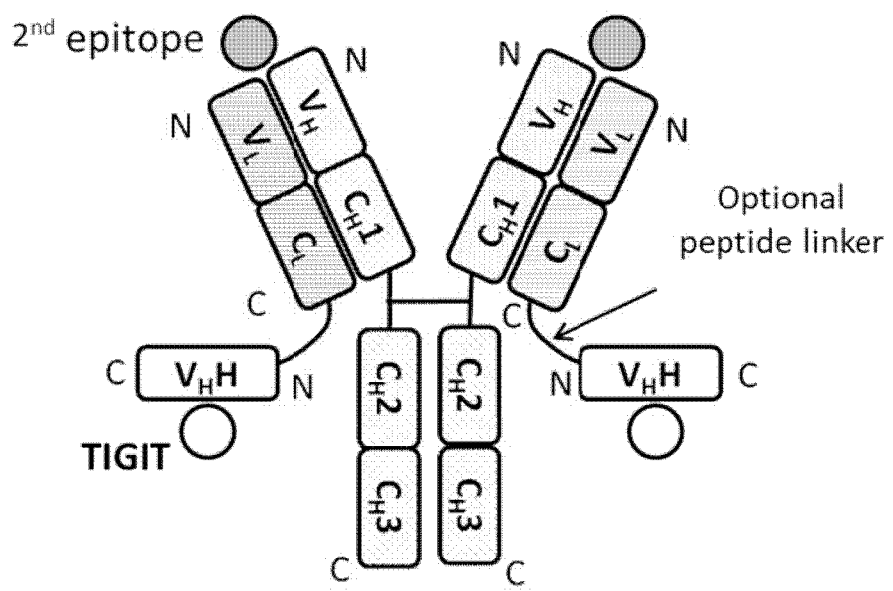
FIG. 20 depicts a schematic structure of an exemplary BABP comprising a monospecific full-length antibody having two identical heavy chains and two identical light chains, and two identical anti-TIGIT sdAbs, wherein the N-terminus of each anti-TIGIT sdAb is fused to the C-terminus of one light chain via an optional peptide linker. The two anti-TIGIT sdAbs specifically bind a first epitope. The full-length antibody has two antigen binding sites that specifically bind a second epitope. For example, the BABP can consist of four polypeptide chains with structures from the N-terminus to the C-terminus as follows: (1) $V_L$—$C_L$—$V_HH$; (2) $V_H$—$C_H1$-$C_H2$-$C_H3$; (3) $V_H$—$C_H1$-$C_H2$-$C_H3$; and (4) $V_L$—$C_L$—$V_HH$, wherein $V_H$ and $V_L$ of polypeptide chains (1) and (2) forms an antigen binding site that specifically binds a first copy of the second epitope, $V_H$ and $V_L$ of polypeptide chains (3) and (4) forms an antigen binding site that specifically binds a second copy of the second epitope, and each $V_HH$ specifically binds a copy of the first epitope (TIGIT). In alternative formats, each anti-TIGIT sdAb may be omitted, or replaced with two identical or different anti-TIGIT sdAbs fused to each other. The monospecific full-length antibody may be replaced with a bispecific full-length antibody to further expand binding specificity.

In some embodiments, there is provided an isolated anti-TIGIT construct comprising an sdAb moiety specifically recognizing TIGIT and an anti-PD-1 full-length antibody, wherein the C-terminus of the anti-TIGIT sdAb moiety is fused to the N-terminus of at least one of the heavy chains of the anti-PD-1 full-length antibody, wherein the anti-PD-1 full-length antibody comprises a heavy chain comprising the amino acid sequence of SEQ ID NO: 390, and a light chain comprising the amino acid sequence of SEQ ID NO: 391 or 395, and wherein the heavy chain fusion polypeptide comprises the amino acid sequence of SEQ ID NO: 394 (hereinafter denoted as "BTP-11"). In some embodiments, the C-terminus of the anti-TIGIT sdAb moiety is fused to the N-terminus of both heavy chains of the anti-PD-1 full-length antibody. In some embodiments, there is provided an isolated anti-TIGIT construct comprising an sdAb moiety specifically recognizing TIGIT and an anti-PD-1 full-length antibody, wherein the N-terminus of the anti-TIGIT sdAb moiety is fused to the C-terminus of at least one of the heavy chains of the anti-PD-1 full-length antibody, wherein the anti-PD-1 full-length antibody comprises a heavy chain comprising the amino acid sequence of SEQ ID NO: 390, and a light chain comprising the amino acid sequence of SEQ ID NO: 391 or 397, and wherein the heavy chain fusion polypeptide comprises the amino acid sequence of SEQ ID NO: 396 (hereinafter denoted as "BTP-12"). In some embodiments, the C-terminus of the anti-TIGIT sdAb moiety is fused to the N-terminus of both heavy chains of the anti-PD-1 full-length antibody. In some embodiments, there is provided an isolated anti-TIGIT construct comprising an sdAb moiety specifically recognizing TIGIT and an anti-PD-1 full-length antibody, wherein the C-terminus of the anti-TIGIT sdAb moiety is fused to the N-terminus of at least one of the light chains of the anti-PD-1 full-length antibody, wherein the anti-PD-1 full-length antibody comprises a heavy chain comprising the amino acid sequence of SEQ ID NO: 390 or 398, and a light chain comprising the amino acid sequence of SEQ ID NO: 391, and wherein the light chain fusion polypeptide comprises the amino acid sequence of SEQ ID NO: 399 (hereinafter denoted as "BTP-13"). In some embodiments, the C-terminus of the anti-TIGIT sdAb moiety is fused to the N-terminus of both light chains of the anti-PD-1 full-length antibody. In some embodiments, there is provided an isolated anti-TIGIT construct comprising an sdAb moiety specifically recognizing TIGIT and an anti-PD-1 full-length antibody, wherein the N-terminus of the anti-TIGIT sdAb moiety is fused to the C-terminus of at least one of the light chains of the anti-PD-1 full-length antibody, wherein the anti-PD-1 full-length antibody comprises a heavy chain comprising the amino acid sequence of SEQ ID NO: 390 or 400, and a light chain comprising the amino acid sequence of SEQ ID NO: 391, and wherein the light chain fusion polypeptide comprises the amino acid sequence of SEQ ID NO: 401 (hereinafter denoted as "BTP-14"). In some embodiments, the N-terminus of the anti-TIGIT sdAb moiety is fused to the C-terminus of both light chains of the anti-PD-1 full-length antibody. In some embodiments, there is provided an isolated anti-TIGIT construct comprising two identical copies of heavy chain fusion polypeptide comprising the amino acid sequence of any one of SEQ ID NOs: 394 and 396, and two identical copies of light chain comprising the amino acid sequence of any one of SEQ ID NOs: 391, 395 or 397. In some embodiments, the anti-TIGIT construct has the structure as shown in FIGS. 17 and 18. In some embodiments, there is provided an isolated anti-TIGIT construct comprising two identical copies of heavy chain comprising the amino acid sequence of any one of SEQ ID NOs: 390, 398 or 400 and two identical copies of light chain fusion polypeptide comprising the amino acid sequence of SEQ ID NO: 399 or 401. In some embodiments, the anti-TIGIT construct has the structure as shown in FIGS. 19 and 20.

Thus in some embodiments, there is provided an isolated anti-TIGIT construct comprising an sdAb moiety specifically recognizing TIGIT and an anti-PD-L1 full-length antibody, wherein the anti-TIGIT sdAb moiety comprises a CDR1 comprising the amino acid sequence of any one of SEQ ID NOs: 36-42, 54, 56-59, 63, 65-67, 69-70, or a variant thereof comprising up to about 3 (such as about any of 1, 2, or 3) amino acid substitutions; a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210, or a variant thereof comprising up to about 3 (such as about any of 1, 2, or 3) amino acid substitutions; and wherein the anti-PD-L1 full-length antibody comprises a $V_H$ comprising HC-CDR1, HC-CDR2, and HC-CDR3 of the amino acid sequence of SEQ ID NO: 381, and a $V_L$ comprising LC-CDR1, LC-CDR2, and LC-CDR3 of the amino acid sequence of SEQ ID NO: 382.

In some embodiments, there is provided an isolated anti-TIGIT construct comprising an sdAb moiety specifically recognizing TIGIT and an anti-PD-L1 full-length antibody, wherein the anti-TIGIT sdAb moiety comprises a CDR1 comprising the amino acid sequence of any one of SEQ ID NOs: 36-42, 54, 56-59, 63, 65-67, 69-70; a CDR2 comprising the amino acid sequence of any one of SEQ ID NOs: 106-112, 124, 126-129, 133, 135-137, 139-140; and a CDR3 comprising the amino acid sequence of any one of SEQ ID NOs: 176-182, 194, 196-199, 203, 205-207, 209-210; and wherein the anti-PD-L1 full-length antibody comprises a $V_H$ comprising HC-CDR1, HC-CDR2, and HC-CDR3 of the amino acid sequence of SEQ ID NO: 381, and a $V_L$ comprising LC-CDR1, LC-CDR2, and LC-CDR3 of the amino acid sequence of SEQ ID NO: 382. In some embodiments, there is provided an isolated anti-TIGIT construct comprising a sdAb moiety specifically recognizing TIGIT and an anti-PD-L1 full-length antibody, wherein the sdAb comprises a $V_H H$ domain comprising the amino acid sequence of any one of SEQ ID NOs: 253-259, 271, 273-276, 280, 282-284, 286-287, or a variant thereof having at least about 80% (such as at least about any of 80%, 85%, 90%, 91%, 92%, 93%, 94%, 95%, 96%, 97%, 98%, or 99%) sequence identify to any one of SEQ ID NOs: 253-259, 271, 273-276, 280, 282-284, 286-287; and wherein the anti-PD-L1 full-length antibody comprises a $V_H$ comprising HC-CDR1, HC-CDR2, and HC-CDR3 of the amino acid sequence of SEQ ID NO: 381, and a $V_L$ comprising LC-CDR1, LC-CDR2, and LC-CDR3 of the amino acid sequence of SEQ ID NO: 382. In some embodiments, there is provided an isolated anti-TIGIT construct comprising an sdAb moiety specifically recognizing TIGIT and an anti-PD-L1 full-length antibody, wherein the sdAb comprises a $V_H H$ domain comprising the amino acid sequence of any one of SEQ ID NOs: 253-259, 271, 273-276, 280, 282-284, 286-287; and wherein the anti-PD-L1 full-length antibody comprises a $V_H$ comprising HC-CDR1, HC-CDR2, and HC-CDR3 of the amino acid sequence of SEQ ID NO: 381, and a $V_L$ comprising LC-CDR1, LC-CDR2, and LC-CDR3 of the amino acid sequence of SEQ ID NO: 382. In some embodiments, there is provided an isolated anti-TIGIT construct comprising an sdAb moiety specifically recognizing TIGIT and an anti-PD-L1 full-length antibody, wherein the sdAb moiety comprises CDR1, CDR2, and CDR3 of any one of SEQ ID NOs: 253-259, 271, 273-276, 280, 282-284, 286-287; and wherein the anti-PD-L1 full-length antibody comprises a $V_H$ comprising HC-CDR1, HC-CDR2, and HC-CDR3 of the amino acid sequence of SEQ ID NO: 381, and a $V_L$ comprising LC-CDR1, LC-CDR2, and LC-CDR3 of the amino acid sequence of SEQ ID NO: 382. In some embodiments, the Fc fragment of the full-length antibody comprises the amino acid sequence of any one of SEQ ID NOs: 355, 356, and 389. In some embodiments, the anti-PD-L1 antibody comprises a heavy chain comprising the amino acid sequence of SEQ ID NO: 331, and a light chain comprising the amino acid sequence of SEQ ID NO: 332. In some embodiments, the anti-PD-L1 antibody comprises a heavy chain comprising the amino acid sequence of SEQ ID NO: 333, and a light chain comprising the amino acid sequence of SEQ ID NO: 334.

In some embodiments, there is provided an isolated anti-TIGIT construct comprising an sdAb moiety specifically recognizing TIGIT and an anti-PD-L1 full-length antibody, wherein the C-terminus of the anti-TIGIT sdAb moiety is fused to the N-terminus of at least one of the heavy chains of the anti-PD-L1 full-length antibody, wherein the anti-PD-L1 full-length antibody comprises a heavy chain comprising the amino acid sequence of SEQ ID NO: 331, and a light chain comprising the amino acid sequence of SEQ ID NO: 332 or 348, and wherein the heavy chain fusion polypeptide comprises the amino acid sequence of SEQ ID NO: 347 (hereinafter denoted as "BTP-7"). In some embodiments, there is provided an isolated anti-TIGIT construct comprising an sdAb moiety specifically recognizing TIGIT and an anti-PD-L1 full-length antibody, wherein the C-terminus of the anti-TIGIT sdAb moiety is fused to the N-terminus of at least one of the heavy chains of the anti-PD-L1 full-length antibody, wherein the anti-PD-L1 full-length antibody comprises a heavy chain comprising the amino acid sequence of SEQ ID NO: 333, and a light chain comprising the amino acid sequence of SEQ ID NO: 334 or 346, and wherein the heavy chain fusion polypeptide comprises the amino acid sequence of SEQ ID NO: 345 (hereinafter denoted as "BTP-6"). In some embodiments, the C-terminus of the anti-TIGIT sdAb moiety is fused to the N-terminus of both heavy chains of the anti-PD-L1 full-length antibody. In some embodiments, there is provided an isolated anti-TIGIT construct comprising two identical copies of heavy chain fusion polypeptide comprising the amino acid sequence of SEQ ID NO: 345 or 347, and two identical copies of light chain comprising the amino acid sequence of any one of SEQ ID NOs: 332, 334, 346 and 348. In some embodiments, the anti-TIGIT construct has the structure as shown in FIG. 17.

In some embodiments according to any of the anti-TIGIT/ anti-PD-L1 constructs described herein, the anti-PD-L1 full-length antibody comprises 1) a $V_H$ comprising an HC-CDR1 comprising the amino acid sequence of SEQ ID NO: 349, an HC-CDR2 comprising the amino acid sequence of SEQ ID NO: 350, and an HC-CDR3 comprising the amino acid sequence of SEQ ID NO: 351, and 2) a $V_L$ comprising an LC-CDR1 comprising the amino acid sequence of SEQ ID NO: 352, an LC-CDR2 comprising the amino acid sequence of SEQ ID NO: 353, and an LC-CDR3 comprising the amino acid sequence of SEQ ID NO: 354.

In some embodiments, there is provided an isolated anti-TIGIT construct comprising an sdAb moiety specifically recognizing TIGIT and an anti-PD-L1 full-length antibody, wherein the C-terminus of the anti-TIGIT sdAb moiety is fused to the N-terminus of at least one of the heavy chains of the anti-PD-L1 full-length antibody, wherein the anti-PD-L1 full-length antibody comprises a heavy chain comprising the amino acid sequence of SEQ ID NO: 329, and a light chain comprising the amino acid sequence of SEQ ID NO: 330 or 342, and wherein the heavy chain fusion polypeptide comprises the amino acid sequence of SEQ ID NO: 341 (hereinafter denoted as "BTP-4"). In some embodiments, there is provided an isolated anti-TIGIT construct comprising an sdAb moiety specifically recognizing TIGIT and an anti-PD-L1 full-length antibody, wherein the C-terminus of the anti-TIGIT sdAb moiety is fused to the N-terminus of at least one of the heavy chains of the anti-PD-L1 full-length antibody, wherein the anti-PD-L1 full-length antibody comprises a heavy chain comprising the amino acid sequence of SEQ ID NO: 327, and a light chain comprising the amino acid sequence of SEQ ID NO: 328 or 344, and wherein the heavy chain fusion polypeptide comprises the amino acid sequence of SEQ ID NO: 343 (hereinafter denoted as "BTP-5"). In some embodiments, there is provided an isolated anti-TIGIT construct comprising an sdAb moiety specifically recognizing TIGIT and an anti-PD-L1 full-length antibody, wherein the C-terminus of the anti-TIGIT sdAb moiety is fused to the N-terminus of at least one of the heavy chains of the anti-PD-L1 full-length antibody, wherein the anti-PD-L1 full-length antibody comprises a heavy chain comprising the amino acid sequence of SEQ ID NO: 323, and a light chain comprising the amino acid sequence of SEQ ID NO: 328 or 358, and wherein the heavy chain fusion polypeptide comprises the amino acid sequence of SEQ ID NO: 357 (hereinafter denoted as "BTP-15"). In some embodiments, the C-terminus of the anti-TIGIT sdAb moiety is fused to the N-terminus of both heavy chains of the anti-PD-L1 full-length antibody. In some embodiments, there is provided an isolated anti-TIGIT construct comprising an sdAb moiety specifically recognizing TIGIT and an anti-PD-L1 full-length antibody, wherein the N-terminus of the anti-TIGIT sdAb moiety is fused to the C-terminus of at least one of the heavy chains of the anti-PD-L1 full-length antibody, wherein the anti-PD-L1 full-length antibody comprises a heavy chain comprising the amino acid sequence of SEQ ID NO: 323, and a light chain comprising the amino acid sequence of SEQ ID NO: 328 or 360, and wherein the heavy chain fusion polypeptide comprises the amino acid sequence of SEQ ID NO: 359 (hereinafter denoted as "BTP-16"). In some embodiments, the N-terminus of the anti-TIGIT sdAb moiety is fused to the C-terminus of both heavy chains of the anti-PD-L1 full-length antibody. In some embodiments, there is provided an isolated anti-TIGIT construct comprising an sdAb moiety specifically recognizing TIGIT and an anti-PD-L1 full-length antibody, wherein the C-terminus of the anti-TIGIT sdAb moiety is fused to the N-terminus of at least one of the light chains of the anti-PD-L1 full-length antibody, wherein the anti-PD-L1 full-length antibody comprises a heavy chain comprising the amino acid sequence of SEQ ID NO: 323 or 361, and a light chain comprising the amino acid sequence of SEQ ID NO: 328, and wherein the light chain fusion polypeptide comprises the amino acid sequence of SEQ ID NO: 362 (hereinafter denoted as "BTP-17"). In some embodiments, the C-terminus of the anti-TIGIT sdAb moiety is fused to the N-terminus of both light chains of the anti-PD-L1 full-length antibody. In some embodiments, there is provided an isolated anti-TIGIT construct comprising an sdAb moiety specifically recognizing TIGIT and an anti-PD-L1 full-length antibody, wherein the N-terminus of the anti-TIGIT sdAb moiety is fused to the C-terminus of at least one of the light chains of the anti-PD-L1 full-length antibody, wherein the anti-PD-L1 full-length antibody comprises a heavy chain comprising the amino acid sequence of SEQ ID NO: 323 or 363, and a light chain comprising the amino acid sequence of SEQ ID NO: 328, and wherein the light chain fusion polypeptide comprises the amino acid sequence of SEQ ID NO: 364 (hereinafter denoted as "BTP-18"). In some embodiments, the N-terminus of the anti-TIGIT sdAb moiety is fused to the C-terminus of both light chains of the anti-PD-L1 full-length antibody. In some embodiments, there is provided an isolated anti-TIGIT construct comprising an sdAb moiety specifically recognizing TIGIT and an anti-PD-L1 full-length antibody, wherein the C-terminus of the anti-TIGIT sdAb moiety is fused to the N-terminus of at least one of the heavy chains of the anti-PD-L1 full-length antibody, wherein the anti-PD-L1 full-length antibody comprises a heavy chain comprising the amino acid sequence of SEQ ID NO: 329, and a light chain comprising the amino acid sequence of SEQ ID NO: 330 or 403, and wherein the heavy chain fusion polypeptide comprises the amino acid sequence of SEQ ID NO: 402 (hereinafter denoted as "BTP-21"). In some embodiments, the C-terminus of the anti-TIGIT sdAb moiety is fused to the N-terminus of both heavy chains of the anti-PD-L1 full-length antibody. In some embodiments, there is provided an isolated anti-TIGIT construct comprising an sdAb moiety specifically recognizing TIGIT and an anti-PD-L1 full-length antibody, wherein the C-terminus of the anti-TIGIT sdAb moiety is fused to the N-terminus of at least one of the light chains of the anti-PD-L1 full-length antibody, wherein the anti-PD-L1 full-length antibody comprises a heavy chain comprising the amino acid sequence of SEQ ID NO: 329 or 404, and a light chain comprising the amino acid sequence of SEQ ID NO: 330, and wherein the light chain fusion polypeptide comprises the amino acid sequence of SEQ ID NO: 405 (hereinafter denoted as "BTP-22"). In some embodiments, the C-terminus of the anti-TIGIT sdAb moiety is fused to the N-terminus of both light chains of the anti-PD-L1 full-length antibody. In some embodiments, there is provided an isolated anti-TIGIT construct comprising two identical copies of heavy chain fusion polypeptide comprising the amino acid sequence of any one of SEQ ID NOs: 341, 343, 357, 359 and 402, and two identical copies of light chain comprising the amino acid sequence of any one of SEQ ID NOs: 328, 330, 342, 344, 358, 360 and 403. In some embodiments, the anti-TIGIT construct has the structure as shown in FIGS. 17 and 18. In some embodiments, there is provided an isolated anti-TIGIT construct comprising two identical copies of heavy chain comprising the amino acid sequence of any one of SEQ ID NOs: 323, 329, 361, 363, and 404 and two identical copies of light chain fusion polypeptide comprising the amino acid sequence of any one of SEQ ID NO: 362, 364 and 405. In some embodiments, the anti-TIGIT construct has the structure as shown in FIGS. 19 and 20.

In some embodiments according to any of the anti-TIGIT/anti-PD-L1 constructs described herein, the anti-PD-L1 full-length antibody comprises a $V_H$ comprising HC-CDR1, HC-CDR2, and HC-CDR3 of the amino acid sequence of SEQ ID NO: 379, and a $V_L$ comprising LC-CDR1, LC-CDR2, and LC-CDR3 of the amino acid sequence of SEQ ID NO: 380. In some embodiments, there is provided an isolated anti-TIGIT construct comprising an sdAb moiety specifically recognizing TIGIT and an anti-PD-L1 full-length antibody, wherein the sdAb comprises a $V_H$H domain comprising the amino acid sequence of any one of SEQ ID NOs: 253-259, 271, 273-276, 280, 282-284, 286-287; and wherein the anti-PD-L1 full-length antibody comprises a $V_H$ comprising HC-CDR1, HC-CDR2, and HC-CDR3 of the amino acid sequence of SEQ ID NO: 379, and a $V_L$ comprising LC-CDR1, LC-CDR2, and LC-CDR3 of the amino acid sequence of SEQ ID NO: 380. In some embodiments, there is provided an isolated anti-TIGIT construct comprising an sdAb moiety specifically recognizing TIGIT and an anti-PD-L1 full-length antibody, wherein the sdAb moiety comprises CDR1, CDR2, and CDR3 of any one of SEQ ID NOs: 253-259, 271, 273-276, 280, 282-284, 286-287; and wherein the anti-PD-L1 full-length antibody comprises a $V_H$ comprising HC-CDR1, HC-CDR2, and HC-CDR3 of the amino acid sequence of SEQ ID NO: 379, and a $V_L$ comprising LC-CDR1, LC-CDR2, and LC-CDR3 of the amino acid sequence of SEQ ID NO: 380.

In some embodiments according to any of the anti-TIGIT/anti-PD-L1 constructs described herein, the anti-PD-L1 full-length antibody comprises a $V_H$ comprising HC-CDR1, HC-CDR2, and HC-CDR3 of the amino acid sequence of SEQ ID NO: 383, and a $V_L$ comprising LC-CDR1, LC-CDR2, and LC-CDR3 of the amino acid sequence of SEQ ID NO: 384. In some embodiments, there is provided an isolated anti-TIGIT construct comprising an sdAb moiety specifically recognizing TIGIT and an anti-PD-L1 full-length antibody, wherein the sdAb comprises a $V_H$H domain comprising the amino acid sequence of any one of SEQ ID NOs: 253-259, 271, 273-276, 280, 282-284, 286-287; and wherein the anti-PD-L1 full-length antibody comprises a $V_H$ comprising HC-CDR1, HC-CDR2, and HC-CDR3 of the amino acid sequence of SEQ ID NO: 383, and a $V_L$ comprising LC-CDR1, LC-CDR2, and LC-CDR3 of the amino acid sequence of SEQ ID NO: 384. In some embodiments, there is provided an isolated anti-TIGIT construct comprising an sdAb moiety specifically recognizing TIGIT and an anti-PD-L1 full-length antibody, wherein the sdAb moiety comprises CDR1, CDR2, and CDR3 of any one of SEQ ID NOs: 253-259, 271, 273-276, 280, 282-284, 286-287; and wherein the anti-PD-L1 full-length antibody comprises a $V_H$ comprising HC-CDR1, HC-CDR2, and HC-CDR3 of the amino acid sequence of SEQ ID NO: 383, and a $V_L$ comprising LC-CDR1, LC-CDR2, and LC-CDR3 of the amino acid sequence of SEQ ID NO: 384.

In some embodiments, there is also provided an anti-TIGIT construct comprising an sdAb moiety specifically recognizing TIGIT (hereinafter referred to as "competing anti-TIGIT construct") that specifically binds to TIGIT competitively with any one of the anti-TIGIT constructs described herein (such as anti-TIGIT sdAb moiety, anti-TIGIT sdAb-Fc fusion protein, multispecific or monospecific anti-TIGIT construct comprising an anti-TIGIT sdAb moiety descried herein, e.g., PD-1×TIGIT BABP or PD-L1× TIGIT BABP described herein).

Anti-TIGIT Multispecific Antigen Binding Proteins (MABPs)

The present application generally provides an anti-TIGIT construct comprising an anti-TIGIT sdAb moiety described herein fused to a full-length antibody or antigen binding fragment that comprises a $V_H$ and a $V_L$, wherein the anti-TIGIT construct is multispecific (hereinafter referred to as "multispecific anti-TIGIT construct" or "anti-TIGIT multispecific antigen binding protein (MABP)"). In some embodiments, the anti-TIGIT MABP is bispecific (hereinafter referred to as "bispecific anti-TIGIT construct" or "anti-TIGIT bispecific antigen binding protein (BABP)"). The anti-TIGIT sdAb moiety specifically binds TIGIT that is distinct from the target(s) recognized by the full-length antibody or antigen binding fragment comprising a $V_H$ and a $V_L$, thereby conferring a broadened targeting capability. Due to the small size of the sdAb, in some embodiments the anti-TIGIT MABPs (or BABPs) described herein can have similar molecular weight and pharmacokinetic properties compared to those of the full-length antibody or antigen binding fragment component. For example, an anti-TIGIT MABP can be designed by fusing one or more anti-TIGIT sdAb moieties to a monoclonal antibody with proven clinical efficacy and safety to provide increased clinical benefits and desirable pharmacokinetic properties without impeding the expressibility of the multispecific construct. In some embodiments, the one or more anti-TIGIT sdAb moiety described herein is fused to the full-length antibody or antigen binding fragment by an optional peptide linker. The anti-TIGIT MABPs (or BABPs) described herein can be adopted to target a variety of disease-related epitope or antigen combinations besides TIGIT, such as TIGIT with the combination of immune checkpoint molecules, cell surface antigens (such as tumor antigens), or pro-inflammatory molecules, thereby providing agents that are useful for treating a variety of diseases and conditions, such as cancer, inflammation, and autoimmune diseases. The anti-TIGIT MABP can be of any format, such as those disclosed in PCT/CN2017/093644, which is incorporated herein by reference in their entirety.

Thus, for example, in some embodiments, there is provided an anti-TIGIT construct (e.g., MABP or BABP) comprising: (a) a first antigen binding portion comprising an anti-TIGIT sdAb moiety comprising a CDR1 comprising the amino acid sequence of any one of SEQ ID NOs: 36-42, 54, 56-59, 63, 65-67, 69-70, or a variant thereof comprising up to about 3 (such as about any of 1, 2, or 3) amino acid substitutions; a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210, or a variant thereof comprising up to about 3 (such as about any of 1, 2, or 3) amino acid substitutions, and (b) a second antigen binding portion comprising a $V_H$ and a $V_L$, wherein the $V_H$ and $V_L$ together form an antigen-binding site that specifically binds a second epitope (e.g., PD-1, PD-L1), wherein the first antigen binding portion and the second antigen binding portion are fused to each other. In some embodiments, there is provided an anti-TIGIT construct (e.g., MABP or BABP) comprising: (a) a first antigen binding portion comprising an anti-TIGIT sdAb moiety that comprises CDR1, CDR2, and CDR3 of any one of SEQ ID NOs: 253-259, 271, 273-276, 280, 282-284, 286-287, and (b) a second antigen binding portion comprising a $V_H$ and a $V_L$, wherein the $V_H$ and $V_L$ together form an antigen-binding site that specifically binds a second epitope (e.g., PD-1, PD-L1), wherein the first antigen binding portion and the second antigen binding portion are fused to each other. In some embodiments, the $K_d$ of the binding between the anti-TIGIT sdAb moiety and TIGIT is about $10^{-5}$ M to about $10^{-12}$ M (such as about $10^{-7}$ M to about $10^{-12}$ M, or about $10^{-8}$ M to about $10^{-12}$ M). In some embodiments, the anti-TIGIT sdAb moiety is camelid, chimeric, human, partially humanized, or fully humanized. In some embodiments, the second epitope is an immune checkpoint molecule (e.g., PD-1, PD-L1). In some embodiments, the second epitope is a pro-inflammatory molecule. In some embodiments, the second epitope is a cell surface antigen (such as tumor antigen, or a cell surface antigen on an immune effector cell). In some embodiments, the second antigen binding portion comprises a heavy chain comprising the $V_H$ and a light chain comprising the $V_L$. In some embodiments, the first antigen binding portion is fused to the second antigen binding portion at the N-terminus of the heavy chain, the N-terminus of the light chain, the N-terminus of the Fc region, the C-terminus of the heavy chain, or the C-terminus of the light chain. In some embodiments, the second antigen binding portion comprises a Fab or an scFv. In some embodiments, the first antigen binding portion is fused to the second antigen binding portion at the C-terminus of the Fab or scFv. In some embodiments, the second antigen binding portion comprises a full-length 4-chain antibody. In some embodiments, the second antigen binding portion comprises an anti-PD-1 full-length antibody. In some embodiments, the anti-PD-1 full-length antibody (or Fab, scFv) comprises a $V_H$ comprising HC-CDR1, HC-CDR2, and HC-CDR3 of the amino acid sequence of SEQ ID NO: 385, and a $V_L$ comprising LC-CDR1, LC-CDR2, and LC-CDR3 of the amino acid sequence of SEQ ID NO: 386. In some embodiments, the anti-PD-1 full-length antibody (or Fab, scFv) comprises a $V_H$ comprising the amino acid sequence of SEQ ID NO: 385, and a $V_L$ comprising the amino acid sequence of SEQ ID NO: 386. In some embodiments, the anti-PD-1 full-length antibody comprises a heavy chain comprising the amino acid sequence of SEQ ID NO: 325, and a light chain comprising the amino acid sequence of SEQ ID NO: 326. In some embodiments, the anti-PD-1 full-length antibody (or Fab, scFv) comprises a $V_H$ comprising HC-CDR1, HC-CDR2, and HC-CDR3 of the amino acid sequence of SEQ ID NO: 387, and a $V_L$ comprising LC-CDR1, LC-CDR2, and LC-CDR3 of the amino acid sequence of SEQ ID NO: 388. In some embodiments, the anti-PD-1 full-length antibody (or Fab, scFv) comprises a $V_H$ comprising the amino acid sequence of SEQ ID NO: 387, and a $V_L$ comprising the amino acid sequence of SEQ ID NO: 388. In some embodiments, the anti-PD-1 full-length antibody (or Fab, scFv) comprises a $V_H$ comprising HC-CDR1, HC-CDR2, and HC-CDR3 of the amino acid sequence of SEQ ID NO: 406, and a $V_L$ comprising LC-CDR1, LC-CDR2, and LC-CDR3 of the amino acid sequence of SEQ ID NO: 407. In some embodiments, the anti-PD-1 full-length antibody (or Fab, scFv) comprises a $V_H$ comprising the amino acid sequence of SEQ ID NO: 406, and a $V_L$ comprising the amino acid sequence of SEQ ID NO: 407. In some embodiments, the second antigen binding portion comprises an anti-PD-L1 full-length antibody (or Fab, scFv). In some embodiments, the anti-PD-L1 full-length antibody (or Fab, scFv) comprises a $V_H$ comprising HC-CDR1, HC-CDR2, and HC-CDR3 of the amino acid sequence of SEQ ID NO: 381, and a $V_L$ comprising LC-CDR1, LC-CDR2, and LC-CDR3 of the amino acid sequence of SEQ ID NO: 382. In some embodiments, the anti-PD-L1 full-length antibody (or Fab, scFv) comprises a $V_H$ comprising the amino acid sequence of SEQ ID NO: 381, and a $V_L$ comprising the amino acid sequence of SEQ ID NO: 382. In some embodiments, the anti-PD-L1 full-length antibody comprises a heavy chain comprising the amino acid sequence of SEQ ID NO: 331, and a light chain comprising the amino acid sequence of SEQ ID NO: 332. In some embodiments, the anti-PD-L1 full-length antibody comprises a heavy chain comprising the amino acid sequence of SEQ ID NO: 333, and a light chain comprising the amino acid sequence of SEQ ID NO: 334. In some embodiments, the anti-PD-L1 full-length antibody (or Fab, scFv) comprises a $V_H$ comprising HC-CDR1, HC-CDR2, and HC-CDR3 of the amino acid sequence of SEQ ID NO: 379, and a $V_L$ comprising LC-CDR1, LC-CDR2, and LC-CDR3 of the amino acid sequence of SEQ ID NO: 380. In some embodiments, the anti-PD-L1 full-length antibody (or Fab, scFv) comprises a $V_H$ comprising the amino acid sequence of SEQ ID NO: 379, and a $V_L$ comprising the amino acid sequence of SEQ ID NO: 380. In some embodiments, the anti-PD-L1 full-length antibody (or Fab, scFv) comprises a $V_H$ comprising HC-CDR1, HC-CDR2, and HC-CDR3 of the amino acid sequence of SEQ ID NO: 383, and a $V_L$ comprising LC-CDR1, LC-CDR2, and LC-CDR3 of the amino acid sequence of SEQ ID NO: 384. In some embodiments, the anti-PD-L1 full-length antibody (or Fab, scFv) comprises a $V_H$ comprising the amino acid sequence of SEQ ID NO: 383, and a $V_L$ comprising the amino acid sequence of SEQ ID NO: 384. In some embodiments, the anti-PD-L1 full-length antibody (or Fab, scFv) comprises 1) a $V_H$ comprising an HC-CDR1 comprising the amino acid sequence of SEQ ID NO: 349, an HC-CDR2 comprising the amino acid sequence of SEQ ID NO: 350, and an HC-CDR3 comprising the amino acid sequence of SEQ ID NO: 351, and 2) a $V_L$ comprising an LC-CDR1 comprising the amino acid sequence of SEQ ID NO: 352, an LC-CDR2 comprising the amino acid sequence of SEQ ID NO: 353, and an LC-CDR3 comprising the amino acid sequence of SEQ ID NO: 354. In some embodiments, the anti-PD-L1 full-length antibody (or Fab, scFv) comprises a $V_H$ comprising the amino acid sequence of SEQ ID NO: 339, and a $V_L$ comprising the amino acid sequence of SEQ ID NO: 340. In some embodiments, the anti-PD-L1 full-length antibody comprises a heavy chain comprising the amino acid sequence of SEQ ID NO: 323 or 327, and a light chain comprising the amino acid sequence of SEQ ID NO: 328. In some embodiments, the anti-PD-L1 full-length antibody comprises a heavy chain comprising the amino acid sequence of SEQ ID NO: 329, and a light chain comprising the amino acid sequence of SEQ ID NO: 330. In some embodiments, the first antigen binding portion is fused to the second antigen binding portion chemically. In some embodiments, the first antigen binding portion is fused to the second antigen binding portion via a peptide linker. In some embodiments, the peptide linker is no more than about 30 (such as no more than about any one of 25, 20, or 15) amino acids long. In some embodiments, the peptide linker comprises the amino acid sequence of any one of SEQ ID NOs: 324 and 370-378. In some embodiments, the second antigen binding fragment comprises an Fc region, such as an IgG1 Fc, effectorless IgG1 Fc, IgG2 Fc, or IgG4 Fc. In some embodiments, the second antigen binding fragment comprises an Fc region comprising the amino acid sequence of any one of SEQ ID NOs: 355, 356, and 389.

In some embodiments, the anti-TIGIT construct (e.g., MABP or BABP) comprises at least two antigen binding portions that can specifically bind at least two different epitopes. Some of the at least two antigen binding portions may be identical, so long as the MABP has binding sites for two different epitopes. The anti-TIGIT MABPs (or BABPs) can be symmetric or asymmetric. For example, the anti-TIGIT MABP (or BABP) may comprise one to eight copies of the first antigen binding portion comprising the anti-TIGIT sdAb moieties described herein, and one or two copies of the second antigen binding portion comprising a $V_H$ and a $V_L$. In some embodiments, the anti-TIGIT MABP (or BABP) comprises two different antigen binding portions that each comprise a $V_H$ domain and a $V_L$ domain that together form a different antigen binding site. For example, the second antigen binding portion can be a bispecific antibody. In some embodiments, the second antigen binding portion is a monospecific full-length antibody or antigen binding fragment thereof, such as a Fab or scFv.

In some embodiments, the anti-TIGIT MABP (or BABP) comprises any one of 1, 2, 3, 4, 5, 6, 7, 8, or more different antigen binding portions that each comprises an anti-TIGIT sdAb moiety described herein. In some embodiments, two identical anti-TIGIT sdAb moieties are fused to each other, which is further fused to the second antigen binding portion. In some embodiments, two different anti-TIGIT sdAb moieties are fused to each other, which is further fused to the second antigen binding portion.

The anti-TIGIT constructs (e.g. MABPs) may have any suitable number of valencies for TIGIT and/or the second epitope (e.g., PD-1, PD-L1), and any suitable number of specificity. In some embodiments, the MABP (or BABP) is bivalent, trivalent, tetravalent, pentavalent, hexavalent, or of higher valencies for TIGIT. In some embodiments, the MABP (or BABP) is bivalent, trivalent, tetravalent, pentavalent, hexavalent, or of higher valencies for the second epitope (e.g., PD-1, PD-L1). In some embodiments, the MABP is bispecific (e.g., PD-1×TIGIT BABP, PD-L1× TIGIT BABP). Exemplary BABPs are depicted in FIGS. 17-26. In some embodiments, the MABP is trispecific. In some embodiments, the MABP is tetraspecific. In some embodiments, the MABP has more than four specificities.

In some embodiments, there is provided an anti-TIGIT BABP comprising: (a) one or more copies (such as 2) of a first antigen binding portion comprising an anti-TIGIT sdAb moiety comprising a CDR1 comprising the amino acid sequence of any one of SEQ ID NOs: 36-42, 54, 56-59, 63, 65-67, 69-70, or a variant thereof comprising up to about 3 (such about any of 1, 2, or 3) amino acid substitutions; a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210, or a variant thereof comprising up to about 3 (such as about any of 1, 2, or 3) amino acid substitutions, and (b) a single copy of a second antigen binding portion comprising a $V_H$ and a $V_L$, wherein the $V_H$ and $V_L$ together form an antigen-binding site that specifically binds a second epitope (e.g., PD-1, PD-L1), wherein each copy of the first antigen binding portion is fused to the second antigen binding portion.

In some embodiments, there is provided an anti-TIGIT MABP comprising: (a) a plurality (such as 2, 3, 4, 5, 6, 7, 8, or more) of identical or different anti-TIGIT sdAb moieties comprising a CDR1 comprising the amino acid sequence of any one of SEQ ID NOs: 36-42, 54, 56-59, 63, 65-67, 69-70, or a variant thereof comprising up to about 3 (such as about any of 1, 2, or 3) amino acid substitutions; a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210, or a variant thereof comprising up to about 3 (such as about any of 1, 2, or 3) amino acid substitutions, and (b) a plurality (such as 2, 3, 4, 5, 6, or more) of a second antigen binding portion comprising a $V_H$ and a $V_L$, wherein the $V_H$ and $V_L$ together form an antigen-binding site that specifically binds a second epitope (e.g., PD-1, PD-L1), and, wherein the anti-TIGIT sdAb moieties are fused to each other, and/or to the second antigen binding portion. In some embodiments, the anti-TIGIT sdAb moiety comprises a CDR1 comprising the amino acid sequence of any one of SEQ ID NOs: 36-42, 54, 56-59, 63, 65-67, 69-70; a CDR2 comprising the amino acid sequence of any one of SEQ ID NOs: 106-112, 124, 126-129, 133, 135-137, 139-140; and a CDR3 comprising the amino acid sequence of any one of SEQ ID NOs: 176-182, 194, 196-199, 203, 205-207, 209-210. In some embodiments, the anti-TIGIT sdAb comprises a $V_H H$ domain comprising the amino acid sequence of any one of SEQ ID NOs: 253-259, 271, 273-276, 280, 282-284, 286-287. In some embodiments, one or more of the anti-TIGIT sdAb moiety is each further fused to another identical or different anti-TIGIT sdAb moiety. In some embodiments, the second antigen binding portion comprises an anti-PD-1 full-length antibody (or Fab, scFv). In some embodiments, the anti-PD-L1 full-length antibody (or Fab, scFv) comprises a $V_H$ comprising the amino acid sequence of SEQ ID NO: 339, and a $V_L$ comprising the amino acid sequence of SEQ ID NO: 340. In some embodiments, the anti-PD-L1 full-length antibody comprises a heavy chain comprising the amino acid sequence of SEQ ID NO: 323 or 327, and a light chain comprising the amino acid sequence of SEQ ID NO: 328. In some embodiments, the anti-PD-L1 full-length antibody comprises a heavy chain comprising the amino acid sequence of SEQ ID NO: 329, and a light chain comprising the amino acid sequence of SEQ ID NO: 330. In some embodiments, the anti-TIGIT sdAb moieties are fused to each other via a peptide linker. In some embodiments, the first antigen binding portion is fused to the second antigen binding portion via a peptide linker. In some embodiments, the peptide linker comprises the amino acid sequence of any one of SEQ ID NOs: 324 and 370-378. In some embodiments, the second antigen binding fragment comprises an Fc region, such as an IgG1 Fc, effectorless IgG1 Fc, IgG2 Fc, or IgG4 Fc. In some embodiments, the second antigen binding fragment comprises an Fc region comprising the amino acid sequence of any one of SEQ ID NOs: 355, 356, and 389. In some embodiments, the $K_d$ of the binding between the anti-TIGIT sdAb moiety and TIGIT is about $10^{-5}$ M to about $10^{-12}$ M (such as about $10^{-7}$ M to about $10^{-12}$ M, or about $10^{-8}$ M to about $10^{-12}$ M). In some embodiments, the anti-TIGIT sdAb moiety is camelid, chimeric, human, partially humanized, or fully humanized.

In some embodiments, there is provided an anti-TIGIT MABP (e.g., BABP) comprising: (a) a single copy of a first antigen binding portion comprising an anti-TIGIT sdAb moiety comprising a CDR1 comprising the amino acid sequence of any one of SEQ ID NOs: 36-42, 54, 56-59, 63, 65-67, 69-70, or a variant thereof comprising up to about 3 (such as about any of 1, 2, or 3) amino acid substitutions; a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210, or a variant thereof comprising up to about 3 (such as about any of 1, 2, or 3) amino acid substitutions, and (b) two copies of a second antigen binding portion each comprising a $V_H$ and a $V_L$, wherein the $V_H$ and $V_L$ together form an antigen-binding site that specifically binds a second epitope (e.g., PD-1, PD-L1), wherein the first antigen binding portion is fused to one of the two copies of the second antigen binding portion.

In some embodiments, there is provided an anti-TIGIT MABP (e.g. BABP) comprising: (a) two copies of a first antigen binding portion each comprising an anti-TIGIT sdAb moiety comprising a CDR1 comprising the amino acid sequence of any one of SEQ ID NOs: 36-42, 54, 56-59, 63, 65-67, 69-70, or a variant thereof comprising up to about 3 (such as about any of 1, 2, or 3) amino acid substitutions; a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210, or a variant thereof comprising up to about 3 (such as about any of 1, 2, or 3) amino acid substitutions, (b) two copies of a second antigen binding portion each comprising a $V_H$ and a $V_L$, wherein the $V_H$ and $V_L$ together form an antigen-binding site that specifically binds a second epitope (e.g., PD-1, PD-L1), wherein one copy of the first antigen binding portion is fused to each copy of the second antigen binding portion (exemplified as FIGS. 17-20, 23 and 24). In some embodiments, one or more of the anti-TIGIT sdAbs is each further fused to another identical or different anti-TIGIT sdAb moiety. In some embodiments, the anti-TIGIT sdAb moiety comprises a CDR1 comprising the amino acid sequence of any one of SEQ ID NOs: 36-42, 54, 56-59, 63, 65-67, 69-70; a CDR2 comprising the amino acid sequence of any one of SEQ ID NOs: 106-112, 124, 126-129, 133, 135-137, 139-140; and a CDR3 comprising the amino acid sequence of any one of SEQ ID NOs: 176-182, 194, 196-199, 203, 205-207, 209-210. In some embodiments, the anti-TIGIT sdAb moiety comprises a $V_HH$ domain comprising the amino acid sequence of any one of SEQ ID NO: 253-259, 271, 273-276, 280, 282-284, 286-287.

a) Fusion Polypeptides

The first antigen binding portion comprising an anti-TIGIT sdAb moiety described herein and the second antigen binding portion comprising a $V_H$ and a $V_L$ of the anti-TIGIT MABP (or BABP) are fused (i.e., covalently linked) to each other. Thus, the anti-TIGIT MABPs (or BABPs) of the present application comprise one or more fusion polypeptides. Each fusion polypeptide may comprise the first antigen binding portion comprising an anti-TIGIT sdAb described herein, and a polypeptide from the second antigen binding portion.

The first antigen binding portion comprising an anti-TIGIT sdAb moiety described herein and the second antigen binding portion comprising a $V_H$ and a $V_L$ may be linked directly by a single chemical bond (such as peptide bond) or via a peptide linker. The first antigen binding portion comprising an anti-TIGIT sdAb moiety may be fused at either the N-terminus or the C-terminus of any one (including each) polypeptide of the second antigen binding portion, or may be fused at an internal position of any one (including each) polypeptide of the second antigen binding portion, such as at the N-terminus of the Fc region in the heavy chain of the second antigen binding portion. The fusion polypeptides may be obtained either recombinantly or chemically. In some embodiments, the C-terminus of the first antigen binding portion comprising an anti-TIGIT sdAb moiety is fused to the N-terminus of any (including each) polypeptide of the second antigen binding portion via a chemical bond (such as peptide bond) or a peptide linker. In some embodiments, the N-terminus of the first antigen binding portion comprising an anti-TIGIT sdAb moiety is fused to the C-terminus of any (including each) polypeptide of the second antigen binding portion via a chemical bond (such as peptide bond) or a peptide linker. In some embodiments, the first antigen binding portion comprising an anti-TIGIT sdAb moiety is fused to the second antigen binding portion via a chemical bond that is not a peptide bond involving the main chain chemical groups of amino acids.

In some embodiments, the second antigen binding portion comprises a single-chain antibody fragment comprising the $V_H$ and $V_L$. In some embodiments, the second antigen binding portion comprises an scFv. In some embodiments, the anti-TIGIT MABP (or BABP) comprises a fusion polypeptide comprising in the N-terminus to C-terminus direction: the first antigen binding portion comprising the anti-TIGIT sdAb moiety described herein, an optional peptide linker, the $V_H$ domain and the $V_L$ domain. In some embodiments, the anti-TIGIT MABP (or BABP) comprises a fusion polypeptide comprising in the N-terminus to C-terminus direction: the first antigen binding portion comprising the anti-TIGIT sdAb moiety described herein, an optional peptide linker, the $V_L$ domain and the $V_H$ domain. In some embodiments, the anti-TIGIT MABP (or BABP) comprises a fusion polypeptide comprising in the N-terminus to C-terminus direction: the $V_H$ domain, the $V_L$ domain, an optional peptide linker, and the first antigen binding portion comprising the anti-TIGIT sdAb moiety described herein. In some embodiments, anti-TIGIT MABP (or BABP) comprises a fusion polypeptide comprising in the N-terminus to C-terminus direction: the $V_L$ domain, the $V_H$ domain, an optional peptide linker, and the first antigen binding portion comprising the anti-TIGIT sdAb moiety described herein.

In some embodiments, the second antigen binding portion comprises a heavy chain comprising the $V_H$ domain, and a light chain comprising the $V_L$ domain. In some embodiments, the heavy chain further comprises one or more heavy chain constant domains, such as $C_H1$, $C_H2$, $C_H3$, and $C_H4$, and/or an antibody hinge region (HR). In some embodiments, the light chain further comprises a light chain constant domain ($C_L$), such as the lambda $C_L$ domain or kappa $C_L$ domain. In some embodiments, the N-terminus of the first antigen binding portion comprising the anti-TIGIT sdAb moiety described herein is fused to the C-terminus of the heavy chain. In some embodiments, the C-terminus of the first antigen binding portion comprising the anti-TIGIT sdAb moiety described herein is fused to the N-terminus of the heavy chain. In some embodiments, the N-terminus of the first antigen binding portion comprising the anti-TIGIT sdAb moiety described herein is fused to the C-terminus of the light chain. In some embodiments, the C-terminus of the first antigen binding portion comprising the anti-TIGIT sdAb moiety described herein is fused to the N-terminus of the light chain. In some embodiments, the anti-TIGIT MABP (or BABP) comprises a first polypeptide comprising from the N-terminus to the C-terminus: the heavy chain, an optional peptide linker, and the first antigen binding portion comprising the anti-TIGIT sdAb moiety described herein; and a second polypeptide comprising the light chain. In some embodiments, the anti-TIGIT MABP (or BABP) comprises a first polypeptide comprising from the N-terminus to the C-terminus: the first antigen binding portion comprising the anti-TIGIT sdAb moiety described herein, an optional peptide linker, and the heavy chain; and a second polypeptide comprising the light chain. In some embodiments, the anti-TIGIT MABP (or BABP) comprises a first polypeptide comprising from the N-terminus to the C-terminus: the light chain, an optional peptide linker, and the first antigen binding portion comprising the anti-TIGIT sdAb moiety described herein; and a second polypeptide comprising the heavy chain. In some embodiments, the anti-TIGIT MABP (or BABP) comprises a first polypeptide comprising from the N-terminus to the C-terminus: the first antigen binding portion comprising the anti-TIGIT sdAb moiety described herein, an optional peptide linker, and the light chain; and a second polypeptide comprising the heavy chain. In some embodiments, the anti-TIGIT MABP (or BABP) comprises two identical first polypeptides and two identical second polypeptides described herein.

In some embodiments, the second antigen binding portion comprises a full-length antibody consisting of two heavy chains and two light chains (e.g., anti-PD-1 or anti-PD-L1 full-length antibody). In some embodiments, the full-length antibody is a full-length monoclonal antibody consisting of two identical heavy chains and two identical light chains. In some embodiments, the anti-TIGIT MABP (or BABP) comprises two identical first polypeptides each comprising from the N-terminus to the C-terminus: the heavy chain, an optional peptide linker, and the first antigen binding portion comprising the anti-TIGIT sdAb moiety described herein; and two identical second polypeptides each comprising the light chain (see, e.g., FIG. 18). In some embodiments, the anti-TIGIT MABP (or BABP) comprises two identical first polypeptides each comprising from the N-terminus to the C-terminus: the first antigen binding portion comprising the anti-TIGIT sdAb moiety described herein, an optional peptide linker, and the heavy chain; and two identical second polypeptides each comprising the light chain (see, e.g., FIG. 17). In some embodiments, the anti-TIGIT MABP (or BABP) comprises two identical first polypeptides each comprising from the N-terminus to the C-terminus: the light chain, an optional peptide linker, and the first antigen binding portion comprising the anti-TIGIT sdAb moiety described herein; and two identical second polypeptides each comprising the heavy chain (see, e.g., FIG. 20). In some embodiments, the anti-TIGIT MABP (or BABP) comprises two identical first polypeptides each comprising from the N-terminus to the C-terminus: the first antigen binding portion comprising the anti-TIGIT sdAb moiety described herein, an optional peptide linker, and the light chain; and two identical second polypeptides comprising the heavy chain (see, e.g., FIG. 19).

In some embodiments, the anti-TIGIT MABP (or BABP) comprises: (a) a full-length antibody consisting of a first and a second heavy chains and a first and a second light chains, wherein the full-length antibody specifically recognizes a first epitope (e.g., PD-1, PD-L1); (b) a first anti-TIGIT sdAb moiety described herein that specifically recognizes a second epitope; (c) a second anti-TIGIT sdAb moiety described herein that specifically recognizes a third epitope; (d) a third anti-TIGIT sdAb moiety described herein that specifically recognizes a fourth epitope; and (e) a fourth anti-TIGIT sdAb moiety described herein that specifically recognizes a fifth epitope; wherein the C-terminus of the first anti-TIGIT sdAb moiety is fused to the N-terminus of the first light chain, wherein the C-terminus of the second anti-TIGIT sdAb moiety is fused to the N-terminus of the second light chain, wherein the C-terminus of the third anti-TIGIT sdAb moiety is fused to the N-terminus of the first heavy chain, and wherein the C-terminus of the fourth anti-TIGIT sdAb moiety is fused to the N-terminus of the second heavy chain. In some embodiments, the four anti-TIGIT sdAb moieties are different. In some embodiments, the four anti-TIGIT sdAb moieties are identical. In some embodiments, the anti-TIGIT MABP (or BABP) comprises two identical first polypeptides each comprising from the N-terminus to the C-terminus: the third or the fourth anti-TIGIT sdAb moiety, an optional peptide linker, and the heavy chain; and two identical second polypeptides each comprising the first or the second anti-TIGIT sdAb moiety, an optional peptide linker, and the light chain. See, for example, FIG. 21.

In some embodiments, the anti-TIGIT MABP (or BABP) comprises: (a) a full-length antibody consisting of two heavy chains and two light chains, wherein the full-length antibody specifically recognizes a first epitope (e.g., PD-1, PD-L1); (b) a first anti-TIGIT sdAb moiety described herein that specifically recognizes a second epitope; (c) a second anti-TIGIT sdAb moiety described herein that specifically recognizes a third epitope; (d) a third anti-TIGIT sdAb moiety described herein that specifically recognizes a fourth epitope; and (e) a fourth anti-TIGIT sdAb moiety described herein that specifically recognizes a fifth epitope; wherein the C-terminus of the first anti-TIGIT sdAb moiety is fused to the N-terminus of the second anti-TIGIT sdAb moiety, and the C-terminus of the second anti-TIGIT sdAb moiety is fused to the N-terminus of one heavy chain, and wherein the C-terminus of the third anti-TIGIT sdAb moiety is fused to the N-terminus of the fourth anti-TIGIT sdAb moiety, and the C-terminus of the fourth anti-TIGIT sdAb moiety is fused to the N-terminus of the other heavy chain. In some embodiments, the four anti-TIGIT sdAb moieties are different. In some embodiments, the four anti-TIGIT sdAb moieties are identical. In some embodiments, the anti-TIGIT MABP (or BABP) comprises two identical first polypeptides each comprising from the N-terminus to the C-terminus: the first or the third anti-TIGIT sdAb moiety, an optional peptide linker, the second or the fourth anti-TIGIT sdAb moiety, an optional peptide linker, and the heavy chain; and two identical second polypeptides each comprising the light chain. See, for example, FIG. 22.

In some embodiments, the anti-TIGIT MABP (or BABP) comprises: (a) a full-length antibody consisting of two heavy chains and two light chains, wherein the full-length antibody specifically recognizes a first epitope (e.g., PD-1, PD-L1); (b) a first anti-TIGIT sdAb moiety described herein that specifically recognizes a second epitope; and (c) a second anti-TIGIT sdAb moiety described herein that specifically recognizes a third epitope, wherein the N-terminus of the first or the second anti-TIGIT sdAb moiety is fused to the C-terminus of the $C_H1$ region of the heavy chain, and the C-terminus of the first or the second anti-TIGIT sdAb moiety is fused to the N-terminus of the $C_H2$ region of the heavy chain. In some embodiments, the two anti-TIGIT sdAb moieties are identical. In some embodiments, the two anti-TIGIT sdAb moieties are different. In some embodiments, the anti-TIGIT MABP (or BABP) comprises two identical first polypeptides each comprising from the N-terminus to the C-terminus: $V_H$—$C_H1$-an optional peptide linker-anti-TIGIT sdAb moiety-$C_H2$-$C_H3$; and two identical second polypeptides each comprising the light chain. See, for example, FIG. 23.

In some embodiments, the anti-TIGIT MABP (or BABP) comprises: (a) a first scFv that specifically recognizes a first epitope (e.g., PD-1, PD-L1); (b) a second scFv that specifically recognizes a second epitope (e.g., PD-1, PD-L1); (c) an Fc region; (d) a first anti-TIGIT sdAb moiety described herein that specifically recognizes a third epitope; and (d) a second anti-TIGIT sdAb moiety described herein that specifically recognizes a fourth epitope, wherein the N-terminus of each anti-TIGIT sdAb moiety is fused to the C-terminus of an scFv and the C-terminus of the anti-TIGIT sdAb moiety is fused to the N-terminus of the Fc region. In some embodiments, the two anti-TIGIT sdAb moieties are identical. In some embodiments, the two anti-TIGIT sdAb moieties are different. In some embodiments, the two scFvs are identical. In some embodiments, the two scFvs are different. In some embodiments, the anti-TIGIT MABP (or BABP) comprises two identical polypeptides each comprising from the N-terminus to the C-terminus: scFv-an optional peptide linker-anti-TIGIT sdAb moiety-$CH_2$—$CH_3$, such as $V_H$—$V_L$-an optional peptide linker-anti-TIGIT sdAb moiety-$CH_2$—$CH_3$, or $V_L$—$V_H$-an optional peptide linker-anti-TIGIT sdAb moiety-$CH_2$—$CH_3$. See, for example, FIG. 24.

In some embodiments, the anti-TIGIT MABP (or BABP) comprises: (a) a first Fab that specifically recognizes a first epitope (e.g., PD-1, PD-L1); (b) a second Fab that specifically recognizes a second epitope (e.g., PD-1, PD-L1); (c) an Fc region; (d) a first Fab-like domain comprising a first anti-TIGIT sdAb moiety described herein that specifically recognizes a third epitope and a second anti-TIGIT sdAb moiety described herein that specifically recognizes a fourth epitope; (e) a second Fab-like domain comprising a third anti-TIGIT sdAb moiety described herein that specifically recognizes a fifth epitope and a fourth anti-TIGIT sdAb moiety described herein that specifically recognizes a sixth epitope, wherein the N-termini of each Fab-like domain are fused to the C-termini of a Fab and one of the two C-termini of the Fab-like domain is fused to the N-terminus of the Fc region. In some embodiments, the four anti-TIGIT sdAb moieties are identical. In some embodiments, the four anti-TIGIT sdAb moieties are different. In some embodiments, the two Fabs are identical. In some embodiments, the two Fabs are different. In some embodiments, the anti-TIGIT MABP (or BABP) comprises two identical first polypeptides each comprising from the N-terminus to the C-terminus: $V_H$—$C_H1$-an optional peptide linker-anti-TIGIT sdAb moiety-$C_H1$-$C_H2$-$C_H3$; and two identical second polypeptides each comprising from the N-terminus to the C-terminus: $V_L$—$C_L$-an optional peptide linker-anti-TIGIT sdAb moiety-$C_L$. See, for example, FIG. 25.

In some embodiments, the anti-TIGIT MABP (or BABP) comprises: (a) a first scFv that specifically recognizes a first epitope (e.g., PD-1, PD-L1); (b) a second scFv that specifically recognizes a second epitope (e.g., PD-1, PD-L1); (c) an Fc region; (d) a first Fab-like domain comprising a first anti-TIGIT sdAb moiety described herein that specifically recognizes a third epitope and a second anti-TIGIT sdAb moiety described herein that specifically recognizes a fourth epitope; (e) a second Fab-like domain comprising a third anti-TIGIT sdAb moiety described herein that specifically recognizes a fifth epitope and a fourth anti-TIGIT sdAb moiety described herein that specifically recognizes a sixth epitope, wherein one of the two N-termini of each Fab-like domain is fused to the C-terminus of an scFv and one of the two C-termini of the Fab-like domain is fused to the N-terminus of the Fc region. In some embodiments, the four anti-TIGIT sdAb moieties are identical. In some embodiments, the four anti-TIGIT sdAb moieties are different. In some embodiments, the two scFvs are identical. In some embodiments, the two scFvs are different. In some embodiments, the anti-TIGIT MABP (or BABP) comprises two identical first polypeptides each comprising from the N-terminus to the C-terminus: scFv-an optional peptide linker-anti-TIGIT sdAb moiety-$C_H1$-$C_H2$-$C_H3$; and two identical second polypeptides each comprising from the N-terminus to the C-terminus: anti-TIGIT sdAb moiety-$C_L$. In some embodiments, the scFv comprises from the N-terminus to the C-terminus: $V_H$—$V_L$ or $V_L$—$V_H$. See, for example, FIG. 26.

The anti-TIGIT MABPs (or BABPs) described herein may comprise one or more peptide linkers situated between the first antigen binding portion and the second antigen binding portion. In some embodiments, the peptide linker between the heavy chain polypeptide of the second antigen binding portion and the first antigen binding portion is the same as the peptide linker between the light chain polypeptide of the second antigen binding portion and the first antigen binding portion. In some embodiments, the peptide linker between the heavy chain polypeptide of the second antigen binding portion and the first antigen binding portion is different from the peptide linker between the light chain polypeptide of the second antigen binding portion and the first antigen binding portion. In some embodiments, the first antigen binding portion and the second antigen binding portion are directly fused to each other without a peptide linker disposed therebetween. The peptide linker between the two or more anti-TIGIT sdAb moieties may be the same as or different from that between the anti-TIGIT sdAb moiety and the second antigen binding portion. Any of the peptide linkers described above in the "Peptide linkers" section can be employed in any of the anti-TIGIT MABPs (or BABPs) described herein.

b) Second Antigen Binding Portion Comprising $V_H$ and $V_L$

The anti-TIGIT MABPs (e.g., BABPs) comprise at least one second antigen binding portion comprising a $V_H$ and a $V_L$. Such antigen binding portion can be a full-length conventional antibody consisting of two heavy chains and two light chains, or an antigen binding fragment derived therefrom.

In some embodiments, the second antigen binding portion is an antigen binding fragment comprising a heavy chain comprising the $V_H$ domain and a light chain comprising the $V_L$ domain. Exemplary antigen binding fragments contemplated herein include, but are not limited to, Fab, Fab', F(ab')$_2$, and Fv fragments; diabodies; linear antibodies; single-chain antibody molecules (such as scFv); and multi-specific antibodies formed from antibody fragments.

In some embodiments, the second antigen binding portion comprises an Fc region, such as a human Fc region. In some embodiments, the Fc region is derived from an IgG molecule, such as any one of the IgG1, IgG2, IgG3, or IgG4 subclass. In some embodiments, the Fc region is capable of mediating an antibody effector function, such as ADCC and/or CDC. For example, antibodies of subclass IgG1, IgG2, and IgG3 with wildtype Fc sequences usually show complement activation including C1q and C3 binding, whereas IgG4 does not activate the complement system and does not bind C1q and/or C3. In some embodiments, the Fc region comprises a modification that reduces binding affinity of the Fc region to an Fc receptor. In some embodiments, the Fc region is an IgG1 Fc. In some embodiments, the IgG1 Fc comprises one or mutations in positions 233-236, such as L234A and/or L235A. In some embodiments, the Fc region is an effectorless IgG1 Fc. In some embodiments, the Fc region is an IgG4 Fc. In some embodiments, the IgG4 Fc comprises a mutation in positions 327, 330 and/or 331. See, for example, Armour K L et al., *Eur J. Immunol.* 1999; 29: 2613; and Shields R L et al., *J. Biol. Chem.* 2001; 276: 6591. In some embodiments, the Fc region comprises a P329G mutation. In some embodiments, the Fc region comprises an amino acid sequence of any one of SEQ ID NOs: 355, 356 and 389.

In some embodiments, the Fc region comprises a modification that promotes heterodimerization of two non-identical heavy chains. Such modified Fc regions may be of particular interest for anti-TIGIT MABPs (e.g., BABPs) described herein having an asymmetric design. In some embodiments, said modification is a knob-into-hole modification, comprising a knob modification in one of the heavy chains or heavy chain fusion polypeptides and a hole modification in the other one of the two heavy chains or heavy chain fusion polypeptides. In one embodiment, the Fc region comprises a modification within the interface between the two heavy chains in the CH3 domain, wherein i) in the CH3 domain of one heavy chain, an amino acid residue is replaced with an amino acid residue having a larger side chain volume, thereby generating a protuberance ("knob") within the interface in the CH3 domain of one heavy chain which is positionable in a cavity ("hole") within the interface in the CH3 domain of the other heavy chain, and ii) in the CH3 domain of the other heavy chain, an amino acid residue is replaced with an amino acid residue having a smaller side chain volume, thereby generating a cavity ("hole") within the interface in the second CH3 domain within which a protuberance ("knob") within the interface in the first CH3 domain is positionable. Examples of knob-into-hole modifications have been described, for example, in US 2011/0287009, US2007/0178552, WO 96/027011, WO 98/050431, and Zhu et al., 1997, *Protein Science* 6:781-788. Other modifications to the Fc region that promote heterodimerization are also contemplated herein. For example, electrostatic steering effects can be engineered into the Fc region to provide Fc-heterodimeric molecules (see, e.g., U.S. Pat. No. 4,676,980, and Brennan et al., *Science*, 229: 81 (1985)).

In some embodiments, the Fc region comprises a modification that inhibits Fab arm exchange. For example, the S228P mutation in IgG4 Fc prevents Fab arm exchange.

In some embodiments, the second antigen binding portion comprises a kappa light chain constant region. In some embodiments, the second antigen binding portion comprises a lambda light chain constant region. In some embodiments, the second antigen binding portion comprises a heavy chain constant region.

In some embodiments, the second antigen binding portion is a full-length antibody consisting of two heavy chains and two light chains. In some embodiments, the second antigen binding portion comprises a monoclonal antibody consisting of two heavy chains and two light chains (also referred herein as "4-chain antibody"). In some embodiments, the second antigen binding portion comprises a multispecific (such as bispecific) full-length antibody consisting of two heavy chains and two light chains. In some embodiments, the second antigen binding portion comprises a full-length antibody of human IgG1 subclass, of effectorless hIgG1 subclass, or of human IgG1 subclass with the mutations L234A and L235A. In some embodiments, the second antigen binding portion comprises a full-length antibody of human IgG2 subclass. In some embodiments, the second antigen binding portion comprises a full-length antibody of human IgG3 subclass. In some embodiments, the second antigen binding portion comprises a full-length antibody of human IgG4 subclass or, of human IgG4 subclass with the additional mutation S228P. In some embodiments, the Fc region of the full-length antibody comprises an amino acid sequence of any one of SEQ ID NOs: 355, 356 and 389.

Any full-length 4-chain antibody known in the art or antigen binding fragments derived therefrom can be used as the second antigen binding portion of the anti-TIGIT MABP (e.g. BABP). Antibodies or antibody fragments with proven clinical efficacy, safety, and pharmacokinetics profile are of particular interest. In some embodiments, the antibody or antibody fragment known in the art is further engineered, such as humanized or mutagenized to select for a variant with a suitable affinity, prior to fusion with the first antigen binding portion to provide the anti-TIGIT MABP (e.g. BABP). In some embodiments, the second antigen binding portion comprises the $V_H$ and $V_L$ domains of a monoclonal antibody or antibody fragment known in the art, and modified heavy chain constant region and/or light chain constant region. In some embodiments, the second antigen binding portion comprises the monoclonal antibody known in the art and a modified Fc region, such as an IgG4 Fc with an S228P mutation, or an effectorless IgG1 Fc. In some embodiments, the second antigen binding portion comprises a human, humanized, or chimeric full-length antibody or antibody fragments.

In some embodiments, the second antigen binding portion is an anti-PD-1 antibody or antigen binding fragment thereof (e.g., Fab or scFv). In some embodiments, the anti-PD-1 antibody is pembrolizumab (e.g., Keytruda®), PD1-BM-min, or nivolumab (e.g., Opdivo®). In some embodiments, the anti-PD-1 antibody or antigen binding fragment thereof (e.g., Fab or scFv) comprises a $V_H$ comprising HC-CDR1, HC-CDR2, and HC-CDR3 of the amino acid sequence of SEQ ID NO: 385, and a $V_L$ comprising LC-CDR1, LC-CDR2, and LC-CDR3 of the amino acid sequence of SEQ ID NO: 386. In some embodiments, the anti-PD-1 antibody or antigen binding fragment thereof (e.g., Fab or scFv) comprises a $V_H$ comprising the amino acid sequence of SEQ ID NO: 385, and a $V_L$ comprising the amino acid sequence of SEQ ID NO: 386. In some embodiments, the anti-PD-1 antibody comprises a heavy chain comprising the amino acid sequence of SEQ ID NO: 325, and a light chain comprising the amino acid sequence of SEQ ID NO: 326. In some embodiments, the anti-PD-1 antibody or antigen binding fragment thereof (e.g., Fab or scFv) comprises a $V_H$ comprising HC-CDR1, HC-CDR2, and HC-CDR3 of the amino acid sequence of SEQ ID NO: 387, and a $V_L$ comprising LC-CDR1, LC-CDR2, and LC-CDR3 of the amino acid sequence of SEQ ID NO: 388. In some embodiments, the anti-PD-1 antibody or antigen binding fragment thereof (e.g., Fab or scFv) comprises a $V_H$ comprising the amino acid sequence of SEQ ID NO: 387, and a $V_L$ comprising the amino acid sequence of SEQ ID NO: 388. In some embodiments, the anti-PD-1 antibody or antigen binding fragment thereof (e.g., Fab or scFv) comprises a $V_H$ comprising HC-CDR1, HC-CDR2, and HC-CDR3 of the amino acid sequence of SEQ ID NO: 406, and a $V_L$ comprising LC-CDR1, LC-CDR2, and LC-CDR3 of the amino acid sequence of SEQ ID NO: 407. In some embodiments, the anti-PD-1 antibody or antigen binding fragment thereof (e.g., Fab or scFv) comprises a $V_H$ comprising the amino acid sequence of SEQ ID NO: 406, and a $V_L$ comprising the amino acid sequence of SEQ ID NO: 407. In some embodiments, the second antigen binding portion is an anti-PD-L1 antibody or antigen binding fragment thereof (e.g., Fab or scFv). In some embodiments, the anti-PD-L1 antibody is atezolizumab (e.g., Tecentriq®), Durvalumab (e.g., MEDI4736, IMFINZI™), avelumab (e.g., Bavencio®), or humanized 53C1 (h53C1). In some embodiments, the anti-PD-L1 antibody or antigen binding fragment thereof (e.g., Fab or scFv) comprises a $V_H$ comprising HC-CDR1, HC-CDR2, and HC-CDR3 of the amino acid sequence of SEQ ID NO: 381, and a $V_L$ comprising LC-CDR1, LC-CDR2, and LC-CDR3 of the amino acid sequence of SEQ ID NO: 382. In some embodiments, the anti-PD-L1 antibody or antigen binding fragment thereof (e.g., Fab or scFv) comprises a $V_H$ comprising the amino acid sequence of SEQ ID NO: 381, and a $V_L$ comprising the amino acid sequence of SEQ ID NO: 382. In some embodiments, the anti-PD-L1 antibody comprises a heavy chain comprising the amino acid sequence of SEQ ID NO: 331, and a light chain comprising the amino acid sequence of SEQ ID NO: 332. In some embodiments, the anti-PD-L1 antibody comprises a heavy chain comprising the amino acid sequence of SEQ ID NO: 333, and a light chain comprising the amino acid sequence of SEQ ID NO: 334. In some embodiments, the anti-PD-L1 antibody or antigen binding fragment thereof (e.g., Fab or scFv) comprises a $V_H$ comprising HC-CDR1, HC-CDR2, and HC-CDR3 of the amino acid sequence of SEQ ID NO: 379, and a $V_L$ comprising LC-CDR1, LC-CDR2, and LC-CDR3 of the amino acid sequence of SEQ ID NO: 380. In some embodiments, the anti-PD-L1 antibody or antigen binding fragment thereof (e.g., Fab or scFv) comprises a $V_H$ comprising the amino acid sequence of SEQ ID NO: 379, and a $V_L$ comprising the amino acid sequence of SEQ ID NO: 380. In some embodiments, the anti-PD-L1 antibody or antigen binding fragment thereof (e.g., Fab or scFv) comprises a $V_H$ comprising HC-CDR1, HC-CDR2, and HC-CDR3 of the amino acid sequence of SEQ ID NO: 383, and a $V_L$ comprising LC-CDR1, LC-CDR2, and LC-CDR3 of the amino acid sequence of SEQ ID NO: 384. In some embodiments, the anti-PD-L1 antibody or antigen binding fragment thereof (e.g., Fab or scFv) comprises a $V_H$ comprising the amino acid sequence of SEQ ID NO: 383, and a $V_L$ comprising the amino acid sequence of SEQ ID NO: 384. In some embodiments, the anti-PD-L1 antibody or antigen binding fragment thereof (e.g., Fab or scFv) comprises 1) a $V_H$ comprising an HC-CDR1 comprising the amino acid sequence of SEQ ID NO: 349, an HC-CDR2 comprising the amino acid sequence of SEQ ID NO: 350, and an HC-CDR3 comprising the amino acid sequence of SEQ ID NO: 351, and 2) a $V_L$ comprising an LC-CDR1 comprising the amino acid sequence of SEQ ID NO: 352, an LC-CDR2 comprising the amino acid sequence of SEQ ID NO: 353, and an LC-CDR3 comprising the amino acid sequence of SEQ ID NO: 354. In some embodiments, the anti-PD-L1 antibody or antigen binding fragment thereof (e.g., Fab or scFv) comprises a $V_H$ comprising the amino acid sequence of SEQ ID NO: 339, and a $V_L$ comprising the amino acid sequence of SEQ ID NO: 340. In some embodiments, the anti-PD-L1 antibody comprises a heavy chain comprising the amino acid sequence of SEQ ID NO: 323 or 327, and a light chain comprising the amino acid sequence of SEQ ID NO: 328. In some embodiments, the anti-PD-L1 antibody comprises a heavy chain comprising the amino acid sequence of SEQ ID NO: 329, and a light chain comprising the amino acid sequence of SEQ ID NO: 330.

c) Exemplary Anti-TIGIT MABPs and BABPs

In some embodiments, the anti-TIGIT MABP (e.g., BABP) comprises (a) a first antigen binding portion comprising an sdAb moiety specifically recognizing TIGIT described herein, and (b) a second antigen binding portion comprising a $V_H$ and a $V_L$, wherein the $V_H$ and $V_L$ together form an antigen-binding site that specifically binds PD-1, wherein the first antigen binding portion and the second antigen binding portion are fused to each other (herein after referred to as "PD-1×TIGIT BABP" or "TIGIT×PD-1 BABP"). In some embodiments, the anti-TIGIT MABP (e.g., BABP) comprises (a) a first antigen binding portion comprising an sdAb moiety specifically recognizing TIGIT described herein, and (b) a second antigen binding portion comprising a $V_H$ and a $V_L$, wherein the $V_H$ and $V_L$ together form an antigen-binding site that specifically binds PD-L1, wherein the first antigen binding portion and the second antigen binding portion are fused to each other (herein after referred to as "PD-L1×TIGIT BABP" or "TIGIT×PD-L1 BABP").

In some embodiments, there is provided an anti-TIGIT MABP (e.g., BABP) comprising: (a) a first antigen binding portion comprising an sdAb moiety specifically recognizing TIGIT comprising a CDR1 comprising the amino acid sequence of any one of SEQ ID NOs: 36-42, 54, 56-59, 63, 65-67, 69-70, or a variant thereof comprising up to about 3 (such as about any of 1, 2, or 3) amino acid substitutions; a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210, or a variant thereof comprising up to about 3 (such as about any of 1, 2, or 3) amino acid substitutions, and (b) a second antigen binding portion comprising a full-length antibody (such as pembrolizumab, PD1-BM-min, or nivolumab) consisting of two heavy chains and two light chains, wherein the full-length antibody specifically binds PD-1; and wherein the first antigen binding portion and the second antigen binding portion are fused to each other. In some embodiments, there is provided an anti-TIGIT MABP (e.g., BABP) comprising: (a) a first antigen binding portion comprising an sdAb moiety specifically recognizing TIGIT comprising a CDR1 comprising the amino acid sequence of any one of SEQ ID NOs: 36-42, 54, 56-59, 63, 65-67, 69-70, or a variant thereof comprising up to about 3 (such as about any of 1, 2, or 3) amino acid substitutions; a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210, or a variant thereof comprising up to about 3 (such as about any of 1, 2, or 3) amino acid substitutions, and (b) a second antigen binding portion comprising a full-length antibody consisting of two heavy chains and two light chains, wherein the full-length antibody specifically binds PD-1; wherein the full-length antibody comprises a $V_H$ comprising HC-CDR1, HC-CDR2, and HC-CDR3 of the amino acid sequence of SEQ ID NO: 385, and a $V_L$ comprising LC-CDR1, LC-CDR2, and LC-CDR3 of the amino acid sequence of SEQ ID NO: 386; and wherein the first antigen binding portion and the second antigen binding portion are fused to each other. In some embodiments, the anti-PD-1 antibody comprises a $V_H$ comprising the amino acid sequence of SEQ ID NO: 385, and a $V_L$ comprising the amino acid sequence of SEQ ID NO: 386. In some embodiments, the anti-PD-1 antibody comprises a heavy chain comprising the amino acid sequence of SEQ ID NO: 325, and a light chain comprising the amino acid sequence of SEQ ID NO: 326. In some embodiments, there is provided an anti-TIGIT MABP (e.g., BABP) comprising: (a) a first antigen binding portion comprising an sdAb moiety specifically recognizing TIGIT comprising a CDR1 comprising the amino acid sequence of any one of SEQ ID NOs: 36-42, 54, 56-59, 63, 65-67, 69-70, or a variant thereof comprising up to about 3 (such as about any of 1, 2, or 3)

amino acid substitutions; a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210, or a variant thereof comprising up to about 3 (such as about any of 1, 2, or 3) amino acid substitutions, and (b) a second antigen binding portion comprising a full-length antibody consisting of two heavy chains and two light chains, wherein the full-length antibody specifically binds PD-1; wherein the full-length antibody comprises a $V_H$ comprising HC-CDR1, HC-CDR2, and HC-CDR3 of the amino acid sequence of SEQ ID NO: 387, and a $V_L$ comprising LC-CDR1, LC-CDR2, and LC-CDR3 of the amino acid sequence of SEQ ID NO: 388; and wherein the first antigen binding portion and the second antigen binding portion are fused to each other. In some embodiments, the anti-PD-1 antibody comprises a $V_H$ comprising the amino acid sequence of SEQ ID NO: 387, and a $V_L$ comprising the amino acid sequence of SEQ ID NO: 388. In some embodiments, there is provided an anti-TIGIT MABP (e.g., BABP) comprising: (a) a first antigen binding portion comprising an sdAb moiety specifically recognizing TIGIT comprising a CDR1 comprising the amino acid sequence of any one of SEQ ID NOs: 36-42, 54, 56-59, 63, 65-67, 69-70, or a variant thereof comprising up to about 3 (such as about any of 1, 2, or 3) amino acid substitutions; a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210, or a variant thereof comprising up to about 3 (such as about any of 1, 2, or 3) amino acid substitutions, and (b) a second antigen binding portion comprising a full-length antibody consisting of two heavy chains and two light chains, wherein the full-length antibody specifically binds PD-1; wherein the full-length antibody comprises a $V_H$ comprising HC-CDR1, HC-CDR2, and HC-CDR3 of the amino acid sequence of SEQ ID NO: 406, and a $V_L$ comprising LC-CDR1, LC-CDR2, and LC-CDR3 of the amino acid sequence of SEQ ID NO: 407; and wherein the first antigen binding portion and the second antigen binding portion are fused to each other. In some embodiments, the anti-PD-1 antibody comprises a $V_H$ comprising the amino acid sequence of SEQ ID NO: 406, and a $V_L$ comprising the amino acid sequence of SEQ ID NO: 407. In some embodiments, the anti-TIGIT sdAb moiety comprises a CDR1 comprising the amino acid sequence of any one of SEQ ID NOs: 36-42, 54, 56-59, 63, 65-67, 69-70; a CDR2 comprising the amino acid sequence of any one of SEQ ID NOs: 106-112, 124, 126-129, 133, 135-137, 139-140; and a CDR3 comprising the amino acid sequence of any one of SEQ ID NOs: 176-182, 194, 196-199, 203, 205-207, 209-210. In some embodiments, the anti-TIGIT sdAb moiety comprises a $V_HH$ domain comprising the amino acid sequence of any one of SEQ ID NOs: 253-259, 271, 273-276, 280, 282-284, 286-287. In some embodiments, the anti-TIGIT sdAb moiety comprises CDR1, CDR2, and CDR3 of any one of SEQ ID NOs: 253-259, 271, 273-276, 280, 282-284, 286-287. In some embodiments, the first antigen binding portion is fused to the second antigen binding portion at the N-terminus of one or each of the two heavy chains, the N-terminus of one or each of the two light chains, the N-terminus of the Fc region, the C-terminus of one or each of the two heavy chains, or the C-terminus of one or each of the two light chains. In some embodiments, the first antigen binding portion is fused to the second antigen binding portion chemically. In some embodiments, the first antigen binding portion is fused to the second antigen binding portion via a peptide bond or a peptide linker. In some embodiments, the peptide linker is no more than about 30 (such as no more than about any one of 25, 20, or 15) amino acids long. In some embodiments, the peptide linker comprises the amino acid sequence of any one of SEQ ID NOs: 324 and 370-378. In some embodiments, the Fc region of the full-length antibody can be, e.g., an IgG1 Fc, effectorless IgG1 Fc, IgG2 Fc, or IgG4 Fc. In some embodiments, the Fc region comprises the amino acid sequence of any one of SEQ ID NOs: 355, 356, and 389. In some embodiments, the $K_d$ of the binding between the anti-TIGIT sdAb moiety and TIGIT is about $10^{-5}$ M to about $10^{-12}$ M (such as about $10^{-7}$ M to about $10^{-12}$ M, or about $10^{-8}$ M to about $10^{-12}$ M). In some embodiments, the anti-TIGIT sdAb moiety is camelid, chimeric, human, partially humanized, or fully humanized.

In some embodiments, there is provided an anti-TIGIT MABP (e.g., BABP) comprising: (a) a first antigen binding portion comprising an sdAb moiety specifically recognizing TIGIT comprising a CDR1 comprising the amino acid sequence of any one of SEQ ID NOs: 36-42, 54, 56-59, 63, 65-67, 69-70, or a variant thereof comprising up to about 3 (such as about any of 1, 2, or 3) amino acid substitutions; a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210, or a variant thereof comprising up to about 3 (such as about any of 1, 2, or 3) amino acid substitutions, and (b) a second antigen binding portion comprising a full-length antibody (such as Atezolizumab, Durvalumab, Avelumab, or h53C1) consisting of two heavy chains and two light chains, wherein the full-length antibody specifically binds PD-L1; and wherein the first antigen binding portion and the second antigen binding portion are fused to each other. In some embodiments, there is provided an anti-TIGIT MABP (e.g., BABP) comprising: (a) a first antigen binding portion comprising an sdAb moiety specifically recognizing TIGIT comprising a CDR1 comprising the amino acid sequence of any one of SEQ ID NOs: 36-42, 54, 56-59, 63, 65-67, 69-70, or a variant thereof comprising up to about 3 (such as about any of 1, 2, or 3) amino acid substitutions; a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210, or a variant thereof comprising up to about 3 (such as about any of 1, 2, or 3) amino acid substitutions, and (b) a second antigen binding portion comprising a full-length antibody consisting of two heavy chains and two light chains, wherein the full-length antibody specifically binds PD-L1; wherein the full-length antibody comprises a $V_H$ comprising HC-CDR1, HC-CDR2, and HC-CDR3 of the amino acid sequence of SEQ ID NO: 381, and a $V_L$ comprising LC-CDR1, LC-CDR2, and LC-CDR3 of the amino acid sequence of SEQ ID NO: 382; and wherein the first antigen binding portion and the second antigen binding portion are fused to each other. In some embodiments, the anti-PD-L1 antibody comprises a $V_H$ comprising the amino acid sequence of SEQ ID NO: 381, and a V$_L$ comprising the amino acid sequence of SEQ ID NO: 382. In some embodiments, the anti-PD-L1 antibody comprises a heavy chain comprising the amino acid sequence of SEQ ID NO: 331, and a light chain comprising the amino acid sequence of SEQ ID NO: 332. In some embodiments, the anti-PD-L1 antibody comprises a heavy chain comprising the amino acid sequence of SEQ ID NO: 333, and a light chain comprising the amino acid sequence of SEQ ID NO: 334. In some embodiments, there is provided an anti-TIGIT MABP (e.g., BABP) comprising: (a) a first antigen binding portion comprising an sdAb moiety specifically recognizing TIGIT comprising a CDR1 comprising the amino acid sequence of any one of SEQ ID NOs: 36-42, 54, 56-59, 63, 65-67, 69-70, or a variant thereof comprising up to about 3 (such as about any of 1, 2, or 3) amino acid substitutions; a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210, or a variant thereof comprising up to about 3 (such as about any of 1, 2, or 3) amino acid substitutions, and (b) a second antigen binding portion comprising a full-length antibody consisting of two heavy chains and two light chains, wherein the full-length antibody specifically binds PD-L1; wherein the full-length antibody comprises a V$_H$ comprising HC-CDR1, HC-CDR2, and HC-CDR3 of the amino acid sequence of SEQ ID NO: 379, and a V$_L$ comprising LC-CDR1, LC-CDR2, and LC-CDR3 of the amino acid sequence of SEQ ID NO: 380; and wherein the first antigen binding portion and the second antigen binding portion are fused to each other. In some embodiments, the anti-PD-L1 antibody comprises a V$_H$ comprising the amino acid sequence of SEQ ID NO: 379, and a V$_L$ comprising the amino acid sequence of SEQ ID NO: 380. In some embodiments, there is provided an anti-TIGIT MABP (e.g., BABP) comprising: (a) a first antigen binding portion comprising an sdAb moiety specifically recognizing TIGIT comprising a CDR1 comprising the amino acid sequence of any one of SEQ ID NOs: 36-42, 54, 56-59, 63, 65-67, 69-70, or a variant thereof comprising up to about 3 (such as about any of 1, 2, or 3) amino acid substitutions; a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210, or a variant thereof comprising up to about 3 (such as about any of 1, 2, or 3) amino acid substitutions, and (b) a second antigen binding portion comprising a full-length antibody consisting of two heavy chains and two light chains, wherein the full-length antibody specifically binds PD-L1; wherein the full-length antibody comprises a V$_H$ comprising HC-CDR1, HC-CDR2, and HC-CDR3 of the amino acid sequence of SEQ ID NO: 383, and a V$_L$ comprising LC-CDR1, LC-CDR2, and LC-CDR3 of the amino acid sequence of SEQ ID NO: 384; and wherein the first antigen binding portion and the second antigen binding portion are fused to each other. In some embodiments, the anti-PD-L1 antibody comprises a V$_H$ comprising the amino acid sequence of SEQ ID NO: 383, and a V$_L$ comprising the amino acid sequence of SEQ ID NO: 384. In some embodiments, there is provided an anti-TIGIT MABP (e.g., BABP) comprising: (a) a first antigen binding portion comprising an sdAb moiety specifically recognizing TIGIT comprising a CDR1 comprising the amino acid sequence of any one of SEQ ID NOs: 36-42, 54, 56-59, 63, 65-67, 69-70, or a variant thereof comprising up to about 3 (such as about any of 1, 2, or 3) amino acid substitutions; a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210, or a variant thereof comprising up to about 3 (such as about any of 1, 2, or 3) amino acid substitutions, and (b) a second antigen binding portion comprising a full-length antibody consisting of two heavy chains and two light chains, wherein the full-length antibody specifically binds PD-L1; wherein the full-length antibody comprises 1) a V$_H$ comprising an HC-CDR1 comprising the amino acid sequence of SEQ ID NO: 349, an HC-CDR2 comprising the amino acid sequence of SEQ ID NO: 350, and an HC-CDR3 comprising the amino acid sequence of SEQ ID NO: 351, and 2) a V$_L$ comprising an LC-CDR1 comprising the amino acid sequence of SEQ ID NO: 352, an LC-CDR2 comprising the amino acid sequence of SEQ ID NO: 353, and an LC-CDR3 comprising the amino acid sequence of SEQ ID NO: 354; and wherein the first antigen binding portion and the second antigen binding portion are fused to each other. In some embodiments, the anti-PD-L1 antibody comprises a V$_H$ comprising the amino acid sequence of SEQ ID NO: 339, and a V$_L$ comprising the amino acid sequence of SEQ ID NO: 340. In some embodiments, the anti-PD-L1 antibody comprises a heavy chain comprising the amino acid sequence of SEQ ID NO: 323 or 327, and a light chain comprising the amino acid sequence of SEQ ID NO: 328. In some embodiments, the anti-PD-L1 antibody comprises a heavy chain comprising the amino acid sequence of SEQ ID NO: 329, and a light chain comprising the amino acid sequence of SEQ ID NO: 330. In some embodiments, the anti-TIGIT sdAb moiety comprises a CDR1 comprising the amino acid sequence of any one of SEQ ID NOs: 36-42, 54, 56-59, 63, 65-67, 69-70; a CDR2 comprising the amino acid sequence of any one of SEQ ID NOs: 106-112, 124, 126-129, 133, 135-137, 139-140; and a CDR3 comprising the amino acid sequence of any one of SEQ ID NOs: 176-182, 194, 196-199, 203, 205-207, 209-210. In some embodiments, the anti-TIGIT sdAb moiety comprises a V$_H$H domain comprising the amino acid sequence of any one of SEQ ID NOs: 253-259, 271, 273-276, 280, 282-284, 286-287. In some embodiments, the anti-TIGIT sdAb moiety comprises CDR1, CDR2, and CDR3 of any one of SEQ ID NOs: 253-259, 271, 273-276, 280, 282-284, 286-287. In some embodiments, the first antigen binding portion is fused to the second antigen binding portion at the N-terminus of one or each of the two heavy chains, the N-terminus of one or each of the two light chains, the N-terminus of the Fc region, the C-terminus of one or each of the two heavy chains, or the C-terminus of one or each of the two light chains. In some embodiments, the first antigen binding portion is fused to the second antigen binding portion chemically. In some embodiments, the first antigen binding portion is fused to the second antigen binding portion via a peptide bond or a peptide linker. In some embodiments, the peptide linker is no more than about 30 (such as no more than about any one of 25, 20, or 15) amino acids long. In some embodiments, the peptide linker comprises the amino acid sequence of any one of SEQ ID NOs: 324 and 370-378. In some embodiments, the Fc region of the full-length antibody can be, e.g., an IgG1 Fc, effectorless IgG1 Fc, IgG2 Fc, or IgG4 Fc. In some embodiments, the Fc region comprises the amino acid sequence of any one of SEQ ID NOs: 355, 356, and 389. In some embodiments, the $K_d$ of the binding between the anti-TIGIT sdAb moiety and TIGIT is about $10^{-5}$ M to about $10^{-12}$ M (such as about $10^{-7}$ M to about $10^{-12}$ M, or about $10^{-8}$ M to about $10^{-12}$ M). In some embodiments, the anti-TIGIT sdAb moiety is camelid, chimeric, human, partially humanized, or fully humanized.

In some embodiments, there is provided an anti-TIGIT BABP comprising: (a) a first polypeptide comprising from N-terminus to C-terminus: $V_H$—$C_H1$-$C_H2$-$C_H3$-anti-TIGIT sdAb moiety; and (b) a second polypeptide comprising from N-terminus to C-terminus: $V_L$—$C_L$, wherein $V_H$ and $V_L$ forms an antigen binding site that specifically binds PD-1, and wherein the anti-TIGIT sdAb moiety comprises a CDR1 comprising the amino acid sequence of any one of SEQ ID NOs: 36-42, 54, 56-59, 63, 65-67, 69-70, or a variant thereof comprising up to about 3 (such as about any of 1, 2, or 3) amino acid substitutions; a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210, or a variant thereof comprising up to about 3 (such as about any of 1, 2, or 3) amino acid substitutions. In some embodiments, the anti-TIGIT sdAb comprises a CDR1 comprising the amino acid sequence of any one of SEQ ID NOs: 36-42, 54, 56-59, 63, 65-67, 69-70; a CDR2 comprising the amino acid sequence of any one of SEQ ID NOs: 106-112, 124, 126-129, 133, 135-137, 139-140; and a CDR3 comprising the amino acid sequence of any one of SEQ ID NOs: 176-182, 194, 196-199, 203, 205-207, 209-210. In some embodiments, the anti-TIGIT sdAb moiety comprises a $V_H H$ domain comprising the amino acid sequence of any one of SEQ ID NO: 253-259, 271, 273-276, 280, 282-284, 286-287. In some embodiments, the $V_H$ and $V_L$ domains are derived from pembrolizumab, PD1-BM-min, or nivolumab. In some embodiments, the $V_H$ comprises the amino acid sequence of SEQ ID NO: 385, and the $V_L$ comprises the amino acid sequence of SEQ ID NO: 386. In some embodiments, the $V_H$ comprises the amino acid sequence of SEQ ID NO: 387, and the $V_L$ comprises the amino acid sequence of SEQ ID NO: 388. In some embodiments, the $V_H$ comprises the amino acid sequence of SEQ ID NO: 406, and the $V_L$ comprises the amino acid sequence of SEQ ID NO: 407. In some embodiments, the $C_H3$ and anti-TIGIT sdAb moiety are fused to each other optionally via a peptide linker, such as a peptide linker comprising the amino acid sequence of any one of SEQ ID NOs: 324 and 370-378. In some embodiments, the $C_H2$ and $C_H3$ domains are derived from an IgG4 Fc, such as SEQ ID NO: 389. In some embodiments, the $C_H2$ and $C_H3$ domains are derived from an IgG1 Fc, such as SEQ ID NO: 356. In some embodiments, the $C_H2$ and $C_H3$ domains are derived from an effectorless IgG1 Fc, such as SEQ ID NO: 355. In some embodiments, the anti-TIGIT BABP comprises two identical copies of the first polypeptide and two identical copies of the second polypeptide. In some embodiments, the anti-TIGIT sdAb moiety is camelid, chimeric, human, partially humanized, or fully humanized. In some embodiments, the anti-TIGIT BABP comprises (a) two identical copies of a first polypeptide comprising the amino acid sequence of SEQ ID NO: 396, and (b) two identical copies of a second polypeptide comprising the amino acid sequence of SEQ ID NO: 397. In some embodiments, the PD-1×TIGIT BABP has the structure as shown in FIG. 18.

In some embodiments, there is provided an anti-TIGIT BABP comprising: (a) a first polypeptide comprising from N-terminus to C-terminus: $V_H$—$C_H1$-$C_H2$-$C_H3$-anti-TIGIT sdAb moiety; and (b) a second polypeptide comprising from N-terminus to C-terminus: $V_L$—$C_L$, wherein $V_H$ and $V_L$ forms an antigen binding site that specifically binds PD-1, and wherein the anti-TIGIT sdAb moiety comprises a CDR1 comprising the amino acid sequence of any one of SEQ ID NOs: 36-42, 54, 56-59, 63, 65-67, 69-70, or a variant thereof comprising up to about 3 (such as about any of 1, 2, or 3) amino acid substitutions; a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210, or a variant thereof comprising up to about 3 (such as about any of 1, 2, or 3) amino acid substitutions. In some embodiments, the anti-TIGIT sdAb comprises a CDR1 comprising the amino acid sequence of any one of SEQ ID NOs: 36-42, 54, 56-59, 63, 65-67, 69-70; a CDR2 comprising the amino acid sequence of any one of SEQ ID NOs: 106-112, 124, 126-129, 133, 135-137, 139-140; and a CDR3 comprising the amino acid sequence of any one of SEQ ID NOs: 176-182, 194, 196-199, 203, 205-207, 209-210. In some embodiments, the anti-TIGIT sdAb moiety comprises a $V_H H$ domain comprising the amino acid sequence of any one of SEQ ID NO: 253-259, 271, 273-276, 280, 282-284, 286-287. In some embodiments, the $V_H$ and $V_L$ domains are derived from atezolizumab, durvalumab, avelumab, or h53C1. In some embodiments, the h53C1 anti-PD-L1 antibody comprises 1) a $V_H$ comprising an HC-CDR1 comprising the amino acid sequence of SEQ ID NO: 349, an HC-CDR2 comprising the amino acid sequence of SEQ ID NO: 350, and an HC-CDR3 comprising the amino acid sequence of SEQ ID NO: 351, and 2) a $V_L$ comprising an LC-CDR1 comprising the amino acid sequence of SEQ ID NO: 352, an LC-CDR2 comprising the amino acid sequence of SEQ ID NO: 353, and an LC-CDR3 comprising the amino acid sequence of SEQ ID NO: 354. In some embodiments, the h53C1 anti-PD-L1 antibody comprises a $V_H$ comprising the amino acid sequence of SEQ ID NO: 339, and a $V_L$ comprising the amino acid sequence of SEQ ID NO: 340. In some embodiments, the $V_H$ comprises the amino acid sequence of SEQ ID NO: 381, and the $V_L$ comprises the amino acid sequence of SEQ ID NO: 382. In some embodiments, the $V_H$ comprises the amino acid sequence of SEQ ID NO: 379, and the $V_L$ comprises the amino acid sequence of SEQ ID NO: 380. In some embodiments, the $V_H$ comprises the amino acid sequence of SEQ ID NO: 383, and the $V_L$ comprises the amino acid sequence of SEQ ID NO: 384. In some embodiments, the $V_H$ comprises the amino acid sequence of SEQ ID NO: 339, and the $V_L$ comprises the amino acid sequence of SEQ ID NO: 340. In some embodiments, the $C_H3$ and anti-TIGIT sdAb moiety are fused to each other optionally via a peptide linker, such as a peptide linker comprising the amino acid sequence of any one of SEQ ID NOs: 324 and 370-378. In some embodiments, the $C_H2$ and $C_H3$ domains are derived from an IgG4 Fc, such as SEQ ID NO: 389. In some embodiments, the $C_H2$ and $C_H3$ domains are derived from an IgG1 Fc, such as SEQ ID NO: 356. In some embodiments, the $C_H2$ and $C_H3$ domains are derived from an effectorless IgG1 Fc, such as SEQ ID NO: 355. In some embodiments, the anti-TIGIT BABP comprises two identical copies of the first polypeptide and two identical copies of the second polypeptide. In some embodiments, the anti-TIGIT sdAb moiety is camelid, chimeric, human, partially humanized, or fully humanized. In some embodiments, the anti-TIGIT BABP comprises (a) two identical copies of a first polypeptide comprising the amino acid sequence of SEQ ID NO: 359, and (b) two identical copies of a second polypeptide comprising the amino acid sequence of SEQ ID NO: 360. In some embodiments, the PD-L1×TIGIT BABP has the structure as shown in FIG. 18.

In some embodiments, there is provided an anti-TIGIT BABP comprising: (a) a first polypeptide comprising from N-terminus to C-terminus: anti-TIGIT sdAb moiety-$V_H$—$C_H1$-$C_H2$-$C_H3$; and (b) a second polypeptide comprising from N-terminus to C-terminus: $V_L$—$C_L$, wherein $V_H$ and $V_L$ forms an antigen binding site that specifically binds PD-1, and wherein the anti-TIGIT sdAb moiety comprises a CDR1 comprising the amino acid sequence of any one of SEQ ID NOs: 36-42, 54, 56-59, 63, 65-67, 69-70, or a variant thereof comprising up to about 3 (such as about any of 1, 2, or 3) amino acid substitutions; a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210, or a variant thereof comprising up to about 3 (such as about any of 1, 2, or 3) amino acid substitutions. In some embodiments, the anti-TIGIT sdAb moiety comprises a CDR1 comprising the amino acid sequence of any one of SEQ ID NOs: 36-42, 54, 56-59, 63, 65-67, 69-70; a CDR2 comprising the amino acid sequence of any one of SEQ ID NOs: 106-112, 124, 126-129, 133, 135-137, 139-140; and a CDR3 comprising the amino acid sequence of any one of SEQ ID NOs: 176-182, 194, 196-199, 203, 205-207, 209-210. In some embodiments, the anti-TIGIT sdAb moiety comprises a $V_H$H domain comprising the amino acid sequence of any one of SEQ ID NO: 253-259, 271, 273-276, 280, 282-284, 286-287. In some embodiments, the $V_H$ and $V_L$ domains are derived from pembrolizumab, PD1-BM-min, or nivolumab. In some embodiments, the $V_H$ comprises the amino acid sequence of SEQ ID NO: 385, and the $V_L$ comprises the amino acid sequence of SEQ ID NO: 386. In some embodiments, the $V_H$ comprises the amino acid sequence of SEQ ID NO: 387, and the $V_L$ comprises the amino acid sequence of SEQ ID NO: 388. In some embodiments, the $V_H$ comprises the amino acid sequence of SEQ ID NO: 406, and the $V_L$ comprises the amino acid sequence of SEQ ID NO: 407. In some embodiments, the $V_H$ and the anti-TIGIT sdAb moiety are fused to each other optionally via a peptide linker, such as a peptide linker comprising the amino acid sequence of any one of SEQ ID NOs: 324 and 370-378. In some embodiments, the $C_H2$ and $C_H3$ domains are derived from an IgG4 Fc, such as SEQ ID NO: 389. In some embodiments, the $C_H2$ and $C_H3$ domains are derived from an IgG1 Fc, such as SEQ ID NO: 356. In some embodiments, the $C_H2$ and $C_H3$ domains are derived from an effectorless IgG1 Fc, such as SEQ ID NO: 355. In some embodiments, the anti-TIGIT BABP comprises two identical copies of the first polypeptide and two identical copies of the second polypeptide. In some embodiments, the anti-TIGIT sdAb moiety is camelid, chimeric, human, partially humanized, or fully humanized. In some embodiments, the anti-TIGIT BABP comprises (a) two identical copies of a first polypeptide comprising the amino acid sequence of SEQ ID NO: 394, and (b) two identical copies of a second polypeptide comprising the amino acid sequence of SEQ ID NO: 395. In some embodiments, the PD-1×TIGIT BABP has the structure as shown in FIG. 17.

In some embodiments, there is provided an anti-TIGIT BABP comprising: (a) a first polypeptide comprising from N-terminus to C-terminus: anti-TIGIT sdAb moiety-$V_H$—$C_H1$-$C_H2$-$C_H3$; and (b) a second polypeptide comprising from N-terminus to C-terminus: $V_L$—$C_L$, wherein $V_H$ and $V_L$ forms an antigen binding site that specifically binds PD-L1, and wherein the anti-TIGIT sdAb moiety comprises a CDR1 comprising the amino acid sequence of any one of SEQ ID NOs: 36-42, 54, 56-59, 63, 65-67, 69-70, or a variant thereof comprising up to about 3 (such as about any of 1, 2, or 3) amino acid substitutions; a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210, or a variant thereof comprising up to about 3 (such as about any of 1, 2, or 3) amino acid substitutions. In some embodiments, the anti-TIGIT sdAb moiety comprises a CDR1 comprising the amino acid sequence of any one of SEQ ID NOs: 36-42, 54, 56-59, 63, 65-67, 69-70; a CDR2 comprising the amino acid sequence of any one of SEQ ID NOs: 106-112, 124, 126-129, 133, 135-137, 139-140; and a CDR3 comprising the amino acid sequence of any one of SEQ ID NOs: 176-182, 194, 196-199, 203, 205-207, 209-210. In some embodiments, the anti-TIGIT sdAb moiety comprises a $V_H$H domain comprising the amino acid sequence of any one of SEQ ID NO: 253-259, 271, 273-276, 280, 282-284, 286-287. In some embodiments, the $V_H$ and $V_L$ domains are derived from atezolizumab, durvalumab, avelumab, or h53C1. In some embodiments, the h53C1 anti-PD-L1 antibody comprises 1) a $V_H$ comprising an HC-CDR1 comprising the amino acid sequence of SEQ ID NO: 349, an HC-CDR2 comprising the amino acid sequence of SEQ ID NO: 350, and an HC-CDR3 comprising the amino acid sequence of SEQ ID NO: 351, and 2) a $V_L$ comprising an LC-CDR1 comprising the amino acid sequence of SEQ ID NO: 352, an LC-CDR2 comprising the amino acid sequence of SEQ ID NO: 353, and an LC-CDR3 comprising the amino acid sequence of SEQ ID NO: 354. In some embodiments, the h53C1 anti-PD-L1 antibody comprises a $V_H$ comprising the amino acid sequence of SEQ ID NO: 339, and a $V_L$ comprising the amino acid sequence of SEQ ID NO: 340. In some embodiments, the $V_H$ comprises the amino acid sequence of SEQ ID NO: 381, and the $V_L$ comprises the amino acid sequence of SEQ ID NO: 382. In some embodiments, the $V_H$ comprises the amino acid sequence of SEQ ID NO: 379, and the $V_L$ comprises the amino acid sequence of SEQ ID NO: 380. In some embodiments, the $V_H$ comprises the amino acid sequence of SEQ ID NO: 383, and the $V_L$ comprises the amino acid sequence of SEQ ID NO: 384. In some embodiments, the $V_H$ comprises the amino acid sequence of SEQ ID NO: 339, and the $V_L$ comprises the amino acid sequence of SEQ ID NO: 340. In some embodiments, the $V_H$ and the anti-TIGIT sdAb moiety are fused to each other optionally via a peptide linker, such as a peptide linker comprising the amino acid sequence of any one of SEQ ID NOs: 324 and 370-378. In some embodiments, the $C_H2$ and $C_H3$ domains are derived from an IgG4 Fc, such as SEQ ID NO: 389. In some embodiments, the $C_H2$ and $C_H3$ domains are derived from an IgG1 Fc, such as SEQ ID NO: 356. In some embodiments, the $C_H2$ and $C_H3$ domains are derived from an effectorless IgG1

Fc, such as SEQ ID NO: 355. In some embodiments, the anti-TIGIT BABP comprises two identical copies of the first polypeptide and two identical copies of the second polypeptide. In some embodiments, the anti-TIGIT sdAb moiety is camelid, chimeric, human, partially humanized, or fully humanized. In some embodiments, the anti-TIGIT BABP comprises (a) two identical copies of a first polypeptide comprising the amino acid sequence of SEQ ID NO: 345, and (b) two identical copies of a second polypeptide comprising the amino acid sequence of SEQ ID NO: 346. In some embodiments, the anti-TIGIT BABP comprises (a) two identical copies of a first polypeptide comprising the amino acid sequence of SEQ ID NO: 347, and (b) two identical copies of a second polypeptide comprising the amino acid sequence of SEQ ID NO: 348. In some embodiments, the anti-TIGIT BABP comprises (a) two identical copies of a first polypeptide comprising the amino acid sequence of SEQ ID NO: 341, and (b) two identical copies of a second polypeptide comprising the amino acid sequence of SEQ ID NO: 342. In some embodiments, the anti-TIGIT BABP comprises (a) two identical copies of a first polypeptide comprising the amino acid sequence of SEQ ID NO: 343, and (b) two identical copies of a second polypeptide comprising the amino acid sequence of SEQ ID NO: 344. In some embodiments, the anti-TIGIT BABP comprises (a) two identical copies of a first polypeptide comprising the amino acid sequence of SEQ ID NO: 357, and (b) two identical copies of a second polypeptide comprising the amino acid sequence of SEQ ID NO: 358. In some embodiments, the anti-TIGIT BABP comprises (a) two identical copies of a first polypeptide comprising the amino acid sequence of SEQ ID NO: 402, and (b) two identical copies of a second polypeptide comprising the amino acid sequence of SEQ ID NO: 403. In some embodiments, the PD-L1×TIGIT BABP has the structure as shown in FIG. 17.

In some embodiments, there is provided an anti-TIGIT BABP comprising: (a) a first polypeptide comprising from N-terminus to C-terminus: $V_H$—$C_H1$-$C_H2$-$C_H3$; and (b) a second polypeptide comprising from N-terminus to C-terminus: $V_L$—$C_L$-anti-TIGIT sdAb moiety, wherein $V_H$ and $V_L$ forms an antigen binding site that specifically binds PD-1, and wherein the anti-TIGIT sdAb moiety comprises a CDR1 comprising the amino acid sequence of any one of SEQ ID NOs: 36-42, 54, 56-59, 63, 65-67, 69-70, or a variant thereof comprising up to about 3 (such as about any of 1, 2, or 3) amino acid substitutions; a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210, or a variant thereof comprising up to about 3 (such as about any of 1, 2, or 3) amino acid substitutions. In some embodiments, the anti-TIGIT sdAb moiety comprises a CDR1 comprising the amino acid sequence of any one of SEQ ID NOs: 36-42, 54, 56-59, 63, 65-67, 69-70; a CDR2 comprising the amino acid sequence of any one of SEQ ID NOs: 106-112, 124, 126-129, 133, 135-137, 139-140; and a CDR3 comprising the amino acid sequence of any one of SEQ ID NOs: 176-182, 194, 196-199, 203, 205-207, 209-210. In some embodiments, the anti-TIGIT sdAb moiety comprises a $V_H H$ domain comprising the amino acid sequence of any one of SEQ ID NO: 253-259, 271, 273-276, 280, 282-284, 286-287. In some embodiments, the $V_H$ and $V_L$ domains are derived from pembrolizumab, PD1-BM-min, or nivolumab. In some embodiments, the $V_H$ comprises the amino acid sequence of SEQ ID NO: 385, and the $V_L$ comprises the amino acid sequence of SEQ ID NO: 386. In some embodiments, the $V_H$ comprises the amino acid sequence of SEQ ID NO: 387, and the $V_L$ comprises the amino acid sequence of SEQ ID NO: 388. In some embodiments, the $V_H$ comprises the amino acid sequence of SEQ ID NO: 406, and the $V_L$ comprises the amino acid sequence of SEQ ID NO: 407. In some embodiments, the $C_L$ and the anti-TIGIT sdAb moiety are fused to each other optionally via a peptide linker, such as a peptide linker comprising the amino acid sequence of any one of SEQ ID NOs: 324 and 370-378. In some embodiments, the $C_H2$ and $C_H3$ domains are derived from an IgG4 Fc, such as SEQ ID NO: 389. In some embodiments, the $C_H2$ and $C_H3$ domains are derived from an IgG1 Fc, such as SEQ ID NO: 356. In some embodiments, the $C_H2$ and $C_H3$ domains are derived from an effectorless IgG1 Fc, such as SEQ ID NO: 355. In some embodiments, the anti-TIGIT BABP comprises two identical copies of the first polypeptide and two identical copies of the second polypeptide. In some embodiments, the anti-TIGIT sdAb moiety is camelid, chimeric, human, partially humanized, or fully humanized. In some embodiments, the anti-TIGIT BABP comprises (a) two identical copies of a first polypeptide comprising the amino acid sequence of SEQ ID NO: 400, and (b) two identical copies of a second polypeptide comprising the amino acid sequence of SEQ ID NO: 401. In some embodiments, the PD-1×TIGIT BABP has the structure as shown in FIG. 20.

In some embodiments, there is provided an anti-TIGIT BABP comprising: (a) a first polypeptide comprising from N-terminus to C-terminus: $V_H$—$C_H1$-$C_H2$-$C_H3$; and (b) a second polypeptide comprising from N-terminus to C-terminus: $V_L$—$C_L$-anti-TIGIT sdAb moiety, wherein $V_H$ and $V_L$ forms an antigen binding site that specifically binds PD-L1, and wherein the anti-TIGIT sdAb moiety comprises a CDR1 comprising the amino acid sequence of any one of SEQ ID NOs: 36-42, 54, 56-59, 63, 65-67, 69-70, or a variant thereof comprising up to about 3 (such as about any of 1, 2, or 3) amino acid substitutions; a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210, or a variant thereof comprising up to about 3 (such as about any of 1, 2, or 3) amino acid substitutions. In some embodiments, the anti-TIGIT sdAb moiety comprises a CDR1 comprising the amino acid sequence of any one of SEQ ID NOs: 36-42, 54, 56-59, 63, 65-67, 69-70; a CDR2 comprising the amino acid sequence of any one of SEQ ID NOs: 106-112, 124, 126-129, 133, 135-137, 139-140; and a CDR3 comprising the amino acid sequence of any one of SEQ ID NOs: 176-182, 194, 196-199, 203, 205-207, 209-210. In some embodiments, the anti-TIGIT sdAb moiety comprises a $V_H H$ domain comprising the amino acid sequence of any one of SEQ ID NO: 253-259, 271, 273-276, 280, 282-284, 286-287. In some embodiments, the $V_H$ and $V_L$ domains are derived from atezolizumab, durvalumab, avelumab, or h53C1. In some embodiments, the h53C1 anti-PD-L1 antibody comprises 1) a $V_H$ comprising an HC-CDR1 comprising the amino acid sequence of SEQ ID NO: 349, an HC-CDR2 comprising the amino acid sequence of SEQ ID NO: 350, and an HC-CDR3 comprising the amino acid sequence of SEQ ID NO: 351, and 2) a $V_L$ comprising an LC-CDR1 comprising the amino acid sequence of SEQ ID NO: 352, an LC-CDR2 comprising the amino acid sequence of SEQ ID NO: 353, and an LC-CDR3 comprising the amino acid sequence of SEQ ID NO: 354. In some embodiments, the h53C1 anti-PD-L1 antibody comprises a $V_H$ comprising the amino acid sequence of SEQ ID NO: 339, and a $V_L$ comprising the amino acid sequence of SEQ ID NO: 340. In some embodiments, the $V_H$ comprises the amino acid sequence of SEQ ID NO: 381, and the $V_L$ comprises the amino acid sequence of SEQ ID NO: 382. In some embodiments, the $V_H$ comprises the amino acid sequence of SEQ ID NO: 379, and the $V_L$ comprises the amino acid sequence of SEQ ID NO: 380. In some embodiments, the $V_H$ comprises the amino acid sequence of SEQ ID NO: 383, and the $V_L$ comprises the amino acid sequence of SEQ ID NO: 384. In some embodiments, the $V_H$ comprises the amino acid sequence of SEQ ID NO: 339, and the $V_L$ comprises the amino acid sequence of SEQ ID NO: 340. In some embodiments, the $C_L$ and the anti-TIGIT sdAb moiety are fused to each other optionally via a peptide linker, such as a peptide linker comprising the amino acid sequence of any one of SEQ ID NOs: 324 and 370-378. In some embodiments, the $C_H2$ and $C_H3$ domains are derived from an IgG4 Fc, such as SEQ ID NO: 389. In some embodiments, the $C_H2$ and $C_H3$ domains are derived from an IgG1 Fc, such as SEQ ID NO: 356. In some embodiments, the $C_H2$ and $C_H3$ domains are derived from an effectorless IgG1 Fc, such as SEQ ID NO: 355. In some embodiments, the anti-TIGIT BABP comprises two identical copies of the first polypeptide and two identical copies of the second polypeptide. In some embodiments, the anti-TIGIT sdAb moiety is camelid, chimeric, human, partially humanized, or fully humanized. In some embodiments, the anti-TIGIT BABP comprises (a) two identical copies of a first polypeptide comprising the amino acid sequence of SEQ ID NO: 363, and (b) two identical copies of a second polypeptide comprising the amino acid sequence of SEQ ID NO: 364. In some embodiments, the PD-L1×TIGIT BABP has the structure as shown in FIG. 20.

In some embodiments, there is provided an anti-TIGIT BABP comprising: (a) a first polypeptide comprising from N-terminus to C-terminus: $V_H$—$C_H1$-$C_H2$-$C_H3$; and (b) a second polypeptide comprising from N-terminus to C-terminus: anti-TIGIT sdAb moiety-$V_L$—$C_L$, wherein $V_H$ and $V_L$ forms an antigen binding site that specifically binds PD-1, and wherein the anti-TIGIT sdAb moiety comprises a CDR1 comprising the amino acid sequence of any one of SEQ ID NOs: 36-42, 54, 56-59, 63, 65-67, 69-70, or a variant thereof comprising up to about 3 (such as about any of 1, 2, or 3) amino acid substitutions; a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210, or a variant thereof comprising up to about 3 (such as about any of 1, 2, or 3) amino acid substitutions. In some embodiments, the anti-TIGIT sdAb moiety comprises a CDR1 comprising the amino acid sequence of any one of SEQ ID NOs: 36-42, 54, 56-59, 63, 65-67, 69-70; a CDR2 comprising the amino acid sequence of any one of SEQ ID NOs: 106-112, 124, 126-129, 133, 135-137, 139-140; and a CDR3 comprising the amino acid sequence of any one of SEQ ID NOs: 176-182, 194, 196-199, 203, 205-207, 209-210. In some embodiments, the anti-TIGIT sdAb moiety comprises a $V_HH$ domain comprising the amino acid sequence of any one of SEQ ID NO: 253-259, 271, 273-276, 280, 282-284, 286-287. In some embodiments, the $V_H$ and $V_L$ domains are derived from pembrolizumab, PD1-BM-min, or nivolumab. In some embodiments, the $V_H$ comprises the amino acid sequence of SEQ ID NO: 385, and the $V_L$ comprises the amino acid sequence of SEQ ID NO: 386. In some embodiments, the $V_H$ comprises the amino acid sequence of SEQ ID NO: 387, and the $V_L$ comprises the amino acid sequence of SEQ ID NO: 388. In some embodiments, the $V_H$ comprises the amino acid sequence of SEQ ID NO: 406, and the $V_L$ comprises the amino acid sequence of SEQ ID NO: 407. In some embodiments, the $V_L$ and the anti-TIGIT sdAb moiety are fused to each other optionally via a peptide linker, such as a peptide linker comprising the amino acid sequence of any one of SEQ ID NOs: 324 and 370-378. In some embodiments, the $C_H2$ and $C_H3$ domains are derived from an IgG4 Fc, such as SEQ ID NO: 389. In some embodiments, the $C_H2$ and $C_H3$ domains are derived from an IgG1 Fc, such as SEQ ID NO: 356. In some embodiments, the $C_H2$ and $C_H3$ domains are derived from an effectorless IgG1 Fc, such as SEQ ID NO: 355. In some embodiments, the anti-TIGIT BABP comprises two identical copies of the first polypeptide and two identical copies of the second polypeptide. In some embodiments, the anti-TIGIT sdAb moiety is camelid, chimeric, human, partially humanized, or fully humanized. In some embodiments, the anti-TIGIT BABP comprises (a) two identical copies of a first polypeptide comprising the amino acid sequence of SEQ ID NO: 398, and (b) two identical copies of a second polypeptide comprising the amino acid sequence of SEQ ID NO: 399. In some embodiments, the PD-1×TIGIT BABP has the structure as shown in FIG. 19.

In some embodiments, there is provided an anti-TIGIT BABP comprising: (a) a first polypeptide comprising from N-terminus to C-terminus: $V_H$—$C_H1$-$C_H2$-$C_H3$; and (b) a second polypeptide comprising from N-terminus to C-terminus: anti-TIGIT sdAb moiety-$V_L$—$C_L$, wherein $V_H$ and $V_L$ forms an antigen binding site that specifically binds PD-L1, and wherein the anti-TIGIT sdAb moiety comprises a CDR1 comprising the amino acid sequence of any one of SEQ ID NOs: 36-42, 54, 56-59, 63, 65-67, 69-70, or a variant thereof comprising up to about 3 (such as about any of 1, 2, or 3) amino acid substitutions; a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210, or a variant thereof comprising up to about 3 (such as about any of 1, 2, or 3) amino acid substitutions. In some embodiments, the anti-TIGIT sdAb moiety comprises a CDR1 comprising the amino acid sequence of any one of SEQ ID NOs: 36-42, 54, 56-59, 63, 65-67, 69-70; a CDR2 comprising the amino acid sequence of any one of SEQ ID NOs: 106-112, 124, 126-129, 133, 135-137, 139-140; and a CDR3 comprising the amino acid sequence of any one of SEQ ID NOs: 176-182, 194, 196-199, 203, 205-207, 209-210. In some embodiments, the anti-TIGIT sdAb moiety comprises a $V_HH$ domain comprising the amino acid sequence of any one of SEQ ID NO: 253-259, 271, 273-276, 280, 282-284, 286-287. In some embodiments, the $V_H$ and $V_L$ domains are derived from atezolizumab, durvalumab, avelumab, or h53C1. In some embodiments, the h53C1 anti-PD-L1 antibody comprises 1) a $V_H$ comprising an HC-CDR1 comprising the amino acid sequence of SEQ ID NO: 349, an HC-CDR2 comprising the amino acid sequence of SEQ ID NO: 350, and an HC-CDR3 comprising the amino acid sequence of SEQ ID NO: 351, and 2) a $V_L$ comprising an LC-CDR1 comprising the amino acid sequence of SEQ ID NO: 352, an LC-CDR2 comprising the amino acid sequence of SEQ ID NO: 353, and an LC-CDR3 comprising the amino acid sequence of SEQ ID NO: 354. In some embodiments, the h53C1 anti-PD-L1 antibody comprises a $V_H$ comprising the amino acid sequence of SEQ ID NO: 339, and a $V_L$ comprising the amino acid sequence of SEQ ID NO: 340. In some embodiments, the $V_H$ comprises the amino acid sequence of SEQ ID NO: 381, and the $V_L$ comprises the amino acid sequence of SEQ ID NO: 382. In some embodiments, the $V_H$ comprises the amino acid sequence of SEQ ID NO: 379, and the $V_L$ comprises the amino acid sequence of SEQ ID NO: 380. In some embodiments, the $V_H$ comprises the amino acid sequence of SEQ ID NO: 383, and the $V_L$ comprises the amino acid sequence of SEQ ID NO: 384. In some embodiments, the $V_H$ comprises the amino acid sequence of SEQ ID NO: 339, and the $V_L$ comprises the amino acid sequence of SEQ ID NO: 340. In some embodiments, the $V_L$ and the anti-TIGIT sdAb moiety are fused to each other optionally via a peptide linker, such as a peptide linker comprising the amino acid sequence of any one of SEQ ID NOs: 324 and 370-378. In some embodiments, the $C_H2$ and $C_H3$ domains are derived from an IgG4 Fc, such as SEQ ID NO: 389. In some embodiments, the $C_H2$ and $C_H3$ domains are derived from an IgG1 Fc, such as SEQ ID NO: 356. In some embodiments, the $C_H2$ and $C_H3$ domains are derived from an effectorless IgG1 Fc, such as SEQ ID NO: 355. In some embodiments, the anti-TIGIT BABP comprises two identical copies of the first polypeptide and two identical copies of the second polypeptide. In some embodiments, the anti-TIGIT sdAb moiety is camelid, chimeric, human, partially humanized, or fully humanized. In some embodiments, the anti-TIGIT BABP comprises (a) two identical copies of a first polypeptide comprising the amino acid sequence of SEQ ID NO: 361, and (b) two identical copies of a second polypeptide comprising the amino acid sequence of SEQ ID NO: 362. In some embodiments, the anti-TIGIT BABP comprises (a) two identical copies of a first polypeptide comprising the amino acid sequence of SEQ ID NO: 404, and (b) two identical copies of a second polypeptide comprising the amino acid sequence of SEQ ID NO: 405. In some embodiments, the PD-L1×TIGIT BABP has the structure as shown in FIG. 19.

Figure 21:
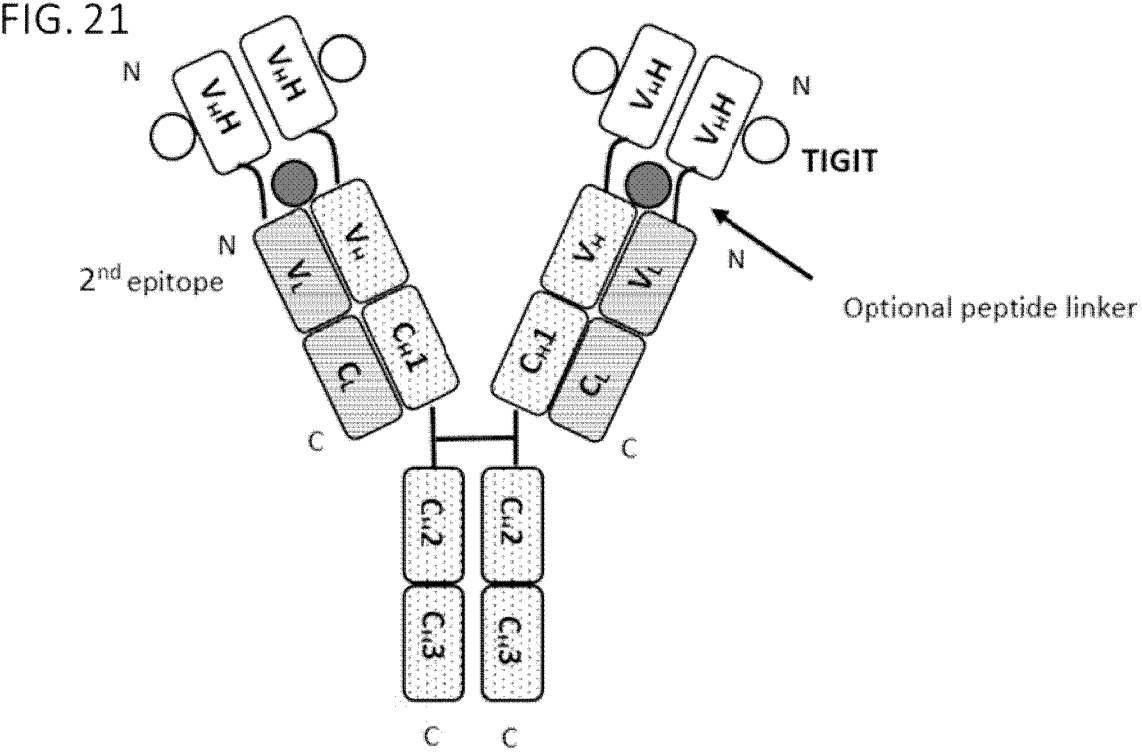
FIG. 21 depicts a schematic structure of an exemplary BABP comprising a monospecific full-length antibody having two identical heavy chains and two identical light chains, and four identical anti-TIGIT sdAbs, wherein the C-terminus of each anti-TIGIT sdAb is fused to the N-terminus of heavy chain or light chain of the monospecific full-length antibody via an optional peptide linker. Each anti-TIGIT sdAb specifically binds to a first epitope (TIGIT). The full-length antibody has two antigen binding sites that each specifically binds a second epitope. For example, the BABP can consist of four polypeptide chains with structures from the N-terminus to the C-terminus as follows: (1) $V_HH$—$V_L$—$C_L$; (2) $V_HH$—$V_H$—$C_H1$-$C_H2$-$C_H3$; (3) $V_HH$—$V_H$—$C_H1$-$C_H2$-$C_H3$; and (4) $V_HH$—$V_L$—$C_L$, wherein $V_H$ and $V_L$ of polypeptide chains (1) and (2) forms an antigen binding site that specifically binds a first copy of the second epitope, $V_H$ and $V_L$ of polypeptide chains (3) and (4) forms an antigen binding site that specifically binds a second copy of the second epitope, and each $V_HH$ specifically binds a copy of the first epitope (TIGIT). In alternative formats, each anti-TIGIT sdAb may be omitted, or replaced with two identical or different anti-TIGIT sdAbs fused to each other. The monospecific full-length antibody may be replaced with a bispecific full-length antibody to further expand binding specificity.

In some embodiments, there is provided an anti-TIGIT MABP (e.g., BABP) comprising: (a) a first polypeptide comprising from N-terminus to C-terminus: anti-TIGIT sdAb1 moiety-$V_H$—$C_H1$-$C_H2$-$C_H3$; and (b) a second polypeptide comprising from N-terminus to C-terminus: anti-TIGIT sdAb2 moiety-$V_L$—$C_L$, wherein $V_H$ and $V_L$ forms an antigen binding site that specifically binds PD-1, and wherein the anti-TIGIT sdAb1 moiety and the anti-TIGIT sdAb2 moiety each comprises a CDR1 comprising the amino acid sequence of any one of SEQ ID NOs: 36-42, 54, 56-59, 63, 65-67, 69-70, or a variant thereof comprising up to about 3 (such as about any of 1, 2, or 3) amino acid substitutions; and a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210, or a variant thereof comprising up to about 3 (such as about any of 1, 2, or 3) amino acid substitutions. In some embodiments, the anti-TIGIT sdAb1 moiety and the anti-TIGIT sdAb2 moiety each comprises a CDR1 comprising the amino acid sequence of any one of SEQ ID NOs: 36-42, 54, 56-59, 63, 65-67, 69-70; a CDR2 comprising the amino acid sequence of any one of SEQ ID NOs: 106-112, 124, 126-129, 133, 135-137, 139-140; and a CDR3 comprising the amino acid sequence of any one of SEQ ID NOs: 176-182, 194, 196-199, 203, 205-207, 209-210. In some embodiments, the anti-TIGIT sdAb1 moiety and the anti-TIGIT sdAb2 moiety each comprises a VOA domain comprising the amino acid sequence of any one of SEQ ID NO: 253-259, 271, 273-276, 280, 282-284, 286-287. In some embodiments, the anti-TIGIT sdAb1 moiety and the anti-TIGIT sdAb2 moiety are the same. In some embodiments, the anti-TIGIT sdAb1 moiety and the anti-TIGIT sdAb2 moiety are different. In some embodiments, the $V_H$ and $V_L$ domains are derived from pembrolizumab, PD1-BM-min, or nivolumab. In some embodiments, the $V_H$ comprises the amino acid sequence of SEQ ID NO: 385, and the $V_L$ comprises the amino acid sequence of SEQ ID NO: 386. In some embodiments, the $V_H$ comprises the amino acid sequence of SEQ ID NO: 387, and the $V_L$ comprises the amino acid sequence of SEQ ID NO: 388. In some embodiments, the $V_H$ comprises the amino acid sequence of SEQ ID NO: 406, and the $V_L$ comprises the amino acid sequence of SEQ ID NO: 407. In some embodiments, the $V_L$ and anti-TIGIT sdAb2 moiety are fused to each other optionally via a peptide linker, such as a peptide linker comprising the amino acid sequence of any one of SEQ ID NOs: 324 and 370-378. In some embodiments, the $V_H$ and anti-TIGIT sdAb1 moiety are fused to each other optionally via a peptide linker, such as a peptide linker comprising the amino acid sequence of any one of SEQ ID NOs: 324 and 370-378. In some embodiments, the $C_H2$ and $C_H3$ domains are derived from an IgG4 Fc, such as SEQ ID NO: 389. In some embodiments, the $C_H2$ and $C_H3$ domains are derived from an IgG1 Fc, such as SEQ ID NO: 356. In some embodiments, the $C_H2$ and $C_H3$ domains are derived from an effectorless IgG1 Fc, such as SEQ ID NO: 355. In some embodiments, the anti-TIGIT MABP (e.g., BABP) comprises two identical copies of the first polypeptide and two identical copies of the second polypeptide. In some embodiments, the anti-TIGIT sdAb moiety is camelid, chimeric, human, partially humanized, or fully humanized. In some embodiments, the PD-1×TIGIT MABP (e.g., BABP) has the structure as shown in FIG. 21.

In some embodiments, there is provided an anti-TIGIT MABP (e.g., BABP) comprising: (a) a first polypeptide comprising from N-terminus to C-terminus: anti-TIGIT sdAb1 moiety-$V_H$—$C_H1$-$C_H2$-$C_H3$; and (b) a second polypeptide comprising from N-terminus to C-terminus: anti-TIGIT sdAb2 moiety-$V_L$—$C_L$, wherein $V_H$ and $V_L$ forms an antigen binding site that specifically binds PD-L1, and wherein the anti-TIGIT sdAb1 moiety and the anti-TIGIT sdAb2 moiety each comprises a CDR1 comprising the amino acid sequence of any one of SEQ ID NOs: 36-42, 54, 56-59, 63, 65-67, 69-70, or a variant thereof comprising up to about 3 (such as about any of 1, 2, or 3) amino acid substitutions; a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210, or a variant thereof comprising up to about 3 (such as about any of 1, 2, or 3) amino acid substitutions. In some embodiments, the anti-TIGIT sdAb1 moiety and the anti-TIGIT sdAb2 moiety each comprises a CDR1 comprising the amino acid sequence of any one of SEQ ID NOs: 36-42, 54, 56-59, 63, 65-67, 69-70; a CDR2 comprising the amino acid sequence of any one of SEQ ID NOs: 106-112, 124, 126-129, 133, 135-137, 139-140; and a CDR3 comprising the amino acid sequence of any one of SEQ ID NOs: 176-182, 194, 196-199, 203, 205-207, 209-210. In some embodiments, the anti-TIGIT sdAb1 moiety and the anti-TIGIT sdAb2 moiety each comprises a $V_H$H domain comprising the amino acid sequence of any one of SEQ ID NO: 253-259, 271, 273-276, 280, 282-284, 286-287. In some embodiments, the anti-TIGIT sdAb1 moiety and the anti-TIGIT sdAb2 moiety are the same. In some embodiments, the anti-TIGIT sdAb1 moiety and the anti-TIGIT sdAb2 moiety are different. In some embodiments, the $V_H$ and $V_L$ domains are derived from atezolizumab, durvalumab, avelumab, or h53C1. In some embodiments, the h53C1 anti-PD-L1 antibody comprises 1) a $V_H$ comprising an HC-CDR1 comprising the amino acid sequence of SEQ ID NO: 349, an HC-CDR2 comprising the amino acid sequence of SEQ ID NO: 350, and an HC-CDR3 comprising the amino acid sequence of SEQ ID NO: 351, and 2) a $V_L$ comprising an LC-CDR1 comprising the amino acid sequence of SEQ ID NO: 352, an LC-CDR2 comprising the amino acid sequence of SEQ ID NO: 353, and an LC-CDR3 comprising the amino acid sequence of SEQ ID NO: 354. In some embodiments, the h53C1 anti-PD-L1 antibody comprises a $V_H$ comprising the amino acid sequence of SEQ ID NO: 339, and a $V_L$ comprising the amino acid sequence of SEQ ID NO: 340. In some embodiments, the $V_H$ comprises the amino acid sequence of SEQ ID NO: 381, and the $V_L$ comprises the amino acid sequence of SEQ ID NO: 382. In some embodiments, the $V_H$ comprises the amino acid sequence of SEQ ID NO: 379, and the $V_L$ comprises the amino acid sequence of SEQ ID NO: 380. In some embodiments, the $V_H$ comprises the amino acid sequence of SEQ ID NO: 383, and the $V_L$ comprises the amino acid sequence of SEQ ID NO: 384. In some embodiments, the $V_H$ comprises the amino acid sequence of SEQ ID NO: 339, and the $V_L$ comprises the amino acid sequence of SEQ ID NO: 340. In some embodiments, the $V_L$ and anti-TIGIT sdAb2 moiety are fused to each other optionally via a peptide linker, such as a peptide linker comprising the amino acid sequence of any one of SEQ ID NOs: 324 and 370-378. In some embodiments, the $V_H$ and anti-TIGIT sdAb1 moiety are fused to each other optionally via a peptide linker, such as a peptide linker comprising the amino acid sequence of any one of SEQ ID NOs: 324 and 370-378. In some embodiments, the $C_H2$ and $C_H3$ domains are derived from an IgG4 Fc, such as SEQ ID NO: 389. In some embodiments, the $C_H2$ and $C_H3$ domains are derived from an IgG1 Fc, such as SEQ ID NO: 356. In some embodiments, the $C_H2$ and $C_H3$ domains are derived from an effectorless IgG1 Fc, such as SEQ ID NO: 355. In some embodiments, the anti-TIGIT MABP (e.g., BABP) comprises two identical copies of the first polypeptide and two identical copies of the second polypeptide. In some embodiments, the anti-TIGIT sdAb moiety is camelid, chimeric, human, partially humanized, or fully humanized. In some embodiments, the PD-L1×TIGIT MABP (e.g., BABP) has the structure as shown in FIG. 21.

Figure 22:
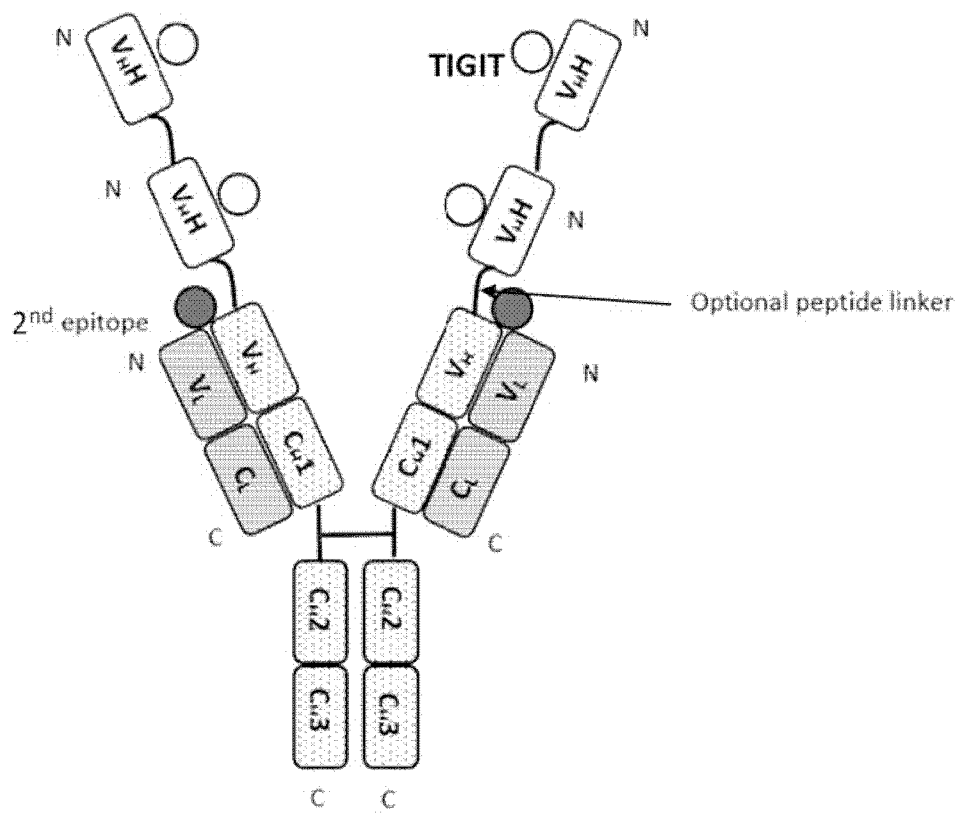
FIG. 22 depicts a schematic structure of an exemplary BABP comprising a monospecific full-length antibody having two identical heavy chains and two identical light chains, and four identical anti-TIGIT sdAbs, wherein fused to the N-terminus of each heavy chain are two identical anti-TIGIT sdAbs, the two anti-TIGIT sdAbs are fused to each other via an optional peptide linker, and the two anti-TIGIT sdAbs are fused to the N-terminus of each heavy chain via an optional peptide linker. Each anti-TIGIT sdAb specifically binds a first epitope (TIGIT). The full-length antibody has two antigen binding sites that each specifically binds a second epitope. For example, the BABP can consist of four polypeptide chains with structures from the N-terminus to the C-terminus as follows: (1) $V_L$—$C_L$; (2) $V_HH$—$V_HH$—$V_H$—$C_H1$-$C_H2$-$C_H3$; (3) $V_HH$—$V_HH$—$V_H$—$C_H1$-$C_H2$-$C_H3$; and (4) $V_L$—$C_L$, wherein $V_H$ and $V_L$ of polypeptide chains (1) and (2) forms an antigen binding site that specifically binds a first copy of the second epitope, $V_H$ and $V_L$ of polypeptide chains (3) and (4) forms an antigen binding site that specifically binds a second copy of the second epitope, and each $V_HH$ specifically binds a copy of the first epitope (TIGIT). In alternative formats, each anti-TIGIT sdAb may be omitted, or replaced with two identical or different anti-TIGIT sdAbs fused to each other. The monospecific full-length antibody may be replaced with a bispecific full-length antibody to further expand binding specificity.

In some embodiments, there is provided an anti-TIGIT MABP (e.g., BABP) comprising: (a) a first polypeptide comprising from N-terminus to C-terminus: anti-TIGIT sdAb1 moiety-anti-TIGIT sdAb2 moiety-$V_H$—$C_H1$-$C_H2$-$C_H3$; and (b) a second polypeptide comprising from N-terminus to C-terminus: $V_L$—$C_L$, wherein $V_H$ and $V_L$ forms an antigen binding site that specifically binds PD-1, and wherein the anti-TIGIT sdAb1 moiety and the anti-TIGIT sdAb2 moiety each comprises a CDR1 comprising the amino acid sequence of any one of SEQ ID NOs: 36-42, 54, 56-59, 63, 65-67, 69-70, or a variant thereof comprising up to about 3 (such as about any of 1, 2, or 3) amino acid substitutions; a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210, or a variant thereof comprising up to about 3 (such as about any of 1, 2, or 3) amino acid substitutions. In some embodiments, the anti-TIGIT sdAb1 moiety and the anti-TIGIT sdAb2 moiety each comprises a CDR1 comprising the amino acid sequence of any one of SEQ ID NOs: 36-42, 54, 56-59, 63, 65-67, 69-70; a CDR2 comprising the amino acid sequence of any one of SEQ ID NOs: 106-112, 124, 126-129, 133, 135-137, 139-140; and a CDR3 comprising the amino acid sequence of any one of SEQ ID NOs: 176-182, 194, 196-199, 203, 205-207, 209-210. In some embodiments, the anti-TIGIT sdAb1 moiety and the anti-TIGIT sdAb2 moiety each comprises a $V_H$H domain comprising the amino acid sequence of any one of SEQ ID NO: 253-259, 271, 273-276, 280, 282-284, 286-287. In some embodiments, the anti-TIGIT sdAb1 moiety and the anti-TIGIT sdAb2 moiety are the same. In some embodiments, the anti-TIGIT sdAb1 moiety and the anti-TIGIT sdAb2 moiety are different. In some embodiments, the $V_H$ and $V_L$ domains are derived from pembrolizumab, PD1-BM-min, or nivolumab. In some embodiments, the $V_H$ comprises the amino acid sequence of SEQ ID NO: 385, and the $V_L$ comprises the amino acid sequence of SEQ ID NO: 386. In some embodiments, the $V_H$ comprises the amino acid sequence of SEQ ID NO: 387, and the $V_L$ comprises the amino acid sequence of SEQ ID NO: 388. In some embodiments, the $V_H$ comprises the amino acid sequence of SEQ ID NO: 406, and the $V_L$ comprises the amino acid sequence of SEQ ID NO: 407. In some embodiments, the anti-TIGIT sdAb1 moiety and the anti-TIGIT sdAb2 moiety, and/or the $V_H$ and anti-TIGIT sdAb2 moiety, are fused to each other optionally via a peptide linker, such as a peptide linker comprising the amino acid sequence of any one of SEQ ID NOs: 324 and 370-378. In some embodiments, the $C_H2$ and $C_H3$ domains are derived from an IgG4 Fc, such as SEQ ID NO: 389. In some embodiments, the $C_H2$ and $C_H3$ domains are derived from an IgG1 Fc, such as SEQ ID NO: 356. In some embodiments, the $C_H2$ and $C_H3$ domains are derived from an effectorless IgG1 Fc, such as SEQ ID NO: 355. In some embodiments, the anti-TIGIT MABP (e.g., BABP) comprises two identical copies of the first polypeptide and two identical copies of the second polypeptide. In some embodiments, the anti-TIGIT sdAb moiety is camelid, chimeric, human, partially humanized, or fully humanized. In some embodiments, the PD-1×TIGIT MABP (e.g., BABP) has the structure as shown in FIG. 22.

In some embodiments, there is provided an anti-TIGIT MABP (e.g., BABP) comprising: (a) a first polypeptide comprising from N-terminus to C-terminus: anti-TIGIT sdAb1 moiety-anti-TIGIT sdAb2 moiety-$V_H$—$C_H1$-$C_H2$-$C_H3$; and (b) a second polypeptide comprising from N-terminus to C-terminus: $V_L$—$C_L$, wherein $V_H$ and $V_L$ forms an antigen binding site that specifically binds PD-L1, and wherein the anti-TIGIT sdAb1 moiety and the anti-TIGIT sdAb2 moiety each comprises a CDR1 comprising the amino acid sequence of any one of SEQ ID NOs: 36-42, 54, 56-59, 63, 65-67, 69-70, or a variant thereof comprising up to about 3 (such as about any of 1, 2, or 3) amino acid substitutions; a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210, or a variant thereof comprising up to about 3 (such as about any of 1, 2, or 3) amino acid substitutions. In some embodiments, the anti-TIGIT sdAb1 moiety and the anti-TIGIT sdAb2 moiety each comprises a CDR1 comprising the amino acid sequence of any one of SEQ ID NOs: 36-42, 54, 56-59, 63, 65-67, 69-70; a CDR2 comprising the amino acid sequence of any one of SEQ ID NOs: 106-112, 124, 126-129, 133, 135-137, 139-140; and a CDR3 comprising the amino acid sequence of any one of SEQ ID NOs: 176-182, 194, 196-199, 203, 205-207, 209-210. In some embodiments, the anti-TIGIT sdAb1 moiety and the anti-TIGIT sdAb2 moiety each comprises a $V_H$H domain comprising the amino acid sequence of any one of SEQ ID NO: 253-259, 271, 273-276, 280, 282-284, 286-287. In some embodiments, the anti-TIGIT sdAb1 moiety and the anti-TIGIT sdAb2 moiety are the same. In some embodiments, the anti-TIGIT sdAb1 moiety and the anti-TIGIT sdAb2 moiety are different. In some embodiments, the $V_H$ and $V_L$ domains are derived from atezolizumab, durvalumab, avelumab, or h53C1. In some embodiments, the h53C1 anti-PD-L1 antibody comprises 1) a $V_H$ comprising an HC-CDR1 comprising the amino acid sequence of SEQ ID NO: 349, an HC-CDR2 comprising the amino acid sequence of SEQ ID NO: 350, and an HC-CDR3 comprising the amino acid sequence of SEQ ID NO: 351, and 2) a $V_L$ comprising an LC-CDR1 comprising the amino acid sequence of SEQ ID NO: 352, an LC-CDR2 comprising the amino acid sequence of SEQ ID NO: 353, and an LC-CDR3 comprising the amino acid sequence of SEQ ID NO: 354. In some embodiments, the h53C1 anti-PD-L1 antibody comprises a $V_H$ comprising the amino acid sequence of SEQ ID NO: 339, and a $V_L$ comprising the amino acid sequence of SEQ ID NO: 340. In some embodiments, the $V_H$ comprises the amino acid sequence of SEQ ID NO: 381, and the $V_L$ comprises the amino acid sequence of SEQ ID NO: 382. In some embodiments, the $V_H$ comprises the amino acid sequence of SEQ ID NO: 379, and the $V_L$ comprises the amino acid sequence of SEQ ID NO: 380. In some embodiments, the $V_H$ comprises the amino acid sequence of SEQ ID NO: 383, and the $V_L$ comprises the amino acid sequence of SEQ ID NO: 384. In some embodiments, the $V_H$ comprises the amino acid sequence of SEQ ID NO: 339, and the $V_L$ comprises the amino acid sequence of SEQ ID NO: 340. In some embodiments, the anti-TIGIT sdAb1 moiety and the anti-TIGIT sdAb2 moiety, and/or the $V_H$ and anti-TIGIT sdAb2 moiety, are fused to each other optionally via a peptide linker, such as a peptide linker comprising the amino acid sequence of any one of SEQ ID NOs: 324 and 370-378. In some embodiments, the $C_H2$ and $C_H3$ domains are derived from an IgG4 Fc, such as SEQ ID NO: 389. In some embodiments, the $C_H2$ and $C_H3$ domains are derived from an IgG1 Fc, such as SEQ ID NO: 356. In some embodiments, the $C_H2$ and $C_H3$ domains are derived from an effectorless IgG1 Fc, such as SEQ ID NO: 355. In some embodiments, the anti-TIGIT MABP (e.g., BABP) comprises two identical copies of the first polypeptide and two identical copies of the second polypeptide. In some embodiments, the anti-TIGIT sdAb moiety is camelid, chimeric, human, partially humanized, or fully humanized. In some embodiments, the PD-L1×TIGIT MABP (e.g., BABP) has the structure as shown in FIG. 22.

Figure 23:
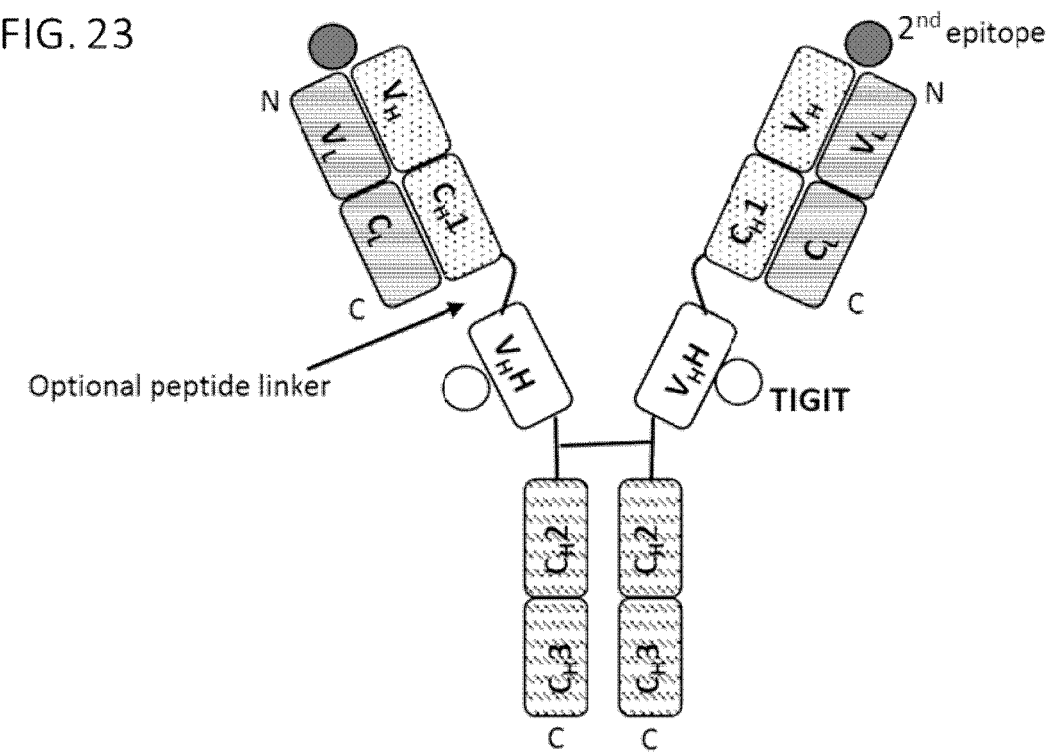
FIG. 23 depicts a schematic structure of an exemplary BABP comprising two identical antigen-binding (Fab) fragments, two identical anti-TIGIT sdAbs, and an Fc region, wherein the N-terminus of each anti-TIGIT sdAb is fused to the C-terminus of the $C_H1$ region of the Fab fragment via an optional peptide linker and the C-terminus of each anti-TIGIT sdAb is fused to the N-terminus of the $C_H2$ region of the Fc region. Each anti-TIGIT sdAb specifically binds a first epitope (TIGIT). Each Fab fragment specifically binds a second epitope. For example, the BABP can consist of four polypeptide chains with structures from the N-terminus to the C-terminus as follows: (1) $V_L$—$C_L$; (2) $V_H$—$C_H1$-$V_HH$—$C_H2$-$C_H3$; (3) $V_H$—$C_H1$-$V_HH$—$C_H2$-$C_H3$; and (4) $V_L$—$C_L$, wherein $V_H$ and $V_L$ of polypeptide chains (1) and (2) forms an antigen binding site that specifically binds a first copy of the second epitope, $V_H$ and $V_L$ of polypeptide chains (3) and (4) forms an antigen binding site that specifically binds a second copy of the second epitope, and each $V_HH$ specifically binds a copy of the first epitope (TIGIT). In alternative formats, each anti-TIGIT sdAb may be omitted, or replaced with two identical or different anti-TIGIT sdAbs fused to each other. In alternative formats, to expand specificity, the two Fab fragments can specifically bind different epitopes, and/or the $V_HH$ fragments can specifically bind different epitopes.

In some embodiments, there is provided an anti-TIGIT BABP comprising: (a) a first polypeptide comprising from N-terminus to C-terminus: $V_H$—$C_H1$-anti-TIGIT sdAb moiety-$C_H2$-$C_H3$; and (b) a second polypeptide comprising from N-terminus to C-terminus: $V_L$—$C_L$, wherein $V_H$ and $V_L$ forms an antigen binding site that specifically binds PD-1, and wherein the anti-TIGIT sdAb moiety comprises a CDR1 comprising the amino acid sequence of any one of SEQ ID NOs: 36-42, 54, 56-59, 63, 65-67, 69-70, or a variant thereof comprising up to about 3 (such as about any of 1, 2, or 3) amino acid substitutions; a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210, or a variant thereof comprising up to about 3 (such as about any of 1, 2, or 3) amino acid substitutions. In some embodiments, the anti-TIGIT sdAb moiety comprises a CDR1 comprising the amino acid sequence of any one of SEQ ID NOs: 36-42, 54, 56-59, 63, 65-67, 69-70; a CDR2 comprising the amino acid sequence of any one of SEQ ID NOs: 106-112, 124, 126-129, 133, 135-137, 139-140; and a CDR3 comprising the amino acid sequence of any one of SEQ ID NOs: 176-182, 194, 196-199, 203, 205-207, 209-210. In some embodiments, the anti-TIGIT sdAb moiety comprises a $V_H$H domain comprising the amino acid sequence of any one of SEQ ID NO: 253-259, 271, 273-276, 280, 282-284, 286-287. In some embodiments, the $V_H$ and $V_L$ domains are derived from pembrolizumab, PD1-BM-min, or nivolumab. In some embodiments, the $V_H$ comprises the amino acid sequence of SEQ ID NO: 385, and the $V_L$ comprises the amino acid sequence of SEQ ID NO: 386. In some embodiments, the $V_H$ comprises the amino acid sequence of SEQ ID NO: 387, and the $V_L$ comprises the amino acid sequence of SEQ ID NO: 388. In some embodiments, the $V_H$ comprises the amino acid sequence of SEQ ID NO: 406, and the $V_L$ comprises the amino acid sequence of SEQ ID NO: 407. In some embodiments, the $C_H1$ and the anti-TIGIT sdAb moiety are fused to each other optionally via a peptide linker, such as a peptide linker comprising the amino acid sequence of any one of SEQ ID NOs: 324 and 370-378. In some embodiments, the $C_H2$ and $C_H3$ domains are derived from an IgG4 Fc, such as SEQ ID NO: 389. In some embodiments, the $C_H2$ and $C_H3$ domains are derived from an IgG1 Fc, such as SEQ ID NO: 356. In some embodiments, the $C_H2$ and $C_H3$ domains are derived from an effectorless IgG1 Fc, such as SEQ ID NO: 355. In some embodiments, the anti-TIGIT BABP comprises two identical copies of the first polypeptide and two identical copies of the second polypeptide. In some embodiments, the anti-TIGIT sdAb moiety is camelid, chimeric, human, partially humanized, or fully humanized. In some embodiments, the PD-1×TIGIT BABP has the structure as shown in FIG. 23.

In some embodiments, there is provided an anti-TIGIT BABP comprising: (a) a first polypeptide comprising from N-terminus to C-terminus: $V_H$—$C_H1$-anti-TIGIT sdAb moiety-$C_H2$-$C_H3$; and (b) a second polypeptide comprising from N-terminus to C-terminus: $V_L$—$C_L$, wherein $V_H$ and $V_L$ forms an antigen binding site that specifically binds PD-L1, and wherein the anti-TIGIT sdAb moiety comprises a CDR1 comprising the amino acid sequence of any one of SEQ ID NOs: 36-42, 54, 56-59, 63, 65-67, 69-70, or a variant thereof comprising up to about 3 (such as about any of 1, 2, or 3) amino acid substitutions; a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210, or a variant thereof comprising up to about 3 (such as about any of 1, 2, or 3) amino acid substitutions. In some embodiments, the anti-TIGIT sdAb moiety comprises a CDR1 comprising the amino acid sequence of any one of SEQ ID NOs: 36-42, 54, 56-59, 63, 65-67, 69-70; a CDR2 comprising the amino acid sequence of any one of SEQ ID NOs: 106-112, 124, 126-129, 133, 135-137, 139-140; and a CDR3 comprising the amino acid sequence of any one of SEQ ID NOs: 176-182, 194, 196-199, 203, 205-207, 209-210. In some embodiments, the anti-TIGIT sdAb moiety comprises a $V_H H$ domain comprising the amino acid sequence of any one of SEQ ID NO: 253-259, 271, 273-276, 280, 282-284, 286-287. In some embodiments, the $V_H$ and $V_L$ domains are derived from atezolizumab, durvalumab, avelumab, or h53C1. In some embodiments, the h53C1 anti-PD-L1 antibody comprises 1) a $V_H$ comprising an HC-CDR1 comprising the amino acid sequence of SEQ ID NO: 349, an HC-CDR2 comprising the amino acid sequence of SEQ ID NO: 350, and an HC-CDR3 comprising the amino acid sequence of SEQ ID NO: 351, and 2) a $V_L$ comprising an LC-CDR1 comprising the amino acid sequence of SEQ ID NO: 352, an LC-CDR2 comprising the amino acid sequence of SEQ ID NO: 353, and an LC-CDR3 comprising the amino acid sequence of SEQ ID NO: 354. In some embodiments, the h53C1 anti-PD-L1 antibody comprises a $V_H$ comprising the amino acid sequence of SEQ ID NO: 339, and a $V_L$ comprising the amino acid sequence of SEQ ID NO: 340. In some embodiments, the $V_H$ comprises the amino acid sequence of SEQ ID NO: 381, and the $V_L$ comprises the amino acid sequence of SEQ ID NO: 382. In some embodiments, the $V_H$ comprises the amino acid sequence of SEQ ID NO: 379, and the $V_L$ comprises the amino acid sequence of SEQ ID NO: 380. In some embodiments, the $V_H$ comprises the amino acid sequence of SEQ ID NO: 383, and the $V_L$ comprises the amino acid sequence of SEQ ID NO: 384. In some embodiments, the $V_H$ comprises the amino acid sequence of SEQ ID NO: 339, and the $V_L$ comprises the amino acid sequence of SEQ ID NO: 340. In some embodiments, the $C_H 1$ and the anti-TIGIT sdAb moiety are fused to each other optionally via a peptide linker, such as a peptide linker comprising the amino acid sequence of any one of SEQ ID NOs: 324 and 370-378. In some embodiments, the $C_H 2$ and $C_H 3$ domains are derived from an IgG4 Fc, such as SEQ ID NO: 389. In some embodiments, the $C_H 2$ and $C_H 3$ domains are derived from an IgG1 Fc, such as SEQ ID NO: 356. In some embodiments, the $C_H 2$ and $C_H 3$ domains are derived from an effectorless IgG1 Fc, such as SEQ ID NO: 355. In some embodiments, the anti-TIGIT BABP comprises two identical copies of the first polypeptide and two identical copies of the second polypeptide. In some embodiments, the anti-TIGIT sdAb moiety is camelid, chimeric, human, partially humanized, or fully humanized. In some embodiments, the PD-L1×TIGIT BABP has the structure as shown in FIG. 23.

Figure 24:
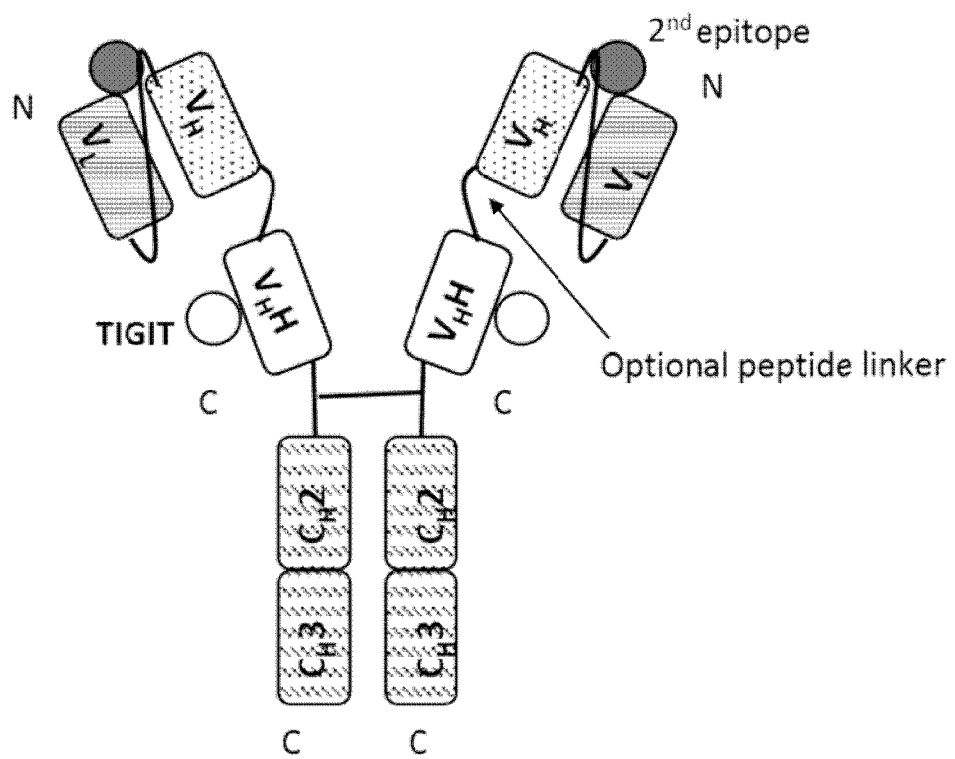
FIG. 24 depicts a schematic structure of an exemplary BABP comprising two identical single chain variable fragments (scFvs), two identical anti-TIGIT sdAbs, and an Fc region, wherein the N-terminus of each anti-TIGIT sdAb is fused to the C-terminus of an scFv via an optional peptide linker and the C-terminus of each anti-TIGIT sdAb is fused to the N-terminus of the Fc region. Each anti-TIGIT sdAb specifically binds a first epitope (TIGIT). Each scFv specifically binds a second epitope. For example, the BABP can consist of two polypeptide chains each with a structure from the N-terminus to the C-terminus as follows: $V_L$—$V_H$—$V_HH$—$C_H2$-$C_H3$, wherein $V_H$ and $V_L$ of each polypeptide chain forms a scFv domain that specifically binds a copy of the second epitope, and each $V_HH$ specifically binds a copy of the first epitope (TIGIT). In alternative formats, the scFv domain can comprise from the N-terminus to the C-terminus: $V_H$—$V_L$. In alternative formats, each anti-TIGIT sdAb may be omitted, or replaced with two identical or different anti-TIGIT sdAbs fused to each other. Additionally, to expand specificity, the two scFvs can specifically bind different epitopes, and/or the $V_HH$ fragments can specifically bind different epitopes.

In some embodiments, there is provided an anti-TIGIT BABP comprising a polypeptide comprising from N-terminus to C-terminus: $V_L$—$V_H$-anti-TIGIT sdAb moiety-$C_H 2$-$C_H 3$, wherein the $V_L$ and $V_H$ together forms an scFv that specifically binds PD-1, and wherein the anti-TIGIT sdAb moiety comprises a CDR1 comprising the amino acid sequence of any one of SEQ ID NOs: 36-42, 54, 56-59, 63, 65-67, 69-70, or a variant thereof comprising up to about 3 (such as about any of 1, 2, or 3) amino acid substitutions; a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210, or a variant thereof comprising up to about 3 (such as about any of 1, 2, or 3) amino acid substitutions. In some embodiments, there is provided an anti-TIGIT BABP comprising a polypeptide comprising from N-terminus to C-terminus: $V_H$—$V_L$-anti-TIGIT sdAb moiety-$C_H 2$-$C_H 3$, wherein the $V_L$ and $V_H$ together forms an scFv that specifically binds PD-1, and wherein the anti-TIGIT sdAb moiety comprises a CDR1 comprising the amino acid sequence of any one of SEQ ID NOs: 36-42, 54, 56-59, 63, 65-67, 69-70, or a variant thereof comprising up to about 3 (such as about any of 1, 2, or 3) amino acid substitutions; a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210, or a variant thereof comprising up to about 3 (such as about any of 1, 2, or 3) amino acid substitutions. In some embodiments, the anti-TIGIT sdAb moiety comprises a CDR1 comprising the amino acid sequence of any one of SEQ ID NOs: 36-42, 54, 56-59, 63, 65-67, 69-70; a CDR2 comprising the amino acid sequence of any one of SEQ ID NOs: 106-112, 124, 126-129, 133, 135-137, 139-140; and a CDR3 comprising the amino acid sequence of any one of SEQ ID NOs: 176-182, 194, 196-199, 203, 205-207, 209-210. In some embodiments, the anti-TIGIT sdAb moiety comprises a $V_H H$ domain comprising the amino acid sequence of any one of SEQ ID NO: 253-259, 271, 273-276, 280, 282-284, 286-287. In some embodiments, the scFv (or the $V_L$ and $V_H$ that forms the scFv) is derived from pembrolizumab, PD1-BM-min, or nivolumab. In some embodiments, the $V_H$ comprises the amino acid sequence of SEQ ID NO: 385, and the $V_L$ comprises the amino acid sequence of SEQ ID NO: 386. In some embodiments, the $V_H$ comprises the amino acid sequence of SEQ ID NO: 387, and the $V_L$ comprises the amino acid sequence of SEQ ID NO: 388. In some embodiments, the $V_H$ comprises the amino acid sequence of SEQ ID NO: 406, and the $V_L$ comprises the amino acid sequence of SEQ ID NO: 407. In some embodiments, the $V_H$ and $V_L$ that forms the scFv, and/or the scFv and the anti-TIGIT sdAb moiety, are fused to each other optionally via a peptide linker, such as a peptide linker comprising the amino acid sequence of any one of SEQ ID NOs: 324 and 370-378. In some embodiments, the $C_H 2$ and $C_H 3$ domains are derived from an IgG4 Fc, such as SEQ ID NO: 389. In some embodiments, the $C_H 2$ and $C_H 3$ domains are derived from an IgG1 Fc, such as SEQ ID NO: 356. In some embodiments, the $C_H 2$ and $C_H 3$ domains are derived from an effectorless IgG1 Fc, such as SEQ ID NO: 355. In some embodiments, the anti-TIGIT BABP comprises two identical copies of the polypeptide. In some embodiments, the anti-TIGIT sdAb moiety is camelid, chimeric, human, partially humanized, or fully humanized. In some embodiments, the PD-1×TIGIT BABP has the structure as shown in FIG. 24.

In some embodiments, there is provided an anti-TIGIT BABP comprising a polypeptide comprising from N-terminus to C-terminus: $V_L$—$V_H$-anti-TIGIT sdAb moiety-$C_H 2$-$C_H 3$, wherein the $V_L$ and $V_H$ together forms an scFv that specifically binds PD-L1, and wherein the anti-TIGIT sdAb moiety comprises a CDR1 comprising the amino acid sequence of any one of SEQ ID NOs: 36-42, 54, 56-59, 63, 65-67, 69-70, or a variant thereof comprising up to about 3 (such as about any of 1, 2, or 3) amino acid substitutions; a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210, or a variant thereof comprising up to about 3 (such as about any of 1, 2, or 3) amino acid substitutions. In some embodiments, there is provided an anti-TIGIT BABP comprising a polypeptide comprising from N-terminus to C-terminus: $V_H$—$V_L$-anti-TIGIT sdAb moiety-$C_H2$-$C_H3$, wherein the $V_L$ and $V_H$ together forms an scFv that specifically binds PD-L1, and wherein the anti-TIGIT sdAb moiety comprises a CDR1 comprising the amino acid sequence of any one of SEQ ID NOs: 36-42, 54, 56-59, 63, 65-67, 69-70, or a variant thereof comprising up to about 3 (such as about any of 1, 2, or 3) amino acid substitutions; a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210, or a variant thereof comprising up to about 3 (such as about any of 1, 2, or 3) amino acid substitutions. In some embodiments, the anti-TIGIT sdAb moiety comprises a CDR1 comprising the amino acid sequence of any one of SEQ ID NOs: 36-42, 54, 56-59, 63, 65-67, 69-70; a CDR2 comprising the amino acid sequence of any one of SEQ ID NOs: 106-112, 124, 126-129, 133, 135-137, 139-140; and a CDR3 comprising the amino acid sequence of any one of SEQ ID NOs: 176-182, 194, 196-199, 203, 205-207, 209-210. In some embodiments, the anti-TIGIT sdAb moiety comprises a $V_HH$ domain comprising the amino acid sequence of any one of SEQ ID NO: 253-259, 271, 273-276, 280, 282-284, 286-287. In some embodiments, the scFv (or the $V_L$ and $V_H$ that forms the scFv) is derived from atezolizumab, durvalumab, avelumab, or h53C1. In some embodiments, the h53C1 anti-PD-L1 antibody comprises 1) a $V_H$ comprising an HC-CDR1 comprising the amino acid sequence of SEQ ID NO: 349, an HC-CDR2 comprising the amino acid sequence of SEQ ID NO: 350, and an HC-CDR3 comprising the amino acid sequence of SEQ ID NO: 351, and 2) a $V_L$ comprising an LC-CDR1 comprising the amino acid sequence of SEQ ID NO: 352, an LC-CDR2 comprising the amino acid sequence of SEQ ID NO: 353, and an LC-CDR3 comprising the amino acid sequence of SEQ ID NO: 354. In some embodiments, the h53C1 anti-PD-L1 antibody comprises a $V_H$ comprising the amino acid sequence of SEQ ID NO: 339, and a $V_L$ comprising the amino acid sequence of SEQ ID NO: 340. In some embodiments, the $V_H$ comprises the amino acid sequence of SEQ ID NO: 381, and the $V_L$ comprises the amino acid sequence of SEQ ID NO: 382. In some embodiments, the $V_H$ comprises the amino acid sequence of SEQ ID NO: 379, and the $V_L$ comprises the amino acid sequence of SEQ ID NO: 380. In some embodiments, the $V_H$ comprises the amino acid sequence of SEQ ID NO: 383, and the $V_L$ comprises the amino acid sequence of SEQ ID NO: 384. In some embodiments, the $V_H$ comprises the amino acid sequence of SEQ ID NO: 339, and the $V_L$ comprises the amino acid sequence of SEQ ID NO: 340. In some embodiments, the $V_H$ and $V_L$ that forms the scFv, and/or the scFv and the anti-TIGIT sdAb moiety, are fused to each other optionally via a peptide linker, such as a peptide linker comprising the amino acid sequence of any one of SEQ ID NOs: 324 and 370-378. In some embodiments, the $C_H2$ and $C_H3$ domains are derived from an IgG4 Fc, such as SEQ ID NO: 389. In some embodiments, the $C_H2$ and $C_H3$ domains are derived from an IgG1 Fc, such as SEQ ID NO: 356. In some embodiments, the $C_H2$ and $C_H3$ domains are derived from an effectorless IgG1 Fc, such as SEQ ID NO: 355. In some embodiments, the anti-TIGIT BABP comprises two identical copies of the polypeptide. In some embodiments, the anti-TIGIT sdAb moiety is camelid, chimeric, human, partially humanized, or fully humanized. In some embodiments, the PD-L1×TIGIT BABP has the structure as shown in FIG. 24.

Figure 25:
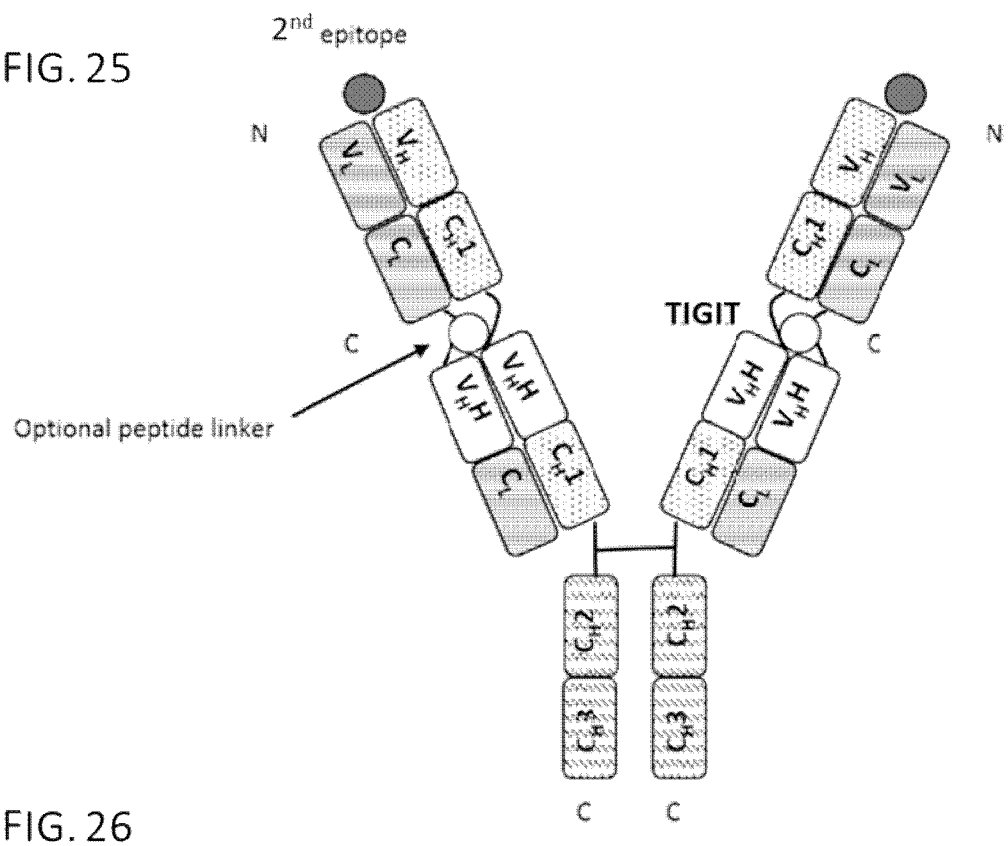
FIG. 25 depicts a schematic structure of an exemplary BABP comprising two identical Fab fragments, two identical Fab-like fragments each comprising two $V_HH$ fragments, and an Fc region. In each Fab-like fragment, the $V_H$ and $V_L$ regions are each replaced by an anti-TIGIT sdAb. Each Fab-like fragment specifically binds a first epitope (TIGIT). Each Fab fragment specifically binds a second epitope. For example, the BABP can consist of four polypeptide chains with structures from the N-terminus to the C-terminus as follows: (1) $V_L$—$C_L$—$V_HH$—$C_L$; (2) $V_H$—$C_H1$-$V_HH$—$C_H1$-$C_H2$-$C_H3$; (3) $V_H$—$C_H1$-$V_HH$—$C_H1$-$C_H2$-$C_H3$; and (4) $V_L$—$C_L$—$V_HH$—$C_L$, wherein $V_H$ and $V_L$ of polypeptide chains (1) and (2) forms an antigen binding site that specifically binds a first copy of the second epitope, $V_H$ and $V_L$ of polypeptide chains (3) and (4) forms an antigen binding site that specifically binds a second copy of the second epitope, and each $V_HH$ specifically binds a copy of the first epitope (TIGIT). In alternative formats, to expand specificity, the two Fab fragments can specifically bind different epitopes, and/or the Fab-like fragments can specifically bind different epitopes (e.g., different epitopes from TIGIT).

In some embodiments, there is provided an anti-TIGIT MABP (e.g., BABP) comprising: (a) a first polypeptide comprising from N-terminus to C-terminus: $V_H$—$C_H1$-anti-TIGIT sdAb1 moiety-$C_H1$-$C_H2$-$C_H3$; and (b) a second polypeptide comprising from N-terminus to C-terminus: $V_L$—$C_L$-anti-TIGIT sdAb2 moiety-$C_L$, wherein $V_H$ and $V_L$ forms an antigen binding site that specifically binds PD-1, and wherein the anti-TIGIT sdAb1 moiety and the anti-TIGIT sdAb2 moiety each comprises a CDR1 comprising the amino acid sequence of any one of SEQ ID NOs: 36-42, 54, 56-59, 63, 65-67, 69-70, or a variant thereof comprising up to about 3 (such as about any of 1, 2, or 3) amino acid substitutions; a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210, or a variant thereof comprising up to about 3 (such as about any of 1, 2, or 3) amino acid substitutions. In some embodiments, the anti-TIGIT sdAb1 moiety and the anti-TIGIT sdAb2 moiety each comprises a CDR1 comprising the amino acid sequence of any one of SEQ ID NOs: 36-42, 54, 56-59, 63, 65-67, 69-70; a CDR2 comprising the amino acid sequence of any one of SEQ ID NOs: 106-112, 124, 126-129, 133, 135-137, 139-140; and a CDR3 comprising the amino acid sequence of any one of SEQ ID NOs: 176-182, 194, 196-199, 203, 205-207, 209-210. In some embodiments, the anti-TIGIT sdAb1 moiety and the anti-TIGIT sdAb2 moiety each comprises a $V_HH$ domain comprising the amino acid sequence of any one of SEQ ID NO: 253-259, 271, 273-276, 280, 282-284, 286-287. In some embodiments, the anti-TIGIT sdAb1 moiety and the anti-TIGIT sdAb2 moiety are the same. In some embodiments, the anti-TIGIT sdAb1 moiety and the anti-TIGIT sdAb2 moiety are different. In some embodiments, the $V_H$ and $V_L$ domains are derived from pembrolizumab, PD1-BM-min, or nivolumab. In some embodiments, the $V_H$ comprises the amino acid sequence of SEQ ID NO: 385, and the $V_L$ comprises the amino acid sequence of SEQ ID NO: 386. In some embodiments, the $V_H$ comprises the amino acid sequence of SEQ ID NO: 387, and the $V_L$ comprises the amino acid sequence of SEQ ID NO: 388. In some embodiments, the $V_H$ comprises the amino acid sequence of SEQ ID NO: 406, and the $V_L$ comprises the amino acid sequence of SEQ ID NO: 407. In some embodiments, the $C_H1$ and the anti-TIGIT sdAb1 moiety, and/or $C_L$ and the anti-TIGIT sdAb2 moiety, are fused to each other optionally via a peptide linker, such as a peptide linker comprising the amino acid sequence of any one of SEQ ID NOs: 324 and 370-378. In some embodiments, the $C_H2$ and $C_H3$ domains are derived from an IgG4 Fc, such as SEQ ID NO: 389. In some embodiments, the $C_H2$ and $C_H3$ domains are derived from an IgG1 Fc, such as SEQ ID NO: 356. In some embodiments, the $C_H2$ and $C_H3$ domains are derived from an effectorless IgG1 Fc, such as SEQ ID NO: 355. In some embodiments, the anti-TIGIT MABP (e.g., BABP) comprises two identical copies of the first polypeptide and two identical copies of the second polypeptide. In some embodiments, the anti-TIGIT sdAb moiety is camelid, chimeric, human, partially humanized, or fully humanized. In some embodiments, the PD-1×TIGIT MABP (e.g., BABP) has the structure as shown in FIG. 25.

In some embodiments, there is provided an anti-TIGIT MABP (e.g., BABP) comprising: (a) a first polypeptide comprising from N-terminus to C-terminus: $V_H$—$C_H1$-anti-TIGIT sdAb1 moiety-$C_H1$-$C_H2$-$C_H3$; and (b) a second polypeptide comprising from N-terminus to C-terminus: $V_L$—$C_L$-anti-TIGIT sdAb2 moiety-$C_L$, wherein $V_H$ and $V_L$ forms an antigen binding site that specifically binds PD-L1, and wherein the anti-TIGIT sdAb1 moiety and the anti-TIGIT sdAb2 moiety each comprises a CDR1 comprising the amino acid sequence of any one of SEQ ID NOs: 36-42, 54, 56-59, 63, 65-67, 69-70, or a variant thereof comprising up to about 3 (such as about any of 1, 2, or 3) amino acid substitutions; a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210, or a variant thereof comprising up to about 3 (such as about any of 1, 2, or 3) amino acid substitutions. In some embodiments, the anti-TIGIT sdAb1 moiety and the anti-TIGIT sdAb2 moiety each comprises a CDR1 comprising the amino acid sequence of any one of SEQ ID NOs: 36-42, 54, 56-59, 63, 65-67, 69-70; a CDR2 comprising the amino acid sequence of any one of SEQ ID NOs: 106-112, 124, 126-129, 133, 135-137, 139-140; and a CDR3 comprising the amino acid sequence of any one of SEQ ID NOs: 176-182, 194, 196-199, 203, 205-207, 209-210. In some embodiments, the anti-TIGIT sdAb1 moiety and the anti-TIGIT sdAb2 moiety each comprises a $V_HH$ domain comprising the amino acid sequence of any one of SEQ ID NO: 253-259, 271, 273-276, 280, 282-284, 286-287. In some embodiments, the anti-TIGIT sdAb1 moiety and the anti-TIGIT sdAb2 moiety are the same. In some embodiments, the anti-TIGIT sdAb1 moiety and the anti-TIGIT sdAb2 moiety are different. In some embodiments, the $V_H$ and $V_L$ domains are derived from atezolizumab, durvalumab, avelumab, or h53C1. In some embodiments, the h53C1 anti-PD-L1 antibody comprises 1) a $V_H$ comprising an HC-CDR1 comprising the amino acid sequence of SEQ ID NO: 349, an HC-CDR2 comprising the amino acid sequence of SEQ ID NO: 350, and an HC-CDR3 comprising the amino acid sequence of SEQ ID NO: 351, and 2) a $V_L$ comprising an LC-CDR1 comprising the amino acid sequence of SEQ ID NO: 352, an LC-CDR2 comprising the amino acid sequence of SEQ ID NO: 353, and an LC-CDR3 comprising the amino acid sequence of SEQ ID NO: 354. In some embodiments, the h53C1 anti-PD-L1 antibody comprises a $V_H$ comprising the amino acid sequence of SEQ ID NO: 339, and a $V_L$ comprising the amino acid sequence of SEQ ID NO: 340. In some embodiments, the $V_H$ comprises the amino acid sequence of SEQ ID NO: 381, and the $V_L$ comprises the amino acid sequence of SEQ ID NO: 382. In some embodiments, the $V_H$ comprises the amino acid sequence of SEQ ID NO: 379, and the $V_L$ comprises the amino acid sequence of SEQ ID NO: 380. In some embodiments, the $V_H$ comprises the amino acid sequence of SEQ ID NO: 383, and the $V_L$ comprises the amino acid sequence of SEQ ID NO: 384. In some embodiments, the $V_H$ comprises the amino acid sequence of SEQ ID NO: 339, and the $V_L$ comprises the amino acid sequence of SEQ ID NO: 340. In some embodiments, the $C_H1$ and the anti-TIGIT sdAb1 moiety, and/or $C_L$ and the anti-TIGIT sdAb2 moiety, are fused to each other optionally via a peptide linker, such as a peptide linker comprising the amino acid sequence of any one of SEQ ID NOs: 324 and 370-378. In some embodiments, the $C_H2$ and $C_H3$ domains are derived from an IgG4 Fc, such as SEQ ID NO: 389. In some embodiments, the $C_H2$ and $C_H3$ domains are derived from an IgG1 Fc, such as SEQ ID NO: 356. In some embodiments, the $C_H2$ and $C_H3$ domains are derived from an effectorless IgG1 Fc, such as SEQ ID NO: 355. In some embodiments, the anti-TIGIT MABP (e.g., BABP) comprises two identical copies of the first polypeptide and two identical copies of the second polypeptide. In some embodiments, the anti-TIGIT sdAb moiety is camelid, chimeric, human, partially humanized, or fully humanized. In some embodiments, the PD-L1×TIGIT MABP (e.g., BABP) has the structure as shown in FIG. 25.

Figure 26:
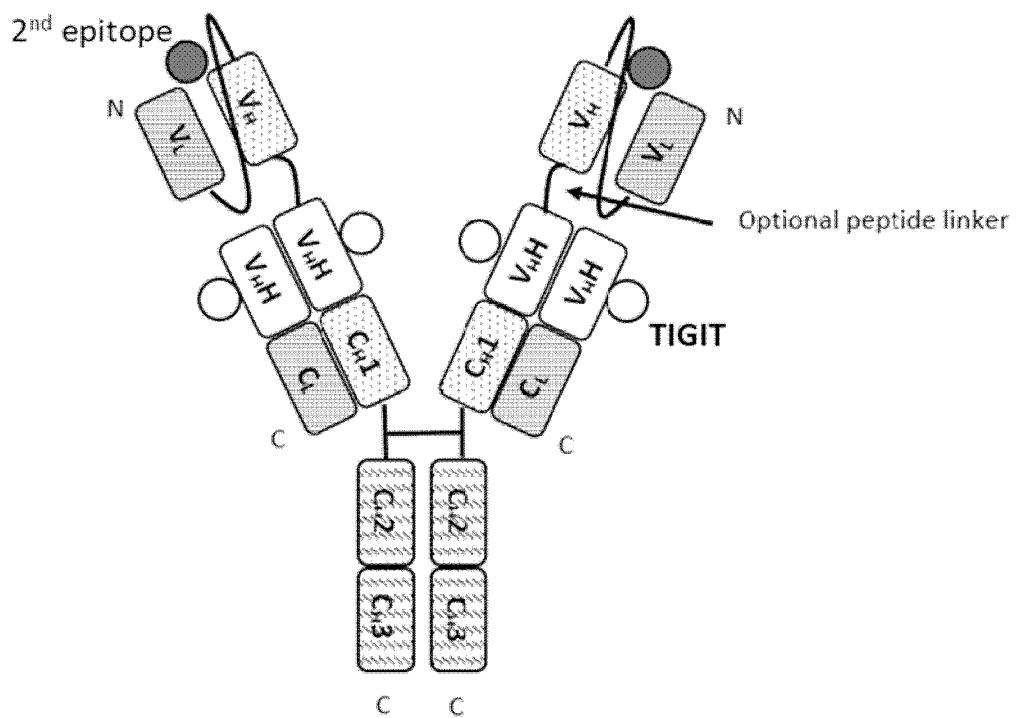
FIG. 26 depicts a schematic structure of an exemplary BABP comprising two identical scFvs, two identical Fab-like fragments each comprising two $V_HH$ fragments, and an Fc region. In each Fab-like fragment, the $V_H$ and $V_L$ regions are each replaced by an anti-TIGIT sdAb. Each Fab-like fragment specifically binds a first epitope (TIGIT). Each scFv specifically binds a second epitope. For example, the BABP can consist of four polypeptide chains with structures from the N-terminus to the C-terminus as follows: (1) $V_HH$—$C_L$; (2) $V_L$—$V_H$—$V_HH$—$C_H1$-$C_H2$-$C_H3$; (3) $V_L$—$V_H$—$V_HH$—$C_H1$-$C_H2$-$C_H3$; and (4) $V_HH$—$C_L$, wherein $V_H$ and $V_L$ of polypeptide chains (2) and (3) each forms an scFv that specifically binds a copy of the second epitope, and each $V_HH$ specifically binds a copy of the first epitope (TIGIT). In alternative formats, the C-terminus of the scFv may be fused to the N-terminus of the chain in the Fab-like fragment comprising $V_HH$—$C_L$; and/or the scFv domain can comprise from the N-terminus to the C-terminus: $V_H$—$V_L$. Additionally, to expand specificity, the two scFvs can specifically bind different epitopes, and/or the $V_H$H fragments can specifically bind different epitopes (e.g., different epitopes from TIGIT).

In some embodiments, there is provided an anti-TIGIT MABP (e.g., BABP) comprising: (a) a first polypeptide comprising from N-terminus to C-terminus: $V_L$—$V_H$-anti-TIGIT sdAb1 moiety-$C_H2$-$C_H3$; and (b) a second polypeptide comprising from N-terminus to C-terminus: anti-TIGIT sdAb2 moiety-$C_L$, wherein the $V_L$ and $V_H$ that forms the scFv specifically binds PD-1, and wherein the anti-TIGIT sdAb1 moiety and the anti-TIGIT sdAb2 moiety each comprises a CDR1 comprising the amino acid sequence of any one of SEQ ID NOs: 36-42, 54, 56-59, 63, 65-67, 69-70, or a variant thereof comprising up to about 3 (such as about any of 1, 2, or 3) amino acid substitutions; a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210, or a variant thereof comprising up to about 3 (such as about any of 1, 2, or 3) amino acid substitutions. In some embodiments, there is provided an anti-TIGIT MABP (e.g., BABP) comprising: (a) a first polypeptide comprising from N-terminus to C-terminus: $V_H$—$V_L$-anti-TIGIT sdAb1 moiety-$C_H2$-$C_H3$; and (b) a second polypeptide comprising from N-terminus to C-terminus: anti-TIGIT sdAb2 moiety-$C_L$, wherein the $V_L$ and $V_H$ that forms the scFv specifically binds PD-1, and wherein the anti-TIGIT sdAb1 moiety and the anti-TIGIT sdAb2 moiety each comprises a CDR1 comprising the amino acid sequence of any one of SEQ ID NOs: 36-42, 54, 56-59, 63, 65-67, 69-70, or a variant thereof comprising up to about 3 (such as about any of 1, 2, or 3) amino acid substitutions; a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210, or a variant thereof comprising up to about 3 (such as about any of 1, 2, or 3) amino acid substitutions. In some embodiments, the anti-TIGIT sdAb1 moiety and the anti-TIGIT sdAb2 moiety each comprises a CDR1 comprising the amino acid sequence of any one of SEQ ID NOs: 36-42, 54, 56-59, 63, 65-67, 69-70; a CDR2 comprising the amino acid sequence of any one of SEQ ID NOs: 106-112, 124, 126-129, 133, 135-137, 139-140; and a CDR3 comprising the amino acid sequence of any one of SEQ ID NOs: 176-182, 194, 196-199, 203, 205-207, 209-210. In some embodiments, the anti-TIGIT sdAb1 moiety and the anti-TIGIT sdAb2 moiety each comprises a $V_H$H domain comprising the amino acid sequence of any one of SEQ ID NO: 253-259, 271, 273-276, 280, 282-284, 286-287. In some embodiments, the anti-TIGIT sdAb1 moiety and the anti-TIGIT sdAb2 moiety are the same. In some embodiments, the anti-TIGIT sdAb1 moiety and the anti-TIGIT sdAb2 moiety are different. In some embodiments, the $V_H$ and $V_L$ domains (or the scFv) are derived from pembrolizumab, PD1-BM-min, or nivolumab. In some embodiments, the $V_H$ comprises the amino acid sequence of SEQ ID NO: 385, and the $V_L$ comprises the amino acid sequence of SEQ ID NO: 386. In some embodiments, the $V_H$ comprises the amino acid sequence of SEQ ID NO: 387, and the $V_L$ comprises the amino acid sequence of SEQ ID NO: 388. In some embodiments, the $V_H$ comprises the amino acid sequence of SEQ ID NO: 406, and the $V_L$ comprises the amino acid sequence of SEQ ID NO: 407. In some embodiments, the $V_H$ and $V_L$ that forms the scFv, and/or the scFv and the anti-TIGIT sdAb1 moiety, are fused to each other optionally via a peptide linker, such as a peptide linker comprising the amino acid sequence of any one of SEQ ID NOs: 324 and 370-378. In some embodiments, the $C_H2$ and $C_H3$ domains are derived from an IgG4 Fc, such as SEQ ID NO: 389. In some embodiments, the $C_H2$ and $C_H3$ domains are derived from an IgG1 Fc, such as SEQ ID NO: 356. In some embodiments, the $C_H2$ and $C_H3$ domains are derived from an effectorless IgG1 Fc, such as SEQ ID NO: 355. In some embodiments, the anti-TIGIT MABP (e.g., BABP) comprises two identical copies of the first polypeptide and two identical copies of the second polypeptide. In some embodiments, the anti-TIGIT sdAb moiety is camelid, chimeric, human, partially humanized, or fully humanized. In some embodiments, the PD-1×TIGIT MABP (e.g., BABP) has the structure as shown in FIG. 26.

In some embodiments, there is provided an anti-TIGIT MABP (e.g., BABP) comprising: (a) a first polypeptide comprising from N-terminus to C-terminus: $V_L$—$V_H$-anti-TIGIT sdAb1 moiety-$C_H2$-$C_H3$; and (b) a second polypeptide comprising from N-terminus to C-terminus: anti-TIGIT sdAb2 moiety-$C_L$, wherein the $V_L$ and $V_H$ that forms the scFv specifically binds PD-L1, and wherein the anti-TIGIT sdAb1 moiety and the anti-TIGIT sdAb2 moiety each comprises a CDR1 comprising the amino acid sequence of any one of SEQ ID NOs: 36-42, 54, 56-59, 63, 65-67, 69-70, or a variant thereof comprising up to about 3 (such as about any of 1, 2, or 3) amino acid substitutions; a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210, or a variant thereof comprising up to about 3 (such as about any of 1, 2, or 3) amino acid substitutions. In some embodiments, there is provided an anti-TIGIT MABP (e.g., BABP) comprising: (a) a first polypeptide comprising from N-terminus to C-terminus: $V_H$—$V_L$-anti-TIGIT sdAb1 moiety-$C_H2$-$C_H3$; and (b) a second polypeptide comprising from N-terminus to C-terminus: anti-TIGIT sdAb2 moiety-$C_L$, wherein the $V_L$ and $V_H$ that forms the scFv specifically binds PD-L1, and wherein the anti-TIGIT sdAb1 moiety and the anti-TIGIT sdAb2 moiety each comprises a CDR1 comprising the amino acid sequence of any one of SEQ ID NOs: 36-42, 54, 56-59, 63, 65-67, 69-70, or a variant thereof comprising up to about 3 (such as about any of 1, 2, or 3) amino acid substitutions; a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210, or a variant thereof comprising up to about 3 (such as about any of 1, 2, or 3) amino acid substitutions. In some embodiments, the anti-TIGIT sdAb1 moiety and the anti-TIGIT sdAb2 moiety each comprises a CDR1 comprising the amino acid sequence of any one of SEQ ID NOs: 36-42, 54, 56-59, 63, 65-67, 69-70; a CDR2 comprising the amino acid sequence of any one of SEQ ID NOs: 106-112, 124, 126-129, 133, 135-137, 139-140; and a CDR3 comprising the amino acid sequence of any one of SEQ ID NOs: 176-182, 194, 196-199, 203, 205-207, 209-210. In some embodiments, the anti-TIGIT sdAb1 moiety and the anti-TIGIT sdAb2 moiety each comprises a $V_H$H domain comprising the amino acid sequence of any one of SEQ ID NO: 253-259, 271, 273-276, 280, 282-284, 286-287. In some embodiments, the anti-TIGIT sdAb1 moiety and the anti-TIGIT sdAb2 moiety are the same. In some embodiments, the anti-TIGIT sdAb1 moiety and the anti-TIGIT sdAb2 moiety are different. In some embodiments, the $V_H$ and $V_L$ domains (or the scFv) are derived from atezolizumab, durvalumab, avelumab, or h53C1. In some embodiments, the h53C1 anti-PD-L1 antibody comprises 1) a $V_H$ comprising an HC-CDR1 comprising the amino acid sequence of SEQ ID NO: 349, an HC-CDR2 comprising the amino acid sequence of SEQ ID NO: 350, and an HC-CDR3 comprising the amino acid sequence of SEQ ID NO: 351, and 2) a $V_L$ comprising an LC-CDR1 comprising the amino acid sequence of SEQ ID NO: 352, an LC-CDR2 comprising the amino acid sequence of SEQ ID NO: 353, and an LC-CDR3 comprising the amino acid sequence of SEQ ID NO: 354. In some embodiments, the h53C1 anti-PD-L1 antibody comprises a $V_H$ comprising the amino acid sequence of SEQ ID NO: 339, and a $V_L$ comprising the amino acid sequence of SEQ ID NO: 340. In some embodiments, the $V_H$ comprises the amino acid sequence of SEQ ID NO: 381, and the $V_L$ comprises the amino acid sequence of SEQ ID NO: 382. In some embodiments, the $V_H$ comprises the amino acid sequence of SEQ ID NO: 379, and the $V_L$ comprises the amino acid sequence of SEQ ID NO: 380. In some embodiments, the $V_H$ comprises the amino acid sequence of SEQ ID NO: 383, and the $V_L$ comprises the amino acid sequence of SEQ ID NO: 384. In some embodiments, the $V_H$ comprises the amino acid sequence of SEQ ID NO: 339, and the $V_L$ comprises the amino acid sequence of SEQ ID NO: 340. In some embodiments, the $V_H$ and $V_L$ that forms the scFv, and/or the scFv and the anti-TIGIT sdAb1 moiety, are fused to each other optionally via a peptide linker, such as a peptide linker comprising the amino acid sequence of any one of SEQ ID NOs: 324 and 370-378. In some embodiments, the $C_H2$ and $C_H3$ domains are derived from an IgG4 Fc, such as SEQ ID NO: 389. In some embodiments, the $C_H2$ and $C_H3$ domains are derived from an IgG1 Fc, such as SEQ ID NO: 356. In some embodiments, the $C_H2$ and $C_H3$ domains are derived from an effectorless IgG1 Fc, such as SEQ ID NO: 355. In some embodiments, the anti-TIGIT MABP (e.g., BABP) comprises two identical copies of the first polypeptide and two identical copies of the second polypeptide. In some embodiments, the anti-TIGIT sdAb moiety is camelid, chimeric, human, partially humanized, or fully humanized. In some embodiments, the PD-L1×TIGIT MABP (e.g., BABP) has the structure as shown in FIG. 26.

In some embodiments, there is also provided an anti-TIGIT MABP (e.g., BABP) comprising an sdAb moiety specifically recognizing TIGIT (hereinafter referred to as "competing anti-TIGIT construct", "competing anti-TIGIT MABP", or "competing anti-TIGIT BABP") that specifically binds to TIGIT competitively with any one of the anti-TIGIT construct described herein (such as anti-TIGIT sdAb moiety, anti-TIGIT sdAb-Fc fusion protein, multispecific (e.g., bispecific) or monospecific anti-TIGIT construct comprising an anti-TIGIT sdAb moiety descried herein, e.g., anti-TIGIT/PD-1 constructs (e.g., MABP or BABP) or anti-TIGIT/PD-L1 constructs (e.g., MABP or BABP) described herein).

(III) Anti-TIGIT Construct Antibody Variants

In some embodiments, amino acid sequence variants of the anti-TIGIT construct (e.g., anti-TIGIT sdAb moiety, anti-TIGIT sdAb-Fc fusion protein, anti-TIGIT MABP/BABP) provided herein are contemplated. For example, it may be desirable to improve the binding affinity and/or other biological properties of the antibody. Amino acid sequence variants of an antibody may be prepared by introducing appropriate modifications into the nucleic acid sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, Deletion and Variants

In some embodiments, antibody variants having one or more amino acid substitutions are provided. Sites of interest for substitutional mutagenesis include the HVRs (or CDRs) and FRs. Conservative substitutions are shown in Table 2 under the heading of "Preferred substitutions." More substantial changes are provided in Table 2 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 2

| Amino acid substitutions | | |
|---|---|---|
| Original Residue | Exemplary Substitutions | Preferred Substitutions |
| Ala (A) | Val; Lew, Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |

TABLE 2-continued

| Amino acid substitutions | | |
|---|---|---|
| Original Residue | Exemplary Substitutions | Preferred Substitutions |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; and (6) aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001)). In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In some embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or CDRs. In some embodiments of the variant $V_HH$ sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

b) Glycosylation Variants

In some embodiments, an anti-TIGIT construct provided herein is altered to increase or decrease the extent to which the construct is glycosylated. Addition or deletion of glycosylation sites to an antibody may be conveniently accomplished by altering the amino acid sequence such that one or more glycosylation sites is created or removed.

Where the anti-TIGIT construct comprises an Fc region (e.g., anti-TIGIT sdAb-Fc fusion protein, PD-1×TIGIT MABP, or PD-L1×TIGIT MABP), the carbohydrate attached thereto may be altered. Native antibodies produced by mammalian cells typically comprise a branched, biantennary oligosaccharide that is generally attached by an N-linkage to Asn297 of the $C_H2$ domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an anti-TIGIT construct of the present application may be made in order to create antibody variants with certain improved properties.

In some embodiments, anti-TIGIT construct antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g., complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004).

Anti-TIGIT construct variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In some embodiments, one or more amino acid modifications may be introduced into the Fc region of the anti-TIGIT construct provided herein (e.g., anti-TIGIT sdAb-Fc fusion protein, PD-1×TIGIT MABP, or PD-L1×TIGIT MABP), thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In some embodiments, the present application contemplates an anti-TIGIT construct (e.g., anti-TIGIT sdAb-Fc fusion protein, PD-1×TIGIT MABP, or PD-L1×TIGIT MABP) variant that possesses some but not all effector functions, which make it a desirable candidate for applications in which the half-life of the anti-TIGIT construct in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 2 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166: 1351-1361 (1987)). Alternatively, non-radioactive assays methods may be employed (see, for example, ACTI™ non-radioactive cytotoxicity assay for flow cytometry (CellTechnology, Inc. Mountain View, CA; and CytoTox 96® non-radioactive cytotoxicity assay (Promega, Madison, WI). Useful effector cells for such assays include peripheral blood mononuclear cells (PBMC) and Natural Killer (NK)

cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed. FcRn binding and in vivo clearance/half-life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In some embodiments, an anti-TIGIT construct variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

In some embodiments, there is provided an anti-TIGIT construct (e.g., anti-TIGIT sdAb-Fc fusion protein, PD-1× TIGIT MABP, or PD-L1×TIGIT MABP) variant comprising a variant Fc region comprising one or more amino acid substitutions which increase half-life and/or improve binding to the neonatal Fc receptor (FcRn). Antibodies with increased half-lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

Anti-TIGIT constructs (such as sdAb-Fc fusion protein, anti-TIGIT sdAb fused to a full-length antibody, or anti-TIGIT MABP/BABP described herein) comprising any of the Fc variants described herein, or combinations thereof, are contemplated.

d) Cysteine Engineered Antibody Variants

In some embodiments, it may be desirable to create cysteine engineered anti-TIGIT constructs, e.g., "thio-MAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In some embodiments, any one or more of the following residues may be substituted with cysteine: A118 (EU numbering) of the heavy chain; and 5400 (EU numbering) of the heavy chain Fc region. Cysteine engineered anti-TIGIT constructs may be generated as described, e.g., in U.S. Pat. No. 7,521,541.

e) Antibody Derivatives

In some embodiments, an anti-TIGIT construct provided herein may be further modified to comprise additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In some embodiments, conjugates of an anti-TIGIT construct and nonproteinaceous moiety that may be selectively heated by exposure to radiation are provided. In some embodiments, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

In some embodiments, an anti-TIGIT construct provided herein (such as anti-TIGIT sdAb, anti-TIGIT sdAb-Fc fusion protein, anti-TIGIT/PD-1 bispecific antibody, anti-TIGIT/PD-L1 bispecific antibody, or anti-TIGIT MABP (e.g., BABP)) may be further modified to comprise one or more biologically active protein, polypeptides or fragments thereof. "Bioactive" or "biologically active", as used herein interchangeably, means showing biological activity in the body to carry out a specific function. For example, it may mean the combination with a particular biomolecule such as protein, DNA, etc., and then promotion or inhibition of the activity of such biomolecule. In some embodiments, the bioactive protein or fragments thereof include proteins and polypeptides that are administered to patients as the active drug substance for prevention of or treatment of a disease or condition, as well as proteins and polypeptides that are used for diagnostic purposes, such as enzymes used in diagnostic tests or in vitro assays, as well as proteins and polypeptides that are administered to a patient to prevent a disease such as a vaccine. In some embodiments, the bioactive protein or fragments thereof have immune-stimulatory/immune-regulatory, membrane transport, or enzymatic activities. In some embodiments, the biologically active protein, polypeptides or fragments thereof is an enzyme, a hormone, a growth factor, a cytokine, or a mixture thereof. In some embodiments, the biologically active protein, polypeptides or fragments can specifically recognize a target peptide (such as antigen, or other proteins).

In some embodiments, the bioactive protein or fragments thereof that can be comprised within the anti-TIGIT construct described herein is a protein-binding protein. In some embodiments, the bioactive protein or fragments thereof that can be comprised within the anti-TIGIT construct described herein is an antibody mimetics, which are small engineered proteins comprising antigen-binding domains reminiscent of antibodies (Geering and Fussenegger, Trends Biotechnol., 33(2):65-79, 2015). These molecules are derived from existing human scaffold proteins and comprise a single polypeptide. Exemplary antibody mimetics that can be comprised within the anti-TIGIT construct described herein can be, but are not limited to, a Designed ankyrin repeat protein (DARPin; comprising 3-5 fully synthetic ankyrin repeats flanked by N- and C-terminal Cap domains), an avidity multimer (avimer; a high-affinity protein comprising multiple A domains, each domain with low affinity for a target), or an Anticalin (based on the scaffold of lipocalins, with four accessible loops, the sequence of each can be randomized). In some embodiments, the bioactive protein or fragments thereof that can be comprised within the anti-TIGIT construct described herein is an Armadillo repeat protein (e.g., β-catenin, α-importin, plakoglobin, adenomatous polyposis coli (APC)), which comprises armadillo repeat units (characteristic, repetitive amino acid sequence of about 40 residues in length). Each Armadillo repeat is composed of a pair of alpha helices that form a hairpin structure. Multiple copies of the repeat form what is known as an alpha solenoid structure. Armadillo repeat proteins are able to bind different types of peptides, relying on a constant way of binding of the peptide backbone without requiring specific conserved side chains or interactions with free N- or C-termini of a peptide. The possibility of recognizing a peptide residue by residue, combined with the intrinsic modularity of a repeat protein, makes the armadillo repeat proteins promising candidates for the design of a generic scaffold for peptide binding.

In some embodiments, the biologically active protein or fragments thereof that can be comprised within the anti-TIGIT construct described herein is a ligand, such as lymphokines and cellular factors which interact with specific cellular receptor. Lymphokines are low molecular weight proteins which are secreted by T cells when antigens or lectins stimulate T cell growth.

III. Pharmaceutical Compositions

Further provided by the present application are pharmaceutical compositions comprising any one of the anti-TIGIT constructs comprising a sdAb specifically recognizing TIGIT as described herein (such as anti-TIGIT sdAb, anti-TIGIT sdAb-Fc fusion protein, anti-TIGIT/PD-1 bispecific antibody (e.g., PD-1×TIGIT BABP), or anti-TIGIT/PD-L1 bispecific antibody (e.g., PD-L1×TIGIT BABP)), and optionally a pharmaceutically acceptable carrier. Pharmaceutical compositions can be prepared by mixing an anti-TIGIT construct described herein having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions.

The pharmaceutical composition is preferably to be stable, in which the anti-TIGIT construct comprising anti-TIGIT sdAb moiety described here essentially retains its physical and chemical stability and integrity upon storage. Stability can be measured at a selected temperature for a selected time period. For rapid screening, the formulation may be kept at 40° C. for 2 weeks to 1 month, at which time stability is measured. Where the formulation is to be stored at 2-8° C., generally the formulation should be stable at 30° C. or 40° C. for at least 1 month, and/or stable at 2-8° C. for at least 2 years. Where the formulation is to be stored at 30° C., generally the formulation should be stable for at least 2 years at 30° C., and/or stable at 40° C. for at least 6 months. For example, the extent of aggregation during storage can be used as an indicator of protein stability. In some embodiments, the stable formulation of anti-TIGIT construct described herein may comprise less than about 10% (preferably less than about 5%) of the anti-TIGIT construct present as an aggregate in the formulation.

Acceptable carriers, excipients, or stabilizers are nontoxic to recipients at the dosages and concentrations employed, and include buffers, antioxidants including ascorbic acid, methionine, Vitamin E, sodium metabisulfite; preservatives, isotonicifiers (e.g. sodium chloride), stabilizers, metal complexes (e.g. Zn-protein complexes); chelating agents such as EDTA and/or non-ionic surfactants.

Examples of physiologically acceptable carriers include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugars such as sucrose, mannitol, trehalose or sorbitol; salt-forming counterions such as sodium; metal complexes (e.g. Zn-protein complexes); and/or nonionic surfactants such as TWEEN™, polyethylene glycol (PEG), and PLURONICS™ or polyethylene glycol (PEG).

Buffers are used to control the pH in a range which optimizes the therapeutic effectiveness, especially if stability is pH dependent. Buffers are preferably present at concentrations ranging from about 50 mM to about 250 mM. Suitable buffering agents for use in the present application include both organic and inorganic acids and salts thereof. For example, citrate, phosphate, succinate, tartrate, fumarate, gluconate, oxalate, lactate, acetate. Additionally, buffers may comprise histidine and trimethylamine salts such as Tris.

Preservatives are added to retard microbial growth, and are typically present in a range from 0.2%-1.0% (w/v). The addition of a preservative may, for example, facilitate the production of a multi-use (multiple-dose) formulation. Suitable preservatives for use in the present application include octadecyldimethylbenzyl ammonium chloride; hexamethonium chloride; benzalkonium halides (e.g., chloride, bromide, iodide), benzethonium chloride; thimerosal, phenol, butyl or benzyl alcohol; alkyl parabens such as methyl or propyl paraben; catechol; resorcinol; cyclohexanol, 3-pentanol, and m-cresol.

Tonicity agents, sometimes known as "stabilizers" are present to adjust or maintain the tonicity of liquid in a composition. When used with large, charged biomolecules such as proteins and antibodies, they are often termed "stabilizers" because they can interact with the charged groups of the amino acid side chains, thereby lessening the potential for inter and intra-molecular interactions. Tonicity agents can be present in any amount between 0.1% to 25% by weight, preferably 1% to 5%, taking into account the relative amounts of the other ingredients. Preferred tonicity agents include polyhydric sugar alcohols, preferably trihydric or higher sugar alcohols, such as glycerin, erythritol, arabitol, xylitol, sorbitol and mannitol.

Additional excipients include agents which can serve as one or more of the following: (1) bulking agents, (2) solubility enhancers, (3) stabilizers and (4) and agents preventing denaturation or adherence to the container wall. Such excipients include: polyhydric sugar alcohols (enumerated above); amino acids such as alanine, glycine, glutamine, asparagine, histidine, arginine, lysine, ornithine, leucine, 2-phenylalanine, glutamic acid, threonine, etc.; organic sugars or sugar alcohols such as sucrose, lactose, lactitol, trehalose, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, α-monothioglycerol and sodium thio sulfate; low molecular weight proteins such as human serum albumin, bovine serum albumin, gelatin or other immunoglobulins; hydrophilic polymers such as polyvinylpyrrolidone; monosaccharides (e.g., xylose, mannose, fructose, glucose; disaccharides (e.g., lactose, maltose, sucrose); trisaccharides such as raffinose; and polysaccharides such as dextrin or dextran.

Non-ionic surfactants or detergents (also known as "wetting agents") are present to help solubilize the therapeutic agent as well as to protect the therapeutic protein against agitation-induced aggregation, which also permits the formulation to be exposed to shear surface stress without causing denaturation of the active therapeutic protein or antibody. Non-ionic surfactants are present in a range of about 0.05 mg/ml to about 1.0 mg/ml, preferably about 0.07 mg/ml to about 0.2 mg/ml.

Suitable non-ionic surfactants include polysorbates (20, 40, 60, 65, 80, etc.), polyoxamers (184, 188, etc.), PLURONIC® polyols, TRITON®, polyoxyethylene sorbitan monoethers (TWEEN®-20, TWEEN®-80, etc.), lauromacrogol 400, polyoxyl 40 stearate, polyoxyethylene hydrogenated castor oil 10, 50 and 60, glycerol monostearate, sucrose fatty acid ester, methyl cellulose and carboxymethyl cellulose. Anionic detergents that can be used include sodium lauryl sulfate, dioctyle sodium sulfosuccinate and dioctyl sodium sulfonate. Cationic detergents include benzalkonium chloride or benzethonium chloride.

In order for the pharmaceutical compositions to be used for in vivo administration, they must be sterile. The pharmaceutical composition may be rendered sterile by filtration through sterile filtration membranes. The pharmaceutical compositions herein generally are placed into a container having a sterile access port, for example, an intravenous solution bag or vial having a stopper pierceable by a hypodermic injection needle.

The route of administration is in accordance with known and accepted methods, such as by single or multiple bolus or infusion over a long period of time in a suitable manner, e.g., injection or infusion by subcutaneous, intravenous, intraperitoneal, intramuscular, intra-arterial, intralesional or intraarticular routes, topical administration, inhalation or by sustained release or extended-release means. In some embodiments, the pharmaceutical composition is administered locally, such as intratumorally.

Sustained-release preparations may be prepared. Suitable examples of sustained-release preparations include semipermeable matrices of solid hydrophobic polymers containing the antagonist, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and. ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The pharmaceutical compositions herein may also contain more than one active compound as necessary for the particular indication being treated, preferably those with complementary activities that do not adversely affect each other. Alternatively, or in addition, the composition may comprise a cytotoxic agent, chemotherapeutic agent, cytokine, immunosuppressive agent, or growth inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 18th edition.

In some embodiments, the pharmaceutical composition is contained in a single-use vial, such as a single-use sealed vial. In some embodiments, the pharmaceutical composition is contained in a multi-use vial. In some embodiments, the pharmaceutical composition is contained in bulk in a container. In some embodiments, the pharmaceutical composition is cryopreserved.

IV. Methods of Treating TIGIT-Related Diseases

The anti-TIGIT construct comprising an sdAb moiety specifically recognizing TIGIT as described herein (such as anti-TIGIT sdAb, anti-TIGIT sdAb-Fc fusion protein, anti-TIGIT/PD-1 bispecific antibody (e.g., PD-1×TIGIT BABP), or anti-TIGIT/PD-L1 bispecific antibody (e.g., PD-L1× TIGIT BABP)), and the compositions (such as pharmaceutical compositions) thereof are useful for a variety of applications, such as in diagnosis, molecular assays, and therapy.

One aspect of the invention provides a method of treating a TIGIT-related disease or a condition in an individual in need thereof, comprising administering to the individual an effective amount of a pharmaceutical composition comprising the anti-TIGIT construct described herein. In some embodiments, the TIGIT-related disease is cancer. In some embodiments, the TIGIT-related disease is pathogenic infection, such as viral infection. In some embodiments, the TIGIT-related disease is an immune-related disease. In some embodiments, immune-related disease is associated with a T cell dysfunctional disorder. In some embodiments, the T cell dysfunctional disorder is characterized by T cell exhaustion. In some embodiments, the immune-related disease is selected from the group consisting of unresolved acute infection, chronic infection, and tumor immunity. In some embodiments, an anti-TIGIT construct described herein may be for use in increasing, enhancing, or stimulating an immune response or function in a subject in need thereof. In some embodiments, the TIGIT-related disease (e.g., cancer, immune-related disease) is partially resistant to PD-1 or PD-L1 blockade (e.g., partially resistant to anti-PD-1 antibody or anti-PD-L1 antibody treatment).

The present invention contemplates, in part, anti-TIGIT protein constructs (such as anti-TIGIT sdAb, anti-TIGIT sdAb-Fc fusion protein, anti-TIGIT/PD-1 bispecific antibody (e.g., PD-1×TIGIT BABP), or anti-TIGIT/PD-L1 bispecific antibody (e.g., PD-L1×TIGIT BABP)), nucleic acid molecules or vectors encoding thereof, host cells comprising nucleic acid molecules or vectors encoding thereof, that can be administered either alone or in any combination with another therapy, and in at least some aspects, together with a pharmaceutically acceptable carrier or excipient. In some embodiments, prior to administration of the anti-TIGIT construct, they may be combined with suitable pharmaceutical carriers and excipients that are well known in the art. The compositions prepared according to the disclosure can be used for the treatment or delaying of worsening of cancer, or increasing, enhancing, or stimulating an immune response or function in a subject in need thereof.

In some embodiments, there is provided a method of treating a TIGIT-related disease (e.g., cancer, immune-related disease such as that associated with a T cell dysfunctional disorder) comprising administering to the individual an effective amount of a pharmaceutical composition comprising an isolated anti-TIGIT construct comprising an sdAb moiety specifically recognizing TIGIT (such as anti-TIGIT sdAb, anti-TIGIT sdAb-Fc fusion protein, anti-TIGIT/PD-1 bispecific antibody (e.g., PD-1×TIGIT BABP), or anti-TIGIT/PD-L1 bispecific antibody (e.g., PD-L1×TIGIT BABP)), wherein the anti-TIGIT sdAb moiety comprises a CDR1 comprising the amino acid sequence of any one of SEQ ID NOs: 36-42, 54, 56-59, 63, 65-67, 69-70, or a variant thereof comprising up to about 3 (such as about any of 1, 2, or 3) amino acid substitutions; a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210, or a variant thereof comprising up to about 3 (such as about any of 1, 2, or 3) amino acid substitutions; and optionally a pharmaceutical acceptable carrier. In some embodiments, the $K_d$ of the binding between the anti-TIGIT sdAb moiety and TIGIT is about $10^{-5}$ M to about $10^{-12}$ M (such as about $10^{-7}$ M to about $10^{-12}$ M, or about $10^{-8}$ M to about $10^{-12}$ M). In some embodiments, the anti-TIGIT sdAb moiety is camelid, chimeric, human, partially humanized, or fully humanized. In some embodiments, the anti-TIGIT sdAb moiety comprises a $V_H H$ domain comprising the amino acid sequence of any one of SEQ ID NOs: 253-259, 271, 273-276, 280, 282-284, 286-287. In some embodiments, the TIGIT-related disease is cancer. In some embodiments, the cancer is a solid tumor (such as colon cancer). In some embodiments, the TIGIT-related disease is an immune-related disease. In some embodiments, immune-related disease is associated with a T cell dysfunctional disorder. In some embodiments, the T cell dysfunctional disorder is characterized by T cell exhaustion. In some embodiments, the immune-related disease is selected from the group consisting of unresolved acute infection, chronic infection, and tumor immunity. In some embodiments, the TIGIT-related disease (e.g., cancer, immune-related disease) is partially resistant to PD-1 or PD-L1 blockade (e.g., partially resistant to anti-PD-1 antibody or anti-PD-L1 antibody treatment). In some embodiments, the method further comprises administering to the individual an additional therapy (e.g., cancer therapy, such as surgery, radiation, chemotherapy, immunotherapy, hormone therapy, or a combination thereof). In some embodiments, the additional therapy is immunotherapy, e.g., by administering to the individual an effective amount of a second pharmaceutical composition comprising an immunomodulator. In some embodiments, the immunomodulator is an immune checkpoint inhibitor, e.g., anti-PD-1 or anti-PD-L1 antibody. In some embodiments, the pharmaceutical composition is administered systemically (such as intravenously or intraperitoneally). In some embodiments, the pharmaceutical composition is administered locally (such as intratumorally). In some embodiments, the individual is a human. In some embodiments, the method of treating cancer has one or more of the following biological activities: (1) killing cancer cells (including bystander killing); (2) inhibiting proliferation of cancer cells; (3) inducing immune response in a tumor; (4) reducing tumor size; (5) alleviating one or more symptoms in an individual having cancer; (6) inhibiting tumor metastasis; (7) prolonging survival; (8) prolonging time to cancer progression; and (9) preventing, inhibiting, or reducing the likelihood of the recurrence of a cancer. In some embodiments, the method of killing cancer cells mediated by the pharmaceutical composition described herein can achieve a tumor cell death rate of at least about any of 40%, 50%, 60%, 70%, 80%, 90%, 95%, or more. In some embodiments, the method of killing cancer cells mediated by the pharmaceutical composition described herein can achieve a bystander tumor cell (e.g., uninfected by oncolytic VV encoding the anti-TIGIT construct) death rate of at least about any of 10%, 20%, 30%, 40%, 50%, 60%, 70%, 80%, 90%, 95%, or more. In some embodiments, the method of reducing tumor size mediated by the pharmaceutical composition described herein can reduce at least about 10% (including for example at least about any of 20%, 30%, 40%, 60%, 70%, 80%, 90%, or 100%) of the tumor size. In some embodiments, the method of inhibiting tumor metastasis mediated by the pharmaceutical composition described herein can inhibit at least about 10% (including for example at least about any of 20%, 30%, 40%, 60%, 70%, 80%, 90%, or 100%) of the metastasis. In some embodiments, the method of prolonging survival of an individual (such as a human) mediated by the pharmaceutical composition described herein can prolongs the survival of the individual by at least any of 1, 2, 3, 4, 5, 6, 7, 8, 9, 10, 11, 12, 18, or 24 months. In some embodiments, the method of prolonging time to cancer progression mediated by the pharmaceutical composition described herein can prolongs the time to cancer progression by at least any of 1, 2, 3, 4, 5, 6, 7, 8, 9, 10, 11, or 12 weeks. In some embodiments, the method of treating immune-related disease can increase, enhance, or stimulate an immune response or function in a subject. In some embodiments, the immune response or function is increased, enhanced, and/or stimulated by activating effector cells (e.g., T cells, e.g., CD8+ and/or CD4+ T cells), expanding (increasing) an effector cell population, and/or killing target cells (e.g., target tumor cells) in the subject. In some embodiments, the CD4 and/or CD8 T cells in the individual have increased or enhanced priming, activation, proliferation, cytokine release and/or cytolytic activity relative to prior to the administration of the pharmaceutical composition comprising the anti-TIGIT construct described herein. In some embodiments, the number of CD4 and/or CD8 T cells is elevated relative to prior to administration of the pharmaceutical composition comprising the anti-TIGIT construct described herein. In some embodiments, the number of activated CD4 and/or CD8 T cells is elevated relative to prior to administration of the pharmaceutical composition comprising the anti-TIGIT construct described herein. In some embodiments, the activated CD4 and/or CD8 T cells is characterized by γ-IFN$^+$ producing CD4 and/or CD8 T cells and/or enhanced cytolytic activity relative to prior to the administration of the pharmaceutical composition comprising the anti-TIGIT construct described herein. In some embodiments, the CD4 and/or CD8 T cells exhibit increased release of cytokines selected from the group consisting of IFN-γ, TNF-α and interleukins. In some embodiments of the methods of this invention, the CD4 and/or CD8 T cell is an effector memory T cell. In some embodiments, the CD4 and/or CD8 effector memory T cell is characterized by γ-IFN$^+$ producing CD4 and/or CD8 T cells and/or enhanced cytolytic activity. In some embodiments, the CD4 and/or CD8 effector memory T cell is characterized by having the expression of CD44$^{high}$ CD62L$^{low}$. In some embodiments, the cancer has elevated levels of T cell infiltration.

The methods described herein are suitable for treating a variety of cancers, including both solid cancer and liquid cancer. The methods are applicable to cancers of all stages, including early stage cancer, non-metastatic cancer, primary cancer, advanced cancer, locally advanced cancer, metastatic cancer, or cancer in remission. The methods described herein may be used as a first therapy, second therapy, third therapy, or combination therapy with other types of cancer therapies known in the art, such as chemotherapy, surgery, hormone therapy, radiation, gene therapy, immunotherapy (such as T-cell therapy or administering immunomodulators), bone marrow transplantation, stem cell transplantation, targeted therapy, cryotherapy, ultrasound therapy, photodynamic therapy, radio-frequency ablation or the like, in an adjuvant setting or a neoadjuvant setting (i.e., the method may be carried out before the primary/definitive therapy). In some embodiments, the method is used to treat an individual who has previously been treated. In some embodiments, the cancer has been refractory to prior therapy. In some embodiments, the method is used to treat an individual who has not previously been treated. In some embodiments, the cancer is partially resistant to PD-1 or PD-L1 blockade (e.g., partially resistant to anti-PD-1 antibody or anti-PD-L1 antibody treatment).

In some embodiments, the method is suitable for treating cancers with aberrant TIGIT expression, activity and/or signaling include, by way of non-limiting example, a non-small cell lung cancer, a small cell lung cancer, a renal cell cancer, a colorectal cancer, an ovarian cancer, a breast cancer, a pancreatic cancer, a gastric carcinoma, a bladder cancer, an esophageal cancer, a mesothelioma, a melanoma, a head and neck cancer, a thyroid cancer, a sarcoma, a prostate cancer, a glioblastoma, a cervical cancer, a thymic carcinoma, a leukemia, a lymphoma, a myeloma (e.g., multiple myeloma (MM)), mycoses fungoides, a merkel cell cancer, and a hematologic malignancy.

Thus in some embodiments, there is provided a method of treating an immunotherapy-responsive solid tumor (such as carcinoma or adenocarcinoma, such as cancers with aberrant TIGIT expression, activity and/or signaling), comprising administering to the individual an effective amount of a pharmaceutical composition comprising an isolated anti-TIGIT construct comprising an sdAb moiety specifically recognizing TIGIT (such as anti-TIGIT sdAb, anti-TIGIT sdAb-Fc fusion protein, anti-TIGIT/PD-1 bispecific antibody (e.g., PD-1×TIGIT BABP), or anti-TIGIT/PD-L1 bispecific antibody (e.g., PD-L1×TIGIT BABP)), wherein the sdAb moiety comprises a CDR1 comprising the amino acid sequence of any one of SEQ ID NOs: 36-42, 54, 56-59, 63, 65-67, 69-70, or a variant thereof comprising up to about 3 (such as about any of 1, 2, or 3) amino acid substitutions; a CDR2 comprising the amino acid sequence of any one of SEQ ID NOs: 106-112, 124, 126-129, 133, 135-137, 139-140, or a variant thereof comprising up to about 3 (such as about any of 1, 2, or 3) amino acid substitutions; and a CDR3 comprising the amino acid sequence of any one of SEQ ID NOs: 176-182, 194, 196-199, 203, 205-207, 209-210, or a variant thereof comprising up to about 3 (such as about any of 1, 2, or 3) amino acid substitutions; and optionally a pharmaceutical acceptable carrier. In some embodiments, the $K_d$ of the binding between the anti-TIGIT sdAb moiety and TIGIT is about 10$^{-5}$ M to about 10$^{-12}$ M (such as about 10$^{-7}$ M to about 10$^{-12}$ M, or about 10$^{-8}$ M to about 10$^{-12}$ M). In some embodiments, the anti-TIGIT sdAb moiety is camelid, chimeric, human, partially humanized, or fully humanized. In some embodiments, the anti-TIGIT sdAb moiety comprises a V$_H$H domain comprising the amino acid sequence of any one of SEQ ID NOs: 253-259, 271, 273-276, 280, 282-284, 286-287. In some embodiments, the cancer is a solid tumor (such as colon cancer). In some embodiments, the pharmaceutical composition is administered systemically (such as intravenously or intraperitoneally). In some embodiments, the pharmaceutical composition is administered locally (such as intratumorally). In some embodiments, the method further comprises administering to the individual an additional cancer therapy (such as surgery, radiation, chemotherapy, immunotherapy, hormone therapy, or a combination thereof). In some embodiments, the additional therapy comprises administering to the individual an effective amount of a second pharmaceutical composition comprising an immunomodulator such as anti-PD-1 or anti-PD-L1 antibody. In some embodiments, the individual is a human. In some embodiments, the immunotherapy-responsive solid tumor is partially resistant to PD-1 or PD-L1 blockade (e.g., partially resistant to anti-PD-1 antibody or anti-PD-L1 antibody treatment).

In some embodiments, the method is suitable for treating cancers with aberrant PD-1 or PD-L1/PD-L2 expression, activity and/or signaling include, by way of non-limiting example, hematological cancer and/or solid tumors. Some cancers whose growth may be inhibited using the antibodies of the invention include cancers typically responsive to immunotherapy. Non-limiting examples of other cancers for treatment include melanoma (e.g., metastatic malignant melanoma), renal cancer (e.g. clear cell carcinoma), prostate cancer (e.g. hormone refractory prostate adenocarcinoma), breast cancer, colon cancer and lung cancer (e.g. non-small cell lung cancer). Additionally, the invention includes refractory or recurrent malignancies whose growth may be inhibited using the antibodies of the invention. Examples of other cancers that may be treated using the antibodies of the invention include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The present invention is also useful for treatment of metastatic cancers, especially metastatic cancers that express PD-L1 (Iwai et al. (2005) *Int. Immunol.* 17:133-144). In some embodiments, the cancer with aberrant PD-1 or PD-L1/PD-L2 expression, activity and/or signaling is partially resistant to PD-1 or PD-L1 blockade (e.g., partially resistant to anti-PD-1 antibody or anti-PD-L1 antibody treatment).

In some embodiments, the method described herein is suitable for treating a colorectal cancer, such as adenocarcinoma, gastrointestinal carcinoid tumor, gastrointestinal stromal tumor, Leiomyosarcoma, melanoma, or squamous cell carcinoma.

Dosages and desired drug concentrations of pharmaceutical compositions of the present application may vary depending on the particular use envisioned. The determination of the appropriate dosage or route of administration is well within the skill of an ordinary artisan Animal experiments provide reliable guidance for the determination of effective doses for human therapy. Interspecies scaling of effective doses can be performed following the principles laid down by Mordenti, J. and Chappell, W. "The Use of Interspecies Scaling in Toxicokinetics," In *Toxicokinetics and New Drug Development*, Yacobi et al., Eds, Pergamon Press, New York 1989, pp. 42-46.

When in vivo administration of the anti-TIGIT construct comprising an anti-TIGIT sdAb moiety described herein (such as anti-TIGIT sdAb, anti-TIGIT sdAb-Fc fusion protein, anti-TIGIT/PD-1 bispecific antibody (e.g., PD-1× TIGIT BABP), or anti-TIGIT/PD-L1 bispecific antibody (e.g., PD-L1×TIGIT BABP)) are used, normal dosage amounts may vary from about 10 ng/kg up to about 100 mg/kg of mammal body weight or more per day, preferably about 1 mg/kg/day to 10 mg/kg/day, such as about 1-3 mg/kg/day, about 2-4 mg/kg/day, about 3-5 mg/kg/day, about 4-6 mg/kg/day, about 5-7 mg/kg/day, about 6-8 mg/kg/day, about 6-6.5 mg/kg/day, about 6.5-7 mg/kg/day, about 7-9 mg/kg/day, or about 8-10 mg/kg/day, depending upon the route of administration. It is within the scope of the present application that different formulations will be effective for different treatments and different disorders, and that administration intended to treat a specific organ or tissue may necessitate delivery in a manner different from that to another organ or tissue. Moreover, dosages may be administered by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays.

In some embodiments, the pharmaceutical composition is administered for a single time (e.g. bolus injection). In some embodiments, the pharmaceutical composition is administered for multiple times (such as any of 2, 3, 4, 5, 6, or more times). If multiple administrations, they may be performed by the same or different routes and may take place at the same site or at alternative sites. The pharmaceutical composition may be administered twice per week, 3 times per week, 4 times per week, 5 times per week, daily, daily without break, once per week, weekly without break, once per 2 weeks, once per 3 weeks, once per month, once per 2 months, once per 3 months, once per 4 months, once per 5 months, once per 6 months, once per 7 months, once per 8 months, once per 9 months, once per 10 months, once per 11 months, or once per year. The interval between administrations can be about any one of 24 h to 48 h, 2 days to 3 days, 3 days to 5 days, 5 days to 1 week, 1 week to 2 weeks, 2 weeks to 1 month, 1 month to 2 months, 2 month to 3 months, 3 months to 6 months, or 6 months to a year. Intervals can also be irregular (e.g. following tumor progression). In some embodiments, there is no break in the dosing schedule. In some embodiments, the pharmaceutical composition is administered every 4 days for 4 times. The optimal dosage and treatment regime for a particular patient can readily be determined by one skilled in the art of medicine by monitoring the patient for signs of disease and adjusting the treatment accordingly.

The pharmaceutical compositions of the present application, including but not limited to reconstituted and liquid formulations, are administered to an individual in need of treatment with the anti-TIGIT construct described herein (such as anti-TIGIT sdAb, anti-TIGIT sdAb-Fc fusion protein, anti-TIGIT/PD-1 bispecific antibody (e.g., PD-1× TIGIT BABP), or anti-TIGIT/PD-L1 bispecific antibody (e.g., PD-L1×TIGIT BABP)), preferably a human, in accord with known methods, such as intravenous administration as a bolus or by continuous infusion over a period of time, by intramuscular, intraperitoneal, intracerobrospinal, subcutaneous, intravenous (i.v.), intra-articular, intrasynovial, intrathecal, oral, topical, or inhalation routes. A reconstituted formulation can be prepared by dissolving a lyophilized anti-TIGIT construct described herein in a diluent such that the protein is dispersed throughout. Exemplary pharmaceutically acceptable (safe and non-toxic for administration to a human) diluents suitable for use in the present application include, but are not limited to, sterile water, bacteriostatic water for injection (BWFI), a pH buffered solution (e.g. phosphate-buffered saline), sterile saline solution, Ringer's solution or dextrose solution, or aqueous solutions of salts and/or buffers.

In some embodiments, the pharmaceutical compositions are administered to the individual by subcutaneous (i.e. beneath the skin) administration. For such purposes, the pharmaceutical compositions may be injected using a syringe. However, other devices for administration of the pharmaceutical compositions are available such as injection devices; injector pens; auto-injector devices, needleless devices; and subcutaneous patch delivery systems. In some embodiments, the pharmaceutical compositions are administered to the individual intravenously. In some embodiments, the pharmaceutical composition is administered to an individual by infusion, such as intravenous infusion.

V. Methods of Preparation

The anti-TIGIT construct described herein (such as anti-TIGIT sdAb, anti-TIGIT sdAb-Fc fusion protein, anti- TIGIT/PD-1 bispecific antibody (e.g., PD-1×TIGIT BABP), or anti-TIGIT/PD-L1 bispecific antibody (e.g., PD-L1× TIGIT BABP)) may be prepared using any methods known in the art or as described herein. Also see Examples 1, 2, 4 and 6. In some embodiments, there is provided a method of producing an anti-TIGIT construct, comprising: (a) culturing a host cell comprising an isolated nucleic acid or vector encoding the anti-TIGIT construct described herein under conditions effective to express the encoded anti-TIGIT construct; and (b) obtaining the expressed anti-TIGIT construct from said host cell. In some embodiments, the method of step (a) further comprises producing a host cell comprising the isolated nucleic acid or vector encoding the anti-TIGIT construct described herein.

Methods of preparing sdAbs have been described. See, for example, Els Pardon et al., *Nature Protocol*, 2014; 9(3): 674. sdAbs (such as $V_H$Hs) may be obtained using methods known in the art such as by immunizing a Camelid species (such as camel or llama) and obtaining hybridomas therefrom, or by cloning a library of single-domain antibodies using molecular biology techniques known in the art and subsequent selection by ELISA with individual clones of unselected libraries or by using phage display.

For recombinant production of the sdAbs, the nucleic acids encoding the single-domain antibodies are isolated and inserted into a replicable vector for further cloning (amplification of the DNA) or for expression. DNA encoding the single-domain antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, preferred host cells are of either prokaryotic or eukaryotic (generally mammalian) origin. In some embodiments, the isolated nucleic acid encoding the anti-TIGIT construct described herein comprises the nucleic acid sequence of any one of SEQ ID NOs: 246-252.

1. Recombinant Production in Prokaryotic Cells a) Vector Construction

Polynucleic acid sequences encoding the antibodies of the present application can be obtained using standard recombinant techniques. Desired polynucleic acid sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells.

In addition, phage vectors containing replicon and control sequences that are compatible with the host microorganism can be used as transforming vectors in connection with these hosts. For example, bacteriophage such as GEM™-11 may be utilized in making a recombinant vector which can be used to transform susceptible host cells such as *E. coli* LE392.

The expression vector of the present application may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the present application. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the -galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleic acid sequences have been published, thereby enabling a skilled worker operably to ligate them to cistrons encoding the target light and heavy chains (Siebenlist et al. (1980) *Cell* 20: 269) using linkers or adaptors to supply any required restriction sites.

In one aspect, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. In some embodiments of the present application, the signal sequences used in both cistrons of the expression system are STII signal sequences or variants thereof.

In some embodiments, the production of the anti-TIGIT construct according to the present application can occur in the cytoplasm of the host cell, and therefore does not require the presence of secretion signal sequences within each cistron. In some embodiments, polypeptide components, such as the polypeptide encoding the $V_H$ domain of the second antigen binding portion optionally fused to the first antigen binding portion, and the polypeptide encoding the $V_L$ domain of the second antigen binding portion optionally fused to the first antigen binding portion, are expressed, folded and assembled to form functional antibodies within the cytoplasm. Certain host strains (e.g., the *E. coli* trxB⁻ strains) provide cytoplasm conditions that are favorable for disulfide bond formation, thereby permitting proper folding and assembly of expressed protein subunits. Proba and Pluckthun *Gene,* 159:203 (1995).

The present invention provides an expression system in which the quantitative ratio of expressed polypeptide components can be modulated in order to maximize the yield of secreted and properly assembled the antibodies of the present application. Such modulation is accomplished at least in part by simultaneously modulating translational strengths for the polypeptide components. One technique for modulating translational strength is disclosed in Simmons et al., U.S. Pat. No. 5,840,523. It utilizes variants of the translational initiation region (TIR) within a cistron. For a given TIR, a series of amino acid or nucleic acid sequence variants can be created with a range of translational strengths, thereby providing a convenient means by which to adjust this factor for the desired expression level of the specific chain. TIR variants can be generated by conventional mutagenesis techniques that result in codon changes which can alter the amino acid sequence, although silent changes in the nucleic acid sequence are preferred. Alterations in the TIR can include, for example, alterations in the number or spacing of Shine-Dalgarno sequences, along with alterations in the signal sequence. One method for generating mutant signal sequences is the generation of a "codon bank" at the beginning of a coding sequence that does not change the amino acid sequence of the signal sequence (i.e., the changes are silent). This can be accomplished by changing the third nucleotide position of each codon; additionally, some amino acids, such as leucine, serine, and arginine, have multiple first and second positions that can add complexity in making the bank.

Preferably, a set of vectors is generated with a range of TIR strengths for each cistron therein. This limited set provides a comparison of expression levels of each chain as well as the yield of the desired protein products under various TIR strength combinations. TIR strengths can be determined by quantifying the expression level of a reporter gene as described in detail in Simmons et al. U.S. Pat. No. 5,840,523. Based on the translational strength comparison, the desired individual TIRs are selected to be combined in the expression vector constructs of the present application.

b) Prokaryotic Host Cells

Prokaryotic host cells suitable for expressing the antibodies of the present application include Archaebacteria and Eubacteria, such as Gram-negative or Gram-positive organisms. Examples of useful bacteria include *Escherichia* (e.g., *E. coli*), Bacilli (e.g., *B. subtilis*), Enterobacteria, *Pseudomonas* species (e.g., *P. aeruginosa*), *Salmonella typhimurium, Serratia marcescans, Klebsiella, Proteus, Shigella, Rhizobia, Vitreoscilla,* or *Paracoccus.* In some embodiments, gram-negative cells are used. In some embodiments, *E. coli* cells are used as hosts for the invention. Examples of *E. coli* strains include strain W3110 and derivatives thereof, including strain 33D3 having genotype W3110 ΔfhuA (ΔtonA) ptr3 lac Iq lacL8 ΔompT Δ(nmpc-fepE) degP41 kan$^R$ (U.S. Pat. No. 5,639,635). Other strains and derivatives thereof, such as *E. coli* 294 (ATCC 31,446), *E. coli* B, *E. coli* 1776 (ATCC 31,537) and *E. coli* RV308 (ATCC 31,608) are also suitable. These examples are illustrative rather than limiting. It is generally necessary to select the appropriate bacteria taking into consideration replicability of the replicon in the cells of a bacterium. For example, *E. coli, Serratia,* or *Salmonella* species can be suitably used as the host when well known plasmids such as pBR322, pBR325, pACYC177, or pKN410 are used to supply the replicon.

Typically the host cell should secrete minimal amounts of proteolytic enzymes, and additional protease inhibitors may desirably be incorporated in the cell culture.

c) Protein Production

Host cells are transformed with the above-described expression vectors and cultured in conventional nutrient media modified as appropriate for inducing promoters, selecting transformants, or amplifying the genes encoding the desired sequences. Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Host cells are transformed with the above-described expression vectors and cultured in conventional nutrient media modified as appropriate for inducing promoters, selecting transformants, or amplifying the genes encoding the desired sequences. Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the antibodies of the present application are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol. The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli,* the pH is preferably from about 6.8 to about 7.4, and more preferably about 7.0.

If an inducible promoter is used in the expression vector of the present application, protein expression is induced under conditions suitable for the activation of the promoter. In one aspect of the present application, PhoA promoters are used for controlling transcription of the polypeptides. Accordingly, the transformed host cells are cultured in a phosphate-limiting medium for induction. Preferably, the phosphate-limiting medium is the C.R.A.P medium. A variety of other inducers may be used, according to the vector construct employed, as is known in the art.

The expressed anti-TIGIT construct of the present application are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

Alternatively, protein production is conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (the preferred carbon/energy source). Small scale fermentation refers generally to fermentation in a fermentor that is no more than approximately 100 liters in volumetric capacity, and can range from about 1 liter to about 100 liters.

During the fermentation process, induction of protein expression is typically initiated after the cells have been grown under suitable conditions to a desired density, e.g., an $OD_{550}$ of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the antibodies of the present application, various fermentation conditions can be modified. For example, to improve the proper assembly and folding of the secreted polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof.

*E. coli* strains deficient for proteolytic enzymes and transformed with plasmids overexpressing one or more chaperone proteins may be used as host cells in the expression system encoding the antibodies of the present application.

d) Protein Purification

The anti-TIGIT construct produced herein are further purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In some embodiments, Protein A immobilized on a solid phase is used for immunoaffinity purification of the antibodies comprising an Fc region of the present application. Protein A is a 411 (D cell wall protein from *Staphylococcus aureas* which binds with a high affinity to the Fc region of antibodies. Lindmark et al (1983) *J. Immunol.* Meth. 62:1-13. The solid phase to which Protein A is immobilized is preferably a column comprising a glass or silica surface, more preferably a controlled pore glass column or a silicic acid column. In some applications, the column has been coated with a reagent, such as glycerol, in an attempt to prevent nonspecific adherence of contaminants. The solid phase is then washed to remove contaminants non-specifically bound to the solid phase. Finally the antibodies of interest are recovered from the solid phase by elution.

2. Recombinant Production in Eukaryotic Cells

For eukaryotic expression, the vector components generally include, but are not limited to, one or more of the following, a signal sequence, an origin of replication, one or more marker genes, and enhancer element, a promoter, and a transcription termination sequence.

a) Signal Sequence Component

A vector for use in a eukaryotic host may also an insert that encodes a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. In mammalian cell expression, mammalian signal sequences as well as viral secretory leaders, for example, the herpes simplex gD signal, are available.

The DNA for such precursor region is ligated in reading frame to DNA encoding the antibodies of the present application.

b) Origin of Replication

Generally, the origin of replication component is not needed for mammalian expression vectors (the SV40 origin may typically be used only because it contains the early promoter).

c) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up nucleic acid encoding the antibodies of the present application, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with the polypeptide encoding-DNA sequences, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418.

d) Promoter Component

Expression and cloning vectors usually contain a promoter that is recognized by the host organism and is operably linked to the nucleic acid encoding the desired polypeptide sequences. Virtually all eukaryotic genes have an AT-rich region located approximately 25 to 30 based upstream from the site where transcription is initiated. Another sequence found 70 to 80 bases upstream from the start of the transcription of many genes is a CNCAAT region where N may be any nucleotide. At the 3' end of most eukaryotic is an AATAAA sequence that may be the signal for addition of the poly A tail to the 3' end of the coding sequence. All of these sequences may be inserted into eukaryotic expression vectors.

Other promoters suitable for use with prokaryotic hosts include the phoA promoter, -lactamase and lactose promoter systems, alkaline phosphatase promoter, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the antibodies.

Polypeptide transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., *Nature* 297:598-601 (1982) on expression of human-interferon cDNA in mouse cells under the control of a thymidine kinase promoter from herpes simplex virus. Alternatively, the Rous Sarcoma Virus long terminal repeat can be used as the promoter.

e) Enhancer Element Component

Transcription of a DNA encoding the antibodies of the present application by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (100-270 bp), the cytomegalovirus early promoter enhancer, the polyoma enhancer on the late side of the replication origin, and adenovirus enhancers. The enhancer may be spliced into the vector at a position 5' or 3' to the polypeptide encoding sequence, but is preferably located at a site 5' from the promoter.

f) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the polypeptide-encoding mRNA. One useful transcription termination component is the bovine growth hormone polyadenylation region. See WO94/11026 and the expression vector disclosed therein.

g) Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., *Annals N.Y. Acad. Sci.* 383:44-68 (1982)); MRC 5 cells; FS4 cells; and a human hepatoma line (Hep G2).

Host cells are transformed with the above-described expression or cloning vectors for antibodies production and cultured in conventional nutrient media modified as appropriate for inducing promoters, selecting transformants, or amplifying the genes encoding the desired sequences.

h) Culturing the Host Cells

The host cells used to produce the antibodies of the present application may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. The media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

i) Protein Purification

When using recombinant techniques, the antibodies can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., *Bio/Technology* 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The protein composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify the antibodies that are based on human immunoglobulins containing 1, 2, or 4 heavy chains. Protein G is recommended for all mouse isotypes and for human 3. The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25 M salt).

3. Polyclonal Antibodies

Polyclonal antibodies are generally raised in animals by multiple subcutaneous (s.c.) or intraperitoneal (i.p.) injections of the relevant antigen and an adjuvant. It may be useful to conjugate the relevant antigen to a protein that is immunogenic in the species to be immunized, e.g., keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N{=}C{=}NR$, where R and $R^1$ are independently lower alkyl groups. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The animals are immunized against the antigen, immunogenic conjugates, or derivatives by combining, e.g., 100 μg or 5 μg or the protein or conjugate (for rabbits or mice, respectively) with 3 volumes of Freund's complete adjuvant and injecting the solution intradermally at multiple sites. One month later, the animals are boosted with ⅕ to ¹⁄₁₀ the original amount of peptide or conjugate in Freund's complete adjuvant by subcutaneous injection at multiple sites. Seven to fourteen days later, the animals are bled and the serum is assayed for antibody titer. Animals are boosted until the titer plateaus. Conjugates also can be made in recombinant cell culture as protein fusions. Also, aggregating agents such as alum are suitable to enhance the immune response. Also see Example 1 for immunization in Camels.

4. Monoclonal Antibodies

Monoclonal antibodies are obtained from a population of substantially homogeneous antibodies, i.e., the individual antibodies comprising the population are identical except for possible naturally occurring mutations and/or post-translational modifications (e.g., isomerizations, amidations) that may be present in minor amounts. Thus, the modifier "monoclonal" indicates the character of the antibody as not being a mixture of discrete antibodies. For example, the monoclonal antibodies may be made using the hybridoma method first described by Kohler et al., *Nature*, 256:495 (1975), or may be made by recombinant DNA methods (U.S. Pat. No. 4,816,567). In the hybridoma method, a mouse or other appropriate host animal, such as a hamster or a llama, is immunized as hereinabove described to elicit lymphocytes that produce or are capable of producing antibodies that will specifically bind the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986). Also see Example 1 for immunization in Camels.

The immunizing agent will typically include the antigenic protein or a fusion variant thereof. Generally either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell. Goding, *Monoclonal Antibodies: Principles and Practice*, Academic Press (1986), pp. 59-103.

Immortalized cell lines are usually transformed mammalian cells, particularly myeloma cells of rodent, bovine and human origin. Usually, rat or mouse myeloma cell lines are employed. The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which are substances that prevent the growth of HGPRT-deficient cells.

Preferred immortalized myeloma cells are those that fuse efficiently, support stable high-level production of antibody by the selected antibody-producing cells, and are sensitive to a medium such as HAT medium. Among these, preferred are murine myeloma lines, such as those derived from MOPC-21 and MPC-11 mouse tumors available from the Salk Institute Cell Distribution Center, San Diego, Calif. USA, and SP-2 cells (and derivatives thereof, e.g., X63-Ag8-653) available from the American Type Culture Collection, Manassas, Va. USA.

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The culture medium in which the hybridoma cells are cultured can be assayed for the presence of monoclonal antibodies directed against the desired antigen. Preferably, the binding affinity and specificity of the monoclonal antibody can be determined by immunoprecipitation or by an in vitro binding assay, such as radioimmunoassay (RIA) or enzyme-linked assay (ELISA). Such techniques and assays are known in the in art. For example, binding affinity may be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, supra). Suitable culture media for this purpose include, for example, D-MEM or RPMI-1640 medium. In addition, the hybridoma cells may be grown in vivo as tumors in a mammal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Monoclonal antibodies may also be made by recombinant DNA methods. DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, in order to synthesize monoclonal antibodies in such recombinant host cells.

In a further embodiment, antibodies can be isolated from antibody phage libraries generated using the techniques described in McCafferty et al., *Nature*, 348:552-554 (1990). Clackson et al., *Nature*, 352:624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nucl. Acids Res.*, 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., Proc. Natl Acad. Sci. USA, 81:6851 (1984)), or by covalently joining to the immunoglobulin coding sequence all or part of the coding sequence for a non-immunoglobulin polypeptide. Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

The monoclonal antibodies described herein may by monovalent, the preparation of which is well known in the art. For example, one method involves recombinant expression of immunoglobulin light chain and a modified heavy chain. The heavy chain is truncated generally at any point in the Fc region so as to prevent heavy chain crosslinking. Alternatively, the relevant cysteine residues may be substituted with another amino acid residue or are deleted so as to prevent crosslinking. In vitro methods are also suitable for preparing monovalent antibodies. Digestion of antibodies to produce fragments thereof, particularly Fab fragments, can be accomplished using routine techniques known in the art.

Chimeric or hybrid antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

Also, see, Example 1 for monoclonal sdAb production.

5. Humanized Antibodies

Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a CDR of the recipient are replaced by residues from a CDR of a non-human species (donor antibody) such as mouse, rat, rabbit, camelid, or llama having the desired specificity, affinity, and capacity. In some instances, Fv framework residues of the human immunoglobulin are replaced by corresponding non-human residues. Humanized antibodies can also comprise residues that are found neither in the recipient antibody nor in the imported CDR or framework sequences. In general, the humanized antibody can comprise substantially all of at least one, and typically two, variable domains, in which all or substantially all of the CDR regions correspond to those of a non-human immunoglobulin, and all or substantially all of the FR regions are those of a human immunoglobulin consensus sequence. In some embodiments, the humanized antibody will comprise at least a portion of an immunoglobulin constant region (Fc), typically that of a human immunoglobulin. See, e.g., Jones et al., *Nature*, 321: 522-525 (1986); Riechmann et al., *Nature*, 332: 323-329 (1988); Presta, *Curr. Op. Struct. Biol.*, 2:593-596 (1992).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers, Jones et al., Nature 321:522-525 (1986); Riechmann et al., Nature 332:323-327 (1988); Verhoeyen et al., Science 239:1534-1536 (1988), or through substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody. Sims et al., J. Immunol., 151:2296 (1993); Chothia et al., J. Mol. Biol., 196:901 (1987). Another method uses a particular framework derived from the consensus sequence of all human antibodies of a particular subgroup of light or heavy chains. The same framework may be used for several different humanized antibodies.

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

In some embodiments, the sdAbs are modified, such as humanized, without diminishing the native affinity of the domain for antigen and while reducing its immunogenicity with respect to a heterologous species. For example, the amino acid residues of the antibody variable domain ($V_HH$) of an llama antibody can be determined, and one or more of the Camelidae amino acids, for example, in the framework regions, are replaced by their human counterpart as found in the human consensus sequence, without that polypeptide losing its typical character, i.e. the humanization does not significantly affect the antigen binding capacity of the resulting polypeptide. Humanization of Camelidae sdAbs requires the introduction and mutagenesis of a limited amount of amino acids in a single polypeptide chain. This is in contrast to humanization of scFv, Fab', (Fab')$_2$ and IgG, which requires the introduction of amino acid changes in two chains, the light and the heavy chain and the preservation of the assembly of both chains.

6. Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice will result in the production of human antibodies upon antigen challenge.

Alternatively, phage display technology can be used to produce human antibodies and antibody fragments in vitro, from immunoglobulin variable (V) domain gene repertoires from unimmunized donors. McCafferty et al., Nature 348: 552-553 (1990); Hoogenboom and Winter, J. Mol. Biol. 227: 381 (1991). According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats. Several sources of V-gene segments can be used for phage display. Clackson et al., Nature 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-597 (1991), or Griffith et al., EMBO J. 12:725-734 (1993). See also, U.S. Pat. Nos. 5,565,332 and 5,573,905.

The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., J Immunol., 147(1): 86-95 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed that closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; and 5,661,016, and Marks et al., *Bio/Technology*, 10: 779-783 (1992); Lonberg et al., *Nature*, 368: 856-859 (1994); Morrison, *Nature*, 368: 812-813 (1994); Fishwild et al., *Nature Biotechnology*, 14: 845-851 (1996); Neuberger, *Nature Biotechnology*, 14: 826 (1996); Lonberg and Huszar, *Intern. Rev. Immunol.*, 13: 65-93 (1995). For example, in some embodiments, human antibodies (e.g., human DAbs) can be generated by immunization of human HCAb mice. For example, HCAb (e.g., sdAb-Fc fusion proteins) can be produced by immunizing a transgenic mouse in which endogenous murine antibody expression has been eliminated and human transgenes have been introduced. HCAb mice are disclosed in U.S. Pat. Nos. 8,883,150, 8,921,524, 8,921,522, 8,507,748, 8,502,014, US2014/0356908, US2014/0033335, US2014/0037616, US2014/0356908, US2013/0344057, 052013/0323235, US2011/0118444, and US2009/0307787, all of which are incorporated herein by reference for all they disclose regarding heavy chain only antibodies and their production in transgenic mice. The HCAb mice are immunized and the resulting primed spleen cells fused with a murine myeloma cells to form hybridomas. The resultant HCAb can then be made fully human by replacing the murine CH2 and CH3 regions with human sequences.

Finally, human antibodies may also be generated by in vitro activated B cells (see U.S. Pat. Nos. 5,567,610 and 5,229,275) or by using various techniques known in the art, including phage display libraries (Hoogenboom and Winter, *J. Mol. Biol.*, 227:381 (1991); Marks et al., *J. Mol. Biol.*, 222:581 (1991).

VI. Articles of Manufacture and Kits

Further provided are kits and articles of manufacture comprising any of the isolated anti-TIGIT constructs (such as anti-TIGIT sdAb, anti-TIGIT sdAb-Fc fusion protein, PD-1×TIGIT bispecific construct (e.g., BABP), PD-L1× TIGIT bispecific construct (e.g., BABP)), isolated nucleic acids or vectors encoding thereof, or isolated host cells comprising the isolated nucleic acids or vectors encoding the anti-TIGIT constructs described herein. In some embodiments, a kit is provided which comprises any one of the pharmaceutical compositions described herein and preferably provides instructions for its use.

The kits of the present application are in suitable packaging. Suitable packaging includes, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The article of manufacture can comprise a container and a label or package insert on or associated with the container. Suitable containers include, for example, bottles, vials, syringes, etc. The containers may be formed from a variety of materials such as glass or plastic. Generally, the container holds a composition which is effective for treating a disease or disorder (such as cancer) described herein, and may have a sterile access port (for example the container may be an intravenous solution bag or a vial having a stopper pierceable by a hypodermic injection needle). The label or package insert indicates that the composition is used for treating the particular condition in an individual. The label or package insert will further comprise instructions for administering the composition to the individual. The label may indicate directions for reconstitution and/or use. The container holding the pharmaceutical composition may be a multi-use vial, which allows for repeat administrations (e.g. from 2-6 administrations) of the reconstituted formulation. Package insert refers to instructions customarily included in commercial packages of therapeutic products that contain information about the indications, usage, dosage, administration, contraindications and/or warnings concerning the use of such therapeutic products. Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kits or article of manufacture may include multiple unit doses of the pharmaceutical composition and instructions for use, packaged in quantities sufficient for storage and use in pharmacies, for example, hospital pharmacies and compounding pharmacies.

EXAMPLES

The examples below are intended to be purely exemplary of the invention and should therefore not be considered to limit the invention in any way. The following examples and detailed description are offered by way of illustration and not by way of limitation.

Example 1: Generation of Anti-TIGIT sdAbs

Immunization

Camels were immunized with recombinant TIGIT-Fc (Acrobiosystems) protein under all current animal welfare regulations. For immunization, the antigen was formulated as an emulsion with CFA (Complete Freund's adjuvant; primary immunization) or IFA (incomplete Freund's adjuvant; boost immunizations). The antigen was administered subcutaneously at the neck. Each animal received 5 injections of the emulsion, containing 100 µg of TIGIT-Fc in CFA emulsion and 4 subsequent injections of TIGIT-Fc in IFA emulsion at two-week intervals. At different time points during immunization, 10 ml blood samples were collected from the animal and sera were prepared. The induction of an antigen specific humoral immune response was verified using the serum samples in an ELISA-based experiment with immobilized TIGIT-His protein (FIG. 1 and FIG. 2), showing an adequate elicit of response including heavy chain immunoglobulins (HCAbs). Five days after the last immunization, a blood sample of 300 ml was collected. Peripheral blood lymphocytes (PBLs), as the genetic source of the camel HCAbs, were isolated from the 300 ml blood sample using a Ficoll-Paque gradient (Amersham Biosciences), yielding $1 \times 10^9$ PBLs.

Library Construction

RNA extracted from PBLs was used as starting material for RT-PCR to amplify sdAb encoding gene fragments. These fragments were cloned into an in-house phagemid vector. In frame with the sdAb coding sequence, the vector coded for a C-terminal His-Tag. The library size is around $6 \times 10^8$. The library phage was prepared according to a standard protocol and stored after filter sterilization at 4° C. for further use.

Selections and High-Throughput Screening

Selections were carried out with the above libraries using solid panning as well as cell-based panning. Only a single round of selection was performed for both conditions. Each selection output was analyzed for enrichment factor (# of phage present in eluate relative to control), diversity and percentage of TIGIT positive clones (ELISA). Based on these parameters the best selections were chosen for further analysis. To this end, the output from each selection was recloned as a pool into a soluble expression vector for high-throughput screening. In frame with the sdAb coding sequence, the vector coded for a C-terminal His-Tag. Colonies were picked and grown in 96 deep well plates (1 mL volume) and induced by adding IPTG and 0.1% Triton for sdAb expression in the supernatant.

The supernatant was analyzed for their ability to bind to TIGIT protein (by ELISA) and TIGIT-expressing CHO—K1 stable cell line (by FACS). The positive binders were sequenced and the unique clones were selected for further characterization.

The unique clones were grown in 2XYT medium and induced by IPTG for sdAb expression in the supernatant. The supernatant of unique binders were analyzed for their ability to inhibit the interaction between CD155 and TIGIT. To this end, TIGIT-expressing stable CHO cells were incubated with the sdAb-containing supernatant first, then with CD155-Fc (Acrobiosystems) followed by fluorophore-labelled secondary antibody against human Fc. Shift in mean fluorescent intensity (MFI) as compared with samples without anti-TIGIT sdAb blocking represents the blockade of CD155/TIGIT binding.

All potential inhibitors were selected for $K_D$ analysis by surface plasmon resonance (SPR) on a BIAcore T200 instrument. The dissociation phase was used to calculate the $k_{off}$ values for each individual sdAb.

Example 2: Preparation and In Vitro Evaluation of Anti-TIGIT sdAb-Fc Fusion Proteins Production of sdAb-Fc Fusion Protein The anti-TIGIT sdAb-Fc fusion protein constructs were generated by fusion of anti-TIGIT sdAbs with human IgG1 Fc region. The maxiprep of the constructs were prepared for CHO—K1 cell transient expression and purification. The expressed anti-TIGIT sdAb-Fc fusion proteins were purified by chromatography through a column containing Protein A agarose resin. Protein purity was determined by SEC-HPLC. An anti-TIGIT antibody generated by Bristol-Myers Squibb, 22G2, was produced according to sequence in a published patent (See US2016/0176963, SEQ ID NOs: 7 and 9) in a human IgG1 backbone. A hamster antibody that blocks murine TIGIT, 10A7, was produced according to sequence reported in a published patent (See US2015/0216970, SEQ ID NOs: 13 and 15) in a human IgG1 backbone.

Target Protein Binding and Cross-Species Reaction Test by Surface Plasmon Resonance (SPR)

BIAcore T200 instrument was utilized to determine affinity constant ($K_D$) of each anti-TIGIT sdAb-Fc fusion protein by SPR. Briefly, human, cynomolgus or mouse TIGIT-His protein (Acrobiosystems) was amine-coupled to a CM5 sensor chip at a density of no higher than 100 RU. Anti-TIGIT sdAb-Fc fusion proteins were injected at no less than 5 different concentrations. The kinetics data of several exemplary anti-TIGIT sdAb-Fc fusion proteins were summarized in Table 3.

TABLE 3

Affinity determination of unhumanized anti-TIGIT sdAb-Fc fusion proteins against TIGIT

| Target | Construct | $k_a$ (1/Ms) | $k_d$ (1/s) | $K_D$ (M) |
|---|---|---|---|---|
| Human TIGIT-His | AS19584-Fc | 7.9E+05 | 4.3E−04 | 5.4E−10 |
|  | AS19886-Fc | 1.0E+06 | 1.9E−03 | 1.9E−09 |
|  | A520160-Fc | 6.8E+05 | 1.9E−03 | 2.7E−09 |
|  | 22G2 | 1.4E+06 | 2.7E−04 | 1.9E−10 |
| Cynomolgus TIGIT-His | AS19584-Fc | 2.7E+05 | 1.4E−02 | 5.1E−08 |
|  | A519886-Fc | 1.9E+05 | 1.6E−02 | 8.2E−08 |
|  | A520160-Fc | 1.3E+05 | 2.5E−02 | 2.0E−07 |
|  | 22G2 | 2.0E+06 | 6.8E−03 | 3.4E−09 |
| Mouse TIGIT-His | AS19584-Fc | 1.4E+06 | 7.2E−04 | 5.0E−10 |
|  | A519886-Fc | / | / | / |
|  | A520160-Fc | / | / | / |
|  | 22G2 | / | / | / |

CHO-TIGIT Cell Binding and Inhibition of Ligand Binding by FACS Analysis

To determine cell binding $EC_{50}$, CHO—K1 cells expressing human, cynomolgus or murine TIGIT were harvested and incubated with gradient concentrations of anti-TIGIT sdAb-Fc fusion proteins, followed by fluorophore-labeled secondary antibodies against human Fc. For blocking assay, a fixed concentration of biotinylated CD155-Fc protein (Acrobiosystems) was added to the incubation and the binding of CD155-Fc to CHO/human TIGIT cells were detected with fluorophore-labeled streptavidin. Samples were analyzed with flow cytometry. EC50 of binding and blocking capability of the anti-TIGIT sdAb-Fc fusion proteins were summarized in Table 4. The anti-TIGIT sdAb-Fc fusion proteins had similar or better binding capability to human TIGIT expressed on CHO cells than the positive control 22G2, while AS19584-Fc, AS19886-Fc and AS20160-Fc demonstrated superior ligand blocking capability to 22G2. Additionally, AS19584-Fc was found to bind mouse TIGIT expressed on CHO cells with similar EC50 of its binding to human TIGIT expressed on CHO cells. The mouse TIGIT cross-binder control, 10A7, was detected with a CHO/mouse TIGIT binding $EC_{50}$ of 0.709 nM, similar with AS19584-Fc.

TABLE 4

Binding and blocking of ligand binding data of unhumanized
anti-TIGIT sdAb-Fc fusion proteins against TIGIT

| EC50 (nM) | Binding Assay | | | Blocking Assay |
| --- | --- | --- | --- | --- |
| | Human | Cynomolgus | Mouse | Human |
| AS19584-Fc | 0.571 | 3.851 | 0.806 | 1.085 |
| AS19852-Fc | 0.383 | >100 | / | / |
| AS19858-Fc | 0.223 | >100 | / | / |
| AS19886-Fc | 0.340 | 1.172 | / | 0.643 |
| AS19887-Fc | 0.497 | >100 | / | / |
| AS19888-Fc | 1.004 | >100 | / | / |
| AS20160-Fc | 0.876 | 14.48 | / | 1.177 |
| 22G2 | 1.140 | 0.604 | / | 2.699 |
| 10A7 | 4.057 | >100 | 0.709 | 5.273 |

CT26, a murine colon cancer cell line, has high expression of murine CD155 (data not shown). As AS19584-Fc cross-reacts with murine TIGIT, to assess its capability of blocking TIGIT interaction with its major ligand, CD155, CT26 cells were incubated with murine TIGIT-Fc at the presence of gradient concentrations of AS19584-Fc fusion protein. Murine TIGIT-Fc binding to CT26 cells were evaluated by staining with fluorochrome-conjugated secondary antibody against human Fc and detection by FACS. EC50 of the blockade was 77.90 nM for AS19584-Fc and 71.33 nM for 10A7, a murine TIGIT blocker. Thus, AS19584-Fc and 10A7 have comparable capability of blocking TIGIT ligand CD155.

TIGIT/CD155 Blockade Reporter Assay

TIGIT/CD155 blockade reporter assay was performed using Promega TIGIT/CD155 blockade reporter assay kit (Promega, Cat #CS198811), according to the manual of assay kit (Promega, Cat #CS198811). Briefly, Thaw-and-Use TIGIT Effector Cells were plated overnight and then incubated with a serial dilution of anti-TIGIT antibody or anti-TIGIT sdAb-Fc fusion protein, followed by addition of CD155 aAPC/CHO—K1 Cells at a suitable E:T ratio. After 6 hours induction at 37° C., 5% $CO_2$, Bio-Glo™ Luciferase Assay Reagent was added and luminescence was determined. Four-parameter logistic curve analysis was performed with GraphPad Prism 6 software. Data curves are shown in FIG. 3 and summarized in Table 5. AS19584-Fc, AS19886-Fc and AS20160-Fc have comparable or superior blocking function to 22G2.

TABLE 5

TIGIT/CD155 blockade reporter assay

| Construct | EC50 (nM) | Signal span |
| --- | --- | --- |
| AS19584-Fc | 1.470 | 111.5 |
| AS19886-Fc | 3.044 | 101.5 |
| AS20160-Fc | 5.464 | 88.8 |
| 22G2 | 7.922 | 107.9 |

Example 3: In Vivo Efficacy of Anti-TIGIT sdAb-Fc Fusion Protein in Syngeneic Tumor Models Efficacy Study Comparing 10A7 and AS19584-Fc in CT26 Syngeneic Tumor Model As AS19584-Fc fusion protein and 10A7 has very close cell binding and blocking EC50 to mouse TIGIT (see Table 4), a study was conducted to compare the two antibodies in different molecular modality at a same molar dose. CT26 tumor cells expressing murine CD155 were cultured, suspended in magnesium- and calcium-free $HBSS^{-/-}$, and $5×10^5$ cells were injected subcutaneously at the flank of female Balb/c mice at 6-8 weeks of age. Tumor volumes were measured using caliper and calculated with a formula (Length×Width×Width)/2. When average tumor volume reached 90-100 $mm^3$, mice were randomized to initiate treatment. Test articles were dosed once every 4 days via i.p. Body weights were measured throughout the study. The animals were sacrificed and tumor tissues were harvested at Day 18 post-dosing, digested with Collagenase IV/DNase I to prepare single cell suspension for the staining of surface markers CD3/CD4/CD8 and flow cytometry analysis.

Figure 4B:
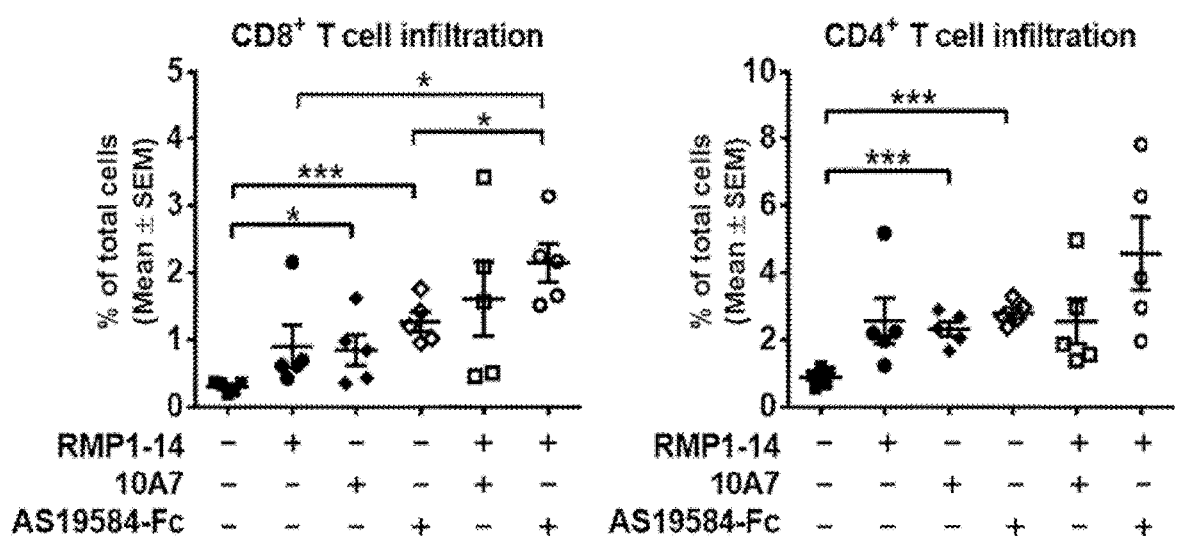

CT26 tumor model is partially resistant to PD-1 blockade. As shown in FIGS. 4A and 4C, a rat anti-murine PD-1 antibody, RMP1-14 (Bioxcell), has limited inhibition to CT26 tumor growth at 5 mg/kg. Both AS19584-Fc and 10A7 significantly delayed tumor progression at a same molar dose (10 mg/kg and 18.8 mg/kg, respectively), either alone or in combination with RMP1-14. Notably, AS19584-Fc demonstrated a faster response within a week post-dosing and eventually a more uniform response than 10A7 at the tested molar dose. The phenomenon was also observed in other studies on different targets for oncology (data not shown). This may be associated with the smaller molecular weight of sdAb-Fc fusion proteins as compared to full-length monoclonal antibodies (~80 kDa vs. 150 kDa, respectively). In PK studies in mouse, anti-TIGIT sdAb-Fc fusion proteins had an about 1.5~2-fold larger apparent volume of distribution at steady state (Vss) and a lower peak plasma concentration (Cmax) than anti-TIGIT full-length antibodies did (FIG. 9; additional data not shown). The difference was not relevant to whether the antibody cross-reacts with mouse TIGIT or not. The observation indicates that sdAb-Fc fusion proteins may have a faster and stronger tissue (including tumor) penetration than full-length antibodies due to its small size, and the faster drug efficacy may also be associated with this unique property. As assessed with flow cytometry, treatment with AS19584-Fc enhanced CD8+ and CD4+ T cell intratumoral infiltration, while its combination with RMP1-14 further enhanced such filtration (FIG. 4B).

Efficacy Study Testing PD-1/TIGIT Dual Blockade in CT26 Syngeneic Tumor Model

CT26 tumor cells were cultured, suspended in magnesium- and calcium-free $HBSS^{-/-}$, and $5×10^5$ cells were injected subcutaneously at the flank of female Balb/c mice at 6-8 weeks of age. Tumor volumes were measured using caliper and calculated with a formula (Length×Width× Width)/2. When average tumor volume reached 90-100 $mm^3$, mice were randomized to initiate treatment. Test articles were dosed once every 4 days via i.p. Body weights were measured throughout the study.

Figure 5A:
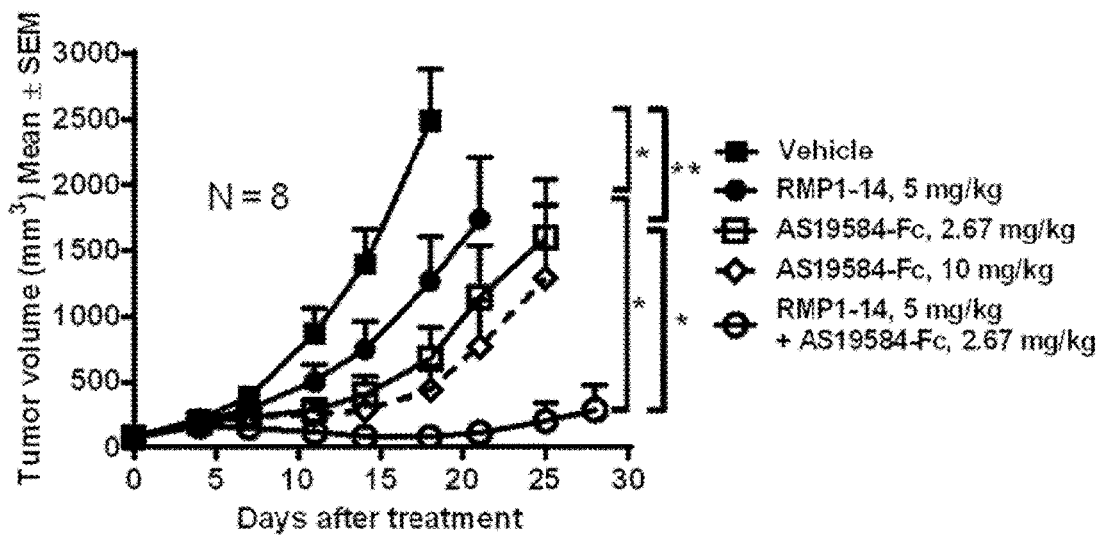
FIGS. 5A-5B depict in vivo efficacy of unhumanized anti-TIGIT sdAb-Fc fusion protein (AS19584-Fc) in CT26 syngeneic tumor model, alone or in combination with anti-PD-1 antibody RMP1-14.
Figure 5B:
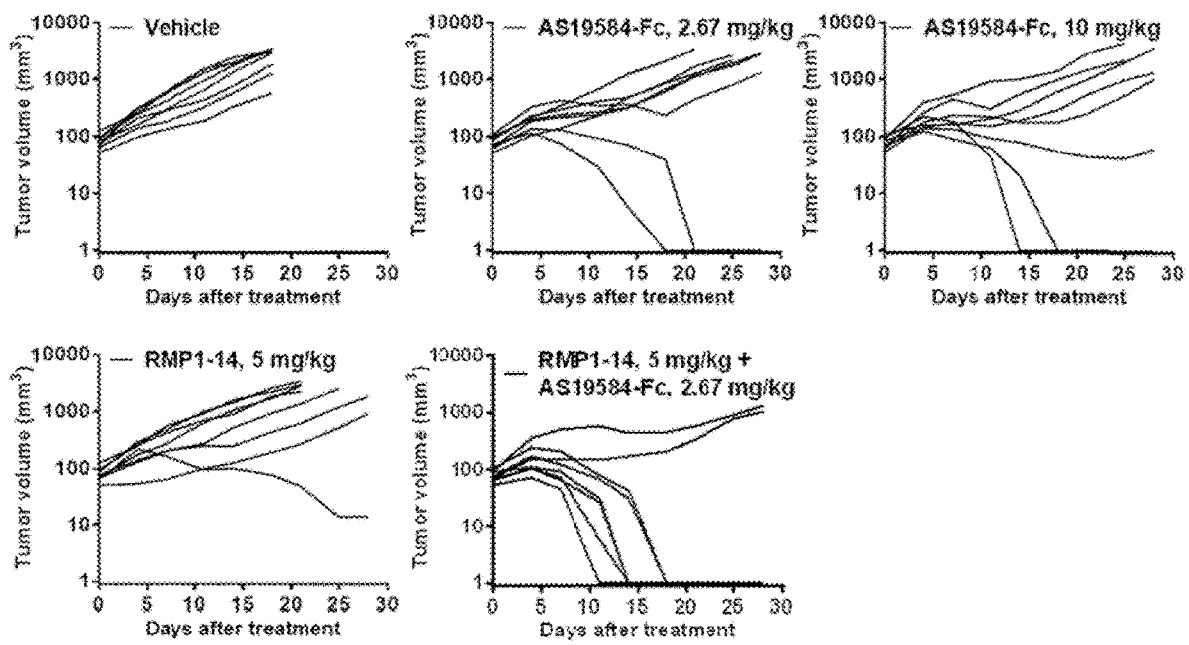

CT26 tumor model is partially resistant to PD-1 blockade. As shown in FIGS. 5A and 5B, the rat anti-murine PD-1 antibody, RMP1-14 (Bioxcell), moderately but significantly inhibited CT26 tumor growth at 5 mg/kg. AS19584-Fc fusion protein showed prominent tumor inhibition at a same molar dose with RMP1-14. The combination of RMP1-14 and AS19584-Fc at a same molar dose (5 mg/kg and 2.67 mg/kg, respectively) demonstrated significantly improved efficacy, with tumor complete regression observed in 6 out of 8 mice.

Efficacy Study Testing PD-1/TIGIT Dual Blockade in MC38 Syngeneic Tumor Model

MC38 tumor cells were cultured, suspended in magnesium- and calcium-free HBSS$^{-/-}$, and $1\times10^6$ cells were injected subcutaneously at the flank of female C57BL/6 mice at 6-8 weeks of age. Tumor volumes were measured using caliper and calculated with a formula (Length×Width×Width)/2. When average tumor volume reached 90-100 mm$^3$, mice were randomized to initiate treatment. Test articles were dosed once every 4 days via i.p. Body weights were measured throughout the study.

Figure 6A:
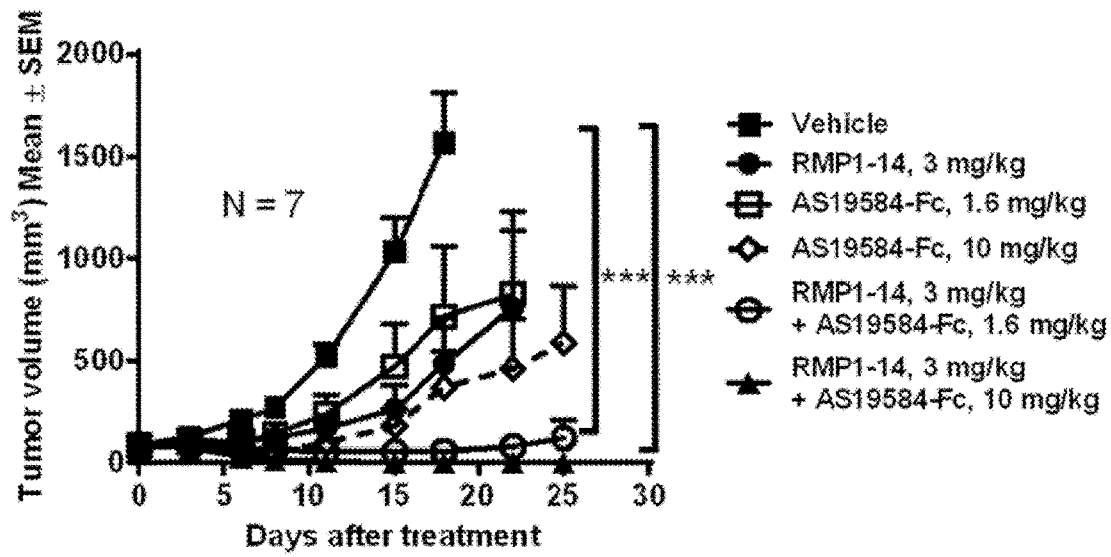
FIGS. 6A-6B depict in vivo efficacy of unhumanized anti-TIGIT sdAb-Fc fusion protein (AS19584-Fc) in MC38 syngeneic tumor model, alone or in combination with anti-PD-1 antibody RMP1-14.
Figure 6B:
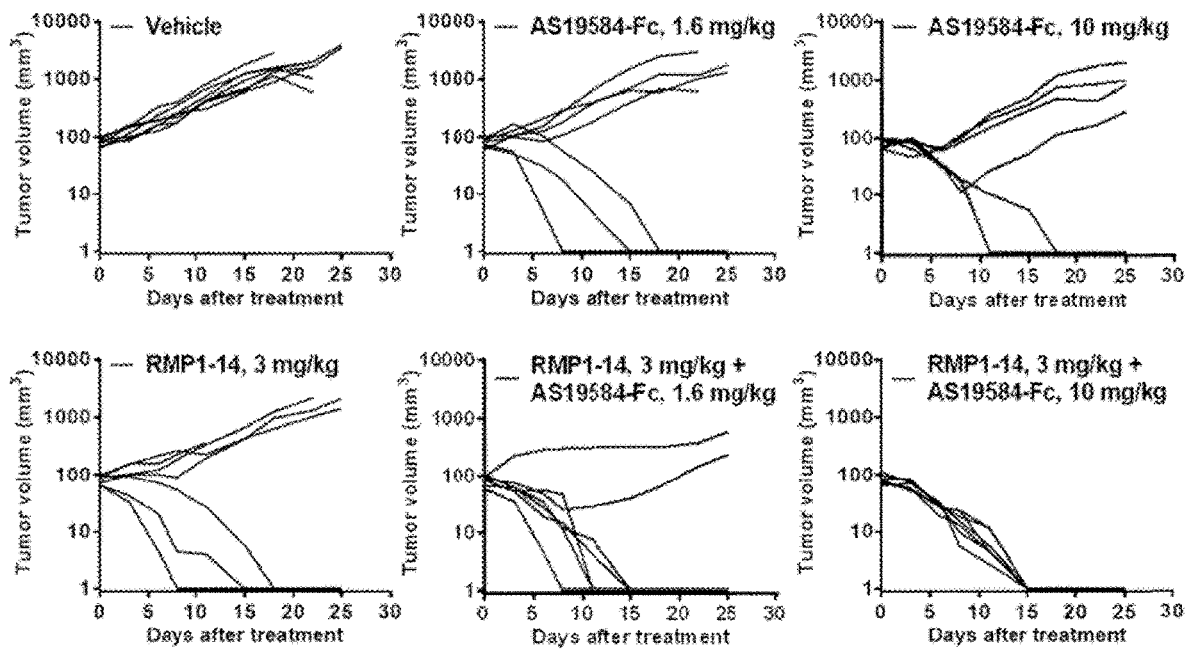

MC38 tumor model is sensitive to PD-1 blockade. As shown in FIGS. 6A and 6B, RMP1-14 substantially delayed MC38 tumor growth at 3 mg/kg. AS19584-Fc fusion protein inhibited tumor growth in a dose-dependent manner. The combination of RMP1-14 and AS19584-Fc at a same molar dose (3 mg/kg and 1.6 mg/kg, respectively) demonstrated synergy of targeting PD-1 and TIGIT simultaneously, resulting in a dramatically improved efficacy and complete regression in 5 out of 7 mice. The combination of RMP1-14 and a high dose of AS19584-Fc (3 mg/kg and 10 mg/kg, respectively) completely abrogated tumor engraftment in all the animals (7 out of 7).

Example 4: Humanization, Production and Characterization of Anti-TIGIT sdAb-Fc Fusion Proteins Humanization of Anti-TIGIT sdAbs Protein sequences of sdAb AS19584 and AS19886 were aligned with the 5 closest human germline sequences sharing the highest degree of homology. The best human germline sequence was selected as human acceptor. Homology model was made. According to the model analysis data, residues potentially critical for antigen binding or antibody scaffold formation were left untouched while the rest were selected for conversion into the human counterpart. Initially a panel of 4-6 sequence optimized variants was generated (stage 1). These variants were analyzed for a number of parameters and the results obtained were used to design a second set of sdAbs (stage 2). Humanized sdAbs are indicated with "VH" in their names.

Production of Humanized Anti-TIGIT sdAb-Fc Fusion Proteins

Among humanized variants, AS19584VH28, AS19886VH5 and AS19886VH8 were selected for production and characterization according to affinity and small scale production level. The humanized anti-TIGIT sdAb-Fc fusion protein constructs were generated by fusing humanized anti-TIGIT sdAbs with human IgG1 Fc region. The maxiprep of the constructs were prepared for HEK293 cell transient expression and purification. The expressed humanized anti-TIGIT sdAb-Fc fusion proteins were purified by chromatography through a column containing Protein A agarose resin. Protein purity was determined by SEC-HPLC. Expression results were summarized in Table 6.

TABLE 6

Expression of humanized anti-TIGIT sdAb-Fc fusion proteins

| Construct | Transient expression (mg/L) | Purity (%) | Endotoxin level (EU/mg) |
|---|---|---|---|
| AS19584VH28-Fc | 212.0 | 98.83 | 0.1 |
| AS19886VH5-Fc | 76.8 | 98.36 | 0.1 |
| AS19886VH8-Fc | 70.0 | 96.47 | 0.2 |

Stability Analysis

The formation of larger protein aggregates during heating was detected using dynamic light scattering (DLS). A temperature ramp from 25° C. to 75° C. with temperature interval at about 0.75° C. was performed for anti-TIGIT sdAb-Fc fusion protein samples at 1.5 mg/ml using the DYNAPRO® NANOSTAR® plate reader (Wyatt, Santa Barbara, California). 20 μl of each sample was added to a WYATT® disposable cuvette followed by covering the sample with 10 μl of mineral oil (Sigma 8410) to prevent evaporation. Triplicate measurements (5 acquisitions/each measurement) were averaged for each anti-TIGIT sdAb-Fc fusion protein sample. In the duration of an experiment with the chosen temperature interval, the thermal scan rate was calculated to be 1.5° C./min. Each sample was measured while the temperature was continuously increased until the target temperature reached 75° C. (~40 min). The aggregation temperature ($T_{agg}$) was analyzed with onset analysis method in the DYNAMICS™ 7.6.0.48 software (Wyatt, Santa Barbara, California). The measured aggregation onset temperatures ($T_{agg}$) of various samples were shown in Table 7.

The acidic stability was assessed as below. Each anti-TIGIT sdAb-Fc fusion protein sample was prepared at 10 mg/ml in 50 mM sodium citrate buffer with different pH: 3.6, 3.3, 3.0 and 2.7, one control was prepared in pH 7.2 sodium phosphate buffer. After 1 hour exposure in the acidic condition at R.T., the sample was neutralized to pH 7.2 by sodium phosphate buffer. Each sample was then detected with SDS-PAGE for purity analysis and SPR activity. The percent of active concentrations at various acidic conditions were summarized in Table 7.

Freeze-thaw stability was tested as below. Anti-TIGIT sdAb-Fc fusion protein samples at concentration of >50 mg/ml in a buffer with 4% sucrose, 50 mM Histidine and 50 mM Arginine, pH 6.0, were completely freeze-thawed for five cycles. Fractions of intact full monomeric molecules of all samples were evaluated by SEC-HPLC, and the data were recorded and analyzed using CHROMELEON™ software supplied by the manufacturer. The recovery rate of each anti-TIGIT sdAb-Fc fusion protein after freeze-thaw cycles was shown in Table 7.

Data in Table 7 demonstrated that all tested humanized anti-TIGIT sdAb-Fc fusion proteins were stable in thermal, acidic, and freeze-thaw stability tests.

TABLE 7

Stability analysis of humanized anti-TIGIT sdAb-Fc fusion proteins

| Construct | Thermal stability $T_{agg}$ (° C.) | Acidic stability Active concentration (%) | | | | | Freeze-thaw stability Recovery rate (%) |
| --- | --- | --- | --- | --- | --- | --- | --- |
| | | Control | pH 3.6 | pH 3.3 | pH 3.0 | pH 2.7 | |
| AS19584VH28-Fc | 66.0 | 100 | 99.9 | 100 | 100 | 100 | 101 |
| AS19886VH5-Fc | 60.2 | 100 | 99.9 | 100 | 100 | 100 | 112 |
| AS19886VH8-Fc | 66.0 | 100 | 100.4 | 100.3 | 99.7 | 99 | 103 |

Hydrophobicity Analysis

The hydrophobicity of the humanized anti-TIGIT sdAb-Fc fusion proteins was tested by hydrophobic interaction chromatography (HIC). Each sample was analyzed on the TSKgel® Butyl-NPR HPLC Column with increasing amount of $(NH4)_2SO_4$ containing Tris buffer (pH 7.0) as the mobile phase at a flow rate of 1 ml/min. Retention time was used to compare the hydrophobicity of each sample. As shown in Table 8, all the humanized anti-TIGIT sdAb-Fc fusion proteins are qualified in terms of hydrophobicity.

TABLE 8

Hydrophobicity analysis of humanized anti-TIGIT sdAb-Fc fusion proteins

| Construct | Retention time (min) |
| --- | --- |
| AS19584VH28-Fc | 21.6 |
| AS19886VH5-Fc | 18.7 |
| AS19886VH8-Fc | 18.7 |

Solubility Analysis

To evaluate the solubility, purified humanized anti-TIGIT sdAb-Fc fusion proteins were measured using a cross-interaction chromatography (CIC) column. Murine polyclonal antibodies purified from pooled mouse serum were purchased from Sigma-Aldrich (15381). Murine polyclonal antibodies were coupled to the resin matrix at ~30 mg/mL. Purified anti-TIGIT sdAb-Fc fusion proteins in PBS buffer were injected to the murine IgG-coupled column and the control column, respectively, with concentrations ranging from 0.05 to 0.20 mg/mL. The retention time was used to calculate the retention factor k' values reported in Table 9: k'=(Vr−Vo)/Vo=(Tr−Tm)/Tm. Vr represents the elution volume of the sample on the protein coupled column, Vo represents the elution volume from a control column, Tr represents the retention time on the protein coupled column, and Tm represents the retention time on the control column. A number of samples were run twice on the same column. Proteins with k' values >0.6 are generally significantly less soluble. According to Table 9, all humanized anti-TIGIT sdAb-Fc fusion protein samples exhibited excellent solubility.

TABLE 9

Solubility analysis of humanized anti-TIGIT sdAb-Fc fusion proteins

| Construct | K' |
| --- | --- |
| AS19584VH28-Fc | 0.041 |
| AS19886VH5-Fc | −0.037 |
| AS19886VH8-Fc | 0.030 |

Target Protein Binding and Cross-Species Reaction Test by Surface Plasmon Resonance (SPR)

BIAcore T200 instrument was utilized to determine affinity constant ($K_D$) of each anti-TIGIT sdAb-Fc fusion protein by SPR. Briefly, human, cynomolgus or mouse TIGIT-His (Acrobiosystems) was amine-coupled to a CM5 sensor chip at a density of no higher than 100 RU. Anti-TIGIT sdAb-Fc fusion proteins were injected at no less than 5 different concentrations. The kinetics data were summarized in Table 10.

TABLE 10

Affinity determination of anti-TIGIT sdAb-Fc fusion proteins against TIGIT

| Target | Construct | $k_a$ (1/Ms) | $k_d$ (1/s) | $K_D$ (M) |
| --- | --- | --- | --- | --- |
| Human TIGIT-His | AS19584VH28-Fc | 7.3E+05 | 2.1E−04 | 2.9E−10 |
| | AS19886VH5-Fc | 5.5E+05 | 1.6E−03 | 2.9E−09 |
| | AS19886VH8-Fc | 7.3E+05 | 1.7E−03 | 2.4E−09 |
| | AS19584-Fc | 9.5E+05 | 3.4E−04 | 3.5E−10 |
| | AS19886-Fc | 8.8E+05 | 2.3E−03 | 2.6E−09 |
| | 22G2 | 1.4E+06 | 1.6E−04 | 1.2E−10 |
| Cynomolgus TIGIT-His | AS19584VH28-Fc | 3.4E+05 | 1.2E−02 | 3.4E−08 |
| | AS19886VH5-Fc | 9.5E+04 | 2.7E−02 | 2.8E−07 |
| | AS19886VH8-Fc | 1.4E+05 | 2.3E−02 | 1.6E−07 |
| | AS19584-Fc | 4.6E+05 | 1.7E−02 | 3.8E−08 |
| | AS19886-Fc | 1.4E+05 | 1.1E−02 | 7.6E−08 |
| | 22G2 | 1.3E+06 | 5.6E−03 | 4.1E−09 |
| Mouse TIGIT-His | AS19584VH28-Fc | 6.2E+05 | 4.9E−04 | 7.8E−10 |
| | AS19886VH5-Fc | / | / | / |
| | AS19886VH8-Fc | / | / | / |
| | AS19584-Fc | 8.8E+05 | 4.9E−04 | 5.5E−10 |
| | AS19886-Fc | / | / | / |
| | 22G2 | / | / | / |

CHO-TIGIT Cell Binding and Inhibition of Ligand Binding by FACS Analysis

The ability of anti-TIGIT sdAb-Fc fusion proteins to bind to TIGIT expressed on CHO—K1 cells and block CD155 ligand binding was determined with the same methods described in Example 2. EC50 of binding and blocking capability of anti-TIGIT sdAb-Fc fusion proteins were summarized in Table 11. All humanized anti-TIGIT sdAb-Fc fusion proteins have comparable binding and blocking capability to their parental anti-TIGIT sdAb-Fc fusion proteins.

TABLE 11

Binding and blocking data of anti-TIGIT sdAb-Fc fusion proteins against TIGIT

| Construct | Binding Assay EC50 (nM) | | Blocking Assay EC50 (nM) |
| --- | --- | --- | --- |
| | Human | Cynomolgus | Human |
| AS19584VH28-Fc | 0.432 | 1.017 | 1.651 |
| AS19886VH5-Fc | 0.657 | 2.062 | 2.818 |
| AS19886VH8-Fc | 0.676 | 2.277 | 2.486 |
| AS19584-Fc | 0.391 | 0.664 | 1.700 |
| AS19886-Fc | 0.541 | 1.354 | 2.377 |
| 22G2 | 0.494 | 1.120 | 1.944 |

TIGIT/CD155 Blockade Reporter Assay and IL-2 Release Assay

TIGIT/CD155 Blockade Reporter Assay:

The study was conducted according to the method described in Example 2. 22G2 served as a positive control. Data curves are shown in FIG. 7 and summarized in Table 12. The results indicate that the humanized anti-TIGIT sdAb-Fc fusion proteins have comparable function to their parental clones in terms of ligand blockade.

IL-2 Release Assay:

CD155-expressing target cells developed by GenScript were plated in 96-w plate overnight and then incubated with a serial dilution of anti-TIGIT antibody or anti-TIGIT sdAb-Fc fusion protein, followed by addition of in-house developed TIGIT effector cells at a suitable E:T ratio. After 24 hours induction at 37° C., 5% $CO_2$, the concentration of interleukin 2 (IL-2) in cell-culture supernatants was measured by human IL-2 HTRF assay kit. Four-parameter logistic curve analysis was performed with GraphPad Prism 6 software. Data curves are shown in FIG. 8 and summarized in Table 12. 22G2 served as a positive control. The results indicate that the humanized anti-TIGIT sdAb-Fc fusion proteins have comparable function to their parental clones in terms of induction of IL-2 release in effector T cells.

TABLE 12

Functional assays for anti-TIGIT sdAb-Fc fusion proteins

| Construct | Reporter assay EC50 (nM) | IL-2 release assay EC50 (nM) |
| --- | --- | --- |
| AS19584VH28-Fc | 2.12 | 0.818 |
| AS19886VH5-Fc | 3.54 | 3.150 |
| AS19886VH8-Fc | 3.27 | 5.850 |
| AS19584-Fc | 2.20 | 1.025 |
| AS19886-Fc | 3.16 | 2.644 |
| 22G2 | 3.04 | 3.072 |

Example 5: In Vivo Studies of Humanized Anti-TIGIT sdAb-Fc Fusion Proteins

Pharmacokinetic Study of Humanized Anti-TIGIT sdAb-Fc Fusion Protein

C57BL/6 mice at 8 weeks of age received a single i.v. bolus of either 22G2 or AS19584VH28-Fc fusion protein, at a dose of 3 mg/kg. At various time points, peripheral blood samples were harvested to prepare plasma and the concentrations of test antibody were determined using sandwich ELISA. WinNonlin was used to model the pharmacokinetic profile of each test antibody with non-compartmental analysis (Model 201). Data were summarized in Table 13 and pharmacokinetic curve was shown in FIG. 9. The results of this study and several others (data now shown) indicate that, as compared to monoclonal antibodies, anti-TIGIT sdAb-Fc fusion proteins have shorter half-life, higher clearance but larger apparent volume of distribution at steady state.

TABLE 13

Pharmacokinetic profile of monoclonal anti-TIGIT antibody and humanized anti-TIGIT sdAb-Fc fusion protein

| Parameters | Unit | 22G2 | AS19584V1128-Fc |
| --- | --- | --- | --- |
| $t_{1/2}$ (Terminal half-life) | hr | 267.031 ± 8.071 | 207.153 ± 14.739 |
| CL | ml/hr/kg | 0.262 ± 0.005 | 0.459 ± 0.064 |
| Cmax | μg/ml | 55.973 ± 6.805 | 51.344 ± 7.644 |
| Vss | ml/kg | 102.086 ± 3.562 | 138.449 ± 6.166 |
| MRT | hr | 389.45 ± 6.564 | 304.32 ± 33.505 |
| $AUC_{0-t}$ | hr*μg/ml | 9535.171 ± 260.896 | 5910.564 ± 673.563 |
| $AUC_{0-\infty}$ | hr*μg/ml | 11449.56 ± 207.903 | 6616.818 ± 941.466 |

Efficacy of Humanized Anti-TIGIT sdAb-Fc Fusion Proteins in TIGIT-Humanized Mice Bearing MC38 Tumor MC38 tumor cells were cultured, suspended in magnesium- and calcium-free $HBSS^{-/-}$, and $1×10^6$ cells were injected subcutaneously at the flank of female C57BL/6 mice with human TIGIT knock-in (KI) at 6-8 weeks of age (Biocytogen). Tumor volumes were measured using caliper and calculated with a formula (Length×Width×Width)/2. When average tumor volume reached 90-100 $mm^3$, mice were randomized to initiate treatment. Test articles were dosed once every 4 days via i.p. Body weights were measured throughout the study.

Figure 10A:
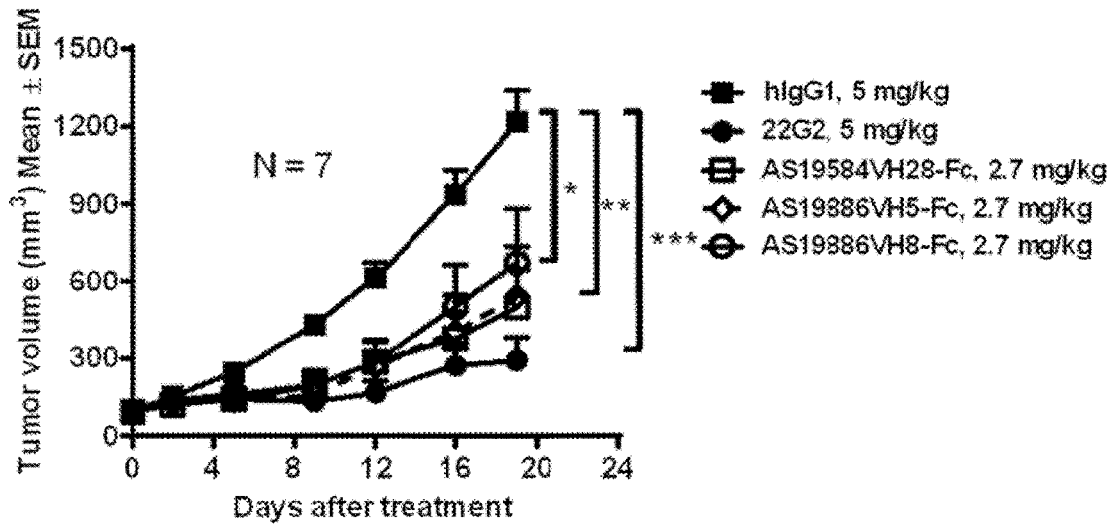
FIGS. 10A-10B depict in vivo efficacy of humanized anti-TIGIT sdAb-Fc fusion proteins in TIGIT humanized mice bearing MC38 tumor model.
Figure 10B:
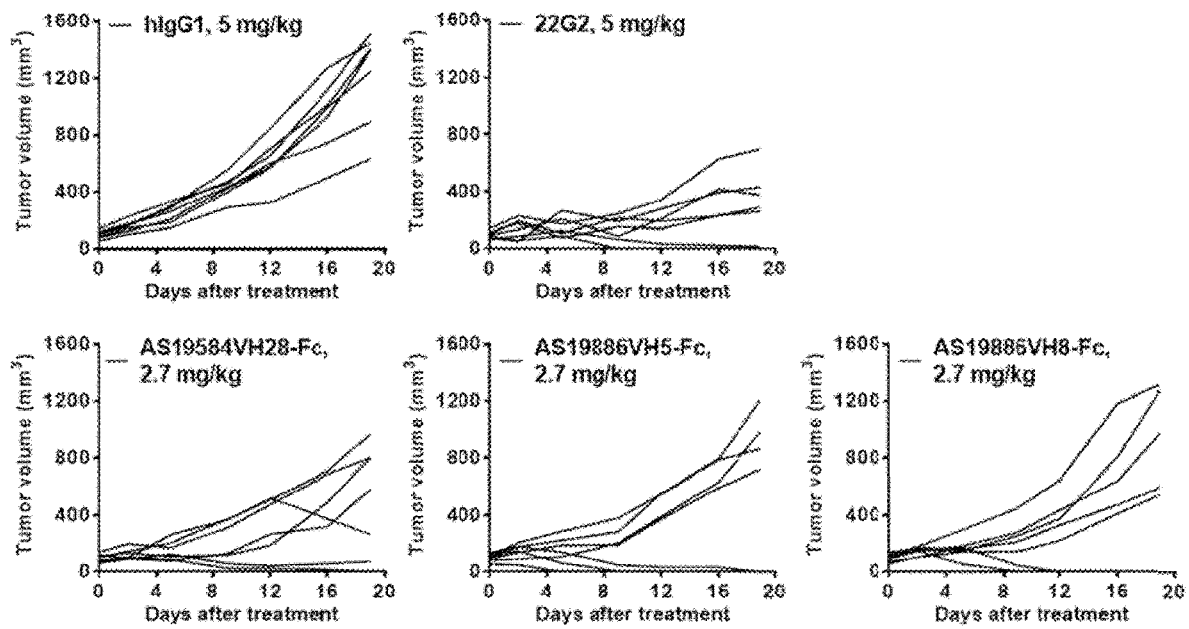

As shown in FIGS. 10A and 10B, all tested antibodies including 3 humanized anti-TIGIT sdAb-Fc fusion proteins and the positive control 22G2 inhibited the growth of MC38 tumor significantly, demonstrating the in vivo efficacy of the humanized anti-TIGIT sdAb-Fc fusion proteins. The superior efficacy of 22G2 to the humanized anti-TIGIT sdAb-Fc fusion proteins in this study, which is inconsistent with the in vitro study results, is most probably due to the shorter half-life of anti-TIGIT sdAb-Fc fusion proteins as compared to regular full-length antibodies (also see FIG. 9 and Table 13), as well as due to a low test dose adopted in this case.

Example 6: Generation and In Vitro Characterization of Proof-of-Concept (POC) Bispecific Molecules Targeting PD-1/PD-L1 and TIGIT Construction and Expression of PD-1×TIGIT and PD-L1×TIGIT POC Bispecific Antigen Binding Proteins (BABPs)

BABPs can be constructed with an anti-TIGIT sdAb fused to a full-length antibody, or scFv or Fab region derived from the full-length antibody with an Fc region at the C-terminus, such as anti-PD-1 antibodies, e.g., Keytruda® (Pembrolizumab), PD1-BM-min, Opdivo® (nivolumab), or anti-PD-L1 antibodies, e.g., Tecentriq® (Atezolizumab), IMFINZI™ (Durvalumab), Bavencio® (Avelumab), or humanized 53C1 (h53C1). The anti-TIGIT sdAb can be connected to the full-length antibody (or scFv or Fab region derived from the full-length antibody with Fc region at the C-terminus) via a linker (such as 9-amino acid Gly/Ser linker (9GS linker), human IgG1 (hIgG1) hinge, or mutated hIgG1 hinge), or without a linker. The BABP can be of any configuration exemplified in FIGS. 17-26. For example, anti-TIGIT sdAb can be fused to at least one of the heavy chains, at least one of the light chains, or both heavy chains and light chains, via N- or C-terminus (see FIGS. 17-20).

This example describes the construction and expression of PD-L1×TIGIT BABPs for proof-of-concept (POC). Anti-TIGIT sdAb AS19584 was fused to the N-terminus of the heavy chain of anti-PD-L1 antibody h53C1 (BTP-4 and BTP-5) or Tecentriq biosimilar (BTP-6 and BTP-7), via a mutated human IgG1 (hIgG1) hinge. A wild-type human IgG1 Fc was used for BTP-5 and BTP-7, while an effectorless human IgG1 (inert hIgG1) Fc was used for BTP-4 and BTP-6. All the POC PD-L1×TIGIT BABP constructs have the structure shown in FIG. 17. The POC BABP constructs were transiently expressed in Expi293F cells and the proteins were purified with Protein A affinity column. Protein purity was determined with SEC-HPLC. Results were summarized in Table 14.

TABLE 14

Expression of POC PD-L1 × TIGIT BABPs

| Construct | Production (mg/L) | Purity (%) | Endotoxin level (EU/mg) |
| --- | --- | --- | --- |
| BTP-4 | 98.4 | 97.09 | 0.1 |
| BTP-5 | 114.1 | 99.52 | 0.1 |
| BTP-6 | 269.8 | 95.27 | 0.1 |
| BTP-7 | 318.6 | 95.15 | 0.1 |

Affinity Determination of BABPs

To compare the POC PD-L1×TIGIT BABPs with its parental elements (anti-PD-L1 Ab and anti-TIGIT sdAb-Fc fusion protein), the Fc region of Tecentriq® was changed to a wild-type human IgG1 (hIgG1) Fc as a control, and h53C1 and AS19584-Fc fusion protein were produced with either wild-type hIgG1 Fc or effectorless human IgG1 (inert hIgG1) Fc as controls. Human and mouse TIGIT-His and human PD-L1 were purchased from Acrobiosystems. The affinities of the POC PD-L1×TIGIT BABPs were tested as described in Example 2 and the data were shown in Table 15. The PD-L1×TIGIT BABPs have comparable or slightly decreased affinity to the target proteins, as compared to their parental elements monoclonal antibody and anti-TIGIT sdAb-Fc fusion protein with corresponding isotype.

TABLE 15

Affinity determination of POC PD-L1 × TIGIT BABPs

| Affinity ($K_D$, M) | Human PD-L1 | Human TIGIT | Mouse TIGIT |
| --- | --- | --- | --- |
| BTP-4 (h53C1 inert IgG1) | 5.1E−10 | 4.1E−10 | 5.6E−10 |
| BTP-5 (h53C1 IgG1) | 4.9E−10 | 4.1E−10 | 5.9E−10 |
| BTP-6 (Tecentriq biosimilar inert IgG1) | 3.4E−10 | 3.6E−10 | 5.4Ev10 |
| BTP-7 (Tecentriq biosimilar IgG1) | 3.4E−10 | 4.1E−10 | 5.6E−10 |
| h53C1 (IgG1) | 5.0E−10 | / | / |
| h53C1 (inert IgG1) | 4.1E−10 | / | / |
| Tecentriqbiosimilar (IgG1) | 3.1E−10 | / | / |
| Tecentriqbiosimilar (inert IgG1) | 2.8E−10 | / | / |
| AS19584-Fc (IgG1) | / | 4.0E−10 | 5.7E−10 |
| AS19584-Fc (inert IgG1) | / | 4.9E−10 | 7.1E−10 |

CHO-TIGIT or CHO-PD-L1 Cell Binding and Inhibition of Ligand Binding by FACS Analysis POC PD-L1×TIGIT BABPs' ability of binding to TIGIT expressed on CHO cells and blocking of CD155 binding to CHO-TIGIT cells were assessed as described in Example 2. The ability of binding to PD-L1 expressed on CHO cells and blocking of PD-1 binding to CHO-PD-L1 cells were also similarly assessed as described in Example 2. 22G2 was used as a positive anti-TIGIT Ab control. Results are summarized in Table 16. The PD-L1×TIGIT BABPs have comparable or slightly decreased target cell binding and ligand blocking capabilities, as compared to their parental elements monoclonal antibody (anti-PD-L1 Ab) and anti-TIGIT sdAb-Fc fusion protein with corresponding isotype.

TABLE 16

Binding and blocking data of POC PD-L1 × TIGIT BABPs

| | PD-L1 | | TIGIT | |
| --- | --- | --- | --- | --- |
| EC50 (nM) | Binding | Blocking | Binding | Blocking |
| BTP-4 (h53C1 inert IgG1) | 0.627 | 0.469 | 1.008 | 0.913 |
| BTP-5 (h53C1 IgG1) | 0.636 | 0.468 | 0.829 | 1.013 |
| BTP-6 (Tecentriq biosimilar inert IgG1) | 2.957 | 2.275 | 3.729 | 6.166 |
| BTP-7 (Tecentriq biosimilar IgG1) | 1.692 | 1.285 | 1.427 | 2.473 |
| h53C1 (IgG1) | 0.466 | 0.432 | / | / |
| h53C1 (inert IgG1) | 0.451 | 0.339 | / | / |
| Tecentriqbiosimilar (IgG1) | 1.292 | 0.872 | / | / |
| Tecentriqbiosimilar (inert IgG1) | 1.288 | 0.873 | / | / |
| AS19584-Fc (IgG1) | / | / | 0.713 | 0.884 |
| AS19584-Fc (inert IgG1) | / | / | 1.036 | 1.415 |
| 22G2 (IgG1) | / | / | 2.455 | 1.113 |

In Vitro Functional Assays for POC PD-L1×TIGIT BABPs

PD-L1 Cell-Based Assay:

PD-L1 Target cells (GS-C2/PD-L1, GenScript, Cat #M00613) were plated overnight and then incubated with a serial dilution of test samples, followed by addition of PD-1 Effector cells (GS-J2/PD-1, GenScript, Cat #M00612) at a suitable E:T ratio. After 6 hours induction at 37° C., 5% $CO_2$, One-Glo™ Luciferase Assay Reagent was added and luminescence was determined. Four-parameter logistic curve analysis was performed with GraphPad Prism 6 software. The results are shown in FIG. 11.

Mixed Lymphocyte Reaction (MLR): Dendritic cells (DCs) and CD4+ T cells were isolated from human Peripheral blood mononuclear cells (PBMC). DCs were analyzed for their expressions of costimulatory molecules and MHC class II in FACS assay (the expression data of their surface markers, CD1a, CD83, CD86, and HLA-DR were verified, data not shown). A suitable ratio of CD4+ T cells and DCs were seeded into the wells of a 96-well plate and treated with the testing antibody. Assay plate were incubated in a 37° C./5% $CO_2$ incubator for 72 hours and IL-2 released by cells was measured using human IL2 HTRF Kit (Cisbio, cat #64IL2PEB). The results are shown in FIG. 12.

TIGIT/CD155 blockade reporter assay and IL-2-release assay were conducted according to methods described in Example 2 and Example 4, respectively. The results are shown in FIG. 13 and FIG. 14, respectively.

Results for all the above in vitro cell-based functional assays were summarized in Table 17. The POC PD-L1×TIGIT BABPs showed comparable or slightly decreased in vitro functions, as compared to their parental elements monoclonal antibody (anti-PD-L1 Ab) and anti-TIGIT sdAb-Fc fusion protein with corresponding isotype.

TABLE 17

In vitro functional assays for POC PD-L1 x TIGIT BABPs

| EC50 (nM) | PD-L1 | MLR | TIGIT Reporter assay | IL-2 release |
|---|---|---|---|---|
| BTP-4 (h53C1inert IgG1) | 1.792 | 0.924 | 4.00 | 1.562 |
| BTP-5 (h53C1IgG1) | 1.968 | 1.045 | 3.99 | 2.403 |
| BTP-6 (Tecentriqbiosimilar inert IgG1) | 3.202 | 1.753 | 4.37 | 6.428 |
| BTP-7 (Tecentriqbiosimilar IgG1) | 1.812 | 1.534 | 3.76 | 4.083 |
| h53C1 (IgG1) | 1.871 | 0.270 | / | / |
| h53C1 (inert IgG1) | 1.810 | 0.499 | / | / |
| Tecentriqbiosimilar (IgG1) | 2.060 | 1.942 | / | / |
| Tecentriq biosimilar (inert IgG1) | 1.534 | 1.590 | / | / |
| AS19584 (IgG1) | / | >100 | 2.44 | 1.992 |
| AS19584 (inert IgG1) | / | >100 | 3.40 | 1.820 |
| 22G2 (IgG1) | / | >100 | 6.01 | 2.263 |

PD-L1/TIGIT Cell-Based Bifunctional Reporter Assay:

PD-L1/CD155 target cells (cells expressing PD-L1 and CD155) were plated overnight and then incubated with a serial dilution of test antibodies, followed by addition of PD-1/TIGIT effector cells (cells expressing PD-1 and TIGIT) at a suitable E:T ratio. After 6 hours induction at 37° C., 5% $CO_2$, One-Glo™ Luciferase Assay Reagent was added and luminescence was determined to represent effector cell activation.

As shown in FIG. 15, h53C1, by blocking PD-L1, was able to induce IL-2 expression in T cells. There was minimal difference in the effect between low and high dose. The TIGIT blocker AS19584-Fc (IgG1 or inert IgG1) alone cannot activate T cells in the assay condition. In comparison, POC PD-L1×TIGIT BABPs (BTP-4 and BTP-5) demonstrated superior capability to enhance T cell function by inducing IL-2 expression in effector cells, as compared to their parental elements monoclonal antibodies (anti-PD-L1 Ab) and anti-TIGIT sdAb-Fc fusion proteins with corresponding isotype. The effects of POC PD-L1×TIGIT BABPs were comparable to those of corresponding combinations (h53C1+AS19584-Fc, with either IgG1 or inert IgG1 Fc fragment).

Example 7: In Vivo Efficacy of POC PD-L1×TIGIT BABPs Targeting PD-L1 and TIGIT

Efficacy Study in C57BL/6 Human PD-1 Knock-In (KI) Mice Bearing MC38-hPD-L1 Tumor Model Mouse PD-L1 gene in MC38 tumor cells was knocked out, and human PD-L1 was stably expressed by lentivirus transduction. The generated MC38-hPD-L1 cells were cultured, suspended in magnesium- and calcium-free $HBSS^{-/-}$, and $1\times10^6$ cells were injected subcutaneously at the flank of female C57BL/6 human PD-1 KI mice (Biocytogen) at 6-8 weeks of age, of which the extracellular domain of murine PD-1 gene had been replaced with human counterpart. Tumor volumes were measured using caliper and calculated with a formula (Length×Width×Width)/2. When average tumor volume reached 90-100 mm³, mice were randomized to initiate treatment. Test articles were dosed three times a week via i.p. Body weights were measured throughout the study.

Figure 16A:
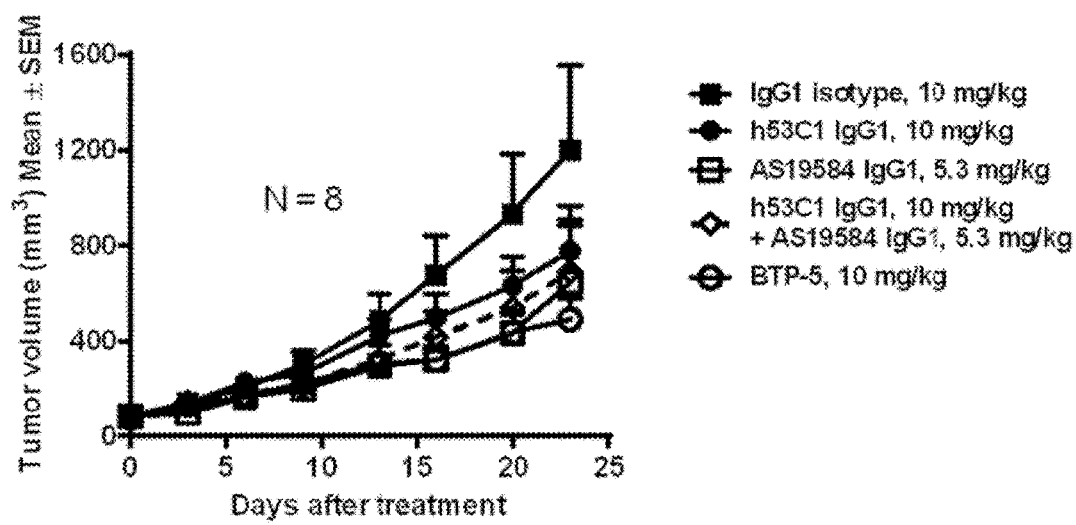
FIGS. 16A-16B depict in vivo efficacy of POC PD-L1× TIGIT BABP BTP-5 in C57BL/6 human PD-1 KI mice bearing MC38-hPD-L1 tumor, compared to its parental elements (h53C1 and AS19584-Fc) and their combination therapy.
Figure 16B:
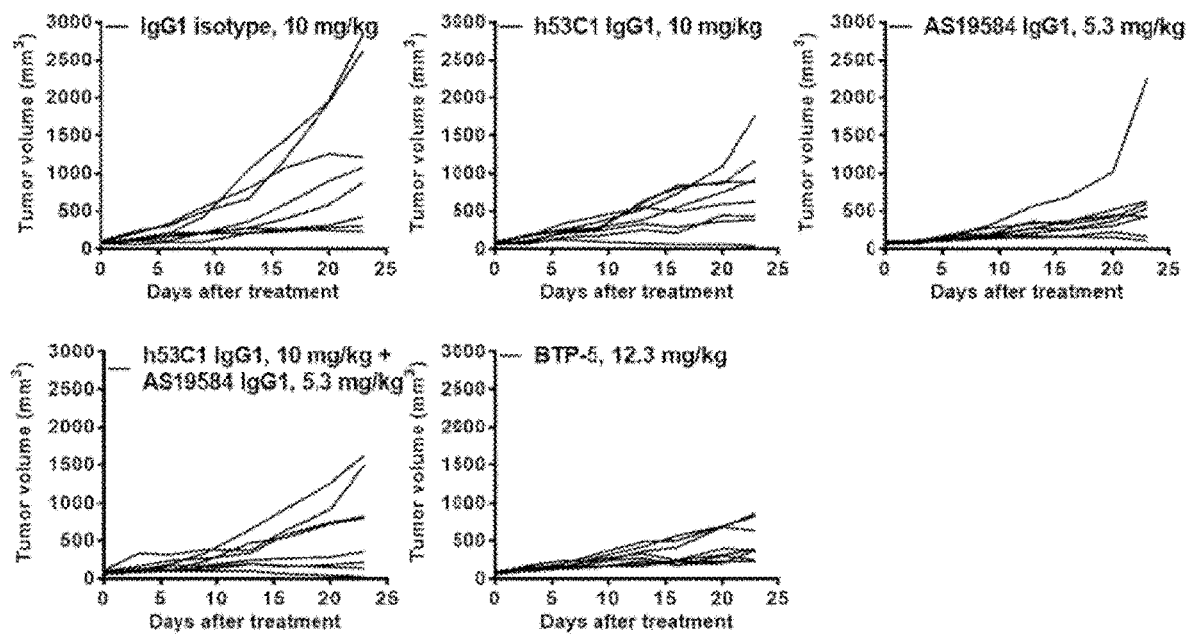

As shown in FIGS. 16A and 16B, both h53C1 and AS19584-Fc (with wild-type IgG1) alone, by blocking PD-L1 and TIGIT respectively, moderately delayed MC38-hPD-L1 tumor growth, with no statistical significance. The combination therapy of h53C1 and AS19584-Fc did not improve the efficacy of either monotherapy, with part of the animals non-responsive. However, animals who received BTP-5 had tumor growth consistently delayed, indicating that POC PD-L1×TIGIT BABP has better therapeutic efficacy than any of the monotherapies and the combination therapy in vivo.

Example 8: Generation of PD-1×TIGIT and PD-L1×TIGIT BABPs

Construction of PD-1×TIGIT and PD-L1×TIGIT BABPs

This example describes the construction of PD-L1×TIGIT and PD-1×TIGIT BABPs.

Humanized anti-TIGIT sdAb AS19584VH28 was fused to heavy chain N-terminus, heavy chain C-terminus, light chain N-terminus, or light chain C-terminus of anti-PD-L1 monoclonal Ab h53C1, to generate PD-L1×TIGIT BABPs BTP-15, BTP-16, BTP-17, and BTP-18, respectively, via a mutated human IgG1 (hIgG1) hinge as the linker. The heavy chain of h53C1 comprises wild-type human IgG1 Fc region. BTP-15, BTP-16, BTP-17, and BTP-18 have the exemplary structures shown in FIG. 17, FIG. 18, FIG. 19, and FIG. 20, respectively.

Humanized anti-TIGIT sdAb AS19584VH28 is fused to heavy chain N-terminus, heavy chain C-terminus, light chain N-terminus, or light chain C-terminus of an anti-PD-1 antibody to generate PD-1×TIGIT BABPs, via a mutated human IgG1 (hIgG1) hinge as the linker. The heavy chain of the anti-PD-1 antibody comprises human IgG4 Fc region. The PD-1×TIGIT BABPs have the exemplary structures shown in FIGS. 17-20.

Example 9: Generation and Characterization of PD-1×TIGIT and PD-L1×TIGIT BABPs

Construction of PD-1×TIGIT and PD-L1×TIGIT BABPs

This example describes the construction of PD-L1×TIGIT and PD-1×TIGIT BABPs.

Humanized anti-TIGIT sdAb AS19584VH28 was fused to heavy chain N-terminus, heavy chain C-terminus, light chain N-terminus, or light chain C-terminus of anti-PD-1 monoclonal Ab PD1-BM-min, to generate PD-1×TIGIT BABPs BTP-11, BTP-12, BTP-13, and BTP-14, respectively, via a mutated human IgG1 (hIgG1) hinge as the linker. The heavy chain of PD1-BM-min comprises human IgG4 Fc region. BTP-11, BTP-12, BTP-13, and BTP-14 have the exemplary structures shown in FIG. 17, FIG. 18, FIG. 19, and FIG. 20, respectively.

Humanized anti-TIGIT sdAb AS19584VH28 was fused to heavy chain N-terminus, heavy chain C-terminus, light chain N-terminus, or light chain C-terminus of anti-PD-L1 monoclonal Ab h53C1, to generate PD-L1×TIGIT BABPs BTP-15, BTP-16, BTP-17, and BTP-18, respectively, via a mutated human IgG1 (hIgG1) hinge as the linker. The heavy chain of h53C1 comprises wild-type human IgG1 Fc region. BTP-15, BTP-16, BTP-17, and BTP-18 have the exemplary structures shown in FIG. 17, FIG. 18, FIG. 19, and FIG. 20, respectively.

Humanized anti-TIGIT sdAb AS19584VH28 was fused to heavy chain N-terminus, or light chain N-terminus of anti-PD-L1 monoclonal Ab h53C1, to generate PD-L1×TIGIT BABPs BTP-21 and BTP-22, respectively, via a mutated human IgG1 (hIgG1) hinge as the linker. The heavy chain of h53C1 comprises inert human IgG1 Fc region. BTP-21 and BTP-22 have the exemplary structures shown in FIG. 17 and FIG. 19, respectively.

Affinity Determination of BABPs

Affinity of the BABPs against human PD-1, PD-L1, human TIGIT and mouse TIGIT was assessed as described before. Results were summarized in Table 18. Briefly, to compare the PD-1×TIGIT BABPs with its parental elements (anti-PD-1 Ab and anti-TIGIT sdAb-Fc fusion protein), PD1-BM-min and AS19584VH28-Fc fusion protein were produced with wild-type human IgG4 Fc as controls. To compare the PD-L1×TIGIT BABPs with its parental elements (anti-PD-L1 Ab and anti-TIGIT sdAb-Fc fusion protein), h53C1 and AS19584VH28-Fc fusion protein were produced with effectorless human IgG1 (inert hIgG1) Fc as controls. Human and mouse TIGIT-His, and human PD-1 and PD-L1 were purchased from Acrobiosystems. The affinities of the PD-1×TIGIT BABPs and PD-L1×TIGIT BABPs were tested as described in Example 2 and the data are shown in Table 18. Both the PD-1×TIGIT BABPs and PD-L1×TIGIT BABPs have comparable or only slightly decreased affinity to the target proteins, as compared to their respective parental elements monoclonal antibody and anti-TIGIT sdAb-Fc fusion protein with corresponding isotype.

TABLE 18

Affinity determination of PD-1 × TIGIT BABPs and PD-L1 × TIGIT BABPs

| Experiment | Affinity ($K_D$, M) | Human PD-1 | Human TIGIT | Mouse TIGIT |
|---|---|---|---|---|
| #1 PD-1/ TIGIT (IgG4) | BTP-11 (IgG4) | 4.0E−09 | 2.8E−10 | 5.0E−10 |
| | BTP-13 (IgG4) | 4.2E−10 | 2.6E−10 | 6.2E−10 |
| | PD1-BM-min (IgG4) | 1.2E−09 | / | / |
| | AS19584VH28 (IgG4) | / | 6.8E−10 | 1.1E−09 |

| | Affinity ($K_D$, M) | Human PD-L1 | Human TIGIT | Mouse TIGIT |
|---|---|---|---|---|
| #2 PD-L1/ TIGIT (IgG1) | BTP-15 (IgG1) | 5.4E−10 | 2.5E−10 | 7.5E−10 |
| | BTP-17 (IgG1) | 6.5E−10 | 2.6E−10 | 8.1E−10 |
| | h53C1 (IgG1) | 3.5E−10 | / | / |
| | AS19584VH28 (IgG1) | / | 2.9E−10 | 1.0E−09 |
| #3 PD-L1/ TIGIT (inert IgG1) | BTP-21 (inert IgG1) | 5.0E−10 | 3.0E−10 | 7.9E−10 |
| | BTP-22 (inert IgG1) | 7.9E−10 | 3.1E−10 | 7.7E−10 |
| | h53C1 (inert IgG1) | 4.4E−10 | / | / |
| | AS19584VH28 (inert IgG1) | / | 3.6E−10 | 1.1E−09 |

CHO-TIGIT, CHO-PD-1 or CHO-PD-L1 Cell Binding and Inhibition of Ligand Binding by FACS Analysis The ability of PD-1×TIGIT BABP's and PD-L1×TIGIT BABP's in binding to PD-1, PD-L1 or TIGIT expressed on CHO cells and their ability in blocking of the binding of PD-1 to CHO-PD-L1 cells, the binding of PD-L1 to CHO-PD-1 cells or the binding of CD155 to CHO-TIGIT cells were assessed as described in Example 2. 22G2 (IgG1) is an anti-TIGIT monoclonal antibody and is expressed according to the published sequence. Tiragolumab (an anti-TIGIT monoclonal antibody in clinical trial), Durvalumab and Atezolizumab (both as commercially available anti-PD-L1 antibodies) were expressed according to their published sequences and used as additional controls. Results are summarized in Table 19. The PD-1×TIGIT BABPs have comparable or only slightly decreased target cell binding and ligand blocking capabilities, as compared to their parental elements monoclonal antibody (anti-PD-1 Ab, PD-1-BM min) and anti-TIGIT sdAb-Fc fusion protein with corresponding isotype. The PD-L1×TIGIT BABPs have comparable or only slightly decreased target cell binding and ligand blocking capabilities, as compared to their parental elements monoclonal antibody (anti-PD-L1 Ab, h53C1) and anti-TIGIT sdAb-Fc fusion protein with corresponding isotype.

TABLE 19

Binding and blocking data of PD-1 × TIGIT BABPs and PD-L1 × TIGIT BABPs

| | | PD-1 | | TIGIT | |
|---|---|---|---|---|---|
| Experiment | EC50 (nM) | Binding | Blocking | Binding | Blocking |
| #1 PD-1/ TIGIT (IgG4) | BTP-11 (IgG4) | 6.308 | 8.681 | 1.405 | 0.9255 |
| | BTP-13 (IgG4) | 1.921 | 2.211 | 1.354 | 1.111 |
| | PD1-BM-min (IgG4) | 1.715 | 1.508 | / | / |
| | AS19584VH28 (IgG4) | / | / | 2.398 | 0.8913 |

| | | PD-L1 | | TIGIT | |
|---|---|---|---|---|---|
| | EC50 (nM) | Binding | Blocking | Binding | Blocking |
| #2 PD-L1/ TIGIT (IgG1) | BTP-15 (IgG1) | 3.530 | 1.834 | 1.792 | 0.2166 |
| | BTP-17 (IgG1) | 3.564 | 2.352 | 0.8443 | 0.6238 |
| | h53C1 (IgG1) | 1.248 | 0.6361 | / | / |
| | AS19584VH28 (IgG1) | / | / | 0.8914 | 0.3353 |
| #3 PD-L1/ TIGIT (inert IgG1) | BTP-21 (inert IgG1) | 3.357 | 3.662 | 3.096 | 3.139 |
| | BTP-22 (inert IgG1) | 4.856 | 5.910 | 4.590 | 4.471 |
| | h53C1 (inert IgG1) | 2.006 | 1.967 | / | / |
| | AS19584VH28 (inert IgG1) | / | / | 5.762 | 4.779 |
| | Atezolizumab | 2.940 | 3.355 | / | / |
| | Durvalumab | 0.7440 | 0.8597 | / | / |
| | 22G2 (IgG1) | / | / | 1.600 | 2.307 |
| | Tiragolumab | / | / | 2.236 | 2.421 |

In Vitro Functional Assays

In vitro functions of the PD-1×TIGIT BABPs and the PD-L1×TIGIT BABPs were analyzed by PD-1 cell based assay, PD-L1 cell based assay, TIGIT cell based reporter assay and IL-2 release assay for TIGIT similarly as described in Examples 2, 4 and 6. 22G2 (IgG1) is an anti-TIGIT monoclonal antibody and is expressed according to the published sequence. Tiragolumab (an anti-TIGIT monoclonal antibody in clinical trial), Durvalumab and Atezolizumab (both as commercially available anti-PD-L1 antibodies) were expressed according to their published sequences and used as additional controls. Results are summarized in Table 20. The PD-1×TIGIT BABPs and PD-L1×TIGIT BABPs showed comparable or only slightly decreased in vitro functions, as compared to their parental elements monoclonal antibody (PD1-BM-min and h53C1 respectively) and anti-TIGIT sdAb-Fc fusion protein with corresponding isotype. PD-L1×TIGIT BABPs BTP-21 and BTP-22 even exhibited better TIGIT blocking function compared to commercial anti-TIGIT antibody Tiragolumab.

TABLE 20

In vitro functional assays for PD-1 × TIGIT BABPs and PD-L1 × TIGIT BABPs

| | | | TIGIT | |
|---|---|---|---|---|
| Experiment | EC50 (nM) | PD-1 | Reporter assay | IL-2 release |
| #1 PD-1/ TIGIT (IgG4) | BTP-11 (IgG4) | 8.514 | 7.814 | 0.778 |
| | BTP-13 (IgG4) | 2.326 | 4.027 | 0.565 |
| | PD1-BM-min (IgG4) | 1.209 | / | / |
| | AS19584VH28 (IgG4) | / | 4.058 | 0.737 |
| | Pembrolizumab (anti-PD-1) | 1.596 | / | / |

TABLE 20-continued

In vitro functional assays for PD-1 × TIGIT BABPs and PD-L1 × TIGIT BABPs

| | | | TIGIT | |
|---|---|---|---|---|
| | EC50 (nM) | PD-L1 | Reporter assay | IL-2 release |
| #2 PD-L1/ TIGIT (IgG1) | BTP-15 (IgG1) | 8.106 | 21.65 | 2.450 |
| | BTP-17 (IgG1) | 3.836 | 2.611 | 0.509 |
| | h53C1 (IgG1) (anti-PD-L1) | 4.017 | / | / |
| | AS19584VH28 (IgG1) | / | 3.123 | 0.223 |
| #3 PD-L1/ TIGIT (inert IgG1) | BTP-21 (inert IgG1) | 5.042 | 5.913 | Not tested |
| | BTP-22 (inert IgG1) | 5.826 | 5.353 | |
| | h53C1 (inert IgG1) | 6.875 | / | |
| | AS19584VH28 (inert IgG1) | / | 5.420 | |
| | Atezolizumab (anti-PD-L1) | 5.146 | / | |
| | Durvalumab (anti-PD-L1) | 5.499 | / | |
| | 22G2 (IgG1) (anti-TIGIT) | / | 4.648 | |
| | Tiragolumab (anti-TIGIT) | / | 11.36 | |

Figure 27A:
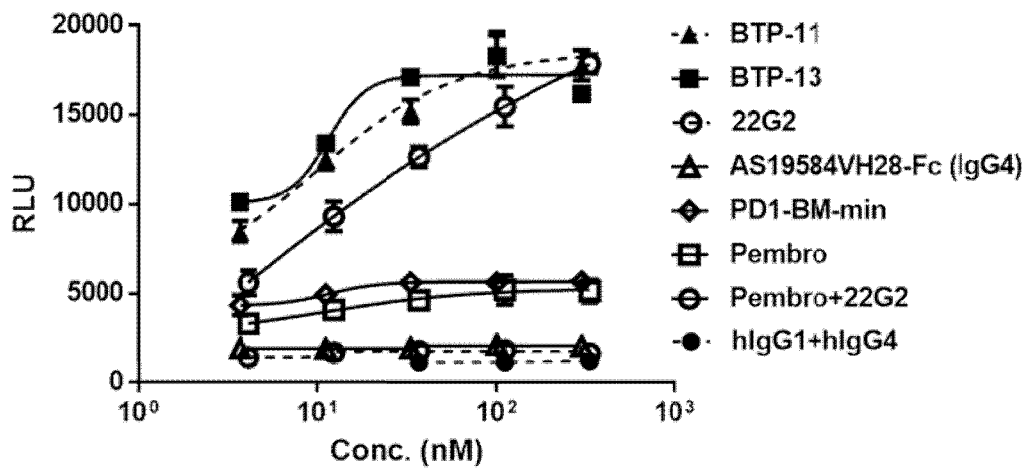
FIGS. 27A-27C depict PD-1/TIGIT and PD-L1/TIGIT bifunctional reporter assay to assess the in vitro synergistic effect of the BABPs by targeting PD-L1/PD-1 pathway and CD155/TIGIT pathways simultaneously. BTP-11 and BTP-13 were tested and compared with monotherapies blocking PD-1 or TIGIT (FIG. 27A). BTP-15, BTP-17, BTP-21 and BTP-22 were tested and compared with monotherapies blocking PD-L1 or TIGIT (FIGS. 27B and 27C).
Figure 27B:
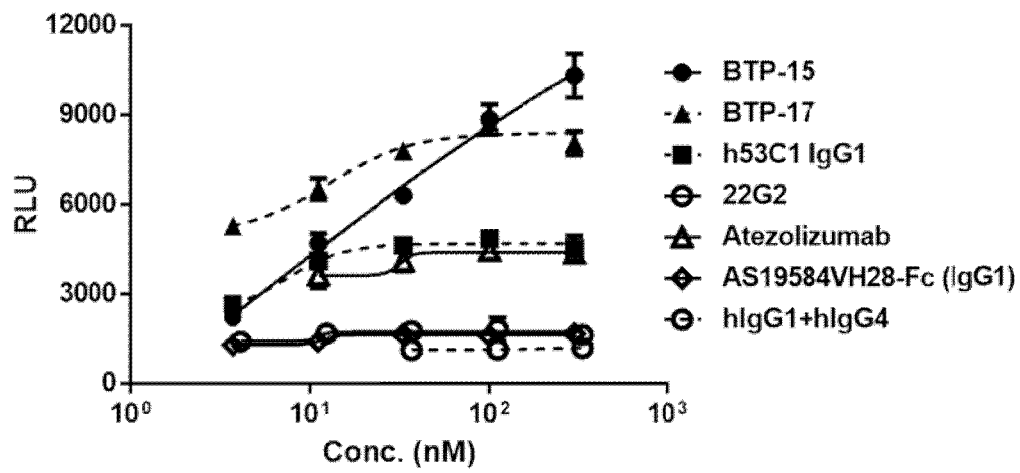
Figure 27C:
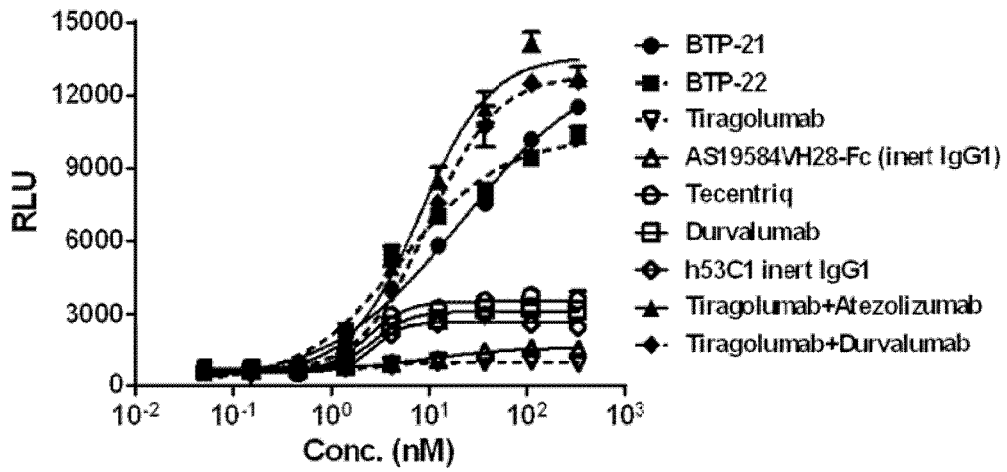

PD-L1/TIGIT Bifunctional Reporter Assay:

To evaluate the capability of the PD-1×TIGIT BABPs or PD-L1×TIGIT BABPs to activate T cells in a synergistic manner by targeting PD-L1/PD-1 pathway and CD155/TIGIT pathways simultaneously, PD-L1/TIGIT bifunctional reporter assay was conducted as described in Example 6. Briefly, PD-L1/CD155 target cells (cells expressing PD-L1 and CD155) were plated overnight and then incubated with a serial dilution of test antibodies, followed by addition of PD-1/TIGIT effector cells (cells expressing PD-1 and TIGIT) at a suitable E:T ratio. After 6 hours induction at 37° C., 5% $CO_2$, One-Glo™ Luciferase Assay Reagent was added and luminescence was determined to represent effector cell activation. 22G2 (IgG1) is an anti-TIGIT monoclonal antibody and is expressed according to the published sequence. Tiragolumab (an anti-TIGIT monoclonal antibody in clinical trial), Pembrolizumab (a commercially available anti-PD-1 monoclonal antibody; abbreviated as Pembro), Durvalumab and Atezolizumab/Tecentriq® (both as commercially available anti-PD-L1 antibodies), were expressed according to their published sequences and used as additional controls. As can be seen from FIGS. 27A-27C, monotherapy using anti-PD-1, anti-PD-L1, or anti-TIGIT Ab could not effectively block PD-L1/PD-1 and CD155/TIGIT pathways simultaneously to trigger effector cell activation. BTP-11, BTP-13 (as shown in FIG. 27A), BTP-15, BTP-17 (as shown in FIG. 27B), BTP-21 and BTP-22 (as shown in FIG. 27C and Table 21) synergistically triggered signal in the reporter cell by blocking PD-L1/PD-1 and/or CD155/TIGIT pathways, showing a dramatically increased maximal signal as compared to any of the monotherapies tested. BTP-11 and BTP-13 even exhibited superior effector cell activating function compared to that of Pembrolizumab (anti-PD-1) and 22G2 (anti-TIGIT) combination therapy (FIG. 27A). BTP-21 and BTP-22 BABPs showed comparable or even better (BTP-22) simultaneous PD-L1/PD-1 and CD155/TIGIT blocking activity compared to that of Tiragolumab+Atezolizumab or Tiragolumab+Durvalumab combination therapies (FIG. 27C).

TABLE 21

PD-L1/TIGIT bifunctional reporter assay for PD-L1 × TIGIT BABPs

| | Upper plateau of signal | EC50 (nM) |
|---|---|---|
| BTP-21 | 11524 | 12.88 |
| BTP-22 | 10263 | 5.47 |
| h53C1 inert IgG1 (anti-PD-L1) | 2660 | 2.76 |
| Atezolizumab (anti-PD-L1 Ab) | 3527 | 2.36 |
| Durvalumab (anti-PD-L1 Ab) | 3109 | 2.66 |
| AS19584VH28-Fc inert IgG1 | 1608 | 10.57 |
| Tiragolumab (anti-TIGIT) | 983 | 3.61 |
| Tiragolumab + Atezolizumab | 13636 | 7.99 |
| Tiragolumab + Durvalumab | 12851 | 9.68 |

Figure 28A:
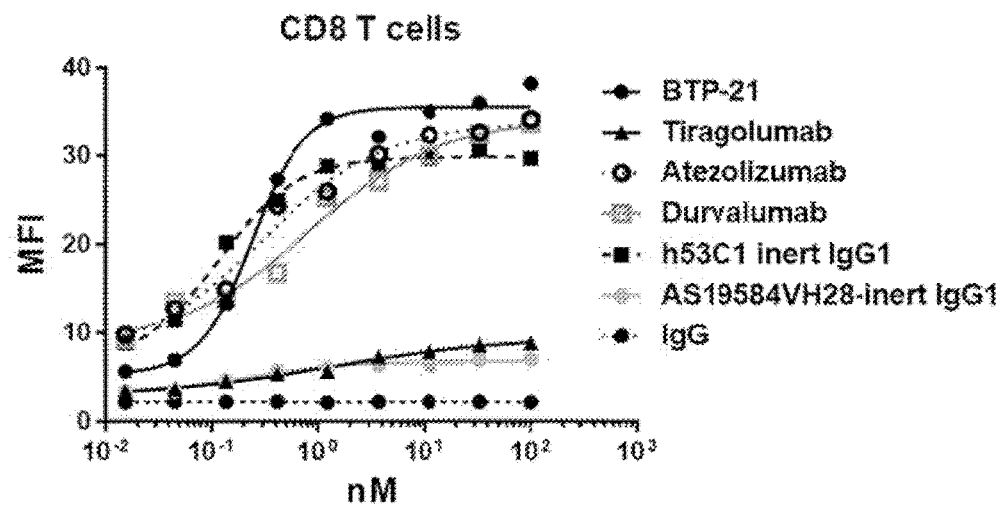
FIGS. 28A and 28B depict the binding of BTP-21, Tiragolumab, Atezolizumab, Durvalumab, h53C1 and AS19584VH28 to primary CD8 and CD4 T cells, respectively, detected by FACS.
Figure 28B:
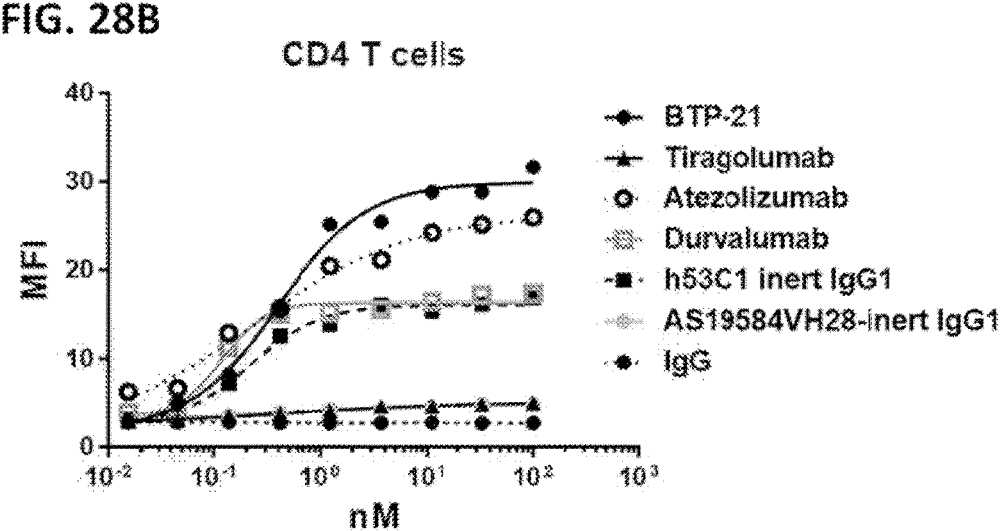

Primary T Cell Binding:

To assess the capability of the PD-L1×TIGIT BABPs to bind to primary cells, human primary T cells were isolated from PBMCs (HemaCare) with either CD8+ T Cell Isolation Kit (Miltenyi, Cat #130-096-495) or CD4+ T Cell Isolation Kit (Miltenyi, Cat #130-096-533). The isolated T cells were activated and expanded with T Cell Activation/Expansion Kit (Miltenyi, Cat #130-092-919). FACS analysis was done as described in Example 2 to determine the binding of PD-L1×TIGIT BABPs to the activated CD8+ and CD4+ T cells, respectively. As shown in FIGS. 28A and 28B, BTP-21 has demonstrated potent binding capability to primary CD8 and CD4 T cells, comparable to the benchmark antibodies or parental antibodies.

PBMC IFN-γ Release Assay:

Freshly thawed human PBMCs (HemaCare) from healthy donors were co-cultured with PD-L1 target cells (GS-C2/PD-L1, GenScript, Cat #M00613) at a ratio of 3:1 in RPMI 1640 medium supplemented with 10% FBS for 72 hours in a incubator at 37° C. with 5% $CO_2$, at the presence of gradient concentrations of test articles. The cells were then spun down and the supernatant were collected for IFN-γ concentration determination using Human IFN-γ HTRF kit (Cisbio, Cat #62HIFNGPEH) and PHERAstarPlus machine (BMG Labtech). The study was conducted with 3 different donors. Results indicated that the BTP-21 had a comparable EC50 with the benchmark antibodies and parental antibodies, while its maximum potential of cytokine release induction was consistently higher in BTP-21 than that in other PD-L1 antibodies (FIG. 29).

In Vivo Efficacy Study for PD-1×TIGIT BABP

The in vivo anti-tumor activity of BTP-11 was evaluated in syngeneic CT26 colon cancer model (expressing murine CD155) established in Balb/c mice with human PD-1 KI. This CT26 tumor model was constructed as in Example 3 Animals started to receive therapies when tumor size reached about 100 mm³. Test articles were dosed once every 4 days via i.p. Body weights were measured throughout the study. Animals with tumor volume less than 10 mm³ were considered tumor-free (TF).

As shown in FIG. 30, CT26 tumor model was partially resistant to anti-TIGIT mono-blockade (see AS19584VH28 IgG4), only resulting in 1 out of 8 mice being tumor-free. The anti-PD-1 antibody (PD1-BM-min) alone, moderately inhibited CT26 tumor growth in PD-1 KI mice at 10 mg/kg, resulted in 3 out of 8 mice being tumor-free. BTP-11 demonstrated a superior effect in causing tumor regression at a same molar dose (12.33 mg/kg), resulting in 5 out of 8 mice being tumor-free. This effect is even better than the combination treatment using PD1-BM-min and AS19584VH28 IgG4 at a same molar dose (10 mg/kg and 5.33 mg/kg, respectively), which only resulted in 1 out of 8 mice being tumor-free.

In Vivo Efficacy Study for PD-L1×TIGIT BABP

To assess the in vivo anti-tumor activity of BTP-21, murine MC38 colon cancer cells overexpressing human PD-L1 (MC38-hPDL1) were implanted in C57BL/6 human PD-1/PD-L1 double KI mice, similarly as described in Example 3. Atezolizumab (a commercially available anti-PD-L1 antibody) was expressed according to published sequences and used as an additional control. The animals were randomized for treatment when tumor size reached 100 mm$^3$. Test articles were dosed on Days 0, 4, 6, and 8, via i.p. Body weights were measured throughout the study.

As can be seen from FIG. 31, Atezolizumab and h53C1 (inert IgG1) mono-blockade were both able to inhibit MC38-hPD-L1 tumor growth at 5 mg/kg, resulting in respectively 4 out of 8 and 3 out of 8 mice being tumor free by Day 30 post-treatment. Mono-blockade using AS19584VH28 inert IgG1 at 2.67 mg/kg resulted in 4 out of 8 tumor-free mice. BTP-21 and the combination therapy (of h53C1 (inert IgG1) and AS19584VH28 inert IgG1) demonstrated a higher rate of tumor-free mice (6 out of 8 and 6 out of 7, respectively). It is also noteworthy that BTP-21 and the combination therapy had much earlier onset of tumor-free status than any monotherapy tested. The earliest responders in BTP-21 or combination therapy treatment groups reached tumor-free status at between Day 10 to 15 after treatment, while the monotherapy groups took 20 to 25 days before any mice reaching tumor-free status. Furthermore, BTP-21 demonstrated similar excellent therapeutic effect even at a lower dose (2.06 mg/kg), compared to when administering BTP-21 at higher dose (6.17 mg/kg) or combination therapy of same molar dose (5 mg/kg h53C1+2.67 mg/kg AS19584VH28 inert IgG1) (FIG. 31).

The above studies demonstrated that BABPs described herein, by blocking PD-L1/PD-1 and CD155/TIGIT pathways simultaneously, displayed superior anti-tumor activity as compared to the monotherapies targeting either of the two pathways in mouse tumor models carrying humanized targets.

SEQUENCE LISTING

TABLE 22

Anti-TIGIT sdAb SEQ ID NOs

| | SEQ ID NO: FR1 | | SEQ ID NO: CDR1 | | SEQ ID NO: FR2 | | SEQ ID NO: CDR2 | | SEQ ID NO: FR3 | | SEQ ID NO: CDR3 | | SEQ ID NO: FR4 |
|---|---|---|---|---|---|---|---|---|---|---|---|---|---|
| AS19584 | 1 | QVQLAESGGGSVQAGGSLRLSCAAS | 36 | GYKYGVYSMG | 71 | WFRLAPGKEREGVA | 106 | AICSGGRTTYSDSVKG | 141 | RFTISKDSANQILYLQMNSLKPEDTAMYYCAA | 176 | RPLWTGDCDLSSSWYKT | 211 | WGQGTQVTVSS |
| AS19852 | 2 | QVQLAESGGGSVQTGGSLRLSCAAS | 37 | GNTGSRRYVA | 72 | WFRQAPGKEREGVA | 107 | RLITDSGSTYYADSVKG | 142 | RFIISQDNAKNTVYLQMNTLKEPDTAMYYCAE | 177 | ELAPARSGGIWFGGRYFSY | 212 | WGQGTQVTVSS |
| AS19858 | 3 | QIQLVESGGGSVQAGGSLRLSCATS | 38 | GYTRYQKCMG | 73 | WFRQAPGKEREGVA | 108 | AIYTSVGGSRTYVADSAKG | 143 | RFTVSQDNAKNTVYLQMNSLKPEDTAMYYCAA | 178 | KSPYDGACSYEADFTY | 213 | WGQGTQVTVSS |
| AS19886 | 4 | QVQLVESGGGSVQAGGSLRLSCVA | 39 | SGYTYSRKCRG | 74 | WFRQAPGKEREGVA | 109 | TLYTSSGGTYFDTYADSVRG | 144 | RFTISQDNAKNTVYLQMNNLKPEDSGIYYCAA | 179 | RLSTDFCGPRADFDY | 214 | WGQGTQVTVSS |
| AS19887 | 5 | QVQLAESGGGSVQAGGSLRLSCAAS | 40 | GVTSDSYHMG | 75 | WFRQAPGKEREGVA | 110 | VIKTGDASTYYTDSVKG | 145 | RFTISQDNAKNTLYLQMNSLKPEDTAMYYCAA | 180 | RRGWVPAPLSQYNYNY | 215 | WGQGTQVTVSS |
| AS19888 | 6 | QVQLAESGGGSVQTGGSLTLSCEAS | 41 | GVAASGYCMA | 76 | WFRQAPGKERERVA | 111 | AISSNDLVAYADSVKG | 146 | RFTISKDNAKTTLYLQMNNLKPEDTAMYYCAA | 181 | DGGYGGYCGRLRPGTGY | 216 | WGQGTQVTVSS |
| AS20160 | 7 | EVQLAESGGGSVQAGGSLRLSCTTS | 42 | GYTYSRNCMG | 77 | WFRQAPGKEREGVA | 112 | TIYVSAASTSFATYADSVKG | 147 | RFTISLDKAKNTVYLQMNSLKPEDTAMYYCAA | 182 | DPPDRISNPCGPRRPDFGY | 217 | WGQGTQVTVSS |
| AS19584VH26 | 19 | EVQLVESGGGLVQPGGSLRLSCAAS | 54 | GYKYGVYSMG | 89 | WFRQAPGKGLEWVS | 124 | AICSGGRTTYSDSVKG | 159 | RFTISRDNSKQTLYLQMNSLRAEDTAVYYCAA | 194 | RPLWTGDCDLSSSWYKT | 229 | WGQGTLVTVSS |
| AS19584VH28 | 21 | EVQLVESGGGLVQPGGSLRLSCAAS | 56 | GYKYGVYSMG | 91 | WVRQAPGKGLEGVS | 126 | AICSGGRTTYSDSVKG | 161 | RFTISRDNSNQILYLAMNSLRAEDTAVYYCAA | 196 | RPLWTGDCDLSSSWYKT | 231 | WGQGTLVTVSS |

TABLE 22-continued

Anti-TIGIT sdAb SEQ ID NOs

| | SEQ ID NO:FR1 | SEQ ID NO:CDR1 | SEQ ID NO:FR2 | SEQ ID NO:CDR2 | SEQ ID NO:FR3 | SEQ ID NO:CDR3 | SEQ ID NO:FR4 |
|---|---|---|---|---|---|---|---|
| AS19584VH29 | 22 EVQLVESGGGLVQPGGSLRLSCAAS | 57 GYKYGVYSMG | 92 WFRQAPGKEREGVS | 127 AICSGGRTTYSDSVKG | 162 RFTISRDNSKQTLYLQMNSLRAEDTAVYYCAA | 197 RPLWTGDCDLSSSWYKT | 232 WGQGTLVTVSS |
| AS19584VH30 | 23 EVQLVESGGGLVQPGGSLRLSCAAS | 58 GYKYGVYSMG | 93 WFRQAPGKEREGVS | 128 AICSGGRTTYSDSVKG | 163 RFTISRDNSNNILYLQMNSLRAEDTAVYYCAA | 198 RPLWTGDCDLSSSWYKT | 233 WGQGTLVTVSS |
| AS19584VH31 | 24 EVQLVESGGGLVQPGGSLRLSCAAS | 59 RYKYGVYSMG | 94 WFRQAPGKEREGVS | 129 AICSGGRTTYSDSVKG | 164 RFTISRDNSNQILYLQMNSLRAEDTAVYYCAA | 199 RPLWTGDCDLSSSWYKT | 234 WGQGTLVTVSS |
| AS19886VH5 | 28 EVQLVESGGGLVQPGGSLRLSCAAS | 63 GYTYSRKCRG | 98 WFRQAPGKGLEGVA | 133 TLYTSSGGTYFDTYADSVRG | 168 RFTISRDNSKNTVYLQMNSLRAEDTGVYYCAA | 203 RLSTDFCGPRADFDY | 238 WGQGTLVTVSS |
| AS19886VH8 | 30 EVQLVESGGGLVQPGGSLRLSCAAS | 65 GYTYSRKCRG | 100 WFRQAPGKGLEGVA | 135 TLYTSSGGTYFDTYADSVRG | 170 RFTISQDNSKNTLYLQMNSLRAEDTAVYYCAA | 205 RLSTDFCGPRADFDY | 240 WGQGTLVTVSS |
| AS19886VH9 | 31 EVQLVESGGGLVQPGGSLRLSCAAS | 66 GYTYSRKCRG | 101 WFRQAPGKGLEWVA | 136 TLYTSSGGTYFDTYADSVRG | 171 RFTISRDNSKNTLYLQMNSLRAEDTAVYYCAA | 206 RLSTDFCGPRADFDY | 241 WGQGTLVTVSS |
| AS19886VH10 | 32 EVQLVESGGGLVQPGGSLRLSCAAS | 67 GYTYSRKCRG | 102 WFRQAPGKGLEGVA | 137 TLYTSSGGTYFDTYADSVRG | 172 RFTISRDNSKNTVYLQMNSLRAEDTAVYYCAA | 207 RLSTDFCGPRADFDY | 242 WGQGTLVTVSS |
| AS19886VH19 | 34 EVQLVESGGGLVQPGGSLRLSCAAS | 69 GYTYSRKCRG | 104 WFRQAPGKGREGVA | 139 TLYTSSGGTYFDTYADSVRG | 174 RFTISRDNAKNTLYLQMNSLRPEDTAVYYCAA | 209 RLSTDFCGPRADFDY | 244 WGQGTLVTVSS |
| AS19886VH20 | 35 EVLQVESGGGLVQPGGSLRLSCAAS | 70 GYTYSRKCRG | 105 WFRQAPGKGREGVA | 140 TLYTSSGGTYFDTYADSVRG | 175 RFTISRDNAKNTVYLQMNSLRPEDTAVYYCAA | 210 RLSTDFCGPRADFDY | 245 WGQGTLVTVSS |

(AS19584 sdAb nucleic acid sequence)
SEQ ID NO: 246
CAGGTGCAACTGGCGGAGTCTGGGGGAGGCTCGGTGCAGGCTGGAGGGTCTCTGAGACTCTCCTGTGCAGCCTCTGGATACAAGTACGGTGTCT
ACTCCATGGGCTGGTTCCGCCTGGCTCCAGGGAAGGAGCGCGAGGGGGTCGCAGCCATTTGTAGTGGCGGTAGAACCACATACTCAGACTCCGT
GAAGGGCCGATTCACCATCTCCAAAGACAGCGCCAACCAATTCTGTATCTACAGATGAACAGCCTGAAACCTGAAGACACTGCCATGTACTAC
TGTGCGGCCCGACCTCTATGGACTGGGGACTGCGATTTAAGCTCATCTTGGTATAAAACCTGGGGCCAGGGGACCCAGGTCACCGTCTCCTCA (AS19852 sdAb nucleic acid sequence)
SEQ ID NO: 247
CAGGTGCAGCTGGCGGAGTCTGGAGGAGGCTCGGTGCAGACTGGAGGGTCTCTGAGACTCTCCTGTGCAGCCTCTGGAAACACCGGTAGTCGCC
GGTATGTGGCATGGTTCCGCCAGGCGCCAGGGAAGGAGCGCGAGGGTGTCGCACGACTCATTACTGATAGTGGCAGCACATACTATGCCGACTC
CGTGAAGGGCCGATTCATCATCTCCCAAGACAACGCCAAGAACACGGTGTATCTGCAAATGAACACCCTGAAACCTGAGGACACTGCCATGTAC
TACTGTGCGGAAGAATTAGCACCAGCTCGCAGCGGTGGTATTTGGTTTGGTGGACGGTACTTCAGTTACTGGGGCCAGGGGACCCAGGTCACCG
TCTCCTCA (AS19858 sdAb nucleic acid sequence)
SEQ ID NO: 248
CAGATTCAGCTGGTGGAGTCTGGGGGAGGCTCGGTGCAGGCTGGAGGGTCTCTGAGACTCTCCTGTGCAACGTCTGGATACACGTACAGACAGA
AATGCATGGGCTGGTTCCGCCAGGCTCCAGGGAAGGAGCGCGAGGGGGTCGCAGCCGATTTATACTTCTGTTGGTGGTAGTAGGACATACGTTGC
CGACTCCGCGAAGGGCCGATTCACCGTCTCCCAAGACAACGCCAAAAACACGGTGTATCTGCAAATGAACAGCCTGAAACCTGAGGACACTGCC
ATGTACTACTGTGCGGCCAAGAGTCCGTACGATGGTGCATGCTCTTACGAAGCTGACTTTACTTACTGGGGCCAGGGGACCCAGGTCACCGTCT
CCTCA (AS19886 sdAb nucleic acid sequence)
SEQ ID NO: 249
CAGGTTCAGCTGGTGGAGTCTGGGGGAGGCTCGGTGCAGGCTGGAGGGTCTCTGAGACTCTCCTGTGTAGCCTCTGGATACACCTATAGTAGGA
AATGTAGGGGCTGGTTCCGCCAGGCTCCAGGGAAGGAGCGCGAGGGGGTCGCGACTCTTTATACTAGTTCAGGGGGGACATATTTTGACACCTA
TGCCGACTCCGTGAGGGGCCGGTTCACCATCTCCCAAGACAACGCCAAGAACACGGTGTATCTGCAAATGAACAACCTGAAACCGGAGGACAGT TABLE 22-continued Anti-TIGIT sdAb SEQ ID NOs

| SEQ ID NO:FR1 | SEQ ID NO:CDR1 | SEQ ID NO:FR2 | SEQ ID NO:CDR2 | SEQ ID NO:FR3 | SEQ ID NO:CDR3 | SEQ ID NO:FR4 |
|---|---|---|---|---|---|---|

GGCATATACTACTGTGCGGCACGCCTGAGTACGGACTTTTGCGGACCAAGAGCTGACTTTGATTACTGGGGCCAGGGGACCCAGGTCACCGTCT
CCTCA (AS19887 sdAb nucleic acid sequence)

SEQ ID NO: 250

CAGGTGCAGCTGGCGGAGTCTGGGGGAGGCTCGGTGCAGGCTGGAGGGTCTCTGAGACTCTCCTGTGCAGCCTCTGGAGTCACCTCCGATAGTT
ACCACATGGGCTGGTTCCGCCAGGCTCCAGGGAAGGAGCGCGAGGGGGTCGCAGTTATTAAAACTGGTGATGCCAGCACATACTATACCGACTC
CGTGAAGGGCCGATTCACCATCTCCCAAGACAACGCCAAGAACACGCTGTACCTGCAAATGAACAGCCTGAAACCTGAGGACACTGCCATGTAC
TACTGTGCGGCAAGACGGGGTTGGGTGCCGGCTCCCCTCTCGCAATATAATTATAACTATTGGGGCCAGGGGACCCAGGTCACCGTCTCCTCA (AS19888 sdAb nucleic acid sequence)

SEQ ID NO: 251

CAGGTGCAACTGGCGGAGTCTGGGGGAGGCTCGGTGCAGACTGGAGGGTCTCTGAGACTTTCCTGTGAAGCCTCTGGAGTGGCCGCCAGTGGCT
ACTGCATGGCCTGGTTCCGCCAGGCTCCGGGGAAGGAGCGCGAAAGGGTCGCAGCTATTAGTAGTAATGATCTAGTTGCTTACGCAGACTCCGT
GAAGGGCCGATTCACCATCTCCAAGGACAACGCCAAGACCACTCTGTATCTACAAATGAACAACCTGAAACCTGAGGACACTGCCATGTACTAC
TGTGCGGCAGATGGAGGTTATGGTGGTTACTGCGGACGGTTGCGACCTGGCACTGGTTACTGGGGCCAGGGGACCCAGGTCACCGTCTCCTCA (AS20160 sdAb nucleic acid sequence)

SEQ ID NO: 252

GAGGTGCAGCTGGCGGAGTCTGGGGGAGGCTCGGTGCAGGCTGGAGGGTCTCTGAGACTCTCCTGTACAACCTCTGGATACACCTACAGTCGCA
ACTGCATGGGCTGGTTCCGCCAGGCTCCAGGGAAGGAGCGCGAGGGGGTCGCAACTATTTATGTAAGTGCTGCAAGCACAAGTTTTGCCACATA
TGCCGACTCCGTAAAGGGCCGATTCACCATCTCCCTAGACAAGGCCAAGAACACGGTATATCTGCAAATGAACAGCCTGAAACCTGAGGACACT
GCCATGTACTACTGTGCGGCAGATCCCCCCGATCGTATCTCGAACCCCTGCGGACCCCGCCGCCCTGACTTTGGATACTGGGGCCAGGGAACCC
AGGTCACCGTCTCCTCA (AS19584 sdAb amino acid sequence; CDRs are underlined)

SEQ ID NO: 253

QVQLAESGGGSVQAGGSLRLSCAASGYKYGVYSMGWFRLAPGKEREGVAAICSGGRTTYSDSVKGRFTISKDSANQILYLQMNSLKPEDTAMYY
CAARPLWTGDCDLSSSWYKTWGQGTQVTVSS (AS19852 sdAb amino acid sequence; CDRs are underlined)

SEQ ID NO: 254

QVQLAESGGGSVQTGGSLRLSCAASGNTGSRRYVAWFRQAPGKEREGVARLITDSGSTYYADSVKGRFIISQDNAKNTVYLQMNTLKPEDTAMY
YCAEELAPARSGGIWFGGRYFSYWGQGTQVTVSS (AS19858 sdAb amino acid sequence; CDRs are underlined)

SEQ ID NO: 255

QIQLVESGGGSVQAGGSLRLSCATSGYTYRQKCMGWFRQAPGKEREGVAAIYTSVGGSRTYVADSAKGRFTVSQDNAKNTVYLQMNSLKPEDTA
MYYCAAKSPYDGACSYEADFTYWGQGTQVTVSS (AS19886 sdAb amino acid sequence; CDRs are underlined)

SEQ ID NO: 256

QVQLVESGGGSVQAGGSLRLSCVASGYTYSRKCRGWFRQAPGKEREGVATLYTSSGGTYFDTYADSVRGRFTISQDNAKNTVYLQMNNLKPEDS
GIYYCAARLSTDFCGPRADFDYWGQGTQVTVSS (AS19887 sdAb amino acid sequence; CDRs are underlined)

SEQ ID NO: 257

QVQLAESGGGSVQAGGSLRLSCAASGVTSDSYHMGWFRQAPGKEREGVAVIKTGDASTYYTDSVKGRFTISQDNAKNTLYLQMNSLKPEDTAMY
YCAARRGWVPAPLSQYNYNYWGQGTQVTVSS (AS19888 sdAb amino acid sequence; CDRs are underlined)

SEQ ID NO: 258

QVQLAESGGGSVQTGGSLRLSCEASGVAASGYCMAWFRQAPGKERERVAAISSNDLVAYADSVKGRFTISKDNAKTTLYLQMNNLKPEDTAMYY
CAADGGYGGYCGRLRPGTGYWGQGTQVTVSS (AS20160 sdAb amino acid sequence; CDRs are underlined)

SEQ ID NO: 259

EVQLAESGGGSVQAGGSLRLSCTTSGYTYSRNCMGWFRQAPGKEREGVATIYVSAASTSFATYADSVKGRFTISLDKAKNTVYLQMNSLKPEDT
AMYYCAADPPDRISNPCGPRRPDFGYWGQGTQVTVSS (AS19584VH26 humanized sdAb amino acid sequence; CDRs are underlined)

SEQ ID NO: 271

EVQLVESGGGLVQPGGSLRLSCAASGYKYGVYSMGWFRQAPGKGLEGVSAICSGGRTTYSDSVKGRFTISRDNSKQTLYLQMNSLRAEDTAVYY
CAARPLWTGDCDLSSSWYKTWGQGTLVTVSS (AS19584VH28 humanized sdAb amino acid sequence; CDRs are underlined)

SEQ ID NO: 273

EVQLVESGGGLVQPGGSLRLSCAASGYKYGVYSMGWFRQAPGKGLEGVSAICSGGRTTYSDSVKGRFTISRDNSNQILYLQMNSLRAEDTAVYY
CAARPLWTGDCDLSSSWYKTWGQGTLVTVSS (AS19584VH29 humanized sdAb amino acid sequence; CDRs are underlined)

SEQ ID NO: 274

EVQLVESGGGLVQPGGSLRLSCAASGYKYGVYSMGWFRQAPGKEREGVSAICSGGRTTYSDSVKGRFTISRDNSKQTLYLQMNSLRAEDTAVYY
CAARPLWTGDCDLSSSWYKTWGQGTLVTVSS

TABLE 22-continued

Anti-TIGIT sdAb SEQ ID NOs

| SEQ ID NO:FR1 | SEQ ID NO:CDR1 | SEQ ID NO:FR2 | SEQ ID NO:CDR2 | SEQ ID NO:FR3 | SEQ ID NO:CDR3 | SEQ ID NO:FR4 |
|---|---|---|---|---|---|---|

(AS19584VH30 humanized sdAb amino acid sequence; CDRs are underlined)

SEQ ID NO: 275

EVQLVESGGGLVQPGGSLRLSCAASGYKYGVYSMGWFRQAPGKEREGVSAICSGGRTTYSDSVKGRFTISRDNSNNILYLQMNSLRAEDTAVYY
CAARPLWTGDCDLSSSWYKTWGQGTLVTVSS (AS19584VH31 humanized sdAb amino acid sequence; CDRs are underlined)

SEQ ID NO: 276

EVQLVESGGGLVQPGGSLRLSCAASGYKYGVYSMGWFRQAPGKEREGVSAICSGGRTTYSDSVKGRFTISRDNSNQILYLQMNSLRAEDTAVYY
CAARPLWTGDCDLSSSWYKTWGQGTLVTVSS (AS19886VH5 humanized sdAb amino acid sequence; CDRs are underlined)

SEQ ID NO: 280

EVQLVESGGGLVQPGGSLRLSCAASGYTYSRKCRGWFRQAPGKGLEGVATLYTSSGGTYFDTYADSVRGRFTISRDNSKNTVYLQMNSLRAEDT
GVYYCAARLSTDFCGPRADFDYWGQGTLVTVSS (AS19886VH8 humanized sdAb amino acid sequence; CDRs are underlined)

SEQ ID NO: 282

EVQLVESGGGLVQPGGSLRLSCAASGYTYSRKCRGWFRQAPGKGLEGVATLYTSSGGTYFDTYADSVRGRFTISQDNSKNTLYLQMNSLRAEDT
AVYYCAARLSTDFCGPRADFDYWGQGTLVTVSS (AS19886VH9 humanized sdAb amino acid sequence; CDRs are underlined)

SEQ ID NO: 283

EVQLVESGGGLVQPGGSLRLSCAASGYTYSRKCRGWFRQAPGKGLEGVATLYTSSGGTYFDTYADSVRGRFTISRDNSKNTLYLQMNSLRAEDT
AVYYCAARLSTDFCGPRADFDYWGQGTLVTVSS (AS19886VH10 humanized sdAb amino acid sequence; CDRs are underlined)

SEQ ID NO: 284

EVQLVESGGGLVQPGGSLRLSCAASGYTYSRKCRGWERQAPGKGLEGVATLYTSSGGTYFDTYADSVRGRFTISRDNSKNTVYLQMNSLRAEDT
AVYYCAARLSTDFCGPRADFDYWGQGTLVTVSS (AS19886VH19 humanized sdAb amino acid sequence; CDRs are underlined)

SEQ ID NO: 286

EVQLVESGGGLVQPGGSLRLSCAASGYTYSRKCRGWERQAPGKGREGVATLYTSSGGTYFDTYADSVRGRFTISRDNAKNTLYLQMNSLRPEDT
AVYYCAARLSTDFCGPRADFDYWGQGTLVTVSS (AS19886VH20 humanized sdAb amino acid sequence; CDRs are underlined)

SEQ ID NO: 287

EVQLVESGGGLVQPGGSLRLSCAASGYTYSRKCRGWERQAPGKGREGVATLYTSSGGTYFDTYADSVRGRFTISRDNAKNTVYLQMNSLRPEDT
AVYYCAARLSTDFCGPRADFDYWGQGTLVTVSS (AS19584 sdAb-Fc (IgG1) fusion protein dimeric form amino acid sequence;
CDRs are underlined, linker is bolded)

SEQ ID NO: 288

QVQLAESGGGSVQAGGSLRLSCAASGYKYGVYSMGWERLAPGKEREGVAAICSGGRTTYSDSVKGRFTISKDSANQILYLQMNSLKPEDTAMYY
CAARPLWTGDCDLSSSWYKTWGQGTQVTVSSEPKSCDKTHTCPPCPAPELLGGPSVFLEPPKPKDTLMISRTPEVTCVVVDVSHEDPEVKFNWY
VDGVEVHNAKTKPREEQYNSTYRVVSVLTVLHQDWLNGKEYKCKVSNKALPAPIEKTISKAKGQPREPQVYTLPPSRDELTKNQVSLTCLVKGF
YPSDIAVEWESNGQPENNYKTTPPVLDSDGSFELYSKLTVDKSRWQQGNVESCSVMHEALHNHYTQKSLSLSPGK (AS19852 sdAb-Fc (IgG1) fusion protein dimeric form amino acid sequence;
CDRs are underlined, linker is bolded)

SEQ ID NO: 289

QVQLAESGGGSVQTGGSLRLSCAASGNTGSRRYVAWFRQAPGKEREGVARLITDSGSTYYADSVKGRFIISQDNAKNTVYLQMNTLKPEDTAMY
YCAEEELAPARSGGIWEGGRYFSYWGQGTQVTVSSEPKSCDKTHTCPPCPAPELLGGPSVFLEPPKPKDTLMISRTPEVTCVVVDVSHEDPEVKF
NWYVDGVEVHNAKTKPREEQYNSTYRVVSVLTVLHQDWLNGKEYKCKVSNKALPAPIEKTISKAKGQPREPQVYTLPPSRDELTKNQVSLTCLV
KGFYPSDIAVEWESNGQPENNYKTTPPVLDSDGSFELYSKLTVDKSRWQQGNVESCSVMHEALHNHYTQKSLSLSPGK (AS19858 sdAb-Fc (IgG1) fusion protein dimeric form amino acid sequence;
CDRs are underlined, linker is bolded)

SEQ ID NO: 290

QIQLVESGGGSVQAGGSLRLSCATSGYTYRQKCMGWERQAPGKEREGVAAIYTSVGGSRTYVADSAKGRFTVSQDNAKNTVYLQMNSLKPEDTA
MYYCAAKSPYDGACSYEADFTYWGQGTQVTVSSEPKSCDKTHTCPPCPAPELLGGPSVFLEPPKPKDTLMISRTPEVTCVVVDVSHEDPEVKFN
WYVDGVEVHNAKTKPREEQYNSTYRVVSVLTVLHQDWLNGKEYKCKVSNKALPAPIEKTISKAKGQPREPQVYTLPPSRDELTKNQVSLTCLVK
GFYPSDIAVEWESNGQPENNYKTTPPVLDSDGSFELYSKLTVDKSRWQQGNVESCSVMHEALHNHYTQKSLSLSPGK (AS19886 sdAb-Fc (IgG1) fusion protein dimeric form amino acid sequence;
CDRs are underlined, linker is bolded)

SEQ ID NO: 291

QVQLVESGGGSVQAGGSLRLSCVASGYTYSRKCRGWERQAPGKEREGVATLYTSSGGTYFDTYADSVRGRFTISQDNAKNTVYLQMNNLKPEDS
GIYYCAARLSTDFCGPRADFDYWGQGTQVTVSSEPKSCDKTHTCPPCPAPELLGGPSVFLEPPKPKDTLMISRTPEVTCVVVDVSHEDPEVKFN
WYVDGVEVHNAKTKPREEQYNSTYRVVSVLTVLHQDWLNGKEYKCKVSNKALPAPIEKTISKAKGQPREPQVYTLPPSRDELTKNQVSLTCLVK
GFYPSDIAVEWESNGQPENNYKTTPPVLDSDGSFELYSKLTVDKSRWQQGNVESCSVMHEALHNHYTQKSLSLSPGK

TABLE 22-continued

Anti-TIGIT sdAb SEQ ID NOs

| SEQ ID NO:FR1 | SEQ ID NO:CDR1 | SEQ ID NO:FR2 | SEQ ID NO:CDR2 | SEQ ID NO:FR3 | SEQ ID NO:CDR3 | SEQ ID NO:FR4 |
|---|---|---|---|---|---|---|

(AS19887 sdAb-Fc (IgG1) fusion protein dimeric form amino acid sequence;
CDRs are underlined, linker is bolded)

SEQ ID NO: 292

QVQLAESGGGSVQAGGSLRLSCAASGVTSDSYHMGWERQAPGKEREGVAVIKTGDASTYYTDSVKGRFTISQDNAKNTLYLQMNSLKPEDTAMY
YCAARRGWVPAPLSQYNYNYWGQGTQVTVSSEPKSCDKTHTCPPCPAPELLGGPSVFLEPPKPKDTLMISRTPEVTCVVVDVSHEDPEVKFNWY
VDGVEVHNAKTKPREEQYNSTYRVVSVLTVLHQDWLNGKEYKCKVSNKALPAPIEKTISKAKGQPREPQVYTLPPSRDELTKNQVSLTCLVKGF
YPSDIAVEWESNGQPENNYKTTPPVLDSDGSFELYSKLTVDKSRWQQGNVFSCSVMHEALHNHYTQKSLSLSPGK (AS19888 sdAb-Fc (IgG1) fusion protein dimeric form amino acid sequence;
CDRs are underlined, linker is bolded)

SEQ ID NO: 293

QVQLAESGGGSVQTGGSLRLSCEASGVAASGYCMAWFRQAPGKERERVAAISSNDLVAYADSVKGRFTISKDNAKTTLYLAMNNLKPEDTAMYY
CAADGGYGGYCGRLRPGTGYWGQGTQVTVSSEPKSCDKTHTCPPCPAPELLGGPSVFLEPPKPKDTLMISRTPEVTCVVVDVSHEDPEVKFNWY
VDGVEVHNAKTKPREEQYNSTYRVVSVLTVLHQDWLNGKEYKCKVSNKALPAPIEKTISKAKGQPREPQVYTLPPSRDELTKNQVSLTCLVKGF
YPSDIAVEWESNGQPENNYKTTPPVLDSDGSFELYSKLTVDKSRWQQGNVFSCSVMHEALHNHYTQKSLSLSPGK (AS20160 sdAb-Fc (IgG1) fusion protein dimeric form amino acid sequence;
CDRs are underlined, linker is bolded)

SEQ ID NO: 294

EVQLAESGGGSVQAGGSLRLSCTTSGYTYSRNCMGWERQAPGKEREGVATIYVSAASTSFATYADSVKGRFTISLDKAKNTVYLQMNSLKPEDT
AMYYCAADPPDRISNPCGPRRPDEGYWGQGTQVTVSSEPKSCDKTHTCPPCPAPELLGGPSVFLEPPKPKDTLMISRTPEVTCVVVDVSHEDPE
VKFNWYVDGVEVHNAKTKPREEQYNSTYRVVSVLTVLHQDWLNGKEYKCKVSNKALPAPIEKTISKAKGQPREPQVYTLPPSRDELTKNQVSLT
CLVKGFYPSDIAVEWESNGQPENNYKTTPPVLDSDGSFELYSKLTVDKSRWQQGNVFSCSVMHEALHNHYTQKSLSLSPGK (AS19584VH26 sdAb-Fc (IgG1) fusion protein dimeric form amino acid sequence;
CDRs are underlined, linker is bolded)

SEQ ID NO: 306

EVQLVESGGGLVQPGGSLRLSCAASGYKYGVYSMGWERQAPGKGLEGVSAICSGGRTTYSDSVKGRFTISRDNSKQTLYLQMNSLRAEDTAVYY
CAARPLWTGDCDLSSSWYKTWGQGTLVTVSSEPKSCDKTHTCPPCPAPELLGGPSVFLEPPKPKDTLMISRTPEVTCVVVDVSHEDPEVKFNWY
VDGVEVHNAKTKPREEQYNSTYRVVSVLTVLHQDWLNGKEYKCKVSNKALPAPIEKTISKAKGQPREPQVYTLPPSRDELTKNQVSLTCLVKGF
YPSDIAVEWESNGQPENNYKTTPPVLDSDGSFELYSKLTVDKSRWQQGNVFSCSVMHEALHNHYTQKSLSLSPGK (AS19584VH28 sdAb-Fc (IgG1) fusion protein dimeric form amino acid sequence;
CDRs are underlined, linker is bolded)

SEQ ID NO: 308

EVQLVESGGGLVQPGGSLRLSCAASGYKYGVYSMGWERQAPGKGLEGVSAICSGGRTTYSDSVKGRFTISRDNSNQILYLQMNSLRAEDTAVYY
CAARPLWTGDCDLSSSWYKTWGQGTLVTVSSEPKSCDKTHTCPPCPAPELLGGPSVFLEPPKPKDTLMISRTPEVTCVVVDVSHEDPEVKFNWY
VDGVEVHNAKTKPREEQYNSTYRVVSVLTVLHQDWLNGKEYKCKVSNKALPAPIEKTISKAKGQPREPQVYTLPPSRDELTKNQVSLTCLVKGF
YPSDIAVEWESNGQPENNYKTTPPVLDSDGSFELYSKLTVDKSRWQQGNVFSCSVMHEALHNHYTQKSLSLSPGK (AS19584VH29 sdAb-Fc (IgG1) fusion protein dimeric form amino acid sequence;
CDRs are underlined, linker is bolded)

SEQ ID NO: 309

EVQLVESGGGLVQPGGSLRLSCAASGYKYGVYSMGWERQAPGKEREGVSAICSGGRTTYSDSVKGRFTISRDNSKQTLYLQMNSLRAEDTAVYY
CAARPLWTGDCDLSSSWYKTWGQGTLVTVSSEPKSCDKTHTCPPCPAPELLGGPSVFLEPPKPKDTLMISRTPEVTCVVVDVSHEDPEVKFNWY
VDGVEVHNAKTKPREEQYNSTYRVVSVLTVLHQDWLNGKEYKCKVSNKALPAPIEKTISKAKGQPREPQVYTLPPSRDELTKNQVSLTCLVKGF
YPSDIAVEWESNGQPENNYKTTPPVLDSDGSFELYSKLTVDKSRWQQGNVFSCSVMHEALHNHYTQKSLSLSPGK (AS19584VH30 sdAb-Fc (IgG1) fusion protein dimeric form amino acid sequence;
CDRs are underlined, linker is bolded)

SEQ ID NO: 310

EVQLVESGGGLVQPGGSLRLSCAASGYKYGVYSMGWERQAPGKEREGVSAICSGGRTTYSDSVKGRFTISRDNSNNILYLQMNSLRAEDTAVYY
CAARPLWTGDCDLSSSWYKTWGQGTLVTVSSEPKSCDKTHTCPPCPAPELLGGPSVFLEPPKPKDTLMISRTPEVTCVVVDVSHEDPEVKFNWY
VDGVEVHNAKTKPREEQYNSTYRVVSVLTVLHQDWLNGKEYKCKVSNKALPAPIEKTISKAKGQPREPQVYTLPPSRDELTKNQVSLTCLVKGF
YPSDIAVEWESNGQPENNYKTTPPVLDSDGSFELYSKLTVDKSRWQQGNVFSCSVMHEALHNHYTQKSLSLSPGK (AS19584VH31 sdAb-Fc (IgG1) fusion protein dimeric form amino acid sequence;
CDRs are underlined, linker is bolded)

SEQ ID NO: 311

EVQLVESGGGLVQPGGSLRLSCAASGYKYGVYSMGWERQAPGKEREGVSAICSGGRTTYSDSVKGRFTISRDNSNQILYLQMNSLRAEDTAVYY
CAARPLWTGDCDLSSSWYKTWGQGTLVTVSSEPKSCDKTHTCPPCPAPELLGGPSVFLEPPKPKDTLMISRTPEVTCVVVDVSHEDPEVKFNWY
VDGVEVHNAKTKPREEQYNSTYRVVSVLTVLHQDWLNGKEYKCKVSNKALPAPIEKTISKAKGQPREPQVYTLPPSRDELTKNQVSLTCLVKGF
YPSDIAVEWESNGQPENNYKTTPPVLDSDGSFELYSKLTVDKSRWQQGNVFSCSVMHEALHNHYTQKSLSLSPGK (AS19886VH5 sdAb-Fc (IgG1) fusion protein dimeric form amino acid sequence;
CDRs are underlined, linker is bolded)

SEQ ID NO: 315

EVQLVESGGGLVQPGGSLRLSCAASGYTYSRKCRGWERQAPGKGLEGVATLYTSSGGTYFDTVADSVRGRFTISRDNSKNTVYLQMNSLRAEDT
GVYYCAARLSTDFCGPRADFDYWGQGTLVTVSSEPKSCDKTHTCPPCPAPELLGGPSVFLEPPKPKDTLMISRTPEVTCVVVDVSHEDPEVKFN
WYVDGVEVHNAKTKPREEQYNSTYRVVSVLTVLHQDWLNGKEYKCKVSNKALPAPIEKTISKAKGQPREPQVYTLPPSRDELTKNQVSLTCLVK
GFYPSDIAVEWESNGQPENNYKTTPPVLDSDGSFELYSKLTVDKSRWQQGNVFSCSVMHEALHNHYTQKSLSLSPGK

TABLE 22-continued

Anti-TIGIT sdAb SEQ ID NOs

| SEQ ID NO:FR1 | SEQ ID NO:CDR1 | SEQ ID NO:FR2 | SEQ ID NO:CDR2 | SEQ ID NO:FR3 | SEQ ID NO:CDR3 | SEQ ID NO:FR4 |
| --- | --- | --- | --- | --- | --- | --- |

(AS19886VH8 sdAb-Fc (IgG1) fusion protein dimeric form amino acid sequence;
CDRs are underlined, linker is bolded)

SEQ ID NO: 317

EVQLVESGGGLVQPGGSLRLSCAASGYTYSRKCRGWERQAPGKGLEGVATLYTSSGGTYFDTYADSVRGRFTISQDNSKNTLYLQMNSLRAEDT
AVYYCAARLSTDFCGPRADFDYWGQGTLVTVSSEPKSCDKTHTCPPCPAPELLGGPSVFLEPPKPKDTLMISRTPEVTCVVVDVSHEDPEVKFN
WYVDGVEVHNAKTKPREEQYNSTYRVVSVLTVLHQDWLNGKEYKCKVSNKALPAPIEKTISKAKGQPREPQVYTLPPSRDELTKNQVSLTCLVK
GFYPSDIAVEWESNGQPENNYKTTPPVLDSDGSFELYSKLTVDKSRWQQGNVESCSVMHEALHNHYTQKSLSLSPGK (AS19886VH9 sdAb-Fc (IgG1) fusion protein dimeric form amino acid sequence;
CDRs are underlined, linker is bolded)

SEQ ID NO: 318

EVQLVESGGGLVQPGGSLRLSCAASGYTYSRKCRGWERQAPGKGLEGVATLYTSSGGTYFDTYADSVRGRFTISRDNSKNTLYLQMNSLRAEDT
AVYYCAARLSTDFCGPRADFDYWGQGTLVTVSSEPKSCDKTHTCPPCPAPELLGGPSVFLEPPKPKDTLMISRTPEVTCVVVDVSHEDPEVKFN
WYVDGVEVHNAKTKPREEQYNSTYRVVSVLTVLHQDWLNGKEYKCKVSNKALPAPIEKTISKAKGQPREPQVYTLPPSRDELTKNQVSLTCLVK
GFYPSDIAVEWESNGQPENNYKTTPPVLDSDGSFELYSKLTVDKSRWQQGNVESCSVMHEALHNHYTQKSLSLSPGK (AS19886VH10 sdAb-Fc (IgG1) fusion protein dimeric form amino acid sequence;
CDRs are underlined, linker is bolded)

SEQ ID NO: 319

EVQLVESGGGLVQPGGSLRLSCAASGYTYSRKCRGWERQAPGKGLEGVATLYTSSGGTYFDTYADSVRGRFTISRDNSKNTVYLQMNSLRAEDT
AVYYCAARLSTDFCGPRADFDYWGQGTLVTVSSEPKSCDKTHTCPPCPAPELLGGPSVFLEPPKPKDTLMISRTPEVTCVVVDVSHEDPEVKFN
WYVDGVEVHNAKTKPREEQYNSTYRVVSVLTVLHQDWLNGKEYKCKVSNKALPAPIEKTISKAKGQPREPQVYTLPPSRDELTKNQVSLTCLVK
GFYPSDIAVEWESNGQPENNYKTTPPVLDSDGSFELYSKLTVDKSRWQQGNVESCSVMHEALHNHYTQKSLSLSPGK (AS19886VH19 sdAb-Fc (IgG1) fusion protein dimeric form amino acid sequence;
CDRs are underlined, linker is bolded)

SEQ ID NO: 321

EVQLVESGGGLVQPGGSLRLSCAASGYTYSRKCRGWERQAPGKGREGVATLYTSSGGTYFDTYADSVRGRFTISRDNAKNTLYLQMNSLRPEDT
AVYYCAARLSTDFCGPRADFDYWGQGTLVTVSSEPKSCDKTHTCPPCPAPELLGGPSVFLEPPKPKDTLMISRTPEVTCVVVDVSHEDPEVKFN
WYVDGVEVHNAKTKPREEQYNSTYRVVSVLTVLHQDWLNGKEYKCKVSNKALPAPIEKTISKAKGQPREPQVYTLPPSRDELTKNQVSLTCLVK
GFYPSDIAVEWESNGQPENNYKTTPPVLDSDGSFELYSKLTVDKSRWQQGNVESCSVMHEALHNHYTQKSLSLSPGK (AS19886VH20 sdAb-Fc (IgG1) fusion protein dimeric form amino acid sequence;
CDRs are underlined, linker is bolded)

SEQ ID NO: 322

EVQLVESGGGLVQPGGSLRLSCAASGYTYSRKCRGWERQAPGKGREGVATLYTSSGGTYFDTYADSVRGRFTISRDNAKNTVYLQMNSLRPEDT
AVYYCAARLSTDFCGPRADFDYWGQGTLVTVSSEPKSCDKTHTCPPCPAPELLGGPSVFLEPPKPKDTLMISRTPEVTCVVVDVSHEDPEVKFN
WYVDGVEVHNAKTKPREEQYNSTYRVVSVLTVLHQDWLNGKEYKCKVSNKALPAPIEKTISKAKGQPREPQVYTLPPSRDELTKNQVSLTCLVK
GFYPSDIAVEWESNGQPENNYKTTPPVLDSDGSFELYSKLTVDKSRWQQGNVESCSVMHEALHNHYTQKSLSLSPGK (h53C1 (IgG1) mAb HC amino acid sequence; CDRs are underlined)

SEQ ID NO: 323

EVQLVQSGAEVKKPGASVKVSCKASGYIFTGYGITWVRQAPGQGLEWMGEIFPRRVQTYYSEKFKGRVTMTTDTSTSTAYMELRSLRSDDTAVY
YCARDYDPYFALDYWGQGTTVTVSSASTKGPSVFPLAPSSKSTSGGTAALGCLVKDYFPEPVTVSWNSGALTSGVHTFPAVLQSSGLYSLSSVV
TVPSSSLGTQTYICNVNHKPSNTKVDKKVEPKSCDKTHTCPPCPAPELLGGPSVFLEPPKPKDTLMISRTPEVTCVVVDVSHEDPEVKFNWYVD
GVEVHNAKTKPREEQYNSTYRVVSVLTVLHQDWLNGKEYKCKVSNKALPAPIEKTISKAKGQPREPQVYTLPPSRDELTKNQVSLTCLVKGFYP
SDIAVEWESNGQPENNYKTTPPVLDSDGSFELYSKLTVDKSRWQQGNVESCSVMHEALHNHYTQKSLSLSPGK (human IgG4 (hIgG4) hinge amino acid sequence)

SEQ ID NO: 324

ESKYGPPCPPCP (Keytruda biosimilar (IgG4) mAb_HC amino acid sequence; CDRs are underlined)

SEQ ID NO: 325

QVQLVQSGVEVKKPGASVKVSCKASGYTFTNYYMYWVRQAPGQGLEWMGGINPSNGGTNFNEKFKNRVTLTTDSSTTTAYMELKSLQFDDTAVY
YCARRDYRFDMGFDYWGQGTTVTVSSASTKGPSVFPLAPCSRSTSESTAALGCLVKDYFPEPVTVSWNSGALTSGVHTFPAVLQSSGLYSLSSV
VTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGV
EVHNAKTKPREEQFNSTYRVVSVLTVLHQDWLNGKEYKCKVSNKGLPSSIEKTISKAKGQPREPQVYTLPPSQEEMTKNQVSLTCLVKGFYPSD
IAVEWESNGQPENNYKTTPPVLDSDGSFFLYSRLTVDKSRWQEGNVFSCSVMHEALHNHYTQKSLSLSLGK (Keytruda biosimilar (IgG4) mAb_LC amino acid sequence; CDRs are underlined)

SEQ ID NO: 326

EIVLTQSPATLSLSPGERATLSCRASKGVSTSGYSYLHWYQQKPGQAPRLLIYLASYLESGVPARFSGSGSGTDFTLTISSLEPEDFAVYYCQH
SRDLPLTFGGGTKVEIKRTVAAPSVFIFPPSDEQLKSGTASVVCLLNNFYPREAKVQWKVDNALQSGNSQESVTEQDSKDSTYSLSSTLTLSKA
DYEKHKVYACEVTHQGLSSPVTKSFNRGEC (h53C1 (IgG1) mAb_HC amino acid sequence; CDRs are underlined)

SEQ ID NO: 327

EVQLVQSGAEVKKPGASVKVSCKASGYIFTGYGITWVRQAPGQGLEWMGEIFPRRVQTYYSEKFKGRVTMTTDTSTSTAYMELRSLRSDDTAVY
YCARDYDPYFALDYWGQGTTVTVSSASTKGPSVFPLAPSSKSTSGGTAALGCLVKDYFPEPVTVSWNSGALTSGVHTFPAVLQSSGLYSLSSVV
TVPSSSLGTQTYICNVNHKPSNTKVDKRVEPKSCDKTHTCPPCPAPELLGGPSVFLEPPKPKDTLMISRTPEVTCVVVDVSHEDPEVKFNWYVD
GVEVHNAKTKPREEQYNSTYRVVSVLTVLHQDWLNGKEYKCKVSNKALPAPIEKTISKAKGQPREPQVYTLPPSRDELTKNQVSLTCLVKGFYP
SDIAVEWESNGQPENNYKTTPPVLDSDGSFELYSKLTVDKSRWQQGNVESCSVMHEALHNHYTQKSLSLSPGK

TABLE 22-continued

Anti-TIGIT sdAb SEQ ID NOs

| SEQ ID NO:FR1 | SEQ ID NO:CDR1 | SEQ ID NO:FR2 | SEQ ID NO:CDR2 | SEQ ID NO:FR3 | SEQ ID NO:CDR3 | SEQ ID NO:FR4 |
|---|---|---|---|---|---|---|

(h53C1 (IgG1) mAb_LC amino acid sequence; CDRs are underlined)

SEQ ID NO: 328

DIQMTQSPSSLSASVGDRVTITCRASQDVSTAVDWYQQKPGKAPKWYSASYRYTGVPDRFSGSGSGTDFTFTISSLQPEDIATYYCQQHYSIPF
TFGQGTKLEIKRTVAAPSVFIFPPSDEQLKSGTASVVCLLNNFYPREAKVQWKVDNALQSGNSQESVTEQDSKDSTYSLSSTLTLSKADYEKHK
VYACEVTHQGLSSPVTKSFNRGEC (h53C1 (inert IgG1) mAb_HC amino acid sequence; CDRs are underlined)

SEQ ID NO: 329

EVQLVQSGAEVKKPGASVKVSCKASGYIFTGYGITWVRQAPGQGLEWMGEIFPRRVQTYYSEKFKGRVTMTTDTSTSTAYMELRSLRSDDTAVY
YCARDYDPYFALDYWGQGTTVTVSSASTKGPSVFPLAPSSKSTSGGTAALGCLVKDYFPEPVTVSWNSGALTSGVHTFPAVLQSSGLYSLSSVV
TVPSSSLGTQTYICNVNHKPSNTKVDKKVEPKSCDKTHTCPPCPAPELLGGPSVFLFPPKPKDTLMISRTPEVTCVVVDVSHEDPEVKFNWYVD
GVEVHNAKTKPREEQYASTYRVVSVLTVLHQDWLNGKEYKCKVSNKALPAPIEKTISKAKGQPREPQVYTLPPSREEMTKNQVSLTCLVKGFYP
SDIAVEWESNGQPENNYKTTPPVLDSDGSFFLYSKLTVDKSRWQQGNVFSCSVMHEALHNHYTQKSLSLSPGK (h53C1 (inert IgG1) mAb_LC amino acid sequence; CDRs are underlined)

SEQ ID NO: 330

DIQMTQSPSSLSASVGDRVTITCRASQDVSTAVDWYQQKPGKAPKLLIYSASYRYTGVPDRFSGSGSGTDFTFTISSLQPEDIATYYCQQHYSI
PFTFGQGTKLEIKRTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC (Tecentriq biosimilar (IgG1) mAb_HC amino acid sequence; CDRs are underlined)

SEQ ID NO: 331

EVQLVESGGGLVQPGGSLRLSCAASGFTFSDSWIHWVRQAPGKGLEWVAWISPYGGSTYYADSVKGRFTISADTSKNTAYLQMNSLRAEDTAVY
YCARRHWPGGFDYWGQGTLVTVSSASTKGPSVFPLAPSSKSTSGGTAALGCLVKDYFPEPVTVSWNSGALTSGVHTFPAVLQSSGLYSLSSVVT
VPSSSLGTQTYICNVNHKPSNTKVDKKVEPKSCDKTHTCPPCPAPELLGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALPAPIEKTISKAKGQPREPQVYTLPPSRDELTKNQVSLTCLVKGFYPS
DIAVEWESNGQPENNYKTTPPVLDSDGSFFLYSKLTVDKSRWQQGNVFSCSVMHEALHNHYTQKSLSLSPGK (Tecentriq biosimilar (IgG1) mAb_LC amino acid sequence; CDRs are underlined)

SEQ ID NO: 332

DIQMTQSPSSLSASVGDRVTITCRASQDVSTAVAWYQQKPGKAPKLLIYSASFLYSGVPSRFSGSGSGTDFTLTISSLQPEDFATYYCQQYLYH
PATFGQGTKVEIKRTVAAPSVFIEPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC (Tecentriq biosimilar (inert IgG1) mAb_HC amino acid sequence; CDRs are underlined)

SEQ ID NO: 333

EVQLVESGGGLVQPGGSLRLSCAASGFTFSDSWIHWVRQAPGKGLEWVAWISPYGGSTYYADSVKGRFTISADTSKNTAYLQMNSLRAEDTAVY
YCARRHWPGGFDYWGQGTLVTVSSASTKGPSVFPLAPSSKSTSGGTAALGCLVKDYFPEPVTVSWNSGALTSGVHTFPAVLQSSGLYSLSSVVT
VPSSSLGTQTYICNVNHKPSNTKVDKKVEPKSCDKTHTCPPCPAPELLGGPSVFLFPPKPKDTLMISRTPEVTCVVVDVSHEDPEVKFNWYVDG
VEVHNAKTKPREEQYASTYRVVSVLTVLHQDWLNGKEYKCKVSNKALPAPIEKTISKAKGQPREPQVYTLPPSREEMTKNQVSLTCLVKGFYPS
DIAVEWESNGQPENNYKTTPPVLDSDGSFFLYSKLTVDKSRWQQGNVFSCSVMHEALHNHYTQKSLSLSPGK (Tecentriq biosimilar (inert IgG1) mAb_LC amino acid sequence; CDRs are underlined)

SEQ ID NO: 334

DIQMTQSPSSLSASVGDRVTITCRASQDVSTAVAWYQQKPGKAPKLLIYSASFLYSGVPSRFSGSGSGTDFTLTISSLQPEDFATYYCQQYLYH
PATFGQGTKVEIKRTVAAPSVFIEPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC (22G2 (IgG1) mAb_HC amino acid sequence; CDRs are underlined)

SEQ ID NO: 335

SQVQLQESGPGLVKPSETLSLTCTVSGGSVSSGIYYWSWIRQPPGKGLEWIGYIYYSGSTNYNPSLKSRVTISVDTSKNQFSLKLSSVTAADTA
VYYCARDYYVSGNYYNVDYYFFGVDVWGQGTTVTVSSASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKRVEPKSCDKTHTCPPCPAPELLGGPSVFLFPPKPKDTLMISRTPEVTCVVVDVSH
EDPEVKFNWYVDGVEVHNAKTKPREEQYNSTYRVVSVLTVLHQDWLNGKEYKCKVSNKALPAPIEKTISKAKGQPREPQVYTLPPSRDELTKNQ
VSLTCLVKGFYPSDIAVEWESNGQPENNYKTTPPVLDSDGSFFLYSKLTVDKSRWQQGNVFSCSVMHEALHNHYTQKSLSLSPGK (22G2 (IgG1) mAb _LC amino acid sequence; CDRs are underlined)

SEQ ID NO: 336

EIVLTQSPATLSLSPGERATLSCRASQSVSSYLAWYQQKPGQAPRLLIYDASNRATGIPARFSGSGSGTDFTLTISSLEPEDFAVYYCQQRSNW
PPLFTFGPGTKVDIKRTVAAPSVFIEPPSDEQLKSGTASVVCLLNNFYPREAKVQWKVDNALQSGNSQESVTEQDSKDSTYSLSSTLTLSKADY
EKHKVYACEVTHQGLSSPVTKSFNRGEC (10A7 mAb_HC amino acid sequence; CDRs are underlined)

SEQ ID NO: 337

EVQLVESGGGLTQPGKSLKLSCEASGFTFSSFTMHWVRQSPGKGLEWVAFIRSGSGIVFYADAVRGRFTISRDNAKNLLFLQMNDLKSEDTAMY
YCARRPLGHNTFDSWGQGTLVTVSSASTKGPSVFPLAPSSKSTSGGTAALGCLVKDYFPEPVTVSWNSGALTSGVHTFPAVLQSSGLYSLSSVV
TVPSSSLGTQTYICNVNHKPSNTKVDKKVEPKSCDKTHTCPPCPAPELLGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPAPIEKTISKAKGQPREPQVYTLPPSRDELTKNQVSLTCLVKGFYP
SDIAVEWESNGQPENNYKTTPPVLDSDGSFFLYSKLTVDKSRWQQGNVFSCSVMHEALHNHYTQKSLSLSPGK

TABLE 22-continued

Anti-TIGIT sdAb SEQ ID NOs

| SEQ ID NO:FR1 | SEQ ID NO:CDR1 | SEQ ID NO:FR2 | SEQ ID NO:CDR2 | SEQ ID NO:FR3 | SEQ ID NO:CDR3 | SEQ ID NO:FR4 |
|---|---|---|---|---|---|---|

(10A7 mAb_LC amino acid sequence; CDRs are underlined)  
SEQ ID NO: 338  
DIVMTQSPSSLAVSPGEKVTMTCKSSQSLYYSGVKENLLAWYQQKPGQSPKLLIYYASIRFTGVPDRFTGSGSGTDYTLTITSVQAEDMGQYFC
QQGINNPLTFGDGTKLEIKRTVAAPSVFIEPPSDEQLKSGTASVVCLLNNFYPREAKVQWKVDNALQSGNSQESVTEQDSKDSTYSLSSTLTLS
KADYEKHKVYACEVTHQGLSSPVTKSFNRGEC (h53C1 VH amino acid sequence; CDRs are underlined)  
SEQ ID NO: 339  
EVQLVQSGAEVKKPGASVKVSCKASGYIFTGYGITWVRQAPGQGLEWMGEIFPRRVQTYYSEKFKGRVTMTTDTSTSTAYMELRSLRSDDTAVY
YCARDYDPYFALDYWGQGTTVTVSS (h53C1 VLamino acid sequence; CDRs are underlined)  
SEQ ID NO: 340  
DIQMTQSPSSLSASVGDRVTITCRASQDVSTAVDWYQQKPGKAPKLLIYSASYRYTGVPDRFSGSGSGTDFTFTISSLQPEDIATYYCQQHYSI
PFTFGQGTKLEIK (h53C1 HC-CDR1 amino acid sequence)  
SEQ ID NO: 349  
GYIFTGYGIT (h53C1 HC-CDR2 amino acid sequence)  
SEQ ID NO: 350  
EIFPRRVQTYYSEKFKG (h53C1 HC-CDR3 amino acid sequence)  
SEQ ID NO: 351  
DYDPYFALDY (h53C1 LC-CDR1 amino acid sequence)  
SEQ ID NO: 352  
RASQDVSTAVD (h53C1 LC-CDR2 amino acid sequence)  
SEQ ID NO: 353  
SASYRYT (h53C1 LC-CDR3 amino acid sequence)  
SEQ ID NO: 354  
QQHYSIPFTF (Human inert IgG1 Fc region amino acid sequence)  
SEQ ID NO: 355  
APELLGGPSVFLFPPKPKDTLMISRTPEVTCVVVDVSHEDPEVKFNWYVDGVEVHNAKTKPREEQYASTYRVVSVLTVLHQDWLNGKEYKCKVS
NKALPAPIEKTISKAKGQPREPQVYTLPPSREEMTKNQVSLTCLVKGFYPSDIAVEWESNGQPENNYKTTPPVLDSDGSFFLYSKLTVDKSRWQ
QGNVFSCSVMHEALHNHYTQKSLSLSPGK (Human IgG1 Fc region amino acid sequence)  
SEQ ID NO: 356  
APELLGGPSVFLFPPKPKDTLMISRTPEVTCVVVDVSHEDPEVKFNWYVDGVEVHNAKTKPREEQYNSTYRVVSVLTVLHQDWLNGKEYKCKVS
NKALPAPIEKTISKAKGQPREPQVYTLPPSRDELTKNQVSLTCLVKGFYPSDIAVEWESNGQPENNYKTTPPVLDSDGSFFLYSKLTVDKSRWQ
QGNVFSCSVMHEALHNHYTQKSLSLSPGK

TABLE 23

Anti-TIGIT/PD-1 and Anti-TIGIT/PD-L1 bispecific antibody amino acid sequences
(sdAb sequence is underlined, linker sequence is bolded)

| | |
|---|---|
| SEQ ID NO: 341<br>BTP-4_HC<br>(AS19584-mutated<br>hIgG1 hinge-h53C1<br>(inert IgG1)<br>HC) | QVQLAESGGGSVQAGGSLRLSCAASGYKYGVYSMGWFRLAPGKEREGVAAICSGGRTTYSDSVKGRFTISKDSANQ<br>ILYLQMNSLKPEDTAMYYCAARPLWTGDCDLSSSWYKTWGQGTQVTVSSEPKSSDKTHTSPPSPEVQLVQSGAEVK<br>KPGASVKVSCKASGYIFTGYGITWVRQAPGQGLEWMGEIFPRRVQTYYSEKFKGRVTMTTDTSTSTAYMELRSLRS<br>DDTAVYYCARDYDPYFALDYWGQGTTVTVSSASTKGPSVFPLAPSSKSTSGGTAALGCLVKDYFPEPVTVSWNSGA<br>LTSGVHTFPAVLQSSGLYSLSSVVTVPSSSLGTQTYICNVNHKPSNTKVDKKVEPKSCDKTHTCPPCPAPELLGGP<br>SVFLFPPKPKDTLMISRTPEVTCVVVDVSHEDPEVKFNWYVDGVEVHNAKTKPREEQYASTYRVVSVLTVLHQDWL<br>NGKEYKCKVSNKALPAPIEKTISKAKGQPREPQVYTLPPSREEMTKNQVSLTCLVKGFYPSDIAVEWESNGQPENN<br>YKTTPPVLDSDGSFLLYSKLTVDKSRWQQGNVLSCSVMHEALHNHYTQKSLSLSPGK |
| SEQ ID NO: 342<br>BTP-4_LC<br>(h53C1 (inert<br>IgG1) LC) | DIQMTQSPSSLSASVGDRVTITCRASQDVSTAVDWYQQKPGKAPKLLIYSASYRYTGVPDRFSGSGSGTDFTFTIS<br>SLQPEDIATYYCQQHYSIPFTEGQGTKLEIKRTVAAPSVFIEPPSDEQLKSGTASVVCLLNNEYPREAKVQWKVDN<br>ALQSGNSQESVTEQDSKDSTYSLSSTLTLSKADYEKHKVYACEVTHQGLSSPVTKSFNRGEC |

TABLE 23-continued

Anti-TIGIT/PD-1 and Anti-TIGIT/PD-L1 bispecific antibody amino acid sequences
(sdAb sequence is underlined, linker sequence is bolded)

| | |
|---|---|
| SEQ ID NO: 343<br>BTP-5_HC<br>(AS19584-mutated<br>hIgG1 hinge-<br>h53C1 (IgG1) HC) | <u>QVQLAESGGGSVQAGGSLRLSCAASGYKYGVYSMGWFRLAPGKEREGVAAICSGGRTTYSDSVKGRFTISKDSANQ<br>ILYLQMNSLKPEDTAMYYCAARPLWTGDCDLSSSWYKTWGQGTQVTVSS</u>EPKSSDKTHTSPPSPEVQLVQSGAEVK<br>KPGASVKVSCKASGYIFTGYGITWVRQAPGQGLEWMGEIFPRRVQTYYSEKFKGRVTMTTDTSTSTAYMELRSLRS<br>DDTAVYYCARDYDPYFALDYWGQGTTVTVSSASTKGPSVFPLAPSSKSTSGGTAALGCLVKDYFPEPVTVSWNSGA<br>LTSGVHTFPAVLQSSGLYSLSSVVTVPSSSLGTQTVNHKPSNTKVDKRVEPKSCDKTHTCPPCPAPELLGGPSVFL<br>FPPKPKDTLMISRTPEVTCVVVDVSHEDPEVKFNWYVDGVEVHNAKTKPREEQYNSTYRVVSVLTVLHQDWLNGKE<br>YKCKVSNKALPAPIEKTISKAKGQPREPQVYTLPPSRDELTKNQVSLTCLVKGFYPSDIAVEWESNGQPENNYKTT<br>PPVLDSDGSFELYSKLTVDKSRWQQGNVFSCSVMHEALHNHYTQKSLSLSPGK |
| SEQ ID NO: 344<br>hIgG1 hinge-h53C1<br>(IgG1) HC | DIQMTQSPSSLSASVGDRVTITCRASQDVSTAVDWYQQKPGKAPKLLIYSASYRYTGVPDRFSGSGSGTDFTFTIS<br>SLQPEDIATYYCQQHYSIPFTEGQGTKLEIKRTVAAPSVFIFPPSDEQLKSGTASVVCLLNNFYPREAKVQWKVDN<br>ALQSGNSQESVTEQDSKDSTYSLSSTLTLSKADYEKHKVYACEVTHQGLSSPVTKSFNRGEC |
| SEQ ID NO: 345<br>BTP-6_HC<br>(AS19584-mutated<br>hIgG1 hinge-<br>Tecentriq<br>biosimilar<br>(inert IgG1) HC | <u>QVQLAESGGGSVQAGGSLRLSCAASGYKYGVYSMGWERLAPGKEREGVAAICSGGRTTYSDSVKGRFTISKDSANQ<br>ILYLQMNSLKPEDTAMYYCAARPLWTGDCDLSSSWYKTWGQGTQVTVSS</u>EPKSSDKTHTSPPSPEVQLVESGGGLA<br>VQPGGSLRLSCAASGFTESDSWIHWVRQAPGKGLEWVAWISPYGGSTYYADSVKGRFTISADTSKNTAYLQMNSLR<br>EDTAVYYCARRHWPGGFDYWGQGTLVTVSSASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNTKVDKKVEPKSCDKTHTCPPCPAPELLGGPS<br>VFLFPPKPKDTLMISRTPEVTCVVVDVSHEDPEVKFNWYVDGVEVHNAKTKPREEQASTYRVVSVLTVLHQDWLN<br>GKEYKCKVSNKALPAPIEKTISKAKGQPREPQVYTLPPSREEMTKNQVSLTCLVKGFYPSDIAVEWESNGQPENNY<br>KTTPPVLDSDGSFELYSKLTVDKSRWQQGNVFSCSVMHEALHNHYTQKSLSLSPGK |
| SEQ ID NO: 346<br>BTP-6_LC<br>Tecentriq<br>biosimilar<br>(inert IgG1) LC | DIQMTQSPSSLSASVGDRVTITCRASQDVSTAVAWYQQKPGKAPKLLIYSASFLYSGVPSRFSGSGSGTDFTLTIS<br>SLQPEDFATYYCQQYLYHPATEGQGTKVEIKRTVAAPSVFIFPPSDEQLKSGTASVVCLLNNFYPREAKVQWKVDN<br>ALQSGNSQESVTEQDSKDSTYSLSSTLTLSKADYEKHKVYACEVTHQGLSSPVTKSFNRGEC |
| SEQ ID NO: 347<br>BTP-7_HC<br>(AS19584-mutated<br>hIgG1 hinge-<br>Tecentriq<br>biosimilar<br>(inert IgG1) HC) | <u>QVQLAESGGGSVQAGGSLRLSCAASGYKYGVYSMGWERLAPGKEREGVAAICSGGRTTYSDSVKGRFTISKDSANQ<br>ILYLQMNSLKPEDTAMYYCAARPLWTGDCDLSSSWYKTWGQGTQVTVSS</u>EPKSSDKTHTSPPSPEVQLVESGGGLV<br>QPGGSLRLSCAASGFTESDSWIHWVRQAPGKGLEWVAWISPYGGSTYYADSVKGRFTISADTSKNTAYLQMNSLRA<br>EDTAVYYCARRHWPGGFDYWGQGTLVTVSSASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNTKVDKKVEPKSCDKTHTCPPCPAPELLGGPS<br>VFLFPPKPKDTLMISRTPEVTCVVVDVSHEDPEVKFNWYVDGVEVHNAKTKPREEQYNSTYRVVSVLTVLHQDWLN<br>GKEYKCKVSNKALPAPIEKTISKAKGQPREPQVYTLPPSRDELTKNQVSLTCLVKGFYPSDIAVEWESNGQPENNY<br>KTTPPVLDSDGSFELYSKLTVDKSRWQQGNVFSCSVMHEALHNHYTQKSLSLSPGK |
| SEQ ID NO: 348<br>Tecentriq<br>biosimilar<br>(inert IgG1) LC | DIQMTQSPSSLSASVGDRVTITCRASQDVSTAVAWYQQKPGKAPKLLIYSASFLYSGVPSRFSGSGSGTDFTLTIS<br>SLQPEDFATYYCQQYLYHPATEGQGTKVEIKRTVAAPSVFIFPPSDEQLKSGTASVVCLLNNFYPREAKVQWKVDN<br>ALQSGNSQESVTEQDSKDSTYSLSSTLTLSKADYEKHKVYACEVTHQGLSSPVTKSFNRGEC |
| SEQ ID NO: 357<br>BTP-15_HC<br>(AS195784VH28-<br>mutated hIgG1<br>hinge-h53C1<br>(IgG1) HC) | <u>EVQLVESGGGLVQPGGSLRLSCAASGYKYGVYSMGWERQAPGKGLEGVSAICSGGRTTYSDSVKGRFTISRDNSNQ<br>ILYLQMNSLRAEDTAVYYCAARPLWTGDCDLSSSWYKTWGQGTLVTVSS</u>EPKSSDKTHTSPPSPEVQLVQSGAEVK<br>KPGASVKVSCKASGYIFTGYGITWVRQAPGQGLEWMGEIFPRRVQTYYSEKFKGRVTMTTDTSTSTAYMELRSLRS<br>DDTAVYYCARDYDPYFALDYWGQGTTVTVSSASTKGPSVFPLAPSSKSTSGGTAALGCLVKDYFPEPVTVSWNSGA<br>LTSGVHTFPAVLQSSGLYSLSSVVTVPSSSLGTQTYICNVNHKPSNTKVDKKVEPKSCDKTHTCPPCPAPELLGGP<br>SVFLFPPKPKDTLMISRTPEVTCVVVDVSHEDPEVKFNWYVDGVEVHNAKTKPREEQYNSTYRVVSVLTVLHQDWL<br>NGKEYKCKVSNKALPAPIEKTISKAKGQPREPQVYTLPPSRDELTKNQVSLTCLVKGFYPSDIAVEWESNGQPENN<br>YKTTPPVLDSDGSFELYSKLTVDKSRWQQGNVFSCSVMHEALHNHYTQKSLSLSPGK |
| SEQ ID NO: 358<br>BTP-15_LC<br>(h53C1 (IgG1) LC) | DIQMTQSPSSLSASVGDRVTITCRASQDVSTAVDWYQQKPGKAPKLLIYSASYRYTGVPDRFSGSGSGTDFTFTIS<br>SLQPEDIATYYCQQHYSIPFTEGQGTKLEIKRTVAAPSVFIFPPSDEQLKSGTASVVCLLNNFYPREAKVQWKVDN<br>ALQSGNSQESVTEQDSKDSTYSLSSTLTLSKADYEKHKVYACEVTHQGLSSPVTKSFNRGEC |
| SEQ ID NO: 359<br>BTP-16_HC<br>(h53C1 (IgG1)<br>HC-mutated hIgG1<br>hinge-<br>AS19584VH28) | EVQLVQSGAEVKKPGASVKVSCKASGYIFTGYGITWVRQAPGQGLEWMGEIFPRRVQTYYSEKFKGRVTMTTDTST<br>STAYMELRSLRSDDTAVYYCARDYDPYFALDYWGQGTTVTVSSASTKGPSVFPLAPSSKSTSGGTAALGCLVKDYF<br>PEPVTVSWNSGALTSGVHTFPAVLQSSGLYSLSSVVTVPSSSLGTQTYICNVNHKPSNTKVDKKVEPKSCDKTHTC<br>PPCPAPELLGGPSVFLFPPKPKDTLMISRTPEVTCVVVDVSHEDPEVKFNWYVDGVEVHNAKTKPREEQYNSTYRV<br>VSVLTVLHQDWLNGKEYKCKVSNKALPAPIEKTISKAKGQPREPQVYTLPPSRDELTKNQVSLTCLVKGFYPSDIA<br>VEWESNGQPENNYKTTPPVLDSDGSFFLYSKLTVDKSRWQQGNVFSCSVMHEALHNHYTQKSLSLSPGKEPKSSDK<br>THTSPPSP<u>EVQLVESGGGLVQPGGSLRLSCAASGYKYGVYSMGWERQAPGKGLEGVSAICSGGRTTYSDSVKGRFT<br>ISRDNSNQILYLQMNSLRAEDTAVYYCAARPLWTGDCDLSSSWYKTWGQGTLVTVSS</u> |
| SEQ ID NO: 360<br>BTP-16_LC<br>(h53C1 (IgG1) LC) | DIQMTQSPSSLSASVGDRVTITCRASQDVSTAVDWYQQKPGKAPKLLIYSASYRYTGVPDRFSGSGSGTDFTFTIS<br>SLQPEDIATYYCQQHYSIPFTEGQGTKLEIKRTVAAPSVFIFPPSDEQLKSGTASVVCLLNNFYPREAKVQWKVDN<br>ALQSGNSQESVTEQDSKDSTYSLSSTLTLSKADYEKHKVYACEVTHQGLSSPVTKSFNRGEC |
| SEQ ID NO: 361<br>BTP-17_HC<br>(h53C1 (IgG1) HC) | EVQLVQSGAEVKKPGASVKVSCKASGYIFTGYGITWVRQAPGQGLEWMGEIFPRRVQTYYSEKFKGRVTMTTDTST<br>STAYMELRSLRSDDTAVYYCARDYDPYFALDYWGQGTTVTVSSASTKGPSVFPLAPSSKSTSGGTAALGCLVKDYF<br>PEPVTVSWNSGALTSGVHTFPAVLQSSGLYSLSSVVTVPSSSLGTQTYICNVNHKPSNTKVDKKVEPKSCDKTHTC<br>PPCPAPELLGGPSVFLFPPKPKDTLMISRTPEVTCVVVDVSHEDPEVKFNWYVDGVEVHNAKTKPREEQYNSTYRV<br>VSVLTVLHQDWLNGKEYKCKVSNKALPAPIEKTISKAKGQPREPQVYTLPPSRDELTKNQVSLTCLVKGFYPSDIA<br>VEWESNGQPENNYKTTPPVLDSDGSFFLYSKLTVDKSRWQQGNVFSCSVMHEALHNHYTQKSLSLSPGK |

TABLE 23-continued

Anti-TIGIT/PD-1 and Anti-TIGIT/PD-L1 bispecific antibody amino acid sequences
(sdAb sequence is underlined, linker sequence is bolded)

| | |
|---|---|
| SEQ ID NO: 362<br>BTP-17_LC<br>(AS19584VH28-<br>mutated hIgG1<br>hinge-h53C1<br>(IgG1) LC) | EVQLVESGGGLVQPGGSLRLSCAASGYKYGVYSMGWERQAPGKGLEGVSAICSGGRTTYSDSVKGRFTISRDNSNQ<br>ILYLQMNSLRAEDTAVYYCAARPLWTGDCDLSSSWYKTWGQGTLVTVSSEPKSSDKTHTSPPSPDIQMTQSPSSLS<br>ASVGDRVTITCRASQDVSTAVDWYQQKPGKAPKLLIYSASYRYTGVPDRFSGSGSGTDFTFTISSLQPEDIATYYC<br>QQHYSIPFTEGQGTKLEIKRTVAAPSVFIFPPSDEQLKSGTASVVCLLNNFYPREAKVQWKVDNALQSGNSQESVT<br>EQDSKDSTYSLSSTLTLSKADYEKHKVYACEVTHQGLSSPVTKSFNRGEC |
| SEQ ID NO: 363<br>BTP-18_HC<br>(h53C1 (IgG1) HC) | EVQLVQSGAEVKKPGASVKVSCKASGYIFTGYGITWVRQAPGQGLEWMGEIFPRRVQTYYSEKFKGRVTMTTDTST<br>STAYMELRSLRSDDTAVYYCARDYDPYFALDYWGQGTTVTVSSASTKGPSVFPLAPSSKSTSGGTAALGCLVKDYF<br>PEPVTVSWNSGALTSGVHTFPAVLQSSGLYSLSSVVTVPSSSLGTQTYICNVNHKPSNTKVDKKVEPKSCDKTHTC<br>PPCPAPELLGGPSVFLFPPKPKDTLMISRTPEVTCVVVDVSHEDPEVKFNWYVDGVEVHNAKTKPREEQYNSTYRV<br>VSVLTVLHQDWLNGKEYKCKVSNKALPAPIEKTISKAKGQPREPQVYTLPPSRDELTKNQVSLTCLVKGFYPSDIA<br>VEWESNGQPENNYKTTPPVLDSDGSFFLYSKLTVDKSRWQQGNVFSCSVMHEALHNHYTQKSLSLSPGK |
| SEQ ID NO: 364<br>BTP-18_LC<br>(h53C1 (IgG1) LC-<br>mutated hIgG1<br>hinge-<br>AS19584VH28) | DIQMTQSPSSLSASVGDRVTITCRASQDVSTAVDWYQQKPGKAPKLLIYSASYRYTGVPDRFSGSGSGTDFTFTIS<br>SLQPEDIATYYCQQHYSIPFTEGQGTKLEIKRTVAAPSVFIEPPSDEQLKSGTASVVCLLNNFYPREAKVQWKVDN<br>ALQSGNSQESVTEQDSKDSTYSLSSTLTLSKADYEKHKVYACEVTHQGLSSPVTKSFNRGECEPKSSDKTHTSPPS<br>PEVQLVESGGGLVQPGGSLRLSCAASGYKYGVYSMGWERQAPGKGLEGVSAICSGGRTTYSDSVKGRFTISRDNSN<br>QILYLQMNSLRAEDTAVYYCAARPLWTGDCDLSSSWYKTWGQGTLVTVSS |

SEQ ID NO: 365 (AS19584 sdAb-Fc (inert IgG1) fusion protein dimeric form amino acid sequence;
CDRs are underlined, linker is bolded)
QVQLAESGGGSVQAGGSLRLSCAAS<u>GYKYGVYSMG</u>WERLAPGKEREGVAA<u>ICSGGRTTYSDSVKG</u>RFTISKDSANQILYLQMNSLKPEDTAMYY
CAAR<u>PLWTGDCDLSSSWYKTW</u>GQGTQVTVSSEPKSCDKTHTCPPCPAPELLGGPSVFLEPPKPKDTLMISRTPEVTCVVVDVSHEDPEVKFNWY
VDG<u>VEVHNAKTKPREEQYA</u>STYRVVSVLTVLHQDWLNGKEYKCKVSNKALPAPIEKTSKAKGQPREPQVTLPPSREEMTKNQVSLTCLVKGF
YPSDIAVEWESNGQPENNYKTTPPVLDSDGSFELYSKLTVDKSRWQQGNVESCSVMHEALHNHYTQKSLSLSPGK SEQ ID NO: 366 (AS19584 sdAb-Fc (IgG4) fusion protein dimeric form amino acid sequence;
CDRs are underlined)
QVQLAESGGGSVQAGGSLRLSCAAS<u>GYKYGVYSMG</u>WERLAPGKEREGVAA<u>ICSGGRTTYSDSVKG</u>RFTISKDSANQILYLQMNSLKPEDTAMYY
CAAR<u>PLWTGDCDLSSSWYKTW</u>GQGTQVTVSSESKYGPPCPPCPAPEFLGGPSVFLEPPKPKDTLMISRTPEVTCVVVDVSQEDPEVQFNWYVDG
VEVHNAKTKPREEQFNSTYRVVSVLTVLHQDWLNGKEYKCKVSNKGLPSSIEKTISKAKGQPREPQVYTLPPSQEEMTKNQVSLTCLVKGFYPS
DIAVEWESNGQPENNYKTTPPVLDSDGSFELYSRLTVDKSRWQEGNVESCSVMHEALHNHYTQKSLSLSLGK SEQ ID NO: 367 (AS19584VH28 sdAb-Fc (IgG4) fusion protein dimeric form amino acid sequence;
CDRs are underlined)
EVQLVESGGGLVQPGGSLRLSCAASGYKYGVYSMGWERQAPGKGLEGVSAICSGGRTTYSDSVKGRFTISRDNSNQILYLQMNSLRAEDTAVYY
CAARPLWTGDCDLSSSWYKTWGQGTLVTVSSESKYGPPCPPCPAPEFLGGPSVFLEPPKPKDTLMISRTPEVTCVVVDVSQEDPEVQFNWYVDG
VEVHNAKTKPREEQFNSTYRVVSVLTVLHQDWLNGKEYKCKVSNKGLPSSIEKTISKAKGQPREPQVYTLPPSQEEMTKNQVSLTCLVKGFYPS
DIAVEWESNGQPENNYKTTPPVLDSDGSFELYSRLTVDKSRWQEGNVESCSVMHEALHNHYTQKSLSLSLGK SEQ ID NO: 368 (full-length human TIGIT amino acid sequence, without signal peptide)
MMTGTIETTGNISAEKGGSIILQCHLSSTTAQVTQVNWEQQDQLLAICNADLGWHISPSFKDRVAPGPGLGLTLQSLTVNDTGEYECIYHTYPD
GTYTGRIFLEVLESSVAEHGARFQIPLLGAMAATLVVICTAVIVVVALTRKKKALRIHSVEGDLRRKSAGQEEWSPSAPSPPGSCVQAEAAPAG
LCGEQRGEDCAELHDYFNVLSYRSLGNCSFFTETG SEQ ID NO: 369 (extracellular domain of human TIGIT amino acid sequence)
MMTGTIETTGNISAEKGGSIILQCHLSSTTAQVTQVNWEQQDQLLAICNADLGWHISPSFKDRVAPGPGLGLTLQSLTVNDTGEYECIYHTYPD
GTYTGRIELEVLESSVAEHGARFQIP SEQ ID NO: 370 (human IgG1 (hIgG1) hinge amino acid sequence)
EPKSCDKTHTCPPCP SEQ ID NO: 371 (mutated human IgG1 (hIgG1) hinge amino acid sequence)
EPKSSDKTHTSPPSP SEQ ID NO: 372 (Linker peptide (9G5) amino acid sequence)
GGGGSGGGS SEQ ID NO: 373 (Linker peptide amino acid sequence)
GGGGSGGGGSGGGGS SEQ ID NO: 374 (Linker peptide amino acid sequence, n is an integer of at least one)
$(G)_n$ SEQ ID NO: 375 (Linker peptide amino acid sequence, n is an integer of at least one)
$(GS)_n$ SEQ ID NO: 376 (Linker peptide amino acid sequence, n is an integer of at least one)
$(GSGGS)_n$ SEQ ID NO: 377 (Linker peptide amino acid sequence, n is an integer of at least one)
$(GGGS)_n$

US 11,905,327 B2

169
170

TABLE 23-continued

Anti-TIGIT/PD-1 and Anti-TIGIT/PD-L1 bispecific antibody amino acid sequences
(sdAb sequence is underlined, linker sequence is bolded)

SEQ ID NO: 378 (Linker peptide amino acid sequence, n is an integer of at least one)
(GGGGS)$_n$ SEQ ID NO: 379 (Durvalumab VH amino acid sequence; CDRs are underlined)
EVQLVESGGGLVQPGGSLRLSCAASGFTFSRYWMSWVRQAPGKGLEWVANIKQDGSEKYYVDSVKGRFTISRDNAKNSLYLQMNSLRAEDTAVY
YCAREGGWFGELAFDYWGQGTLVTVSS SEQ ID NO: 380 (Durvalumab VL amino acid sequence; CDRs are underlined)
EIVLTQSPGTLSLSPGERATLSCRASQRVSSSYLAWYQQKPGQAPRLLIYDASSRATGIPDRFSGSGSGTDFTLTISRLEPEDFAVYYCQQYGS
LPWTFGQGTKVEIK SEQ ID NO: 381 (Tecentriq VH amino acid sequence; CDRs are underlined)
EVQLVESGGGLVQPGGSLRLSCAASGFTFSDSWIHWVRQAPGKGLEWVAWISPYGGSTYYADSVKGRFTISADTSKNTAYLQMNSLRAEDTAVY
YCARRHWPGGFDYWGQGTLVTVSS SEQ ID NO: 382 (Tecentriq VL amino acid sequence; CDRs are underlined)
DIQMTQSPSSLSASVGDRVTITCRASQDVSTAVAWYQQKPGKAPKLLIYSASFLYSGVPSRFSGSGSGTDFTLTISSLQPEDFATYYCQQYLYH
PATFGQGTKVEIK SEQ ID NO: 383 (Avelumab VH amino acid sequence; CDRs are underlined)
EVQLLESGGGLVQPGGSLRLSCAASGFTFSSYIMMWVRQAPGKGLEWVSSIYPSGGITFYADTVKGRFTISRDNSKNTLYLQMNSLRAEDTAVY
YCARIKLGTVTTVDYWGQGTLVTVSS SEQ ID NO: 384 (Avelumab VL amino acid sequence; CDRs are underlined)
QSALTQPASVSGSPGQSITISCTGTSSDVGGYNYVSWYQQHPGKAPKLMIYDVSNRPSGVSNRFSGSKSGNTASLTISGLQAEDEADYYCSSYT
SSSTRVFGTGTKVTVL SEQ ID NO: 385 (Keytruda VH amino acid sequence; CDRs are underlined)
QVQLVQSGVEVKKPGASVKVSCKASGYTFTNYYMYWVRQAPGQGLEWMGGINPSNGGTNFNEKFKNRVTLTTDSSTTTAYMELKSLQFDDTAVY
YCARRDYRFDMGFDYWGQGTTVTVSS SEQ ID NO: 386 (Keytruda VL amino acid sequence; CDRs are underlined)
EIVLTQSPATLSLSPGERATLSCRASKGVSTSGYSYLHWYQQKPGQAPRLLIYLASYLESGVPARFSGSGSGTDFTLTISSLEPEDFAVYYCQH
SRDLPLTFGGGTKVEIK SEQ ID NO: 387 (Opdivo VH amino acid sequence; CDRs are underlined)
QVQLVESGGGVVQPGRSLRLDCKASGITFSNSGMHWVRQAPGKGLEWVAVIWYDGSKRYVADSVKGRFTISRDNSKNTLFLQMNSLRAEDTAVY
YCATNDDYWGQGTLVTVSS SEQ ID NO: 388 (Opdivo VL amino acid sequence; CDRs are underlined)
EIVLTQSPATLSLSPGERATLSCRASQSVSSYLAWYQQKPGQAPRLLIYDASNRATGIPARFSGSGSGTDFTLTISSLEPEDFAVYYCQQSSNW
PRTFGQGTKVEIK SEQ ID NO: 389 (Human IgG4 Fc region amino acid sequence)
APEFLGGPSVFLFPPKPKDTLMISRTPEVTCVVVDVSQEDPEVQFNWYVDGVEVHNAKTKPREEQFNSTYRVVSVLTVLHQDWLNGKEYKCKVS
NKGLPSSIEKTISKAKGQPREPQVYTLPPSQEEMTKNQVSLTCLVKGFYPSDIAVEWESNGQPENNYKTTPPVLDSDGSFFLYSRLTVDKSRWQ
EGNVFSCSVMHEALHNHYTQKSLSLSLGK SEQ ID NO: 390 (PD1-BM-min_HC amino acid sequence; CDRs are underlined)
EVQLVESGGGLVQPGGSLRLSCAASGFVFSRYDMAWVRQAPGKGLEWVSFISGGGSNTYYPDTVKGRFTISRDNSKNTLYLQMNSLRAEDTAVY
YCISPYYYAMEYWGQGTTVTVSSASTKGPSVFPLAPCSRSTSESTAALGCLVKDYFPEPVTVSWNSGALTSGVHTFPAVLQSSGLYSLSSVVTV
PSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVH
NAKTKPREEQFNSTYRVVSVLTVLHQDWLNGKEYKCKVSNKGLPSSIEKTISKAKGQPREPQVYTLPPSQEEMTKNQVSLTCLVKGFYPSDIAV
EWESNGQPENNYKTTPPVLDSDGSFFLYSRLTVDKSRWQEGNVFSCSVMHEALHNHYTQKSLSLSLGK SEQ ID NO: 391 (PD1-BM-min_LC amino acid sequence; CDRs are underlined)
DIQMTQSPSSVSASVGDRVTITCKASQDVDTAVAWYQQKPGKAPKLLIYWASTRHTGVPSRFSGSGSGTDFTLTISSLQPEDFATYYCQQYSTF
PWTFGGGTKVEIKRTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC SEQ ID NO: 392 (Tiragolumab_HC amino acid sequence; CDRs are underlined)
EVQLQQSGPGLVKPSQTLSLTCAISGDSVSSNSAAWNWIRQSPSRGLEWLGKTYYRFKWYSDYAVSVKGRITINPDTSKNQFSLQLNSVTPEDT
AVFYCTRESTTYDLLAGPFDYWGQGTLVTVSSASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSNKALPAPIEKTISKAKGQPREPQVYTLPPSREEMTKNQVSLTC
LVKGFYPSDIAVEWESNGQPENNYKTTPPVLDSDGSFFLYSKLTVDKSRWQQGNVFSCSVMHEALHNHYTQKSLSLSPGK SEQ ID NO: 393 (Tiragolumab_LC amino acid sequence; CDRs are underlined)
DIVMTQSPDSLAVSLGERATINCKSSQTVLYSSNNKKYLAWYQQKPGQPPNLLIYWASTRESGVPDRFSGSGSGTDFTLTISSLQAEDVAVYYC
QQYYSTPFTFGPGTKVEIKRTVAAPSVFIFPPSDEQLKSGTASVVCLLNNFYPREAKVQWKVDNALQSGNSQESVTEQDSKDSTYSLSSTLTLS
KADYEKHKVYACEVTHQGLSSPVTKSFNRGEC

TABLE 24

Anti-TIGIT/PD-1 and Anti-TIGIT/PD-L1 bispecific antibody amino acid sequences
(sdAb sequence is underlined, linker sequence is bolded)

| | |
|---|---|
| SEQ ID NO: 394<br>BTP-11_HC<br>(AS19584VH28-<br>mutated hIgG1<br>hinge-PD1-BM-<br>min HC) | EVQLVESGGGLVQPGGSLRLSCAASGYKYGVYSMGWFRQAPGKGLEGVSAICSGGRTTYSDSVKGRFTISRDNSNQI<br>LYLQMNSLRAEDTAVYYCAARPLWTGDCDLSSSWYKTWGQGTLVTVSSEPKSSDKTHTSPPSPEVQLVESGGGLVQP<br>GGSLRLSCAASGFVFSRYDMAWVRQAPGKGLEWVSFISGGGSNTYYPDTVKGRFTISRDNSKNTLYLQMNSLRAEDT<br>AVYYCISPYYYAMEYWGQGTTVTVSSASTKGPSVFPLAPCSRSTSESTAALGCLVKDYFPEPVTVSWNSGALTSGVH<br>TFPAVLQSSGLYSLSSVVTVPSSSLGTKTYTCNVDHKPSNTKVDKRVESKYGPPCPPCPAPEFLGGPSVFLFPPKPK<br>DTLMISRTPEVTCVVVDVSQEDPEVQFNWYVDGVEVHNAKTKPREEQFNSTYRVVSVLTVLHQDWLNGKEYKCKVSN<br>KGLPSSIEKTISKAKGQPREPQVYTLPPSQEEMTKNQVSLTCLVKGFYPSDIAVEWESNGQPENNYKTTPPVLDSDG<br>SFFLYSRLTVDKSRWQEGNVFSCSVMHEALHNHYTQKSLSLSLGK |
| SEQ ID NO: 395<br>BTP-11_LC<br>(PD1-BM-min<br>LC) | DIQMTQSPSSVSASVGDRVTITCKASQDVDTAVAWYQQKPGKAPKLLIYWASTRHTGVPSRFSGSGSGTDFTLTISS<br>LQPEDFATYYCQQYSTFPWTFGGGTKVEIKRTVAAPSVFIFPPSDEQLKSGTASVVCLLNNFYPREAKVQWKVDNAL<br>QSGNSQESVTEQDSKDSTYSLSSTLTLSKADYEKHKVYACEVTHQGLSSPVTKSFNRGEC |
| SEQ ID NO: 396<br>BTP-12_HC<br>(PD1-BM-min<br>HC-mutated<br>hIgG1 hinge-<br>AS19584VH28) | EVQLVESGGGLVQPGGSLRLSCAASGFVFSRYDMAWVRQAPGKGLEWVSFISGGGSNTYYPDTVKGRFTISRDNSKN<br>TLYLQMNSLRAEDTAVYYCISPYYYAMEYWGQGTTVTVSSASTKGPSVFPLAPCSRSTSESTAALGCLVKDYFPEPV<br>TVSWNSGALTSGVHTFPAVLQSSGLYSLSSVVTVPSSSLGTKTYTCNVDHKPSNTKVDKRVESKYGPPCPPCPAPEF<br>LGGPSVFLFPPKPKDTLMISRTPEVTCVVVDVSQEDPEVQFNWYVDGVEVHNAKTKPREEQFNSTYRVVSVLTVLHQ<br>DWLNGKEYKCKVSNKGLPSSIEKTISKAKGQPREPQVYTLPPSQEEMTKNQVSLTCLVKGFYPSDIAVEWESNGQPE<br>NNYKTTPPVLDSDGSFFLYSRLTVDKSRWQEGNVFSCSVMHEALHNHYTQKSLSLSLGKEPKSSDKTHTSPPSPEVQ<br>LVESGGGLVQPGGSLRLSCAASGYKYGVYSMGWFRQAPGKGLEGVSAICSGGRTTYSDSVKGRFTISRDNSNQILYL<br>QMNSLRAEDTAVYYCAARPLWTGDCDLSSSWYKTWGQGTLVTVSS |
| SEQ ID NO: 397<br>BTP-12_LC<br>(PD1-BM-min<br>LC) | DIQMTQSPSSVSASVGDRVTITCKASQDVDTAVAWYQQKPGKAPKLLIYWASTRHTGVPSRFSGSGSGTDFTLTISS<br>LQPEDFATYYCQQYSTFPWTFGGGTKVEIKRTVAAPSVFIFPPSDEQLKSGTASVVCLLNNFYPREAKVQWKVDNAL<br>QSGNSQESVTEQDSKDSTYSLSSTLTLSKADYEKHKVYACEVTHQGLSSPVTKSFNRGEC |
| SEQ ID NO: 398<br>BTP-13_HC<br>(PD1-BM-min<br>HC) | EVQLVESGGGLVQPGGSLRLSCAASGFVFSRYDMAWVRQAPGKGLEWVSFISGGGSNTYYPDTVKGRFTISRDNSKN<br>TLYLQMNSLRAEDTAVYYCISPYYYAMEYWGQGTTVTVSSASTKGPSVFPLAPCSRSTSESTAALGCLVKDYFPEPV<br>TVSWNSGALTSGVHTFPAVLQSSGLYSLSSVVTVPSSSLGTKTYTCNVDHKPSNTKVDKRVESKYGPPCPPCPAPEF<br>LGGPSVFLFPPKPKDTLMISRTPEVTCVVVDVSQEDPEVQFNWYVDGVEVHNAKTKPREEQFNSTYRVVSVLTVLHQ<br>DWLNGKEYKCKVSNKGLPSSILKTISKAKGQPREPQVYTLPPSQEEMTKNQVSLTCLVKGFYPSDIAVEWESNGQPE<br>NNYKTTPPVLDSDGSFFLYSRLTVDKSRWQEGNVFSCSVMHEALHNHYTQKSLSLSLGK |
| SEQ ID NO: 399<br>BTP-13_LC<br>(AS19584VH28-<br>mutated hIgG1<br>hinge-PD1-BM-<br>min LC) | EVQLVESGGGLVQPGGSLRLSCAASGYKYGVYSMGWFRQAPGKGLEGVSAICSGGRTTYSDSVKGRFTISRDNSNQI<br>LYLQMNSLRAEDTAVYYCAARPLWTGDCDLSSSWYKTWGQGTLVTVSSEPKSSDKTHTSPPSPDIQMTQSPSSVSAS<br>VGDRVTITCKASQDVDTAVAWYQQKPGKAPKLLIYWASTRHTGVPSRFSGSGSGTDFTLTISSLQPEDFATYYCQQY<br>STFPWTFGGGTKVEIKRTVAAPSVFIFPPSDEQLKSGTASVVCLLNNFYPREAKVQWKVDNALQSGNSQESVTEQDS<br>KDSTYSLSSTLTLSKADYEKHKVYACEVTHQGLSSPVTKSFNRGEC |
| SEQ ID NO: 400<br>BTP-14_HC<br>(PD1-BM-min<br>LC-mutated<br>hIgG1 hinge-<br>AS19584VH28) | EVQLVESGGGLVQPGGSLRLSCAASGFVFSRYDMAWVRQAPGKGLEWVSFISGGGSNTYYPDTVKGRFTISRDNSKN<br>TLYLQMNSLRAEDTAVYYCISPYYYAMEYWGQGTTVTVSSASTKGPSVFPLAPCSRSTSESTAALGCLVKDYFPEPV<br>TVSWNSGALTSGVHTFPAVLQSSGLYSLSSVVTVPSSSLGTKTYTCNVDHKPSNTKVDKRVESKYGPPCPPCPAPEF<br>LGGPSVFLFPPKPKDTLMISRTPEVTCVVVDVSQEDPEVQFNWYVDGVEVHNAKTKPREEQFNSTYRVVSVLTVLHQ<br>DWLNGKEYKCKVSNKGLPSSIEKTISKAKGQPREPQVYTLPPSQEEMTKNQVSLTCLVKGFYPSDIAVEWESNGQPE<br>NNYKTTPPVLDSDGSFFLYSRLTVDKSRWQEGNVFSCSVMHEALHNHYTQKSLSLSLGK |
| SEQ ID NO: 401<br>BTP-14_LC<br>(PD1-BM-min<br>LC-mutated<br>hIgG1 hinge-<br>AS19584VH28) | DIQMTQSPSSVSASVGDRVTITCKASQDVDTAVAWYQQKPGKAPKLLIYWASTRHTGVPSRFSGSGSGTDFTLTISS<br>LQPEDFATYYCQQYSTFPWTFGGGTKVEIKRTVAAPSVFIFPPSDEQLKSGTASVVCLLNNFYPREAKVQWKVDNAL<br>QSGNSQESVTEQDSKDSTYSLSSTLTLSKADYEKHKVYACEVTHQGLSSPVTKSFNRGECEPKSSDKTHTSPPSPEV<br>QLVESGGGLVQPGGSLRLSCAASGYKYGVYSMGWFRQAPGKGLEGVSAICSGGRTTYSDSVKGRFTISRDNSNQILY<br>LQMNSLRAEDTAVYYCAARPLWTGDCDLSSSWYKTWGQGTLVTVSS |
| SEQ ID NO: 402<br>BTP-21_HC<br>(AS19584VH28-<br>mutated hIgG1<br>hinge-h53C1<br>(inert IgG1)<br>HC) | EVQLVESGGGLVQPGGSLRLSCAASGYKYGVYSMGWFRQAPGKGLEGVSAICSGGRTTYSDSVKGRFTISRDNSNQI<br>LYLQMNSLRAEDTAVYYCAARPLWTGDCDLSSSWYKTWGQGTLVTVSSEPKSSDKTHTSPPSPEVQLVQSGAEVKKP<br>GASVKVSCKASGYIFTGYGITWVRQAPGQGLEWMGEIFPRRVQTYYSEKFKGRVTMTTDTSTSTAYMELRSLRSDDT<br>AVYYCARDYDPYFALDYWGQGTTVTVSSASTKGPSVFPLAPSSKSTSGGTAALGCLVKDYFPEPVTVSWNSGALTSG<br>VHTFPAVLQSSGLYSLSSVVTVPSSSLGTQTYICNVNHKPSNTKVDKKVEPKSCDKTHTCPPCPAPELLGGPSVFLF<br>PPKPKDTLMISRTPEVTCVVVDVSHEDPEVKFNWYVDGVEVHNAKTKPREEQYASTYRVVSVLTVLHQDWLNGKEYK<br>CKVSNKALPAPIEKTISKAKGQPREPQVYTLPPSREEMTKNQVSLTCLVKGFYPSDIAVEWESNGQPENNYKTTPPV<br>LDSDGSFFLYSKLTVDKSRWQQGNVFSCSVMHEALHNHYTQKSLSLSPGK |
| SEQ ID NO: 403<br>BTP-21_LC<br>(h53C1<br>(inert IgG1)<br>LC) | DIQMTQSPSSLSASVGDRVTITCRASQDVSTAVDWYQQKPGKAPKLLIYSASYRYTGVPDRFSGSGSGTDFTFTISS<br>LQPEDIATYYCQQHYSIPFTFGQGTKLEIKRTVAAPSVFIEPPSDEQLKSGTASVVCLLNNFYPREAKVQWKVDNAL<br>QSGNSQESVTEQDSKDSTYSLSSTLTLSKADYEKHKVYACEVTHQGLSSPVTKSFNRGEC |
| SEQ ID NO: 404<br>BTP-22_HC<br>(h53C1<br>(inert IgG1)<br>HC) | EVQLVQSGAEVKKPGASVKVSCKASGYIFTGYGITWVRQAPGQGLEWMGEIFPRRVQTYYSEKFKGRVTMTTDTSTS<br>TAYMELRSLRSDDTAVYYCARDYDPYFALDYWGQGTTVTVSSASTKGPSVFPLAPSSKSTSGGTAALGCLVKDYFPE<br>PVTVSWNSGALTSGVHTFPAVLQSSGLYSLSSVVTVPSSSLGTQTYICNVNHKPSNTKVDKKVEPKSCDKTHTCPPC<br>PAPELLGGPSVFLFPPKPKDTLMISRTPEVTCVVVDVSHEDPEVKFNWYVDGVEVHNAKTKPREEQYASTYRVVSVL<br>TVLHQDWLNGKEYKCKVSNKALPAPIEKTISKAKGQPREPQVYTLPPSREEMTKNQVSLTCLVKGFYPSDIAVEWES<br>NGQPENNYKTTPPVLDSDGSFFLYSKLTVDKSRWQQGNVFSCSVMHEALHNHYTQKSLSLSPGK |

TABLE 24-continued

Anti-TIGIT/PD-1 and Anti-TIGIT/PD-L1 bispecific antibody amino acid sequences
(sdAb sequence is underlined, linker sequence is bolded)

SEQ ID NO: 405
BTP-22_LC
(AS19584VH28-
mutated hIgG1
hinge-h53C1
(inert IgG1)
LC)
EVQLVESGGGLVQPGGSLRLSCAASGYKYGVYSMGWFRQAPGKGLEGVSAICSGGRTTYSDSVKGRFTISRDNSNQI
LYLQMNSLRAEDTAVYYCAARPLWTGDCDLSSSWYKTWGQGTLVTVSSEPKSSDKTHTSPPSPDIQMTQSPSSLSAS
VGDRVTITCRASQDVSTAVDWYQQKPGKAPKLLIYSASYRYTGVPDRFSGSGSGTDFTFTISSLQPEDIATYYCQQH
YSIPFTFGQGTKLEIKRTVAAPSVFIFPPSDEQLKSGTASVVCLLNNFYPREAKVQWKVDNALQSGNSQESVTEQDS
KDSTYSLSSTLTLSKADYEKHKVYACEVTHQGLSSPVTKSFNRGEC SEQ ID NO: 406 (PD1-BM-min_VH amino acid sequence; CDRs are underlined)
EVQLVESGGGLVQPGGSLRLSCAASGFVFSRYDMAWVRQAPGKGLEWVSFISGGGSNTYYPDTVKGRFTISRDNSKNTLYLQMNSLRAEDT
AVYYCISPYYYAMEYWGQGTTVTVSS SEQ ID NO: 407 (PD1-BM-min_VL amino acid sequence; CDRs are underlined)
DIQMTQSPSSVSASVGDRVTITCKASQDVDTAVAWYQQKPGKAPKLLIYWASTRHTGVPSRFSGSGSGTDFTLTISSLQPEDFATYYCQQY
STFPWTFGGGTKVEIK

What is claimed is:

1. An anti-TIGIT construct comprising a single-domain antibody (sdAb) moiety specifically recognizing TIGIT, wherein the sdAb moiety comprises a CDR1 comprising the amino acid sequence of SEQ ID NO: 36; a CDR2 comprising the amino acid sequence of SEQ ID NO: 106; and a CDR3 comprising the amino acid sequence of SEQ ID NO: 176.

2. The anti-TIGIT construct of claim 1, wherein the sdAb moiety comprises a $V_H H$ domain comprising the amino acid sequence of any one of SEQ ID NOs: 253, 271, and 273-276, or a variant thereof having at least 90% sequence identity to any one of SEQ ID NOs: 253, 271, and 273-276.

3. The anti-TIGIT construct of claim 1, wherein the sdAb moiety specifically recognizing TIGIT is camelid, chimeric, human, partially humanized, or fully humanized.

4. The anti-TIGIT construct of claim 1, wherein the anti-TIGIT construct is an sdAb-Fc fusion protein.

5. The anti-TIGIT construct of claim 4, wherein the Fc fragment is a human IgG1 (hIgG1) Fc, effectorless (inert) hIgG1 Fc, or hIgG4 Fc.

6. The anti-TIGIT construct of claim 4, wherein the sdAb-Fc fusion protein comprises the amino acid sequence of any one of SEQ ID NOs: 288, 306, 308-311 and 365-367.

7. The anti-TIGIT construct of claim 1, wherein the anti-TIGIT construct further comprises a second antibody moiety specifically recognizing a second epitope.

8. The anti-TIGIT construct of claim 7, wherein the sdAb moiety specifically recognizing TIGIT and the second antibody moiety are connected by a peptide linker.

9. The anti-TIGIT construct of claim 8, wherein the peptide linker comprises the amino acid sequence of any one of SEQ ID NOs: 324 and 370-378.

10. The anti-TIGIT construct of claim 7, wherein the second antibody moiety is a full-length antibody consisting of two heavy chains and two light chains.

11. The anti-TIGIT construct of claim 10, wherein the full-length antibody comprises an Fc that is selected from the group consisting of IgG1 Fc, effectorless IgG1 Fc, IgG2 Fc, and IgG4 Fc.

12. The anti-TIGIT construct of claim 10, wherein the anti-TIGIT construct comprises a configuration selected from the group consisting of:
   (a) the N-terminus of the sdAb moiety specifically recognizing TIGIT is fused to the C-terminus of at least one of the heavy chains of the full-length antibody;
   (b) the C-terminus of the sdAb moiety specifically recognizing TIGIT is fused to the N-terminus of at least one of the heavy chains of the full-length antibody;
   (c) the N-terminus of the sdAb moiety specifically recognizing TIGIT is fused to the C-terminus of at least one of the light chains of the full-length antibody; and
   (d) the C-terminus of the sdAb moiety specifically recognizing TIGIT is fused to the N-terminus of at least one of the light chains of the full-length antibody.

13. The anti-TIGIT construct of claim 10, wherein the full-length antibody specifically recognizes PD-1, and wherein the full-length antibody comprises heavy chain complementarity determining regions (HC-CDRs) and light chain complementarity determining regions (LC-CDRs) of:
   (a) a heavy chain variable domain (VH) comprising the amino acid sequence of SEQ ID NO: 385, and a light chain variable domain (VL) comprising the amino acid sequence of SEQ ID NO: 386;
   (b) a $V_H$ comprising the amino acid sequence of SEQ ID NO: 387, and a $V_L$ comprising the amino acid sequence of SEQ ID NO: 388; or
   (c) a $V_H$ comprising the amino acid sequence of SEQ ID NO: 406, and a $V_L$ comprising the amino acid sequence of SEQ ID NO: 407.

14. The anti-TIGIT construct of claim 10, wherein the full-length antibody specifically recognizes PD-L1, and wherein the full-length antibody comprises:
   (a) an HC-CDR1 comprising the amino acid sequence of SEQ ID NO: 349, an HC-CDR2 comprising the amino acid sequence of SEQ ID NO: 350, an HC-CDR3 comprising the amino acid sequence of SEQ ID NO: 351, an LC-CDR1 comprising the amino acid sequence of SEQ ID NO: 352, an LC-CDR2 comprising the amino acid sequence of SEQ ID NO: 353, and an LC-CDR3 comprising the amino acid sequence of SEQ ID NO: 354;
   (b) a $V_H$ comprising the amino acid sequence of SEQ ID NO: 339, and a $V_L$ comprising the amino acid sequence of SEQ ID NO: 340;
   (c) a heavy chain comprising the amino acid sequence of SEQ ID NO: 323 or 327, and a light chain comprising the amino acid sequence of SEQ ID NO: 328;
   (d) a heavy chain comprising the amino acid sequence of SEQ ID NO: 329, and a light chain comprising the amino acid sequence of SEQ ID NO: 330;
   (e) HC-CDRs of a $V_H$ comprising the amino acid sequence of SEQ ID NO: 379, and LC-CDRs of a $V_L$ comprising the amino acid sequence of SEQ ID NO: 380;
   (f) HC-CDRs of a $V_H$ comprising the amino acid sequence of SEQ ID NO: 383, and LC-CDRs of a $V_L$ comprising the amino acid sequence of SEQ ID NO: 384;
   (g) HC-CDRs of a $V_H$ comprising the amino acid sequence of SEQ ID NO: 381, and LC-CDRs of a $V_L$ comprising the amino acid sequence of SEQ ID NO: 382;
   (h) a heavy chain comprising the amino acid sequence of SEQ ID NO: 331, and a light chain comprising the amino acid sequence of SEQ ID NO: 332; or
   (i) a heavy chain comprising the amino acid sequence of SEQ ID NO: 333, and a light chain comprising the amino acid sequence of SEQ ID NO: 334.

15. The anti-TIGIT construct of claim 10, wherein the full-length antibody specifically recognizes PD-L1, and:
   (a) wherein the full-length antibody comprises a heavy chain comprising the amino acid sequence of SEQ ID NO: 329, and a light chain comprising the amino acid sequence of SEQ ID NO: 330, wherein at least one of the heavy chains of the full-length antibody is fused to the sdAb moiety specifically recognizing TIGIT, and wherein the heavy chain fusion polypeptide comprises the amino acid sequence of SEQ ID NO: 402 or 341;
   (b) wherein the full-length antibody comprises a heavy chain comprising the amino acid sequence of SEQ ID NO: 323, and a light chain comprising the amino acid sequence of SEQ ID NO: 328, wherein at least one of the heavy chains of the full-length antibody is fused to the sdAb moiety specifically recognizing TIGIT, and wherein the heavy chain fusion polypeptide comprises the amino acid sequence of SEQ ID NO: 357 or 359;
   (c) wherein the full-length antibody comprises a heavy chain comprising the amino acid sequence of SEQ ID NO: 390, and a light chain comprising the amino acid sequence of SEQ ID NO: 391, wherein at least one of the heavy chains of the full-length antibody is fused to the sdAb moiety specifically recognizing TIGIT, and wherein the heavy chain fusion polypeptide comprises the amino acid sequence of SEQ ID NO: 394 or 396;

(d) wherein the full-length antibody comprises a heavy chain comprising the amino acid sequence of SEQ ID NO: 390, and a light chain comprising the amino acid sequence of SEQ ID NO: 391, wherein at least one of the light chains of the full-length antibody is fused to the sdAb moiety specifically recognizing TIGIT, and wherein the light chain fusion polypeptide comprises the amino acid sequence of SEQ ID NO: 399 or 401;

(e) wherein the full-length antibody comprises a heavy chain comprising the amino acid sequence of SEQ ID NO: 329, and a light chain comprising the amino acid sequence of SEQ ID NO: 330, wherein at least one of the light chains of the full-length antibody is fused to the sdAb moiety specifically recognizing TIGIT, and wherein the light chain fusion polypeptide comprises the amino acid sequence of SEQ ID NO: 405;

(f) wherein the full-length antibody comprises a heavy chain comprising the amino acid sequence of SEQ ID NO: 327, and a light chain comprising the amino acid sequence of SEQ ID NO: 328, wherein at least one of the heavy chains of the full-length antibody is fused to the sdAb moiety specifically recognizing TIGIT, and wherein the heavy chain fusion polypeptide comprises the amino acid sequence of SEQ ID NO: 343;

(g) wherein the full-length antibody comprises a heavy chain comprising the amino acid sequence of SEQ ID NO: 333, and a light chain comprising the amino acid sequence of SEQ ID NO: 334, wherein at least one of the heavy chains of the full-length antibody is fused to the sdAb moiety specifically recognizing TIGIT, and wherein the heavy chain fusion polypeptide comprises the amino acid sequence of SEQ ID NO: 345;

(h) wherein the full-length antibody comprises a heavy chain comprising the amino acid sequence of SEQ ID NO: 331, and a light chain comprising the amino acid sequence of SEQ ID NO: 332, wherein at least one of the heavy chains of the full-length antibody is fused to the sdAb moiety specifically recognizing TIGIT, and wherein the heavy chain fusion polypeptide comprises the amino acid sequence of SEQ ID NO: 347; or (i) wherein the full-length antibody comprises a heavy chain comprising the amino acid sequence of SEQ ID NO: 323, and a light chain comprising the amino acid sequence of SEQ ID NO: 328, wherein at least one of the light chains of the full-length antibody is fused to the sdAb moiety specifically recognizing TIGIT, and wherein the light chain fusion polypeptide comprises the amino acid sequence of SEQ ID NO: 362 or 364.

16. An anti-TIGIT construct comprising an sdAb moiety specifically recognizing TIGIT, wherein the sdAb moiety comprises CDR1, CDR2, and CDR3 of any one of SEQ ID NOs: 253, 271, and 273-276.

17. A method of treating an individual having a TIGIT-related disease, comprising administering to the individual an effective amount of an anti-TIGIT construct of claim 1.

18. A method of producing an anti-TIGIT construct, comprising: (a) culturing a host cell comprising a nucleic acid encoding the anti-TIGIT construct of claim 1 under conditions effective to express the encoded anti-TIGIT construct; and (b) obtaining the expressed anti-TIGIT construct from said host cell.

\* \* \* \* \*